(12) United States Patent
Simard et al.

(10) Patent No.: US 8,637,305 B2
(45) Date of Patent: **\*Jan. 28, 2014**

(54) EXPRESSION VECTORS ENCODING EPITOPES OF TARGET-ASSOCIATED ANTIGENS AND METHODS FOR THEIR DESIGN

(75) Inventors: John J. L. Simard, Vancouver (CA); David C. Diamond, West Hills, CA (US); Zhiyong Qiu, Los Angeles, CA (US); Xiang-Dong Lei, West Hills, CA (US)

(73) Assignee: Mannkind Corporation, Sylmar, CA (US)

( * ) Notice: Subject to any disclaimer, the term of this patent is extended or adjusted under 35 U.S.C. 154(b) by 1144 days.

This patent is subject to a terminal disclaimer.

(21) Appl. No.: 10/292,413

(22) Filed: Nov. 7, 2002

(65) Prior Publication Data

US 2003/0228634 A1   Dec. 11, 2003

Related U.S. Application Data

(60) Provisional application No. 60/336,968, filed on Nov. 7, 2001.

(51) Int. Cl.
| C12N 15/63 | (2006.01) |
| A61K 38/04 | (2006.01) |
| C07K 4/00 | (2006.01) |

(52) U.S. Cl.
USPC ........................................ 435/320.1

(58) Field of Classification Search
USPC ........................................ 435/320.1
See application file for complete search history.

(56) References Cited

U.S. PATENT DOCUMENTS

| | | |
|---|---|---|
| 4,439,199 A | 3/1984 | Amkraut et al. |
| 4,683,199 A | 7/1987 | Palladino |
| 4,937,190 A | 6/1990 | Palmenberg et al. |
| 5,093,242 A | 3/1992 | Bachmair et al. |
| 5,132,213 A | 7/1992 | Bachmair et al. |
| 5,168,062 A | 12/1992 | Stinski |
| 5,258,294 A | 11/1993 | Boyle et al. |
| 5,385,839 A | 1/1995 | Stinski |
| 5,405,940 A | 4/1995 | Boon et al. |
| 5,478,556 A | 12/1995 | Elliott et al. |
| 5,487,974 A | 1/1996 | Boon-Falleur et al. |
| 5,496,721 A | 3/1996 | Bachmair et al. |
| 5,519,117 A | 5/1996 | Wolfel et al. |
| 5,530,096 A | 6/1996 | Wolfel et al. |
| 5,554,506 A | 9/1996 | van der Bruggen et al. |
| 5,554,724 A | 9/1996 | Melief et al. |
| 5,558,995 A | 9/1996 | van der Bruggen et al. |
| 5,580,859 A | 12/1996 | Felgner et al. |
| 5,585,461 A | 12/1996 | Townsend et al. |
| 5,589,466 A | 12/1996 | Felgner et al. |
| 5,646,017 A | 7/1997 | Bachmair et al. |
| 5,648,226 A | 7/1997 | Van den Eynde et al. |
| 5,679,647 A | 10/1997 | Carson et al. |
| 5,698,396 A | 12/1997 | Pfreundschuh |
| 5,733,548 A | 3/1998 | Restifo et al. |
| 5,744,316 A | 4/1998 | Lethe et al. |
| 5,747,269 A | 5/1998 | Rammensee et al. |
| 5,844,075 A | 12/1998 | Kawakami et al. |
| 5,846,540 A | 12/1998 | Restifo et al. |
| 5,847,097 A | 12/1998 | Bachmair et al. |
| 5,856,187 A | 1/1999 | Restifo et al. |
| 5,925,565 A | 7/1999 | Berlioz et al. |
| 5,962,428 A | 10/1999 | Carrano et al. |
| 5,989,565 A | 11/1999 | Storkus et al. |
| 5,993,828 A | 11/1999 | Morton |
| 5,994,523 A | 11/1999 | Kawakami et al. |
| 6,004,777 A | 12/1999 | Tartaglia et al. |
| 6,037,135 A | 3/2000 | Kubo et al. |
| 6,060,273 A | 5/2000 | Dirks et al. |
| 6,074,817 A | 6/2000 | Landini et al. |
| 6,130,066 A | 10/2000 | Tartaglia et al. |
| 6,287,569 B1 | 9/2001 | Kipps et al. |
| 7,084,239 B1 | 8/2006 | Wang et al. |

(Continued)

FOREIGN PATENT DOCUMENTS

| CA | 2147863 | 5/1994 |
| DE | 44 23 392 A1 | 1/1996 |

(Continued)

OTHER PUBLICATIONS

Manickan, E et al. Crit. Rev. Immunol. [1997] 17(2):139-154.*
Chen et al. Journal of Immunol. 2000, 165: 948-955.*
US 6,008,200, 12/1999, Krieg (withdrawn).
Aid et al., "Interferon-( Induces Different Subunit Organizations and Functional Diversity of Proteasomes," *J. Biochem.*, 115: 257-269(1994).
Altuvia et al., "A structure-based algorithm to predict potential binding peptides to MHC molecules with hydrophobic binding pockets," *Human Immunology*, 58: 1-11 (1997).

(Continued)

*Primary Examiner* — Gerald R Ewoldt
*Assistant Examiner* — Marianne Dibrino
(74) *Attorney, Agent, or Firm* — Davis Wright Tremaine LLP

(57) ABSTRACT

The invention disclosed herein is directed to methods of identifying a polypeptide suitable for epitope liberation including, for example, the steps of identifying an epitope of interest; providing a substrate polypeptide sequence including the epitope, wherein the substrate polypeptide permits processing by a proteasome; contacting the substrate polypeptide with a composition including the proteasome, under conditions that support processing of the substrate polypeptide by the proteasome; and assaying for liberation of the epitope. The invention further relates to vectors including a housekeeping epitope expression cassette. The housekeeping epitope(s) can be derived from a target-associated antigen, and the housekeeping epitope can be liberatable, that is capable of liberation, from a translation product of the cassette by immunoproteasome processing. The invention also relates to a method of activating a T cell comprising contacting a substrate polypeptide with an APC and contacting the APC with a T cell.

4 Claims, 10 Drawing Sheets

(56) References Cited

U.S. PATENT DOCUMENTS

| | | |
|---|---|---|
| 2003/0220239 A1 | 11/2003 | Simard et al. |
| 2004/0203051 A1 | 10/2004 | Simard et al. |
| 2004/0214284 A1 | 10/2004 | Tureci et al. |
| 2005/0130920 A1 | 6/2005 | Simard et al. |

FOREIGN PATENT DOCUMENTS

| | | |
|---|---|---|
| EP | 93/03175 | 4/1995 |
| EP | 1118860 A1 | 7/2001 |
| EP | 1181314 A1 | 2/2002 |
| IE | 74899 | 8/1997 |
| WO | WO 92/21033 | 11/1992 |
| WO | WO 96/01429 | 1/1996 |
| WO | WO 96/03144 A1 | 2/1996 |
| WO | WO 96/40209 | 12/1996 |
| WO | WO 97/34613 | 9/1997 |
| WO | WO 97/41440 A1 | 11/1997 |
| WO | WO 98/13489 | 4/1998 |
| WO | WO 98/14464 | 4/1998 |
| WO | WO 98/40501 A1 | 9/1998 |
| WO | WO 99/02183 | 1/1999 |
| WO | WO 99/24596 A1 | 5/1999 |
| WO | WO 99/45954 | 9/1999 |
| WO | WO 99/55730 A2 | 11/1999 |
| WO | WO 00/06723 A1 | 2/2000 |
| WO | WO 00/29008 A2 | 5/2000 |
| WO | WO 00/40261 A2 | 7/2000 |
| WO | WO 00/52157 A1 | 9/2000 |
| WO | WO 00/52451 A1 | 9/2000 |
| WO | WO 00/66727 A1 | 11/2000 |
| WO | WO 00/73438 A1 | 12/2000 |
| WO | WO 01/11040 A1 | 2/2001 |
| WO | WO 01/18035 A2 | 3/2001 |
| WO | WO 01/19408 A1 | 3/2001 |
| WO | WO 01/23577 A3 | 4/2001 |
| WO | WO 01/55393 | 8/2001 |
| WO | WO 01/58478 A1 | 8/2001 |
| WO | WO 01/82963 A | 11/2001 |
| WO | WO 01/89281 A2 | 11/2001 |
| WO | WO 01/90197 A1 | 11/2001 |
| WO | WO 02/068654 A2 | 9/2002 |
| WO | WO 00/71158 A1 | 11/2002 |
| WO | WO 03/011331 A | 2/2003 |
| WO | WO 03/82963 | 2/2003 |
| WO | WO 2004/018666 | 3/2004 |
| WO | WO 2004/022709 A2 | 3/2004 |

OTHER PUBLICATIONS

An et al. "A Multivalent Minigene Vaccine, Containing B-Cell, Cytoxic T-Lymphocyte, and $T_h$ Epitopes from Several Microbes, Induces Appropriate Responses in Vivo and Confers Protection against More than One Pathogen", *J Virol*; 71(3):2292-302 (1997).
Aria et al., "Isolation of Highly Purified Lysosomes from Rat Liver: Identification of Electron Carrier Components on Lysosomal Membranes", *J. Biochem.*, 110:541-7 (1991).
Arnold et al., "Proteasome subunits encoded in the MHC are not generally required for the processing of peptides bound by MHC class I molecules," *Nature*, 360: 171-174 (1992).
Ausubel et al., *Short Protocols in Molecular Biology*, Unit 11.2 (3d ed. 1997).
Ayyoub, et al., "Lack of tumor recognition by hTERT peptide 540-548-specific CD8⁺T cells from melanoma patients reveals inefficient antigen processing," *Eur. J. Jmmunol.*, 31:2642-2651 (2001).
Bachmann et al., "In vivo vs. in vitro assays for the assessment of T- and B-cell function," *Curr. Opin. Immunol.*, 6:320-326 (1994).
Bettinotti et al., "Stringent Allele/Epitope Requirements for MART-1/Melan A Immunodominance: Implications for Peptide-Based immunotherapy," *J. Immunol.*, 161: 877-889.(1998).
Boes et al., "Interferon y Stimulation Modulates the Proteolytic Activity and Cleavage Site Preference of 20S Mouse Proteasomes,"*J. Exp. Med.*, 179: 901-909 (1994).

Brown et al., "Structural and serological simularity of MHC-linked LMP and proteasome (rnulticatalytie proteinase) complexes," *Nature*, 353: 355-357 (1991).
Butterfield et al., "Generation of Melanoma-Specific Cytotoxic T Lymphocytes by Dendritic Cells Tranduced with a MART-1 Adenovirus," *J. Immunol.*, 161: 5607-5613 (1998).
Carulli et al., "High Throughput Analysis of Differential Gene Expression", *J. Cellular Biochem Suppl.*, 30/31:286-96(1998).
Chattergoon, et al., "Genetic Immunization: a new era in vaccines and immune therapeutics," *FASEB J.*, 11:753-763 (1997).
Chaux et al., "Identification of Five MAGE-A1 Epitopes Recognized by Cytolytic T Lymphocytes Obtained by in Vitro Stimulation with Dendritic Cells Transduced with MAGE-A1," *The Journal of Immunology*, 163: 2928-2936 (1999).
Cleland et al., "Design and developmental strategy", *Formulation and Delivery of Proteins and Peptides*, American Chemical Society Symposium Series, No. 567, (1994).
Davis, H. L., "Plasmid DNA expression systems for the purpose of immunization," *Current Opinion in Immunology*, 8: 635-640 (1997).
Dean et al., "Proteolysis in Mitochondrial Preparations and in Lysosomal Preparations Derived from Rat Liver", *Arch. Biochem. Biophys.*, 227:154-63 (1983).
Dean et al., "Sequence requirements for plasmid nuclear import," *Experimental Cell Research*, 253: 713-722 (1999).
DeGroot et al., "An Interactive Web Site Providing Major Histocompatibility Ligand Predictions: Application to HIV Research," *Aids Res. and Human Retrov*, 13: 529-531 (1997).
Dick et al., "Coordinated Dual Cleavages Induced by the Protcasome Regulator PA28 Lead to Dominant MHC Ligands," *Cell*, 86: 253-262 (1996).
Dick, et al., "Proteolytic Processing of Ovalbumin and 3-galactosidase by the Proteasome to Yield Antigenic Peptides," *J. of Immunology*, 152:3884-3894-(1994).
Driscoll et al., "MHC-linked LMP gene products specifically alter peptidase activities of the proteasome,"*Nature*, 365: 262-264 (1993).
Durrant, L.G., "Cancer vaccines," *Anti-cancer drugs*, 8: 727-733 (1997).
Elliot et al., "Intercellular Trafficking and Protein Delivery by a Herpesvirus Structural Protein", *Cell* 88:223-233 (1997).
Escola et al., "Characterization of a Lysozyme-Major Histocompatibility Complex Class II Molecule-loading Compartment as a Specialized Recycling Endosome in Murine B Lymphocytes", *J. Biol. Chem.* 271:27360-65 (1996).
Falk et al., "Allele-specific Motifs Revealed by Sequencing of Self-peptides Eluted from MHC Molecules", *Nature*, 351:290-296 (1991).
Fang et al., "Expression of Vaccinia E3L and K3L Genes by a Novel Recombinant Canarypox HIV Vaccine Vector Enhances HIV-1 Pseudovirion Production and Inhibits Apoptosis in Human Cells", *Virology* 291(2):272-84 (2001).
Farrar et al., "The molecular cell biology of interferon-( and its receptor," *Annu. Rev. Immunol.*, 11: 571-611 (1993).
Fayolle et al., "Delivery of Multiple Epitopes by Recombinant Detoxified Adenylate Cyclase of *Bordetella pertussis* Induces Protective Antiviral Immunity", *J Virol* 75(161:7330-8 (2001).
Fiette et al, "Theiler's virus infection of 129Sv mice that lack the interferon α/β or interferon y receptors," *J. Exp. Med.*, 181: 2069-2076 (1995).
Firat et al., "Design of a Polyepitope Construct for the Induction of HLA-A0201-restricted HIV 1-specific CTL Responses Using HLA-A*0201 Transgenic, H-2 Class I KO Mice", *Eur J Immunol* 31(101:3064-74 (2001).
Firat et al., "H-2 Class 1 Knockout, HLA-A2.1-Transgenic Mice: a Versatile Animal Model for Preclinical Evaluation or Antitumor Immunotherapeutic Strategies", *Eur J Immunol* 29(10):3112-21 (1999).
Firat et al., "Use of a Lentiviral Flap Vector for Induction of CTL Immunity Against Melanoma. Perspectives for Immunotherapy", *J Gene Med*; 4(1):38-45 (2001).
Fomsgaard et al., "Induction of Cytotoxic T-cell-RespoliSes by Gene Gun DNA Vaccination with Minigenes Encoding Influenza A Virus HA and NP CTL-Epitopes", *Vaccine* 18(7-8):681-91 (2000).

(56) References Cited

OTHER PUBLICATIONS

Ford et al., "Protein Transduction: an Alternative to Genetic Intervention?", *Gene Ther.* 8:1-4, (2001).
Gaczynska et al., "γγ-Interferon and expression of Mhc genes regulate peptide hydrolysis by proteasomes," *Nature*, 365: 264-267 (1993).
Gale et al., "Evidence that hepatitis C Virus resistance to interferon is mediated through repression of the PKR protein kinase by the onostructural 5A protein," *Virology*, 230: 217-227 (1997).
Gariglio et al., "Therapeutic Uterine-Cervix Cancer Vaccines in Humans", *Arch Med Res* 29(4):279-84 (1998).
Gilbert et al., Nat. Biotech. 15:1280-1284, 1997.
Gileadi et al., "Generation of an Immunodominant CTL Epitope is Affected by Proteasome Subunit Composition and Stability of the Antigenic Protein," *Am. Assoc. of Immunol.*, 163: 6045-6052 (1999).
Glynne et al., "A proteasome-related gene between the two Abc transporter loci in the class II region of the human MHC," *Nature*, 353: 357-360 (1991).
Groettrup et al., "A role for the proteasome regulator PA28a in antigen presentation," *Nature*, 381: 166-168 (1996).
Gulukota et al., "Two complementary methods for predicting peptides binding major histocompatibility complex molecules," *J. Mol. Biol.*, 267: 1258-1267 (1997).
Gurunathan et al., "DNA vaccines: a key for inducing long-term cellular immunity," *Current Opinion in Immunology*, 12:442-447 (2000).
Hammond et al., "Heavy Endosomes Isolated from the Rat Renal Cortex Show Attributes of Intermicrovillar Clefts", *Am. J. Physiol.* 267:F516-27 (1994).
Hanke et al., "DNA Multi-CTL Epitope Vaccines for HIV and *Plasmodium Falciparum*: Immunogenicity in Mice", Vaccine 16(4):426-35 (1998).
Heemskerk et al., "Enrichment of an Antigen-Specific T Cell Response by Retrovirally Transduced Human Dendritic Cells", *Cell Immunol.* 195(1): 10-7 (1999).
Heim et al., "Expression of hepatitis C virus proteins inhibits signal transduction through the Jak-STAT pathway," *Journal of Virology*, 73: 8469-8475 (1999).
Hirano et al., "Expression of a Mutant ER-retained Polytope Membrane Protein in Cultured Rat Hepatocytes Results in Mallory Body Formation", *Histochem. Cell Biol.* 117(1):41-53 (2002).
Huang et al., "Immune response in mice that lack the interferon-( receptor," *Science*, 259: 1742-1745 (1993).
Hung et al., "Improving DNA Vaccine Potency by Linking Marek's Disease Virus Type 1 VP22 to an Antigen", *J. Virol.* 76:2676-2682 (2002).
hypertext transfer protocol address syfpeithi.bmi-heidelberg.com/Scripts/MHCServer.dll/EpPredict.htm (Apr. 3, 2003).
Inaba et al., "Identification of Proliferating Dendritic Cell Precursors in Mouse Blood,"*J. Exp. Med.* 175:1157-67 (1992).
International Search Report from co-pending Application No. PCT/US01/13806.
Jager et al., "Granulocyte-macrophage-colony-stimulating Factor Enhances Immune Responses to Melanoma-associated Peptides in Vivo", *Int. J Cancer* 67, 54-62 (1996).
Jager et al., "Simultaneous humoral and cellular immune response against cancer-testis antigen NY-ESO-1: definition of human histocompatibility leukocyte antigen (HLA)-A2-binding Peptide Epitopes," *J. Exp. Med.*, 187: 265-270 (1998).
Kang et al., "Induction of Melanoma Reactive T Cells by Stimulator Cells Expressing Melanoma Epitope-Major Histocompatibility Complex Class 1 Fusion Proteins," *Cancer Res.*, 57: 202-205 (1997).
Kawakami et al., "The Use of Melanosomal Proteins in the Immunotherapy of Melanoma,"*J. Immunother.*, 21:237-246 (1998).
Kawashima et al., "A Simple Procedure for the Isolation of Rat Kidney Lysosomes", *Kidney Int.* 54:275-8 (1998).
Kawashima et al., "The Multi-epitope Approach for Immunotherapy for Cancer: Identification of Several CTL Epitopes from Various Tumor-associated Antigens Expressed on Solid Epithelial Tumors", *Human Immunology* 59:1-14 (1998).

Kelly et al., "Second proteasome-related gene in the human MHC class II region," *Nature*, 353:667-668 (1991).
Kittlesen et al., "Human Melanoma Patients Recognize an HLA-A1-Restricted CTL Epitope from Tyrosinase Containing Two Cysteine Residues: Implications for Tumor Vaccine Development," *J. Immunol.*, 160: 2099-2106 (1998).
Kuby, Janis, "Cell-mediated Immunity", *Immunology* Chapter 15 (2d ed., W.H. Freeman and Company 1991).
Kundig et al., "Skin Test to Assess Virus-Specific Cytotoxic T-cell Activity," *Proc. Natl. Acad Sci. USA* 89:7757-7761 (1992).
Kündig et al., "Fibroblasts as efficient antigen-presenting cells in lymphoid organs," *Proc. Natl. Acad. Sci.*, 268:1343-1347 (1995).
Kündig et al., "On the Role of Antigen in Maintaining Cytotoxic T-cell Memory," *Proc. Natl. Acad Sci. USA* 93:9716-23 (1996).
Larregina et al., "Direct Transfection and Activation of Human Cutaneous Dendritic Cells," *Gene Ther.*, 8:608-617 (2001).
Le et al., "Cytotoxic T Cell Polyepitope Vaccines Delivered by ISCOMs", *Vaccine* 19(32):4669-75 (2001).
Lee et al., "Characterization of circulating T cells specific for tumor-associated antigens in melanoma patients," *Nature Medicine*, 5:677-685 (1999).
Leitner, et al., "DNA and RNA-based vaccines: principles, progress and prospects," *Vaccine*, 18:765-777 (2000).
Levy et al., "Using ubiquitin to follow the metabolic fate of a protein," *Proc. Natl. Acad. Sci USA*, 93: 4907-4912 (1996).
Linette et al., "In Vitro Priming with Adenovirus/gp100 Antigen-Transduced Dendritic Cells Reveals the Epitope Specificity of HLA-A*0201-Restricted CD8+T Cells in Patients with Melanoma, "*J. Immunol.*, 164: 3402-3412 (2000).
Lisman et al., "A Separation Method by Means of Alteration of Mitochondrial and Synaptosomal Sedimentation Properties", *Biochem. J.* 178:79-87 0979).
Liu et al., "Papillomavirus Virus-like Particles for the Delivery of Multiple Cytotoxic T Cell Epitopes",. *Virology* 273(2):374-82 (2000).
Loftus et al., "Peptides Derived from Self-Proteins as Partial Agonists and Antagonists of Human CD8+T-cell Clones Reactive to Melanoma/Melanocyte Epitope MART1(27-35)," *Cancer Res.*, 11: 2433-2439 (1998).
Malcsymowych et al, "Invasion by Salmonella typhimurium-Induces Increased Expression of the LMP, MECL, and PA28 Proteasome Genes and Changes in the Peptide Repertoire of HLA-B27, *Infection and Immunity*, 66:4624-4632 (1998)".
Marsh, M., "Endosome and Lysosome Purification by Free-flow Electrophoresis", *Methods Cell Biol.* 31:319-34 (1989).
Martinez et al., "Homology of proteasome subunits to a major histocompatibility complex-linked LMP gene," *Nature*, 353:664-667 (1991).
Mateo et al., "An HLA-A2 polyepitope vaccine for melanoma immunotherapy," *The Journal of Immunology*, 163: 4058-4063 (1999).
McCluskie, et al., "Route and Method of Delivery of DNA Vaccine Influence Immune Response in Mice and Non-Human Primates," *Molecular Medicine*, 5:287-300 (1999).
Meister et al., "Two novel T cell epitope prediction algorithms based on Mhc-binding motifs; comparison of predicted and published epitopes from Mycobacterium tuberculosis and HIV protein sequences," *Vaccine*, 13: 581-591 (1995).
Melief, C. J., *Cancerlit*, Database Accession No. 1998625858, "Towards T-cell immunotherapy of cancer," Meeting Abstract (1996).
Miconnet et al., "Amino acid identity and/or position determine the proteasomal cleavage of the HLA-A *0201-restricted peptide tumor antigen MAGE-3," *The American Society for Biochemistry and Molecular Biology, Inc.*, p. 20 (2000).
Missale et al., "HLA-A31-and HLA-Aw68-restricted Cytotoxic T cell Responses to a Single Hepatitis B Virus Nucelocapsid Epitope during Acute Viral Hepatitis," *J. Exp. Med.*, 177: 751-762 (1993).
Momburg et al., "Proteasome subunits encoded by the major histocompatilbity complex are not essential for antigen presentation," *Nature*, 360: 174-177 (1992).

(56) References Cited

OTHER PUBLICATIONS

Morel et al., Processing of Some Antigens by the Standard Proteasome but not by the Immunoproteasome Results in Poor Presentation by Dendritic Cells, *Immunity* 12:107-117 (2000).
Morris et al., "A Peptide Carrier for the Delivery of Biologically Active Proteins into Mammalian Cells", *Nat. Biotech.* 19:1173-1176 (2001).
Moskophidis et al., "Immuriobiology of Cytotoxic T-cell escape mutants of lymphocytic choriomentingitis virus," *Journal of Virology*, 69: 7423-7429 (1995).
Murphy et al., "Higher-Dose and Less Frequent Dendritic Cell Infusions with PSMA Peptides in Hormone-Refractory Metastatic Prostate Cancer Patients," *The Prostate*, 43: 59-62 (2000).
Nakabayshi et al., "Isolation and Characterization of Chicken Liver Lysosomes", *Biochem. Int.* 16:1119-25 (1988).
NCBI Blast Accession No. NP_005502.
Noppen et al., Naturally processed and concealed HLA-A2.1-restricted epitopes from tumor-associated antigen tyrosinase-related protein-2, *Int. J. Cancer*, 87: 241-246 (2000).
Normand et al., "Particle Formation by a Conserved Domain of the Herpes Simplex Virus Protein VP22 Facilitating Protein and Nucleic Acid Delivery", *J. Biol. Chem.* 276:15042-15050 (2001).
Nussbaum et al., "Cleavage motifs of the yeast 20S proteasome 13 subunits deduced from digest of enolase 1," *Proc. Natl. Acad. Sci USA*, 95: 12504-12509 (1998).
Oehen et al., "Antivirally protective cytotoxic T cell memory to lymphocytic choriomeningitis virus is governed by persisting antigen," *J.Exp.Med.* 176: 1273-1281 (1992).
Oess et al., Novel Cell Permeable Motif Derived from the PreS2-domain of Hepatitis-B Virus Surface Antigens, *Gene Ther.* 7:750-758 (2000).
Otaita et al., "Simple Preparation of Rat Brain-Lysosomes and Their Proteolytic Properties", *Anal. Biochem.* 230:41-47 (1995).
Oldstone et al., "Discriminated selection among viral peptides with the appropriate anchor residues: Implications for the size of the cytotoxic T-lymphocyte repertoire and control of viral infection," *Journal of Virology*, 69: 7423-7429 (1995).
Oliveira et al., "A Genetic Immunization Adjuvant System based on BVP22-Antigen Fusion", *Hum. Gene Ther.* 12:1353-1359 (2001).
Ortiz-Navarrete et al., "Subunit of the '20S proteasome (multicatalytic proteinase) encoded by the major histocompatibility complex," *Nature*, 353: 662-664 (1991).
Overdijk et al., "Isolation of Lysosomes from Bovine Brain Tissue a New Zonal Centrifugation Technique", *Adv. Exp: Med. Biol./Enzymes of Lipid Metabolism* 101:601-10 (1978).
Palmowski et al., "Competition Between CTL Narrows the Immune Response Induced by Prime-Boost Vaccination Protocols", *J Immunol* 168(9):4391-8 (2002).
Pantaleo et al., "Evidence for rapid disappearance of initially expanded HIV-specific CD8+T cell clones during primary HIV infection," *Proc. Natl. Acad. Sci*., 94: 9848-9853 (1997).
Parker et al., "Scheme for Ranking Potential HLA-A2 Binding Peptides Based on Independent Binding of Individual Peptide Sidechains,"*J. Immunol.* 152:163-175 (1994).
Pascolo et al., "HLA-A2.1-restricted Education and Cytolytic Activity of CD8 T Lymphocytes from β2 Microglobulin (132m) HLA-A2.1 Monochain Transgenic H-2D$^b$ β2m Double Knockout Mice" *J. Exp. Med.* 185:2043-2051 (1997).
Perez-Diez et al., "Generation of CD8+and CD4+T-cell Response to Dendritic Cells Genetically Engineered to Express the MART-1/Melan-A Gene," *Cancer Res.*, 58: 5305-5309 (1998).
Preckel et al., "Impaired ImmunoproteasOme Assembly and Immune Reponses in PA28-I-Mice," *Science*, 286: 2162-2165 (1999).
Puccetti et al., "Use of skin test assay to determine tumor-specific CD8+T cell reactivity," *Eur. J. Immunol.* 24: 1446-1452 (1994).
Rammensee et al., "MHC ligands and peptide motifs: first listing," *Immunogenetics*, 41: 178-228 (1995).
Rammensee et al., "Peptide motifs: amino acids in peptide-MHC interactions," *Landes Bioscence Austin Texas*, Chapter 4: 217-369 (1997).

Rammensee et al., "SYFPEITHI: Database for MHC ligands and peptide motifs, " *Immunogenetics*, 50: 213-219 (1999).
Raz et al., "Preferential induction of a Th$_1$ immune response and inhibition of specific IgE antibody formation by plasmid DNA immunization," *Proc. Natl. Acad. Sci. USA*, 93: 5141-5145 (1996).
Reeves et al., "Retroviral Transduction of Human Dendritic Cells with a Tumor-Associated Antigen Gene," *Cancer Res.*, 56: 5672-5677 (1996).
Rehermann et al., "The Cytotoxic T Lymphocyte Response to. Multiple Hepatitis B Virus Polymerase Epitopes During and After Acute Viral Hepatitis," *Journal of Exp. Medicine*, 181: 1047-1058 (1995).
Remington, *The Science and Practice of Pharmacy*, Nineteenth Edition, Chapters 86-88 (1985).
Ripalti et al., "Construction of Polyepitope Fusion Antigens of Human Cytomegalovirus ppUL32: Reactivity with Human Antibodies",*J Clin Microbiol* 32(2):358-63 (1994).
Roberts et al., "Prediction of HIV Peptide Epitopes by a Novel Algorithm," *Aids Research and Human Retroviruses*, 12: 593-610 (1996).
Rock et al., "Degradation of cell proteins and the generation of MHC class I-presented peptides," *Annu. Rev. Immunol.*, 17: 739-779 (1999).
Roman et al., "Immunostimulatory DNA sequences function as T helper-1-promoting adjuvants," *Nature Medicine*, 3: 849-854 (1997).
Rosmorduc et al., "Inhibition of interferon-inducible MxA protein expression by hepatitis B virus capsid protein," *Journal of General Virology*, 80: 1253-1262 (1999).
Ryan et al., "A model for nonstoichiometric, cotranslational protein scission in eukaryotic ribosomes," *Bioorganic Chemistry*, 27: 55-79 (1999).
Ryser et al., "The Cellular Uptake of Horseradish Peroxidase and its Poly(Lysine) Conjugate by Cultured Fibroblasts is Qualitively Similar Despite a 900-Fold Difference in Rate"; *J. Cell Physiol.* 113:167-178 (1982).
Salmi et al., "Tumor endothelium selectively supports binding of IL-2 propagated tumor-infiltrating lymphocytes," *The Journal of Immunology*, 154: 6002-6012 (1995).
Santus et al., "Osmotic Drug Delivery: A Review of the Patent Literature," *Journal of Controlled Release*, 35:1-21 (1995).
Sato et al., "Immunostimulatory DNA sequences necessary for effective intradermal gene immunization," *Science*, 273: 352-354 (1996).
Schirle et al., "Combining computer algorithms with experimental approaches permits the rapid and accurate identification of T cell epitopes from defined antigens," *Journal of Immunological Methods*, 257: 1-16 (2001).
Schmid et al., "Isolation of Functionally Distinct Endosome Subpopulations by Free-Flow Electrophoresis", *Prog. Clin. Biol. Res./Cell-Free Analysis of Membrane Traffic* 270:35-49 (1988).
Schneider, et al., "Overlapping peptides of melanocyte differentiation antigen Melan-A/MART-1 recognized by autologous cytolytic T lymphocytes in association with HLA-B45.1 and HLA-A2.1," *Int. J. Cancer*, 75(3):451-458 (1998).
Schwartz, J.J. & Zhang, S., "Peptide-mediated cellular delivery", *Curr. Opin. Mol. Ther.* 2:162-167 (2000).
Seipelt et al., "The Structures of Picornaviral Proteinases," *Virus Research* 62:159-68 (1999).
Sewell et al., "IFN-( Exposes a Cryptic Cytotoxic T Lymphocyte Epitope in HIV-1 Reverse Transcriptase," *J. Immunol.*, 162: 7075-7079 (1999).
Sheldon et al., "Loligomers: Design of *de novo* Peptide-based Intracular Vehicles"; *Proc. Natl. Aced. Sci: USA* 92:2056-2060 (1995).
Shen et al., "Conjugation of Poly-L-lysine to Albumin and Horseradish Peroxidase: A Novel Method of Enhancing the Cellular Uptake of Proteins", *Proc. Natl. Aced. Sci. USA* 75:1872-1876 (1978).
Sijts et al., "Efficient Generation of a Hepatitis B Virus Cytotoxic T Lymphocyte Epitope Requires the Structural Features of Immunoproteasomes," *Journal of Exp. Medicine*, 191: 503-513 (2000).
Smith et al., "Human Dendritic Cells Genetically Engineered to Express a Melanoma Polyepitope DNA Vaccine Induce Multiple Cytotoxic T-Cell Responses", *Clin Cancer Res*; 7(12):4253-61 (2001).

(56) References Cited

OTHER PUBLICATIONS

Smith, "The polyepitope approach to DNA vaccination", *Curr Opin Mol Ther* 1(1):10-5 (1999).
Speiser et al., "Self antigens expressed by solid tumors do not efficiently stimulate naive or activated T cells: implications for immunotherapy,"*Journal Exp. Medicine*, 186: 645-653 (1997).
Stauss et al., "Induction of Cytotoxic T Lymphocytes with Peptides in Vitro: Identification of Candidate T-cell Epitopes in Human Papilloma," *Proc. Natl. Acad. Sci*, 89: 7871-7875 (199D).
Steinmann et al., "The Dendritic Cells System and Its Role in Immunogenicity," *Ann. Rev. Immunol.* 9:271-96 (1991).
Street et al., "Limitations of HLA-transgenic Mice in Presentation of Hla-restricted Cytotoxic T-cell Epitopes from Endogenously Processed Human Papillomavirus type 16 E7 Protein", *Immunology* 106(4):526-36 (2002).
Stromhaug et al., "Purification and Characterization of Autophagosomes from Rat Hepatocytes", *Biochem. J.* 335:217-24 (1998).
Stumiolo et al., "Generation of tissue-specific and promiscuous HLA ligand databases using DNA microarrays and virtual HLA class II matrices," *Nature Biotechnology*, 17: 555-561 (1999).
Suhrbier A, "Multi-epitope DNA Vaccines", *Immunol Cell Biol* 75(4):402-8 (1997).
Taylor et al., "Inhibition of the interferon-inducible protein kinase PKR by HCV E2 protein," *Science*, 285: 107-110 (1999).
Thomson et al., "Delivery of Multiple CD8 Cytotoxic T Cell Epitopes by DNA Vaccination", *J Immunol* 160(4):1717-23 (1998).
Thomson et al., "Minimal Epitopes Expressed in a Recombinant Polyepitope Protein are Processed and Presented to CD8 Cytotoxic T cells: Implications for Vaccine Design", *Proc. Natl Acad Sci USA* 92(13):5845-9 (1995).
Thomson et al., "Recombinant Polyepitope Vaccines for the Delivery of Multiple CD8 Cytotoxic T Cell Epitopes", *J Immunol* 157(2):822-6 (1996).
Tjoa et al., "Evaluation of Phase I/II Clinical Trials in Prostate Cancer with Dendritic Cells and PSMA Peptides," *The Prostate*, 36: 39-44 (1998).
Toes et al., "Discrete Cleavage Motifs of Constitutive and Immunoproteasomes Revealed by Quantitative Analysis of Cleavage Products", *J. Exp. Med.* 194:1-12 (2001).
Toes et al., "Protective Anti-tumor Immunity Induced by Vaccination with Recombinant Adenoviruses Encoding Multiple Tumor-associated Cytotoxic T Lymphocyte Epitopes in a String-of-beads Fashion", *Proc Natl Acad Sci USA* 94(26):14660-5 (1997).
Türeci et al., "Serological Analysis of Human Tumor Antigens: Molecular Definition and Implications," *Molecular Medicine Today* 3:342 (1997).
Twu et al., "Transcription of the human beta interferon gene is inhibited by hepatitis B virus," *Journal of Virology*, 63: 3065-3071 (1989).
Valmori et al., "Induction of Potent-Antitumor CTL Responses by-Recombinant Vaccinia Encoding a Melan-A Peptide Analogue," *J. Immunol.*, 164: 1125-1131 (2000).
Van den Eynde et al., "Differential Processing of Class-I-Restricted Epitopes by the Standard Proteasome and the Immunoproteasome," *Curr. Opinion in Immunol.*, 13: 147-153 (2001).
Van Kaer et al., "Altered Peptidase and Viral-Specific T Cell Response in LMP2 Mutant Mice," *Immunity* 1: 533-541 (1994).
Vitiello et al., "Comparison of Cytotoxic T lymphocyte responses induced by peptide or DNA immunization: implications on immunogenicity and immunodominance," *Euro. Jr. Immunol.*, 27: 671-678 (1997).
Vonderheide et al., "Characterization of HLA-A3-restricted Cytotoxic T Lymphocytes Reactive Against the Widely Expressed Tumor Antigen Telomerase", *Clin Cancer Res* 7(11):3343-8 (2001).
Wang et al., "Phase 1 Trial of a MART-1 Peptide Vaccine with Incomplete Freund's Adjuvant for Resected High-Risk Melanoma," *Clin. Cancer Res.*, 10: 2756-2765 (1999).
Ward et al., "Development and Characterisation of Recombinant Hepatitis Delta Virus-like Particle", *Virus Genes* 23(I):97-104 (2001).

Wattiaux et al., "Isolation of Rat Liver Lysosomes by Isopycnic Centrifugation in a Metrizamide Gradient", *J. Cell Biol.* 78:349-68 (1978).
Whitton et al., "A "String-of-Beads" Vaccine, Comprising Linked Minigenes, Confers Protection from Lethal-Dose Virus Challenge", *J Virol* 67(1):348-52 (1993).
Williams et al., "Isolation of a Membrane-Associated Cathes-pin D-like Enzyme form the Model Antigen Presenting Cell, A20, and Its Ability to Generate Antigenic Fragments from a Protein Antigen in a Cell-Free System", *Arch. Biochem. Biophys.* 305:298-306 (1993).
Woodberry et al., "Immunogenicity of a Human Immunodeficiency Virus (HIV) Polytope Vaccine Containing Multiple HLA A2 HIV CD8 Cytotoxic T-Cell Epitopes", *J Virol* 73(7):5320-5 (1999).
Yamada et al., "A Simple Procedure for the Isolation of Highly Purified Lysosomes from Normal Rat Liver" *J Biochem.* 95:1155-60 (1984).
Yang et al., "Proteasomes Are Regulated by Interferon (: Implications for Antigen Processing," *Proc. Natl. Acad. Sci.*, 89: 4928-4932 (1992).
Yewedell, et al., " MHC-Encoded Proteasome Subunits LMP2 and LMP7 Are Not Required for Efficient Antigen Presentation," *J. Immunology* 1994, 152:1163-1170 (1994).
Young et al., "Dendritic Cells as Adjuvants for Class I Major Histocompatibility Complex-restricted Anti-tumor Immunity," *J Exp Med* 183:7-11 (1996).
Zajac et al., "Enhanced Generation of Cytotoxic T Lymphocytes Using Recombinant Vaccinia Virus Expressing Human Tumor-Associated Antigens and B7 Costimulatory Molecules," *Cancer Res.*, 58: 4567-4571 (1998).
Zajac et al., "Generation of Tumoricidal Cytotoxic T Lymphocytes from Healthy Donors after in Vitro Stimulation with a Replication-Incompetent Vaccinia Virus Encoding MART-1/Melan-A 27-35 Epitope," *Int. J. Cancer*, 71: 491-496 (1997).
Zhai et al., "Antigen-Specific Tumor Vaccines. Development and Characterization of Recombinant Adenoviruses Encoding MART1 or gp100 for Cancer Therapy," *J. Immunol.*, 156: 700-710 (1996).
Zipkin, I., "Cancer vaccines," *Bio Century*, 6: A1-A6 (1998).
Ayyoub et al. *J. Immunol.* 168(4):1717-1722 (2002).
Gene Therapy Advisory Committee. "Ninth Annual Report," Health Departments of the UK 2003; entire document.
Clark, J et al. Nature Genetics [1994] 7(4):502-508.
Crew, AJ et al. The EMBO Journal [1995] 14(10):2333-2340.
Campbell, A. Monoclonal Antibody Technology [1985] pp. 1-32.
Lim et al. "A KRAB-related domain and a novel transcription repression domain in proteins encoded by Ssx genes that are disrupted in human sarcomas," Oncogene, 1998, 17: 2013-2018.
Invitrogen, www.invitrogen.com/content/sfs/vectors/pcdna3_1mychie/020_map.pdf, one page (Apr. 2007).
Kessler et al., *J Exp Med* 193, 73-88 (2001).
Qiagen, www.qiagen.com/literature/pqesequences/pqe9.pdf, one page (Apr. 2007).
Shadendorf et al. "Listeria expression vector for immunotherapy, particularly of malignant melanoma, comprises a DNA sequence encoding tumor-associated antigens," Database Geneseq (online) Jul. 16, 2001, database accession No. AAB86042.
Bergmann, et al. 1994. "Differential Effects of Flanking Residues on Presentation of Epitopes from Chimeric Peptides." *J. Virol.* 68(8):5306-5310.
Borbulevych, et al. 2005. "Increased Immunogenicity of an Anchor-Modified Tumor-Associated Antigen is Due to the Enhanced Stability of the Peptide/MHC Complex: Implications for Vaccine Design." *J. Immunol.* 174:4812-4820.
Celts, et al. 1994. "Identification of Potential CTL Epitopes of Tumor-Associated Antigen Mage-1 for Five Common HLA-A Alleles." *Mol. Immunol.* 31(18): 1423-1430.
Chaux, et al. 1998. "Estimation of the Frequencies of Anti-Mage-3 Cytolytic T-Lymphocyte Precursors in blood from Individuals without Cancer." *Int. J. Cancer.* 77:538-542.
Eisenlohr, et al. 1992. "Flanking Sequences Influence the Presentation of an Endogenously Synthesized Peptide to Cytotoxic T Lymphocytes." *J. Exp. Med.* 175: 481-487.

(56) References Cited

OTHER PUBLICATIONS

Gileadi, et al. 1999. "Effect of Epitope Flanking Residues on the Presentation of N-Terminal Cytotoxic T Lymphocyte Epitopes." *Eur. J. Immunol.* 29: 2213-2222.

Gnjatic, et al. 2003. "Cross-Presentation of HLA Class I Epitopes from Exogenous Nyeso-1 Polypeptides by Nonprofessional APCs." *J. Immunol.* 170: 1191-1196.

Gnjatic, et al. 2003. "Survey of naturally occurring CD4+T cell responses against NY-ESO-1 in cancer patients: Correlation with antibody reponses." *PNAS USA.* 100(15): 8862-8867.

Lu, J. et al. 2004. "Multiepitope Trojan Antigen Peptide Vaccines for the Induction of Antitumor CTL and Th Immune Responses." *J. Immunol.* 172:4575-4582.

Ochoa-Garay, et al. 1997. "The Ability of Peptides to Induce Ctotoxic T Cells in Vitro Does Not Strongly Correlate with their Affinity for the H-21d Molecule: Implications for Vaccine Design and Immunotherapy." *Molecular Immunology* 34(3): 273-281.

Perkins, et al. 1991. "Immunodominance: Intramolecular Competition Between T Cell Epitopes." *J. Immunol.* 146: 2137-2144.

Shastri, et al. 1995. "Presentation of Endogenous Peptide/MHC Class I Complexes is Profoundly Influenced by Specific C-Terminal Flanking Residues." *J. Immunol.* 155: 4339-4346.

Simard, et al. 2001. "Novel nucleic acid encoding tumor-associated antigen SSx-2, useful in inducing an immune response and in treating cancer." N_Geneseq Accession No. AAD14184, Nov. 6, 2001, p. 2.

Supplementary European Search Report for Application No. EP 02 80 6695.9 dated Dec. 30, 2005.

Theobald, et al. 1998. "The Sequence Alteration Associated with a Mutational Hotspot in P53 Protects Cells from Lysis by Cytotoxic T Lymphocytes Specific for a Flanking Peptide Epitope." *J. Exp. Med.* 188(6): 1017-1028.

Wang, et al. 1992. "Silencing of Immunodominant Epitopes by Contiguous Sequences in Complex Synthetic Peptides." *Cell. Immunol.* 143: 284-297.

Zheng, et al. 2001. "CD4+cell recognition of MHC class II-restricted epitopes from NY-ESO-1 presented by a prevalent HLA allele: Association with NY-ESO-1 anitbody production." *PHAN* 98(7):3964-3969.

SYPEITHI search report, Jan. 4, 2010, 2 pages.

Swiss-Prot P78358, 2011, 7 pages.

\* cited by examiner

FIGURE 1. pMA2M

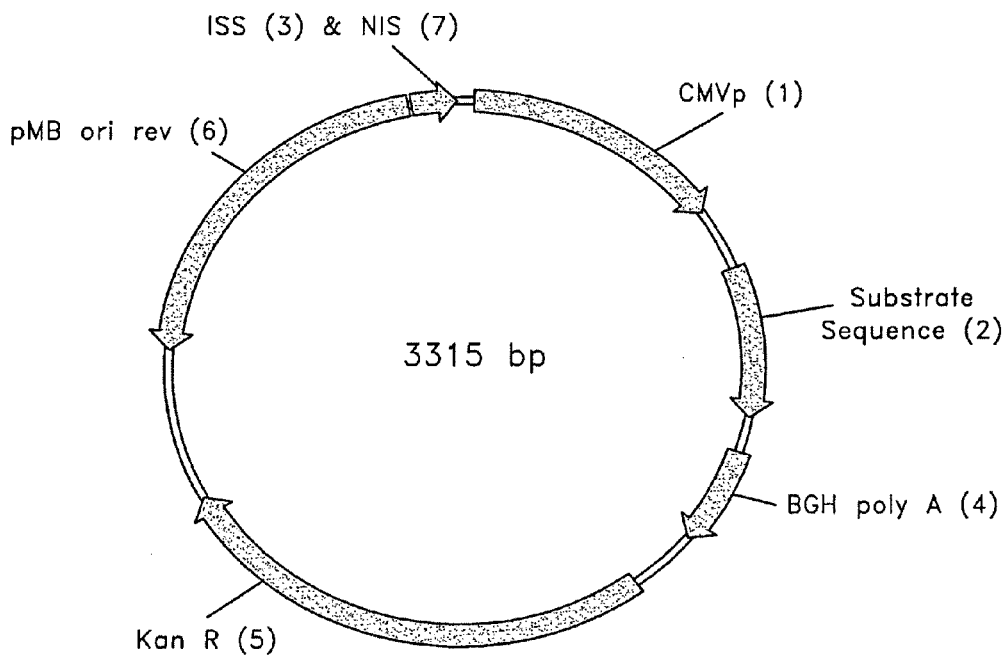

Figure Legend:

| Code in Figure | Genetic Element | Region |
|---|---|---|
| 1. CMVp | Cytomeglovirus Enhancer/Promoter | 63–637 |
| 2. Substrate Sequence | Substrate Sequence Containing Epitope | 696–983 |
| 3. ISS | Immunostimulatory Sequence | 3220–3226 |
| 4. BGH poly A | Bovine Growth Hormone Polyadenylation Signal | 1028–1045 |
| 5. Kan R | Kanamycin Resistance Gene | 1431–2225 |
| 6. pMB ori rev | Bacterial pMB Origin of Replication | 3165–2492 |
| 7. NIS | Nuclear Import Sequence from Simian Virus 40–72bp repeat | 3227–3304 |

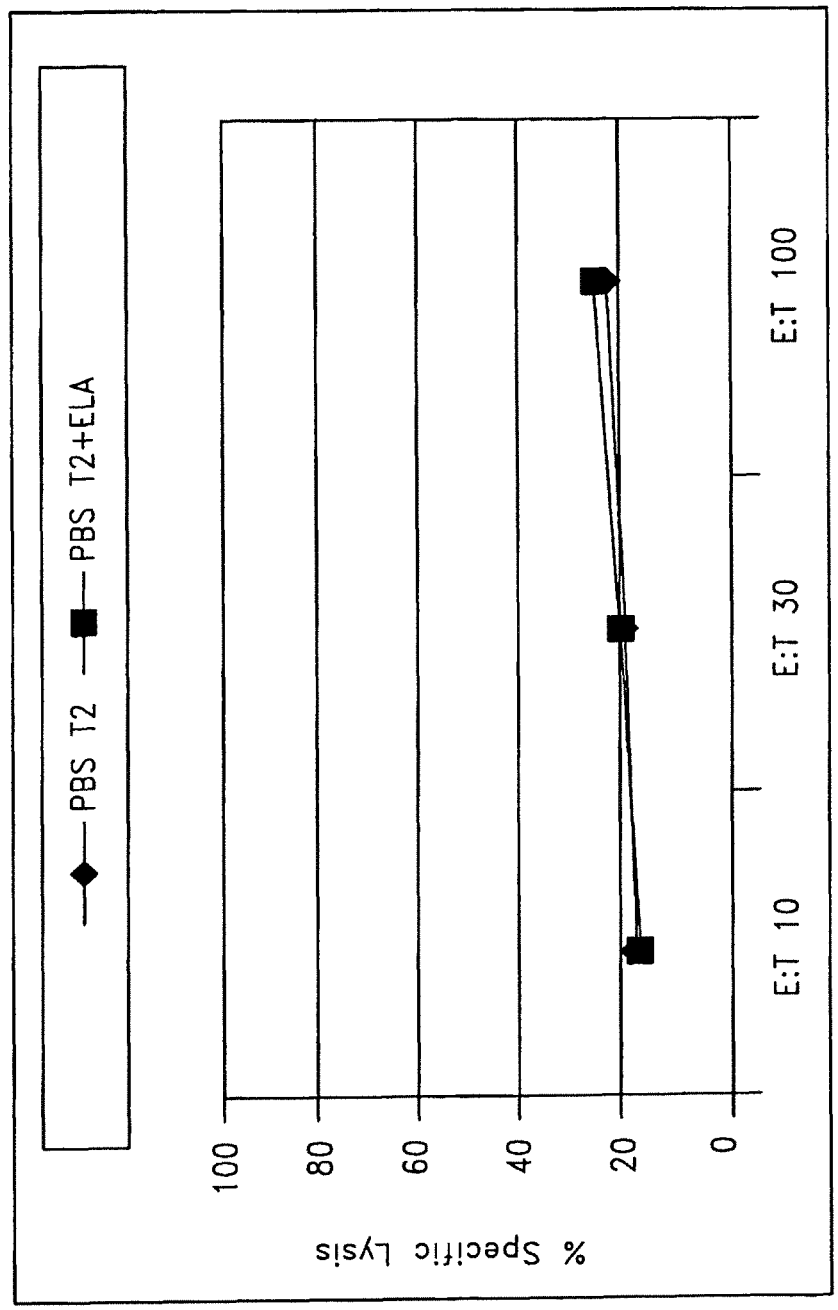
FIGURE 2. Lysis of ELAGIGILTV (SEQ ID NO.1) - pulsed and unpulsed T2 target cells by mock immunized CTL.

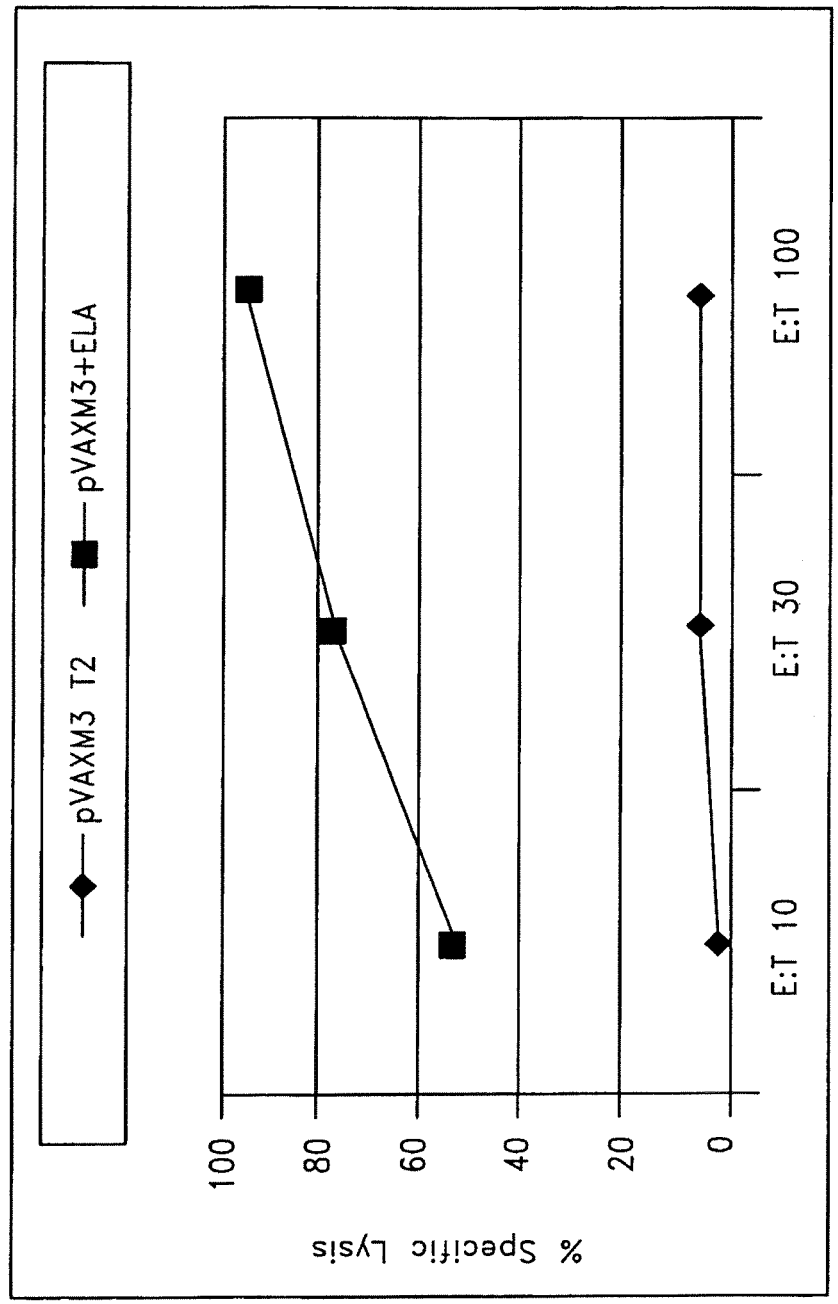
FIGURE 3. Lysis of ELAGIGILTV (SEQ ID NO.1) - pulsed and unpulsed T2 target cells by pVAXM3 immunized CTL.

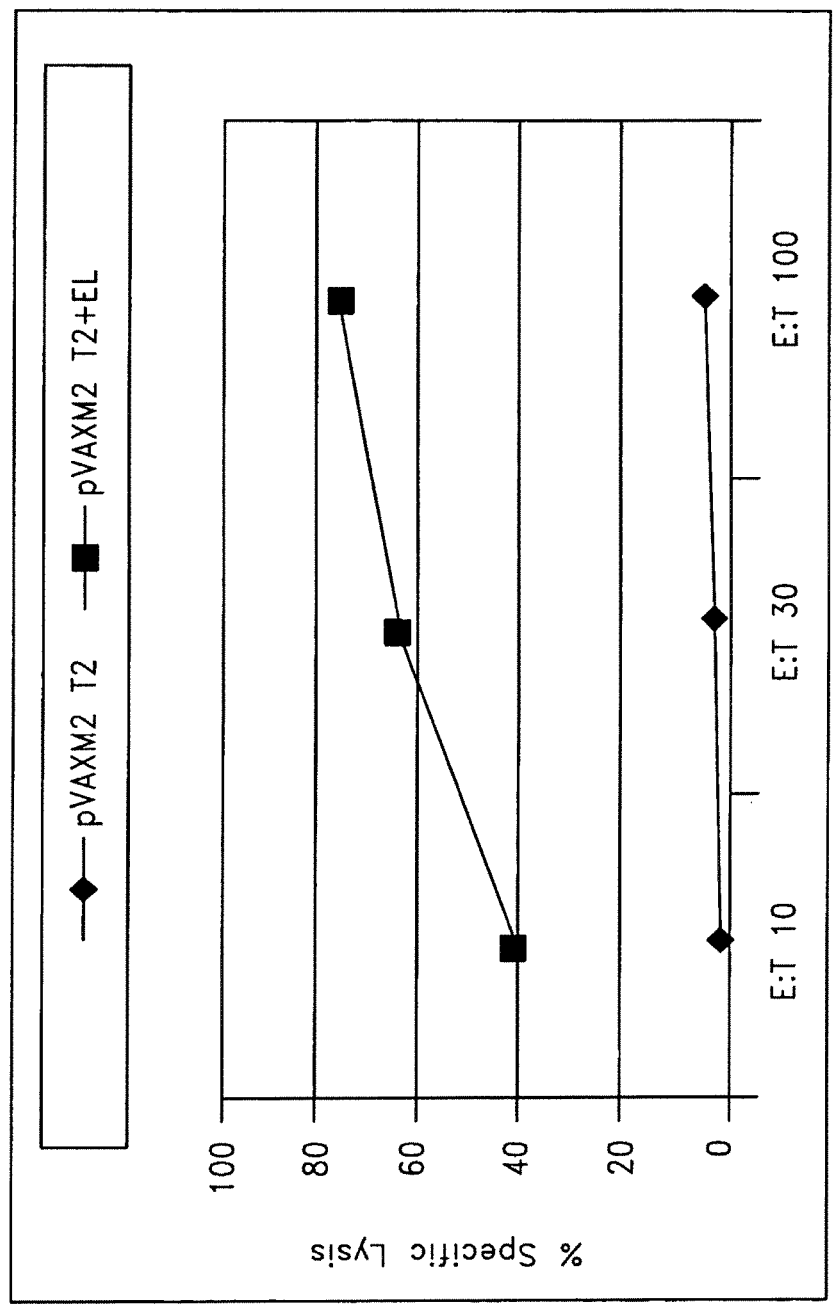
FIGURE 4. Lysis of ELAGIGILTV (SEQ ID NO.1) - pulsed and unpulsed T2 target cells by pVAXM2 immunized CTL.

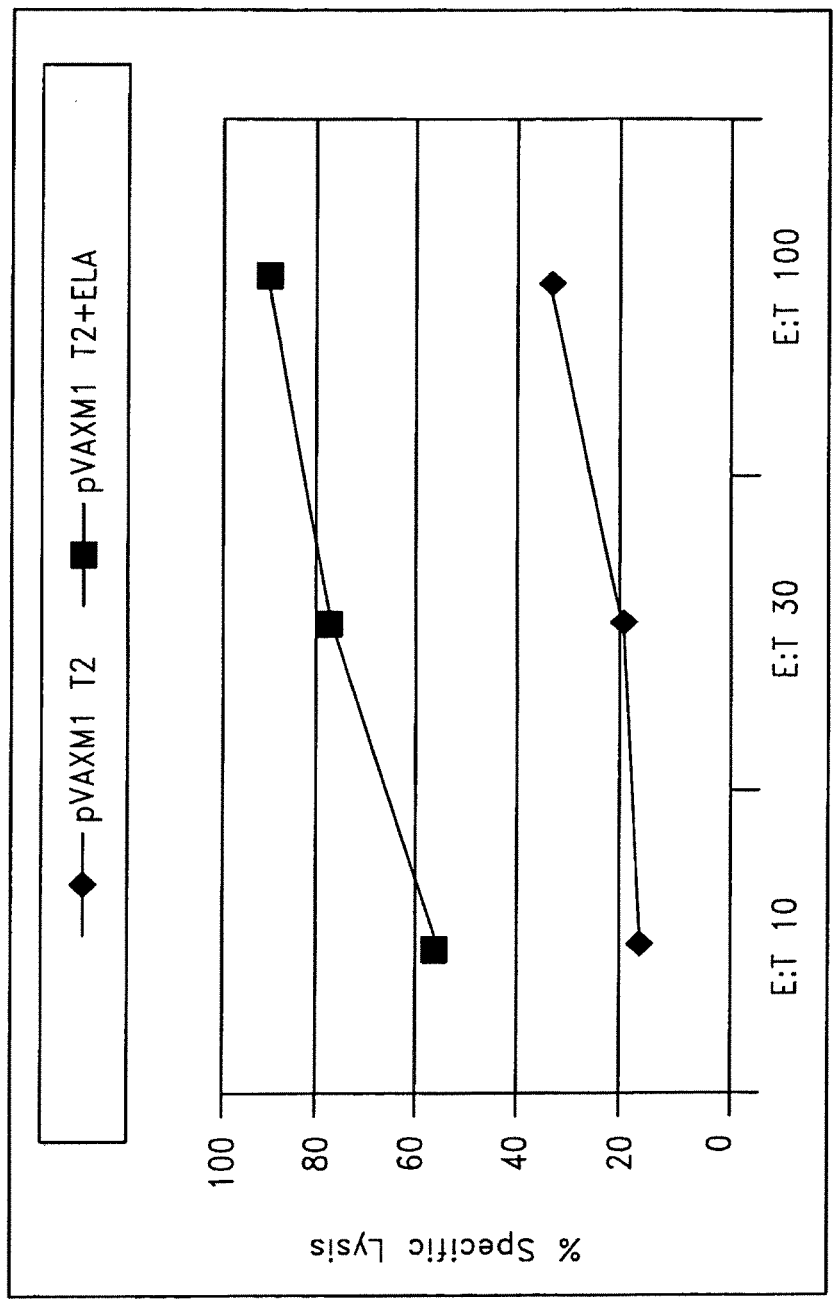
FIGURE 5. Lysis of ELAGIGILTV (SEQ ID NO.1) - pulsed and unpulsed T2 target cells by pVAXM1 immunized CTL.

Cleavage sites in the NY-ESO-1 150-177 (SEQ ID NO. 1579) substrate upon digestion with 20S housekeeping proteasome (upper arrows) and immunoproteasome (lower arrows). The size of each arrow indicates the efficiency of cleavage as determined by pool sequencing analysis. The epitope NY-ESO-1 157-165 (SEQ ID NO. 12) is underlined.

Cleavage sites in the CTLS1-2 substrate upon digestion with immunoproteasome (isolated from γ-IFN treated HeLa cells). The sequence of epitope SSX2 41-49 (SEQ ID NO. 13) is underlined.

Comparisons of CTLS1-2 substrate (SEQ ID NO. 31) digested by 20S human immunoproteasome versus mouse immunoproteasome. The size of each arrow indicates the efficiency of cleavage as determined by N-terminal pool sequencing analysis. The sequence of epitope SSX2 41-49 (SEQ ID NO. 13) is underlined.

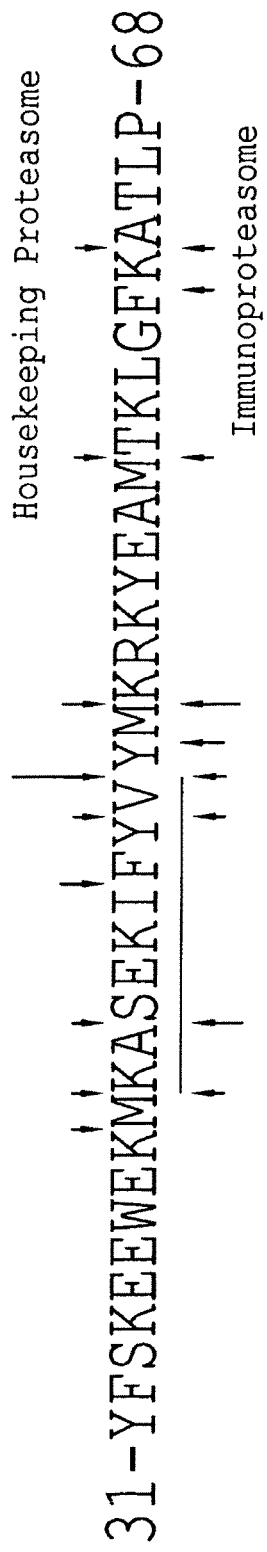

Cleavage sites in the SSX2 31-68 (SEQ ID NO. 1580) substrate upon digestion with 20S housekeeping proteasome (isolated from erythrocytes) (upper arrows) and immunoproteasome (isolated from γ-IFN treated HeLa cells) (lower arrows). The size of each arrow indicates the efficiency of cleavage as determined by N-terminal pool sequencing analysis. The epitope SSX2 41-49 (SEQ ID NO. 13) is underlined.

FIGURE 9

SEQUENCE LISTING

<160> NUMBER OF SEQ ID NOS: 1584

<210> SEQ ID NO 1

```
<211> LENGTH: 10
<212> TYPE: PRT
<213> ORGANISM: Homo sapiens

<400> SEQUENCE: 1

Glu Leu Ala Gly Ile Gly Ile Leu Thr Val
1               5                   10

<210> SEQ ID NO 2
<211> LENGTH: 118
<212> TYPE: PRT
<213> ORGANISM: Homo sapiens

<400> SEQUENCE: 2

Met Pro Arg Glu Asp Ala His Phe Ile Tyr Gly Tyr Pro Lys Lys Gly
1               5                   10                  15

His Gly His Ser Tyr Thr Thr Ala Glu Ala Ala Gly Ile Gly Ile
            20                  25                  30

Leu Thr Val Ile Leu Gly Val Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 3
<211> LENGTH: 529
<212> TYPE: PRT
<213> ORGANISM: Homo sapiens

<400> SEQUENCE: 3

Met Leu Leu Ala Val Leu Tyr Cys Leu Leu Trp Ser Phe Gln Thr Ser
1               5                   10                  15

Ala Gly His Phe Pro Arg Ala Cys Val Ser Ser Lys Asn Leu Met Glu
            20                  25                  30

Lys Glu Cys Cys Pro Pro Trp Ser Gly Asp Arg Ser Pro Cys Gly Gln
        35                  40                  45

Leu Ser Gly Arg Gly Ser Cys Gln Asn Ile Leu Leu Ser Asn Ala Pro
    50                  55                  60

Leu Gly Pro Gln Phe Pro Phe Thr Gly Val Asp Asp Arg Glu Ser Trp
65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
            100                 105                 110

Thr Glu Arg Arg Leu Leu Val Arg Arg Asn Ile Phe Asp Leu Ser Ala
        115                 120                 125

Pro Glu Lys Asp Lys Phe Phe Ala Tyr Leu Thr Leu Ala Lys His Thr
    130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
```

```
                    165                 170                 175
Val Trp Met His Tyr Val Ser Met Asp Ala Leu Leu Gly Gly Ser
            180                 185                 190

Glu Ile Trp Arg Asp Ile Asp Phe Ala His Glu Ala Pro Ala Phe Leu
            195                 200                 205

Pro Trp His Arg Leu Phe Leu Leu Arg Trp Glu Gln Glu Ile Gln Lys
            210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255

Pro Thr Asn Pro Asn Leu Leu Ser Pro Ala Ser Phe Phe Ser Ser Trp
            260                 265                 270

Gln Ile Val Cys Ser Arg Leu Glu Glu Tyr Asn Ser His Gln Ser Leu
            275                 280                 285

Cys Asn Gly Thr Pro Glu Gly Pro Leu Arg Arg Asn Pro Gly Asn His
            290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                325                 330                 335

Asn Phe Ser Phe Arg Asn Thr Leu Glu Gly Phe Ala Ser Pro Leu Thr
            340                 345                 350

Gly Ile Ala Asp Ala Ser Gln Ser Ser Met His Asn Ala Leu His Ile
            355                 360                 365

Tyr Met Asn Gly Thr Met Ser Gln Val Gln Gly Ser Ala Asn Asp Pro
            370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                405                 410                 415

Pro Ile Gly His Asn Arg Glu Ser Tyr Met Val Pro Phe Ile Pro Leu
            420                 425                 430

Tyr Arg Asn Gly Asp Phe Phe Ile Ser Ser Lys Asp Leu Gly Tyr Asp
            435                 440                 445

Tyr Ser Tyr Leu Gln Asp Ser Asp Pro Asp Ser Phe Gln Asp Tyr Ile
            450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
            500                 505                 510

Pro Leu Leu Met Glu Lys Glu Asp Tyr His Ser Leu Tyr Gln Ser His
            515                 520                 525

Leu

<210> SEQ ID NO 4
<211> LENGTH: 94
<212> TYPE: PRT
<213> ORGANISM: Artificial Sequence
<220> FEATURE:
<223> OTHER INFORMATION: Synthetic peptide

<400> SEQUENCE: 4
```

Met Leu Leu Ala Val Leu Tyr Cys Leu Glu Leu Ala Gly Ile Gly Ile
1               5                   10                  15

Leu Thr Val Tyr Met Asp Gly Thr Met Ser Gln Val Gly Ile Leu Thr
            20                  25                  30

Val Ile Leu Gly Val Leu Leu Ile Gly Cys Trp Tyr Cys Arg Arg
        35                  40                  45

Arg Asn Gly Tyr Arg Ala Leu Met Asp Lys Ser Leu His Val Gly Thr
    50                  55                  60

Gln Cys Ala Leu Thr Arg Arg Cys Pro Gln Glu Gly Phe Asp His Arg
65              70                  75                  80

Asp Ser Lys Val Ser Leu Gln Glu Lys Asn Cys Glu Pro Val
            85                  90

<210> SEQ ID NO 5
<211> LENGTH: 28
<212> TYPE: PRT
<213> ORGANISM: Artificial Sequence
<220> FEATURE:
<223> OTHER INFORMATION: Synthetic peptide

<400> SEQUENCE: 5

Met Leu Leu Ala Val Leu Tyr Cys Leu Glu Leu Ala Gly Ile Gly Ile
1               5                   10                  15

Leu Thr Val Tyr Met Asp Gly Thr Met Ser Gln Val
            20                  25

<210> SEQ ID NO 6
<211> LENGTH: 9
<212> TYPE: PRT
<213> ORGANISM: Homo sapiens

<400> SEQUENCE: 6

Met Leu Leu Ala Val Leu Tyr Cys Leu
1               5

<210> SEQ ID NO 7
<211> LENGTH: 9
<212> TYPE: PRT
<213> ORGANISM: Homo sapiens

<400> SEQUENCE: 7

Tyr Met Asp Gly Thr Met Ser Gln Val
1               5

<210> SEQ ID NO 8
<211> LENGTH: 10
<212> TYPE: PRT
<213> ORGANISM: Homo sapiens

<400> SEQUENCE: 8

Glu Ala Ala Gly Ile Gly Ile Leu Thr Val
1               5                   10

<210> SEQ ID NO 9
<211> LENGTH: 307
<212> TYPE: DNA
<213> ORGANISM: Artificial Sequence
<220> FEATURE:
<223> OTHER INFORMATION: Synthetic peptide

<400> SEQUENCE: 9
cttaagccac catgttacta gctgttttgt actgcctgga actagcaggg atcggcatat      60
tgacagtgta tatggatgga acaatgtccc aggtaggaat tctgacagtg atcctgggag     120

```
tcttactgct catcggctgt tggtattgta gaagacgaaa tggatacaga gccttgatgg      180
ataaaagtct tcatgttggc actcaatgtg ccttaacaag aagatgccca caagaagggt     240
ttgatcatcg ggacagcaaa gtgtctcttc aagagaaaaa ctgtgaacct gtgtagtgag     300
cggccgc                                                                307
```

<210> SEQ ID NO 10
<211> LENGTH: 85
<212> TYPE: PRT
<213> ORGANISM: Artificial Sequence
<220> FEATURE:
<223> OTHER INFORMATION: Synthetic peptide

<400> SEQUENCE: 10

```
Met Val Leu Tyr Cys Leu Glu Leu Ala Gly Ile Gly Ile Leu Thr Val
 1               5                  10                  15
Tyr Met Asp Gly Thr Ala Val Leu Tyr Cys Leu Glu Leu Ala Gly Ile
            20                  25                  30
Gly Ile Leu Thr Val Tyr Met Asp Gly Thr Met Leu Ala Val Leu Tyr
        35                  40                  45
Cys Leu Glu Leu Ala Gly Ile Gly Ile Leu Thr Val Tyr Met Asp Gly
    50                  55                  60
Thr Met Ser Leu Leu Ala Val Leu Tyr Cys Leu Glu Leu Ala Gly Ile
65                  70                  75                  80
Gly Ile Leu Thr Val
            85
```

<210> SEQ ID NO 11
<211> LENGTH: 180
<212> TYPE: PRT
<213> ORGANISM: Homo sapiens

<400> SEQUENCE: 11

```
Met Gln Ala Glu Gly Arg Gly Thr Gly Gly Ser Thr Gly Asp Ala Asp
 1               5                  10                  15
Gly Pro Gly Gly Pro Gly Ile Pro Asp Gly Pro Gly Gly Asn Ala Gly
            20                  25                  30
Gly Pro Gly Glu Ala Gly Ala Thr Gly Gly Arg Gly Pro Arg Gly Ala
        35                  40                  45
Gly Ala Ala Arg Ala Ser Gly Pro Gly Gly Gly Ala Pro Arg Gly Pro
    50                  55                  60
His Gly Gly Ala Ala Ser Gly Leu Asn Gly Cys Cys Arg Cys Gly Ala
65                  70                  75                  80
Arg Gly Pro Glu Ser Arg Leu Leu Glu Phe Tyr Leu Ala Met Pro Phe
                85                  90                  95
Ala Thr Pro Met Glu Ala Glu Leu Ala Arg Arg Ser Leu Ala Gln Asp
            100                 105                 110
Ala Pro Pro Leu Pro Val Pro Gly Val Leu Leu Lys Glu Phe Thr Val
        115                 120                 125
Ser Gly Asn Ile Leu Thr Ile Arg Leu Thr Ala Ala Asp His Arg Gln
    130                 135                 140
Leu Gln Leu Ser Ile Ser Ser Cys Leu Gln Gln Leu Ser Leu Leu Met
145                 150                 155                 160
Trp Ile Thr Gln Cys Phe Leu Pro Val Phe Leu Ala Gln Pro Pro Ser
                165                 170                 175
Gly Gln Arg Arg
            180
```

```
<210> SEQ ID NO 12
<211> LENGTH: 9
<212> TYPE: PRT
<213> ORGANISM: Homo sapiens

<400> SEQUENCE: 12

Ser Leu Leu Met Trp Ile Thr Gln Cys
 1               5

<210> SEQ ID NO 13
<211> LENGTH: 9
<212> TYPE: PRT
<213> ORGANISM: Homo sapiens

<400> SEQUENCE: 13

Lys Ala Ser Glu Lys Ile Phe Tyr Val
 1               5

<210> SEQ ID NO 14
<211> LENGTH: 9
<212> TYPE: PRT
<213> ORGANISM: Homo sapiens

<400> SEQUENCE: 14

Thr Gln Cys Phe Leu Pro Val Phe Leu
 1               5

<210> SEQ ID NO 15
<211> LENGTH: 10
<212> TYPE: PRT
<213> ORGANISM: Homo sapiens

<400> SEQUENCE: 15

Gly Leu Pro Ser Ile Pro Val His Pro Ile
 1               5                  10

<210> SEQ ID NO 16
<211> LENGTH: 6
<212> TYPE: PRT
<213> ORGANISM: Homo sapiens

<400> SEQUENCE: 16

Ala Val Leu Tyr Cys Leu
 1               5

<210> SEQ ID NO 17
<211> LENGTH: 123
<212> TYPE: PRT
<213> ORGANISM: Artificial Sequence
<220> FEATURE:
<223> OTHER INFORMATION: Synthetic peptide

<400> SEQUENCE: 17

Met Ser Leu Leu Met Trp Ile Thr Gln Cys Lys Ala Ser Glu Lys Ile
 1               5                  10                  15

Phe Tyr Val Arg Cys Gly Ala Arg Gly Pro Glu Ser Arg Leu Leu Glu
             20                  25                  30

Phe Tyr Leu Ala Met Pro Phe Ala Thr Pro Met Glu Ala Glu Leu Ala
         35                  40                  45

Arg Arg Ser Leu Ala Gln Asp Ala Pro Pro Leu Pro Val Pro Gly Val
     50                  55                  60

Leu Leu Lys Glu Phe Thr Val Ser Gly Asn Ile Leu Thr Ile Arg Leu
 65                  70                  75                  80
```

```
Thr Ala Ala Asp His Arg Gln Leu Gln Leu Ser Ile Ser Ser Cys Leu
                 85                  90                  95

Gln Gln Leu Ser Leu Leu Met Trp Ile Thr Gln Cys Phe Leu Pro Val
            100                 105                 110

Phe Leu Ala Gln Pro Pro Ser Gly Gln Arg Arg
        115                 120
```

<210> SEQ ID NO 18
<211> LENGTH: 19
<212> TYPE: PRT
<213> ORGANISM: Artificial Sequence
<220> FEATURE:
<223> OTHER INFORMATION: Synthetic peptide

<400> SEQUENCE: 18

```
Met Ser Leu Leu Met Trp Ile Thr Gln Cys Lys Ala Ser Glu Lys Ile
 1               5                  10                  15

Phe Tyr Val
```

<210> SEQ ID NO 19
<211> LENGTH: 392
<212> TYPE: DNA
<213> ORGANISM: Artificial Sequence
<220> FEATURE:
<223> OTHER INFORMATION: Synthetic peptide

<400> SEQUENCE: 19

```
cttaagccac catgtccctg ttgatgtgga tcacgcagtg caaagcttcg agaaaatct      60 tctacgtacg gtgcggtgcc aggggggccgg agagccgcct gcttgagttc tacctcgcca    120
tgcctttcgc gacacccatg aagcagagc tggcccgcag gagcctggcc caggatgccc      180
caccgcttcc cgtgccaggg gtgcttctga aggagttcac tgtgtccggc aacatactga    240
ctatccgact gactgctgca gaccaccgcc aactgcagct ctccatcagc tcctgtctcc    300
agcagctttc cctgttgatg tggatcacgc agtgctttct gcccgtgttt ttggctcagc    360
ctccctcagg gcagaggcgc tagtgagaat tc                                   392
```

<210> SEQ ID NO 20
<211> LENGTH: 179
<212> TYPE: PRT
<213> ORGANISM: Artificial Sequence
<220> FEATURE:
<223> OTHER INFORMATION: Synthetic peptide

<400> SEQUENCE: 20

```
Met Ser Leu Leu Met Trp Ile Thr Gln Cys Lys Ala Ser Glu Lys Ile
 1               5                  10                  15

Phe Tyr Val Gly Leu Pro Ser Ile Pro Val His Pro Ile Gly Leu Pro
            20                  25                  30

Ser Ile Pro Val His Pro Ile Lys Ala Ser Glu Lys Ile Phe Tyr Val
        35                  40                  45

Ser Leu Leu Met Trp Ile Thr Gln Cys Lys Ala Ser Glu Lys Ile Phe
    50                  55                  60

Tyr Val Lys Ala Ser Glu Lys Ile Phe Tyr Val Arg Cys Gly Ala Arg
65                  70                  75                  80

Gly Pro Glu Ser Arg Leu Leu Glu Phe Tyr Leu Ala Met Pro Phe Ala
                85                  90                  95

Thr Pro Met Glu Ala Glu Leu Ala Arg Arg Ser Leu Ala Gln Asp Ala
            100                 105                 110
```

```
Pro Pro Leu Pro Val Pro Gly Val Leu Leu Lys Glu Phe Thr Val Ser
        115                 120                 125

Gly Asn Ile Leu Thr Ile Arg Leu Thr Ala Ala Asp His Arg Gln Leu
    130                 135                 140

Gln Leu Ser Ile Ser Ser Cys Leu Gln Gln Leu Ser Leu Leu Met Trp
145                 150                 155                 160

Ile Thr Gln Cys Phe Leu Pro Val Phe Leu Ala Gln Pro Pro Ser Gly
                165                 170                 175

Gln Arg Arg

<210> SEQ ID NO 21
<211> LENGTH: 543
<212> TYPE: DNA
<213> ORGANISM: Artificial Sequence
<220> FEATURE:
<223> OTHER INFORMATION: Synthetic peptide

<400> SEQUENCE: 21
atgtccctgt tgatgtggat cacgcagtgc aaagcttcgg agaaaatctt ctatgtgggt    60
cttccaagta ttcctgttca tccaattggt cttccaagta ttcctgttca tccaattaaa   120
gcttcggaga aaatcttcta tgtgtccctg ttgatgtgga tcacgcagtg caaagcttcg   180
gagaaaatct tctatgtgaa agcttcggag aaaatcttct acgtacggtg cggtgccagg   240
gggccggaga gccgcctgct tgagttctac ctcgccatgc ctttcgcgac acccatggaa   300
gcagagctgg cccgcaggag cctggcccag gatgcccac cgcttcccgt gccagggtg    360 cttctgaagg agttcactgt gtccggcaac atactgacta tccgactgac tgctgcagac   420
caccgccaac tgcagctctc catcagctcc tgtctccagc agctttccct gttgatgtgg   480
atcacgcagt gctttctgcc cgtgtttttg gctcagcctc cctcagggca gaggcgctag   540
tga                                                                543

<210> SEQ ID NO 22
<211> LENGTH: 29
<212> TYPE: PRT
<213> ORGANISM: Artificial Sequence
<220> FEATURE:
<223> OTHER INFORMATION: Synthetic peptide

<400> SEQUENCE: 22

Ile Lys Ala Ser Glu Lys Ile Phe Tyr Val Ser Leu Leu Met Trp Ile
1               5                   10                  15

Thr Gln Cys Lys Ala Ser Glu Lys Ile Phe Tyr Val Lys
            20                  25

<210> SEQ ID NO 23
<211> LENGTH: 9
<212> TYPE: PRT
<213> ORGANISM: Homo sapiens

<400> SEQUENCE: 23

Val Met Thr Lys Leu Gly Phe Lys Val
1               5

<210> SEQ ID NO 24
<211> LENGTH: 10
<212> TYPE: PRT
<213> ORGANISM: Homo sapiens

<400> SEQUENCE: 24

Arg Gln Ile Tyr Val Ala Ala Phe Thr Val
```

<210> SEQ ID NO 25
<211> LENGTH: 169
<212> TYPE: PRT
<213> ORGANISM: Homo sapiens

<400> SEQUENCE: 25

```
Ala Gln Ile Pro Glu Lys Ile Gln Lys Ala Phe Asp Asp Ile Ala Lys
 1               5                  10                  15

Tyr Phe Ser Lys Glu Glu Trp Glu Lys Met Lys Ala Ser Glu Lys Ile
             20                  25                  30

Phe Tyr Val Tyr Met Lys Arg Lys Tyr Glu Ala Met Thr Lys Leu Gly
         35                  40                  45

Phe Lys Ala Thr Leu Pro Pro Phe Met Cys Asn Lys Arg Ala Glu Asp
     50                  55                  60

Phe Gln Gly Asn Asp Leu Asp Asn Asp Pro Asn Arg Gly Asn Gln Val
 65                  70                  75                  80

Glu Arg Pro Gln Met Thr Phe Gly Arg Leu Gln Gly Ile Ser Pro Lys
                 85                  90                  95

Ile Met Pro Lys Lys Pro Ala Glu Glu Gly Asn Asp Ser Glu Glu Val
            100                 105                 110

Pro Glu Ala Ser Gly Pro Gln Asn Asp Gly Lys Glu Leu Cys Pro Pro
        115                 120                 125

Gly Lys Pro Thr Thr Ser Glu Lys Ile His Glu Arg Ser Gly Pro Lys
    130                 135                 140

Arg Gly Glu His Ala Trp Thr His Arg Leu Arg Glu Arg Lys Gln Leu
145                 150                 155                 160

Val Ile Tyr Glu Glu Ile Ser Asp Pro
                165
```

<210> SEQ ID NO 26
<211> LENGTH: 245
<212> TYPE: PRT
<213> ORGANISM: Artificial Sequence
<220> FEATURE:
<223> OTHER INFORMATION: Synthetic peptide

<400> SEQUENCE: 26

```
Met Val Met Thr Lys Leu Gly Phe Lys Val Lys Ala Ser Glu Lys Ile
 1               5                  10                  15

Phe Tyr Val Arg Gln Ile Tyr Val Ala Ala Phe Thr Val Gly Leu Pro
             20                  25                  30

Ser Ile Pro Val His Pro Ile Thr Gln Cys Phe Leu Pro Val Phe Leu
         35                  40                  45

Val Met Thr Lys Leu Gly Phe Lys Val Arg Gln Ile Tyr Val Ala Ala
     50                  55                  60

Phe Thr Val Lys Ala Ser Glu Lys Ile Phe Tyr Val Ala Gln Ile Pro
 65                  70                  75                  80

Glu Lys Ile Gln Lys Ala Phe Asp Asp Ile Ala Lys Tyr Phe Ser Lys
                 85                  90                  95

Glu Glu Trp Glu Lys Met Lys Ala Ser Glu Lys Ile Phe Tyr Val Tyr
            100                 105                 110

Met Lys Arg Lys Tyr Glu Ala Met Thr Lys Leu Gly Phe Lys Ala Thr
        115                 120                 125

Leu Pro Pro Phe Met Cys Asn Lys Arg Ala Glu Asp Phe Gln Gly Asn
    130                 135                 140
```

```
Asp Leu Asp Asn Asp Pro Asn Arg Gly Asn Gln Val Glu Arg Pro Gln
145                 150                 155                 160

Met Thr Phe Gly Arg Leu Gln Gly Ile Ser Pro Lys Ile Met Pro Lys
            165                 170                 175

Lys Pro Ala Glu Glu Gly Asn Asp Ser Glu Glu Val Pro Glu Ala Ser
            180                 185                 190

Gly Pro Gln Asn Asp Gly Lys Glu Leu Cys Pro Pro Gly Lys Pro Thr
            195                 200                 205

Thr Ser Glu Lys Ile His Glu Arg Ser Gly Pro Lys Arg Gly Glu His
        210                 215                 220

Ala Trp Thr His Arg Leu Arg Glu Arg Lys Gln Leu Val Ile Tyr Glu
225                 230                 235                 240

Glu Ile Ser Asp Pro
                245

<210> SEQ ID NO 27
<211> LENGTH: 245
<212> TYPE: PRT
<213> ORGANISM: Artificial Sequence
<220> FEATURE:
<223> OTHER INFORMATION: Synthetic peptide

<400> SEQUENCE: 27

Met Ala Gln Ile Pro Glu Lys Ile Gln Lys Ala Phe Asp Asp Ile Ala
1               5                   10                  15

Lys Tyr Phe Ser Lys Glu Glu Trp Glu Lys Met Lys Ala Ser Glu Lys
            20                  25                  30

Ile Phe Tyr Val Tyr Met Lys Arg Lys Tyr Glu Ala Met Thr Lys Leu
        35                  40                  45

Gly Phe Lys Ala Thr Leu Pro Pro Phe Met Cys Asn Lys Arg Ala Glu
    50                  55                  60

Asp Phe Gln Gly Asn Asp Leu Asp Asn Asp Pro Asn Arg Gly Asn Gln
65                  70                  75                  80

Val Glu Arg Pro Gln Met Thr Phe Gly Arg Leu Gln Gly Ile Ser Pro
                85                  90                  95

Lys Ile Met Pro Lys Lys Pro Ala Glu Glu Gly Asn Asp Ser Glu Glu
            100                 105                 110

Val Pro Glu Ala Ser Gly Pro Gln Asn Asp Gly Lys Glu Leu Cys Pro
        115                 120                 125

Pro Gly Lys Pro Thr Thr Ser Glu Lys Ile His Glu Arg Ser Gly Pro
    130                 135                 140

Lys Arg Gly Glu His Ala Trp Thr His Arg Leu Arg Glu Arg Lys Gln
145                 150                 155                 160

Leu Val Ile Tyr Glu Glu Ile Ser Asp Pro Val Met Thr Lys Leu Gly
                165                 170                 175

Phe Lys Val Lys Ala Ser Glu Lys Ile Phe Tyr Val Arg Gln Ile Tyr
            180                 185                 190

Val Ala Ala Phe Thr Val Gly Leu Pro Ser Ile Pro Val His Pro Ile
        195                 200                 205

Thr Gln Cys Phe Leu Pro Val Phe Leu Val Met Thr Lys Leu Gly Phe
    210                 215                 220

Lys Val Arg Gln Ile Tyr Val Ala Ala Phe Thr Val Lys Ala Ser Glu
225                 230                 235                 240

Lys Ile Phe Tyr Val
                245
```

```
<210> SEQ ID NO 28
<211> LENGTH: 208
<212> TYPE: PRT
<213> ORGANISM: Artificial Sequence
<220> FEATURE:
<223> OTHER INFORMATION: Synthetic peptide

<400> SEQUENCE: 28

Met Val Met Thr Lys Leu Gly Phe Lys Val Lys Ala Ser Glu Lys Ile
 1               5                  10                  15

Phe Tyr Val Arg Gln Ile Tyr Val Ala Ala Phe Thr Val Gly Leu Pro
                20                  25                  30

Ser Ile Pro Val His Pro Ile Ala Gln Ile Pro Glu Lys Ile Gln Lys
            35                  40                  45

Ala Phe Asp Asp Ile Ala Lys Tyr Phe Ser Lys Glu Glu Trp Glu Lys
 50                  55                  60

Met Lys Ala Ser Glu Lys Ile Phe Tyr Val Tyr Met Lys Arg Lys Tyr
 65                  70                  75                  80

Glu Ala Met Thr Lys Leu Gly Phe Lys Ala Thr Leu Pro Pro Phe Met
                85                  90                  95

Cys Asn Lys Arg Ala Glu Asp Phe Gln Gly Asn Asp Leu Asp Asn Asp
            100                 105                 110

Pro Asn Arg Gly Asn Gln Val Glu Arg Pro Gln Met Thr Phe Gly Arg
        115                 120                 125

Leu Gln Gly Ile Ser Pro Lys Ile Met Pro Lys Lys Pro Ala Glu Glu
130                 135                 140

Gly Asn Asp Ser Glu Glu Val Pro Glu Ala Ser Gly Pro Gln Asn Asp
145                 150                 155                 160

Gly Lys Glu Leu Cys Pro Pro Gly Lys Pro Thr Thr Ser Glu Lys Ile
                165                 170                 175

His Glu Arg Ser Gly Pro Lys Arg Gly Glu His Ala Trp Thr His Arg
            180                 185                 190

Leu Arg Glu Arg Lys Gln Leu Val Ile Tyr Glu Glu Ile Ser Asp Pro
        195                 200                 205

<210> SEQ ID NO 29
<211> LENGTH: 207
<212> TYPE: PRT
<213> ORGANISM: Artificial Sequence
<220> FEATURE:
<223> OTHER INFORMATION: Synthetic peptide

<400> SEQUENCE: 29

Met Ala Gln Ile Pro Glu Lys Ile Gln Lys Ala Phe Asp Asp Ile Ala
 1               5                  10                  15

Lys Tyr Phe Ser Lys Glu Glu Trp Glu Lys Met Lys Ala Ser Glu Lys
                20                  25                  30

Ile Phe Tyr Val Tyr Met Lys Arg Lys Tyr Glu Ala Met Thr Lys Leu
            35                  40                  45

Gly Phe Lys Ala Thr Leu Pro Pro Phe Met Cys Asn Lys Arg Ala Glu
 50                  55                  60

Asp Phe Gln Gly Asn Asp Leu Asp Asn Asp Pro Asn Arg Gly Asn Gln
 65                  70                  75                  80

Val Glu Arg Pro Gln Met Thr Phe Gly Arg Leu Gln Gly Ile Ser Pro
                85                  90                  95

Lys Ile Met Pro Lys Lys Pro Ala Glu Glu Gly Asn Asp Ser Glu Glu
            100                 105                 110

Val Pro Glu Ala Ser Gly Pro Gln Asn Asp Gly Lys Glu Leu Cys Pro
```

```
                 115                 120                 125
Pro Gly Lys Pro Thr Thr Ser Glu Lys Ile His Glu Arg Ser Gly Pro
    130                 135                 140

Lys Arg Gly Glu His Ala Trp Thr His Arg Leu Arg Glu Arg Lys Gln
145                 150                 155                 160

Leu Val Ile Tyr Glu Glu Ile Ser Asp Pro Thr Gln Cys Phe Leu Pro
                165                 170                 175

Val Phe Leu Val Met Thr Lys Leu Gly Phe Lys Val Arg Gln Ile Tyr
            180                 185                 190

Val Ala Ala Phe Thr Val Lys Ala Ser Glu Lys Ile Phe Tyr Val
        195                 200                 205

<210> SEQ ID NO 30
<211> LENGTH: 741
<212> TYPE: DNA
<213> ORGANISM: Artificial Sequence
<220> FEATURE:
<223> OTHER INFORMATION: Synthetic peptide

<400> SEQUENCE: 30
atggtcatga ctaaactagg tttcaaggtc aaagcttcgg agaaaatctt ctatgtgaga      60
cagatttatg ttgcagcctt cacagtgggt cttccaagta ttcctgttca tccaattacg     120
cagtgctttc tgcccgtgtt tttggtcatg actaaactag gtttcaaggt cagacagatt     180
tatgttgcag ccttcacagt gaaagcttcg gagaaaatct tctacgtagc tcaaatacca     240
gagaagatcc aaaaggcctt cgatgatatt gccaaatact ctctaaggga agagtgggaa     300
aagatgaaag cctcggagaa aatcttctat gtgtatatga agagaaagta tgaggctatg     360
actaaactag gtttcaaggc caccctccca cctttcatgt gtaataaacg ggccgaagac     420
ttccagggga tgatttgga taatgaccct aaccgtggga atcaggttga acgtcctcag     480
atgactttcg gcaggctcca gggaatctcc ccgaagatca tgcccaagaa gccagcagag     540
gaaggaaatg attcggagga agtgccagaa gcatctggcc acaaaatga tgggaaagag     600 ctgtgccccc cgggaaaacc aactacctct gagaagattc acgagagatc tggacccaaa     660 agggggaac atgcctggac ccacagactg cgtgagagaa acagctggt gatttatgaa       720 gagatcagcg acccttagtg a                                               741

<210> SEQ ID NO 31
<211> LENGTH: 28
<212> TYPE: PRT
<213> ORGANISM: Artificial Sequence
<220> FEATURE:
<223> OTHER INFORMATION: Synthetic peptide

<400> SEQUENCE: 31

Arg Gln Ile Tyr Val Ala Ala Phe Thr Val Lys Ala Ser Glu Lys Ile
1               5                   10                  15

Phe Tyr Val Ala Gln Ile Pro Glu Lys Ile Gln Lys
            20                  25

<210> SEQ ID NO 32
<211> LENGTH: 9
<212> TYPE: PRT
<213> ORGANISM: Homo sapiens

<400> SEQUENCE: 32

Phe Leu Pro Trp His Arg Leu Phe Leu
1               5
```

```
<210> SEQ ID NO 33
<211> LENGTH: 104
<212> TYPE: PRT
<213> ORGANISM: Artificial Sequence
<220> FEATURE:
<223> OTHER INFORMATION: Synthetic peptide

<400> SEQUENCE: 33

Met Leu Leu Ala Val Leu Tyr Cys Leu Leu Trp Ser Phe Gln Thr Ser
 1               5                  10                  15

Ala Phe Leu Pro Trp His Arg Leu Phe Leu Met Leu Leu Ala Val Leu
            20                  25                  30

Tyr Cys Leu Leu Trp Ser Phe Gln Thr Ser Ala Phe Leu Pro Trp His
        35                  40                  45

Arg Leu Phe Leu Met Leu Leu Ala Val Leu Tyr Cys Leu Leu Trp Ser
    50                  55                  60

Phe Gln Thr Ser Ala Phe Leu Pro Trp His Arg Leu Phe Leu Met Leu
65                  70                  75                  80

Leu Ala Val Leu Tyr Cys Leu Leu Trp Ser Phe Gln Thr Ser Ala Phe
                85                  90                  95

Leu Pro Trp His Arg Leu Phe Leu
            100

<210> SEQ ID NO 34
<211> LENGTH: 318
<212> TYPE: DNA
<213> ORGANISM: Artificial Sequence
<220> FEATURE:
<223> OTHER INFORMATION: Synthetic peptide

<400> SEQUENCE: 34
atgctcctgg ctgttttgta ctgcctgctg tggagtttcc agacctccgc ttttctgcct     60
tggcatagac tcttcttgat gctcctggct gttttgtact gcctgctgtg gagtttccag    120
acctccgctt ttctgccttg gcatagactc ttcttgatgc tcctggctgt tttgtactgc    180
ctgctgtgga gtttccagac ctccgctttt ctgccttggc atagactctt cttgatgctc    240
ctggctgttt tgtactgcct gctgtggagt ttccagacct ccgcttttct gccttggcat    300
agactcttct tgtagtga                                                  318

<210> SEQ ID NO 35
<211> LENGTH: 1524
<212> TYPE: DNA
<213> ORGANISM: Homo sapiens

<400> SEQUENCE: 35
agcagacaga ggactctcat taaggaaggt gtcctgtgcc ctgaccctac aagatgccaa     60
gagaagatgc tcacttcatc tatggttacc ccaagaaggg gcacggccac tcttacacca    120
cggctgaaga ggccgctggg atcggcatcc tgacagtgat cctgggagtc ttactgctca    180
tcggctgttg gtattgtaga agacgaaatg gatacagagc cttgatggat aaaagtcttc    240
atgttggcac tcaatgtgcc ttaacaagaa gatgcccaca agaagggttt gatcatcggg    300
acagcaaagt gtctcttcaa gagaaaaact gtgaacctgt ggttcccaat gctccacctg    360
cttatgagaa actctctgca gaacagtcac caccacctta ttcaccttaa gagccagcga    420
gacacctgag acatgctgaa attatttctc tcacactttt gcttgaattt aatacagaca    480
tctaatgttc tcctttggaa tggtgtagga aaatgcaag ccatctctaa taataagtca     540
gtgttaaaat tttagtaggt ccgctagcag tactaatcat gtgaggaaat gatgagaaat    600
```

```
attaaattgg gaaaactcca tcaataaatg ttgcaatgca tgatactatc tgtgccagag      660
gtaatgttag taaatccatg gtgttatttt ctgagagaca gaattcaagt gggtattctg      720
gggccatcca atttctcttt acttgaaatt tggctaataa caaactagtc aggttttcga      780
accttgaccg acatgaactg tacacagaat tgttccagta ctatggagtg ctcacaaagg      840
atacttttac aggttaagac aaaggggttga ctggcctatt tatctgatca agaacatgtc      900
agcaatgtct ctttgtgctc taaaattcta ttatactaca ataatatatt gtaaagatcc      960
tatagctctt ttttttttgag atggagtttc gcttttgttg cccaggctgg agtgcaatgg     1020
cgcgatcttg gctcaccata acctccgcct cccaggttca agcaattctc ctgccttagc     1080
ctcctgagta gctgggatta caggcgtgcg ccactatgcc tgactaattt tgtagtttta     1140
gtagagacgg ggtttctcca tgttggtcag gctggtctca actcctgac ctcaggtgat      1200 ctgcccgcct cagcctccca aagtgctgga attacaggcg tgagccacca cgcctggctg     1260
gatcctatat cttaggtaag acatataacg cagtctaatt acatttcact tcaaggctca     1320
atgctattct aactaatgac aagtattttc tactaaacca gaaattggta gaaggattta     1380
aataagtaaa agctactatg tactgcctta gtgctgatgc ctgtgtactg ccttaaatgt     1440
acctatggca atttagctct cttgggttcc caaatccctc tcacaagaat gtgcagaaga     1500
aatcataaag gatcagagat tctg                                             1524

<210> SEQ ID NO 36
<211> LENGTH: 1964
<212> TYPE: DNA
<213> ORGANISM: Homo sapiens

<400> SEQUENCE: 36
atcactgtag tagtagctgg aaagagaaat ctgtgactcc aattagccag ttcctgcaga       60
ccttgtgagg actagaggaa gaatgctcct ggctgttttg tactgcctgc tgtggagttt      120
ccagacctcc gctggccatt tccctagagc ctgtgtctcc tctaagaacc tgatggagaa      180
ggaatgctgt ccaccgtgga gcggggacag gagtccctgt ggccagcttt caggcagagg      240
ttcctgtcag aatatccttc tgtccaatgc accacttggg cctcaatttc ccttcacagg      300
ggtggatgac cgggagtcgt ggccttccgt cttttataat aggacctgcc agtgctctgg      360
caacttcatg ggattcaact gtggaaactg caagtttggc ttttggggac caaactgcac      420
agagagacga ctcttggtga aagaaacat cttcgatttg agtgccccag agaaggacaa      480 atttttttgcc tacctcactt tagcaaagca taccatcagc tcagactatg tcatccccat      540
agggacctat ggccaaatga aaatggatc aacacccatg tttaacgaca tcaatattta      600
tgacctcttt gtctggatgc attattatgt gtcaatggat gcactgcttg ggggatctga      660
aatctggaga gacattgatt ttgcccatga agcaccagct tttctgcctt ggcatagact      720
cttcttgttg cggtgggaac aagaaatcca gaagctgaca ggagatgaaa acttcactat      780
tccatattgg gactggcggg atgcagaaaa gtgtgacatt tgcacagatg agtacatggg      840
aggtcagcac cccacaaatc ctaacttact cagcccagca tcattcttct cctcttggca      900
gattgtctgt agccgattgg aggagtacaa cagccatcag tctttatgca atggaacgcc      960
cgagggacct ttacggcgta atcctggaaa ccatgacaaa tccagaaccc caaggctccc     1020
ctcttcagct gatgtagaat tttgcctgag tttgacccaa tatgaatctg gttccatgga     1080
taaagctgcc aatttcagct ttagaaatac actggaagga tttgctagtc cacttactgg     1140
gatagcggat gcctctcaaa gcagcatgca caatgccttg cacatctata tgaatggaac     1200
```

```
aatgtcccag gtacagggat ctgccaacga tcctatcttc cttcttcacc atgcatttgt    1260
tgacagtatt tttgagcagt ggctccgaag gcaccgtcct cttcaagaag tttatccaga    1320
agccaatgca cccattggac ataaccggga atcctacatg gttccttttta taccactgta   1380 cagaaatggt gatttcttta tttcatccaa agatctgggc tatgactata gctatctaca    1440
agattcagac ccagactctt ttcaagacta cattaagtcc tatttggaac aagcgagtcg    1500
gatctggtca tggctccttg gggcggcgat ggtaggggcc gtcctcactg ccctgctggc    1560
agggcttgtg agcttgctgt gtcgtcacaa gagaaagcag cttcctgaag aaaagcagcc    1620
actcctcatg gagaaagagg attaccacag cttgtatcag agccatttat aaaaggctta    1680
ggcaatagag tagggccaaa aagcctgacc tcactctaac tcaaagtaat gtccaggttc    1740
ccagagaata tctgctggta ttttttctgta aagaccattt gcaaaattgt aacctaatac    1800
aaagtgtagc cttcttccaa ctcaggtaga acacacctgt ctttgtcttg ctgttttcac    1860
tcagcccttt taacatttc ccctaagccc atatgtctaa ggaaaggatg ctatttggta     1920
atgaggaact gttatttgta tgtgaattaa agtgctctta tttt                    1964
```

<210> SEQ ID NO 37
<211> LENGTH: 752
<212> TYPE: DNA
<213> ORGANISM: Homo sapiens

<400> SEQUENCE: 37

```
atcctcgtgg gccctgacct tctctctgag agccgggcag aggctccgga gccatgcagg     60
ccgaaggccg gggcacaggg ggttcgacgg gcgatgctga tgggcccagga ggccctggca   120 ttcctgatgg cccaggggc aatgctggcg gcccaggaga ggcgggtgcc acgggcggca    180
gaggtccccg gggcgcaggg gcagcaaggg cctcggggcc gggaggaggc gccccgcggg   240
gtccgcatgg cggcgcggct tcagggctga atggatgctg cagatgcggg gccaggggc    300 cggagagccg cctgcttgag ttctacctcg ccatgccttt cgcgacaccc atggaagcag   360
agctggcccg caggagcctg gcccaggatg ccccaccgct tcccgtgcca ggggtgcttc   420
tgaaggagtt cactgtgtcc ggcaacatac tgactatccg actgactgct gcagaccacc   480
gccaactgca gctctccatc agctcctgtc tccagcagct ttccctgttg atgtggatca   540
cgcagtgctt tctgcccgtg ttttttggctc agcctccctc agggcagagg cgctaagccc   600
agcctggcgc cccttcctag gtcatgcctc ctccccctagg gaatggtccc agcacgagtg   660
gccagttcat tgtgggggcc tgattgtttg tcgctggagg aggacggctt acatgttttgt   720 ttctgtagaa aataaaactg agctacgaaa aa                                  752
```

<210> SEQ ID NO 38
<211> LENGTH: 750
<212> TYPE: PRT
<213> ORGANISM: Homo sapiens

<400> SEQUENCE: 38

```
Met Trp Asn Leu Leu His Glu Thr Asp Ser Ala Val Ala Thr Ala Arg
  1               5                  10                  15

Arg Pro Arg Trp Leu Cys Ala Gly Ala Leu Val Leu Ala Gly Gly Phe
             20                  25                  30

Phe Leu Leu Gly Phe Leu Phe Gly Trp Phe Ile Lys Ser Ser Asn Glu
         35                  40                  45

Ala Thr Asn Ile Thr Pro Lys His Asn Met Lys Ala Phe Leu Asp Glu
     50                  55                  60
```

```
Leu Lys Ala Glu Asn Ile Lys Lys Phe Leu Tyr Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
```

485                 490                 495
Trp Thr Lys Lys Ser Pro Ser Pro Glu Phe Ser Gly Met Pro Arg Ile
            500                 505                 510
Ser Lys Leu Gly Ser Gly Asn Asp Phe Glu Val Phe Gln Arg Leu
            515                 520                 525
Gly Ile Ala Ser Gly Arg Ala Arg Tyr Thr Lys Asn Trp Glu Thr Asn
        530                 535                 540
Lys Phe Ser Gly Tyr Pro Leu Tyr His Ser Val Tyr Glu Thr Tyr Glu
545                 550                 555                 560
Leu Val Glu Lys Phe Tyr Asp Pro Met Phe Lys Tyr His Leu Thr Val
                565                 570                 575
Ala Gln Val Arg Gly Gly Met Val Phe Glu Leu Ala Asn Ser Ile Val
            580                 585                 590
Leu Pro Phe Asp Cys Arg Asp Tyr Ala Val Val Leu Arg Lys Tyr Ala
            595                 600                 605
Asp Lys Ile Tyr Ser Ile Ser Met Lys His Pro Gln Glu Met Lys Thr
        610                 615                 620
Tyr Ser Val Ser Phe Asp Ser Leu Phe Ser Ala Val Lys Asn Phe Thr
625                 630                 635                 640
Glu Ile Ala Ser Lys Phe Ser Glu Arg Leu Gln Asp Phe Asp Lys Ser
                645                 650                 655
Asn Pro Ile Val Leu Arg Met Met Asn Asp Gln Leu Met Phe Leu Glu
            660                 665                 670
Arg Ala Phe Ile Asp Pro Leu Gly Leu Pro Asp Arg Pro Phe Tyr Arg
            675                 680                 685
His Val Ile Tyr Ala Pro Ser Ser His Asn Lys Tyr Ala Gly Glu Ser
        690                 695                 700
Phe Pro Gly Ile Tyr Asp Ala Leu Phe Asp Ile Glu Ser Lys Val Asp
705                 710                 715                 720
Pro Ser Lys Ala Trp Gly Glu Val Lys Arg Gln Ile Tyr Val Ala Ala
                725                 730                 735
Phe Thr Val Gln Ala Ala Ala Glu Thr Leu Ser Glu Val Ala
            740                 745                 750

<210> SEQ ID NO 39
<211> LENGTH: 2653
<212> TYPE: DNA
<213> ORGANISM: Homo sapiens

<400> SEQUENCE: 39
ctcaaaaggg gccggatttc cttctcctgg aggcagatgt tgcctctctc tctcgctcgg      60
attggttcag tgcactctag aaacactgct gtggtggaga aactggaccc caggtctgga    120
gcgaattcca gcctgcaggg ctgataagcg aggcattagt gagattgaga gagactttac    180
cccgccgtgg tggttggagg gcgcgcagta gagcagcagc acaggcgcgg gtcccgggag    240
gccggctctg ctcgcgccga gatgtggaat ctccttcacg aaaccgactc ggctgtggcc    300
accgcgcgcc gccgcgcgcc gctgtgcgct ggggcgctgg tgctggcggg tggcttcttt    360
ctcctcggct tcctcttcgg gtggtttata aaatcctcca atgaagctac taacattact    420
ccaaagcata tatgaaagc attttttggat gaattgaaag ctgagaacat caagaagttc    480
ttatataatt ttacacagat accacattta gcaggaacag aacaaaactt tcagcttgca    540
aagcaaattc aatcccagtg aaagaattt ggcctggatt ctgttgagct agcacattat    600
gatgtcctgt tgtcctaccc aaataagact catcccaact acatctcaat aattaatgaa    660

-continued

```
gatggaaatg agattttcaa cacatcatta tttgaaccac ctcctccagg atatgaaaat      720
gtttcggata ttgtaccacc tttcagtgct ttctctcctc aaggaatgcc agagggcgat      780
ctagtgtatg ttaactatgc acgaactgaa gacttctttta aattggaacg ggacatgaaa      840
atcaattgct ctgggaaaat tgtaattgcc agatatggga agttttcag aggaaataag      900
gttaaaaatg cccagctggc aggggccaaa ggagtcattc tctactccga ccctgctgac      960
tactttgctc ctggggtgaa gtcctatcca gatggttgga atcttcctgg aggtggtgtc     1020
cagcgtggaa atatcctaaa tctgaatggt gcaggagacc ctctcacacc aggttaccca     1080
gcaaatgaat atgcttatag cgtggaattc agaggctg ttggtcttcc aagtattcct      1140
gttcatccaa ttggatacta tgatgcacag aagctcctag aaaaaatggg tggctcagca     1200
ccaccagata gcagctggag aggaagtctc aaagtgccct acaatgttgg acctggcttt     1260
actggaaact tttctacaca aaaagtcaag atgcacatcc actctaccaa tgaagtgaca     1320
agaatttaca atgtgatagg tactctcaga ggagcagtgg aaccagacag atatgtcatt     1380
ctgggaggtc accgggactc atgggtgttt ggtggtattg accctcagag tggagcagct     1440
gttgttcatg aaattgtgag gagctttgga acactgaaaa aggaagggtg agacctaga     1500
agaacaattt tgtttgcaag ctgggatgca aagaatttg gtcttcttgg ttctactgag     1560
tgggcagagg agaattcaag actccttcaa gagcgtggcg tggcttatat taatgctgac     1620
tcatctatag aaggaaacta cactctgaga gttgattgta caccgctgat gtacagcttg     1680
gtacacaacc taacaaaaga gctgaaaagc cctgatgaag ctttgaagg caaatctctt     1740
tatgaaagtt ggactaaaaa aagtccttcc ccagagttca gtggcatgcc aggataagc      1800
aaattgggat ctgaaatga ttttgaggtg ttcttccaac gacttggaat tgcttcaggc     1860
agagcacggt atactaaaaa ttgggaaaca acaaattca gcggctatcc actgtatcac     1920
agtgtctatg aaacatatga gttggtggaa aagtttatg atccaatgtt taaatatcac     1980
ctcactgtgg cccaggttcg aggagggatg gtgtttgagc tagccaattc catagtgctc     2040
ccttttgatt gtcgagatta tgctgtagtt ttaagaaagt atgctgacaa aatctacagt     2100
atttctatga acatcccaca ggaaatgaag acatacagtg tatcatttga ttcactttt      2160
tctgcagtaa agaattttac agaaattgct tccaagttca gtgagagact ccaggacttt     2220
gacaaaagca acccaatagt attaagaatg atgaatgatc aactcatgtt tctggaaaga     2280
gcatttattg atccattagg gttaccagac aggccttttt ataggcatgt catctatgct     2340
ccaagcagcc acaacaagta tgcagggag tcattcccag gaatttatga tgctctgttt     2400
gatattgaaa gcaaagtgga cccttccaag gcctgggag aagtgaagag acagatttat     2460
gttgcagcct tcacagtgca ggcagctgca gagactttga gtgaagtagc ctaagaggat     2520
tcttagaga atccgtattg aatttgtgtg gtatgtcact cagaaagaat cgtaatgggt     2580
atattgataa attttaaat tggtatattt gaaataaagt tgaatattat atataaaaaa     2640
aaaaaaaaa aaa                                                         2653
```

<210> SEQ ID NO 40
<211> LENGTH: 188
<212> TYPE: PRT
<213> ORGANISM: Homo sapiens

<400> SEQUENCE: 40

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe

```
                    20                  25                  30
Ser Lys Glu Glu Trp Glu Lys Met Lys Ala Ser Glu Lys Ile Phe Tyr
        35                  40                  45

Val Tyr Met Lys Arg Lys Tyr Glu Ala Met Thr Lys Leu Gly Phe Lys
    50                  55                  60

Ala Thr Leu Pro Pro Phe Met Cys Asn Lys Arg Ala Glu Asp Phe Gln
65                  70                  75                  80

Gly Asn Asp Leu Asp Asn Asp Pro Asn Arg Gly Asn Gln Val Glu Arg
                85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Glu Val Pro Glu
        115                 120                 125

Ala Ser Gly Pro Gln Asn Asp Gly Lys Glu Leu Cys Pro Pro Gly Lys
    130                 135                 140

Pro Thr Thr Ser Glu Lys Ile His Glu Arg Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Asp Glu
            180                 185

<210> SEQ ID NO 41
<211> LENGTH: 766
<212> TYPE: DNA
<213> ORGANISM: Homo sapiens

<400> SEQUENCE: 41
ctctctttcg attcttccat actcagagta cgcacggtct gattttctct ttggattctt      60
ccaaaatcag agtcagactg ctcccggtgc catgaacgga gacgacgcct ttgcaaggag     120
acccacggtt ggtgctcaaa taccagagaa gatccaaaag gccttcgatg atattgccaa     180
atacttctct aaggaagagt gggaaaagat gaaagcctcg agaaaatct tctatgtgta      240 tatgaagaga agtatgagg ctatgactaa actaggtttc aaggccaccc tcccaccttt      300
catgtgtaat aaacgggccg aagacttcca ggggaatgat ttggataatg accctaaccg     360
tgggaatcag gttgaacgtc ctcagatgac tttcggcagg ctccagggaa tctccccgaa     420
gatcatgccc aagaagccag cagaggaagg aaatgattcg gaggaagtgc cagaagcatc     480
tggcccacaa aatgatggga aagagctgtg ccccccggga aaaccaacta cctctgagaa     540
gattcacgag agatctggac ccaaaagggg ggaacatgcc tggacccaca gactgcgtga     600
gagaaaacag ctggtgattt atgaagagat cagcgaccct gaggaagatg acgagtaact     660
cccctcaggg atacgacaca tgcccatgat gagaagcaga acgtggtgac ctttcacgaa     720
catgggcatg gctgcggacc cctcgtcatc aggtgcatag caagtg                    766

<210> SEQ ID NO 42
<211> LENGTH: 903
<212> TYPE: DNA
<213> ORGANISM: Herpes Simplex Virus

<400> SEQUENCE: 42
atgacctctc gccgctccgt gaagtcgggt ccgcgggagg ttccgcgcga tgagtacgag      60
gatctgtact acaccccgtc ttcaggtatg gcgagtccg atagtccgcc tgacacctcc     120
cgccgtggcg ccctacagac acgctcgcgc cagaggggcg aggtccgttt cgtccagtac     180
```

-continued

```
gacgagtcgg attatgccct ctacgggggc tcgtcatccg aagacgacga acacccggag    240
gtcccccgga cgcggcgtcc cgtttccggg gcggttttgt ccggcccggg gcctgcgcgg    300
gcgcctccgc cacccgctgg gtccggaggg gccggacgca cacccaccac cgcccccgg     360 gccccccgaa cccagcgggt ggcgactaag gcccccgcgg ccccggcggc ggagaccacc    420
cgcggcagga aatcggccca gccagaatcc gccgcactcc cagacgcccc cgcgtcgacg    480
gcgccaaccc gatccaagac acccgcgcag gggctggcca gaaagctgca ctttagcacc    540
gcccccccaa accccgacgc gccatggacc ccccgggtgg ccggctttaa caagcgcgtc    600
ttctgcgccg cggtcgggcg cctggcggcc atgcatgccc ggatggcggc ggtccagctc    660
tgggacatgt cgcgtccgcg cacagacgaa gacctcaacg aactccttgg catcaccacc    720
atccgcgtga cggtctgcga gggcaaaaac ctgcttcagc gcgccaacga gttggtgaat    780
ccagacgtgg tgcaggacgt cgacgcggcc acggcgactc gagggcgttc tgcggcgtcg    840
cgccccaccg agcgacctcg agccccagcc cgctccgctt ctcgcccag acggcccgtc     900 gag                                                                 903
```

```
<210> SEQ ID NO 43
<211> LENGTH: 311
<212> TYPE: PRT
<213> ORGANISM: Herpes Simplex Virus

<400> SEQUENCE: 43
```

Met Thr Ser Arg Arg Ser Val Lys Ser Gly Pro Arg Glu Val Pro Arg
1               5                   10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Phe Thr Gln
        35                  40                  45

Thr Arg Ser Arg Gln Arg Gly Glu Val Arg Phe Val Gln Tyr Asp Glu
    50                  55                  60

Ser Asp Tyr Ala Leu Tyr Gly Gly Ser Ser Glu Asp Asp Glu His
65                  70                  75                  80

Pro Glu Val Pro Arg Thr Arg Arg Pro Val Ser Gly Ala Val Leu Ser
                85                  90                  95

Gly Pro Gly Pro Ala Arg Ala Pro Pro Pro Phe Thr Pro Ala Gly Ser
            100                 105                 110

Gly Gly Ala Gly Arg Thr Pro Thr Thr Ala Pro Arg Ala Pro Arg Thr
        115                 120                 125

Gln Arg Val Ala Thr Lys Ala Pro Ala Ala Pro Ala Ala Glu Thr Thr
    130                 135                 140

Arg Gly Arg Lys Ser Ala Gln Pro Glu Ser Ala Ala Leu Pro Asp Ala
145                 150                 155                 160

Pro Ala Ser Thr Ala Pro Thr Phe Thr Arg Ser Lys Thr Pro Ala Gln
                165                 170                 175

Gly Leu Ala Arg Lys Leu His Phe Ser Thr Ala Pro Pro Asn Pro Asp
            180                 185                 190

Ala Pro Trp Thr Pro Arg Val Ala Gly Phe Asn Lys Arg Val Phe Cys
        195                 200                 205

Ala Ala Val Gly Arg Leu Ala Ala Met His Ala Arg Met Ala Ala Val
    210                 215                 220

Gln Leu Trp Asp Phe Thr Met Ser Arg Pro Arg Thr Asp Glu Asp Leu
225                 230                 235                 240

Asn Glu Leu Leu Gly Ile Thr Thr Ile Arg Val Thr Val Cys Glu Gly

```
                   245                 250                 255
Lys Asn Leu Leu Gln Arg Ala Asn Glu Leu Val Asn Pro Asp Val Val
                260                 265                 270

Gln Asp Val Asp Ala Ala Thr Ala Thr Arg Gly Arg Ser Ala Ala Ser
            275                 280                 285

Arg Phe Thr Pro Thr Glu Arg Pro Arg Ala Pro Ala Arg Ser Ala Ser
        290                 295                 300

Arg Pro Arg Arg Pro Val Glu
305                 310

<210> SEQ ID NO 44
<211> LENGTH: 9
<212> TYPE: PRT
<213> ORGANISM: Adenovirus 3

<400> SEQUENCE: 44

Leu Ile Val Ile Gly Ile Leu Ile Leu
1               5

<210> SEQ ID NO 45
<211> LENGTH: 10
<212> TYPE: PRT
<213> ORGANISM: Adenovirus 5

<400> SEQUENCE: 45

Ser Gly Pro Ser Asn Thr Pro Pro Glu Ile
1               5                  10

<210> SEQ ID NO 46
<211> LENGTH: 8
<212> TYPE: PRT
<213> ORGANISM: Adenovirus 5

<400> SEQUENCE: 46

Val Asn Ile Arg Asn Cys Cys Tyr
1               5

<210> SEQ ID NO 47
<211> LENGTH: 10
<212> TYPE: PRT
<213> ORGANISM: Adenovirus 5

<400> SEQUENCE: 47

Ser Gly Pro Ser Asn Ile Pro Pro Glu Ile
1               5                  10

<210> SEQ ID NO 48
<211> LENGTH: 9
<212> TYPE: PRT
<213> ORGANISM: Classical Swine Fever Virus

<400> SEQUENCE: 48

Glu Asn Ala Leu Leu Val Ala Leu Phe
1               5

<210> SEQ ID NO 49
<211> LENGTH: 9
<212> TYPE: PRT
<213> ORGANISM: Dengue Virus 4

<400> SEQUENCE: 49

Thr Pro Glu Gly Ile Ile Pro Thr Leu
1               5
```

```
<210> SEQ ID NO 50
<211> LENGTH: 9
<212> TYPE: PRT
<213> ORGANISM: Epstein-Barr Virus

<400> SEQUENCE: 50

Cys Leu Gly Gly Leu Leu Thr Met Val
 1               5

<210> SEQ ID NO 51
<211> LENGTH: 9
<212> TYPE: PRT
<213> ORGANISM: Epstein-Barr Virus

<400> SEQUENCE: 51

Asn Ile Ala Glu Gly Leu Arg Ala Leu
 1               5

<210> SEQ ID NO 52
<211> LENGTH: 9
<212> TYPE: PRT
<213> ORGANISM: Epstein-Barr Virus

<400> SEQUENCE: 52

Asn Leu Arg Arg Gly Thr Ala Leu Ala
 1               5

<210> SEQ ID NO 53
<211> LENGTH: 9
<212> TYPE: PRT
<213> ORGANISM: Epstein-Barr Virus

<400> SEQUENCE: 53

Ala Leu Ala Ile Pro Gln Cys Arg Leu
 1               5

<210> SEQ ID NO 54
<211> LENGTH: 9
<212> TYPE: PRT
<213> ORGANISM: Epstein-Barr Virus

<400> SEQUENCE: 54

Val Leu Lys Asp Ala Ile Lys Asp Leu
 1               5

<210> SEQ ID NO 55
<211> LENGTH: 9
<212> TYPE: PRT
<213> ORGANISM: Epstein-Barr Virus

<400> SEQUENCE: 55

Phe Met Val Phe Leu Gln Thr His Ile
 1               5

<210> SEQ ID NO 56
<211> LENGTH: 9
<212> TYPE: PRT
<213> ORGANISM: Epstein-Barr Virus

<400> SEQUENCE: 56

His Leu Ile Val Asp Thr Asp Ser Leu
 1               5

<210> SEQ ID NO 57
<211> LENGTH: 9
```

```
<212> TYPE: PRT
<213> ORGANISM: Epstein-Barr Virus

<400> SEQUENCE: 57

Ser Leu Gly Asn Pro Ser Leu Ser Val
1               5

<210> SEQ ID NO 58
<211> LENGTH: 9
<212> TYPE: PRT
<213> ORGANISM: Epstein-Barr Virus

<400> SEQUENCE: 58

Pro Leu Ala Ser Ala Met Arg Met Leu
1               5

<210> SEQ ID NO 59
<211> LENGTH: 8
<212> TYPE: PRT
<213> ORGANISM: Epstein-Barr Virus

<400> SEQUENCE: 59

Arg Met Leu Trp Met Ala Asn Tyr
1               5

<210> SEQ ID NO 60
<211> LENGTH: 9
<212> TYPE: PRT
<213> ORGANISM: Epstein-Barr Virus

<400> SEQUENCE: 60

Met Leu Trp Met Ala Asn Tyr Ile Val
1               5

<210> SEQ ID NO 61
<211> LENGTH: 9
<212> TYPE: PRT
<213> ORGANISM: Epstein-Barr Virus

<400> SEQUENCE: 61

Ile Leu Pro Gln Gly Pro Gln Thr Ala
1               5

<210> SEQ ID NO 62
<211> LENGTH: 9
<212> TYPE: PRT
<213> ORGANISM: Epstein-Barr Virus

<400> SEQUENCE: 62

Pro Leu Arg Pro Thr Ala Pro Thr Ile
1               5

<210> SEQ ID NO 63
<211> LENGTH: 9
<212> TYPE: PRT
<213> ORGANISM: Epstein-Barr Virus

<400> SEQUENCE: 63

Pro Leu Pro Pro Ala Thr Leu Thr Val
1               5

<210> SEQ ID NO 64
<211> LENGTH: 9
<212> TYPE: PRT
<213> ORGANISM: Epstein-Barr Virus
```

-continued

<400> SEQUENCE: 64

Arg Met His Leu Pro Val Leu His Val
1               5

<210> SEQ ID NO 65
<211> LENGTH: 9
<212> TYPE: PRT
<213> ORGANISM: Epstein-Barr Virus

<400> SEQUENCE: 65

Pro Met Pro Leu Pro Pro Ser Gln Leu
1               5

<210> SEQ ID NO 66
<211> LENGTH: 9
<212> TYPE: PRT
<213> ORGANISM: Epstein-Barr Virus

<400> SEQUENCE: 66

Gln Leu Pro Pro Pro Ala Ala Pro Ala
1               5

<210> SEQ ID NO 67
<211> LENGTH: 9
<212> TYPE: PRT
<213> ORGANISM: Epstein-Barr Virus

<400> SEQUENCE: 67

Ser Met Pro Glu Leu Ser Pro Val Leu
1               5

<210> SEQ ID NO 68
<211> LENGTH: 9
<212> TYPE: PRT
<213> ORGANISM: Epstein-Barr Virus

<400> SEQUENCE: 68

Asp Leu Asp Glu Ser Trp Asp Tyr Ile
1               5

<210> SEQ ID NO 69
<211> LENGTH: 9
<212> TYPE: PRT
<213> ORGANISM: Epstein-Barr Virus

<400> SEQUENCE: 69

Pro Leu Pro Cys Val Leu Trp Pro Val
1               5

<210> SEQ ID NO 70
<211> LENGTH: 9
<212> TYPE: PRT
<213> ORGANISM: Epstein-Barr Virus

<400> SEQUENCE: 70

Ser Leu Glu Glu Cys Asp Ser Glu Leu
1               5

<210> SEQ ID NO 71
<211> LENGTH: 9
<212> TYPE: PRT
<213> ORGANISM: Epstein-Barr Virus

<400> SEQUENCE: 71

Glu Ile Lys Arg Tyr Lys Asn Arg Val

```
<210> SEQ ID NO 72
<211> LENGTH: 9
<212> TYPE: PRT
<213> ORGANISM: Epstein-Barr Virus

<400> SEQUENCE: 72

Gln Leu Leu Gln His Tyr Arg Glu Val
1               5

<210> SEQ ID NO 73
<211> LENGTH: 9
<212> TYPE: PRT
<213> ORGANISM: Epstein-Barr Virus

<400> SEQUENCE: 73

Leu Leu Gln His Tyr Arg Glu Val Ala
1               5

<210> SEQ ID NO 74
<211> LENGTH: 9
<212> TYPE: PRT
<213> ORGANISM: Epstein-Barr Virus

<400> SEQUENCE: 74

Leu Leu Lys Gln Met Cys Pro Ser Leu
1               5

<210> SEQ ID NO 75
<211> LENGTH: 9
<212> TYPE: PRT
<213> ORGANISM: Epstein-Barr Virus

<400> SEQUENCE: 75

Ser Ile Ile Pro Arg Thr Pro Asp Val
1               5

<210> SEQ ID NO 76
<211> LENGTH: 10
<212> TYPE: PRT
<213> ORGANISM: Epstein-Barr Virus

<400> SEQUENCE: 76

Leu Leu Asp Phe Val Arg Phe Met Gly Val
1               5                   10

<210> SEQ ID NO 77
<211> LENGTH: 9
<212> TYPE: PRT
<213> ORGANISM: Epstein-Barr Virus

<400> SEQUENCE: 77

Ser Val Arg Asp Arg Leu Ala Arg Leu
1               5

<210> SEQ ID NO 78
<211> LENGTH: 9
<212> TYPE: PRT
<213> ORGANISM: Epstein-Barr Virus

<400> SEQUENCE: 78

Ile Val Thr Asp Phe Ser Val Ile Lys
1               5
```

```
<210> SEQ ID NO 79
<211> LENGTH: 10
<212> TYPE: PRT
<213> ORGANISM: Epstein-Barr Virus

<400> SEQUENCE: 79

Ala Val Phe Asp Arg Lys Ser Asp Ala Lys
1               5                   10

<210> SEQ ID NO 80
<211> LENGTH: 8
<212> TYPE: PRT
<213> ORGANISM: Epstein-Barr Virus

<400> SEQUENCE: 80

Arg Tyr Ser Ile Phe Phe Asp Tyr
1               5

<210> SEQ ID NO 81
<211> LENGTH: 9
<212> TYPE: PRT
<213> ORGANISM: Epstein-Barr Virus

<400> SEQUENCE: 81

Gln Pro Arg Ala Pro Ile Arg Pro Ile
1               5

<210> SEQ ID NO 82
<211> LENGTH: 9
<212> TYPE: PRT
<213> ORGANISM: Epstein-Barr Virus

<400> SEQUENCE: 82

Arg Pro Pro Ile Phe Ile Arg Arg Ile
1               5

<210> SEQ ID NO 83
<211> LENGTH: 9
<212> TYPE: PRT
<213> ORGANISM: Epstein-Barr Virus

<400> SEQUENCE: 83

Glu Pro Asp Val Pro Pro Gly Ala Ile
1               5

<210> SEQ ID NO 84
<211> LENGTH: 9
<212> TYPE: PRT
<213> ORGANISM: Epstein-Barr Virus

<400> SEQUENCE: 84

Ile Pro Gln Cys Arg Leu Thr Pro Leu
1               5

<210> SEQ ID NO 85
<211> LENGTH: 9
<212> TYPE: PRT
<213> ORGANISM: Epstein-Barr Virus

<400> SEQUENCE: 85

Gly Pro Gly Pro Gln Pro Gly Pro Leu
1               5

<210> SEQ ID NO 86
<211> LENGTH: 9
<212> TYPE: PRT
```

<213> ORGANISM: Epstein-Barr Virus

<400> SEQUENCE: 86

Gln Pro Gly Pro Leu Arg Glu Ser Ile
1               5

<210> SEQ ID NO 87
<211> LENGTH: 9
<212> TYPE: PRT
<213> ORGANISM: Epstein-Barr Virus

<400> SEQUENCE: 87

Arg Pro Gln Lys Arg Pro Ser Cys Ile
1               5

<210> SEQ ID NO 88
<211> LENGTH: 9
<212> TYPE: PRT
<213> ORGANISM: Epstein-Barr Virus

<400> SEQUENCE: 88

Pro Pro Thr Pro Leu Leu Thr Val Leu
1               5

<210> SEQ ID NO 89
<211> LENGTH: 9
<212> TYPE: PRT
<213> ORGANISM: Epstein-Barr Virus

<400> SEQUENCE: 89

Thr Pro Ser Pro Pro Arg Met His Leu
1               5

<210> SEQ ID NO 90
<211> LENGTH: 9
<212> TYPE: PRT
<213> ORGANISM: Epstein-Barr Virus

<400> SEQUENCE: 90

Pro Pro Arg Met His Leu Pro Val Leu
1               5

<210> SEQ ID NO 91
<211> LENGTH: 9
<212> TYPE: PRT
<213> ORGANISM: Epstein-Barr Virus

<400> SEQUENCE: 91

Val Pro Asp Gln Ser Met His Pro Leu
1               5

<210> SEQ ID NO 92
<211> LENGTH: 9
<212> TYPE: PRT
<213> ORGANISM: Epstein-Barr Virus

<400> SEQUENCE: 92

Pro Pro Ser Ile Asp Pro Ala Asp Leu
1               5

<210> SEQ ID NO 93
<211> LENGTH: 9
<212> TYPE: PRT
<213> ORGANISM: Epstein-Barr Virus

<400> SEQUENCE: 93

```
Leu Pro Cys Val Leu Trp Pro Val Leu
1               5

<210> SEQ ID NO 94
<211> LENGTH: 10
<212> TYPE: PRT
<213> ORGANISM: Epstein-Barr Virus

<400> SEQUENCE: 94

Cys Pro Ser Leu Asp Val Asp Ser Ile Ile
1               5                   10

<210> SEQ ID NO 95
<211> LENGTH: 9
<212> TYPE: PRT
<213> ORGANISM: Epstein-Barr Virus

<400> SEQUENCE: 95

Thr Pro Asp Val Leu His Glu Asp Leu
1               5

<210> SEQ ID NO 96
<211> LENGTH: 9
<212> TYPE: PRT
<213> ORGANISM: Epstein-Barr Virus

<400> SEQUENCE: 96

Phe Leu Arg Gly Arg Ala Tyr Gly Leu
1               5

<210> SEQ ID NO 97
<211> LENGTH: 9
<212> TYPE: PRT
<213> ORGANISM: Epstein-Barr Virus

<400> SEQUENCE: 97

Gln Ala Lys Trp Arg Leu Gln Thr Leu
1               5

<210> SEQ ID NO 98
<211> LENGTH: 9
<212> TYPE: PRT
<213> ORGANISM: Epstein-Barr Virus

<400> SEQUENCE: 98

Ala Tyr Pro Leu His Glu Gln His Gly
1               5

<210> SEQ ID NO 99
<211> LENGTH: 9
<212> TYPE: PRT
<213> ORGANISM: Epstein-Barr Virus

<400> SEQUENCE: 99

Tyr Leu Lys Ser Phe Val Ser Asp Ala
1               5

<210> SEQ ID NO 100
<211> LENGTH: 9
<212> TYPE: PRT
<213> ORGANISM: Epstein-Barr Virus

<400> SEQUENCE: 100

Arg Arg Arg Trp Arg Arg Leu Thr Val
1               5
```

<210> SEQ ID NO 101
<211> LENGTH: 9
<212> TYPE: PRT
<213> ORGANISM: Epstein-Barr Virus

<400> SEQUENCE: 101

Arg Arg Ile Tyr Asp Leu Ile Glu Leu
1               5

<210> SEQ ID NO 102
<211> LENGTH: 9
<212> TYPE: PRT
<213> ORGANISM: Epstein-Barr Virus

<400> SEQUENCE: 102

Tyr Pro Leu His Glu Gln His Gly Met
1               5

<210> SEQ ID NO 103
<211> LENGTH: 9
<212> TYPE: PRT
<213> ORGANISM: Epstein-Barr Virus

<400> SEQUENCE: 103

Tyr Pro Leu His Glu Gln His Gly Met
1               5

<210> SEQ ID NO 104
<211> LENGTH: 9
<212> TYPE: PRT
<213> ORGANISM: Hepatitis C Virus

<400> SEQUENCE: 104

His Ser Lys Lys Lys Cys Asp Glu Leu
1               5

<210> SEQ ID NO 105
<211> LENGTH: 8
<212> TYPE: PRT
<213> ORGANISM: Hepatitis C Virus

<400> SEQUENCE: 105

Ala Ser Arg Cys Trp Val Ala Met
1               5

<210> SEQ ID NO 106
<211> LENGTH: 9
<212> TYPE: PRT
<213> ORGANISM: Hepatitis C Virus

<400> SEQUENCE: 106

Gly Gln Ile Val Gly Gly Val Tyr Leu
1               5

<210> SEQ ID NO 107
<211> LENGTH: 10
<212> TYPE: PRT
<213> ORGANISM: Hepatitis C Virus

<400> SEQUENCE: 107

Pro Pro Leu Thr Asp Phe Asp Gln Gly Trp
1               5                   10

<210> SEQ ID NO 108

-continued

<211> LENGTH: 10
<212> TYPE: PRT
<213> ORGANISM: Hepatitis C Virus

<400> SEQUENCE: 108

Leu Met Gly Tyr Ile Pro Leu Val Gly Ala
1 5 10

<210> SEQ ID NO 109
<211> LENGTH: 10
<212> TYPE: PRT
<213> ORGANISM: Hepatitis C Virus

<400> SEQUENCE: 109

Ala Asp Leu Met Gly Tyr Ile Pro Leu Val
1 5 10

<210> SEQ ID NO 110
<211> LENGTH: 16
<212> TYPE: PRT
<213> ORGANISM: Hepatitis C Virus

<400> SEQUENCE: 110

Met Ser Tyr Ser Trp Thr Gly Ala Leu Val Thr Pro Cys Ala Glu Glu
1 5 10 15

<210> SEQ ID NO 111
<211> LENGTH: 9
<212> TYPE: PRT
<213> ORGANISM: Hepatitis C Virus

<400> SEQUENCE: 111

Lys His Pro Asp Ala Thr Tyr Ser Arg
1 5

<210> SEQ ID NO 112
<211> LENGTH: 10
<212> TYPE: PRT
<213> ORGANISM: Hepatitis C Virus 1

<400> SEQUENCE: 112

Lys Leu Val Ala Leu Gly Ile Asn Ala Val
1 5 10

<210> SEQ ID NO 113
<211> LENGTH: 9
<212> TYPE: PRT
<213> ORGANISM: Hepatitis C Virus 1

<400> SEQUENCE: 113

Gly Asp Phe Asp Ser Val Ile Asp Cys
1 5

<210> SEQ ID NO 114
<211> LENGTH: 9
<212> TYPE: PRT
<213> ORGANISM: Hepatitis C Virus 1

<400> SEQUENCE: 114

Gly Asn Ala Ser Arg Cys Trp Val Ala
1 5

<210> SEQ ID NO 115
<211> LENGTH: 9
<212> TYPE: PRT
<213> ORGANISM: Hepatitis C Virus 1

```
<400> SEQUENCE: 115

Thr Arg Pro Pro Leu Gly Asn Trp Phe
  1               5

<210> SEQ ID NO 116
<211> LENGTH: 9
<212> TYPE: PRT
<213> ORGANISM: Hepatitis C Virus 1

<400> SEQUENCE: 116

Val Pro His Pro Asn Ile Glu Glu Val
  1               5

<210> SEQ ID NO 117
<211> LENGTH: 9
<212> TYPE: PRT
<213> ORGANISM: Hepatitis C Virus 1

<400> SEQUENCE: 117

Tyr Thr Gly Asp Phe Asp Ser Val Ile
  1               5

<210> SEQ ID NO 118
<211> LENGTH: 8
<212> TYPE: PRT
<213> ORGANISM: Hepatitis C Virus 1

<400> SEQUENCE: 118

Ser Trp Ala Ile Lys Trp Glu Tyr
  1               5

<210> SEQ ID NO 119
<211> LENGTH: 9
<212> TYPE: PRT
<213> ORGANISM: Hepatitis C Virus 1

<400> SEQUENCE: 119

Lys His Pro Asp Ala Thr Tyr Ser Arg
  1               5

<210> SEQ ID NO 120
<211> LENGTH: 9
<212> TYPE: PRT
<213> ORGANISM: Hepatitis C Virus 1

<400> SEQUENCE: 120

Gly Asp Phe Asp Ser Val Ile Asp Cys
  1               5

<210> SEQ ID NO 121
<211> LENGTH: 9
<212> TYPE: PRT
<213> ORGANISM: Human Immunodeficiency Virus

<400> SEQUENCE: 121

Arg Tyr Leu Lys Asp Gln Gln Leu Leu
  1               5

<210> SEQ ID NO 122
<211> LENGTH: 9
<212> TYPE: PRT
<213> ORGANISM: Human Immunodeficiency Virus

<400> SEQUENCE: 122
```

```
Ile Val Gly Leu Asn Lys Ile Val Arg
1               5

<210> SEQ ID NO 123
<211> LENGTH: 9
<212> TYPE: PRT
<213> ORGANISM: Human Immunodeficiency Virus

<400> SEQUENCE: 123

Glu Ile Tyr Lys Arg Trp Ile Ile Leu
1               5

<210> SEQ ID NO 124
<211> LENGTH: 8
<212> TYPE: PRT
<213> ORGANISM: Human Immunodeficiency Virus

<400> SEQUENCE: 124

Gly Glu Leu Tyr Lys Arg Trp Ile
1               5

<210> SEQ ID NO 125
<211> LENGTH: 9
<212> TYPE: PRT
<213> ORGANISM: Human Immunodeficiency Virus

<400> SEQUENCE: 125

Glu Ile Lys Asp Thr Lys Glu Ala Leu
1               5

<210> SEQ ID NO 126
<211> LENGTH: 8
<212> TYPE: PRT
<213> ORGANISM: Human Immunodeficiency Virus

<400> SEQUENCE: 126

Tyr Leu Lys Asp Gln Gln Leu Leu
1               5

<210> SEQ ID NO 127
<211> LENGTH: 11
<212> TYPE: PRT
<213> ORGANISM: Human Immunodeficiency Virus

<400> SEQUENCE: 127

Ile Leu Gly Leu Asn Lys Ile Val Arg Met Tyr
1               5                   10

<210> SEQ ID NO 128
<211> LENGTH: 9
<212> TYPE: PRT
<213> ORGANISM: Human Immunodeficiency Virus

<400> SEQUENCE: 128

Glu Arg Tyr Leu Lys Asp Gln Gln Leu
1               5

<210> SEQ ID NO 129
<211> LENGTH: 11
<212> TYPE: PRT
<213> ORGANISM: Human Immunodeficiency Virus

<400> SEQUENCE: 129

Tyr His Thr Gln Gly Tyr Phe Pro Gln Trp Gln
1               5                   10
```

```
<210> SEQ ID NO 130
<211> LENGTH: 12
<212> TYPE: PRT
<213> ORGANISM: Human Immunodeficiency Virus

<400> SEQUENCE: 130

Thr Gln Gly Tyr Phe Pro Gln Trp Gln Asn Tyr Thr
1               5                   10

<210> SEQ ID NO 131
<211> LENGTH: 9
<212> TYPE: PRT
<213> ORGANISM: Human Immunodeficiency Virus

<400> SEQUENCE: 131

Gly Arg Ala Phe Val Thr Leu Gly Lys
1               5

<210> SEQ ID NO 132
<211> LENGTH: 9
<212> TYPE: PRT
<213> ORGANISM: Human Immunodeficiency Virus

<400> SEQUENCE: 132

Lys Arg Trp Ile Ile Leu Gly Leu Asn
1               5

<210> SEQ ID NO 133
<211> LENGTH: 10
<212> TYPE: PRT
<213> ORGANISM: Human Immunodeficiency Virus

<400> SEQUENCE: 133

Gln Val Pro Leu Arg Pro Met Thr Tyr Lys
1               5                   10

<210> SEQ ID NO 134
<211> LENGTH: 9
<212> TYPE: PRT
<213> ORGANISM: Human Immunodeficiency Virus

<400> SEQUENCE: 134

Thr Gln Gly Tyr Phe Pro Gln Trp Gln
1               5

<210> SEQ ID NO 135
<211> LENGTH: 9
<212> TYPE: PRT
<213> ORGANISM: Human Immunodeficiency Virus

<400> SEQUENCE: 135

His Gln Ala Ile Ser Pro Arg Thr Ile
1               5

<210> SEQ ID NO 136
<211> LENGTH: 12
<212> TYPE: PRT
<213> ORGANISM: Human Immunodeficiency Virus

<400> SEQUENCE: 136

Gln Met Val His Gln Ala Ile Ser Pro Arg Thr Leu
1               5                   10

<210> SEQ ID NO 137
<211> LENGTH: 10
```

```
<212> TYPE: PRT
<213> ORGANISM: Human Immunodeficiency Virus

<400> SEQUENCE: 137

Met Tyr Ala Pro Pro Ile Gly Gly Gln Ile
1               5                   10

<210> SEQ ID NO 138
<211> LENGTH: 10
<212> TYPE: PRT
<213> ORGANISM: Human Immunodeficiency Virus

<400> SEQUENCE: 138

Arg Gly Pro Gly Arg Ala Phe Val Thr Ile
1               5                   10

<210> SEQ ID NO 139
<211> LENGTH: 9
<212> TYPE: PRT
<213> ORGANISM: Human Immunodeficiency Virus

<400> SEQUENCE: 139

Met Pro Gly Arg Ala Phe Val Thr Ile
1               5

<210> SEQ ID NO 140
<211> LENGTH: 9
<212> TYPE: PRT
<213> ORGANISM: Human Immunodeficiency Virus 1

<400> SEQUENCE: 140

Ile Leu Lys Glu Pro Val His Gly Val
1               5

<210> SEQ ID NO 141
<211> LENGTH: 9
<212> TYPE: PRT
<213> ORGANISM: Human Immunodeficiency Virus 1

<400> SEQUENCE: 141

Ala Phe His His Val Ala Arg Glu Leu
1               5

<210> SEQ ID NO 142
<211> LENGTH: 9
<212> TYPE: PRT
<213> ORGANISM: Human Immunodeficiency Virus 1

<400> SEQUENCE: 142

Lys Leu Thr Pro Leu Cys Val Thr Leu
1               5

<210> SEQ ID NO 143
<211> LENGTH: 10
<212> TYPE: PRT
<213> ORGANISM: Human Immunodeficiency Virus 1

<400> SEQUENCE: 143

Ser Leu Leu Asn Ala Thr Asp Ile Ala Val
1               5                   10

<210> SEQ ID NO 144
<211> LENGTH: 9
<212> TYPE: PRT
<213> ORGANISM: Human Immunodeficiency Virus 1
```

```
<400> SEQUENCE: 144

Val Ile Tyr Gln Tyr Met Asp Asp Leu
 1               5

<210> SEQ ID NO 145
<211> LENGTH: 9
<212> TYPE: PRT
<213> ORGANISM: Human Immunodeficiency Virus 1

<400> SEQUENCE: 145

Ser Leu Tyr Asn Thr Val Ala Thr Leu
 1               5

<210> SEQ ID NO 146
<211> LENGTH: 9
<212> TYPE: PRT
<213> ORGANISM: Human Immunodeficiency Virus 1

<400> SEQUENCE: 146

Arg Gly Pro Gly Arg Ala Phe Val Thr
 1               5

<210> SEQ ID NO 147
<211> LENGTH: 11
<212> TYPE: PRT
<213> ORGANISM: Human Immunodeficiency Virus 1

<400> SEQUENCE: 147

Arg Leu Arg Asp Leu Leu Leu Ile Val Thr Arg
 1               5                   10

<210> SEQ ID NO 148
<211> LENGTH: 10
<212> TYPE: PRT
<213> ORGANISM: Human Immunodeficiency Virus 1

<400> SEQUENCE: 148

Gln Val Pro Leu Arg Pro Met Thr Tyr Lys
 1               5                   10

<210> SEQ ID NO 149
<211> LENGTH: 10
<212> TYPE: PRT
<213> ORGANISM: Human Immunodeficiency Virus 1

<400> SEQUENCE: 149

Thr Val Tyr Tyr Gly Val Pro Val Trp Lys
 1               5                   10

<210> SEQ ID NO 150
<211> LENGTH: 9
<212> TYPE: PRT
<213> ORGANISM: Human Immunodeficiency Virus 1

<400> SEQUENCE: 150

Arg Leu Arg Pro Gly Gly Lys Lys Lys
 1               5

<210> SEQ ID NO 151
<211> LENGTH: 9
<212> TYPE: PRT
<213> ORGANISM: Human Immunodeficiency Virus 1

<400> SEQUENCE: 151

Val Tyr Tyr Gly Val Pro Val Trp Lys
```

-continued

```
<210> SEQ ID NO 152
<211> LENGTH: 9
<212> TYPE: PRT
<213> ORGANISM: Human Immunodeficiency Virus 1

<400> SEQUENCE: 152

Val Pro Leu Arg Pro Met Thr Tyr Lys
1               5

<210> SEQ ID NO 153
<211> LENGTH: 9
<212> TYPE: PRT
<213> ORGANISM: Human Immunodeficiency Virus 1

<400> SEQUENCE: 153

Ala Ile Phe Gln Ser Ser Met Thr Lys
1               5

<210> SEQ ID NO 154
<211> LENGTH: 10
<212> TYPE: PRT
<213> ORGANISM: Human Immunodeficiency Virus 1

<400> SEQUENCE: 154

Gln Val Pro Leu Arg Pro Met Thr Tyr Lys
1               5                   10

<210> SEQ ID NO 155
<211> LENGTH: 12
<212> TYPE: PRT
<213> ORGANISM: Human Immunodeficiency Virus 1

<400> SEQUENCE: 155

Ala Ala Val Asp Leu Ser His Phe Leu Lys Glu Lys
1               5                   10

<210> SEQ ID NO 156
<211> LENGTH: 12
<212> TYPE: PRT
<213> ORGANISM: Human Immunodeficiency Virus 1

<400> SEQUENCE: 156

Ala Cys Gln Gly Val Gly Gly Pro Gly Gly His Lys
1               5                   10

<210> SEQ ID NO 157
<211> LENGTH: 10
<212> TYPE: PRT
<213> ORGANISM: Human Immunodeficiency Virus 1

<400> SEQUENCE: 157

Glu Thr Ile Asn Glu Glu Ala Ala Glu Trp
1               5                   10

<210> SEQ ID NO 158
<211> LENGTH: 10
<212> TYPE: PRT
<213> ORGANISM: Human Immunodeficiency Virus 1

<400> SEQUENCE: 158

Thr Pro Gly Pro Gly Val Arg Tyr Pro Leu
1               5                   10
```

```
<210> SEQ ID NO 159
<211> LENGTH: 8
<212> TYPE: PRT
<213> ORGANISM: Human Immunodeficiency Virus 1

<400> SEQUENCE: 159

Gly Gly Lys Lys Lys Tyr Lys Leu
 1               5

<210> SEQ ID NO 160
<211> LENGTH: 9
<212> TYPE: PRT
<213> ORGANISM: Human Immunodeficiency Virus 1

<400> SEQUENCE: 160

Arg Val Lys Glu Lys Tyr Gln His Leu
 1               5

<210> SEQ ID NO 161
<211> LENGTH: 9
<212> TYPE: PRT
<213> ORGANISM: Human Immunodeficiency Virus 1

<400> SEQUENCE: 161

Asp Arg Phe Tyr Lys Thr Leu Arg Ala
 1               5

<210> SEQ ID NO 162
<211> LENGTH: 16
<212> TYPE: PRT
<213> ORGANISM: Human Immunodeficiency Virus 1

<400> SEQUENCE: 162

Gly Val Arg Tyr Pro Leu Thr Phe Gly Trp Cys Tyr Lys Leu Val Pro
 1               5                  10                  15

<210> SEQ ID NO 163
<211> LENGTH: 10
<212> TYPE: PRT
<213> ORGANISM: Human Immunodeficiency Virus 1

<400> SEQUENCE: 163

Lys Arg Trp Ile Ile Leu Gly Leu Asn Lys
 1               5                  10

<210> SEQ ID NO 164
<211> LENGTH: 9
<212> TYPE: PRT
<213> ORGANISM: Human Immunodeficiency Virus 1

<400> SEQUENCE: 164

Ala Phe His His Val Ala Arg Glu Leu
 1               5

<210> SEQ ID NO 165
<211> LENGTH: 9
<212> TYPE: PRT
<213> ORGANISM: Epstein-Barr Virus

<400> SEQUENCE: 165

Lys Glu His Val Ile Gln Asn Ala Phe
 1               5

<210> SEQ ID NO 166
<211> LENGTH: 10
<212> TYPE: PRT
```

-continued

```
<213> ORGANISM: Epstein-Barr Virus

<400> SEQUENCE: 166

Glu Glu Asn Leu Leu Asp Phe Val Arg Phe
1               5                   10

<210> SEQ ID NO 167
<211> LENGTH: 10
<212> TYPE: PRT
<213> ORGANISM: Epstein-Barr Virus

<400> SEQUENCE: 167

Asp Thr Pro Leu Ile Pro Leu Thr Ile Phe
1               5                   10

<210> SEQ ID NO 168
<211> LENGTH: 10
<212> TYPE: PRT
<213> ORGANISM: Epstein-Barr Virus

<400> SEQUENCE: 168

Gln Asn Gly Ala Leu Ala Ile Asn Thr Phe
1               5                   10

<210> SEQ ID NO 169
<211> LENGTH: 9
<212> TYPE: PRT
<213> ORGANISM: Epstein-Barr Virus

<400> SEQUENCE: 169

Arg Leu Arg Ala Glu Ala Gly Val Lys
1               5

<210> SEQ ID NO 170
<211> LENGTH: 10
<212> TYPE: PRT
<213> ORGANISM: Hepatitis B Virus

<400> SEQUENCE: 170

Gly Leu Ser Pro Thr Val Trp Leu Ser Val
1               5                   10

<210> SEQ ID NO 171
<211> LENGTH: 9
<212> TYPE: PRT
<213> ORGANISM: Hepatitis B Virus

<400> SEQUENCE: 171

Trp Leu Ser Leu Leu Val Pro Phe Val
1               5

<210> SEQ ID NO 172
<211> LENGTH: 10
<212> TYPE: PRT
<213> ORGANISM: Hepatitis B Virus

<400> SEQUENCE: 172

Phe Leu Pro Ser Asp Phe Phe Pro Ser Val
1               5                   10

<210> SEQ ID NO 173
<211> LENGTH: 10
<212> TYPE: PRT
<213> ORGANISM: Hepatitis B Virus

<400> SEQUENCE: 173
```

Phe Leu Pro Ser Asp Phe Phe Pro Ser Val
1               5                   10

<210> SEQ ID NO 174
<211> LENGTH: 10
<212> TYPE: PRT
<213> ORGANISM: Hepatitis B Virus

<400> SEQUENCE: 174

Phe Leu Pro Ser Asp Phe Phe Pro Ser Val
1               5                   10

<210> SEQ ID NO 175
<211> LENGTH: 10
<212> TYPE: PRT
<213> ORGANISM: Hepatitis B Virus

<400> SEQUENCE: 175

Phe Leu Pro Ser Asp Phe Phe Pro Ser Val
1               5                   10

<210> SEQ ID NO 176
<211> LENGTH: 9
<212> TYPE: PRT
<213> ORGANISM: Hepatitis B Virus

<400> SEQUENCE: 176

Phe Leu Leu Ser Leu Gly Ile His Leu
1               5

<210> SEQ ID NO 177
<211> LENGTH: 9
<212> TYPE: PRT
<213> ORGANISM: Hepatitis B Virus

<400> SEQUENCE: 177

Ser Leu Tyr Ala Asp Ser Pro Ser Val
1               5

<210> SEQ ID NO 178
<211> LENGTH: 9
<212> TYPE: PRT
<213> ORGANISM: Hepatitis B Virus

<400> SEQUENCE: 178

Gly Leu Ser Arg Tyr Val Ala Arg Leu
1               5

<210> SEQ ID NO 179
<211> LENGTH: 10
<212> TYPE: PRT
<213> ORGANISM: Hepatitis B Virus

<400> SEQUENCE: 179

Leu Leu Val Pro Phe Val Gln Trp Phe Val
1               5                   10

<210> SEQ ID NO 180
<211> LENGTH: 9
<212> TYPE: PRT
<213> ORGANISM: Hepatitis B Virus

<400> SEQUENCE: 180

Ala Leu Met Pro Leu Tyr Ala Cys Ile
1               5

```
<210> SEQ ID NO 181
<211> LENGTH: 10
<212> TYPE: PRT
<213> ORGANISM: Hepatitis B Virus

<400> SEQUENCE: 181

Leu Leu Pro Ile Phe Phe Cys Leu Trp Val
 1               5                  10

<210> SEQ ID NO 182
<211> LENGTH: 9
<212> TYPE: PRT
<213> ORGANISM: Hepatitis B Virus

<400> SEQUENCE: 182

Tyr Met Asp Asp Val Val Leu Gly Ala
 1               5

<210> SEQ ID NO 183
<211> LENGTH: 9
<212> TYPE: PRT
<213> ORGANISM: Hepatitis B Virus

<400> SEQUENCE: 183

Leu Leu Leu Cys Leu Ile Phe Leu Leu
 1               5

<210> SEQ ID NO 184
<211> LENGTH: 10
<212> TYPE: PRT
<213> ORGANISM: Hepatitis B Virus

<400> SEQUENCE: 184

Leu Leu Asp Tyr Gln Gly Met Leu Pro Val
 1               5                  10

<210> SEQ ID NO 185
<211> LENGTH: 10
<212> TYPE: PRT
<213> ORGANISM: Hepatitis B Virus

<400> SEQUENCE: 185

Ser Ile Val Ser Pro Phe Ile Pro Leu Leu
 1               5                  10

<210> SEQ ID NO 186
<211> LENGTH: 9
<212> TYPE: PRT
<213> ORGANISM: Hepatitis B Virus

<400> SEQUENCE: 186

Phe Leu Leu Thr Arg Ile Leu Thr Ile
 1               5

<210> SEQ ID NO 187
<211> LENGTH: 9
<212> TYPE: PRT
<213> ORGANISM: Hepatitis B Virus

<400> SEQUENCE: 187

Tyr Val Asn Val Asn Met Gly Leu Lys
 1               5

<210> SEQ ID NO 188
```

<211> LENGTH: 11
<212> TYPE: PRT
<213> ORGANISM: Hepatitis B Virus

<400> SEQUENCE: 188

Ser Thr Leu Pro Glu Thr Thr Val Val Arg Arg
1 5 10

<210> SEQ ID NO 189
<211> LENGTH: 11
<212> TYPE: PRT
<213> ORGANISM: Hepatitis B Virus

<400> SEQUENCE: 189

Ser Thr Leu Pro Glu Thr Thr Val Val Arg Arg
1 5 10

<210> SEQ ID NO 190
<211> LENGTH: 10
<212> TYPE: PRT
<213> ORGANISM: Hepatitis B Virus

<400> SEQUENCE: 190

Phe Leu Pro Ser Asp Phe Phe Pro Ser Val
1 5 10

<210> SEQ ID NO 191
<211> LENGTH: 12
<212> TYPE: PRT
<213> ORGANISM: Hepatitis B Virus

<400> SEQUENCE: 191

Ile Pro Gln Ser Leu Asp Ser Trp Trp Thr Ser Leu
1 5 10

<210> SEQ ID NO 192
<211> LENGTH: 8
<212> TYPE: PRT
<213> ORGANISM: Hepatitis B Virus

<400> SEQUENCE: 192

Met Gly Leu Lys Phe Arg Gln Leu
1 5

<210> SEQ ID NO 193
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 4, 8
<223> OTHER INFORMATION: Xaa = Any Amino Acid

<400> SEQUENCE: 193

Ser Thr Asx Xaa Gln Ser Gly Xaa Gln
1 5

<210> SEQ ID NO 194
<211> LENGTH: 11
<212> TYPE: PRT
<213> ORGANISM: Human Cytomegalovirus

<400> SEQUENCE: 194

Phe Ile Ala Gly Asn Ser Ala Tyr Glu Tyr Val
1 5 10

<210> SEQ ID NO 195
<211> LENGTH: 12
<212> TYPE: PRT
<213> ORGANISM: Human Cytomegalovirus

<400> SEQUENCE: 195

Ser Asp Glu Glu Phe Ala Ile Val Ala Tyr Thr Leu
1               5                   10

<210> SEQ ID NO 196
<211> LENGTH: 15
<212> TYPE: PRT
<213> ORGANISM: Human Cytomegalovirus

<400> SEQUENCE: 196

Asp Asp Val Trp Thr Ser Gly Ser Asp Ser Asp Glu Glu Leu Val
1               5                   10                  15

<210> SEQ ID NO 197
<211> LENGTH: 9
<212> TYPE: PRT
<213> ORGANISM: Human Cytomegalovirus

<400> SEQUENCE: 197

Ile Pro Ser Ile Asn Val His His Tyr
1               5

<210> SEQ ID NO 198
<211> LENGTH: 9
<212> TYPE: PRT
<213> ORGANISM: Human Cytomegalovirus

<400> SEQUENCE: 198

Asn Leu Val Pro Met Val Ala Thr Val
1               5

<210> SEQ ID NO 199
<211> LENGTH: 9
<212> TYPE: PRT
<213> ORGANISM: Human Cytomegalovirus

<400> SEQUENCE: 199

Asp Leu Met Gly Tyr Ile Pro Leu Val
1               5

<210> SEQ ID NO 200
<211> LENGTH: 9
<212> TYPE: PRT
<213> ORGANISM: Hepatitis C Virus

<400> SEQUENCE: 200

Asp Leu Met Gly Tyr Ile Pro Leu Val
1               5

<210> SEQ ID NO 201
<211> LENGTH: 10
<212> TYPE: PRT
<213> ORGANISM: Hepatitis C Virus

<400> SEQUENCE: 201

Leu Leu Ala Leu Leu Ser Cys Leu Thr Val
1               5                   10

<210> SEQ ID NO 202

-continued

<211> LENGTH: 8
<212> TYPE: PRT
<213> ORGANISM: Hepatitis C Virus

<400> SEQUENCE: 202

Ile Leu His Thr Pro Gly Cys Val
1 5

<210> SEQ ID NO 203
<211> LENGTH: 10
<212> TYPE: PRT
<213> ORGANISM: Hepatitis C Virus

<400> SEQUENCE: 203

Gln Leu Arg Arg His Ile Asp Leu Leu Val
1 5 10

<210> SEQ ID NO 204
<211> LENGTH: 9
<212> TYPE: PRT
<213> ORGANISM: Hepatitis C Virus

<400> SEQUENCE: 204

Asp Leu Cys Gly Ser Val Phe Leu Val
1 5

<210> SEQ ID NO 205
<211> LENGTH: 9
<212> TYPE: PRT
<213> ORGANISM: Hepatitis C Virus

<400> SEQUENCE: 205

Ser Met Val Gly Asn Trp Ala Lys Val
1 5

<210> SEQ ID NO 206
<211> LENGTH: 10
<212> TYPE: PRT
<213> ORGANISM: Hepatitis C Virus

<400> SEQUENCE: 206

His Leu Ile Ile Gln Asn Ile Val Asp Val
1 5 10

<210> SEQ ID NO 207
<211> LENGTH: 9
<212> TYPE: PRT
<213> ORGANISM: Hepatitis C Virus

<400> SEQUENCE: 207

Phe Leu Leu Leu Ala Asp Ala Arg Val
1 5

<210> SEQ ID NO 208
<211> LENGTH: 13
<212> TYPE: PRT
<213> ORGANISM: Hepatitis C Virus

<400> SEQUENCE: 208

Gly Leu Arg Asp Leu Ala Val Ala Val Glu Pro Val Val
1 5 10

<210> SEQ ID NO 209
<211> LENGTH: 11
<212> TYPE: PRT
<213> ORGANISM: Hepatitis C Virus -continued

```
<400> SEQUENCE: 209

Ser Leu Leu Ala Pro Gly Ala Lys Gln Asn Val
1               5                   10

<210> SEQ ID NO 210
<211> LENGTH: 10
<212> TYPE: PRT
<213> ORGANISM: Hepatitis C Virus

<400> SEQUENCE: 210

Leu Leu Ala Pro Gly Ala Lys Gln Asn Val
1               5                   10

<210> SEQ ID NO 211
<211> LENGTH: 10
<212> TYPE: PRT
<213> ORGANISM: Hepatitis C Virus

<400> SEQUENCE: 211

Leu Leu Phe Asn Ile Leu Gly Gly Trp Val
1               5                   10

<210> SEQ ID NO 212
<211> LENGTH: 9
<212> TYPE: PRT
<213> ORGANISM: Hepatitis C Virus

<400> SEQUENCE: 212

Tyr Leu Val Ala Tyr Gln Ala Thr Val
1               5

<210> SEQ ID NO 213
<211> LENGTH: 10
<212> TYPE: PRT
<213> ORGANISM: Hepatitis C Virus

<400> SEQUENCE: 213

Tyr Leu Leu Pro Arg Arg Gly Pro Arg Leu
1               5                   10

<210> SEQ ID NO 214
<211> LENGTH: 10
<212> TYPE: PRT
<213> ORGANISM: Hepatitis C Virus

<400> SEQUENCE: 214

Leu Leu Ala Leu Leu Ser Cys Leu Thr Ile
1               5                   10

<210> SEQ ID NO 215
<211> LENGTH: 9
<212> TYPE: PRT
<213> ORGANISM: Hepatitis C Virus

<400> SEQUENCE: 215

Ser Leu Met Ala Phe Thr Ala Ala Val
1               5

<210> SEQ ID NO 216
<211> LENGTH: 9
<212> TYPE: PRT
<213> ORGANISM: Hepatitis C Virus

<400> SEQUENCE: 216
```

```
Cys Ile Asn Gly Val Cys Trp Thr Val
1               5
```

<210> SEQ ID NO 217
<211> LENGTH: 9
<212> TYPE: PRT
<213> ORGANISM: Hepatitis C Virus

<400> SEQUENCE: 217

```
Leu Leu Cys Pro Ala Gly His Ala Val
1               5
```

<210> SEQ ID NO 218
<211> LENGTH: 9
<212> TYPE: PRT
<213> ORGANISM: Hepatitis C Virus

<400> SEQUENCE: 218

```
Ile Leu Asp Ser Phe Asp Pro Leu Val
1               5
```

<210> SEQ ID NO 219
<211> LENGTH: 9
<212> TYPE: PRT
<213> ORGANISM: Hepatitis C Virus

<400> SEQUENCE: 219

```
Ile Leu Ala Gly Tyr Gly Ala Gly Val
1               5
```

<210> SEQ ID NO 220
<211> LENGTH: 9
<212> TYPE: PRT
<213> ORGANISM: Hepatitis C Virus

<400> SEQUENCE: 220

```
Gly Leu Gln Asp Cys Thr Met Leu Val
1               5
```

<210> SEQ ID NO 221
<211> LENGTH: 10
<212> TYPE: PRT
<213> ORGANISM: Hepatitis C Virus

<400> SEQUENCE: 221

```
Thr Gly Ala Pro Val Thr Tyr Ser Thr Tyr
1               5                   10
```

<210> SEQ ID NO 222
<211> LENGTH: 9
<212> TYPE: PRT
<213> ORGANISM: Hepatitis C Virus

<400> SEQUENCE: 222

```
His Met Trp Asn Phe Ile Ser Gly Ile
1               5
```

<210> SEQ ID NO 223
<211> LENGTH: 9
<212> TYPE: PRT
<213> ORGANISM: Hepatitis C Virus

<400> SEQUENCE: 223

```
Arg Val Cys Glu Lys Met Ala Leu Tyr
1               5
```

<210> SEQ ID NO 224
<211> LENGTH: 8
<212> TYPE: PRT
<213> ORGANISM: Hepatitis C Virus

<400> SEQUENCE: 224

Thr Ile Asn Tyr Thr Ile Phe Lys
1               5

<210> SEQ ID NO 225
<211> LENGTH: 8
<212> TYPE: PRT
<213> ORGANISM: Hepatitis C Virus

<400> SEQUENCE: 225

Tyr Ile Ser Trp Cys Leu Trp Trp
1               5

<210> SEQ ID NO 226
<211> LENGTH: 9
<212> TYPE: PRT
<213> ORGANISM: Hepatitis C Virus

<400> SEQUENCE: 226

Gly Pro Arg Leu Gly Val Arg Ala Thr
1               5

<210> SEQ ID NO 227
<211> LENGTH: 9
<212> TYPE: PRT
<213> ORGANISM: Human Immunodeficiency Virus 1

<400> SEQUENCE: 227

Ser Phe Asn Cys Gly Gly Glu Phe Phe
1               5

<210> SEQ ID NO 228
<211> LENGTH: 9
<212> TYPE: PRT
<213> ORGANISM: Human Immunodeficiency Virus 1

<400> SEQUENCE: 228

Thr Glu Met Glu Lys Glu Gly Lys Ile
1               5

<210> SEQ ID NO 229
<211> LENGTH: 9
<212> TYPE: PRT
<213> ORGANISM: Human Immunodeficiency Virus 1

<400> SEQUENCE: 229

Lys Ile Arg Leu Arg Pro Gly Gly Lys
1               5

<210> SEQ ID NO 230
<211> LENGTH: 10
<212> TYPE: PRT
<213> ORGANISM: Human Immunodeficiency Virus 1

<400> SEQUENCE: 230

Arg Leu Arg Pro Gly Gly Lys Lys Lys Tyr
1               5                   10

<210> SEQ ID NO 231
<211> LENGTH: 9

<212> TYPE: PRT
<213> ORGANISM: Human Immunodeficiency Virus 1

<400> SEQUENCE: 231

Ala Ile Phe Gln Ser Ser Met Thr Lys
 1               5

<210> SEQ ID NO 232
<211> LENGTH: 9
<212> TYPE: PRT
<213> ORGANISM: Human Immunodeficiency Virus 1

<400> SEQUENCE: 232

Thr Leu Tyr Cys Val His Gln Arg Ile
 1               5

<210> SEQ ID NO 233
<211> LENGTH: 10
<212> TYPE: PRT
<213> ORGANISM: Human Immunodeficiency Virus 1

<400> SEQUENCE: 233

Ile Tyr Gln Glu Pro Phe Lys Asn Leu Lys
 1               5                  10

<210> SEQ ID NO 234
<211> LENGTH: 9
<212> TYPE: PRT
<213> ORGANISM: Human Immunodeficiency Virus 1

<400> SEQUENCE: 234

Lys Tyr Lys Leu Lys His Ile Val Trp
 1               5

<210> SEQ ID NO 235
<211> LENGTH: 10
<212> TYPE: PRT
<213> ORGANISM: Human Immunodeficiency Virus 1

<400> SEQUENCE: 235

Leu Phe Cys Ala Ser Asp Ala Lys Ala Tyr
 1               5                  10

<210> SEQ ID NO 236
<211> LENGTH: 11
<212> TYPE: PRT
<213> ORGANISM: Human Immunodeficiency Virus 1

<400> SEQUENCE: 236

Gln Ala Ile Ser Pro Arg Thr Leu Asn Ala Trp
 1               5                  10

<210> SEQ ID NO 237
<211> LENGTH: 9
<212> TYPE: PRT
<213> ORGANISM: Human Immunodeficiency Virus 1

<400> SEQUENCE: 237

Glu Val Ile Pro Met Phe Ser Ala Leu
 1               5

<210> SEQ ID NO 238
<211> LENGTH: 11
<212> TYPE: PRT
<213> ORGANISM: Human Immunodeficiency Virus 1

```
<400> SEQUENCE: 238

Glu Thr Phe Tyr Val Asp Gly Ala Ala Asn Arg
1               5                   10

<210> SEQ ID NO 239
<211> LENGTH: 11
<212> TYPE: PRT
<213> ORGANISM: Human Immunodeficiency Virus 1

<400> SEQUENCE: 239

Arg Leu Arg Asp Leu Leu Ile Val Thr Arg
1               5                   10

<210> SEQ ID NO 240
<211> LENGTH: 10
<212> TYPE: PRT
<213> ORGANISM: Human Immunodeficiency Virus 1

<400> SEQUENCE: 240

Pro Ile Gln Lys Glu Thr Trp Glu Thr Trp
1               5                   10

<210> SEQ ID NO 241
<211> LENGTH: 9
<212> TYPE: PRT
<213> ORGANISM: Human Immunodeficiency Virus 1

<400> SEQUENCE: 241

Arg Ile Lys Gln Ile Ile Asn Met Trp
1               5

<210> SEQ ID NO 242
<211> LENGTH: 9
<212> TYPE: PRT
<213> ORGANISM: Human Immunodeficiency Virus 1

<400> SEQUENCE: 242

Ile Thr Leu Trp Gln Arg Pro Leu Val
1               5

<210> SEQ ID NO 243
<211> LENGTH: 9
<212> TYPE: PRT
<213> ORGANISM: Human Immunodeficiency Virus 1

<400> SEQUENCE: 243

Asp Thr Val Leu Glu Glu Met Asn Leu
1               5

<210> SEQ ID NO 244
<211> LENGTH: 9
<212> TYPE: PRT
<213> ORGANISM: Human Immunodeficiency Virus 1

<400> SEQUENCE: 244

Ile Thr Leu Trp Gln Arg Pro Leu Val
1               5

<210> SEQ ID NO 245
<211> LENGTH: 9
<212> TYPE: PRT
<213> ORGANISM: Human Immunodeficiency Virus 1

<400> SEQUENCE: 245

Ser Pro Arg Thr Leu Asn Ala Trp Val
```

```
<210> SEQ ID NO 246
<211> LENGTH: 9
<212> TYPE: PRT
<213> ORGANISM: Human Immunodeficiency Virus 1

<400> SEQUENCE: 246

Ala Thr Pro Gln Asp Leu Asn Thr Met
1               5

<210> SEQ ID NO 247
<211> LENGTH: 10
<212> TYPE: PRT
<213> ORGANISM: Human Immunodeficiency Virus 1

<400> SEQUENCE: 247

Arg Pro Asn Asn Asn Thr Arg Lys Ser Ile
1               5                   10

<210> SEQ ID NO 248
<211> LENGTH: 9
<212> TYPE: PRT
<213> ORGANISM: Human Immunodeficiency Virus 1

<400> SEQUENCE: 248

Ile Pro Arg Arg Ile Arg Gln Gly Leu
1               5

<210> SEQ ID NO 249
<211> LENGTH: 9
<212> TYPE: PRT
<213> ORGANISM: Human Immunodeficiency Virus 1

<400> SEQUENCE: 249

Glu Leu Arg Ser Leu Tyr Asn Thr Val
1               5

<210> SEQ ID NO 250
<211> LENGTH: 8
<212> TYPE: PRT
<213> ORGANISM: Human Immunodeficiency Virus 1

<400> SEQUENCE: 250

Trp Pro Thr Val Arg Glu Arg Met
1               5

<210> SEQ ID NO 251
<211> LENGTH: 8
<212> TYPE: PRT
<213> ORGANISM: Human Immunodeficiency Virus 1

<400> SEQUENCE: 251

Phe Leu Lys Glu Lys Gly Gly Leu
1               5

<210> SEQ ID NO 252
<211> LENGTH: 9
<212> TYPE: PRT
<213> ORGANISM: Human Immunodeficiency Virus 1

<400> SEQUENCE: 252

Asp Leu Asn Thr Met Leu Asn Thr Val
1               5
```

```
<210> SEQ ID NO 253
<211> LENGTH: 10
<212> TYPE: PRT
<213> ORGANISM: Human Immunodeficiency Virus 1

<400> SEQUENCE: 253

Lys Ile Arg Leu Arg Pro Gly Gly Lys Lys
1               5                   10

<210> SEQ ID NO 254
<211> LENGTH: 9
<212> TYPE: PRT
<213> ORGANISM: Human Immunodeficiency Virus 1

<400> SEQUENCE: 254

Ile Arg Leu Arg Pro Gly Gly Lys Lys
1               5

<210> SEQ ID NO 255
<211> LENGTH: 10
<212> TYPE: PRT
<213> ORGANISM: Human Immunodeficiency Virus 1

<400> SEQUENCE: 255

Gly Arg Arg Gly Trp Glu Ala Leu Lys Tyr
1               5                   10

<210> SEQ ID NO 256
<211> LENGTH: 10
<212> TYPE: PRT
<213> ORGANISM: Human Immunodeficiency Virus 1

<400> SEQUENCE: 256

Gln Val Pro Leu Arg Pro Met Thr Tyr Lys
1               5                   10

<210> SEQ ID NO 257
<211> LENGTH: 8
<212> TYPE: PRT
<213> ORGANISM: Human Immunodeficiency Virus 1

<400> SEQUENCE: 257

Arg Tyr Leu Lys Asp Gln Gln Leu
1               5

<210> SEQ ID NO 258
<211> LENGTH: 10
<212> TYPE: PRT
<213> ORGANISM: Human Immunodeficiency Virus 1

<400> SEQUENCE: 258

Arg Arg Gln Asp Ile Leu Asp Leu Trp Ile
1               5                   10

<210> SEQ ID NO 259
<211> LENGTH: 8
<212> TYPE: PRT
<213> ORGANISM: Human Immunodeficiency Virus 1

<400> SEQUENCE: 259

Arg Tyr Pro Leu Thr Phe Gly Trp
1               5

<210> SEQ ID NO 260
<211> LENGTH: 9
<212> TYPE: PRT
```

<213> ORGANISM: Human Immunodeficiency Virus 1

<400> SEQUENCE: 260

Trp Ala Ser Arg Glu Leu Glu Arg Phe
1               5

<210> SEQ ID NO 261
<211> LENGTH: 9
<212> TYPE: PRT
<213> ORGANISM: Human Immunodeficiency Virus 1

<400> SEQUENCE: 261

Thr Val Leu Asp Val Gly Asp Ala Tyr
1 5

<210> SEQ ID NO 262
<211> LENGTH: 11
<212> TYPE: PRT
<213> ORGANISM: Human Immunodeficiency Virus 1

<400> SEQUENCE: 262

Val Pro Val Trp Lys Glu Ala Thr Thr Thr Leu
1 5 10

<210> SEQ ID NO 263
<211> LENGTH: 9
<212> TYPE: PRT
<213> ORGANISM: Human Immunodeficiency Virus 1

<400> SEQUENCE: 263

Asn Ser Ser Lys Val Ser Gln Asn Tyr
1 5

<210> SEQ ID NO 264
<211> LENGTH: 9
<212> TYPE: PRT
<213> ORGANISM: Human Immunodeficiency Virus 1

<400> SEQUENCE: 264

Pro Pro Ile Pro Val Gly Asp Ile Tyr
1 5

<210> SEQ ID NO 265
<211> LENGTH: 9
<212> TYPE: PRT
<213> ORGANISM: Human Immunodeficiency Virus 1

<400> SEQUENCE: 265

His Pro Asp Ile Val Ile Tyr Gln Tyr
1 5

<210> SEQ ID NO 266
<211> LENGTH: 9
<212> TYPE: PRT
<213> ORGANISM: Human Immunodeficiency Virus 1

<400> SEQUENCE: 266

Thr Ala Val Pro Trp Asn Ala Ser Trp
1 5

<210> SEQ ID NO 267
<211> LENGTH: 9
<212> TYPE: PRT
<213> ORGANISM: Human Immunodeficiency Virus 1

<400> SEQUENCE: 267

Asn Pro Val Pro Val Gly Asn Leu Tyr
1               5

<210> SEQ ID NO 268
<211> LENGTH: 9
<212> TYPE: PRT
<213> ORGANISM: Human Immunodeficiency Virus 1

<400> SEQUENCE: 268

Tyr Phe Pro Asp Trp Gln Asn Tyr Thr
1               5

<210> SEQ ID NO 269
<211> LENGTH: 9
<212> TYPE: PRT
<213> ORGANISM: Human Immunodeficiency Virus 1

<400> SEQUENCE: 269

Gly His Gln Ala Ala Met Gln Met Leu
1               5

<210> SEQ ID NO 270
<211> LENGTH: 10
<212> TYPE: PRT
<213> ORGANISM: Human Immunodeficiency Virus 1

<400> SEQUENCE: 270

Arg Leu Arg Pro Gly Gly Lys Lys Lys Tyr
1               5                   10

<210> SEQ ID NO 271
<211> LENGTH: 9
<212> TYPE: PRT
<213> ORGANISM: Human Immunodeficiency Virus 1

<400> SEQUENCE: 271

Tyr Pro Gly Ile Lys Val Arg Gln Leu
1               5

<210> SEQ ID NO 272
<211> LENGTH: 10
<212> TYPE: PRT
<213> ORGANISM: Human Immunodeficiency Virus 1

<400> SEQUENCE: 272

Gly Ala Glu Thr Phe Tyr Val Asp Gly Ala
1               5                   10

<210> SEQ ID NO 273
<211> LENGTH: 9
<212> TYPE: PRT
<213> ORGANISM: Human Immunodeficiency Virus 1

<400> SEQUENCE: 273

Asn Ala Asn Pro Asp Cys Lys Thr Ile
1               5

<210> SEQ ID NO 274
<211> LENGTH: 8
<212> TYPE: PRT
<213> ORGANISM: Human Immunodeficiency Virus 1

<400> SEQUENCE: 274

Arg Met Tyr Ser Pro Thr Ser Ile
1               5

<210> SEQ ID NO 275
<211> LENGTH: 10
<212> TYPE: PRT
<213> ORGANISM: Human Immunodeficiency Virus 1

<400> SEQUENCE: 275

Val Pro Val Trp Lys Glu Ala Thr Thr Thr
1               5                   10

<210> SEQ ID NO 276
<211> LENGTH: 9
<212> TYPE: PRT
<213> ORGANISM: Human Immunodeficiency Virus 1

<400> SEQUENCE: 276

Ile Ser Pro Arg Thr Leu Asn Ala Trp
1               5

<210> SEQ ID NO 277
<211> LENGTH: 10
<212> TYPE: PRT
<213> ORGANISM: Human Immunodeficiency Virus 1

<400> SEQUENCE: 277

Thr Ser Thr Leu Gln Glu Gln Ile Gly Trp
1               5                   10

<210> SEQ ID NO 278
<211> LENGTH: 11
<212> TYPE: PRT
<213> ORGANISM: Human Immunodeficiency Virus 1

<400> SEQUENCE: 278

Lys Ala Phe Ser Pro Glu Val Ile Pro Met Phe
1               5                   10

<210> SEQ ID NO 279
<211> LENGTH: 9
<212> TYPE: PRT
<213> ORGANISM: Human Immunodeficiency Virus 1

<400> SEQUENCE: 279

Gln Ala Ser Gln Glu Val Lys Asn Trp
1               5

<210> SEQ ID NO 280
<211> LENGTH: 9
<212> TYPE: PRT
<213> ORGANISM: Human Immunodeficiency Virus 1

<400> SEQUENCE: 280

Gln Ala Ser Gln Asp Val Lys Asn Trp
1               5

<210> SEQ ID NO 281
<211> LENGTH: 10
<212> TYPE: PRT
<213> ORGANISM: Human Immunodeficiency Virus 1

<400> SEQUENCE: 281

His Thr Gln Gly Tyr Phe Pro Asp Trp Gln
1               5                   10

<210> SEQ ID NO 282

```
<211> LENGTH: 9
<212> TYPE: PRT
<213> ORGANISM: Human Immunodeficiency Virus 1

<400> SEQUENCE: 282

Tyr Phe Pro Asp Trp Gln Asn Tyr Thr
1               5

<210> SEQ ID NO 283
<211> LENGTH: 10
<212> TYPE: PRT
<213> ORGANISM: Human Immunodeficiency Virus 1

<400> SEQUENCE: 283

Thr Ser Thr Leu Gln Glu Gln Ile Gly Trp
1               5                   10

<210> SEQ ID NO 284
<211> LENGTH: 10
<212> TYPE: PRT
<213> ORGANISM: Human Immunodeficiency Virus 1

<400> SEQUENCE: 284

Arg Leu Arg Pro Gly Gly Lys Lys Lys Tyr
1               5                   10

<210> SEQ ID NO 285
<211> LENGTH: 9
<212> TYPE: PRT
<213> ORGANISM: Human Immunodeficiency Virus 1

<400> SEQUENCE: 285

Leu Gly Leu Asn Lys Val Arg Met Tyr
1               5

<210> SEQ ID NO 286
<211> LENGTH: 12
<212> TYPE: PRT
<213> ORGANISM: Human Immunodeficiency Virus 1

<400> SEQUENCE: 286

Leu Val Gly Lys Leu Asn Trp Ala Ser Gln Ile Tyr
1               5                   10

<210> SEQ ID NO 287
<211> LENGTH: 10
<212> TYPE: PRT
<213> ORGANISM: Human Immunodeficiency Virus 1

<400> SEQUENCE: 287

Ile Leu Lys Glu Pro Val His Gly Val Tyr
1               5                   10

<210> SEQ ID NO 288
<211> LENGTH: 11
<212> TYPE: PRT
<213> ORGANISM: Human Immunodeficiency Virus 1

<400> SEQUENCE: 288

Thr Gln Gly Tyr Phe Pro Asp Trp Gln Asn Tyr
1               5                   10

<210> SEQ ID NO 289
<211> LENGTH: 8
<212> TYPE: PRT
<213> ORGANISM: Human Immunodeficiency Virus 1
```

```
<400> SEQUENCE: 289

Ala Val Asp Leu Ser His Phe Leu
1               5

<210> SEQ ID NO 290
<211> LENGTH: 8
<212> TYPE: PRT
<213> ORGANISM: Human Immunodeficiency Virus 1

<400> SEQUENCE: 290

Val Ile Pro Met Phe Ser Ala Leu
1               5

<210> SEQ ID NO 291
<211> LENGTH: 9
<212> TYPE: PRT
<213> ORGANISM: Human Immunodeficiency Virus 1

<400> SEQUENCE: 291

Phe Asn Cys Gly Gly Glu Phe Phe Tyr
1               5

<210> SEQ ID NO 292
<211> LENGTH: 9
<212> TYPE: PRT
<213> ORGANISM: Human Immunodeficiency Virus 1

<400> SEQUENCE: 292

Ser Phe Asn Cys Gly Gly Glu Phe Phe
1               5

<210> SEQ ID NO 293
<211> LENGTH: 10
<212> TYPE: PRT
<213> ORGANISM: Human Immunodeficiency Virus 1

<400> SEQUENCE: 293

Pro Leu Thr Phe Gly Trp Cys Tyr Lys Leu
1               5                   10

<210> SEQ ID NO 294
<211> LENGTH: 10
<212> TYPE: PRT
<213> ORGANISM: Human Immunodeficiency Virus 1

<400> SEQUENCE: 294

Val Leu Glu Trp Arg Phe Asp Ser Arg Leu
1               5                   10

<210> SEQ ID NO 295
<211> LENGTH: 10
<212> TYPE: PRT
<213> ORGANISM: Human Immunodeficiency Virus 1

<400> SEQUENCE: 295

Phe Pro Val Thr Pro Gln Val Pro Leu Arg
1               5                   10

<210> SEQ ID NO 296
<211> LENGTH: 10
<212> TYPE: PRT
<213> ORGANISM: Human Immunodeficiency Virus 1

<400> SEQUENCE: 296
```

```
Thr Pro Gly Pro Gly Val Arg Tyr Pro Leu
1               5                   10

<210> SEQ ID NO 297
<211> LENGTH: 9
<212> TYPE: PRT
<213> ORGANISM: Human Immunodeficiency Virus 1

<400> SEQUENCE: 297

Gln Ala Ser Gln Glu Val Lys Asn Trp
1               5

<210> SEQ ID NO 298
<211> LENGTH: 10
<212> TYPE: PRT
<213> ORGANISM: Human Immunodeficiency Virus 1 IIIB

<400> SEQUENCE: 298

Val Pro Leu Asp Glu Asp Phe Arg Lys Tyr
1               5                   10

<210> SEQ ID NO 299
<211> LENGTH: 9
<212> TYPE: PRT
<213> ORGANISM: Human Immunodeficiency Virus 1 IIIB

<400> SEQUENCE: 299

Asn Pro Asp Ile Val Ile Tyr Gln Tyr
1               5

<210> SEQ ID NO 300
<211> LENGTH: 9
<212> TYPE: PRT
<213> ORGANISM: Human Immunodeficiency Virus 1 IIIB

<400> SEQUENCE: 300

Arg Ala Ile Glu Ala Gln Ala His Leu
1               5

<210> SEQ ID NO 301
<211> LENGTH: 8
<212> TYPE: PRT
<213> ORGANISM: Human Immunodeficiency Virus 1 IIIB

<400> SEQUENCE: 301

Thr Ala Phe Thr Ile Pro Ser Ile
1               5

<210> SEQ ID NO 302
<211> LENGTH: 10
<212> TYPE: PRT
<213> ORGANISM: Human Immunodeficiency Virus 1 IIIB

<400> SEQUENCE: 302

Val His Pro Val His Ala Gly Pro Ile Ala
1               5                   10

<210> SEQ ID NO 303
<211> LENGTH: 10
<212> TYPE: PRT
<213> ORGANISM: Human Immunodeficiency Virus 1 IIIB

<400> SEQUENCE: 303

Asn Cys Ser Phe Asn Ile Ser Thr Ser Ile
1               5                   10
```

<210> SEQ ID NO 304
<211> LENGTH: 9
<212> TYPE: PRT
<213> ORGANISM: Human Immunodeficiency Virus 1 IIIB

<400> SEQUENCE: 304

Cys Thr Asn Val Ser Thr Val Gln Cys
1               5

<210> SEQ ID NO 305
<211> LENGTH: 9
<212> TYPE: PRT
<213> ORGANISM: Human Immunodeficiency Virus 1 5F2

<400> SEQUENCE: 305

Ile Gly Pro Gly Arg Ala Phe His Thr
1               5

<210> SEQ ID NO 306
<211> LENGTH: 9
<212> TYPE: PRT
<213> ORGANISM: Human Immunodeficiency Virus 1 5F2

<400> SEQUENCE: 306

Asn Pro Asp Ile Val Ile Tyr Gln Tyr
1               5

<210> SEQ ID NO 307
<211> LENGTH: 10
<212> TYPE: PRT
<213> ORGANISM: Human Immunodeficiency Virus 1 5F2

<400> SEQUENCE: 307

Glu Pro Ile Val Gly Ala Glu Thr Phe Tyr
1               5                   10

<210> SEQ ID NO 308
<211> LENGTH: 9
<212> TYPE: PRT
<213> ORGANISM: Human Immunodeficiency Virus 1 5F2

<400> SEQUENCE: 308

Glu Pro Ile Val Gly Ala Glu Thr Phe
1               5

<210> SEQ ID NO 309
<211> LENGTH: 9
<212> TYPE: PRT
<213> ORGANISM: Human Immunodeficiency Virus 1 5F2

<400> SEQUENCE: 309

Ser Pro Ala Ile Phe Gln Ser Ser Met
1               5

<210> SEQ ID NO 310
<211> LENGTH: 10
<212> TYPE: PRT
<213> ORGANISM: Human Immunodeficiency Virus 1 5F2

<400> SEQUENCE: 310

Val Pro Leu Asp Lys Asp Phe Arg Lys Tyr
1               5                   10

<210> SEQ ID NO 311
<211> LENGTH: 9

```
<212> TYPE: PRT
<213> ORGANISM: Human Immunodeficiency Virus 1 5F2

<400> SEQUENCE: 311

Ile Pro Leu Thr Glu Glu Ala Glu Leu
 1               5

<210> SEQ ID NO 312
<211> LENGTH: 11
<212> TYPE: PRT
<213> ORGANISM: Human Immunodeficiency Virus 1 5F2

<400> SEQUENCE: 312

Arg Pro Gln Val Pro Leu Arg Pro Met Thr Tyr
 1               5                  10

<210> SEQ ID NO 313
<211> LENGTH: 9
<212> TYPE: PRT
<213> ORGANISM: Human Immunodeficiency Virus 1 5F2

<400> SEQUENCE: 313

Phe Pro Val Arg Pro Gln Val Pro Leu
 1               5

<210> SEQ ID NO 314
<211> LENGTH: 9
<212> TYPE: PRT
<213> ORGANISM: Human Immunodeficiency Virus 1 5F2

<400> SEQUENCE: 314

Asp Pro Asn Pro Gln Glu Val Val Leu
 1               5

<210> SEQ ID NO 315
<211> LENGTH: 9
<212> TYPE: PRT
<213> ORGANISM: Human Immunodeficiency Virus 1 5F2

<400> SEQUENCE: 315

Arg Pro Ile Val Ser Thr Gln Leu Leu
 1               5

<210> SEQ ID NO 316
<211> LENGTH: 9
<212> TYPE: PRT
<213> ORGANISM: Human Immunodeficiency Virus 1 5F2

<400> SEQUENCE: 316

Ile Pro Leu Thr Glu Glu Ala Glu Leu
 1               5

<210> SEQ ID NO 317
<211> LENGTH: 9
<212> TYPE: PRT
<213> ORGANISM: Human Immunodeficiency Virus 1 5F2

<400> SEQUENCE: 317

Asp Pro Asn Pro Gln Glu Val Val Leu
 1               5

<210> SEQ ID NO 318
<211> LENGTH: 9
<212> TYPE: PRT
<213> ORGANISM: Human Immunodeficiency Virus 1 5F2
```

```
<400> SEQUENCE: 318

Ala Met Gln Met Leu Lys Glu Thr Ile
 1               5

<210> SEQ ID NO 319
<211> LENGTH: 9
<212> TYPE: PRT
<213> ORGANISM: Human Immunodeficiency Virus 2

<400> SEQUENCE: 319

Thr Pro Tyr Asp Arg Asn Gln Met Leu
 1               5

<210> SEQ ID NO 320
<211> LENGTH: 11
<212> TYPE: PRT
<213> ORGANISM: Human Immunodeficiency Virus 2

<400> SEQUENCE: 320

Arg Arg Trp Ile Gln Leu Gly Leu Gln Lys Val
 1               5                   10

<210> SEQ ID NO 321
<211> LENGTH: 15
<212> TYPE: PRT
<213> ORGANISM: Human Immunodeficiency Virus 1 5F2

<400> SEQUENCE: 321

Gly Ile Trp Gly Cys Ser Gly Lys Leu Ile Cys Thr Thr Ala Val
 1               5                   10                  15

<210> SEQ ID NO 322
<211> LENGTH: 15
<212> TYPE: PRT
<213> ORGANISM: Human Immunodeficiency Virus 1 5F2

<400> SEQUENCE: 322

Ala Leu Ile Trp Glu Asp Leu Arg Ser Leu Cys Leu Phe Ser Tyr
 1               5                   10                  15

<210> SEQ ID NO 323
<211> LENGTH: 9
<212> TYPE: PRT
<213> ORGANISM: Human Papillomavirus 6b

<400> SEQUENCE: 323

Gly Leu His Cys Tyr Glu Gln Leu Val
 1               5

<210> SEQ ID NO 324
<211> LENGTH: 9
<212> TYPE: PRT
<213> ORGANISM: Human Papillomavirus 6b

<400> SEQUENCE: 324

Pro Leu Lys Gln His Phe Gln Ile Val
 1               5

<210> SEQ ID NO 325
<211> LENGTH: 9
<212> TYPE: PRT
<213> ORGANISM: Human Papillomavirus 11

<400> SEQUENCE: 325

Arg Leu Val Thr Leu Lys Asp Ile Val
```

<210> SEQ ID NO 326
<211> LENGTH: 9
<212> TYPE: PRT
<213> ORGANISM: Human Papillomavirus 16

<400> SEQUENCE: 326

Thr Leu Gly Ile Val Cys Pro Ile Cys
 1               5

<210> SEQ ID NO 327
<211> LENGTH: 9
<212> TYPE: PRT
<213> ORGANISM: Human Papillomavirus 16

<400> SEQUENCE: 327

Gly Thr Leu Gly Ile Val Cys Pro Ile
 1               5

<210> SEQ ID NO 328
<211> LENGTH: 9
<212> TYPE: PRT
<213> ORGANISM: Human Papillomavirus 16

<400> SEQUENCE: 328

Met Leu Asp Leu Gln Pro Glu Thr Thr
 1               5

<210> SEQ ID NO 329
<211> LENGTH: 10
<212> TYPE: PRT
<213> ORGANISM: Human Papillomavirus 16

<400> SEQUENCE: 329

Tyr Met Leu Asp Leu Gln Pro Glu Thr Thr
 1               5                  10

<210> SEQ ID NO 330
<211> LENGTH: 8
<212> TYPE: PRT
<213> ORGANISM: Human Papillomavirus 16

<400> SEQUENCE: 330

Arg Pro Arg Lys Leu Pro Gln Leu
 1               5

<210> SEQ ID NO 331
<211> LENGTH: 9
<212> TYPE: PRT
<213> ORGANISM: Human Papillomavirus 16

<400> SEQUENCE: 331

Arg Ala His Tyr Asn Ile Val Thr Phe
 1               5

<210> SEQ ID NO 332
<211> LENGTH: 8
<212> TYPE: PRT
<213> ORGANISM: Herpes Simplex Virus

<400> SEQUENCE: 332

Ser Ser Ile Glu Phe Ala Arg Leu
 1               5

```
<210> SEQ ID NO 333
<211> LENGTH: 9
<212> TYPE: PRT
<213> ORGANISM: Herpes Simplex Virus 1

<400> SEQUENCE: 333

Gly Ile Gly Ile Gly Val Leu Ala Ala
1               5

<210> SEQ ID NO 334
<211> LENGTH: 9
<212> TYPE: PRT
<213> ORGANISM: Herpes Simplex Virus 1

<400> SEQUENCE: 334

Asp Tyr Ala Thr Leu Gly Val Gly Val
1               5

<210> SEQ ID NO 335
<211> LENGTH: 11
<212> TYPE: PRT
<213> ORGANISM: Herpes Simplex Virus 1

<400> SEQUENCE: 335

Leu Tyr Arg Thr Phe Ala Gly Asn Pro Arg Ala
1               5                   10

<210> SEQ ID NO 336
<211> LENGTH: 8
<212> TYPE: PRT
<213> ORGANISM: Herpes Simplex Virus 1

<400> SEQUENCE: 336

Gln Thr Phe Asp Phe Gly Arg Leu
1               5

<210> SEQ ID NO 337
<211> LENGTH: 9
<212> TYPE: PRT
<213> ORGANISM: Herpes Simplex Virus 2

<400> SEQUENCE: 337

Gly Ala Gly Ile Gly Val Ala Val Leu
1               5

<210> SEQ ID NO 338
<211> LENGTH: 9
<212> TYPE: PRT
<213> ORGANISM: Human T-lymphotropic Virus 1

<400> SEQUENCE: 338

Leu Leu Phe Gly Tyr Pro Val Tyr Val
1               5

<210> SEQ ID NO 339
<211> LENGTH: 9
<212> TYPE: PRT
<213> ORGANISM: Influenza

<400> SEQUENCE: 339

Gly Ile Leu Gly Phe Val Phe Thr Leu
1               5

<210> SEQ ID NO 340
<211> LENGTH: 10
<212> TYPE: PRT
```

-continued

<213> ORGANISM: Influenza

<400> SEQUENCE: 340

Ile Leu Gly Phe Val Phe Thr Leu Thr Val
1 5 10

<210> SEQ ID NO 341
<211> LENGTH: 9
<212> TYPE: PRT
<213> ORGANISM: Influenza

<400> SEQUENCE: 341

Ile Leu Arg Gly Ser Val Ala His Lys
1 5

<210> SEQ ID NO 342
<211> LENGTH: 9
<212> TYPE: PRT
<213> ORGANISM: Influenza

<400> SEQUENCE: 342

Lys Thr Gly Gly Pro Ile Tyr Lys Arg
1 5

<210> SEQ ID NO 343
<211> LENGTH: 9
<212> TYPE: PRT
<213> ORGANISM: Influenza

<400> SEQUENCE: 343

Glu Leu Arg Ser Arg Tyr Trp Ala Ile
1 5

<210> SEQ ID NO 344
<211> LENGTH: 8
<212> TYPE: PRT
<213> ORGANISM: Influenza

<400> SEQUENCE: 344

Leu Arg Ser Arg Tyr Trp Ala Ile
1 5

<210> SEQ ID NO 345
<211> LENGTH: 9
<212> TYPE: PRT
<213> ORGANISM: Influenza

<400> SEQUENCE: 345

Glu Asp Leu Arg Val Leu Ser Phe Ile
1 5

<210> SEQ ID NO 346
<211> LENGTH: 9
<212> TYPE: PRT
<213> ORGANISM: Influenza

<400> SEQUENCE: 346

Gly Glu Ile Ser Pro Leu Pro Ser Leu
1 5

<210> SEQ ID NO 347
<211> LENGTH: 9
<212> TYPE: PRT
<213> ORGANISM: Influenza

<400> SEQUENCE: 347

Phe Glu Asp Leu Arg Val Leu Ser Phe
1               5

<210> SEQ ID NO 348
<211> LENGTH: 9
<212> TYPE: PRT
<213> ORGANISM: Influenza

<400> SEQUENCE: 348

Gly Glu Ile Ser Pro Leu Pro Ser Leu
1               5

<210> SEQ ID NO 349
<211> LENGTH: 9
<212> TYPE: PRT
<213> ORGANISM: Influenza

<400> SEQUENCE: 349

Phe Glu Asp Leu Arg Val Leu Ser Phe
1               5

<210> SEQ ID NO 350
<211> LENGTH: 9
<212> TYPE: PRT
<213> ORGANISM: Influenza

<400> SEQUENCE: 350

Val Ser Asp Gly Gly Pro Lys Leu Tyr
1               5

<210> SEQ ID NO 351
<211> LENGTH: 9
<212> TYPE: PRT
<213> ORGANISM: Influenza A

<400> SEQUENCE: 351

Cys Thr Glu Leu Lys Leu Ser Asp Tyr
1               5

<210> SEQ ID NO 352
<211> LENGTH: 9
<212> TYPE: PRT
<213> ORGANISM: Influenza

<400> SEQUENCE: 352

Ala Ile Met Asp Lys Asn Ile Ile Leu
1               5

<210> SEQ ID NO 353
<211> LENGTH: 10
<212> TYPE: PRT
<213> ORGANISM: Influenza A

<400> SEQUENCE: 353

Ile Met Asp Lys Asn Ile Ile Leu Lys Ala
1               5                   10

<210> SEQ ID NO 354
<211> LENGTH: 9
<212> TYPE: PRT
<213> ORGANISM: Influenza A

<400> SEQUENCE: 354

Ser Arg Tyr Trp Ala Ile Arg Thr Arg
1               5

<210> SEQ ID NO 355
<211> LENGTH: 9
<212> TYPE: PRT
<213> ORGANISM: Influenza A

<400> SEQUENCE: 355

Thr Tyr Gln Arg Thr Arg Ala Leu Val
1               5

<210> SEQ ID NO 356
<211> LENGTH: 10
<212> TYPE: PRT
<213> ORGANISM: Influenza A

<400> SEQUENCE: 356

Thr Tyr Val Ser Val Ser Thr Ser Thr Leu
1               5                   10

<210> SEQ ID NO 357
<211> LENGTH: 9
<212> TYPE: PRT
<213> ORGANISM: Influenza A

<400> SEQUENCE: 357

Ile Tyr Ser Thr Val Ala Ser Ser Leu
1               5

<210> SEQ ID NO 358
<211> LENGTH: 8
<212> TYPE: PRT
<213> ORGANISM: Influenza A

<400> SEQUENCE: 358

Phe Glu Ala Asn Gly Asn Leu Ile
1               5

<210> SEQ ID NO 359
<211> LENGTH: 9
<212> TYPE: PRT
<213> ORGANISM: Influenza A

<400> SEQUENCE: 359

Ile Glu Gly Gly Trp Thr Gly Met Leu
1               5

<210> SEQ ID NO 360
<211> LENGTH: 8
<212> TYPE: PRT
<213> ORGANISM: Influenza A

<400> SEQUENCE: 360

Ser Asp Tyr Glu Gly Arg Leu Ile
1               5

<210> SEQ ID NO 361
<211> LENGTH: 9
<212> TYPE: PRT
<213> ORGANISM: Influenza A

<400> SEQUENCE: 361

Glu Glu Gly Ala Ile Val Gly Glu Ile
1               5

<210> SEQ ID NO 362

```
<211> LENGTH: 9
<212> TYPE: PRT
<213> ORGANISM: Influenza A34

<400> SEQUENCE: 362

Ala Ser Asn Glu Asn Met Glu Thr Met
1               5

<210> SEQ ID NO 363
<211> LENGTH: 9
<212> TYPE: PRT
<213> ORGANISM: Influenza A68

<400> SEQUENCE: 363

Ala Ser Asn Glu Asn Met Asp Ala Met
1               5

<210> SEQ ID NO 364
<211> LENGTH: 10
<212> TYPE: PRT
<213> ORGANISM: Influenza B

<400> SEQUENCE: 364

Lys Leu Gly Glu Phe Tyr Asn Gln Met Met
1               5                   10

<210> SEQ ID NO 365
<211> LENGTH: 10
<212> TYPE: PRT
<213> ORGANISM: Influenza B

<400> SEQUENCE: 365

Lys Ala Gly Glu Phe Tyr Asn Gln Met Met
1               5                   10

<210> SEQ ID NO 366
<211> LENGTH: 9
<212> TYPE: PRT
<213> ORGANISM: Influenza JAP

<400> SEQUENCE: 366

Leu Tyr Gln Asn Val Gly Thr Tyr Val
1               5

<210> SEQ ID NO 367
<211> LENGTH: 10
<212> TYPE: PRT
<213> ORGANISM: Influenza JAP

<400> SEQUENCE: 367

Thr Tyr Val Ser Val Gly Thr Ser Thr Leu
1               5                   10

<210> SEQ ID NO 368
<211> LENGTH: 9
<212> TYPE: PRT
<213> ORGANISM: Influenza JAP

<400> SEQUENCE: 368

Val Tyr Gln Ile Leu Ala Thr Tyr Ala
1               5

<210> SEQ ID NO 369
<211> LENGTH: 9
<212> TYPE: PRT
<213> ORGANISM: Influenza JAP
```

```
<400> SEQUENCE: 369

Ile Tyr Ala Thr Val Ala Gly Ser Leu
 1               5

<210> SEQ ID NO 370
<211> LENGTH: 10
<212> TYPE: PRT
<213> ORGANISM: Influenza JAP

<400> SEQUENCE: 370

Thr Tyr Val Ser Val Gly Thr Ser Thr Ile
 1               5                  10

<210> SEQ ID NO 371
<211> LENGTH: 8
<212> TYPE: PRT
<213> ORGANISM: Influenza JAP

<400> SEQUENCE: 371

Phe Glu Ser Thr Gly Asn Leu Ile
 1               5

<210> SEQ ID NO 372
<211> LENGTH: 9
<212> TYPE: PRT
<213> ORGANISM: Mouse Hepatitis Virus Strain JHM

<400> SEQUENCE: 372

Ala Pro Thr Ala Gly Ala Phe Phe Phe
 1               5

<210> SEQ ID NO 373
<211> LENGTH: 9
<212> TYPE: PRT
<213> ORGANISM: Lymphocytic Choriomeningitis Virus

<400> SEQUENCE: 373

Arg Pro Gln Ala Ser Gly Val Tyr Met
 1               5

<210> SEQ ID NO 374
<211> LENGTH: 9
<212> TYPE: PRT
<213> ORGANISM: Lymphocytic Choriomeningitis Virus

<400> SEQUENCE: 374

Phe Gln Pro Gln Asn Gly Gln Phe Ile
 1               5

<210> SEQ ID NO 375
<211> LENGTH: 11
<212> TYPE: PRT
<213> ORGANISM: Lymphocytic Choriomeningitis Virus

<400> SEQUENCE: 375

Ser Gly Val Glu Asn Pro Gly Gly Tyr Cys Leu
 1               5                  10

<210> SEQ ID NO 376
<211> LENGTH: 10
<212> TYPE: PRT
<213> ORGANISM: Lymphocytic Choriomeningitis Virus

<400> SEQUENCE: 376
```

Lys Ala Val Tyr Asn Phe Ala Thr Cys Gly
1               5                   10

<210> SEQ ID NO 377
<211> LENGTH: 9
<212> TYPE: PRT
<213> ORGANISM: Murine Cytomegalovirus

<400> SEQUENCE: 377

Tyr Pro His Phe Met Pro Thr Asn Leu
1               5

<210> SEQ ID NO 378
<211> LENGTH: 9
<212> TYPE: PRT
<213> ORGANISM: Mouse Hepatitis Virus

<400> SEQUENCE: 378

Cys Leu Ser Trp Asn Gly Pro His Leu
1               5

<210> SEQ ID NO 379
<211> LENGTH: 9
<212> TYPE: PRT
<213> ORGANISM: Mouse Mammarytumor Virus

<400> SEQUENCE: 379

Ser Phe Ala Val Ala Thr Thr Ala Leu
1               5

<210> SEQ ID NO 380
<211> LENGTH: 9
<212> TYPE: PRT
<213> ORGANISM: Mouse Mammarytumor Virus

<400> SEQUENCE: 380

Ser Tyr Glu Thr Phe Ile Ser Arg Leu
1               5

<210> SEQ ID NO 381
<211> LENGTH: 8
<212> TYPE: PRT
<213> ORGANISM: Mouse Mammarytumor Virus

<400> SEQUENCE: 381

Ala Asn Tyr Asp Phe Ile Cys Val
1               5

<210> SEQ ID NO 382
<211> LENGTH: 8
<212> TYPE: PRT
<213> ORGANISM: Murine Leukemia Virus

<400> SEQUENCE: 382

Lys Ser Pro Trp Phe Thr Thr Leu
1               5

<210> SEQ ID NO 383
<211> LENGTH: 8
<212> TYPE: PRT
<213> ORGANISM: Murine Leukemia Virus

<400> SEQUENCE: 383

Ser Ser Trp Asp Phe Ile Thr Val
1               5

<210> SEQ ID NO 384
<211> LENGTH: 9
<212> TYPE: PRT
<213> ORGANISM: Murine Leukemia Virus

<400> SEQUENCE: 384

Cys Cys Leu Cys Leu Thr Val Phe Leu
1               5

<210> SEQ ID NO 385
<211> LENGTH: 9
<212> TYPE: PRT
<213> ORGANISM: Murine Leukemia Virus

<400> SEQUENCE: 385

Ser Pro Ser Tyr Val Tyr His Gln Phe
1               5

<210> SEQ ID NO 386
<211> LENGTH: 11
<212> TYPE: PRT
<213> ORGANISM: Measles Virus

<400> SEQUENCE: 386

Ser Arg Arg Tyr Pro Asp Ala Val Tyr Leu His
1               5                   10

<210> SEQ ID NO 387
<211> LENGTH: 9
<212> TYPE: PRT
<213> ORGANISM: Measles Virus

<400> SEQUENCE: 387

Arg Arg Tyr Pro Asp Ala Val Tyr Leu
1               5

<210> SEQ ID NO 388
<211> LENGTH: 9
<212> TYPE: PRT
<213> ORGANISM: Measles Virus

<400> SEQUENCE: 388

Tyr Pro Ala Leu Gly Leu His Glu Phe
1               5

<210> SEQ ID NO 389
<211> LENGTH: 9
<212> TYPE: PRT
<213> ORGANISM: Measles Virus

<400> SEQUENCE: 389

Asp Pro Val Ile Asp Arg Leu Tyr Leu
1               5

<210> SEQ ID NO 390
<211> LENGTH: 9
<212> TYPE: PRT
<213> ORGANISM: Measles Virus

<400> SEQUENCE: 390

Ser Pro Gly Arg Ser Phe Ser Tyr Phe
1               5

<210> SEQ ID NO 391
<211> LENGTH: 8

<212> TYPE: PRT
<213> ORGANISM: Poliovirus

<400> SEQUENCE: 391

Thr Tyr Lys Asp Thr Val Gln Leu
1 5

<210> SEQ ID NO 392
<211> LENGTH: 10
<212> TYPE: PRT
<213> ORGANISM: Poliovirus

<400> SEQUENCE: 392

Phe Tyr Asp Gly Phe Ser Lys Val Pro Leu
1 5 10

<210> SEQ ID NO 393
<211> LENGTH: 9
<212> TYPE: PRT
<213> ORGANISM: Pseudorabies virus gp

<400> SEQUENCE: 393

Ile Ala Gly Ile Gly Ile Leu Ala Ile
1 5

<210> SEQ ID NO 394
<211> LENGTH: 9
<212> TYPE: PRT
<213> ORGANISM: Rabiesvirus

<400> SEQUENCE: 394

Val Glu Ala Glu Ile Ala His Gln Ile
1 5

<210> SEQ ID NO 395
<211> LENGTH: 8
<212> TYPE: PRT
<213> ORGANISM: Rotavirus

<400> SEQUENCE: 395

Leu Leu Tyr Arg Phe Leu Leu Leu
1 5

<210> SEQ ID NO 396
<211> LENGTH: 9
<212> TYPE: PRT
<213> ORGANISM: Rotavirus

<400> SEQUENCE: 396

Val Gly Pro Val Phe Pro Pro Gly Met
1 5

<210> SEQ ID NO 397
<211> LENGTH: 9
<212> TYPE: PRT
<213> ORGANISM: Rotavirus

<400> SEQUENCE: 397

Tyr Ser Gly Tyr Ile Phe Arg Asp Leu
1 5

<210> SEQ ID NO 398
<211> LENGTH: 9
<212> TYPE: PRT
<213> ORGANISM: Respiratory Syncytial Virus

```
<400> SEQUENCE: 398

Ser Tyr Ile Gly Ser Ile Asn Asn Ile
1               5

<210> SEQ ID NO 399
<211> LENGTH: 12
<212> TYPE: PRT
<213> ORGANISM: Simian Immunodeficiency Virus

<400> SEQUENCE: 399

Glu Gly Cys Thr Pro Tyr Asp Thr Asn Gln Met Leu
1               5                   10

<210> SEQ ID NO 400
<211> LENGTH: 9
<212> TYPE: PRT
<213> ORGANISM: Sendai Virus

<400> SEQUENCE: 400

Phe Ala Pro Gly Asn Tyr Pro Ala Leu
1               5

<210> SEQ ID NO 401
<211> LENGTH: 10
<212> TYPE: PRT
<213> ORGANISM: Sendai Virus

<400> SEQUENCE: 401

Phe Ala Pro Cys Thr Asn Tyr Pro Ala Leu
1               5                   10

<210> SEQ ID NO 402
<211> LENGTH: 8
<212> TYPE: PRT
<213> ORGANISM: Sendai Virus 40

<400> SEQUENCE: 402

Val Val Tyr Asp Phe Leu Lys Cys
1               5

<210> SEQ ID NO 403
<211> LENGTH: 10
<212> TYPE: PRT
<213> ORGANISM: Sendai Virus 40

<400> SEQUENCE: 403

Ser Ala Ile Asn Asn Tyr Ala Gln Lys Leu
1               5                   10

<210> SEQ ID NO 404
<211> LENGTH: 9
<212> TYPE: PRT
<213> ORGANISM: Sendai Virus 40

<400> SEQUENCE: 404

Cys Lys Gly Val Asn Lys Glu Tyr Leu
1               5

<210> SEQ ID NO 405
<211> LENGTH: 9
<212> TYPE: PRT
<213> ORGANISM: Sendai Virus 40

<400> SEQUENCE: 405

Gln Gly Ile Asn Asn Leu Asp Asn Leu
```

<210> SEQ ID NO 406
<211> LENGTH: 10
<212> TYPE: PRT
<213> ORGANISM: Sendai Virus 40

<400> SEQUENCE: 406

Asn Asn Leu Asp Asn Leu Arg Asp Tyr Leu
1 5 10

<210> SEQ ID NO 407
<211> LENGTH: 9
<212> TYPE: PRT
<213> ORGANISM: Sendai Virus 40

<400> SEQUENCE: 407

Ser Glu Phe Leu Leu Glu Lys Arg Ile
1 5

<210> SEQ ID NO 408
<211> LENGTH: 8
<212> TYPE: PRT
<213> ORGANISM: Vesicular Stomatitis Virus

<400> SEQUENCE: 408

Arg Gly Tyr Val Tyr Gln Gly Leu
1 5

<210> SEQ ID NO 409
<211> LENGTH: 9
<212> TYPE: PRT
<213> ORGANISM: Homo sapiens

<400> SEQUENCE: 409

Glu Ala Asp Pro Thr Gly His Ser Tyr
1 5

<210> SEQ ID NO 410
<211> LENGTH: 9
<212> TYPE: PRT
<213> ORGANISM: Influenza

<400> SEQUENCE: 410

Val Ser Asp Gly Gly Pro Asn Leu Tyr
1 5

<210> SEQ ID NO 411
<211> LENGTH: 9
<212> TYPE: PRT
<213> ORGANISM: Influenza

<400> SEQUENCE: 411

Cys Thr Glu Leu Lys Leu Ser Asp Tyr
1 5

<210> SEQ ID NO 412
<211> LENGTH: 9
<212> TYPE: PRT
<213> ORGANISM: Homo sapiens

<400> SEQUENCE: 412

Glu Val Asp Pro Ile Gly His Leu Tyr
1 5

```
<210> SEQ ID NO 413
<211> LENGTH: 10
<212> TYPE: PRT
<213> ORGANISM: Homo sapiens (Calreticulin)

<400> SEQUENCE: 413

Met Leu Leu Ser Val Pro Leu Leu Leu Gly
 1               5                  10

<210> SEQ ID NO 414
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 4, 8
<223> OTHER INFORMATION: Xaa = Any Amino Acid

<400> SEQUENCE: 414

Ser Thr Asx Xaa Gln Ser Gly Xaa Gln
 1               5

<210> SEQ ID NO 415
<211> LENGTH: 9
<212> TYPE: PRT
<213> ORGANISM: Homo sapiens

<400> SEQUENCE: 415

Tyr Met Asp Gly Thr Met Ser Gln Val
 1               5

<210> SEQ ID NO 416
<211> LENGTH: 9
<212> TYPE: PRT
<213> ORGANISM: Human Immunodeficiency Virus 1

<400> SEQUENCE: 416

Ile Leu Lys Glu Pro Val His Gly Val
 1               5

<210> SEQ ID NO 417
<211> LENGTH: 10
<212> TYPE: PRT
<213> ORGANISM: Influenza MP

<400> SEQUENCE: 417

Leu Leu Gly Phe Val Phe Thr Leu Thr Val
 1               5                  10

<210> SEQ ID NO 418
<211> LENGTH: 10
<212> TYPE: PRT
<213> ORGANISM: Human T-lymphotropic Virus 1

<400> SEQUENCE: 418

Leu Leu Phe Gly Tyr Pro Val Tyr Val Val
 1               5                  10

<210> SEQ ID NO 419
<211> LENGTH: 10
<212> TYPE: PRT
<213> ORGANISM: Hepatitis B Virus

<400> SEQUENCE: 419

Gly Leu Ser Pro Thr Val Trp Leu Ser Val
```

```
                1               5                  10
```

<210> SEQ ID NO 420
<211> LENGTH: 9
<212> TYPE: PRT
<213> ORGANISM: Hepatitis B Virus

<400> SEQUENCE: 420

```
Trp Leu Ser Leu Leu Val Pro Phe Val
 1               5
```

<210> SEQ ID NO 421
<211> LENGTH: 10
<212> TYPE: PRT
<213> ORGANISM: Hepatitis B Virus

<400> SEQUENCE: 421

```
Phe Leu Pro Ser Asp Phe Phe Pro Ser Val
 1               5                  10
```

<210> SEQ ID NO 422
<211> LENGTH: 8
<212> TYPE: PRT
<213> ORGANISM: Epstein-Barr Virus

<400> SEQUENCE: 422

```
Cys Leu Gly Leu Leu Thr Met Val
 1               5
```

<210> SEQ ID NO 423
<211> LENGTH: 11
<212> TYPE: PRT
<213> ORGANISM: Human Cytomegalovirus

<400> SEQUENCE: 423

```
Phe Leu Ala Gly Asn Ser Ala Tyr Glu Tyr Val
 1               5                  10
```

<210> SEQ ID NO 424
<211> LENGTH: 10
<212> TYPE: PRT
<213> ORGANISM: Influenza

<400> SEQUENCE: 424

```
Lys Leu Gly Glu Phe Tyr Asn Gln Met Met
 1               5                  10
```

<210> SEQ ID NO 425
<211> LENGTH: 10
<212> TYPE: PRT
<213> ORGANISM: Hepatitis C Virus 1

<400> SEQUENCE: 425

```
Lys Leu Val Ala Leu Gly Ile Asn Ala Val
 1               5                  10
```

<210> SEQ ID NO 426
<211> LENGTH: 9
<212> TYPE: PRT
<213> ORGANISM: Hepatitis C Virus

<400> SEQUENCE: 426

```
Asp Leu Met Gly Tyr Ile Pro Leu Val
 1               5
```

```
<210> SEQ ID NO 427
<211> LENGTH: 9
<212> TYPE: PRT
<213> ORGANISM: Human Papillomavirus

<400> SEQUENCE: 427

Arg Leu Val Thr Leu Lys Asp Ile Val
1               5

<210> SEQ ID NO 428
<211> LENGTH: 9
<212> TYPE: PRT
<213> ORGANISM: Homo sapiens

<400> SEQUENCE: 428

Met Leu Leu Ala Val Leu Tyr Cys Leu
1               5

<210> SEQ ID NO 429
<211> LENGTH: 9
<212> TYPE: PRT
<213> ORGANISM: Homo sapiens

<400> SEQUENCE: 429

Ala Ala Gly Ile Gly Ile Leu Thr Val
1               5

<210> SEQ ID NO 430
<211> LENGTH: 9
<212> TYPE: PRT
<213> ORGANISM: Homo sapiens

<400> SEQUENCE: 430

Tyr Leu Glu Pro Gly Pro Val Thr Ala
1               5

<210> SEQ ID NO 431
<211> LENGTH: 10
<212> TYPE: PRT
<213> ORGANISM: Homo sapiens

<400> SEQUENCE: 431

Ile Leu Asp Gly Thr Ala Thr Leu Arg Leu
1               5                   10

<210> SEQ ID NO 432
<211> LENGTH: 10
<212> TYPE: PRT
<213> ORGANISM: Homo sapiens

<400> SEQUENCE: 432

Leu Leu Asp Gly Thr Ala Thr Leu Arg Leu
1               5                   10

<210> SEQ ID NO 433
<211> LENGTH: 9
<212> TYPE: PRT
<213> ORGANISM: Homo sapiens

<400> SEQUENCE: 433

Ile Thr Asp Gln Val Pro Phe Ser Val
1               5

<210> SEQ ID NO 434
<211> LENGTH: 9
<212> TYPE: PRT
```

```
<213> ORGANISM: Homo sapiens

<400> SEQUENCE: 434

Lys Thr Trp Gly Gln Tyr Trp Gln Val
  1               5

<210> SEQ ID NO 435
<211> LENGTH: 10
<212> TYPE: PRT
<213> ORGANISM: Homo sapiens

<400> SEQUENCE: 435

Thr Ile Thr Asp Gln Val Pro Phe Ser Val
  1               5                  10

<210> SEQ ID NO 436
<211> LENGTH: 10
<212> TYPE: PRT
<213> ORGANISM: Human Immunodeviciency Virus 1

<400> SEQUENCE: 436

Ala Phe His Ile Ile Val Ala Arg Glu Leu
  1               5                  10

<210> SEQ ID NO 437
<211> LENGTH: 9
<212> TYPE: PRT
<213> ORGANISM: Plasmodium Falciparum

<400> SEQUENCE: 437

Tyr Leu Asn Lys Ile Gln Asn Ser Leu
  1               5

<210> SEQ ID NO 438
<211> LENGTH: 10
<212> TYPE: PRT
<213> ORGANISM: Plasmodium Falciparum

<400> SEQUENCE: 438

Met Met Arg Lys Leu Ala Ile Leu Ser Val
  1               5                  10

<210> SEQ ID NO 439
<211> LENGTH: 10
<212> TYPE: PRT
<213> ORGANISM: Influenza

<400> SEQUENCE: 439

Lys Ala Gly Glu Phe Tyr Asn Gln Met Met
  1               5                  10

<210> SEQ ID NO 440
<211> LENGTH: 9
<212> TYPE: PRT
<213> ORGANISM: Epstein-Barr Virus (EBNA)

<400> SEQUENCE: 440

Asn Ile Ala Glu Gly Leu Arg Ala Leu
  1               5

<210> SEQ ID NO 441
<211> LENGTH: 9
<212> TYPE: PRT
<213> ORGANISM: Epstein-Barr Virus (EBNA)

<400> SEQUENCE: 441
```

Asn Leu Arg Arg Gly Thr Ala Leu Ala
1               5

<210> SEQ ID NO 442
<211> LENGTH: 9
<212> TYPE: PRT
<213> ORGANISM: Epstein-Barr Virus (EBNA)

<400> SEQUENCE: 442

Ala Leu Ala Ile Pro Gln Cys Arg Leu
1               5

<210> SEQ ID NO 443
<211> LENGTH: 9
<212> TYPE: PRT
<213> ORGANISM: Epstein-Barr Virus (EBNA)

<400> SEQUENCE: 443

Val Leu Lys Asp Ala Ile Lys Asp Leu
1               5

<210> SEQ ID NO 444
<211> LENGTH: 9
<212> TYPE: PRT
<213> ORGANISM: Epstein-Barr Virus (EBNA)

<400> SEQUENCE: 444

Phe Met Val Phe Leu Gln Thr His Ile
1               5

<210> SEQ ID NO 445
<211> LENGTH: 9
<212> TYPE: PRT
<213> ORGANISM: Epstein-Barr Virus (EBNA)

<400> SEQUENCE: 445

His Leu Ile Val Asp Thr Asp Ser Leu
1               5

<210> SEQ ID NO 446
<211> LENGTH: 9
<212> TYPE: PRT
<213> ORGANISM: Epstein-Barr Virus (EBNA)

<400> SEQUENCE: 446

Ser Leu Gly Asn Pro Ser Leu Ser Val
1               5

<210> SEQ ID NO 447
<211> LENGTH: 9
<212> TYPE: PRT
<213> ORGANISM: Epstein-Barr Virus (EBNA)

<400> SEQUENCE: 447

Pro Leu Ala Ser Ala Met Arg Met Leu
1               5

<210> SEQ ID NO 448
<211> LENGTH: 9
<212> TYPE: PRT
<213> ORGANISM: Epstein-Barr Virus (EBNA)

<400> SEQUENCE: 448

Arg Met Leu Trp Met Ala Asn Tyr Ile
1               5

-continued

```
<210> SEQ ID NO 449
<211> LENGTH: 9
<212> TYPE: PRT
<213> ORGANISM: Epstein-Barr Virus (EBNA)

<400> SEQUENCE: 449

Met Leu Trp Met Ala Asn Tyr Ile Val
1               5

<210> SEQ ID NO 450
<211> LENGTH: 9
<212> TYPE: PRT
<213> ORGANISM: Epstein-Barr Virus (EBNA)

<400> SEQUENCE: 450

Ile Leu Pro Gln Gly Pro Gln Thr Ala
1               5

<210> SEQ ID NO 451
<211> LENGTH: 10
<212> TYPE: PRT
<213> ORGANISM: Epstein-Barr Virus (EBNA)

<400> SEQUENCE: 451

Pro Leu Arg Pro Thr Ala Pro Thr Thr Ile
1               5                   10

<210> SEQ ID NO 452
<211> LENGTH: 9
<212> TYPE: PRT
<213> ORGANISM: Epstein-Barr Virus (EBNA)

<400> SEQUENCE: 452

Pro Leu Pro Pro Ala Thr Leu Thr Val
1               5

<210> SEQ ID NO 453
<211> LENGTH: 9
<212> TYPE: PRT
<213> ORGANISM: Epstein-Barr Virus (EBNA)

<400> SEQUENCE: 453

Arg Met His Leu Pro Val Leu His Val
1               5

<210> SEQ ID NO 454
<211> LENGTH: 9
<212> TYPE: PRT
<213> ORGANISM: Epstein-Barr Virus (EBNA)

<400> SEQUENCE: 454

Pro Met Pro Leu Pro Pro Ser Gln Leu
1               5

<210> SEQ ID NO 455
<211> LENGTH: 9
<212> TYPE: PRT
<213> ORGANISM: Epstein-Barr Virus (EBNA)

<400> SEQUENCE: 455

Gln Leu Pro Pro Pro Ala Ala Pro Ala
1               5

<210> SEQ ID NO 456
```

```
<211> LENGTH: 9
<212> TYPE: PRT
<213> ORGANISM: Epstein-Barr Virus (EBNA)

<400> SEQUENCE: 456

Ser Met Pro Glu Leu Ser Pro Val Leu
1               5

<210> SEQ ID NO 457
<211> LENGTH: 9
<212> TYPE: PRT
<213> ORGANISM: Epstein-Barr Virus (EBNA)

<400> SEQUENCE: 457

Asp Leu Asp Glu Ser Trp Asp Tyr Leu
1               5

<210> SEQ ID NO 458
<211> LENGTH: 10
<212> TYPE: PRT
<213> ORGANISM: Epstein-Barr Virus (EBNA)

<400> SEQUENCE: 458

Pro Leu Pro Cys Val Leu Trp Pro Val Val
1               5                   10

<210> SEQ ID NO 459
<211> LENGTH: 9
<212> TYPE: PRT
<213> ORGANISM: Epstein-Barr Virus (EBNA)

<400> SEQUENCE: 459

Ser Leu Glu Glu Cys Asp Ser Glu Leu
1               5

<210> SEQ ID NO 460
<211> LENGTH: 9
<212> TYPE: PRT
<213> ORGANISM: Epstein-Barr Virus (EBNA)

<400> SEQUENCE: 460

Glu Ile Lys Arg Tyr Lys Asn Arg Val
1               5

<210> SEQ ID NO 461
<211> LENGTH: 10
<212> TYPE: PRT
<213> ORGANISM: Epstein-Barr Virus (EBNA)

<400> SEQUENCE: 461

Gln Leu Leu Gln Phe Ile Tyr Arg Glu Val
1               5                   10

<210> SEQ ID NO 462
<211> LENGTH: 9
<212> TYPE: PRT
<213> ORGANISM: Epstein-Barr Virus (EBNA)

<400> SEQUENCE: 462

Leu Leu Gln His Tyr Arg Glu Val Ala
1               5

<210> SEQ ID NO 463
<211> LENGTH: 9
<212> TYPE: PRT
<213> ORGANISM: Epstein-Barr Virus (EBNA)
```

<400> SEQUENCE: 463

Leu Leu Lys Gln Met Cys Pro Ser Leu
1               5

<210> SEQ ID NO 464
<211> LENGTH: 9
<212> TYPE: PRT
<213> ORGANISM: Epstein-Barr Virus (EBNA)

<400> SEQUENCE: 464

Ser Ile Ile Pro Arg Thr Pro Asp Val
1               5

<210> SEQ ID NO 465
<211> LENGTH: 9
<212> TYPE: PRT
<213> ORGANISM: Influenza A

<400> SEQUENCE: 465

Ala Ile Met Asp Lys Asn Ile Ile Leu
1               5

<210> SEQ ID NO 466
<211> LENGTH: 10
<212> TYPE: PRT
<213> ORGANISM: Influenza A

<400> SEQUENCE: 466

Ile Met Asp Lys Asn Ile Ile Leu Lys Ala
1               5                   10

<210> SEQ ID NO 467
<211> LENGTH: 10
<212> TYPE: PRT
<213> ORGANISM: Hepatitis C Virus

<400> SEQUENCE: 467

Leu Leu Ala Leu Leu Ser Cys Leu Thr Val
1               5                   10

<210> SEQ ID NO 468
<211> LENGTH: 8
<212> TYPE: PRT
<213> ORGANISM: Hepatitis C Virus

<400> SEQUENCE: 468

Ile Leu His Thr Pro Gly Cys Val
1               5

<210> SEQ ID NO 469
<211> LENGTH: 10
<212> TYPE: PRT
<213> ORGANISM: Hepatitis C Virus

<400> SEQUENCE: 469

Gln Leu Arg Arg His Ile Asp Leu Leu Val
1               5                   10

<210> SEQ ID NO 470
<211> LENGTH: 9
<212> TYPE: PRT
<213> ORGANISM: Hepatitis C Virus

<400> SEQUENCE: 470

```
Asp Leu Cys Gly Ser Val Phe Leu Val
1               5
```

<210> SEQ ID NO 471
<211> LENGTH: 9
<212> TYPE: PRT
<213> ORGANISM: Hepatitis C Virus

<400> SEQUENCE: 471

```
Ser Met Val Gly Asn Trp Ala Lys Val
1               5
```

<210> SEQ ID NO 472
<211> LENGTH: 9
<212> TYPE: PRT
<213> ORGANISM: Hepatitis C Virus

<400> SEQUENCE: 472

```
His Leu His Gln Asn Ile Val Asp Val
1               5
```

<210> SEQ ID NO 473
<211> LENGTH: 9
<212> TYPE: PRT
<213> ORGANISM: Hepatitis C Virus

<400> SEQUENCE: 473

```
Phe Leu Leu Leu Ala Asp Ala Arg Val
1               5
```

<210> SEQ ID NO 474
<211> LENGTH: 13
<212> TYPE: PRT
<213> ORGANISM: Hepatitis C Virus

<400> SEQUENCE: 474

```
Gly Leu Arg Asp Leu Ala Val Ala Val Glu Pro Val Val
1               5                   10
```

<210> SEQ ID NO 475
<211> LENGTH: 11
<212> TYPE: PRT
<213> ORGANISM: Hepatitis C Virus

<400> SEQUENCE: 475

```
Ser Leu Leu Ala Pro Gly Ala Lys Gln Asn Val
1               5                   10
```

<210> SEQ ID NO 476
<211> LENGTH: 10
<212> TYPE: PRT
<213> ORGANISM: Hepatitis C Virus

<400> SEQUENCE: 476

```
Leu Leu Ala Pro Gly Ala Lys Gln Asn Val
1               5                   10
```

<210> SEQ ID NO 477
<211> LENGTH: 9
<212> TYPE: PRT
<213> ORGANISM: Hepatitis B Virus

<400> SEQUENCE: 477

```
Phe Leu Leu Ser Leu Gly Ile His Leu
1               5
```

<210> SEQ ID NO 478
<211> LENGTH: 9
<212> TYPE: PRT
<213> ORGANISM: Hepatitis B Virus

<400> SEQUENCE: 478

Ser Leu Tyr Ala Asp Ser Pro Ser Val
1               5

<210> SEQ ID NO 479
<211> LENGTH: 9
<212> TYPE: PRT
<213> ORGANISM: Hepatitis B Virus

<400> SEQUENCE: 479

Gly Leu Ser Arg Tyr Val Ala Arg Leu
1               5

<210> SEQ ID NO 480
<211> LENGTH: 9
<212> TYPE: PRT
<213> ORGANISM: Homo sapiens

<400> SEQUENCE: 480

Lys Ile Phe Gly Ser Leu Ala Phe Leu
1               5

<210> SEQ ID NO 481
<211> LENGTH: 9
<212> TYPE: PRT
<213> ORGANISM: Homo sapiens

<400> SEQUENCE: 481

Glu Leu Val Ser Glu Phe Ser Arg Met
1               5

<210> SEQ ID NO 482
<211> LENGTH: 9
<212> TYPE: PRT
<213> ORGANISM: Human Immunodeficiency Virus 1

<400> SEQUENCE: 482

Lys Leu Thr Pro Leu Cys Val Thr Leu
1               5

<210> SEQ ID NO 483
<211> LENGTH: 10
<212> TYPE: PRT
<213> ORGANISM: Human Immunodeficiency Virus 1

<400> SEQUENCE: 483

Ser Leu Leu Asn Ala Thr Asp Ile Ala Val
1               5                   10

<210> SEQ ID NO 484
<211> LENGTH: 10
<212> TYPE: PRT
<213> ORGANISM: Homo sapiens

<400> SEQUENCE: 484

Val Leu Tyr Arg Tyr Gly Ser Phe Ser Val
1               5                   10

<210> SEQ ID NO 485
<211> LENGTH: 9

```
<212> TYPE: PRT
<213> ORGANISM: Homo sapiens

<400> SEQUENCE: 485

Tyr Ile Gly Glu Val Leu Val Ser Val
 1               5

<210> SEQ ID NO 486
<211> LENGTH: 10
<212> TYPE: PRT
<213> ORGANISM: Hepatitis C Virus

<400> SEQUENCE: 486

Leu Leu Phe Asn Ile Leu Gly Gly Trp Val
 1               5                  10

<210> SEQ ID NO 487
<211> LENGTH: 10
<212> TYPE: PRT
<213> ORGANISM: Hepatitis B Virus

<400> SEQUENCE: 487

Leu Leu Val Pro Phe Val Gln Trp Phe Trp
 1               5                  10

<210> SEQ ID NO 488
<211> LENGTH: 9
<212> TYPE: PRT
<213> ORGANISM: Hepatitis B Virus

<400> SEQUENCE: 488

Ala Leu Met Pro Leu Tyr Ala Cys Ile
 1               5

<210> SEQ ID NO 489
<211> LENGTH: 9
<212> TYPE: PRT
<213> ORGANISM: Hepatitis C Virus

<400> SEQUENCE: 489

Tyr Leu Val Ala Tyr Gln Ala Thr Val
 1               5

<210> SEQ ID NO 490
<211> LENGTH: 9
<212> TYPE: PRT
<213> ORGANISM: Himetobi P Virus (HiPV)

<400> SEQUENCE: 490

Thr Leu Gly Ile Val Cys Pro Ile Cys
 1               5

<210> SEQ ID NO 491
<211> LENGTH: 10
<212> TYPE: PRT
<213> ORGANISM: Hepatitis C Virus

<400> SEQUENCE: 491

Tyr Leu Leu Pro Arg Arg Gly Pro Arg Leu
 1               5                  10

<210> SEQ ID NO 492
<211> LENGTH: 10
<212> TYPE: PRT
<213> ORGANISM: Hepatitis B Virus
```

-continued

```
<400> SEQUENCE: 492

Leu Leu Pro Ile Phe Phe Cys Leu Trp Val
1               5                   10

<210> SEQ ID NO 493
<211> LENGTH: 9
<212> TYPE: PRT
<213> ORGANISM: Hepatitis B Virus

<400> SEQUENCE: 493

Tyr Met Asp Asp Val Val Leu Gly Ala
1               5

<210> SEQ ID NO 494
<211> LENGTH: 9
<212> TYPE: PRT
<213> ORGANISM: Human Papillomavirus

<400> SEQUENCE: 494

Gly Thr Leu Gly Ile Val Cys Pro Ile
1               5

<210> SEQ ID NO 495
<211> LENGTH: 10
<212> TYPE: PRT
<213> ORGANISM: Hepatitis C Virus

<400> SEQUENCE: 495

Leu Leu Ala Leu Leu Ser Cys Leu Thr Ile
1               5                   10

<210> SEQ ID NO 496
<211> LENGTH: 9
<212> TYPE: PRT
<213> ORGANISM: Human Papillomavirus

<400> SEQUENCE: 496

Met Leu Asp Leu Gln Pro Glu Thr Thr
1               5

<210> SEQ ID NO 497
<211> LENGTH: 9
<212> TYPE: PRT
<213> ORGANISM: Hepatitis C Virus

<400> SEQUENCE: 497

Ser Leu Met Ala Phe Thr Ala Ala Val
1               5

<210> SEQ ID NO 498
<211> LENGTH: 9
<212> TYPE: PRT
<213> ORGANISM: Hepatitis C Virus

<400> SEQUENCE: 498

Cys Ile Asn Gly Val Cys Trp Thr Val
1               5

<210> SEQ ID NO 499
<211> LENGTH: 10
<212> TYPE: PRT
<213> ORGANISM: Homo sapiens

<400> SEQUENCE: 499

Val Met Asn Ile Leu Leu Gln Tyr Val Val
```

-continued

<210> SEQ ID NO 500
<211> LENGTH: 9
<212> TYPE: PRT
<213> ORGANISM: Homo sapiens

<400> SEQUENCE: 500

Ile Leu Thr Val Ile Leu Gly Val Leu
1               5

<210> SEQ ID NO 501
<211> LENGTH: 9
<212> TYPE: PRT
<213> ORGANISM: Homo sapiens

<400> SEQUENCE: 501

Phe Leu Trp Gly Pro Arg Ala Leu Val
1               5

<210> SEQ ID NO 502
<211> LENGTH: 9
<212> TYPE: PRT
<213> ORGANISM: Hepatitis C Virus

<400> SEQUENCE: 502

Leu Leu Cys Pro Ala Gly His Ala Val
1               5

<210> SEQ ID NO 503
<211> LENGTH: 9
<212> TYPE: PRT
<213> ORGANISM: Hepatitis C Virus

<400> SEQUENCE: 503

Ile Leu Asp Ser Phe Asp Pro Leu Val
1               5

<210> SEQ ID NO 504
<211> LENGTH: 9
<212> TYPE: PRT
<213> ORGANISM: Hepatitis B Virus

<400> SEQUENCE: 504

Leu Leu Leu Cys Leu Ile Phe Leu Leu
1               5

<210> SEQ ID NO 505
<211> LENGTH: 10
<212> TYPE: PRT
<213> ORGANISM: Hepatitis B Virus

<400> SEQUENCE: 505

Leu Ile Asp Tyr Gln Gly Met Leu Pro Val
1               5                   10

<210> SEQ ID NO 506
<211> LENGTH: 10
<212> TYPE: PRT
<213> ORGANISM: Hepatitis B Virus

<400> SEQUENCE: 506

Ser Ile Val Ser Pro Phe Ile Pro Leu Leu
1               5                   10

```
<210> SEQ ID NO 507
<211> LENGTH: 9
<212> TYPE: PRT
<213> ORGANISM: Hepatitis B Virus

<400> SEQUENCE: 507

Phe Leu Leu Thr Arg Ile Leu Thr Ile
 1               5

<210> SEQ ID NO 508
<211> LENGTH: 9
<212> TYPE: PRT
<213> ORGANISM: Plasmodium Faciparum

<400> SEQUENCE: 508

His Leu Gly Asn Val Lys Tyr Leu Val
 1               5

<210> SEQ ID NO 509
<211> LENGTH: 9
<212> TYPE: PRT
<213> ORGANISM: Plasmodium Faciparum

<400> SEQUENCE: 509

Gly Ile Ala Gly Gly Leu Ala Leu Leu
 1               5

<210> SEQ ID NO 510
<211> LENGTH: 9
<212> TYPE: PRT
<213> ORGANISM: Hepatitis C Virus

<400> SEQUENCE: 510

Ile Leu Ala Gly Tyr Gly Ala Gly Val
 1               5

<210> SEQ ID NO 511
<211> LENGTH: 9
<212> TYPE: PRT
<213> ORGANISM: Hepatitis C Virus

<400> SEQUENCE: 511

Gly Leu Gln Asp Cys Thr Met Leu Val
 1               5

<210> SEQ ID NO 512
<211> LENGTH: 10
<212> TYPE: PRT
<213> ORGANISM: Hepatitis C Virus

<400> SEQUENCE: 512

Thr Gly Ala Pro Val Thr Tyr Ser Thr Tyr
 1               5                  10

<210> SEQ ID NO 513
<211> LENGTH: 10
<212> TYPE: PRT
<213> ORGANISM: Human Immunodeficiency Virus 1

<400> SEQUENCE: 513

Val Ile Tyr Gln Tyr Met Asp Asp Leu Val
 1               5                  10

<210> SEQ ID NO 514
<211> LENGTH: 10
<212> TYPE: PRT
```

-continued

```
<213> ORGANISM: Homo sapiens

<400> SEQUENCE: 514

Val Leu Pro Asp Val Phe Ile Arg Cys Val
1               5                   10

<210> SEQ ID NO 515
<211> LENGTH: 9
<212> TYPE: PRT
<213> ORGANISM: Homo sapiens

<400> SEQUENCE: 515

Val Leu Pro Asp Val Phe Ile Arg Cys
1               5

<210> SEQ ID NO 516
<211> LENGTH: 9
<212> TYPE: PRT
<213> ORGANISM: Homo sapiens

<400> SEQUENCE: 516

Ala Val Gly Ile Gly Ile Ala Val Val
1               5

<210> SEQ ID NO 517
<211> LENGTH: 9
<212> TYPE: PRT
<213> ORGANISM: Homo sapiens

<400> SEQUENCE: 517

Leu Val Val Leu Gly Leu Leu Ala Val
1               5

<210> SEQ ID NO 518
<211> LENGTH: 9
<212> TYPE: PRT
<213> ORGANISM: Homo sapiens

<400> SEQUENCE: 518

Ala Leu Gly Leu Gly Leu Leu Pro Val
1               5

<210> SEQ ID NO 519
<211> LENGTH: 9
<212> TYPE: PRT
<213> ORGANISM: Herpes Simplex Virus I

<400> SEQUENCE: 519

Gly Ile Gly Ile Gly Val Leu Ala Ala
1               5

<210> SEQ ID NO 520
<211> LENGTH: 9
<212> TYPE: PRT
<213> ORGANISM: Herpes Simplex Virus 2

<400> SEQUENCE: 520

Gly Ala Gly Ile Gly Val Ala Val Leu
1               5

<210> SEQ ID NO 521
<211> LENGTH: 9
<212> TYPE: PRT
<213> ORGANISM: Pseudorabies Virus

<400> SEQUENCE: 521
```

```
Ile Ala Gly Ile Gly Ile Leu Ala Ile
1               5
```

<210> SEQ ID NO 522
<211> LENGTH: 9
<212> TYPE: PRT
<213> ORGANISM: Adenovirus

<400> SEQUENCE: 522

```
Leu Ile Val Ile Gly Ile Leu Ile Leu
1               5
```

<210> SEQ ID NO 523
<211> LENGTH: 9
<212> TYPE: PRT
<213> ORGANISM: Streptomyces Lincolnensis

<400> SEQUENCE: 523

```
Leu Ala Gly Ile Gly Leu Ile Ala Ala
1               5
```

<210> SEQ ID NO 524
<211> LENGTH: 9
<212> TYPE: PRT
<213> ORGANISM: Yeast (YSA-1)

<400> SEQUENCE: 524

```
Val Asp Gly Ile Gly Ile Leu Thr Ile
1               5
```

<210> SEQ ID NO 525
<211> LENGTH: 9
<212> TYPE: PRT
<213> ORGANISM: Bacillus Polymyxa

<400> SEQUENCE: 525

```
Gly Ala Gly Ile Gly Val Leu Thr Ala
1               5
```

<210> SEQ ID NO 526
<211> LENGTH: 9
<212> TYPE: PRT
<213> ORGANISM: Escherichia Coli

<400> SEQUENCE: 526

```
Ala Ala Gly Ile Gly Ile Ile Gln Ile
1               5
```

<210> SEQ ID NO 527
<211> LENGTH: 9
<212> TYPE: PRT
<213> ORGANISM: Escherichia Coli

<400> SEQUENCE: 527

```
Gln Ala Gly Ile Gly Ile Leu Leu Ala
1               5
```

<210> SEQ ID NO 528
<211> LENGTH: 11
<212> TYPE: PRT
<213> ORGANISM: Homo sapiens

<400> SEQUENCE: 528

```
Lys Ala Arg Asp Pro His Ser Gly His Phe Val
1               5                   10
```

<210> SEQ ID NO 529
<211> LENGTH: 13
<212> TYPE: PRT
<213> ORGANISM: Homo sapiens

<400> SEQUENCE: 529

Lys Ala Cys Asp Pro Ile Ile Ser Gly Ile Ile Phe Val
1               5                   10

<210> SEQ ID NO 530
<211> LENGTH: 11
<212> TYPE: PRT
<213> ORGANISM: Homo sapiens

<400> SEQUENCE: 530

Ala Cys Asp Pro Phe Ile Ser Gly His Phe Val
1               5                   10

<210> SEQ ID NO 531
<211> LENGTH: 9
<212> TYPE: PRT
<213> ORGANISM: Human Immunodeficiency Virus I

<400> SEQUENCE: 531

Ser Leu Tyr Asn Thr Val Ala Thr Leu
1               5

<210> SEQ ID NO 532
<211> LENGTH: 9
<212> TYPE: PRT
<213> ORGANISM: Homo sapiens

<400> SEQUENCE: 532

Glu Leu Val Ser Glu Phe Ser Arg Val
1               5

<210> SEQ ID NO 533
<211> LENGTH: 10
<212> TYPE: PRT
<213> ORGANISM: Human Immunodeficiency Virus I

<400> SEQUENCE: 533

Arg Gly Pro Gly Arg Ala Phe Val Thr Ile
1               5                   10

<210> SEQ ID NO 534
<211> LENGTH: 9
<212> TYPE: PRT
<213> ORGANISM: Hepatitis C Virus

<400> SEQUENCE: 534

His Met Trp Asn Phe Ile Ser Gly Ile
1               5

<210> SEQ ID NO 535
<211> LENGTH: 10
<212> TYPE: PRT
<213> ORGANISM: Human Cytomegalovirus

<400> SEQUENCE: 535

Asn Leu Val Pro Met Val Ala Thr Val Gln
1               5                   10

<210> SEQ ID NO 536

```
<211> LENGTH: 9
<212> TYPE: PRT
<213> ORGANISM: Human Papillomavirus

<400> SEQUENCE: 536

Gly Leu His Cys Tyr Glu Gln Leu Val
1               5

<210> SEQ ID NO 537
<211> LENGTH: 9
<212> TYPE: PRT
<213> ORGANISM: Human Papillomavirus

<400> SEQUENCE: 537

Pro Leu Lys Gln His Phe Gln Ile Val
1               5

<210> SEQ ID NO 538
<211> LENGTH: 10
<212> TYPE: PRT
<213> ORGANISM: Epstein-Barr Virus (EBNA)

<400> SEQUENCE: 538

Leu Leu Asp Phe Val Arg Phe Met Gly Val
1               5                   10

<210> SEQ ID NO 539
<211> LENGTH: 9
<212> TYPE: PRT
<213> ORGANISM: Influenza

<400> SEQUENCE: 539

Ala Ile Met Glu Lys Asn Ile Met Leu
1               5

<210> SEQ ID NO 540
<211> LENGTH: 9
<212> TYPE: PRT
<213> ORGANISM: Plasmodium Falciparum

<400> SEQUENCE: 540

Tyr Leu Lys Thr Ile Gln Asn Ser Leu
1               5

<210> SEQ ID NO 541
<211> LENGTH: 9
<212> TYPE: PRT
<213> ORGANISM: Plasmodium Falciparum

<400> SEQUENCE: 541

Tyr Leu Asn Lys Ile Gln Asn Ser Leu
1               5

<210> SEQ ID NO 542
<211> LENGTH: 10
<212> TYPE: PRT
<213> ORGANISM: Human Papillomavirus

<400> SEQUENCE: 542

Tyr Met Leu Asp Leu Gln Pro Glu Thr Thr
1               5                   10

<210> SEQ ID NO 543
<211> LENGTH: 9
<212> TYPE: PRT
<213> ORGANISM: Human Papillomavirus
```

```
<400> SEQUENCE: 543

Leu Leu Met Gly Thr Leu Gly Ile Val
 1               5

<210> SEQ ID NO 544
<211> LENGTH: 8
<212> TYPE: PRT
<213> ORGANISM: Human Papillomavirus

<400> SEQUENCE: 544

Thr Leu Gly Ile Val Cys Pro Ile
 1               5

<210> SEQ ID NO 545
<211> LENGTH: 9
<212> TYPE: PRT
<213> ORGANISM: Human Immunodeficiency Virus 1

<400> SEQUENCE: 545

Thr Leu Thr Ser Cys Asn Thr Ser Val
 1               5

<210> SEQ ID NO 546
<211> LENGTH: 9
<212> TYPE: PRT
<213> ORGANISM: Human Papillomavirus

<400> SEQUENCE: 546

Lys Leu Pro Gln Leu Cys Thr Glu Leu
 1               5

<210> SEQ ID NO 547
<211> LENGTH: 9
<212> TYPE: PRT
<213> ORGANISM: Human Papillomavirus 16

<400> SEQUENCE: 547

Thr Ile His Asp Ile Ile Leu Glu Cys
 1               5

<210> SEQ ID NO 548
<211> LENGTH: 9
<212> TYPE: PRT
<213> ORGANISM: Human Papillomavirus 16

<400> SEQUENCE: 548

Leu Gly Ile Val Cys Pro Ile Cys Ser
 1               5

<210> SEQ ID NO 549
<211> LENGTH: 9
<212> TYPE: PRT
<213> ORGANISM: Homo sapiens

<400> SEQUENCE: 549

Val Ile Leu Gly Val Leu Leu Leu Ile
 1               5

<210> SEQ ID NO 550
<211> LENGTH: 9
<212> TYPE: PRT
<213> ORGANISM: Homo sapiens

<400> SEQUENCE: 550
```

```
Ala Leu Met Asp Lys Ser Leu His Val
1               5

<210> SEQ ID NO 551
<211> LENGTH: 9
<212> TYPE: PRT
<213> ORGANISM: Homo sapiens

<400> SEQUENCE: 551

Gly Ile Leu Thr Val Ile Leu Gly Val
1               5

<210> SEQ ID NO 552
<211> LENGTH: 9
<212> TYPE: PRT
<213> ORGANISM: Plasmodium Falciparum

<400> SEQUENCE: 552

Met Ile Asn Ala Tyr Leu Asp Lys Leu
1               5

<210> SEQ ID NO 553
<211> LENGTH: 9
<212> TYPE: PRT
<213> ORGANISM: Homo sapiens

<400> SEQUENCE: 553

Ala Ala Gly Ile Gly Ile Leu Thr Val
1               5

<210> SEQ ID NO 554
<211> LENGTH: 10
<212> TYPE: PRT
<213> ORGANISM: Hepatitis B Virus

<400> SEQUENCE: 554

Phe Leu Pro Ser Asp Phe Phe Pro Ser Val
1               5                   10

<210> SEQ ID NO 555
<211> LENGTH: 9
<212> TYPE: PRT
<213> ORGANISM: Epstein-Barr Virus (EBNA)

<400> SEQUENCE: 555

Ser Val Arg Asp Arg Leu Ala Arg Leu
1               5

<210> SEQ ID NO 556
<211> LENGTH: 9
<212> TYPE: PRT
<213> ORGANISM: Homo sapiens

<400> SEQUENCE: 556

Ala Ala Gly Ile Gly Ile Leu Thr Val
1               5

<210> SEQ ID NO 557
<211> LENGTH: 9
<212> TYPE: PRT
<213> ORGANISM: Homo sapiens

<400> SEQUENCE: 557

Phe Ala Tyr Asp Gly Lys Asp Tyr Ile
1               5
```

<210> SEQ ID NO 558
<211> LENGTH: 9
<212> TYPE: PRT
<213> ORGANISM: Homo sapiens

<400> SEQUENCE: 558

Ala Ala Gly Ile Gly Ile Leu Thr Val
1               5

<210> SEQ ID NO 559
<211> LENGTH: 10
<212> TYPE: PRT
<213> ORGANISM: Hepatitis B Virus

<400> SEQUENCE: 559

Phe Leu Pro Ser Asp Phe Phe Pro Ser Val
1               5                   10

<210> SEQ ID NO 560
<211> LENGTH: 9
<212> TYPE: PRT
<213> ORGANISM: Homo sapiens

<400> SEQUENCE: 560

Ala Ala Gly Ile Gly Ile Leu Thr Val
1               5

<210> SEQ ID NO 561
<211> LENGTH: 10
<212> TYPE: PRT
<213> ORGANISM: Hepatitis B Virus

<400> SEQUENCE: 561

Phe Leu Pro Ser Asp Phe Phe Pro Ser Val
1               5                   10

<210> SEQ ID NO 562
<211> LENGTH: 9
<212> TYPE: PRT
<213> ORGANISM: Homo sapiens

<400> SEQUENCE: 562

Ala Ala Gly Ile Gly Ile Leu Thr Val
1               5

<210> SEQ ID NO 563
<211> LENGTH: 9
<212> TYPE: PRT
<213> ORGANISM: Homo sapiens

<400> SEQUENCE: 563

Ala Leu Leu Ala Val Gly Ala Thr Lys
1               5

<210> SEQ ID NO 564
<211> LENGTH: 11
<212> TYPE: PRT
<213> ORGANISM: Human Immunodeficiency Virus 1

<400> SEQUENCE: 564

Arg Leu Arg Asp Leu Leu Leu Ile Val Thr Arg
1               5                   10

<210> SEQ ID NO 565
<211> LENGTH: 10

```
<212> TYPE: PRT
<213> ORGANISM: Human Immunodeficiency Virus 1

<400> SEQUENCE: 565

Gln Val Pro Leu Arg Pro Met Thr Tyr Lys
 1               5                  10

<210> SEQ ID NO 566
<211> LENGTH: 10
<212> TYPE: PRT
<213> ORGANISM: Human Immunodeficiency Virus 1

<400> SEQUENCE: 566

Thr Val Tyr Tyr Gly Val Pro Val Trp Lys
 1               5                  10

<210> SEQ ID NO 567
<211> LENGTH: 9
<212> TYPE: PRT
<213> ORGANISM: Human Immunodeficiency Virus 1

<400> SEQUENCE: 567

Arg Leu Arg Pro Gly Gly Lys Lys Lys
 1               5

<210> SEQ ID NO 568
<211> LENGTH: 9
<212> TYPE: PRT
<213> ORGANISM: Influenza

<400> SEQUENCE: 568

Ile Leu Arg Gly Ser Val Ala His Lys
 1               5

<210> SEQ ID NO 569
<211> LENGTH: 9
<212> TYPE: PRT
<213> ORGANISM: Epstein-Barr Virus (EBNA)

<400> SEQUENCE: 569

Arg Leu Arg Ala Glu Ala Gly Val Lys
 1               5

<210> SEQ ID NO 570
<211> LENGTH: 11
<212> TYPE: PRT
<213> ORGANISM: Human Immunodeficiency Virus 1

<400> SEQUENCE: 570

Arg Leu Arg Asp Leu Leu Leu Ile Val Thr Arg
 1               5                  10

<210> SEQ ID NO 571
<211> LENGTH: 9
<212> TYPE: PRT
<213> ORGANISM: Human Immunodeficiency Virus 1

<400> SEQUENCE: 571

Val Tyr Tyr Gly Val Pro Val Trp Lys
 1               5

<210> SEQ ID NO 572
<211> LENGTH: 9
<212> TYPE: PRT
<213> ORGANISM: Hepatitis C Virus
```

```
<400> SEQUENCE: 572

Arg Val Cys Glu Lys Met Ala Leu Tyr
 1               5

<210> SEQ ID NO 573
<211> LENGTH: 9
<212> TYPE: PRT
<213> ORGANISM: Homo sapiens

<400> SEQUENCE: 573

Lys Ile Phe Ser Glu Val Thr Leu Lys
 1               5

<210> SEQ ID NO 574
<211> LENGTH: 9
<212> TYPE: PRT
<213> ORGANISM: Hepatitis B Virus

<400> SEQUENCE: 574

Tyr Val Asn Val Asn Met Gly Leu Lys
 1               5

<210> SEQ ID NO 575
<211> LENGTH: 9
<212> TYPE: PRT
<213> ORGANISM: Epstein-Barr Virus (EBNA)

<400> SEQUENCE: 575

Ile Val Thr Asp Phe Ser Val Ile Lys
 1               5

<210> SEQ ID NO 576
<211> LENGTH: 9
<212> TYPE: PRT
<213> ORGANISM: Homo sapiens

<400> SEQUENCE: 576

Glu Leu Asn Glu Ala Leu Glu Leu Lys
 1               5

<210> SEQ ID NO 577
<211> LENGTH: 9
<212> TYPE: PRT
<213> ORGANISM: Human Immunodeficiency Virus 1

<400> SEQUENCE: 577

Val Pro Leu Arg Pro Met Thr Tyr Lys
 1               5

<210> SEQ ID NO 578
<211> LENGTH: 9
<212> TYPE: PRT
<213> ORGANISM: Human Immunodeficiency Virus 1

<400> SEQUENCE: 578

Ala Ile Phe Gln Ser Ser Met Thr Lys
 1               5

<210> SEQ ID NO 579
<211> LENGTH: 10
<212> TYPE: PRT
<213> ORGANISM: Human Immunodeficiency Virus 1

<400> SEQUENCE: 579

Gln Val Pro Leu Arg Pro Met Thr Tyr Lys
```

<210> SEQ ID NO 580
<211> LENGTH: 11
<212> TYPE: PRT
<213> ORGANISM: Influenza

<400> SEQUENCE: 580

Thr Ile Asn Tyr Thr Ile Phe Lys His Cys Val
 1               5                  10

<210> SEQ ID NO 581
<211> LENGTH: 12
<212> TYPE: PRT
<213> ORGANISM: Human Immunodeficiency Virus 1

<400> SEQUENCE: 581

Ala Ala Val Asp Leu Ser His Phe Leu Lys Glu Lys
 1               5                  10

<210> SEQ ID NO 582
<211> LENGTH: 12
<212> TYPE: PRT
<213> ORGANISM: Human Immunodeficiency Virus 1

<400> SEQUENCE: 582

Ala Cys Gln Gly Val Gly Gly Pro Gly His Lys
 1               5                  10

<210> SEQ ID NO 583
<211> LENGTH: 9
<212> TYPE: PRT
<213> ORGANISM: Homo sapiens

<400> SEQUENCE: 583

Ser Tyr Leu Asp Ser Gly Ile His Phe
 1               5

<210> SEQ ID NO 584
<211> LENGTH: 9
<212> TYPE: PRT
<213> ORGANISM: Human Immunodeficiency Virus 1

<400> SEQUENCE: 584

Arg Tyr Leu Lys Asp Gln Gln Leu Leu
 1               5

<210> SEQ ID NO 585
<211> LENGTH: 9
<212> TYPE: PRT
<213> ORGANISM: Homo sapiens

<400> SEQUENCE: 585

Ala Tyr Gly Leu Asp Phe Tyr Ile Leu
 1               5

<210> SEQ ID NO 586
<211> LENGTH: 10
<212> TYPE: PRT
<213> ORGANISM: Homo sapiens

<400> SEQUENCE: 586

Ala Phe Leu Pro Trp His Arg Leu Phe Leu
 1               5                  10

<210> SEQ ID NO 587
<211> LENGTH: 9
<212> TYPE: PRT
<213> ORGANISM: Homo sapiens

<400> SEQUENCE: 587

Ala Phe Leu Pro Trp His Arg Leu Phe
1               5

<210> SEQ ID NO 588
<211> LENGTH: 8
<212> TYPE: PRT
<213> ORGANISM: Epstein-Barr Virus (EBNA)

<400> SEQUENCE: 588

Arg Tyr Ser Ile Phe Phe Asp Tyr
1               5

<210> SEQ ID NO 589
<211> LENGTH: 10
<212> TYPE: PRT
<213> ORGANISM: Human Immunodeficiency Virus 1

<400> SEQUENCE: 589

Glu Thr Ile Asn Glu Glu Ala Ala Glu Trp
1               5                   10

<210> SEQ ID NO 590
<211> LENGTH: 11
<212> TYPE: PRT
<213> ORGANISM: Hepatitis B Virus

<400> SEQUENCE: 590

Ser Thr Leu Pro Glu Thr Thr Val Val Arg Arg
1               5                   10

<210> SEQ ID NO 591
<211> LENGTH: 9
<212> TYPE: PRT
<213> ORGANISM: Homo sapiens

<400> SEQUENCE: 591

Met Ser Leu Gln Arg Gln Phe Leu Arg
1               5

<210> SEQ ID NO 592
<211> LENGTH: 9
<212> TYPE: PRT
<213> ORGANISM: Homo sapiens

<400> SEQUENCE: 592

Leu Leu Pro Gly Gly Arg Pro Tyr Arg
1               5

<210> SEQ ID NO 593
<211> LENGTH: 9
<212> TYPE: PRT
<213> ORGANISM: Human Immunodeficiency Virus

<400> SEQUENCE: 593

Ile Val Gly Leu Asn Lys Ile Val Arg
1               5

<210> SEQ ID NO 594
<211> LENGTH: 9
<212> TYPE: PRT

```
<213> ORGANISM: Homo sapiens

<400> SEQUENCE: 594

Ala Ala Gly Ile Gly Ile Leu Thr Val
 1               5

<210> SEQ ID NO 595
<211> LENGTH: 9
<212> TYPE: PRT
<213> ORGANISM: Homo sapiens

<400> SEQUENCE: 595

Glu Val Asp Pro Thr Ser Asn Thr Tyr
 1               5

<210> SEQ ID NO 596
<211> LENGTH: 9
<212> TYPE: PRT
<213> ORGANISM: Homo sapiens

<400> SEQUENCE: 596

Glu Ala Asp Pro Thr Ser Asn Thr Tyr
 1               5

<210> SEQ ID NO 597
<211> LENGTH: 9
<212> TYPE: PRT
<213> ORGANISM: Homo sapiens

<400> SEQUENCE: 597

Glu Ala Asp Pro Thr Ser Asn Thr Tyr
 1               5

<210> SEQ ID NO 598
<211> LENGTH: 9
<212> TYPE: PRT
<213> ORGANISM: Homo sapiens

<400> SEQUENCE: 598

Glu Val Asp Pro Ile Gly His Val Tyr
 1               5

<210> SEQ ID NO 599
<211> LENGTH: 10
<212> TYPE: PRT
<213> ORGANISM: Homo sapiens

<400> SEQUENCE: 599

Met Leu Leu Ala Val Leu Tyr Cys Leu Leu
 1               5                  10

<210> SEQ ID NO 600
<211> LENGTH: 9
<212> TYPE: PRT
<213> ORGANISM: Homo sapiens

<400> SEQUENCE: 600

Met Leu Leu Ala Val Leu Tyr Cys Leu
 1               5

<210> SEQ ID NO 601
<211> LENGTH: 10
<212> TYPE: PRT
<213> ORGANISM: Homo sapiens

<400> SEQUENCE: 601
```

```
Ser Glu Ile Trp Arg Asp Ile Asp Phe Ala
1               5                   10

<210> SEQ ID NO 602
<211> LENGTH: 9
<212> TYPE: PRT
<213> ORGANISM: Homo sapiens

<400> SEQUENCE: 602

Ser Glu Ile Trp Arg Asp Ile Asp Phe
1               5

<210> SEQ ID NO 603
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 1
<223> OTHER INFORMATION: Xaa = Any Amino Acid

<400> SEQUENCE: 603

Xaa Glu Ile Trp Arg Asp Ile Asp Phe
1               5

<210> SEQ ID NO 604
<211> LENGTH: 10
<212> TYPE: PRT
<213> ORGANISM: Homo sapiens

<400> SEQUENCE: 604

Ser Thr Leu Val Glu Val Thr Leu Gly Val
1               5                   10

<210> SEQ ID NO 605
<211> LENGTH: 9
<212> TYPE: PRT
<213> ORGANISM: Homo sapiens

<400> SEQUENCE: 605

Leu Val Glu Val Thr Leu Gly Glu Val
1               5

<210> SEQ ID NO 606
<211> LENGTH: 10
<212> TYPE: PRT
<213> ORGANISM: Homo sapiens

<400> SEQUENCE: 606

Val Ile Phe Ser Lys Ala Ser Glu Tyr Leu
1               5                   10

<210> SEQ ID NO 607
<211> LENGTH: 9
<212> TYPE: PRT
<213> ORGANISM: Homo sapiens

<400> SEQUENCE: 607

Ile Ile Val Leu Ala Ile Ile Ala Ile
1               5

<210> SEQ ID NO 608
<211> LENGTH: 11
<212> TYPE: PRT
```

<213> ORGANISM: Homo sapiens

<400> SEQUENCE: 608

Lys Ile Trp Glu Glu Leu Ser Met Leu Glu Tyr
1               5                   10

<210> SEQ ID NO 609
<211> LENGTH: 9
<212> TYPE: PRT
<213> ORGANISM: Homo sapiens

<400> SEQUENCE: 609

Leu Ile Glu Thr Ser Tyr Val Lys Val
1               5

<210> SEQ ID NO 610
<211> LENGTH: 9
<212> TYPE: PRT
<213> ORGANISM: Homo sapiens

<400> SEQUENCE: 610

Phe Leu Trp Gly Pro Arg Ala Leu Val
1               5

<210> SEQ ID NO 611
<211> LENGTH: 10
<212> TYPE: PRT
<213> ORGANISM: Homo sapiens

<400> SEQUENCE: 611

Thr Leu Val Glu Val Thr Leu Gly Glu Val
1               5                   10

<210> SEQ ID NO 612
<211> LENGTH: 10
<212> TYPE: PRT
<213> ORGANISM: Homo sapiens

<400> SEQUENCE: 612

Ala Leu Val Glu Thr Ser Tyr Val Lys Val
1               5                   10

<210> SEQ ID NO 613
<211> LENGTH: 9
<212> TYPE: PRT
<213> ORGANISM: Homo sapiens

<400> SEQUENCE: 613

Lys Ile Trp Glu Glu Leu Ser Val Leu
1               5

<210> SEQ ID NO 614
<211> LENGTH: 9
<212> TYPE: PRT
<213> ORGANISM: Homo sapiens

<400> SEQUENCE: 614

Glu Val Asp Pro Ile Gly His Leu Tyr
1               5

<210> SEQ ID NO 615
<211> LENGTH: 9
<212> TYPE: PRT
<213> ORGANISM: Artificial Sequence
<220> FEATURE:
<223> OTHER INFORMATION: Synthetic peptide

```
<220> FEATURE:
<221> NAME/KEY: VARIANT
<222> LOCATION: 2, 4, 5, 6, 7, 8
<223> OTHER INFORMATION: Xaa = Any Amino Acid

<400> SEQUENCE: 615

Glu Xaa Asp Xaa Xaa Xaa Xaa Xaa Tyr
 1               5

<210> SEQ ID NO 616
<211> LENGTH: 9
<212> TYPE: PRT
<213> ORGANISM: Homo sapiens

<400> SEQUENCE: 616

Glu Ala Asp Pro Thr Gly His Ser Tyr
 1               5

<210> SEQ ID NO 617
<211> LENGTH: 9
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Variant Sequences
<220> FEATURE:
<221> NAME/KEY: misc_feature
<222> LOCATION: (2)..(2)
<223> OTHER INFORMATION: Xaa = A or V
<220> FEATURE:
<221> NAME/KEY: misc_feature
<222> LOCATION: (4)..(8)
<223> OTHER INFORMATION: Xaa = any amino acid

<400> SEQUENCE: 617

Glu Xaa Asp Xaa Xaa Xaa Xaa Xaa Tyr
 1               5

<210> SEQ ID NO 618
<211> LENGTH: 9
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Variant Sequences
<220> FEATURE:
<221> NAME/KEY: misc_feature
<222> LOCATION: (2)..(2)
<223> OTHER INFORMATION: Xaa = A or V
<220> FEATURE:
<221> NAME/KEY: misc_feature
<222> LOCATION: (5)..(8)
<223> OTHER INFORMATION: Xaa = any amino acid

<400> SEQUENCE: 618

Glu Xaa Asp Pro Xaa Xaa Xaa Xaa Tyr
 1               5

<210> SEQ ID NO 619
<211> LENGTH: 9
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Variant Sequences
<220> FEATURE:
<221> NAME/KEY: misc_feature
<222> LOCATION: (2)..(2)
<223> OTHER INFORMATION: Xaa = A or V
```

```
<220> FEATURE:
<221> NAME/KEY: misc_feature
<222> LOCATION: (5)..(5)
<223> OTHER INFORMATION: Xaa = I or A or T
<220> FEATURE:
<221> NAME/KEY: misc_feature
<222> LOCATION: (6)..(8)
<223> OTHER INFORMATION: Xaa = any amino acid

<400> SEQUENCE: 619

Glu Xaa Asp Pro Xaa Xaa Xaa Xaa Tyr
 1               5

<210> SEQ ID NO 620
<211> LENGTH: 9
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Variant Sequences
<220> FEATURE:
<221> NAME/KEY: misc_feature
<222> LOCATION: (2)..(2)
<223> OTHER INFORMATION: Xaa = A or V
<220> FEATURE:
<221> NAME/KEY: misc_feature
<222> LOCATION: (5)..(5)
<223> OTHER INFORMATION: Xaa = I or A or T
<220> FEATURE:
<221> NAME/KEY: misc_feature
<222> LOCATION: (6)..(6)
<223> OTHER INFORMATION: Xaa = G or S
<220> FEATURE:
<221> NAME/KEY: misc_feature
<222> LOCATION: (7)..(8)
<223> OTHER INFORMATION: Xaa = any amino acid

<400> SEQUENCE: 620

Glu Xaa Asp Pro Xaa Xaa Xaa Xaa Tyr
 1               5

<210> SEQ ID NO 621
<211> LENGTH: 9
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Variant Sequences
<220> FEATURE:
<221> NAME/KEY: misc_feature
<222> LOCATION: (2)..(2)
<223> OTHER INFORMATION: Xaa = A or V
<220> FEATURE:
<221> NAME/KEY: misc_feature
<222> LOCATION: (5)..(5)
<223> OTHER INFORMATION: Xaa = I or A or T
<220> FEATURE:
<221> NAME/KEY: misc_feature
<222> LOCATION: (6)..(6)
<223> OTHER INFORMATION: Xaa = G or S
<220> FEATURE:
<221> NAME/KEY: misc_feature
<222> LOCATION: (7)..(7)
<223> OTHER INFORMATION: Xaa = H or N
<220> FEATURE:
<221> NAME/KEY: misc_feature
<222> LOCATION: (8)..(8)
<223> OTHER INFORMATION: Xaa = any amino acid

<400> SEQUENCE: 621

Glu Xaa Asp Pro Xaa Xaa Xaa Xaa Tyr
 1               5
```

```
<210> SEQ ID NO 622
<211> LENGTH: 9
<212> TYPE: PRT
<213> ORGANISM: Artificial Sequence
<220> FEATURE:
<223> OTHER INFORMATION: Synthetic peptide
<220> FEATURE:
<223> OTHER INFORMATION: Variant Sequences
<220> FEATURE:
<221> NAME/KEY: misc_feature
<222> LOCATION: (2)..(2)
<223> OTHER INFORMATION: Xaa = A or V
<220> FEATURE:
<221> NAME/KEY: misc_feature
<222> LOCATION: (5)..(5)
<223> OTHER INFORMATION: Xaa = I or A or T
<220> FEATURE:
<221> NAME/KEY: misc_feature
<222> LOCATION: (6)..(6)
<223> OTHER INFORMATION: Xaa = G or S
<220> FEATURE:
<221> NAME/KEY: misc_feature
<222> LOCATION: (7)..(7)
<223> OTHER INFORMATION: Xaa = H or N
<220> FEATURE:
<221> NAME/KEY: misc_feature
<222> LOCATION: (8)..(8)
<223> OTHER INFORMATION: Xaa = L or T or V

<400> SEQUENCE: 622

Glu Xaa Asp Pro Xaa Xaa Xaa Xaa Tyr
 1               5

<210> SEQ ID NO 623
<211> LENGTH: 16
<212> TYPE: PRT
<213> ORGANISM: Homo sapiens

<400> SEQUENCE: 623

Glu Leu His Ser Ala Tyr Gly Glu Pro Arg Lys Leu Leu Thr Gln Asp
 1               5                  10                  15

<210> SEQ ID NO 624
<211> LENGTH: 12
<212> TYPE: PRT
<213> ORGANISM: Homo sapiens

<400> SEQUENCE: 624

Glu His Ser Ala Tyr Gly Glu Pro Arg Lys Leu Leu
 1               5                  10

<210> SEQ ID NO 625
<211> LENGTH: 9
<212> TYPE: PRT
<213> ORGANISM: Homo sapiens

<400> SEQUENCE: 625

Ser Ala Tyr Gly Glu Pro Arg Lys Leu
 1               5

<210> SEQ ID NO 626
<211> LENGTH: 9
<212> TYPE: PRT
<213> ORGANISM: Homo sapiens

<400> SEQUENCE: 626

Glu Ala Asp Pro Thr Gly His Ser Tyr
 1               5
```

```
<210> SEQ ID NO 627
<211> LENGTH: 22
<212> TYPE: PRT
<213> ORGANISM: Homo sapiens

<400> SEQUENCE: 627

Met Ala Ala Arg Ala Val Phe Leu Ala Leu Ser Ala Gln Leu Leu Gln
 1               5                  10                  15

Ala Arg Leu Met Lys Glu
            20

<210> SEQ ID NO 628
<211> LENGTH: 16
<212> TYPE: PRT
<213> ORGANISM: Homo sapiens

<400> SEQUENCE: 628

Met Ala Ala Arg Ala Val Phe Leu Ala Leu Ser Ala Gln Leu Leu Gln
 1               5                  10                  15

<210> SEQ ID NO 629
<211> LENGTH: 9
<212> TYPE: PRT
<213> ORGANISM: Homo sapiens

<400> SEQUENCE: 629

Ala Ala Arg Ala Val Phe Leu Ala Leu
 1               5

<210> SEQ ID NO 630
<211> LENGTH: 8
<212> TYPE: PRT
<213> ORGANISM: Homo sapiens

<400> SEQUENCE: 630

Tyr Arg Pro Arg Pro Arg Arg Tyr
 1               5

<210> SEQ ID NO 631
<211> LENGTH: 9
<212> TYPE: PRT
<213> ORGANISM: Artificial Sequence
<220> FEATURE:
<223> OTHER INFORMATION: Synthetic peptide

<400> SEQUENCE: 631

Ala Leu Phe Ala Ala Ala Ala Ala Val
 1               5

<210> SEQ ID NO 632
<211> LENGTH: 9
<212> TYPE: PRT
<213> ORGANISM: Artificial Sequence
<220> FEATURE:
<223> OTHER INFORMATION: Synthetic peptide

<400> SEQUENCE: 632

Gly Ile Phe Gly Gly Val Gly Gly Val
 1               5

<210> SEQ ID NO 633
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 633

Gly Leu Asp Lys Gly Gly Gly Val
 1               5

<210> SEQ ID NO 634
<211> LENGTH: 9
<212> TYPE: PRT
<213> ORGANISM: Artificial Sequence
<220> FEATURE:
<223> OTHER INFORMATION: Synthetic peptide

<400> SEQUENCE: 634

Gly Leu Phe Gly Gly Phe Gly Gly Val
 1               5

<210> SEQ ID NO 635
<211> LENGTH: 9
<212> TYPE: PRT
<213> ORGANISM: Artificial Sequence
<220> FEATURE:
<223> OTHER INFORMATION: Synthetic peptide

<400> SEQUENCE: 635

Gly Leu Phe Gly Gly Gly Ala Gly Val
 1               5

<210> SEQ ID NO 636
<211> LENGTH: 9
<212> TYPE: PRT
<213> ORGANISM: Artificial Sequence
<220> FEATURE:
<223> OTHER INFORMATION: Synthetic peptide

<400> SEQUENCE: 636

Gly Leu Phe Gly Gly Gly Glu Gly Val
 1               5

<210> SEQ ID NO 637
<211> LENGTH: 9
<212> TYPE: PRT
<213> ORGANISM: Artificial Sequence
<220> FEATURE:
<223> OTHER INFORMATION: Synthetic peptide

<400> SEQUENCE: 637

Gly Leu Phe Gly Gly Gly Phe Gly Val
 1               5

<210> SEQ ID NO 638
<211> LENGTH: 9
<212> TYPE: PRT
<213> ORGANISM: Artificial Sequence
<220> FEATURE:
<223> OTHER INFORMATION: Synthetic peptide

<400> SEQUENCE: 638

Gly Leu Phe Gly Gly Gly Gly Gly Leu
 1               5

<210> SEQ ID NO 639
<211> LENGTH: 9
<212> TYPE: PRT
<213> ORGANISM: Artificial Sequence
<220> FEATURE:
<223> OTHER INFORMATION: Synthetic peptide

<400> SEQUENCE: 639
```

```
Gly Leu Phe Gly Gly Gly Gly Gly Val
 1               5

<210> SEQ ID NO 640
<211> LENGTH: 9
<212> TYPE: PRT
<213> ORGANISM: Artificial Sequence
<220> FEATURE:
<223> OTHER INFORMATION: Synthetic peptide

<400> SEQUENCE: 640

Gly Leu Phe Gly Gly Gly Val Gly Val
 1               5

<210> SEQ ID NO 641
<211> LENGTH: 9
<212> TYPE: PRT
<213> ORGANISM: Artificial Sequence
<220> FEATURE:
<223> OTHER INFORMATION: Synthetic peptide

<400> SEQUENCE: 641

Gly Leu Phe Gly Gly Val Gly Gly Val
 1               5

<210> SEQ ID NO 642
<211> LENGTH: 9
<212> TYPE: PRT
<213> ORGANISM: Artificial Sequence
<220> FEATURE:
<223> OTHER INFORMATION: Synthetic peptide

<400> SEQUENCE: 642

Gly Leu Phe Gly Gly Val Gly Lys Val
 1               5

<210> SEQ ID NO 643
<211> LENGTH: 9
<212> TYPE: PRT
<213> ORGANISM: Artificial Sequence
<220> FEATURE:
<223> OTHER INFORMATION: Synthetic peptide

<400> SEQUENCE: 643

Gly Leu Phe Lys Gly Val Gly Gly Val
 1               5

<210> SEQ ID NO 644
<211> LENGTH: 9
<212> TYPE: PRT
<213> ORGANISM: Artificial Sequence
<220> FEATURE:
<223> OTHER INFORMATION: Synthetic peptide

<400> SEQUENCE: 644

Gly Leu Gly Gly Gly Gly Phe Gly Val
 1               5

<210> SEQ ID NO 645
<211> LENGTH: 9
<212> TYPE: PRT
<213> ORGANISM: Artificial Sequence
<220> FEATURE:
<223> OTHER INFORMATION: Synthetic peptide

<400> SEQUENCE: 645

Gly Leu Leu Gly Gly Gly Val Gly Val
 1               5
```

<210> SEQ ID NO 646
<211> LENGTH: 9
<212> TYPE: PRT
<213> ORGANISM: Artificial Sequence
<220> FEATURE:
<223> OTHER INFORMATION: Synthetic peptide

<400> SEQUENCE: 646

Gly Leu Tyr Gly Gly Gly Gly Gly Val
 1               5

<210> SEQ ID NO 647
<211> LENGTH: 9
<212> TYPE: PRT
<213> ORGANISM: Artificial Sequence
<220> FEATURE:
<223> OTHER INFORMATION: Synthetic peptide

<400> SEQUENCE: 647

Gly Met Phe Gly Gly Gly Gly Gly Val
 1               5

<210> SEQ ID NO 648
<211> LENGTH: 9
<212> TYPE: PRT
<213> ORGANISM: Artificial Sequence
<220> FEATURE:
<223> OTHER INFORMATION: Synthetic peptide

<400> SEQUENCE: 648

Gly Met Phe Gly Gly Val Gly Gly Val
 1               5

<210> SEQ ID NO 649
<211> LENGTH: 9
<212> TYPE: PRT
<213> ORGANISM: Artificial Sequence
<220> FEATURE:
<223> OTHER INFORMATION: Synthetic peptide

<400> SEQUENCE: 649

Gly Gln Phe Gly Gly Val Gly Gly Val
 1               5

<210> SEQ ID NO 650
<211> LENGTH: 9
<212> TYPE: PRT
<213> ORGANISM: Artificial Sequence
<220> FEATURE:
<223> OTHER INFORMATION: Synthetic peptide

<400> SEQUENCE: 650

Gly Val Phe Gly Gly Val Gly Gly Val
 1               5

<210> SEQ ID NO 651
<211> LENGTH: 9
<212> TYPE: PRT
<213> ORGANISM: Artificial Sequence
<220> FEATURE:
<223> OTHER INFORMATION: Synthetic peptide

<400> SEQUENCE: 651

Lys Leu Phe Gly Gly Gly Gly Gly Val
 1               5

```
<210> SEQ ID NO 652
<211> LENGTH: 9
<212> TYPE: PRT
<213> ORGANISM: Artificial Sequence
<220> FEATURE:
<223> OTHER INFORMATION: Synthetic peptide

<400> SEQUENCE: 652

Lys Leu Phe Gly Gly Val Gly Gly Val
 1               5

<210> SEQ ID NO 653
<211> LENGTH: 9
<212> TYPE: PRT
<213> ORGANISM: Artificial Sequence
<220> FEATURE:
<223> OTHER INFORMATION: Synthetic peptide

<400> SEQUENCE: 653

Ala Ile Leu Gly Phe Val Phe Thr Leu
 1               5

<210> SEQ ID NO 654
<211> LENGTH: 9
<212> TYPE: PRT
<213> ORGANISM: Artificial Sequence
<220> FEATURE:
<223> OTHER INFORMATION: Synthetic peptide

<400> SEQUENCE: 654

Gly Ala Ile Gly Phe Val Phe Thr Leu
 1               5

<210> SEQ ID NO 655
<211> LENGTH: 9
<212> TYPE: PRT
<213> ORGANISM: Artificial Sequence
<220> FEATURE:
<223> OTHER INFORMATION: Synthetic peptide

<400> SEQUENCE: 655

Gly Ala Leu Gly Phe Val Phe Thr Leu
 1               5

<210> SEQ ID NO 656
<211> LENGTH: 9
<212> TYPE: PRT
<213> ORGANISM: Artificial Sequence
<220> FEATURE:
<223> OTHER INFORMATION: Synthetic peptide

<400> SEQUENCE: 656

Gly Glu Leu Gly Phe Val Phe Thr Leu
 1               5

<210> SEQ ID NO 657
<211> LENGTH: 9
<212> TYPE: PRT
<213> ORGANISM: Artificial Sequence
<220> FEATURE:
<223> OTHER INFORMATION: Synthetic peptide

<400> SEQUENCE: 657

Gly Ile Ala Gly Phe Val Phe Thr Leu
 1               5

<210> SEQ ID NO 658
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 658

Gly Ile Glu Gly Phe Val Phe Thr Leu
  1               5

<210> SEQ ID NO 659
<211> LENGTH: 9
<212> TYPE: PRT
<213> ORGANISM: Artificial Sequence
<220> FEATURE:
<223> OTHER INFORMATION: Synthetic peptide

<400> SEQUENCE: 659

Gly Ile Leu Ala Phe Val Phe Thr Leu
  1               5

<210> SEQ ID NO 660
<211> LENGTH: 9
<212> TYPE: PRT
<213> ORGANISM: Artificial Sequence
<220> FEATURE:
<223> OTHER INFORMATION: Synthetic peptide

<400> SEQUENCE: 660

Gly Ile Leu Gly Ala Val Phe Thr Leu
  1               5

<210> SEQ ID NO 661
<211> LENGTH: 9
<212> TYPE: PRT
<213> ORGANISM: Artificial Sequence
<220> FEATURE:
<223> OTHER INFORMATION: Synthetic peptide

<400> SEQUENCE: 661

Gly Ile Leu Gly Glu Val Phe Thr Leu
  1               5

<210> SEQ ID NO 662
<211> LENGTH: 9
<212> TYPE: PRT
<213> ORGANISM: Artificial Sequence
<220> FEATURE:
<223> OTHER INFORMATION: Synthetic peptide

<400> SEQUENCE: 662

Gly Ile Leu Phe Gly Ala Phe Thr Leu
  1               5

<210> SEQ ID NO 663
<211> LENGTH: 9
<212> TYPE: PRT
<213> ORGANISM: Artificial Sequence
<220> FEATURE:
<223> OTHER INFORMATION: Synthetic peptide

<400> SEQUENCE: 663

Gly Ile Leu Gly Phe Glu Phe Thr Leu
  1               5

<210> SEQ ID NO 664
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 664

Gly Ile Leu Gly Phe Lys Phe Thr Leu
 1               5

<210> SEQ ID NO 665
<211> LENGTH: 9
<212> TYPE: PRT
<213> ORGANISM: Artificial Sequence
<220> FEATURE:
<223> OTHER INFORMATION: Synthetic peptide

<400> SEQUENCE: 665

Gly Ile Leu Gly Phe Val Ala Thr Leu
 1               5

<210> SEQ ID NO 666
<211> LENGTH: 9
<212> TYPE: PRT
<213> ORGANISM: Artificial Sequence
<220> FEATURE:
<223> OTHER INFORMATION: Synthetic peptide

<400> SEQUENCE: 666

Gly Ile Leu Gly Phe Val Glu Thr Leu
 1               5

<210> SEQ ID NO 667
<211> LENGTH: 9
<212> TYPE: PRT
<213> ORGANISM: Artificial Sequence
<220> FEATURE:
<223> OTHER INFORMATION: Synthetic peptide

<400> SEQUENCE: 667

Gly Ile Leu Gly Phe Val Phe Ala Leu
 1               5

<210> SEQ ID NO 668
<211> LENGTH: 9
<212> TYPE: PRT
<213> ORGANISM: Artificial Sequence
<220> FEATURE:
<223> OTHER INFORMATION: Synthetic peptide

<400> SEQUENCE: 668

Gly Ile Leu Gly Phe Val Phe Glu Leu
 1               5

<210> SEQ ID NO 669
<211> LENGTH: 9
<212> TYPE: PRT
<213> ORGANISM: Artificial Sequence
<220> FEATURE:
<223> OTHER INFORMATION: Synthetic peptide

<400> SEQUENCE: 669

Gly Ile Leu Gly Phe Val Phe Lys Leu
 1               5

<210> SEQ ID NO 670
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 670

Gly Ile Leu Gly Phe Val Phe Thr Ala
1               5

<210> SEQ ID NO 671
<211> LENGTH: 9
<212> TYPE: PRT
<213> ORGANISM: Artificial Sequence
<220> FEATURE:
<223> OTHER INFORMATION: Synthetic peptide

<400> SEQUENCE: 671

Gly Ile Leu Gly Phe Val Phe Thr Leu
1               5

<210> SEQ ID NO 672
<211> LENGTH: 9
<212> TYPE: PRT
<213> ORGANISM: Artificial Sequence
<220> FEATURE:
<223> OTHER INFORMATION: Synthetic peptide

<400> SEQUENCE: 672

Gly Ile Leu Gly Phe Val Phe Val Leu
1               5

<210> SEQ ID NO 673
<211> LENGTH: 9
<212> TYPE: PRT
<213> ORGANISM: Artificial Sequence
<220> FEATURE:
<223> OTHER INFORMATION: Synthetic peptide

<400> SEQUENCE: 673

Gly Ile Leu Gly Phe Val Lys Thr Leu
1               5

<210> SEQ ID NO 674
<211> LENGTH: 9
<212> TYPE: PRT
<213> ORGANISM: Artificial Sequence
<220> FEATURE:
<223> OTHER INFORMATION: Synthetic peptide

<400> SEQUENCE: 674

Gly Ile Leu Gly Lys Val Phe Thr Leu
1               5

<210> SEQ ID NO 675
<211> LENGTH: 9
<212> TYPE: PRT
<213> ORGANISM: Artificial Sequence
<220> FEATURE:
<223> OTHER INFORMATION: Synthetic peptide

<400> SEQUENCE: 675

Gly Ile Leu Lys Phe Val Phe Thr Leu
1               5

<210> SEQ ID NO 676
<211> LENGTH: 9
<212> TYPE: PRT
<213> ORGANISM: Artificial Sequence
<220> FEATURE:
<223> OTHER INFORMATION: Synthetic peptide

<400> SEQUENCE: 676
```

Gly Ile Leu Pro Phe Val Phe Thr Leu
1               5

<210> SEQ ID NO 677
<211> LENGTH: 9
<212> TYPE: PRT
<213> ORGANISM: Artificial Sequence
<220> FEATURE:
<223> OTHER INFORMATION: Synthetic peptide

<400> SEQUENCE: 677

Gly Ile Val Gly Phe Val Phe Thr Leu
1               5

<210> SEQ ID NO 678
<211> LENGTH: 9
<212> TYPE: PRT
<213> ORGANISM: Artificial Sequence
<220> FEATURE:
<223> OTHER INFORMATION: Synthetic peptide

<400> SEQUENCE: 678

Gly Lys Leu Gly Phe Val Phe Thr Leu
1               5

<210> SEQ ID NO 679
<211> LENGTH: 9
<212> TYPE: PRT
<213> ORGANISM: Artificial Sequence
<220> FEATURE:
<223> OTHER INFORMATION: Synthetic peptide

<400> SEQUENCE: 679

Gly Leu Leu Gly Phe Val Phe Thr Leu
1               5

<210> SEQ ID NO 680
<211> LENGTH: 9
<212> TYPE: PRT
<213> ORGANISM: Artificial Sequence
<220> FEATURE:
<223> OTHER INFORMATION: Synthetic peptide

<400> SEQUENCE: 680

Gly Gln Leu Gly Phe Val Phe Thr Leu
1               5

<210> SEQ ID NO 681
<211> LENGTH: 9
<212> TYPE: PRT
<213> ORGANISM: Artificial Sequence
<220> FEATURE:
<223> OTHER INFORMATION: Synthetic peptide

<400> SEQUENCE: 681

Lys Ala Leu Gly Phe Val Phe Thr Leu
1               5

<210> SEQ ID NO 682
<211> LENGTH: 9
<212> TYPE: PRT
<213> ORGANISM: Artificial Sequence
<220> FEATURE:
<223> OTHER INFORMATION: Synthetic peptide

<400> SEQUENCE: 682

Lys Ile Leu Gly Phe Val Phe Thr Leu

```
<210> SEQ ID NO 683
<211> LENGTH: 9
<212> TYPE: PRT
<213> ORGANISM: Artificial Sequence
<220> FEATURE:
<223> OTHER INFORMATION: Synthetic peptide

<400> SEQUENCE: 683

Lys Ile Leu Gly Lys Val Phe Thr Leu
1               5

<210> SEQ ID NO 684
<211> LENGTH: 9
<212> TYPE: PRT
<213> ORGANISM: Artificial Sequence
<220> FEATURE:
<223> OTHER INFORMATION: Synthetic peptide

<400> SEQUENCE: 684

Ala Ile Leu Leu Gly Val Phe Met Leu
1               5

<210> SEQ ID NO 685
<211> LENGTH: 9
<212> TYPE: PRT
<213> ORGANISM: Artificial Sequence
<220> FEATURE:
<223> OTHER INFORMATION: Synthetic peptide

<400> SEQUENCE: 685

Ala Ile Tyr Lys Arg Trp Ile Ile Leu
1               5

<210> SEQ ID NO 686
<211> LENGTH: 9
<212> TYPE: PRT
<213> ORGANISM: Artificial Sequence
<220> FEATURE:
<223> OTHER INFORMATION: Synthetic peptide

<400> SEQUENCE: 686

Ala Leu Phe Phe Phe Asp Ile Asp Leu
1               5

<210> SEQ ID NO 687
<211> LENGTH: 9
<212> TYPE: PRT
<213> ORGANISM: Artificial Sequence
<220> FEATURE:
<223> OTHER INFORMATION: Synthetic peptide

<400> SEQUENCE: 687

Ala Thr Val Glu Leu Leu Ser Glu Leu
1               5

<210> SEQ ID NO 688
<211> LENGTH: 9
<212> TYPE: PRT
<213> ORGANISM: Artificial Sequence
<220> FEATURE:
<223> OTHER INFORMATION: Synthetic peptide

<400> SEQUENCE: 688

Cys Leu Phe Gly Tyr Pro Val Tyr Val
1               5
```

<210> SEQ ID NO 689
<211> LENGTH: 9
<212> TYPE: PRT
<213> ORGANISM: Artificial Sequence
<220> FEATURE:
<223> OTHER INFORMATION: Synthetic peptide

<400> SEQUENCE: 689

Phe Ile Phe Pro Asn Tyr Thr Ile Val
 1               5

<210> SEQ ID NO 690
<211> LENGTH: 9
<212> TYPE: PRT
<213> ORGANISM: Artificial Sequence
<220> FEATURE:
<223> OTHER INFORMATION: Synthetic peptide

<400> SEQUENCE: 690

Ile Ile Ser Leu Trp Asp Ser Gln Leu
 1               5

<210> SEQ ID NO 691
<211> LENGTH: 9
<212> TYPE: PRT
<213> ORGANISM: Artificial Sequence
<220> FEATURE:
<223> OTHER INFORMATION: Synthetic peptide

<400> SEQUENCE: 691

Ile Leu Ala Ser Leu Phe Ala Ala Val
 1               5

<210> SEQ ID NO 692
<211> LENGTH: 9
<212> TYPE: PRT
<213> ORGANISM: Artificial Sequence
<220> FEATURE:
<223> OTHER INFORMATION: Synthetic peptide

<400> SEQUENCE: 692

Ile Leu Glu Ser Leu Phe Ala Ala Val
 1               5

<210> SEQ ID NO 693
<211> LENGTH: 9
<212> TYPE: PRT
<213> ORGANISM: Artificial Sequence
<220> FEATURE:
<223> OTHER INFORMATION: Synthetic peptide

<400> SEQUENCE: 693

Lys Leu Gly Glu Phe Phe Asn Gln Met
 1               5

<210> SEQ ID NO 694
<211> LENGTH: 9
<212> TYPE: PRT
<213> ORGANISM: Artificial Sequence
<220> FEATURE:
<223> OTHER INFORMATION: Synthetic peptide

<400> SEQUENCE: 694

Lys Leu Gly Glu Phe Tyr Asn Gln Met
 1               5

<210> SEQ ID NO 695

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 695

Leu Leu Phe Gly Tyr Pro Val Tyr Val
 1               5

<210> SEQ ID NO 696
<211> LENGTH: 9
<212> TYPE: PRT
<213> ORGANISM: Artificial Sequence
<220> FEATURE:
<223> OTHER INFORMATION: Synthetic peptide

<400> SEQUENCE: 696

Leu Leu Trp Lys Gly Glu Gly Ala Val
 1               5

<210> SEQ ID NO 697
<211> LENGTH: 9
<212> TYPE: PRT
<213> ORGANISM: Artificial Sequence
<220> FEATURE:
<223> OTHER INFORMATION: Synthetic peptide

<400> SEQUENCE: 697

Leu Met Phe Gly Tyr Pro Val Tyr Val
 1               5

<210> SEQ ID NO 698
<211> LENGTH: 9
<212> TYPE: PRT
<213> ORGANISM: Artificial Sequence
<220> FEATURE:
<223> OTHER INFORMATION: Synthetic peptide

<400> SEQUENCE: 698

Leu Asn Phe Gly Tyr Pro Val Tyr Val
 1               5

<210> SEQ ID NO 699
<211> LENGTH: 9
<212> TYPE: PRT
<213> ORGANISM: Artificial Sequence
<220> FEATURE:
<223> OTHER INFORMATION: Synthetic peptide

<400> SEQUENCE: 699

Leu Gln Phe Gly Tyr Pro Val Tyr Val
 1               5

<210> SEQ ID NO 700
<211> LENGTH: 9
<212> TYPE: PRT
<213> ORGANISM: Artificial Sequence
<220> FEATURE:
<223> OTHER INFORMATION: Synthetic peptide

<400> SEQUENCE: 700

Asn Ile Val Ala His Thr Phe Lys Val
 1               5

<210> SEQ ID NO 701
<211> LENGTH: 8
<212> TYPE: PRT
```

<213> ORGANISM: Artificial Sequence
<220> FEATURE:
<223> OTHER INFORMATION: Synthetic peptide

<400> SEQUENCE: 701

Asn Leu Pro Met Val Ala Thr Val
 1               5

<210> SEQ ID NO 702
<211> LENGTH: 9
<212> TYPE: PRT
<213> ORGANISM: Artificial Sequence
<220> FEATURE:
<223> OTHER INFORMATION: Synthetic peptide

<400> SEQUENCE: 702

Gln Met Leu Leu Ala Ile Ala Arg Leu
 1               5

<210> SEQ ID NO 703
<211> LENGTH: 9
<212> TYPE: PRT
<213> ORGANISM: Artificial Sequence
<220> FEATURE:
<223> OTHER INFORMATION: Synthetic peptide

<400> SEQUENCE: 703

Gln Met Trp Gln Ala Arg Leu Thr Val
 1               5

<210> SEQ ID NO 704
<211> LENGTH: 9
<212> TYPE: PRT
<213> ORGANISM: Artificial Sequence
<220> FEATURE:
<223> OTHER INFORMATION: Synthetic peptide

<400> SEQUENCE: 704

Arg Leu Leu Gln Thr Gly Ile His Val
 1               5

<210> SEQ ID NO 705
<211> LENGTH: 9
<212> TYPE: PRT
<213> ORGANISM: Artificial Sequence
<220> FEATURE:
<223> OTHER INFORMATION: Synthetic peptide

<400> SEQUENCE: 705

Arg Leu Val Asn Gly Ser Leu Ala Leu
 1               5

<210> SEQ ID NO 706
<211> LENGTH: 9
<212> TYPE: PRT
<213> ORGANISM: Artificial Sequence
<220> FEATURE:
<223> OTHER INFORMATION: Synthetic peptide

<400> SEQUENCE: 706

Ser Leu Tyr Asn Thr Val Ala Thr Leu
 1               5

<210> SEQ ID NO 707
<211> LENGTH: 9
<212> TYPE: PRT
<213> ORGANISM: Artificial Sequence
<220> FEATURE:

<223> OTHER INFORMATION: Synthetic peptide

<400> SEQUENCE: 707

Thr Leu Asn Ala Trp Val Lys Val Val
1               5

<210> SEQ ID NO 708
<211> LENGTH: 9
<212> TYPE: PRT
<213> ORGANISM: Artificial Sequence
<220> FEATURE:
<223> OTHER INFORMATION: Synthetic peptide

<400> SEQUENCE: 708

Trp Leu Tyr Arg Glu Thr Cys Asn Leu
1               5

<210> SEQ ID NO 709
<211> LENGTH: 9
<212> TYPE: PRT
<213> ORGANISM: Artificial Sequence
<220> FEATURE:
<223> OTHER INFORMATION: Synthetic peptide

<400> SEQUENCE: 709

Tyr Leu Phe Lys Arg Met Ile Asp Leu
1               5

<210> SEQ ID NO 710
<211> LENGTH: 9
<212> TYPE: PRT
<213> ORGANISM: Artificial Sequence
<220> FEATURE:
<223> OTHER INFORMATION: Synthetic peptide

<400> SEQUENCE: 710

Gly Ala Phe Gly Gly Val Gly Gly Val
1               5

<210> SEQ ID NO 711
<211> LENGTH: 9
<212> TYPE: PRT
<213> ORGANISM: Artificial Sequence
<220> FEATURE:
<223> OTHER INFORMATION: Synthetic peptide

<400> SEQUENCE: 711

Gly Ala Phe Gly Gly Val Gly Gly Tyr
1               5

<210> SEQ ID NO 712
<211> LENGTH: 9
<212> TYPE: PRT
<213> ORGANISM: Artificial Sequence
<220> FEATURE:
<223> OTHER INFORMATION: Synthetic peptide

<400> SEQUENCE: 712

Gly Glu Phe Gly Gly Val Gly Gly Val
1               5

<210> SEQ ID NO 713
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 713

Gly Gly Phe Gly Gly Val Gly Gly Val
 1               5

<210> SEQ ID NO 714
<211> LENGTH: 9
<212> TYPE: PRT
<213> ORGANISM: Artificial Sequence
<220> FEATURE:
<223> OTHER INFORMATION: Synthetic peptide

<400> SEQUENCE: 714

Gly Ile Phe Gly Gly Gly Gly Gly Val
 1               5

<210> SEQ ID NO 715
<211> LENGTH: 9
<212> TYPE: PRT
<213> ORGANISM: Artificial Sequence
<220> FEATURE:
<223> OTHER INFORMATION: Synthetic peptide

<400> SEQUENCE: 715

Gly Ile Gly Gly Phe Gly Gly Gly Leu
 1               5

<210> SEQ ID NO 716
<211> LENGTH: 9
<212> TYPE: PRT
<213> ORGANISM: Artificial Sequence
<220> FEATURE:
<223> OTHER INFORMATION: Synthetic peptide

<400> SEQUENCE: 716

Gly Ile Gly Gly Gly Gly Gly Gly Leu
 1               5

<210> SEQ ID NO 717
<211> LENGTH: 9
<212> TYPE: PRT
<213> ORGANISM: Artificial Sequence
<220> FEATURE:
<223> OTHER INFORMATION: Synthetic peptide

<400> SEQUENCE: 717

Gly Leu Asp Gly Gly Gly Gly Gly Val
 1               5

<210> SEQ ID NO 718
<211> LENGTH: 9
<212> TYPE: PRT
<213> ORGANISM: Artificial Sequence
<220> FEATURE:
<223> OTHER INFORMATION: Synthetic peptide

<400> SEQUENCE: 718

Gly Leu Asp Gly Lys Gly Gly Gly Val
 1               5

<210> SEQ ID NO 719
<211> LENGTH: 9
<212> TYPE: PRT
<213> ORGANISM: Artificial Sequence
<220> FEATURE:
<223> OTHER INFORMATION: Synthetic peptide

<400> SEQUENCE: 719
```

```
Gly Leu Asp Lys Lys Gly Gly Gly Val
1               5
```

<210> SEQ ID NO 720
<211> LENGTH: 9
<212> TYPE: PRT
<213> ORGANISM: Artificial Sequence
<220> FEATURE:
<223> OTHER INFORMATION: Synthetic peptide

<400> SEQUENCE: 720

```
Gly Leu Phe Gly Gly Gly Phe Gly Phe
1               5
```

<210> SEQ ID NO 721
<211> LENGTH: 9
<212> TYPE: PRT
<213> ORGANISM: Artificial Sequence
<220> FEATURE:
<223> OTHER INFORMATION: Synthetic peptide

<400> SEQUENCE: 721

```
Gly Leu Phe Gly Gly Gly Phe Gly Gly
1               5
```

<210> SEQ ID NO 722
<211> LENGTH: 9
<212> TYPE: PRT
<213> ORGANISM: Artificial Sequence
<220> FEATURE:
<223> OTHER INFORMATION: Synthetic peptide

<400> SEQUENCE: 722

```
Gly Leu Phe Gly Gly Gly Phe Gly Asn
1               5
```

<210> SEQ ID NO 723
<211> LENGTH: 9
<212> TYPE: PRT
<213> ORGANISM: Artificial Sequence
<220> FEATURE:
<223> OTHER INFORMATION: Synthetic peptide

<400> SEQUENCE: 723

```
Gly Leu Phe Gly Gly Gly Phe Gly Ser
1               5
```

<210> SEQ ID NO 724
<211> LENGTH: 9
<212> TYPE: PRT
<213> ORGANISM: Artificial Sequence
<220> FEATURE:
<223> OTHER INFORMATION: Synthetic peptide

<400> SEQUENCE: 724

```
Gly Leu Phe Gly Gly Gly Gly Gly Ile
1               5
```

<210> SEQ ID NO 725
<211> LENGTH: 9
<212> TYPE: PRT
<213> ORGANISM: Artificial Sequence
<220> FEATURE:
<223> OTHER INFORMATION: Synthetic peptide

<400> SEQUENCE: 725

```
Gly Leu Phe Gly Gly Gly Gly Gly Met
1               5
```

```
<210> SEQ ID NO 726
<211> LENGTH: 9
<212> TYPE: PRT
<213> ORGANISM: Artificial Sequence
<220> FEATURE:
<223> OTHER INFORMATION: Synthetic peptide

<400> SEQUENCE: 726

Gly Leu Phe Gly Gly Gly Gly Gly Thr
 1               5

<210> SEQ ID NO 727
<211> LENGTH: 9
<212> TYPE: PRT
<213> ORGANISM: Artificial Sequence
<220> FEATURE:
<223> OTHER INFORMATION: Synthetic peptide

<400> SEQUENCE: 727

Gly Leu Phe Gly Gly Gly Gly Gly Tyr
 1               5

<210> SEQ ID NO 728
<211> LENGTH: 9
<212> TYPE: PRT
<213> ORGANISM: Artificial Sequence
<220> FEATURE:
<223> OTHER INFORMATION: Synthetic peptide

<400> SEQUENCE: 728

Gly Leu Gly Phe Gly Gly Gly Gly Val
 1               5

<210> SEQ ID NO 729
<211> LENGTH: 9
<212> TYPE: PRT
<213> ORGANISM: Artificial Sequence
<220> FEATURE:
<223> OTHER INFORMATION: Synthetic peptide

<400> SEQUENCE: 729

Gly Leu Gly Gly Phe Gly Gly Gly Val
 1               5

<210> SEQ ID NO 730
<211> LENGTH: 9
<212> TYPE: PRT
<213> ORGANISM: Artificial Sequence
<220> FEATURE:
<223> OTHER INFORMATION: Synthetic peptide

<400> SEQUENCE: 730

Gly Leu Gly Gly Gly Phe Gly Gly Val
 1               5

<210> SEQ ID NO 731
<211> LENGTH: 9
<212> TYPE: PRT
<213> ORGANISM: Artificial Sequence
<220> FEATURE:
<223> OTHER INFORMATION: Synthetic peptide

<400> SEQUENCE: 731

Gly Leu Gly Gly Gly Gly Gly Phe Val
 1               5
```

```
<210> SEQ ID NO 732
<211> LENGTH: 9
<212> TYPE: PRT
<213> ORGANISM: Artificial Sequence
<220> FEATURE:
<223> OTHER INFORMATION: Synthetic peptide

<400> SEQUENCE: 732

Gly Leu Gly Gly Gly Gly Gly Gly Tyr
 1               5

<210> SEQ ID NO 733
<211> LENGTH: 9
<212> TYPE: PRT
<213> ORGANISM: Artificial Sequence
<220> FEATURE:
<223> OTHER INFORMATION: Synthetic peptide

<400> SEQUENCE: 733

Gly Leu Gly Gly Gly Val Gly Gly Val
 1               5

<210> SEQ ID NO 734
<211> LENGTH: 9
<212> TYPE: PRT
<213> ORGANISM: Artificial Sequence
<220> FEATURE:
<223> OTHER INFORMATION: Synthetic peptide

<400> SEQUENCE: 734

Gly Leu Leu Gly Gly Gly Gly Gly Val
 1               5

<210> SEQ ID NO 735
<211> LENGTH: 9
<212> TYPE: PRT
<213> ORGANISM: Artificial Sequence
<220> FEATURE:
<223> OTHER INFORMATION: Synthetic peptide

<400> SEQUENCE: 735

Gly Leu Pro Gly Gly Gly Gly Gly Val
 1               5

<210> SEQ ID NO 736
<211> LENGTH: 9
<212> TYPE: PRT
<213> ORGANISM: Artificial Sequence
<220> FEATURE:
<223> OTHER INFORMATION: Synthetic peptide

<400> SEQUENCE: 736

Gly Asn Phe Gly Gly Val Gly Gly Val
 1               5

<210> SEQ ID NO 737
<211> LENGTH: 9
<212> TYPE: PRT
<213> ORGANISM: Artificial Sequence
<220> FEATURE:
<223> OTHER INFORMATION: Synthetic peptide

<400> SEQUENCE: 737

Gly Ser Phe Gly Gly Val Gly Gly Val
 1               5

<210> SEQ ID NO 738
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 738

Gly Thr Phe Gly Gly Val Gly Gly Val
 1               5

<210> SEQ ID NO 739
<211> LENGTH: 9
<212> TYPE: PRT
<213> ORGANISM: Artificial Sequence
<220> FEATURE:
<223> OTHER INFORMATION: Synthetic peptide

<400> SEQUENCE: 739

Ala Gly Asn Ser Ala Tyr Glu Tyr Val
 1               5

<210> SEQ ID NO 740
<211> LENGTH: 9
<212> TYPE: PRT
<213> ORGANISM: Artificial Sequence
<220> FEATURE:
<223> OTHER INFORMATION: Synthetic peptide

<400> SEQUENCE: 740

Gly Leu Phe Pro Gly Gln Phe Ala Tyr
 1               5

<210> SEQ ID NO 741
<211> LENGTH: 9
<212> TYPE: PRT
<213> ORGANISM: Artificial Sequence
<220> FEATURE:
<223> OTHER INFORMATION: Synthetic peptide

<400> SEQUENCE: 741

His Ile Leu Leu Gly Val Phe Met Leu
 1               5

<210> SEQ ID NO 742
<211> LENGTH: 9
<212> TYPE: PRT
<213> ORGANISM: Artificial Sequence
<220> FEATURE:
<223> OTHER INFORMATION: Synthetic peptide

<400> SEQUENCE: 742

Ile Leu Glu Ser Leu Phe Arg Ala Val
 1               5

<210> SEQ ID NO 743
<211> LENGTH: 9
<212> TYPE: PRT
<213> ORGANISM: Artificial Sequence
<220> FEATURE:
<223> OTHER INFORMATION: Synthetic peptide

<400> SEQUENCE: 743

Lys Lys Lys Tyr Lys Leu Lys His Ile
 1               5

<210> SEQ ID NO 744
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 744

Met Leu Ala Ser Ile Asp Leu Lys Tyr
 1               5

<210> SEQ ID NO 745
<211> LENGTH: 9
<212> TYPE: PRT
<213> ORGANISM: Artificial Sequence
<220> FEATURE:
<223> OTHER INFORMATION: Synthetic peptide

<400> SEQUENCE: 745

Met Leu Glu Arg Glu Leu Val Arg Lys
 1               5

<210> SEQ ID NO 746
<211> LENGTH: 9
<212> TYPE: PRT
<213> ORGANISM: Artificial Sequence
<220> FEATURE:
<223> OTHER INFORMATION: Synthetic peptide

<400> SEQUENCE: 746

Lys Leu Phe Gly Phe Val Phe Thr Val
 1               5

<210> SEQ ID NO 747
<211> LENGTH: 9
<212> TYPE: PRT
<213> ORGANISM: Artificial Sequence
<220> FEATURE:
<223> OTHER INFORMATION: Synthetic peptide

<400> SEQUENCE: 747

Ile Leu Asp Lys Lys Val Glu Lys Val
 1               5

<210> SEQ ID NO 748
<211> LENGTH: 9
<212> TYPE: PRT
<213> ORGANISM: Artificial Sequence
<220> FEATURE:
<223> OTHER INFORMATION: Synthetic peptide

<400> SEQUENCE: 748

Ile Leu Lys Glu Pro Val His Gly Val
 1               5

<210> SEQ ID NO 749
<211> LENGTH: 9
<212> TYPE: PRT
<213> ORGANISM: Artificial Sequence
<220> FEATURE:
<223> OTHER INFORMATION: Synthetic peptide

<400> SEQUENCE: 749

Ala Leu Phe Ala Ala Ala Ala Ala Tyr
 1               5

<210> SEQ ID NO 750
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 750

Gly Ile Gly Phe Gly Gly Gly Gly Leu
  1               5

<210> SEQ ID NO 751
<211> LENGTH: 9
<212> TYPE: PRT
<213> ORGANISM: Artificial Sequence
<220> FEATURE:
<223> OTHER INFORMATION: Synthetic peptide

<400> SEQUENCE: 751

Gly Lys Phe Gly Gly Val Gly Gly Val
  1               5

<210> SEQ ID NO 752
<211> LENGTH: 9
<212> TYPE: PRT
<213> ORGANISM: Artificial Sequence
<220> FEATURE:
<223> OTHER INFORMATION: Synthetic peptide

<400> SEQUENCE: 752

Gly Leu Phe Gly Gly Gly Gly Gly Lys
  1               5

<210> SEQ ID NO 753
<211> LENGTH: 9
<212> TYPE: PRT
<213> ORGANISM: Artificial Sequence
<220> FEATURE:
<223> OTHER INFORMATION: Synthetic peptide

<400> SEQUENCE: 753

Glu Ile Leu Gly Phe Val Phe Thr Leu
  1               5

<210> SEQ ID NO 754
<211> LENGTH: 9
<212> TYPE: PRT
<213> ORGANISM: Artificial Sequence
<220> FEATURE:
<223> OTHER INFORMATION: Synthetic peptide

<400> SEQUENCE: 754

Gly Ile Lys Gly Phe Val Phe Thr Leu
  1               5

<210> SEQ ID NO 755
<211> LENGTH: 9
<212> TYPE: PRT
<213> ORGANISM: Artificial Sequence
<220> FEATURE:
<223> OTHER INFORMATION: Synthetic peptide

<400> SEQUENCE: 755

Gly Gln Leu Gly Phe Val Phe Thr Lys
  1               5

<210> SEQ ID NO 756
<211> LENGTH: 9
<212> TYPE: PRT
<213> ORGANISM: Artificial Sequence
<220> FEATURE:
<223> OTHER INFORMATION: Synthetic peptide

<400> SEQUENCE: 756
```

Ile Leu Gly Phe Val Phe Thr Leu Thr
1               5

<210> SEQ ID NO 757
<211> LENGTH: 9
<212> TYPE: PRT
<213> ORGANISM: Artificial Sequence
<220> FEATURE:
<223> OTHER INFORMATION: Synthetic peptide

<400> SEQUENCE: 757

Lys Ile Leu Gly Phe Val Phe Thr Lys
1               5

<210> SEQ ID NO 758
<211> LENGTH: 9
<212> TYPE: PRT
<213> ORGANISM: Artificial Sequence
<220> FEATURE:
<223> OTHER INFORMATION: Synthetic peptide

<400> SEQUENCE: 758

Lys Lys Leu Gly Phe Val Phe Thr Leu
1               5

<210> SEQ ID NO 759
<211> LENGTH: 9
<212> TYPE: PRT
<213> ORGANISM: Artificial Sequence
<220> FEATURE:
<223> OTHER INFORMATION: Synthetic peptide

<400> SEQUENCE: 759

Lys Leu Phe Glu Lys Val Tyr Asn Tyr
1               5

<210> SEQ ID NO 760
<211> LENGTH: 9
<212> TYPE: PRT
<213> ORGANISM: Artificial Sequence
<220> FEATURE:
<223> OTHER INFORMATION: Synthetic peptide

<400> SEQUENCE: 760

Leu Arg Phe Gly Tyr Pro Val Tyr Val
1               5

<210> SEQ ID NO 761
<211> LENGTH: 9
<212> TYPE: PRT
<213> ORGANISM: Homo sapiens

<400> SEQUENCE: 761

Ile Arg Arg Gly Val Met Leu Ala Val
1               5

<210> SEQ ID NO 762
<211> LENGTH: 9
<212> TYPE: PRT
<213> ORGANISM: Homo sapiens

<400> SEQUENCE: 762

Lys Arg Ile Gln Glu Ile Ile Glu Gln
1               5

<210> SEQ ID NO 763

<211> LENGTH: 9
<212> TYPE: PRT
<213> ORGANISM: Homo sapiens

<400> SEQUENCE: 763

Lys Arg Thr Leu Lys Ile Pro Ala Met
1               5

<210> SEQ ID NO 764
<211> LENGTH: 9
<212> TYPE: PRT
<213> ORGANISM: Yersenia Pestis

<400> SEQUENCE: 764

Gly Arg Asn Val Val Leu Asp Lys Ser
1 5

<210> SEQ ID NO 765
<211> LENGTH: 9
<212> TYPE: PRT
<213> ORGANISM: Yersenia Pestis

<400> SEQUENCE: 765

Lys Arg Gly Ile Asp Lys Ala Val Ile
1 5

<210> SEQ ID NO 766
<211> LENGTH: 9
<212> TYPE: PRT
<213> ORGANISM: Yersenia Pestis

<400> SEQUENCE: 766

Ile Arg Ala Ala Ser Ala Ile Thr Ala
1 5

<210> SEQ ID NO 767
<211> LENGTH: 9
<212> TYPE: PRT
<213> ORGANISM: Yersenia Pestis

<400> SEQUENCE: 767

Arg Arg Lys Ala Met Phe Glu Asp Ile
1 5

<210> SEQ ID NO 768
<211> LENGTH: 8
<212> TYPE: PRT
<213> ORGANISM: Plasmodium Falciparum

<400> SEQUENCE: 768

Lys Pro Lys Asp Glu Leu Asp Tyr
1 5

<210> SEQ ID NO 769
<211> LENGTH: 9
<212> TYPE: PRT
<213> ORGANISM: Influenza

<400> SEQUENCE: 769

Leu Glu Leu Arg Ser Arg Tyr Trp Ala
1 5

<210> SEQ ID NO 770
<211> LENGTH: 10
<212> TYPE: PRT
<213> ORGANISM: Homo sapiens

<400> SEQUENCE: 770

Gly Pro Pro His Ser Asn Asn Phe Gly Tyr
1               5                   10

<210> SEQ ID NO 771
<211> LENGTH: 8
<212> TYPE: PRT
<213> ORGANISM: Rotavirus

<400> SEQUENCE: 771

Ile Ile Tyr Arg Phe Leu Leu Ile
1               5

<210> SEQ ID NO 772
<211> LENGTH: 9
<212> TYPE: PRT
<213> ORGANISM: Homo sapiens

<400> SEQUENCE: 772

Gln Leu Ser Pro Tyr Pro Phe Asp Leu
1               5

<210> SEQ ID NO 773
<211> LENGTH: 8
<212> TYPE: PRT
<213> ORGANISM: Homo sapiens

<400> SEQUENCE: 773

Val Tyr Asp Phe Phe Val Trp Leu
1               5

<210> SEQ ID NO 774
<211> LENGTH: 8
<212> TYPE: PRT
<213> ORGANISM: Homo sapiens

<400> SEQUENCE: 774

Ser Asn Phe Val Phe Ala Gly Ile
1               5

<210> SEQ ID NO 775
<211> LENGTH: 8
<212> TYPE: PRT
<213> ORGANISM: Rotavirus

<400> SEQUENCE: 775

Ser Val Val Glu Phe Ser Ser Leu
1               5

<210> SEQ ID NO 776
<211> LENGTH: 8
<212> TYPE: PRT
<213> ORGANISM: Artificial Sequence
<220> FEATURE:
<223> OTHER INFORMATION: Synthetic peptide

<400> SEQUENCE: 776

Ala His Tyr Leu Phe Arg Asn Leu
1               5

<210> SEQ ID NO 777
<211> LENGTH: 8
<212> TYPE: PRT
<213> ORGANISM: Artificial Sequence
<220> FEATURE:

<223> OTHER INFORMATION: Synthetic peptide

<400> SEQUENCE: 777

Thr His Tyr Leu Phe Arg Asn Leu
1               5

<210> SEQ ID NO 778
<211> LENGTH: 8
<212> TYPE: PRT
<213> ORGANISM: Artificial Sequence
<220> FEATURE:
<223> OTHER INFORMATION: Synthetic peptide

<400> SEQUENCE: 778

Leu Ile Val Ile Tyr Asn Thr Leu
1               5

<210> SEQ ID NO 779
<211> LENGTH: 8
<212> TYPE: PRT
<213> ORGANISM: Artificial Sequence
<220> FEATURE:
<223> OTHER INFORMATION: Synthetic peptide

<400> SEQUENCE: 779

Leu Ile Tyr Glu Phe Asn Thr Leu
1               5

<210> SEQ ID NO 780
<211> LENGTH: 8
<212> TYPE: PRT
<213> ORGANISM: Artificial Sequence
<220> FEATURE:
<223> OTHER INFORMATION: Synthetic peptide

<400> SEQUENCE: 780

Ile Pro Tyr Ile Tyr Asn Thr Leu
1               5

<210> SEQ ID NO 781
<211> LENGTH: 8
<212> TYPE: PRT
<213> ORGANISM: Artificial Sequence
<220> FEATURE:
<223> OTHER INFORMATION: Synthetic peptide

<400> SEQUENCE: 781

Ile Ile Tyr Ile Tyr His Arg Leu
1               5

<210> SEQ ID NO 782
<211> LENGTH: 8
<212> TYPE: PRT
<213> ORGANISM: Artificial Sequence
<220> FEATURE:
<223> OTHER INFORMATION: Synthetic peptide

<400> SEQUENCE: 782

Leu Ile Tyr Ile Phe Asn Thr Leu
1               5

<210> SEQ ID NO 783
<211> LENGTH: 8
<212> TYPE: PRT
<213> ORGANISM: Hepatitis B Virus

<400> SEQUENCE: 783

```
Met Gly Leu Lys Phe Arg Gln Leu
1               5

<210> SEQ ID NO 784
<211> LENGTH: 9
<212> TYPE: PRT
<213> ORGANISM: Homo sapiens

<400> SEQUENCE: 784

Ile Met Ile Lys Phe Arg Asn Arg Leu
1               5

<210> SEQ ID NO 785
<211> LENGTH: 9
<212> TYPE: PRT
<213> ORGANISM: Mus Musculus

<400> SEQUENCE: 785

Trp Met His His Asn Met Asp Leu Ile
1               5

<210> SEQ ID NO 786
<211> LENGTH: 9
<212> TYPE: PRT
<213> ORGANISM: Mus Musculus

<400> SEQUENCE: 786

Lys Tyr Met Cys Asn Ser Ser Cys Met
1               5

<210> SEQ ID NO 787
<211> LENGTH: 9
<212> TYPE: PRT
<213> ORGANISM: Mus Musculus

<400> SEQUENCE: 787

Gly Arg Pro Lys Asn Gly Cys Ile Val
1               5

<210> SEQ ID NO 788
<211> LENGTH: 9
<212> TYPE: PRT
<213> ORGANISM: Artificial Sequence
<220> FEATURE:
<223> OTHER INFORMATION: Synthetic peptide

<400> SEQUENCE: 788

Ala Gln His Pro Asn Ala Glu Leu Leu
1               5

<210> SEQ ID NO 789
<211> LENGTH: 9
<212> TYPE: PRT
<213> ORGANISM: Murine Leukemia Virus

<400> SEQUENCE: 789

Cys Cys Leu Cys Leu Thr Val Phe Leu
1               5

<210> SEQ ID NO 790
<211> LENGTH: 8
<212> TYPE: PRT
<213> ORGANISM: Plasmodium Falciparum

<400> SEQUENCE: 790

Tyr Glu Asn Asp Ile Glu Lys Lys
```

<210> SEQ ID NO 791
<211> LENGTH: 9
<212> TYPE: PRT
<213> ORGANISM: Plasmodium Falciparum

<400> SEQUENCE: 791

Asp Glu Leu Asp Tyr Glu Asn Asp Ile
1               5

<210> SEQ ID NO 792
<211> LENGTH: 9
<212> TYPE: PRT
<213> ORGANISM: Human Immunodeficiency Virus

<400> SEQUENCE: 792

Thr Glu Met Glu Lys Glu Gly Lys Ile
1               5

<210> SEQ ID NO 793
<211> LENGTH: 9
<212> TYPE: PRT
<213> ORGANISM: Rabies

<400> SEQUENCE: 793

Val Glu Ala Glu Ile Ala His Gln Ile
1               5

<210> SEQ ID NO 794
<211> LENGTH: 9
<212> TYPE: PRT
<213> ORGANISM: Influenza A

<400> SEQUENCE: 794

Glu Glu Gly Ala Ile Val Gly Glu Ile
1               5

<210> SEQ ID NO 795
<211> LENGTH: 8
<212> TYPE: PRT
<213> ORGANISM: Mus Musculus

<400> SEQUENCE: 795

Thr Glu Asn Ser Gly Lys Asp Ile
1               5

<210> SEQ ID NO 796
<211> LENGTH: 9
<212> TYPE: PRT
<213> ORGANISM: Artificial Sequence
<220> FEATURE:
<223> OTHER INFORMATION: Synthetic peptide

<400> SEQUENCE: 796

Ala Met Ala Pro Arg Thr Leu Leu Leu
1               5

<210> SEQ ID NO 797
<211> LENGTH: 11
<212> TYPE: PRT
<213> ORGANISM: Homo sapiens

<400> SEQUENCE: 797

Phe Phe Ile Asn Ile Leu Thr Leu Leu Val Pro
1               5                   10

<210> SEQ ID NO 798
<211> LENGTH: 11
<212> TYPE: PRT
<213> ORGANISM: Homo sapiens

<400> SEQUENCE: 798

Phe Phe Ile Asn Ile Leu Thr Leu Leu Val Pro
1               5                   10

<210> SEQ ID NO 799
<211> LENGTH: 16
<212> TYPE: PRT
<213> ORGANISM: Homo sapiens

<400> SEQUENCE: 799

Phe Phe Ile Asn Ile Leu Thr Leu Leu Val Pro Ile Leu Ile Ala Met
1               5                   10                  15

<210> SEQ ID NO 800
<211> LENGTH: 16
<212> TYPE: PRT
<213> ORGANISM: Homo sapiens

<400> SEQUENCE: 800

Phe Phe Ile Asn Ala Leu Thr Leu Leu Val Pro Ile Leu Ile Ala Met
1               5                   10                  15

<210> SEQ ID NO 801
<211> LENGTH: 5
<212> TYPE: PRT
<213> ORGANISM: Homo sapiens

<400> SEQUENCE: 801

Phe Ile Asn Arg Trp
1               5

<210> SEQ ID NO 802
<211> LENGTH: 5
<212> TYPE: PRT
<213> ORGANISM: Listeria Monocytogenes

<400> SEQUENCE: 802

Ile Gly Trp Ile Ile
1               5

<210> SEQ ID NO 803
<211> LENGTH: 12
<212> TYPE: PRT
<213> ORGANISM: Simian Immunodeficiency Virus

<400> SEQUENCE: 803

Glu Gly Cys Thr Pro Tyr Asp Ile Asn Gln Met Leu
1               5                   10

<210> SEQ ID NO 804
<211> LENGTH: 9
<212> TYPE: PRT
<213> ORGANISM: Homo sapiens

<400> SEQUENCE: 804

Ala Leu Ser Arg Lys Val Ala Glu Leu
1               5

<210> SEQ ID NO 805

```
<211> LENGTH: 9
<212> TYPE: PRT
<213> ORGANISM: Homo sapiens

<400> SEQUENCE: 805

Ile Met Pro Lys Ala Gly Leu Leu Ile
1               5

<210> SEQ ID NO 806
<211> LENGTH: 9
<212> TYPE: PRT
<213> ORGANISM: Homo sapiens

<400> SEQUENCE: 806

Lys Ile Trp Glu Glu Leu Ser Val Leu
1               5

<210> SEQ ID NO 807
<211> LENGTH: 10
<212> TYPE: PRT
<213> ORGANISM: Homo sapiens

<400> SEQUENCE: 807

Ala Leu Val Glu Thr Ser Tyr Val Lys Val
1               5                   10

<210> SEQ ID NO 808
<211> LENGTH: 10
<212> TYPE: PRT
<213> ORGANISM: Homo sapiens

<400> SEQUENCE: 808

Thr Leu Val Glu Val Thr Leu Gly Glu Val
1               5                   10

<210> SEQ ID NO 809
<211> LENGTH: 9
<212> TYPE: PRT
<213> ORGANISM: Homo sapiens

<400> SEQUENCE: 809

Ala Leu Ser Arg Lys Val Ala Glu Leu
1               5

<210> SEQ ID NO 810
<211> LENGTH: 9
<212> TYPE: PRT
<213> ORGANISM: Homo sapiens

<400> SEQUENCE: 810

Ile Met Pro Lys Ala Gly Leu Leu Ile
1               5

<210> SEQ ID NO 811
<211> LENGTH: 9
<212> TYPE: PRT
<213> ORGANISM: Homo sapiens

<400> SEQUENCE: 811

Lys Ile Trp Glu Glu Leu Ser Val Leu
1               5

<210> SEQ ID NO 812
<211> LENGTH: 10
<212> TYPE: PRT
<213> ORGANISM: Homo sapiens
```

<400> SEQUENCE: 812

Ala Leu Val Glu Thr Ser Tyr Val Lys Val
1               5                   10

<210> SEQ ID NO 813
<211> LENGTH: 12
<212> TYPE: PRT
<213> ORGANISM: Homo sapiens

<400> SEQUENCE: 813

Lys Gly Ile Leu Gly Phe Val Phe Thr Leu Thr Val
1               5                   10

<210> SEQ ID NO 814
<211> LENGTH: 9
<212> TYPE: PRT
<213> ORGANISM: Homo sapiens

<400> SEQUENCE: 814

Gly Ile Ile Gly Phe Val Phe Thr Ile
1               5

<210> SEQ ID NO 815
<211> LENGTH: 9
<212> TYPE: PRT
<213> ORGANISM: Homo sapiens

<400> SEQUENCE: 815

Gly Ile Ile Gly Phe Val Phe Thr Leu
1               5

<210> SEQ ID NO 816
<211> LENGTH: 9
<212> TYPE: PRT
<213> ORGANISM: Homo sapiens

<400> SEQUENCE: 816

Gly Ile Leu Gly Phe Val Phe Thr Leu
1               5

<210> SEQ ID NO 817
<211> LENGTH: 9
<212> TYPE: PRT
<213> ORGANISM: Homo sapiens

<400> SEQUENCE: 817

Gly Leu Leu Gly Phe Val Phe Thr Leu
1               5

<210> SEQ ID NO 818
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 1, 2, 5, 6, 9
<223> OTHER INFORMATION: Xaa = Any Amino Acid

<400> SEQUENCE: 818

Xaa Xaa Thr Val Xaa Xaa Gly Val Xaa
1               5

<210> SEQ ID NO 819

```
<211> LENGTH: 9
<212> TYPE: PRT
<213> ORGANISM: Homo sapiens

<400> SEQUENCE: 819

Ile Leu Thr Val Ile Leu Gly Val Leu
 1               5

<210> SEQ ID NO 820
<211> LENGTH: 9
<212> TYPE: PRT
<213> ORGANISM: Homo sapiens

<400> SEQUENCE: 820

Tyr Leu Glu Pro Gly Pro Val Thr Ala
 1               5

<210> SEQ ID NO 821
<211> LENGTH: 10
<212> TYPE: PRT
<213> ORGANISM: Homo sapiens

<400> SEQUENCE: 821

Gln Val Pro Leu Arg Pro Met Thr Tyr Lys
 1               5                  10

<210> SEQ ID NO 822
<211> LENGTH: 11
<212> TYPE: PRT
<213> ORGANISM: Homo sapiens

<400> SEQUENCE: 822

Asp Gly Leu Ala Pro Pro Gln His Leu Ile Arg
 1               5                  10

<210> SEQ ID NO 823
<211> LENGTH: 9
<212> TYPE: PRT
<213> ORGANISM: Homo sapiens

<400> SEQUENCE: 823

Leu Leu Gly Arg Asn Ser Phe Glu Val
 1               5

<210> SEQ ID NO 824
<211> LENGTH: 16
<212> TYPE: PRT
<213> ORGANISM: Homo sapiens

<400> SEQUENCE: 824

Glu His Ser Ala Tyr Gly Glu Pro Arg Lys Leu Leu Thr Gln Asp Leu
 1               5                  10                  15

<210> SEQ ID NO 825
<211> LENGTH: 12
<212> TYPE: PRT
<213> ORGANISM: Homo sapiens

<400> SEQUENCE: 825

Glu His Ser Ala Tyr Gly Glu Pro Arg Lys Leu Leu
 1               5                  10

<210> SEQ ID NO 826
<211> LENGTH: 9
<212> TYPE: PRT
<213> ORGANISM: Homo sapiens
```

```
<400> SEQUENCE: 826

Ser Ala Tyr Gly Glu Pro Arg Lys Leu
1               5

<210> SEQ ID NO 827
<211> LENGTH: 8
<212> TYPE: PRT
<213> ORGANISM: Homo sapiens

<400> SEQUENCE: 827

Tyr Arg Pro Arg Pro Arg Arg Tyr
1               5

<210> SEQ ID NO 828
<211> LENGTH: 9
<212> TYPE: PRT
<213> ORGANISM: Homo sapiens

<400> SEQUENCE: 828

Thr Tyr Arg Pro Arg Pro Arg Arg Tyr
1               5

<210> SEQ ID NO 829
<211> LENGTH: 9
<212> TYPE: PRT
<213> ORGANISM: Homo sapiens

<400> SEQUENCE: 829

Tyr Arg Pro Arg Pro Arg Arg Tyr Val
1               5

<210> SEQ ID NO 830
<211> LENGTH: 10
<212> TYPE: PRT
<213> ORGANISM: Homo sapiens

<400> SEQUENCE: 830

Thr Tyr Arg Pro Arg Pro Arg Arg Tyr Val
1               5                   10

<210> SEQ ID NO 831
<211> LENGTH: 9
<212> TYPE: PRT
<213> ORGANISM: Homo sapiens

<400> SEQUENCE: 831

Arg Pro Arg Pro Arg Arg Tyr Val Glu
1               5

<210> SEQ ID NO 832
<211> LENGTH: 15
<212> TYPE: PRT
<213> ORGANISM: Homo sapiens

<400> SEQUENCE: 832

Met Ser Trp Arg Gly Arg Ser Thr Tyr Arg Pro Arg Pro Arg Arg
1               5                   10                  15

<210> SEQ ID NO 833
<211> LENGTH: 16
<212> TYPE: PRT
<213> ORGANISM: Homo sapiens

<400> SEQUENCE: 833
```

```
Thr Tyr Arg Pro Arg Pro Arg Arg Tyr Val Glu Pro Pro Glu Met Ile
1               5                   10                  15
```

<210> SEQ ID NO 834
<211> LENGTH: 3
<212> TYPE: PRT
<213> ORGANISM: Homo sapiens

<400> SEQUENCE: 834

```
Glu Asp Tyr
1
```

<210> SEQ ID NO 835
<211> LENGTH: 9
<212> TYPE: PRT
<213> ORGANISM: Homo sapiens

<400> SEQUENCE: 835

```
Glu Val Val Pro Ile Ser His Leu Tyr
1               5
```

<210> SEQ ID NO 836
<211> LENGTH: 9
<212> TYPE: PRT
<213> ORGANISM: Homo sapiens

<400> SEQUENCE: 836

```
Glu Val Val Arg Ile Gly His Leu Tyr
1               5
```

<210> SEQ ID NO 837
<211> LENGTH: 9
<212> TYPE: PRT
<213> ORGANISM: Homo sapiens

<400> SEQUENCE: 837

```
Glu Val Asp Pro Ile Gly His Leu Tyr
1               5
```

<210> SEQ ID NO 838
<211> LENGTH: 9
<212> TYPE: PRT
<213> ORGANISM: Homo sapiens

<400> SEQUENCE: 838

```
Glu Val Asp Pro Ala Ser Asn Thr Tyr
1               5
```

<210> SEQ ID NO 839
<211> LENGTH: 9
<212> TYPE: PRT
<213> ORGANISM: Homo sapiens

<400> SEQUENCE: 839

```
Glu Val Asp Pro Thr Ser Asn Thr Tyr
1               5
```

<210> SEQ ID NO 840
<211> LENGTH: 9
<212> TYPE: PRT
<213> ORGANISM: Homo sapiens

<400> SEQUENCE: 840

```
Glu Ala Asp Pro Thr Ser Asn Thr Tyr
1               5
```

```
<210> SEQ ID NO 841
<211> LENGTH: 9
<212> TYPE: PRT
<213> ORGANISM: Homo sapiens

<400> SEQUENCE: 841

Glu Val Asp Pro Ile Gly His Val Tyr
 1               5

<210> SEQ ID NO 842
<211> LENGTH: 27
<212> TYPE: DNA
<213> ORGANISM: Homo sapiens

<400> SEQUENCE: 842
gaagtggtcc ccatcagcca cttgtac                                        27

<210> SEQ ID NO 843
<211> LENGTH: 27
<212> TYPE: DNA
<213> ORGANISM: Homo sapiens

<400> SEQUENCE: 843
gaagtggtcc gcatcggcca cttgtac                                        27

<210> SEQ ID NO 844
<211> LENGTH: 27
<212> TYPE: DNA
<213> ORGANISM: Homo sapiens

<400> SEQUENCE: 844
gaagtggacc ccatcggcca cttgtac                                        27

<210> SEQ ID NO 845
<211> LENGTH: 27
<212> TYPE: DNA
<213> ORGANISM: Homo sapiens

<400> SEQUENCE: 845
gaagtggacc ccgccagcaa cacctac                                        27

<210> SEQ ID NO 846
<211> LENGTH: 27
<212> TYPE: DNA
<213> ORGANISM: Homo sapiens

<400> SEQUENCE: 846
gaagtggacc ccaccagcaa cacctac                                        27

<210> SEQ ID NO 847
<211> LENGTH: 27
<212> TYPE: DNA
<213> ORGANISM: Homo sapiens

<400> SEQUENCE: 847
gaagcggacc ccaccagcaa cacctac                                        27

<210> SEQ ID NO 848
<211> LENGTH: 27
<212> TYPE: DNA
<213> ORGANISM: Homo sapiens

<400> SEQUENCE: 848
gaagcggacc ccaccagcaa cacctac                                        27
```

<210> SEQ ID NO 849
<211> LENGTH: 27
<212> TYPE: DNA
<213> ORGANISM: Homo sapiens

<400> SEQUENCE: 849
gaagtggacc ccatcggcca cgtgtac                27

<210> SEQ ID NO 850
<211> LENGTH: 8
<212> TYPE: PRT
<213> ORGANISM: Homo sapiens

<400> SEQUENCE: 850

Glu Ala Asp Pro Thr Gly His Ser
1               5

<210> SEQ ID NO 851
<211> LENGTH: 8
<212> TYPE: PRT
<213> ORGANISM: Homo sapiens

<400> SEQUENCE: 851

Ala Asp Pro Trp Gly His Ser Tyr
1               5

<210> SEQ ID NO 852
<211> LENGTH: 11
<212> TYPE: PRT
<213> ORGANISM: Homo sapiens

<400> SEQUENCE: 852

Ser Thr Leu Val Glu Val Thr Leu Gly Glu Val
1               5                   10

<210> SEQ ID NO 853
<211> LENGTH: 9
<212> TYPE: PRT
<213> ORGANISM: Homo sapiens

<400> SEQUENCE: 853

Leu Val Glu Val Thr Leu Gly Glu Val
1               5

<210> SEQ ID NO 854
<211> LENGTH: 9
<212> TYPE: PRT
<213> ORGANISM: Homo sapiens

<400> SEQUENCE: 854

Lys Met Val Glu Leu Val His Phe Leu
1               5

<210> SEQ ID NO 855
<211> LENGTH: 10
<212> TYPE: PRT
<213> ORGANISM: Homo sapiens

<400> SEQUENCE: 855

Val Ile Phe Ser Lys Ala Ser Glu Tyr Leu
1               5                   10

<210> SEQ ID NO 856
<211> LENGTH: 10

```
<212> TYPE: PRT
<213> ORGANISM: Homo sapiens

<400> SEQUENCE: 856

Tyr Leu Gln Leu Val Phe Gly Ile Glu Val
1               5                   10

<210> SEQ ID NO 857
<211> LENGTH: 9
<212> TYPE: PRT
<213> ORGANISM: Homo sapiens

<400> SEQUENCE: 857

Gln Leu Val Phe Gly Ile Glu Val Val
1               5

<210> SEQ ID NO 858
<211> LENGTH: 11
<212> TYPE: PRT
<213> ORGANISM: Homo sapiens

<400> SEQUENCE: 858

Gln Leu Val Phe Gly Ile Glu Val Val Glu Val
1               5                   10

<210> SEQ ID NO 859
<211> LENGTH: 9
<212> TYPE: PRT
<213> ORGANISM: Homo sapiens

<400> SEQUENCE: 859

Ile Ile Val Leu Ala Ile Ile Ala Ile
1               5

<210> SEQ ID NO 860
<211> LENGTH: 11
<212> TYPE: PRT
<213> ORGANISM: Homo sapiens

<400> SEQUENCE: 860

Lys Ile Trp Glu Glu Leu Ser Met Leu Glu Val
1               5                   10

<210> SEQ ID NO 861
<211> LENGTH: 10
<212> TYPE: PRT
<213> ORGANISM: Homo sapiens

<400> SEQUENCE: 861

Ala Leu Ile Glu Thr Ser Tyr Val Lys Val
1               5                   10

<210> SEQ ID NO 862
<211> LENGTH: 9
<212> TYPE: PRT
<213> ORGANISM: Homo sapiens

<400> SEQUENCE: 862

Leu Ile Glu Thr Ser Tyr Val Lys Val
1               5

<210> SEQ ID NO 863
<211> LENGTH: 11
<212> TYPE: PRT
<213> ORGANISM: Homo sapiens
```

-continued

```
<400> SEQUENCE: 863

Gly Leu Glu Ala Arg Gly Glu Ala Leu Gly Leu
1               5                   10

<210> SEQ ID NO 864
<211> LENGTH: 9
<212> TYPE: PRT
<213> ORGANISM: Homo sapiens

<400> SEQUENCE: 864

Gly Leu Glu Ala Arg Gly Glu Ala Leu
1               5

<210> SEQ ID NO 865
<211> LENGTH: 9
<212> TYPE: PRT
<213> ORGANISM: Homo sapiens

<400> SEQUENCE: 865

Ala Leu Gly Leu Val Gly Ala Gln Ala
1               5

<210> SEQ ID NO 866
<211> LENGTH: 9
<212> TYPE: PRT
<213> ORGANISM: Homo sapiens

<400> SEQUENCE: 866

Gly Leu Val Gly Ala Gln Ala Pro Ala
1               5

<210> SEQ ID NO 867
<211> LENGTH: 9
<212> TYPE: PRT
<213> ORGANISM: Homo sapiens

<400> SEQUENCE: 867

Asp Leu Glu Ser Glu Phe Gln Ala Ala
1               5

<210> SEQ ID NO 868
<211> LENGTH: 10
<212> TYPE: PRT
<213> ORGANISM: Homo sapiens

<400> SEQUENCE: 868

Asp Leu Glu Ser Glu Phe Gln Ala Ala Ile
1               5                   10

<210> SEQ ID NO 869
<211> LENGTH: 10
<212> TYPE: PRT
<213> ORGANISM: Homo sapiens

<400> SEQUENCE: 869

Ala Ile Ser Arg Lys Met Val Glu Leu Val
1               5                   10

<210> SEQ ID NO 870
<211> LENGTH: 9
<212> TYPE: PRT
<213> ORGANISM: Homo sapiens

<400> SEQUENCE: 870

Ala Ile Ser Arg Lys Met Val Glu Leu
```

```
                1               5

<210> SEQ ID NO 871
<211> LENGTH: 10
<212> TYPE: PRT
<213> ORGANISM: Homo sapiens

<400> SEQUENCE: 871

Lys Met Val Glu Leu Val His Phe Leu Leu
1               5                   10

<210> SEQ ID NO 872
<211> LENGTH: 11
<212> TYPE: PRT
<213> ORGANISM: Homo sapiens

<400> SEQUENCE: 872

Lys Met Val Glu Leu Val His Phe Leu Leu Leu
1               5                   10

<210> SEQ ID NO 873
<211> LENGTH: 11
<212> TYPE: PRT
<213> ORGANISM: Homo sapiens

<400> SEQUENCE: 873

Leu Leu Leu Lys Tyr Arg Ala Arg Glu Pro Val
1               5                   10

<210> SEQ ID NO 874
<211> LENGTH: 10
<212> TYPE: PRT
<213> ORGANISM: Homo sapiens

<400> SEQUENCE: 874

Leu Leu Lys Tyr Arg Ala Arg Glu Pro Val
1               5                   10

<210> SEQ ID NO 875
<211> LENGTH: 11
<212> TYPE: PRT
<213> ORGANISM: Homo sapiens

<400> SEQUENCE: 875

Val Leu Arg Asn Cys Gln Asp Phe Phe Pro Val
1               5                   10

<210> SEQ ID NO 876
<211> LENGTH: 11
<212> TYPE: PRT
<213> ORGANISM: Homo sapiens

<400> SEQUENCE: 876

Tyr Leu Gln Leu Val Phe Gly Ile Glu Val Val
1               5                   10

<210> SEQ ID NO 877
<211> LENGTH: 10
<212> TYPE: PRT
<213> ORGANISM: Homo sapiens

<400> SEQUENCE: 877

Gly Ile Glu Val Val Glu Val Val Pro Ile
1               5                   10
```

-continued

```
<210> SEQ ID NO 878
<211> LENGTH: 9
<212> TYPE: PRT
<213> ORGANISM: Homo sapiens

<400> SEQUENCE: 878

Pro Ile Ser His Leu Tyr Ile Leu Val
1               5

<210> SEQ ID NO 879
<211> LENGTH: 9
<212> TYPE: PRT
<213> ORGANISM: Homo sapiens

<400> SEQUENCE: 879

His Leu Tyr Ile Leu Val Thr Cys Leu
1               5

<210> SEQ ID NO 880
<211> LENGTH: 11
<212> TYPE: PRT
<213> ORGANISM: Homo sapiens

<400> SEQUENCE: 880

His Leu Tyr Ile Leu Val Thr Cys Leu Gly Leu
1               5                   10

<210> SEQ ID NO 881
<211> LENGTH: 9
<212> TYPE: PRT
<213> ORGANISM: Homo sapiens

<400> SEQUENCE: 881

Tyr Ile Leu Val Thr Cys Leu Gly Leu
1               5

<210> SEQ ID NO 882
<211> LENGTH: 9
<212> TYPE: PRT
<213> ORGANISM: Homo sapiens

<400> SEQUENCE: 882

Cys Leu Gly Leu Ser Tyr Asp Gly Leu
1               5

<210> SEQ ID NO 883
<211> LENGTH: 10
<212> TYPE: PRT
<213> ORGANISM: Homo sapiens

<400> SEQUENCE: 883

Cys Leu Gly Leu Ser Tyr Asp Gly Leu Leu
1               5                   10

<210> SEQ ID NO 884
<211> LENGTH: 9
<212> TYPE: PRT
<213> ORGANISM: Homo sapiens

<400> SEQUENCE: 884

Val Met Pro Lys Thr Gly Leu Leu Ile
1               5

<210> SEQ ID NO 885
<211> LENGTH: 10
<212> TYPE: PRT
```

<213> ORGANISM: Homo sapiens

<400> SEQUENCE: 885

Val Met Pro Lys Thr Gly Leu Leu Ile Ile
1               5                   10

<210> SEQ ID NO 886
<211> LENGTH: 11
<212> TYPE: PRT
<213> ORGANISM: Homo sapiens

<400> SEQUENCE: 886

Val Met Pro Lys Thr Gly Leu Leu Ile Ile Val
1               5                   10

<210> SEQ ID NO 887
<211> LENGTH: 9
<212> TYPE: PRT
<213> ORGANISM: Homo sapiens

<400> SEQUENCE: 887

Gly Leu Leu Ile Ile Val Leu Ala Ile
1               5

<210> SEQ ID NO 888
<211> LENGTH: 10
<212> TYPE: PRT
<213> ORGANISM: Homo sapiens

<400> SEQUENCE: 888

Gly Leu Leu Ile Ile Val Leu Ala Ile Ile
1               5                   10

<210> SEQ ID NO 889
<211> LENGTH: 11
<212> TYPE: PRT
<213> ORGANISM: Homo sapiens

<400> SEQUENCE: 889

Gly Leu Leu Ile Ile Val Leu Ala Ile Ile Ala
1               5                   10

<210> SEQ ID NO 890
<211> LENGTH: 9
<212> TYPE: PRT
<213> ORGANISM: Homo sapiens

<400> SEQUENCE: 890

Leu Leu Ile Ile Val Leu Ala Ile Ile
1               5

<210> SEQ ID NO 891
<211> LENGTH: 10
<212> TYPE: PRT
<213> ORGANISM: Homo sapiens

<400> SEQUENCE: 891

Leu Leu Ile Ile Val Leu Ala Ile Ile Ala
1               5                   10

<210> SEQ ID NO 892
<211> LENGTH: 11
<212> TYPE: PRT
<213> ORGANISM: Homo sapiens

<400> SEQUENCE: 892

Leu Leu Ile Ile Val Leu Ala Ile Ala Ile
1               5                   10

<210> SEQ ID NO 893
<211> LENGTH: 9
<212> TYPE: PRT
<213> ORGANISM: Homo sapiens

<400> SEQUENCE: 893

Leu Ile Ile Val Leu Ala Ile Ile Ala
1               5

<210> SEQ ID NO 894
<211> LENGTH: 10
<212> TYPE: PRT
<213> ORGANISM: Homo sapiens

<400> SEQUENCE: 894

Leu Ile Ile Val Leu Ala Ile Ile Ala Ile
1               5                   10

<210> SEQ ID NO 895
<211> LENGTH: 9
<212> TYPE: PRT
<213> ORGANISM: Homo sapiens

<400> SEQUENCE: 895

Ile Ile Ala Ile Glu Gly Asp Cys Ala
1               5

<210> SEQ ID NO 896
<211> LENGTH: 9
<212> TYPE: PRT
<213> ORGANISM: Homo sapiens

<400> SEQUENCE: 896

Lys Ile Trp Glu Glu Leu Ser Met Leu
1               5

<210> SEQ ID NO 897
<211> LENGTH: 11
<212> TYPE: PRT
<213> ORGANISM: Homo sapiens

<400> SEQUENCE: 897

Leu Met Gln Asp Leu Val Gln Glu Asn Tyr Leu
1               5                   10

<210> SEQ ID NO 898
<211> LENGTH: 9
<212> TYPE: PRT
<213> ORGANISM: Homo sapiens

<400> SEQUENCE: 898

Phe Leu Trp Gly Pro Arg Ala Leu Ile
1               5

<210> SEQ ID NO 899
<211> LENGTH: 9
<212> TYPE: PRT
<213> ORGANISM: Homo sapiens

<400> SEQUENCE: 899

Leu Ile Glu Thr Ser Tyr Val Lys Val
1               5

<210> SEQ ID NO 900
<211> LENGTH: 11
<212> TYPE: PRT
<213> ORGANISM: Homo sapiens

<400> SEQUENCE: 900

Ala Leu Ile Glu Thr Ser Tyr Val Lys Val Leu
1               5                   10

<210> SEQ ID NO 901
<211> LENGTH: 10
<212> TYPE: PRT
<213> ORGANISM: Homo sapiens

<400> SEQUENCE: 901

Thr Leu Lys Ile Gly Gly Glu Pro His Ile
1               5                   10

<210> SEQ ID NO 902
<211> LENGTH: 11
<212> TYPE: PRT
<213> ORGANISM: Homo sapiens

<400> SEQUENCE: 902

His Ile Ser Tyr Pro Pro Leu His Glu Arg Ala
1               5                   10

<210> SEQ ID NO 903
<211> LENGTH: 9
<212> TYPE: PRT
<213> ORGANISM: Homo sapiens

<400> SEQUENCE: 903

Gln Thr Ala Ser Ser Ser Ser Thr Leu
1               5

<210> SEQ ID NO 904
<211> LENGTH: 10
<212> TYPE: PRT
<213> ORGANISM: Homo sapiens

<400> SEQUENCE: 904

Gln Thr Ala Ser Ser Ser Ser Thr Leu Val
1               5                   10

<210> SEQ ID NO 905
<211> LENGTH: 9
<212> TYPE: PRT
<213> ORGANISM: Homo sapiens

<400> SEQUENCE: 905

Val Thr Leu Gly Glu Val Pro Ala Ala
1               5

<210> SEQ ID NO 906
<211> LENGTH: 10
<212> TYPE: PRT
<213> ORGANISM: Homo sapiens

<400> SEQUENCE: 906

Val Thr Lys Ala Glu Met Leu Glu Ser Val
1               5                   10

<210> SEQ ID NO 907

```
<211> LENGTH: 11
<212> TYPE: PRT
<213> ORGANISM: Homo sapiens

<400> SEQUENCE: 907

Val Thr Lys Ala Glu Met Leu Glu Ser Val Leu
1               5                   10

<210> SEQ ID NO 908
<211> LENGTH: 11
<212> TYPE: PRT
<213> ORGANISM: Homo sapiens

<400> SEQUENCE: 908

Val Thr Cys Leu Gly Leu Ser Tyr Asp Gly Leu
1               5                   10

<210> SEQ ID NO 909
<211> LENGTH: 9
<212> TYPE: PRT
<213> ORGANISM: Homo sapiens

<400> SEQUENCE: 909

Lys Thr Gly Leu Leu Ile Ile Val Leu
1               5

<210> SEQ ID NO 910
<211> LENGTH: 10
<212> TYPE: PRT
<213> ORGANISM: Homo sapiens

<400> SEQUENCE: 910

Lys Thr Gly Leu Leu Ile Ile Val Leu Ala
1               5                   10

<210> SEQ ID NO 911
<211> LENGTH: 11
<212> TYPE: PRT
<213> ORGANISM: Homo sapiens

<400> SEQUENCE: 911

Lys Thr Gly Leu Leu Ile Ile Val Leu Ala Ile
1               5                   10

<210> SEQ ID NO 912
<211> LENGTH: 11
<212> TYPE: PRT
<213> ORGANISM: Homo sapiens

<400> SEQUENCE: 912

His Thr Leu Lys Ile Gly Gly Glu Pro His Ile
1               5                   10

<210> SEQ ID NO 913
<211> LENGTH: 9
<212> TYPE: PRT
<213> ORGANISM: Homo sapiens

<400> SEQUENCE: 913

Met Leu Asp Leu Gln Pro Glu Thr Thr
1               5

<210> SEQ ID NO 914
<211> LENGTH: 9
<212> TYPE: PRT
<213> ORGANISM: Homo sapiens
```

```
<400> SEQUENCE: 914

Gly Leu Glu Ala Arg Gly Glu Ala Leu
 1               5

<210> SEQ ID NO 915
<211> LENGTH: 9
<212> TYPE: PRT
<213> ORGANISM: Homo sapiens

<400> SEQUENCE: 915

Ala Leu Ser Arg Lys Val Ala Glu Leu
 1               5

<210> SEQ ID NO 916
<211> LENGTH: 9
<212> TYPE: PRT
<213> ORGANISM: Homo sapiens

<400> SEQUENCE: 916

Phe Leu Trp Gly Pro Arg Ala Leu Val
 1               5

<210> SEQ ID NO 917
<211> LENGTH: 10
<212> TYPE: PRT
<213> ORGANISM: Homo sapiens

<400> SEQUENCE: 917

Thr Leu Val Glu Val Thr Leu Gly Glu Val
 1               5                  10

<210> SEQ ID NO 918
<211> LENGTH: 10
<212> TYPE: PRT
<213> ORGANISM: Homo sapiens

<400> SEQUENCE: 918

Ala Leu Ser Arg Lys Val Ala Glu Leu Val
 1               5                  10

<210> SEQ ID NO 919
<211> LENGTH: 10
<212> TYPE: PRT
<213> ORGANISM: Homo sapiens

<400> SEQUENCE: 919

Ala Leu Val Glu Thr Ser Tyr Val Lys Val
 1               5                  10

<210> SEQ ID NO 920
<211> LENGTH: 9
<212> TYPE: PRT
<213> ORGANISM: Homo sapiens

<400> SEQUENCE: 920

Tyr Met Asn Gly Thr Met Ser Gln Val
 1               5

<210> SEQ ID NO 921
<211> LENGTH: 10
<212> TYPE: PRT
<213> ORGANISM: Homo sapiens

<400> SEQUENCE: 921
```

```
Met Leu Leu Ala Val Leu Tyr Cys Leu Leu
1               5                   10

<210> SEQ ID NO 922
<211> LENGTH: 9
<212> TYPE: PRT
<213> ORGANISM: Homo sapiens

<400> SEQUENCE: 922

Met Leu Leu Ala Val Leu Tyr Cys Leu
1               5

<210> SEQ ID NO 923
<211> LENGTH: 9
<212> TYPE: PRT
<213> ORGANISM: Homo sapiens

<400> SEQUENCE: 923

Leu Leu Ala Val Leu Tyr Cys Leu Leu
1               5

<210> SEQ ID NO 924
<211> LENGTH: 13
<212> TYPE: PRT
<213> ORGANISM: Homo sapiens

<400> SEQUENCE: 924

Ser Glu Ile Trp Arg Asp Ile Asp Phe Ala His Glu Ala
1               5                   10

<210> SEQ ID NO 925
<211> LENGTH: 9
<212> TYPE: PRT
<213> ORGANISM: Homo sapiens

<400> SEQUENCE: 925

Ser Glu Ile Trp Arg Asp Ile Asp Phe
1               5

<210> SEQ ID NO 926
<211> LENGTH: 10
<212> TYPE: PRT
<213> ORGANISM: Homo sapiens

<400> SEQUENCE: 926

Glu Glu Asn Leu Leu Asp Phe Val Arg Phe
1               5                   10

<210> SEQ ID NO 927
<211> LENGTH: 10
<212> TYPE: PRT
<213> ORGANISM: Homo sapiens

<400> SEQUENCE: 927

Glu Ala Ala Gly Ile Gly Ile Leu Thr Val
1               5                   10

<210> SEQ ID NO 928
<211> LENGTH: 9
<212> TYPE: PRT
<213> ORGANISM: Homo sapiens

<400> SEQUENCE: 928

Met Leu Leu Ala Val Leu Tyr Cys Leu
1               5
```

```
<210> SEQ ID NO 929
<211> LENGTH: 9
<212> TYPE: PRT
<213> ORGANISM: Homo sapiens

<400> SEQUENCE: 929

Tyr Met Asp Gly Thr Met Ser Gln Val
1               5

<210> SEQ ID NO 930
<211> LENGTH: 9
<212> TYPE: PRT
<213> ORGANISM: Homo sapiens

<400> SEQUENCE: 930

Tyr Leu Glu Pro Gly Pro Val Thr Ala
1               5

<210> SEQ ID NO 931
<211> LENGTH: 10
<212> TYPE: PRT
<213> ORGANISM: Homo sapiens

<400> SEQUENCE: 931

Leu Leu Asp Gly Thr Ala Thr Leu Arg Leu
1               5                   10

<210> SEQ ID NO 932
<211> LENGTH: 9
<212> TYPE: PRT
<213> ORGANISM: Homo sapiens

<400> SEQUENCE: 932

Gly Ile Leu Gly Phe Val Phe Thr Leu
1               5

<210> SEQ ID NO 933
<211> LENGTH: 9
<212> TYPE: PRT
<213> ORGANISM: Homo sapiens

<400> SEQUENCE: 933

Glu Ala Asp Pro Thr Gly His Ser Tyr
1               5

<210> SEQ ID NO 934
<211> LENGTH: 9
<212> TYPE: PRT
<213> ORGANISM: Homo sapiens

<400> SEQUENCE: 934

Glu Ala Asp Pro Thr Gly His Ser Tyr
1               5

<210> SEQ ID NO 935
<211> LENGTH: 22
<212> TYPE: PRT
<213> ORGANISM: Homo sapiens

<400> SEQUENCE: 935

Met Ala Ala Arg Ala Val Phe Leu Ala Leu Ser Ala Gln Leu Leu Gln
1               5                   10                  15

Ala Arg Leu Met Lys Glu
            20
```

```
<210> SEQ ID NO 936
<211> LENGTH: 16
<212> TYPE: PRT
<213> ORGANISM: Homo sapiens

<400> SEQUENCE: 936

Met Ala Ala Arg Ala Val Phe Leu Ala Leu Ser Ala Gln Leu Leu Gln
 1               5                  10                  15

<210> SEQ ID NO 937
<211> LENGTH: 9
<212> TYPE: PRT
<213> ORGANISM: Homo sapiens

<400> SEQUENCE: 937

Ala Ala Arg Ala Val Phe Leu Ala Leu
 1               5

<210> SEQ ID NO 938
<211> LENGTH: 9
<212> TYPE: PRT
<213> ORGANISM: Influenza

<400> SEQUENCE: 938

Ile Tyr Gln Arg Ile Arg Ala Leu Val
 1               5

<210> SEQ ID NO 939
<211> LENGTH: 9
<212> TYPE: PRT
<213> ORGANISM: Homo sapiens

<400> SEQUENCE: 939

Ser Tyr Phe Pro Glu Ile Thr His Ile
 1               5

<210> SEQ ID NO 940
<211> LENGTH: 9
<212> TYPE: PRT
<213> ORGANISM: Influenza

<400> SEQUENCE: 940

Ile Tyr Ala Thr Val Ala Gly Ser Leu
 1               5

<210> SEQ ID NO 941
<211> LENGTH: 9
<212> TYPE: PRT
<213> ORGANISM: Influenza

<400> SEQUENCE: 941

Val Tyr Gln Ile Leu Ala Ile Tyr Ala
 1               5

<210> SEQ ID NO 942
<211> LENGTH: 9
<212> TYPE: PRT
<213> ORGANISM: Influenza

<400> SEQUENCE: 942

Ile Tyr Ser Thr Val Ala Ser Ser Leu
 1               5

<210> SEQ ID NO 943
<211> LENGTH: 9
```

<212> TYPE: PRT
<213> ORGANISM: Influenza

<400> SEQUENCE: 943

Leu Tyr Gln Asn Val Gly Thr Tyr Val
1               5

<210> SEQ ID NO 944
<211> LENGTH: 9
<212> TYPE: PRT
<213> ORGANISM: Homo sapiens

<400> SEQUENCE: 944

Arg Tyr Leu Glu Asn Gln Lys Arg Thr
1               5

<210> SEQ ID NO 945
<211> LENGTH: 9
<212> TYPE: PRT
<213> ORGANISM: Homo sapiens

<400> SEQUENCE: 945

Arg Tyr Leu Lys Asn Gly Lys Glu Thr
1               5

<210> SEQ ID NO 946
<211> LENGTH: 9
<212> TYPE: PRT
<213> ORGANISM: Homo sapiens

<400> SEQUENCE: 946

Lys Tyr Gln Ala Val Thr Thr Thr Leu
1               5

<210> SEQ ID NO 947
<211> LENGTH: 9
<212> TYPE: PRT
<213> ORGANISM: Plasmodium Berghei

<400> SEQUENCE: 947

Ser Tyr Ile Pro Ser Ala Glu Lys Ile
1               5

<210> SEQ ID NO 948
<211> LENGTH: 9
<212> TYPE: PRT
<213> ORGANISM: Plasmodium Yoelii

<400> SEQUENCE: 948

Ser Tyr Val Pro Ser Ala Phe Gln Ile
1               5

<210> SEQ ID NO 949
<211> LENGTH: 8
<212> TYPE: PRT
<213> ORGANISM: Vesicular Stomatitis Virus

<400> SEQUENCE: 949

Arg Gly Tyr Val Tyr Gln Gly Leu
1               5

<210> SEQ ID NO 950
<211> LENGTH: 8
<212> TYPE: PRT
<213> ORGANISM: Gallus Domesticus

```
<400> SEQUENCE: 950

Ser Ile Ile Asn Phe Glu Lys Leu
1               5

<210> SEQ ID NO 951
<211> LENGTH: 8
<212> TYPE: PRT
<213> ORGANISM: Sendai Virus

<400> SEQUENCE: 951

Ala Pro Gly Asn Tyr Pro Ala Leu
1               5

<210> SEQ ID NO 952
<211> LENGTH: 9
<212> TYPE: PRT
<213> ORGANISM: Homo sapiens

<400> SEQUENCE: 952

Val Pro Tyr Gly Ser Phe Lys His Val
1               5

<210> SEQ ID NO 953
<211> LENGTH: 9
<212> TYPE: PRT
<213> ORGANISM: Influenza

<400> SEQUENCE: 953

Thr Tyr Gln Arg Thr Arg Ala Leu Val
1               5

<210> SEQ ID NO 954
<211> LENGTH: 9
<212> TYPE: PRT
<213> ORGANISM: Homo sapiens

<400> SEQUENCE: 954

Ser Tyr Phe Pro Glu Ile Thr His Ile
1               5

<210> SEQ ID NO 955
<211> LENGTH: 9
<212> TYPE: PRT
<213> ORGANISM: Influenza

<400> SEQUENCE: 955

Ile Tyr Ala Thr Val Ala Gly Ser Leu
1               5

<210> SEQ ID NO 956
<211> LENGTH: 9
<212> TYPE: PRT
<213> ORGANISM: Influenza

<400> SEQUENCE: 956

Val Tyr Gln Ile Leu Ala Ile Tyr Ala
1               5

<210> SEQ ID NO 957
<211> LENGTH: 9
<212> TYPE: PRT
<213> ORGANISM: Influenza

<400> SEQUENCE: 957

Ile Tyr Ser Thr Val Ala Ser Ser Leu
```

```
              1               5
```

<210> SEQ ID NO 958
<211> LENGTH: 9
<212> TYPE: PRT
<213> ORGANISM: Influenza

<400> SEQUENCE: 958

```
Leu Tyr Gln Asn Val Gly Thr Tyr Val
  1               5
```

<210> SEQ ID NO 959
<211> LENGTH: 10
<212> TYPE: PRT
<213> ORGANISM: Homo sapiens

<400> SEQUENCE: 959

```
Arg Tyr Leu Glu Asn Gly Lys Glu Thr Leu
  1               5                  10
```

<210> SEQ ID NO 960
<211> LENGTH: 10
<212> TYPE: PRT
<213> ORGANISM: Homo sapiens

<400> SEQUENCE: 960

```
Arg Tyr Leu Lys Asn Gly Lys Glu Thr Leu
  1               5                  10
```

<210> SEQ ID NO 961
<211> LENGTH: 9
<212> TYPE: PRT
<213> ORGANISM: Homo sapiens

<400> SEQUENCE: 961

```
Lys Tyr Gln Ala Val Thr Thr Thr Leu
  1               5
```

<210> SEQ ID NO 962
<211> LENGTH: 9
<212> TYPE: PRT
<213> ORGANISM: Plasmodium Berghei

<400> SEQUENCE: 962

```
Ser Tyr Ile Pro Ser Ala Glu Lys Ile
  1               5
```

<210> SEQ ID NO 963
<211> LENGTH: 9
<212> TYPE: PRT
<213> ORGANISM: Plasmodium Yoelii

<400> SEQUENCE: 963

```
Ser Tyr Val Pro Ser Ala Glu Gln Ile
  1               5
```

<210> SEQ ID NO 964
<211> LENGTH: 9
<212> TYPE: PRT
<213> ORGANISM: Influenza

<400> SEQUENCE: 964

```
Ala Ser Asn Glu Asn Met Glu Thr Met
  1               5
```

<210> SEQ ID NO 965
<211> LENGTH: 10
<212> TYPE: PRT
<213> ORGANISM: Adenovirus

<400> SEQUENCE: 965

Ser Gly Pro Ser Asn Thr Pro Pro Glu Ile
1               5                   10

<210> SEQ ID NO 966
<211> LENGTH: 11
<212> TYPE: PRT
<213> ORGANISM: Lymphocytic Choriomeningitis Virus

<400> SEQUENCE: 966

Ser Gly Val Glu Asn Pro Gly Gly Tyr Cys Leu
1               5                   10

<210> SEQ ID NO 967
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 7, 8, 9
<223> OTHER INFORMATION: Xaa = Any Amino Acid

<400> SEQUENCE: 967

Ser Ala Ile Asn Asn Tyr Xaa Xaa Xaa
1               5

<210> SEQ ID NO 968
<211> LENGTH: 9
<212> TYPE: PRT
<213> ORGANISM: Human Immunodeficiency Virus

<400> SEQUENCE: 968

Ile Leu Lys Glu Pro Val His Gly Val
1               5

<210> SEQ ID NO 969
<211> LENGTH: 9
<212> TYPE: PRT
<213> ORGANISM: Influenza

<400> SEQUENCE: 969

Gly Ile Leu Gly Phe Val Phe Thr Leu
1               5

<210> SEQ ID NO 970
<211> LENGTH: 10
<212> TYPE: PRT
<213> ORGANISM: Influenza

<400> SEQUENCE: 970

Ile Leu Gly Phe Val Phe Thr Leu Thr Val
1               5                   10

<210> SEQ ID NO 971
<211> LENGTH: 9
<212> TYPE: PRT
<213> ORGANISM: Human Immunodeficiency Virus

<400> SEQUENCE: 971

Phe Leu Gln Ser Arg Pro Glu Pro Thr

-continued

```
<210> SEQ ID NO 972
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 8, 9
<223> OTHER INFORMATION: Xaa = Any Amino Acid

<400> SEQUENCE: 972

Ala Met Gln Met Leu Lys Glu Xaa Xaa
1               5

<210> SEQ ID NO 973
<211> LENGTH: 9
<212> TYPE: PRT
<213> ORGANISM: Human Immunodeficiency Virus

<400> SEQUENCE: 973

Pro Ile Ala Pro Gly Gln Met Arg Glu
1               5

<210> SEQ ID NO 974
<211> LENGTH: 9
<212> TYPE: PRT
<213> ORGANISM: Human Immunodeficiency Virus

<400> SEQUENCE: 974

Gln Met Lys Asp Cys Thr Glu Arg Gln
1               5

<210> SEQ ID NO 975
<211> LENGTH: 7
<212> TYPE: PRT
<213> ORGANISM: Human Immunodeficiency Virus

<400> SEQUENCE: 975

Val Tyr Gly Val Ile Gln Lys
1               5

<210> SEQ ID NO 976
<211> LENGTH: 12
<212> TYPE: PRT
<213> ORGANISM: Artificial Sequence
<220> FEATURE:
<223> OTHER INFORMATION: Synthetic peptide

<400> SEQUENCE: 976

Ser Asp Leu Arg Gly Tyr Val Tyr Gln Gly Leu Lys
1               5                   10

<210> SEQ ID NO 977
<211> LENGTH: 15
<212> TYPE: PRT
<213> ORGANISM: Artificial Sequence
<220> FEATURE:
<223> OTHER INFORMATION: Synthetic peptide

<400> SEQUENCE: 977

Arg Pro Gln Ala Ser Gly Val Tyr Met Gly Asn Leu Thr Thr Gln
1               5                   10                  15

<210> SEQ ID NO 978
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 978

Lys Ala Val Tyr Asn Phe Ala Thr Cys
 1               5

<210> SEQ ID NO 979
<211> LENGTH: 9
<212> TYPE: PRT
<213> ORGANISM: Homo sapiens

<400> SEQUENCE: 979

Glu Val Asp Pro Ala Ser Asn Thr Tyr
 1               5

<210> SEQ ID NO 980
<211> LENGTH: 10
<212> TYPE: PRT
<213> ORGANISM: Homo sapiens

<400> SEQUENCE: 980

Phe Leu Pro Trp His Arg Leu Phe Leu Leu
 1               5                  10

<210> SEQ ID NO 981
<211> LENGTH: 529
<212> TYPE: PRT
<213> ORGANISM: Homo sapiens

<400> SEQUENCE: 981

Met Leu Leu Ala Val Leu Tyr Cys Leu Leu Trp Ser Phe Gln Thr Ser
 1               5                  10                  15

Ala Gly His Phe Pro Arg Ala Cys Val Ser Ser Lys Asn Leu Met Glu
                20                  25                  30

Lys Glu Cys Cys Pro Pro Trp Ser Gly Asp Arg Ser Pro Cys Gly Gln
            35                  40                  45

Leu Ser Gly Arg Gly Ser Cys Gln Asn Ile Leu Leu Ser Asn Ala Pro
        50                  55                  60

Leu Gly Pro Gln Phe Pro Phe Thr Gly Val Asp Asp Arg Glu Ser Trp
 65                  70                  75                  80

Pro Ser Val Phe Tyr Asn Arg Thr Cys Gln Cys Ser Gly Asn Phe Met
                85                  90                  95

Gly Phe Asn Cys Gly Asn Cys Lys Phe Gly Phe Trp Gly Pro Asn Cys
            100                 105                 110

Thr Glu Arg Arg Leu Leu Val Arg Arg Asn Ile Phe Asp Leu Ser Ala
        115                 120                 125

Pro Glu Lys Asp Lys Phe Phe Ala Tyr Leu Thr Leu Ala Lys His Thr
    130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
            180                 185                 190

Glu Ile Trp Arg Asp Ile Asp Phe Ala His Glu Ala Pro Ala Phe Leu
        195                 200                 205
```

```
Pro Trp His Arg Leu Phe Leu Leu Arg Trp Glu Gln Glu Ile Gln Lys
    210                 215                 220

Leu Thr Gly Asp Glu Asn Phe Thr Ile Pro Tyr Asp Trp Arg Asp
225                 230                 235                 240

Ala Glu Lys Cys Asp Ile Cys Thr Asp Glu Tyr Met Gly Gly Gln His
                    245                 250                 255

Pro Thr Asn Pro Asn Leu Leu Ser Pro Ala Ser Phe Ser Ser Trp
            260                 265                 270

Gln Ile Val Cys Ser Arg Leu Glu Glu Tyr Asn Ser His Gln Ser Leu
        275                 280                 285

Cys Asn Gly Thr Pro Glu Gly Pro Leu Arg Arg Asn Pro Gly Asn His
    290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                    325                 330                 335

Asn Phe Ser Phe Arg Asn Thr Leu Glu Gly Phe Ala Ser Pro Leu Thr
                340                 345                 350

Gly Ile Ala Asp Ala Ser Gln Ser Ser Met His Asn Ala Leu His Ile
            355                 360                 365

Tyr Met Asn Gly Thr Met Ser Gln Val Gln Gly Ser Ala Asn Asp Pro
    370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                    405                 410                 415

Pro Ile Gly His Asn Arg Glu Ser Tyr Met Val Pro Phe Ile Pro Leu
                420                 425                 430

Tyr Arg Asn Gly Asp Phe Phe Ile Ser Ser Lys Asp Leu Gly Tyr Asp
            435                 440                 445

Tyr Ser Tyr Leu Gln Asp Ser Asp Pro Asp Ser Phe Gln Asp Tyr Ile
    450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                    485                 490                 495

Ser Leu Leu Cys Arg His Lys Arg Lys Gln Leu Pro Glu Glu Lys Gln
                500                 505                 510

Pro Leu Leu Met Glu Lys Glu Asp Tyr His Ser Leu Tyr Gln Ser His
            515                 520                 525

Leu

<210> SEQ ID NO 982
<211> LENGTH: 188
<212> TYPE: PRT
<213> ORGANISM: Homo sapiens

<400> SEQUENCE: 982

Met Asn Gly Asp Asp Ala Phe Ala Arg Arg Pro Thr Val Gly Ala Gln
1               5                   10                  15

Ile Pro Glu Lys Ile Gln Lys Ala Phe Asp Asp Ile Ala Lys Tyr Phe
                20                  25                  30

Ser Lys Glu Glu Trp Glu Lys Met Lys Ala Ser Glu Lys Ile Phe Tyr
            35                  40                  45

Val Tyr Met Lys Arg Lys Tyr Glu Ala Met Thr Lys Leu Gly Phe Lys
```

```
                50                  55                  60
Ala Thr Leu Pro Pro Phe Met Cys Asn Lys Arg Ala Glu Asp Phe Gln
 65                  70                  75                  80

Gly Asn Asp Leu Asp Asn Asp Pro Asn Arg Gly Asn Gln Val Glu Arg
                 85                  90                  95

Pro Gln Met Thr Phe Gly Arg Leu Gln Gly Ile Ser Pro Lys Ile Met
            100                 105                 110

Pro Lys Lys Pro Ala Glu Glu Gly Asn Asp Ser Glu Val Pro Glu
        115                 120                 125

Ala Ser Gly Pro Gln Asn Asp Gly Lys Glu Leu Cys Pro Pro Gly Lys
130                 135                 140

Pro Thr Thr Ser Glu Lys Ile His Glu Arg Ser Gly Pro Lys Arg Gly
145                 150                 155                 160

Glu His Ala Trp Thr His Arg Leu Arg Glu Arg Lys Gln Leu Val Ile
                165                 170                 175

Tyr Glu Glu Ile Ser Asp Pro Glu Glu Asp Glu
            180                 185

<210> SEQ ID NO 983
<211> LENGTH: 750
<212> TYPE: PRT
<213> ORGANISM: Homo sapiens

<400> SEQUENCE: 983

Met Trp Asn Leu Leu His Glu Thr Asp Ser Ala Val Ala Thr Ala Arg
  1               5                  10                  15

Arg Pro Arg Trp Leu Cys Ala Gly Ala Leu Val Leu Ala Gly Gly Phe
                 20                  25                  30

Phe Leu Leu Gly Phe Leu Phe Gly Trp Phe Ile Lys Ser Ser Asn Glu
             35                  40                  45

Ala Thr Asn Ile Thr Pro Lys His Asn Met Lys Ala Phe Leu Asp Glu
         50                  55                  60

Leu Lys Ala Glu Asn Ile Lys Lys Phe Leu Tyr Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
```

```
                245                 250                 255
Asn Ile Leu Asn Leu Asn Gly Ala Gly Asp Pro Leu Thr Pro Gly Tyr
            260                 265                 270
Pro Ala Asn Glu Tyr Ala Tyr Arg Arg Gly Ile Ala Glu Ala Val Gly
            275                 280                 285
Leu Pro Ser Ile Pro Val His Pro Ile Gly Tyr Tyr Asp Ala Gln Lys
            290                 295                 300
Leu Leu Glu Lys Met Gly Gly Ser Ala Pro Pro Asp Ser Ser Trp Arg
305                 310                 315                 320
Gly Ser Leu Lys Val Pro Tyr Asn Val Gly Pro Gly Phe Thr Gly Asn
                325                 330                 335
Phe Ser Thr Gln Lys Val Lys Met His Ile His Ser Thr Asn Glu Val
            340                 345                 350
Thr Arg Ile Tyr Asn Val Ile Gly Thr Leu Arg Gly Ala Val Glu Pro
            355                 360                 365
Asp Arg Tyr Val Ile Leu Gly Gly His Arg Asp Ser Trp Val Phe Gly
            370                 375                 380
Gly Ile Asp Pro Gln Ser Gly Ala Ala Val Val His Glu Ile Val Arg
385                 390                 395                 400
Ser Phe Gly Thr Leu Lys Lys Glu Gly Trp Arg Pro Arg Arg Thr Ile
                405                 410                 415
Leu Phe Ala Ser Trp Asp Ala Glu Glu Phe Gly Leu Leu Gly Ser Thr
            420                 425                 430
Glu Trp Ala Glu Glu Asn Ser Arg Leu Leu Gln Glu Arg Gly Val Ala
            435                 440                 445
Tyr Ile Asn Ala Asp Ser Ser Ile Glu Gly Asn Tyr Thr Leu Arg Val
            450                 455                 460
Asp Cys Thr Pro Leu Met Tyr Ser Leu Val His Asn Leu Thr Lys Glu
465                 470                 475                 480
Leu Lys Ser Pro Asp Glu Gly Phe Glu Gly Lys Ser Leu Tyr Glu Ser
                485                 490                 495
Trp Thr Lys Lys Ser Pro Ser Pro Glu Phe Ser Gly Met Pro Arg Ile
            500                 505                 510
Ser Lys Leu Gly Ser Gly Asn Asp Phe Glu Val Phe Phe Gln Arg Leu
            515                 520                 525
Gly Ile Ala Ser Gly Arg Ala Arg Tyr Thr Lys Asn Trp Glu Thr Asn
            530                 535                 540
Lys Phe Ser Gly Tyr Pro Leu Tyr His Ser Val Tyr Glu Thr Tyr Glu
545                 550                 555                 560
Leu Val Glu Lys Phe Tyr Asp Pro Met Phe Lys Tyr His Leu Thr Val
                565                 570                 575
Ala Gln Val Arg Gly Gly Met Val Phe Glu Leu Ala Asn Ser Ile Val
            580                 585                 590
Leu Pro Phe Asp Cys Arg Asp Tyr Ala Val Val Leu Arg Lys Tyr Ala
            595                 600                 605
Asp Lys Ile Tyr Ser Ile Ser Met Lys His Pro Gln Glu Met Lys Thr
610                 615                 620
Tyr Ser Val Ser Phe Asp Ser Leu Phe Ser Ala Val Lys Asn Phe Thr
625                 630                 635                 640
Glu Ile Ala Ser Lys Phe Ser Glu Arg Leu Gln Asp Phe Asp Lys Ser
                645                 650                 655
Asn Pro Ile Val Leu Arg Met Met Asn Asp Gln Leu Met Phe Leu Glu
            660                 665                 670
```

```
Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
        690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750

<210> SEQ ID NO 984
<211> LENGTH: 1964
<212> TYPE: DNA
<213> ORGANISM: Homo sapiens

<400> SEQUENCE: 984
```

| | | | |
|---|---|---|---|
| atcactgtag tagtagctgg aaagagaaat ctgtgactcc aattagccag ttcctgcaga | 60 |
| ccttgtgagg actagaggaa gaatgctcct ggctgttttg tactgcctgc tgtggagttt | 120 |
| ccagacctcc gctggccatt tccctagagc ctgtgtctcc tctaagaacc tgatggagaa | 180 |
| ggaatgctgt ccaccgtgga gcggggacag gagtccctgt ggccagcttt caggcagagg | 240 |
| ttcctgtcag aatatccttc tgtccaatgc accacttggg cctcaatttc ccttcacagg | 300 |
| ggtggatgac cgggagtcgt ggccttccgt cttttataat aggacctgcc agtgctctgg | 360 |
| caacttcatg ggattcaact gtggaaactg caagtttggc ttttggggac aaaactgcac | 420 |
| agagagacga ctcttggtga agaaacat cttcgatttg agtgcccag agaaggacaa | 480 |
| atttttgcc tacctcactt tagcaaagca taccatcagc tcagactatg tcatccccat | 540 |
| agggacctat ggccaaatga aaatggatc aacacccatg tttaacgaca tcaatattta | 600 |
| tgacctcttt gtctggatgc attattatgt gtcaatggat gcactgcttg ggggatctga | 660 |
| aatctggaga gacattgatt ttgcccatga agcaccagct tttctgcctt ggcatagact | 720 |
| cttcttgttg cggtgggaac aagaaatcca gaagctgaca ggagatgaaa acttcactat | 780 |
| tccatattgg gactggcggg atgcagaaaa gtgtgacatt tgcacagatg agtacatggg | 840 |
| aggtcagcac cccacaaatc ctaacttact cagcccagca tcattcttct cctcttggca | 900 |
| gattgtctgt agccgattgg aggagtacaa cagccatcag tctttatgca atggaacgcc | 960 |
| cgagggacct ttacggcgta atcctggaaa ccatgacaaa tccagaaccc caaggctccc | 1020 |
| ctcttcagct gatgtagaat tttgcctgag tttgacccaa tatgaatctg gttccatgga | 1080 |
| taaagctgcc aatttcagct ttagaaatac actggaagga tttgctagtc cacttactgg | 1140 |
| gatagcggat gcctctcaaa gcagcatgca caatgccttg cacatctata tgaatggaac | 1200 |
| aatgtcccag gtacagggat ctgccaacga tcctatcttc cttcttcacc atgcatttgt | 1260 |
| tgacagtatt tttgagcagt ggctccgaag gcaccgtcct cttcaagaag tttatccaga | 1320 |
| agccaatgca cccattggac ataaccggga atcctacatg gttccttta taccactgta | 1380 |
| cagaaatggt gatttcttta tttcatccaa agatctgggc tatgactata gctatctaca | 1440 |
| agattcagac ccagactctt ttcaagacta cattaagtcc tatttggaac aagcgagtcg | 1500 |
| gatctggtca tggctccttg gggcggcgat ggtaggggcc gtcctcactg ccctgctggc | 1560 |
| agggcttgtg agcttgctgt gtcgtcacaa gagaaagcag cttcctgaag aaaagcagcc | 1620 |
| actcctcatg gagaaagagg attaccacag cttgtatcag agccatttat aaaaggctta | 1680 |
| ggcaatagag tagggccaaa aagcctgacc tcactctaac tcaaagtaat gtccaggttc | 1740 |

```
ccagagaata tctgctggta tttttctgta aagaccattt gcaaaattgt aacctaatac   1800
aaagtgtagc cttcttccaa ctcaggtaga acacacctgt ctttgtcttg ctgttttcac   1860
tcagcccttt taacattttc ccctaagccc atatgtctaa ggaaaggatg ctatttggta   1920
atgaggaact gttatttgta tgtgaattaa agtgctctta tttt                    1964
```

<210> SEQ ID NO 985
<211> LENGTH: 766
<212> TYPE: DNA
<213> ORGANISM: Homo sapiens

<400> SEQUENCE: 985

```
ctctctttcg attcttccat actcagagta cgcacggtct gatttctct ttggattctt    60 ccaaaatcag agtcagactg ctcccggtgc catgaacgga gacgacgcct ttgcaaggag   120
acccacggtt ggtgctcaaa taccagaaa gatccaaaag gccttcgatg atattgccaa   180
atacttctct aaggaagagt gggaaaagat gaaagcctcg gagaaaatct tctatgtgta   240
tatgaagaga agtatgagg ctatgactaa actaggtttc aaggccaccc tcccacctt    300 catgtgtaat aaacgggccg aagacttcca ggggaatgat ttggataatg accctaaccg   360
tgggaatcag gttgaacgtc tcagatgac tttcggcagg ctccagggaa tctccccgaa   420
gatcatgccc aagaagccag cagaggaagg aaatgattcg gaggaagtgc agaagcatc   480 tggcccacaa aatgatggga agagctgtg cccccggga aaaccaacta cctctgagaa   540
gattcacgag agatctggac ccaaaagggg gaacatgcc tggacccaca gactgcgtga   600
gagaaaacag ctggtgattt atgaagagat cagcgaccct gaggaagatg acgagtaact   660
cccctcaggg atacgacaca tgcccatgat gagaagcaga acgtggtgac ctttcacgaa   720
catgggcatg gctgcggacc cctcgtcatc aggtgcatag caagtg                 766
```

<210> SEQ ID NO 986
<211> LENGTH: 2653
<212> TYPE: DNA
<213> ORGANISM: Homo sapiens

<400> SEQUENCE: 986

```
ctcaaaaggg gccggatttc cttctcctgg aggcagatgt tgcctctctc tctcgctcgg    60
attggttcag tgcactctag aaacactgct gtggtggaga aactggaccc caggtctgga   120
gcgaattcca gcctgcaggg ctgataagcg aggcattagt gagattgaga gagactttac   180
cccgccgtgg tggttggagg gcgcgcagta gagcagcagc acaggcgcgg gtcccgggag   240
gccggctctg ctcgcgccga gatgtggaat ctccttcacg aaaccgactc ggctgtggcc   300
accgcgcgcc gcccgcgctg gctgtgcgct ggggcgctgg tgctggcggg tggcttcttt   360
ctcctcggct tcctcttcgg gtggtttata aaatcctcca atgaagctac taacattact   420
ccaaagcata atatgaaagc attttttggat gaattgaaag ctgagaacat caagaagttc   480
ttatataatt ttacacagat accacattta gcaggaacag aacaaaactt tcagcttgca   540
aagcaaattc aatcccagtg gaaagaattt ggcctggatt ctgttgagct agcacattat   600
gatgtcctgt tgtcctaccc aaataagact catcccaact acatctcaat aattaatgaa   660
gatggaaatg agattttcaa cacatcatta tttgaaccac ctcctccagg atatgaaaat   720
gtttcggata ttgtaccacc tttcagtgct ttctctcctc aaggaatgcc agagggcgat   780
ctagtgtatg ttaactatgc acgaactgaa gacttcttta aattggaacg ggacatgaaa   840
atcaattgct ctgggaaaat tgtaattgcc agatatggga aagttttcag aggaaataag   900
```

```
gttaaaaatg cccagctggc aggggccaaa ggagtcattc tctactccga ccctgctgac    960
tactttgctc ctggggtgaa gtcctatcca gatggttgga atcttcctgg aggtggtgtc   1020
cagcgtggaa atatcctaaa tctgaatggt gcaggagacc ctctcacacc aggttaccca   1080
gcaaatgaat atgcttatag gcgtggaatt gcagaggctg ttggtcttcc aagtattcct   1140
gttcatccaa ttggatacta tgatgcacag aagctcctag aaaaaatggg tggctcagca   1200
ccaccagata gcagctggag aggaagtctc aaagtgccct acaatgttgg acctggcttt   1260
actggaaact tttctacaca aaaagtcaag atgcacatcc actctaccaa tgaagtgaca   1320
agaatttaca atgtgatagg tactctcaga ggagcagtgg aaccagacag atatgtcatt   1380
ctggaggtc accgggactc atgggtgttt ggtggtattg accctcagag tggagcagct   1440
gttgttcatg aaattgtgag gagctttgga acactgaaaa aggaagggtg gagacctaga   1500
agaacaattt tgtttgcaag ctgggatgca gaagaatttg tcttcttgg ttctactgag   1560
tgggcagagg agaattcaag actccttcaa gagcgtggcg tggcttatat taatgctgac   1620
tcatctatag aaggaaacta cactctgaga gttgattgta caccgctgat gtacagcttg   1680
gtacacaacc taacaaaaga gctgaaaagc cctgatgaag ctttgaagg caaatctctt   1740
tatgaaagtt ggactaaaaa aagtccttcc ccagagttca gtggcatgcc aggataagc   1800
aaattgggat ctgaaaatga ttttgaggtg ttcttccaac gacttggaat tgcttcaggc   1860
agagcacggt atactaaaaa ttgggaaaca aacaaattca gcggctatcc actgtatcac   1920
agtgtctatg aaacatatga gttggtgaa aagtttatg atccaatgtt taaatatcac   1980
ctcactgtgg cccaggttcg aggagggatg gtgtttgagc tagccaattc catagtgctc   2040
cctttgatt gtcgagatta tgctgtagtt ttaagaaagt atgctgacaa aatctacagt   2100
atttctatga acatccaca ggaaatgaag acatacagtg tatcatttga ttcacttttt   2160
tctgcagtaa agaattttac agaaattgct tccaagttca gtgagagact ccaggacttt   2220
gacaaaagca acccaatagt attaagaatg atgaatgatc aactcatgtt tctggaaaga   2280
gcatttattg atccattagg gttaccagac aggcctttt ataggcatgt catctatgct   2340
ccaagcagcc acaacaagta tgcaggggag tcattcccag gaatttatga tgctctgttt   2400
gatattgaaa gcaaagtgga ccccttccaag gcctggggag aagtgaagag acagatttat   2460
gttgcagcct tcacagtgca ggcagctgca gagactttga gtgaagtagc ctaagaggat   2520
tctttagaga atccgtattg aatttgtgtg gtatgtcact cagaaagaat cgtaatgggt   2580
atattgataa atttaaaat tggtatattt gaaataagt tgaatattat atataaaaaa   2640
aaaaaaaaa aaa                                                       2653
```

<210> SEQ ID NO 987
<211> LENGTH: 9
<212> TYPE: PRT
<213> ORGANISM: Homo sapiens

<400> SEQUENCE: 987

Phe Leu Pro Trp His Arg Leu Phe Leu
 1               5

<210> SEQ ID NO 988
<211> LENGTH: 9
<212> TYPE: PRT
<213> ORGANISM: Homo sapiens

<400> SEQUENCE: 988

Leu Pro Trp His Arg Leu Phe Leu Leu
1               5

<210> SEQ ID NO 989
<211> LENGTH: 38
<212> TYPE: PRT
<213> ORGANISM: Homo sapiens

<400> SEQUENCE: 989

Tyr Phe Ser Lys Glu Glu Trp Glu Lys Met Lys Ala Ser Glu Lys Ile
1               5                   10                  15

Phe Tyr Val Tyr Met Lys Arg Lys Tyr Glu Ala Met Thr Lys Leu Gly
            20                  25                  30

Phe Lys Ala Thr Leu Pro
        35

<210> SEQ ID NO 990
<211> LENGTH: 9
<212> TYPE: PRT
<213> ORGANISM: Homo sapiens

<400> SEQUENCE: 990

Phe Ser Lys Glu Glu Trp Glu Lys Met
1               5

<210> SEQ ID NO 991
<211> LENGTH: 9
<212> TYPE: PRT
<213> ORGANISM: Homo sapiens

<400> SEQUENCE: 991

Lys Met Lys Ala Ser Glu Lys Ile Phe
1               5

<210> SEQ ID NO 992
<211> LENGTH: 9
<212> TYPE: PRT
<213> ORGANISM: Homo sapiens

<400> SEQUENCE: 992

Met Lys Ala Ser Glu Lys Ile Phe Tyr
1               5

<210> SEQ ID NO 993
<211> LENGTH: 10
<212> TYPE: PRT
<213> ORGANISM: Homo sapiens

<400> SEQUENCE: 993

Lys Met Lys Ala Ser Glu Lys Ile Phe Tyr
1               5                   10

<210> SEQ ID NO 994
<211> LENGTH: 9
<212> TYPE: PRT
<213> ORGANISM: Homo sapiens

<400> SEQUENCE: 994

Lys Ala Ser Glu Lys Ile Phe Tyr Val
1               5

<210> SEQ ID NO 995
<211> LENGTH: 10
<212> TYPE: PRT
<213> ORGANISM: Homo sapiens

```
<400> SEQUENCE: 995

Met Lys Ala Ser Glu Lys Ile Phe Tyr Val
1               5                   10

<210> SEQ ID NO 996
<211> LENGTH: 10
<212> TYPE: PRT
<213> ORGANISM: Homo sapiens

<400> SEQUENCE: 996

Lys Ala Ser Glu Lys Ile Phe Tyr Val Tyr
1               5                   10

<210> SEQ ID NO 997
<211> LENGTH: 9
<212> TYPE: PRT
<213> ORGANISM: Homo sapiens

<400> SEQUENCE: 997

Ala Ser Glu Lys Ile Phe Tyr Val Tyr
1               5

<210> SEQ ID NO 998
<211> LENGTH: 9
<212> TYPE: PRT
<213> ORGANISM: Homo sapiens

<400> SEQUENCE: 998

Arg Lys Tyr Glu Ala Met Thr Lys Leu
1               5

<210> SEQ ID NO 999
<211> LENGTH: 10
<212> TYPE: PRT
<213> ORGANISM: Homo sapiens

<400> SEQUENCE: 999

Lys Arg Lys Tyr Glu Ala Met Thr Lys Leu
1               5                   10

<210> SEQ ID NO 1000
<211> LENGTH: 10
<212> TYPE: PRT
<213> ORGANISM: Homo sapiens

<400> SEQUENCE: 1000

Lys Tyr Glu Ala Met Thr Lys Leu Gly Phe
1               5                   10

<210> SEQ ID NO 1001
<211> LENGTH: 9
<212> TYPE: PRT
<213> ORGANISM: Homo sapiens

<400> SEQUENCE: 1001

Tyr Glu Ala Met Thr Lys Leu Gly Phe
1               5

<210> SEQ ID NO 1002
<211> LENGTH: 8
<212> TYPE: PRT
<213> ORGANISM: Homo sapiens

<400> SEQUENCE: 1002
```

```
Glu Ala Met Thr Lys Leu Gly Phe
 1               5
```

<210> SEQ ID NO 1003
<211> LENGTH: 10
<212> TYPE: PRT
<213> ORGANISM: Homo sapiens

<400> SEQUENCE: 1003

```
Phe Leu Pro Ser Asp Tyr Phe Pro Ser Val
 1               5                  10
```

<210> SEQ ID NO 1004
<211> LENGTH: 9
<212> TYPE: PRT
<213> ORGANISM: Homo sapiens

<400> SEQUENCE: 1004

```
Ala Glu Met Gly Lys Tyr Ser Phe Tyr
 1               5
```

<210> SEQ ID NO 1005
<211> LENGTH: 9
<212> TYPE: PRT
<213> ORGANISM: Homo sapiens

<400> SEQUENCE: 1005

```
Lys Tyr Ser Glu Lys Ile Ser Tyr Val
 1               5
```

<210> SEQ ID NO 1006
<211> LENGTH: 9
<212> TYPE: PRT
<213> ORGANISM: Homo sapiens

<400> SEQUENCE: 1006

```
Lys Val Ser Glu Lys Ile Val Tyr Val
 1               5
```

<210> SEQ ID NO 1007
<211> LENGTH: 9
<212> TYPE: PRT
<213> ORGANISM: Homo sapiens

<400> SEQUENCE: 1007

```
Lys Ser Ser Glu Lys Ile Val Tyr Val
 1               5
```

<210> SEQ ID NO 1008
<211> LENGTH: 9
<212> TYPE: PRT
<213> ORGANISM: Homo sapiens

<400> SEQUENCE: 1008

```
Lys Ala Ser Glu Lys Ile Ile Tyr Val
 1               5
```

<210> SEQ ID NO 1009
<211> LENGTH: 30
<212> TYPE: PRT
<213> ORGANISM: Homo sapiens

<400> SEQUENCE: 1009

```
Ala Phe Ser Pro Gln Gly Met Pro Glu Gly Asp Leu Val Tyr Val Asn
 1               5                  10                  15
```

-continued

```
Tyr Ala Arg Thr Glu Asp Phe Phe Lys Leu Glu Arg Asp Met
            20                  25                  30

<210> SEQ ID NO 1010
<211> LENGTH: 23
<212> TYPE: PRT
<213> ORGANISM: Homo sapiens

<400> SEQUENCE: 1010

Gly Met Pro Glu Gly Asp Leu Val Tyr Val Asn Tyr Ala Arg Thr Glu
1               5                   10                  15

Asp Phe Phe Lys Leu Glu Arg
            20

<210> SEQ ID NO 1011
<211> LENGTH: 9
<212> TYPE: PRT
<213> ORGANISM: Homo sapiens

<400> SEQUENCE: 1011

Met Pro Glu Gly Asp Leu Val Tyr Val
1               5

<210> SEQ ID NO 1012
<211> LENGTH: 10
<212> TYPE: PRT
<213> ORGANISM: Homo sapiens

<400> SEQUENCE: 1012

Gly Met Pro Glu Gly Asp Leu Val Tyr Val
1               5                   10

<210> SEQ ID NO 1013
<211> LENGTH: 9
<212> TYPE: PRT
<213> ORGANISM: Homo sapiens

<400> SEQUENCE: 1013

Gly Met Pro Glu Gly Asp Leu Val Tyr
1               5

<210> SEQ ID NO 1014
<211> LENGTH: 10
<212> TYPE: PRT
<213> ORGANISM: Homo sapiens

<400> SEQUENCE: 1014

Gln Gly Met Pro Glu Gly Asp Leu Val Tyr
1               5                   10

<210> SEQ ID NO 1015
<211> LENGTH: 8
<212> TYPE: PRT
<213> ORGANISM: Homo sapiens

<400> SEQUENCE: 1015

Met Pro Glu Gly Asp Leu Val Tyr
1               5

<210> SEQ ID NO 1016
<211> LENGTH: 9
<212> TYPE: PRT
<213> ORGANISM: Homo sapiens

<400> SEQUENCE: 1016
```

Glu Gly Asp Leu Val Tyr Val Asn Tyr
1               5

<210> SEQ ID NO 1017
<211> LENGTH: 10
<212> TYPE: PRT
<213> ORGANISM: Homo sapiens

<400> SEQUENCE: 1017

Pro Glu Gly Asp Leu Val Tyr Val Asn Tyr
1               5                   10

<210> SEQ ID NO 1018
<211> LENGTH: 10
<212> TYPE: PRT
<213> ORGANISM: Homo sapiens

<400> SEQUENCE: 1018

Leu Val Tyr Val Asn Tyr Ala Arg Thr Glu
1               5                   10

<210> SEQ ID NO 1019
<211> LENGTH: 9
<212> TYPE: PRT
<213> ORGANISM: Homo sapiens

<400> SEQUENCE: 1019

Val Asn Tyr Ala Arg Thr Glu Asp Phe
1               5

<210> SEQ ID NO 1020
<211> LENGTH: 10
<212> TYPE: PRT
<213> ORGANISM: Homo sapiens

<400> SEQUENCE: 1020

Tyr Val Asn Tyr Ala Arg Thr Glu Asp Phe
1               5                   10

<210> SEQ ID NO 1021
<211> LENGTH: 9
<212> TYPE: PRT
<213> ORGANISM: Homo sapiens

<400> SEQUENCE: 1021

Asn Tyr Ala Arg Thr Glu Asp Phe Phe
1               5

<210> SEQ ID NO 1022
<211> LENGTH: 8
<212> TYPE: PRT
<213> ORGANISM: Homo sapiens

<400> SEQUENCE: 1022

Tyr Ala Arg Thr Glu Asp Phe Phe
1               5

<210> SEQ ID NO 1023
<211> LENGTH: 9
<212> TYPE: PRT
<213> ORGANISM: Homo sapiens

<400> SEQUENCE: 1023

Arg Thr Glu Asp Phe Phe Lys Leu Glu
1               5

-continued

<210> SEQ ID NO 1024
<211> LENGTH: 30
<212> TYPE: PRT
<213> ORGANISM: Homo sapiens

<400> SEQUENCE: 1024

Arg Gly Ile Ala Glu Ala Val Gly Leu Pro Ser Ile Pro Val His Pro
1               5                   10                  15

Ile Gly Tyr Tyr Asp Ala Gln Lys Leu Leu Glu Lys Met Gly
            20                  25                  30

<210> SEQ ID NO 1025
<211> LENGTH: 25
<212> TYPE: PRT
<213> ORGANISM: Homo sapiens

<400> SEQUENCE: 1025

Ile Ala Glu Ala Val Gly Leu Pro Ser Ile Pro Val His Pro Ile Gly
1               5                   10                  15

Tyr Tyr Asp Ala Gln Lys Leu Leu Glu
            20                  25

<210> SEQ ID NO 1026
<211> LENGTH: 9
<212> TYPE: PRT
<213> ORGANISM: Homo sapiens

<400> SEQUENCE: 1026

Leu Pro Ser Ile Pro Val His Pro Ile
1               5

<210> SEQ ID NO 1027
<211> LENGTH: 10
<212> TYPE: PRT
<213> ORGANISM: Homo sapiens

<400> SEQUENCE: 1027

Gly Leu Pro Ser Ile Pro Val His Pro Ile
1               5                   10

<210> SEQ ID NO 1028
<211> LENGTH: 9
<212> TYPE: PRT
<213> ORGANISM: Homo sapiens

<400> SEQUENCE: 1028

Ile Gly Tyr Tyr Asp Ala Gln Lys Leu
1               5

<210> SEQ ID NO 1029
<211> LENGTH: 10
<212> TYPE: PRT
<213> ORGANISM: Homo sapiens

<400> SEQUENCE: 1029

Pro Ile Gly Tyr Tyr Asp Ala Gln Lys Leu
1               5                   10

<210> SEQ ID NO 1030
<211> LENGTH: 9
<212> TYPE: PRT
<213> ORGANISM: Homo sapiens

<400> SEQUENCE: 1030

```
Ser Ile Pro Val His Pro Ile Gly Tyr
1               5

<210> SEQ ID NO 1031
<211> LENGTH: 10
<212> TYPE: PRT
<213> ORGANISM: Homo sapiens

<400> SEQUENCE: 1031

Pro Ser Ile Pro Val His Pro Ile Gly Tyr
1               5                   10

<210> SEQ ID NO 1032
<211> LENGTH: 8
<212> TYPE: PRT
<213> ORGANISM: Homo sapiens

<400> SEQUENCE: 1032

Ile Pro Val His Pro Ile Gly Tyr
1               5

<210> SEQ ID NO 1033
<211> LENGTH: 9
<212> TYPE: PRT
<213> ORGANISM: Homo sapiens

<400> SEQUENCE: 1033

Tyr Tyr Asp Ala Gln Lys Leu Leu Glu
1               5

<210> SEQ ID NO 1034
<211> LENGTH: 27
<212> TYPE: PRT
<213> ORGANISM: Homo sapiens

<400> SEQUENCE: 1034

Ser Ser Ile Glu Gly Asn Tyr Thr Leu Arg Val Asp Cys Thr Pro Leu
1               5                   10                  15

Met Tyr Ser Leu Val His Leu Thr Lys Glu Leu
            20                  25

<210> SEQ ID NO 1035
<211> LENGTH: 9
<212> TYPE: PRT
<213> ORGANISM: Homo sapiens

<400> SEQUENCE: 1035

Ile Glu Gly Asn Tyr Thr Leu Arg Val
1               5

<210> SEQ ID NO 1036
<211> LENGTH: 10
<212> TYPE: PRT
<213> ORGANISM: Homo sapiens

<400> SEQUENCE: 1036

Ser Ile Glu Gly Asn Tyr Thr Leu Arg Val
1               5                   10

<210> SEQ ID NO 1037
<211> LENGTH: 8
<212> TYPE: PRT
<213> ORGANISM: Homo sapiens

<400> SEQUENCE: 1037
```

```
Glu Gly Asn Tyr Thr Leu Arg Val
1               5

<210> SEQ ID NO 1038
<211> LENGTH: 9
<212> TYPE: PRT
<213> ORGANISM: Homo sapiens

<400> SEQUENCE: 1038

Thr Leu Arg Val Asp Cys Thr Pro Leu
1               5

<210> SEQ ID NO 1039
<211> LENGTH: 10
<212> TYPE: PRT
<213> ORGANISM: Homo sapiens

<400> SEQUENCE: 1039

Tyr Thr Leu Arg Val Asp Cys Thr Pro Leu
1               5                   10

<210> SEQ ID NO 1040
<211> LENGTH: 9
<212> TYPE: PRT
<213> ORGANISM: Homo sapiens

<400> SEQUENCE: 1040

Leu Arg Val Asp Cys Thr Pro Leu Met
1               5

<210> SEQ ID NO 1041
<211> LENGTH: 9
<212> TYPE: PRT
<213> ORGANISM: Homo sapiens

<400> SEQUENCE: 1041

Arg Val Asp Cys Thr Pro Leu Met Tyr
1               5

<210> SEQ ID NO 1042
<211> LENGTH: 10
<212> TYPE: PRT
<213> ORGANISM: Homo sapiens

<400> SEQUENCE: 1042

Leu Arg Val Asp Cys Thr Pro Leu Met Tyr
1               5                   10

<210> SEQ ID NO 1043
<211> LENGTH: 35
<212> TYPE: PRT
<213> ORGANISM: Homo sapiens

<400> SEQUENCE: 1043

Phe Asp Lys Ser Asn Pro Ile Val Leu Arg Met Met Asn Asp Gln Leu
1               5                   10                  15
Met Phe Leu Glu Arg Ala Phe Ile Asp Pro Leu Gly Leu Pro Asp Arg
            20                  25                  30
Pro Phe Tyr
        35

<210> SEQ ID NO 1044
<211> LENGTH: 22
<212> TYPE: PRT
<213> ORGANISM: Homo sapiens
```

<400> SEQUENCE: 1044

Val Leu Arg Met Met Asn Asp Gln Leu Met Phe Leu Glu Arg Ala Phe
1               5                   10                  15

Ile Asp Pro Leu Gly Leu
            20

<210> SEQ ID NO 1045
<211> LENGTH: 9
<212> TYPE: PRT
<213> ORGANISM: Homo sapiens

<400> SEQUENCE: 1045

Met Met Asn Asp Gln Leu Met Phe Leu
1               5

<210> SEQ ID NO 1046
<211> LENGTH: 10
<212> TYPE: PRT
<213> ORGANISM: Homo sapiens

<400> SEQUENCE: 1046

Arg Met Met Asn Asp Gln Leu Met Phe Leu
1               5                   10

<210> SEQ ID NO 1047
<211> LENGTH: 9
<212> TYPE: PRT
<213> ORGANISM: Homo sapiens

<400> SEQUENCE: 1047

Arg Met Met Asn Asp Gln Leu Met Phe
1               5

<210> SEQ ID NO 1048
<211> LENGTH: 17
<212> TYPE: PRT
<213> ORGANISM: Homo sapiens

<400> SEQUENCE: 1048

Met Leu Leu Ala Val Leu Tyr Cys Leu Leu Trp Ser Phe Gln Thr Ser
1               5                   10                  15

Ala

<210> SEQ ID NO 1049
<211> LENGTH: 661
<212> TYPE: PRT
<213> ORGANISM: Homo sapiens

<400> SEQUENCE: 1049

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
                20                  25                  30

Leu Gly Val Ser Arg Gln Leu Arg Thr Lys Ala Trp Asn Arg Gln Leu
            35                  40                  45

Tyr Pro Glu Trp Thr Glu Ala Gln Arg Leu Asp Cys Trp Arg Gly Gly
        50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

```
Leu Pro Asp Gly Gln Val Ile Trp Val Asn Asn Thr Ile Ile Asn Gly
            100                 105                 110

Ser Gln Val Trp Gly Gly Pro Val Tyr Pro Gln Glu Thr Asp Asp
    115                 120                 125

Ala Cys Ile Phe Pro Asp Gly Gly Pro Cys Pro Ser Gly Ser Trp Ser
130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Pro Val Val Thr His Thr Tyr Leu Glu Pro Gly Pro Val Thr Ala
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
```

```
                515                 520                 525
Ser Ser Pro Gly Cys Gln Pro Ala Gln Arg Leu Cys Gln Pro Val
        530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
                580                 585                 590

Leu Gly Gln Val Pro Leu Ile Val Gly Ile Leu Leu Val Leu Met Ala
                595                 600                 605

Val Val Leu Ala Ser Leu Ile Tyr Arg Arg Arg Leu Met Lys Gln Asp
                610                 615                 620

Phe Ser Val Pro Gln Leu Pro His Ser Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
                660

<210> SEQ ID NO 1050
<211> LENGTH: 309
<212> TYPE: PRT
<213> ORGANISM: Homo sapiens

<400> SEQUENCE: 1050

Met Ser Leu Glu Gln Arg Ser Leu His Cys Lys Pro Glu Glu Ala Leu
 1                   5                  10                  15

Glu Ala Gln Gln Glu Ala Leu Gly Leu Val Cys Val Gln Ala Ala Thr
                20                  25                  30

Ser Ser Ser Ser Pro Leu Val Leu Gly Thr Leu Glu Glu Val Pro Thr
                35                  40                  45

Ala Gly Ser Thr Asp Pro Pro Gln Ser Pro Gln Gly Ala Ser Ala Phe
            50                  55                  60

Pro Thr Thr Ile Asn Phe Thr Arg Gln Arg Gln Pro Ser Glu Gly Ser
 65                  70                  75                  80

Ser Ser Arg Glu Glu Glu Gly Pro Ser Thr Ser Cys Ile Leu Glu Ser
                 85                  90                  95

Leu Phe Arg Ala Val Ile Thr Lys Lys Val Ala Asp Leu Val Gly Phe
                100                 105                 110

Leu Leu Leu Lys Tyr Arg Ala Arg Glu Pro Val Thr Lys Ala Glu Met
            115                 120                 125

Leu Glu Ser Val Ile Lys Asn Tyr Lys His Cys Phe Pro Glu Ile Phe
        130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr
```

```
                225                 230                 235                 240
Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Arg Phe Phe Pro Ser Leu Arg Glu Ala Ala Leu Arg Glu
        290                 295                 300

Glu Glu Glu Gly Val
305

<210> SEQ ID NO 1051
<211> LENGTH: 314
<212> TYPE: PRT
<213> ORGANISM: Homo sapiens

<400> SEQUENCE: 1051

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Gln Gln Thr Ala Ser Ser Ser Thr Leu Val Glu Val
        35                  40                  45

Thr Leu Gly Glu Val Pro Ala Ala Asp Ser Pro Ser Pro Pro His Ser
50                  55                  60

Pro Gln Gly Ala Ser Ser Phe Ser Thr Thr Ile Asn Tyr Thr Leu Trp
65                  70                  75                  80

Arg Gln Ser Asp Glu Gly Ser Ser Asn Gln Glu Glu Glu Gly Pro Arg
                85                  90                  95

Met Phe Pro Asp Leu Glu Ser Glu Phe Gln Ala Ala Ile Ser Arg Lys
            100                 105                 110

Met Val Glu Leu Val His Phe Leu Leu Leu Lys Tyr Arg Ala Arg Glu
        115                 120                 125

Pro Val Thr Lys Ala Glu Met Leu Glu Ser Val Leu Arg Asn Cys Gln
    130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Pro Ile Ser His Leu Tyr
                165                 170                 175

Ile Leu Val Thr Cys Leu Gly Leu Ser Tyr Asp Gly Leu Leu Gly Asp
            180                 185                 190

Asn Gln Val Met Pro Lys Thr Gly Leu Leu Ile Ile Val Leu Ala Ile
        195                 200                 205

Ile Ala Ile Glu Gly Asp Cys Ala Pro Glu Glu Lys Ile Trp Glu Glu
    210                 215                 220

Leu Ser Met Leu Glu Val Phe Glu Gly Arg Glu Asp Ser Val Phe Ala
225                 230                 235                 240

His Pro Arg Lys Leu Leu Met Gln Asp Leu Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Ile Glu Thr Ser Tyr Val Lys Val Leu His
        275                 280                 285

His Thr Leu Lys Ile Gly Gly Glu Pro His Ile Ser Tyr Pro Pro Leu
```

```
              290                 295                 300

His Glu Arg Ala Leu Arg Glu Gly Glu Glu
305                 310

<210> SEQ ID NO 1052
<211> LENGTH: 314
<212> TYPE: PRT
<213> ORGANISM: Homo sapiens

<400> SEQUENCE: 1052

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
                20                  25                  30

Thr Glu Gln Glu Ala Ala Ser Ser Ser Thr Leu Val Glu Val
            35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

<210> SEQ ID NO 1053
<211> LENGTH: 180
<212> TYPE: PRT
<213> ORGANISM: Homo sapiens

<400> SEQUENCE: 1053
```

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65              70                  75                  80

Arg Gly Pro Glu Ser Arg Leu Leu Glu Phe Tyr Leu Ala Met Pro Phe
            85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
            130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 1054
<211> LENGTH: 180
<212> TYPE: PRT
<213> ORGANISM: Homo sapiens

<400> SEQUENCE: 1054

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Arg Gly Gly Ala Pro Arg Gly Pro
    50                  55                  60

His Gly Gly Ala Ala Ser Ala Gln Asp Gly Arg Cys Pro Cys Gly Ala
65              70                  75                  80

Arg Arg Pro Asp Ser Arg Leu Leu Glu Leu His Ile Thr Met Pro Phe
            85                  90                  95

Ser Ser Pro Met Glu Ala Glu Leu Val Arg Arg Ile Leu Ser Arg Asp
            100                 105                 110

Ala Ala Pro Leu Pro Arg Pro Gly Ala Val Leu Lys Asp Phe Thr Val
            115                 120                 125

Ser Gly Asn Leu Leu Phe Ile Arg Leu Thr Ala Ala Asp His Arg Gln
            130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Ala Pro Ser
                165                 170                 175

Gly Gln Arg Arg
            180

```
<210> SEQ ID NO 1055
<211> LENGTH: 210
<212> TYPE: PRT
<213> ORGANISM: Homo sapiens

<400> SEQUENCE: 1055

Met Gln Ala Glu Gly Arg Gly Thr Gly Ser Thr Gly Asp Ala Asp
 1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Arg Gly Gly Ala Pro Arg Gly Pro
        50                  55                  60

His Gly Gly Ala Ala Ser Ala Gln Asp Gly Arg Cys Pro Cys Gly Ala
 65                 70                  75                  80

Arg Arg Pro Asp Ser Arg Leu Leu Glu Leu His Ile Thr Met Pro Phe
                85                  90                  95

Ser Ser Pro Met Glu Ala Glu Leu Val Arg Arg Ile Leu Ser Arg Asp
            100                 105                 110

Ala Ala Pro Leu Pro Arg Pro Gly Ala Val Leu Lys Asp Phe Thr Val
        115                 120                 125

Ser Gly Asn Leu Leu Phe Met Ser Val Trp Asp Gln Asp Arg Glu Gly
    130                 135                 140

Ala Gly Arg Met Arg Val Val Gly Trp Gly Leu Gly Ser Ala Ser Pro
145                 150                 155                 160

Glu Gly Gln Lys Ala Arg Asp Leu Arg Thr Pro Lys His Lys Val Ser
                165                 170                 175

Glu Gln Arg Pro Gly Thr Pro Gly Pro Pro Pro Glu Gly Ala Gln
            180                 185                 190

Gly Asp Gly Cys Arg Gly Val Ala Phe Asn Val Met Phe Ser Ala Pro
        195                 200                 205

His Ile
    210

<210> SEQ ID NO 1056
<211> LENGTH: 509
<212> TYPE: PRT
<213> ORGANISM: Homo sapiens

<400> SEQUENCE: 1056

Met Glu Arg Arg Arg Leu Trp Gly Ser Ile Gln Ser Arg Tyr Ile Ser
 1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
 65                 70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110
```

-continued

```
Arg Pro Arg Arg Trp Lys Leu Gln Val Leu Asp Leu Arg Lys Asn Ser
            115                 120                 125

His Gln Asp Phe Trp Thr Val Trp Ser Gly Asn Arg Ala Ser Leu Tyr
        130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ala Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505

<210> SEQ ID NO 1057
<211> LENGTH: 261
<212> TYPE: PRT
<213> ORGANISM: Homo sapiens
```

```
<400> SEQUENCE: 1057

Met Trp Val Pro Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
                35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 1058
<211> LENGTH: 123
<212> TYPE: PRT
<213> ORGANISM: Homo sapiens

<400> SEQUENCE: 1058

Met Lys Ala Val Leu Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
                35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95
```

Ala His Ala Leu Gln Pro Ala Ala Ala Ile Leu Ala Leu Leu Pro Ala
            100                 105                 110

Leu Gly Leu Leu Leu Trp Gly Pro Gly Gln Leu
            115                 120

<210> SEQ ID NO 1059
<211> LENGTH: 2817
<212> TYPE: DNA
<213> ORGANISM: Homo sapiens

<400> SEQUENCE: 1059

| | | | | | |
|---|---|---|---|---|---|
| gtgctaaaaa | gatgccttct | tcatttggct | gtgataggtg | ctttgtggct | gtgggggcta | 60 |
| caaaagtacc | cagaaaccag | gactggcttg | tgtctcaag | gcaactcaga | accaaagcct | 120 |
| ggaacaggca | gctgtatcca | gagtggacag | aagcccagag | acttgactgc | tggagaggtg | 180 |
| gtcaagtgtc | cctcaaggtc | agtaatgatg | ggcctacact | gattggtgca | aatgcctcct | 240 |
| tctctattgc | cttgaacttc | cctggaagcc | aaaaggtatt | gccagatggg | caggttatct | 300 |
| gggtcaacaa | taccatcatc | aatgggagcc | aggtgtgggg | aggacagcca | gtgtatcccc | 360 |
| aggaaactga | cgatgcctgc | atcttccctg | atggtggacc | ttgcccatct | ggctcttggt | 420 |
| ctcagaagag | aagctttgtt | tatgtctgga | agacctgggg | tgagggactc | ccttctcagc | 480 |
| ctatcatcca | cacttgtgtt | tacttctttc | tacctgatca | cctttctttt | ggccgccct | 540 |
| tccaccttaa | cttctgtgat | tttctctaat | cttcattttc | ctcttagatc | ttttctcttt | 600 |
| cttagcacct | agcccccttc | aagctctatc | ataattcttt | ctggcaactc | ttggcctcaa | 660 |
| ttgtagtcct | accccatgga | atgcctcatt | aggacccctt | ccctgtcccc | ccatatcaca | 720 |
| gccttccaaa | caccctcaga | agtaatcata | cttcctgacc | tcccatctcc | agtgccgttt | 780 |
| cgaagcctgt | ccctcagtcc | cctttgacca | gtaatctctt | cttccttgct | tttcattcca | 840 |
| aaaatgcttc | aggccaatac | tggcaagttc | taggggcccc | agtgtctggg | ctgagcattg | 900 |
| ggacaggcag | ggcaatgctg | ggcacacaca | ccatggaagt | gactgtctac | catcgccggg | 960 |
| gatcccggag | ctatgtgcct | cttgctcatt | ccagctcagc | cttcaccatt | actggtaagg | 1020 |
| gttcaggaag | ggcaaggcca | gttgtagggc | aaagagaagg | cagggaggct | tggatggact | 1080 |
| gcaaaggaga | aaggtgaaat | gctgtgcaaa | cttaaagtag | aagggccagg | aagacctagg | 1140 |
| cagagaaatg | tgaggcttag | tgccagtgaa | gggccagcca | gtcagcttgg | agttggaggg | 1200 |
| tgtggctgtg | aaaggagaag | ctgtggctca | ggcctggttc | tcacctttc | tggctccaat | 1260 |
| cccagaccag | gtgcctttct | ccgtgagcgt | gtcccagttg | cgggccttgg | atggagggaa | 1320 |
| caagcacttc | ctgagaaatc | agcctctgac | ctttgccctc | cagctccatg | accccagtgg | 1380 |
| ctatctggct | gaagctgacc | tctcctacac | ctgggacttt | ggagacagta | gtggaaccct | 1440 |
| gatctctcgg | gcacctgtgg | tcactcatac | ttacctggag | cctggcccag | tcactgccca | 1500 |
| ggtggtcctg | caggctgcca | ttcctctcac | ctcctgtggc | tcctcccag | ttccaggcac | 1560 |
| cacagatggg | cacaggccaa | ctgcagaggc | ccctaacacc | acagctggcc | aagtgcctac | 1620 |
| tacagaagtt | gtgggtacta | cacctggtca | ggcgccaact | gcagagccct | ctggaaccac | 1680 |
| atctgtgcag | gtgccaacca | ctgaagtcat | aagcactgca | cctgtgcaga | tgccaactgc | 1740 |
| agagagcaca | ggtatgacac | ctgagaaggt | gccagtttca | gaggtcatgg | gtaccacact | 1800 |
| ggcagagatg | tcaactccag | aggctacagg | tatgacacct | gcagaggtat | caattgtggt | 1860 |
| gctttctgga | accacagctg | cacaggtaac | aactacagag | tgggtggaga | ccacagctag | 1920 |
| agagctacct | atccctgagc | ctgaaggtcc | agatgccagc | tcaatcatgt | ctacggaaag | 1980 |

| | |
|---|---:|
| tattacaggt tccctgggcc ccctgctgga tggtacagcc accttaaggc tggtgaagag | 2040 |
| acaagtcccc ctggattgtg ttctgtatcg atatggttcc ttttccgtca ccctggacat | 2100 |
| tgtccagggt attgaaagtg ccgagatcct gcaggctgtg ccgtccggtg aggggatgc | 2160 |
| atttgagctg actgtgtcct gccaaggcgg gctgcccaag aagcctgca tggagatctc | 2220 |
| atcgccaggg tgccagcccc ctgcccagcg gctgtgccag cctgtgctac ccagcccagc | 2280 |
| ctgccagctg gttctgcacc agatactgaa gggtggctcg gggacatact gcctcaatgt | 2340 |
| gtctctggct gataccaaca gcctggcagt ggtcagcacc cagcttatca tgcctggtag | 2400 |
| gtccttggac agagactaag tgaggaggga agtggataga ggggacagct ggcaagcagc | 2460 |
| agacatgagt gaagcagtgc ctgggattct tctcacaggt caagaagcag gccttgggca | 2520 |
| ggttccgctg atcgtgggca tcttgctggt gttgatggct gtggtccttg catctctgat | 2580 |
| atataggcgc agacttatga agcaagactt ctccgtaccc cagttgccac atagcagcag | 2640 |
| tcactggctg cgtctacccc gcatcttctg ctcttgtccc attggtgaga atagccccct | 2700 |
| cctcagtggg cagcaggtct gagtactctc atatgatgct gtgattttcc tggagttgac | 2760 |
| agaaacacct atatttcccc cagtcttccc tgggagacta ctattaactg aaataaa | 2817 |

<210> SEQ ID NO 1060
<211> LENGTH: 2420
<212> TYPE: DNA
<213> ORGANISM: Homo sapiens

<400> SEQUENCE: 1060

| | |
|---|---:|
| ggatccaggc cctgccagga aaatataag ggccctgcgt gagaacagag ggggtcatcc | 60 |
| actgcatgag agtggggatg tcacagagtc cagcccaccc tcctggtagc actgagaagc | 120 |
| cagggctgtg cttgcggtct gcaccctgag ggcccgtgga ttcctcttcc tggagctcca | 180 |
| ggaaccaggc agtgaggcct tggtctgaga cagtatcctc aggtcacaga gcagaggatg | 240 |
| cacagggtgt gccagcagtg aatgtttgcc ctgaatgcac accaagggcc ccacctgcca | 300 |
| caggacacat aggactccac agagtctggc ctcacctccc tactgtcagt cctgtagaat | 360 |
| cgacctctgc tggccggctg taccctgagt accctctcac ttcctccttc aggttttcag | 420 |
| gggacaggcc aacccagagg acaggattcc ctggaggcca cagaggagca ccaaggagaa | 480 |
| gatctgtaag taggcctttg ttagagtctc caaggttcag ttctcagctg aggcctctca | 540 |
| cacactccct ctctccccag gcctgtgggt cttcattgcc cagctcctgc ccacactcct | 600 |
| gcctgctgcc ctgacgagag tcatcatgtc tcttgagcag aggagtctgc actgcaagcc | 660 |
| tgaggaagcc cttgaggccc aacaagaggc cctgggcctg gtgtgtgtgc aggctgccac | 720 |
| ctcctcctcc tctcctctgg tcctgggcac cctggaggag gtgcccactg ctgggtcaac | 780 |
| agatcctccc cagagtcctc agggagcctc cgcctttccc actaccatca acttcactcg | 840 |
| acagaggcaa cccagtgagg gttccagcag ccgtgaagag gaggggccaa gcacctcttg | 900 |
| tatcctggag tccttgttcc gagcagtaat cactaagaag gtggctgatt tggttggttt | 960 |
| tctgctcctc aaatatcgag ccaggagcc agtcacaaag gcagaaatgc tggagagtgt | 1020 |
| catcaaaaat tacaagcact gttttcctga tcttcggc aaagcctctg agtccttgca | 1080 |
| gctggtcttt ggcattgacg tgaaggaagc agacccacc ggccactcct atgtccttgt | 1140 |
| cacctgccta ggtctctcct atgatggcct gctgggtgat aatcagatca tgcccaagac | 1200 |
| aggcttcctg ataattgtcc tggtcatgat tgcaatggag gcggccatg ctcctgagga | 1260 |
| ggaaatctgg gaggagctga gtgtgatgga ggtgtatgat gggagggagc acagtgccta | 1320 |

```
tggggagccc aggaagctgc tcacccaaga tttggtgcag gaaaagtacc tggagtaccg   1380
gcaggtgccg gacagtgatc ccgcacgcta tgagttcctg tggggtccaa gggccctcgc   1440
tgaaaccagc tatgtgaaag tccttgagta tgtgatcaag gtcagtgcaa gagttcgctt   1500
tttcttccca tccctgcgtg aagcagcttt gagagaggag gaagagggag tctgagcatg   1560
agttgcagcc aaggccagtg ggaggggac tgggccagtg caccttccag ggccgcgtcc    1620
agcagcttcc cctgcctcgt gtgacatgag gcccattctt cactctgaag agagcggtca   1680
gtgttctcag tagtaggttt ctgttctatt gggtgacttg gagatttatc tttgttctct   1740 tttgaattg ttcaaatgtt ttttttaag ggatggttga atgaacttca gcatccaagt      1800
ttatgaatga cagcagtcac acagttctgt gtatatagtt taagggtaag agtcttgtgt   1860
tttattcaga ttgggaaatc cattctattt tgtgaattgg gataataaca gcagtggaat   1920
aagtacttag aaatgtgaaa aatgagcagt aaaatagatg agataaagaa ctaaagaaat   1980
taagagatag tcaattcttg ccttatacct cagtctattc tgtaaaattt ttaaagatat   2040
atgcatacct ggatttcctt ggcttctttg agaatgtaag agaaattaaa tctgaataaa   2100
gaattcttcc tgttcactgg ctcttttctt ctccatgcac tgagcatctg cttttggaa     2160 ggccctgggt tagtagtgga gatgctaagg taagccagac tcatacccac ccatagggtc   2220
gtagagtcta ggagctgcag tcacgtaatc gaggtggcaa gatgtcctct aaagatgtag   2280
ggaaaagtga gagaggggtg agggtgtggg gctccgggtg agagtggtgg agtgtcaatg   2340
ccctgagctg gggcattttg ggctttggga aactgcagtt ccttctgggg gagctgattg   2400
taatgatctt gggtggatcc                                                2420

<210> SEQ ID NO 1061
<211> LENGTH: 4559
<212> TYPE: DNA
<213> ORGANISM: Homo sapiens

<400> SEQUENCE: 1061
attccttcat caaacagcca ggagtgagga agaggaccct cctgagtgag gactgaggat     60
ccaccctcac cacatagtgg gaccacagaa tccagctcag cccctcttgt cagccctggt   120
acacactggc aatgatctca ccccgagcac accctcccc ccaatgccac ttcgggccga    180
ctcagagtca gagacttggt ctgaggggag cagacacaat cggcagagga tggcggtcca   240
ggctcagtct ggcatccaag tcaggacctt gagggatgac caaaggcccc tcccacccc    300 aactccccg accccaccag gatctacagc ctcaggatcc ccgtcccaat ccctacccct    360
acaccaacac catcttcatg cttaccccca ccccccatc cagatcccca tccgggcaga   420
atccggttcc acccttgccg tgaacccagg gaagtcacgg gcccggatgt gacgccactg    480
acttgcacat tggaggtcag aggacagcga gattctcgcc ctgagcaacg gcctgacgtc   540
ggcggaggga agcaggcgca ggctccgtga ggaggcaagg taagacgccg agggaggact   600
gaggcgggcc tcaccccaga cagagggccc ccaataatcc agcgctgcct ctgctgccgg   660
gcctggacca ccctgcaggg gaagacttct caggctcagt cgccaccacc tcaccccgcc   720
accccccgcc gctttaaccg cagggaactc tggcgtaaga gctttgtgtg accagggcag   780
ggctggttag aagtgctcag ggcccagact cagccaggaa tcaaggtcag gaccccaaga   840
ggggactgag ggcaacccac cccctaccct cactaccaat cccatccccc aacaccaacc   900 ccaccccat ccctcaaaca ccaacccac cccaaaccc cattcccatc tcctccccca    960
ccaccatcct ggcagaatcc ggctttgccc ctgcaatcaa cccacggaag ctccgggaat  1020
```

```
ggcggccaag cacgcggatc ctgacgttca catgtacggc taagggaggg aaggggttgg    1080
gtctcgtgag tatggccttt gggatgcaga ggaaggcccc aggcctcctg aagacagtg    1140 gagtccttag gggacccagc atgccaggac agggggccca ctgtacccct gtctcaaact    1200
gagccacctt ttcattcagc cgagggaatc ctagggatgc agacccactt cagcaggggg    1260
ttggggccca gcctgcgagg agtcaagggg aggaagaaga gggaggactg aggggacctt    1320
ggagtccaga tcagtggcaa ccttgggctg gggatcctg gcacagtgg ccgaatgtgc     1380 cccgtgctca ttgcaccttc agggtgacag agagttgagg gctgtggtct gagggctggg    1440
acttcaggtc agcagaggga ggaatcccag gatctgccgg acccaaggtg tgccccttc    1500 atgaggactg gggatacccc cggcccagaa agaagggatg ccacagagtc tggaagtccc    1560
ttgttcttag ctctgggga acctgatcag ggatggccct aagtgacaat ctcatttgta    1620
ccacaggcag gaggttgggg aaccctcagg agataaggt gttggtgtaa agaggagctg     1680
tctgctcatt tcaggggttt gggggttgag aaagggcagt ccctggcagg agtaaagatg    1740
agtaacccac aggaggccat cataacgttc accctagaac caaaggggtc agccctggac    1800
aacgcacgtg ggggtaacag gatgtggccc ctcctcactt gtctttccag atctcaggga    1860
gttgatgacc ttgttttcag aaggtgactc aggtcaacac aggggcccca tctggtcgac    1920
agatgcagtg gttctaggat ctgccaagca tccaggtgga gagcctgagg taggattgag    1980
ggtacccctg gccagaatg cagcaagggg gccccataga aatctgccct gccctgcgg    2040 ttacttcaga gaccctgggc agggctgtca gctgaagtcc ctccattatc ctgggatctt    2100
tgatgtcagg gaaggggagg ccttggtctg aaggggctgg agtcaggtca gtagagggag    2160
ggtctcaggc cctgccagga gtggacgtga ggaccaagcg gactcgtcac ccaggacacc    2220
tggactccaa tgaatttgga catctctcgt tgtccttcgc ggaggacct ggtcacgtat    2280 ggccagatgt gggtcccctc atatccttct gtaccatatc agggatgtga gttcttgaca    2340
tgagagattc tcaagccagc aaaagggtgg gattaggccc tacaaggaga aaggtgaggg    2400
ccctgagtga gcacagaggg gaccctccac ccaagtagag tggggacctc acggagtctg    2460
gccaaccctg ctgagacttc tgggaatccg tggctgtgct tgcagtctgc acactgaagg    2520
cccgtgcatt cctctcccag gaatcaggag ctccaggaac caggcagtga ggccttggtc    2580
tgagtcagtg tcctcaggtc acagagcaga ggggacgcag acagtgccaa cactgaaggt    2640
ttgcctggaa tgcacaccaa gggcccacc cgcccagaac aaatgggact ccagagggcc     2700
tggcctcacc ctcccattc tcagtcctgc agcctgagca tgtgctggcc ggctgtaccc    2760
tgaggtgccc tcccacttcc tccttcaggt tctgaggggg acaggctgac aagtaggacc    2820
cgaggcactg gaggagcatt gaaggagaag atctgtaagt aagcctttgt cagagcctcc    2880
aaggttcagt tcagttctca cctaaggcct cacacacgct ccttctctcc ccaggcctgt    2940
gggtcttcat tgcccagctc ctgcccgcac tcctgcctgc tgccctgacc agagtcatca    3000
tgcctcttga gcagaggagt cagcactgca agcctgaaga aggccttgag gcccgaggag    3060
aggccctggg cctggtgggt gcgcaggctc ctgctactga ggagcagcag accgcttctt    3120
cctcttctac tctagtggaa gttaccctgg gggaggtgcc tgctgccgac tcaccgagtc    3180
ctccccacag tcctcaggga gcctccagct tctcgactac catcaactac actctttgga    3240
gacaatccga tgagggctcc agcaaccaag aagaggaggg gccaagaatg tttcccgacc    3300
tggagtccga gttccaagca gcaatcagta ggaagatggt tgagttggtt cattttctgc    3360
tcctcaagta tcgagccagg gagccggtca caaaggcaga aatgctggag agtgtcctca    3420
```

```
gaaattgcca ggacttcttt cccgtgatct tcagcaaagc ctccgagtac ttgcagctgg    3480
tctttggcat cgaggtggtg gaagtggtcc ccatcagcca cttgtacatc cttgtcacct    3540
gcctgggcct ctcctacgat ggcctgctgg gcgacaatca ggtcatgccc aagacaggcc    3600
tcctgataat cgtcctggcc ataatcgcaa tagagggcga ctgtgcccct gaggagaaaa    3660
tctgggagga gctgagtatg ttggaggtgt tgaggggag ggaggacagt gtcttcgcac    3720
atcccaggaa gctgctcatg caagatctgg tgcaggaaaa ctacctggag taccggcagg    3780
tgcccggcag tgatcctgca tgctacgagt tcctgtgggg tccaagggcc ctcattgaaa    3840
ccagctatgt gaaagtcctg caccatacac taaagatcgg tggagaacct cacatttcct    3900
acccacccct gcatgaacgg gctttgagag agggagaaga gtgagtctca gcacatgttg    3960
cagccagggc cagtgggagg gggtctgggc cagtgcacct tccagggccc catccattag    4020
cttccactgc ctcgtgtgat atgaggccca ttcctgcctc tttgaagaga gcagtcagca    4080
ttcttagcag tgagttctg ttctgttgga tgactttgag atttatcttt ctttcctgtt    4140
ggaattgttc aaatgttcct tttaacaaat ggttggatga acttcagcat ccaagtttat    4200
gaatgacagt agtcacacat agtgctgttt atatagttta ggggtaagag tcctgttttt    4260
tattcagatt gggaaatcca ttccattttg tgagttgtca cataataaca gcagtggaat    4320
atgtatttgc ctatattgtg aacgaattag cagtaaaata catgatacaa ggaactcaaa    4380
agatagttaa ttcttgcctt atacctcagt ctattatgta aaattaaaaa tatgtgtatg    4440
tttttgcttc tttgagaatg caaaagaaat taaatctgaa taaattcttc ctgttcactg    4500
gctcatttct ttaccattca ctcagcatct gctctgtgga aggccctggt agtagtggg    4559

<210> SEQ ID NO 1062
<211> LENGTH: 4204
<212> TYPE: DNA
<213> ORGANISM: Homo sapiens

<400> SEQUENCE: 1062
acgcaggcag tgatgtcacc cagaccacac cccttcccc aatgccactt caggggtac       60 tcagagtcag agacttggtc tgaggggagc agaagcaatc tgcagaggat ggcggtccag    120
gctcagccag gcatcaactt caggaccctg agggatgacc gaaggccccg cccacccacc    180 ccaactccc ccgaccccac caggatctac agcctcagga cccccgtccc aatccttacc    240
ccttgcccca tcaccatctt catgcttacc tccaccccca tccgatcccc atccaggcag    300
aatccagttc cacccctgcc cggaacccag ggtagtaccg ttgccaggat gtgacgccac    360
tgacttgcgc attggaggtc agaagaccgc gagattctcg ccctgagcaa cgagcgacgg    420
cctgacgtcg gcgagggaa gccggcccag gctcggtgag gaggcaaggt aagacgctga    480
gggaggactg aggcgggcct cacctcagac agagggcctc aaataatcca gtgctgcctc    540
tgctgccggg cctgggccac cccgcagggg aagacttcca ggctgggtcg ccactacctc    600
accccgccga ccccgccgc tttagccacg ggaactctg gggacagagc ttaatgtggc      660
cagggcaggc ctggttagaa gaggtcaggg cccacgctgt ggcaggaatc aaggtcagga    720
ccccgagagg gaactgaggg cagcctaacc accaccctca ccaccattcc cgtccccaa    780 cacccaaccc cacccccatc ccccattccc atccccaccc ccaccccctat cctggcagaa    840 tccgggcttt gccctggta tcaagtcacg gaagctccgg gaatggcggc caggcacgtg    900
agtcctgagg ttcacatcta cggctaaggg agggaagggg ttcggtatcg cgagtatggc    960
cgttgggagg cagcgaaagg gcccaggcct cctggaagac agtggagtcc tgaggggacc   1020
```

```
cagcatgcca ggacaggggg cccactgtac ccctgtctca aaccgaggca ccttttcatt   1080
cggctacggg aatcctaggg atgcagaccc acttcagcag ggggttgggg cccagccctg   1140
cgaggagtca tggggaggaa gaagagggag gactgagggg accttggagt ccagatcagt   1200
ggcaaccttg ggctggggga tgctgggcac agtggccaaa tgtgctctgt gctcattgcg   1260
ccttcagggt gaccagagag ttgagggctg tggtctgaag agtgggactt caggtcagca   1320
gagggaggaa tccaggatc tgcagggccc aaggtgtacc cccaagggc ccctatgtgg   1380 tggacagatg cagtggtcct aggatctgcc aagcatccag gtgaagagac tgagggagga   1440
ttgagggtac ccctgggaca gaatgcggac tgggggcccc ataaaaatct gccctgctcc   1500
tgctgttacc tcagagagcc tgggcagggc tgtcagctga ggtccctcca ttatcctagg   1560
atcactgatg tcagggaagg ggaagccttg gtctgagggg gctgcactca gggcagtaga   1620
gggaggctct cagaccctac taggagtgga ggtgaggacc aagcagtctc ctcacccagg   1680
gtacatggac ttcaataaat ttggacatct ctcgttgtcc tttccgggag gacctgggaa   1740
tgtatggcca gatgtgggtc ccctcatgtt tttctgtacc atatcaggta tgtgagttct   1800
tgacatgaga gattctcagg ccagcagaag ggagggatta ggccctataa ggagaaaggt   1860
gagggccctg agtgagcaca gaggggatcc tccaccccag tagagtgggg acctcacaga   1920
gtctggccaa ccctcctgac agttctggga atccgtggct gcgtttgctg tctgcacatt   1980
gggggcccgt ggattcctct cccaggaatc aggagctcca ggaacaaggc agtgaggact   2040
tggtctgagg cagtgtcctc aggtcacaga gtagaggggg ctcagatagt gccaacggtg   2100
aaggtttgcc ttggattcaa accaagggcc ccacctgccc cagaacacat ggactccaga   2160
gcgcctggcc tcaccctcaa tactttcagt cctgcagcct cagcatgcgc tggccggatg   2220
taccctgagg tgccctctca cttcctcctt caggttctga ggggacaggc tgacctggag   2280
gaccagaggc ccccggagga gcactgaagg agaagatctg taagtaagcc tttgttagag   2340
cctccaaggt tccattcagt actcagctga ggtctctcac atgctccctc tctcccagg   2400 ccagtgggtc tccattgccc agctcctgcc cacactcccg cctgttgccc tgaccagagt   2460
catcatgcct cttgagcaga ggagtcagca ctgcaagcct gaagaggcc ttgaggcccg   2520 aggagaggcc ctgggcctgg tgggtgcgca ggctcctgct actgaggagc aggaggctgc   2580
ctcctcctct tctactctag ttgaagtcac cctgggggag gtgcctgctg ccagtcacc   2640 agatcctccc cagagtcctc agggagcctc cagcctcccc actaccatga actaccctct   2700
ctggagccaa tcctatgagg actccagcaa ccaagaagag gaggggccaa gcaccttccc   2760
tgacctggag tccgagttcc aagcagcact cagtaggaag gtggccgagt tggttcattt   2820
tctgctcctc aagtatcgag ccaggagcc ggtcacaaag gcagaaatgc tggggagtgt   2880
cgtcggaaat tggcagtatt tctttcctgt gatcttcagc aaagcttcca gttccttgca   2940
gctggtcttt ggcatcgagc tgatggaagt ggaccccatc ggccacttgt acatctttgc   3000
cacctgcctg ggcctctcct acgatggcct gctgggtgac aatcagatca tgcccaaggc   3060
aggcctcctg ataatcgtcc tggccataat cgcaagagag ggcgactgtg cccctgagga   3120
gaaaatctgg gaggagctga gtgtgttaga ggtgtttgag gggagggaag acagtatctt   3180
gggggatccc aagaagctgc tcacccaaca tttcgtgcag gaaaactacc tggagtaccg   3240
gcaggtcccc ggcagtgatc ctgcatgtta tgaattcctg tggggtccaa gggccctcgt   3300
tgaaaccagc tatgtgaaag tcctgcacca tatggtaaag atcagtggag gacctcacat   3360
ttcctaccca cccctgcatg agtgggtttt gagagagggg gaagagtgag tctgagcacg   3420
```

| | |
|---|---|
| agttgcagcc agggccagtg ggaggggtc tgggccagtg caccttccgg ggccgcatcc | 3480 |
| cttagtttcc actgcctcct gtgacgtgag gcccattctt cactctttga agcgagcagt | 3540 |
| cagcattctt agtagtgggt ttctgttctg ttggatgact ttgagattat tctttgtttc | 3600 |
| ctgttggagt tgttcaaatg ttccttttaa cggatggttg aatgagcgtc agcatccagg | 3660 |
| tttatgaatg acagtagtca cacatagtgc tgtttatata gtttaggagt aagagtcttg | 3720 |
| ttttttactc aaattgggaa atccattcca ttttgtgaat tgtgacataa taatagcagt | 3780 |
| ggtaaaagta tttgcttaaa attgtgagcg aattagcaat aacatacatg agataactca | 3840 |
| agaaatcaaa agatagttga ttcttgcctt gtacctcaat ctattctgta aaattaaaca | 3900 |
| aatatgcaaa ccaggatttc cttgacttct ttgagaatgc aagcgaaatt aaatctgaat | 3960 |
| aaataattct tcctcttcac tggctcgttt cttttccgtt cactcagcat ctgctctgtg | 4020 |
| ggaggccctg ggttagtagt ggggatgcta aggtaagcca gactcacgcc tacccatagg | 4080 |
| gctgtagagc ctaggacctg cagtcatata attaaggtgg tgagaagtcc tgtaagatgt | 4140 |
| agaggaaatg taagagaggg gtgagggtgt ggcgctccgg gtgagagtag tggagtgtca | 4200 |
| gtgc | 4204 |

<210> SEQ ID NO 1063
<211> LENGTH: 752
<212> TYPE: DNA
<213> ORGANISM: Homo sapiens

<400> SEQUENCE: 1063

| | |
|---|---|
| atcctcgtgg gccctgacct tctctctgag agccgggcag aggctccgga gccatgcagg | 60 |
| ccgaaggccg gggcacaggg ggttcgacgg gcgatgctga tggcccagga ggccctggca | 120 |
| ttcctgatgg cccagggggc aatgctggcg gcccaggaga ggcgggtgcc acgggcggca | 180 |
| gaggtccccg gggcgcaggg gcagcaaggg cctcggggcc gggaggaggc gccccgcggg | 240 |
| gtccgcatgg cggcgcggct tcagggctga atggatgctg cagatgcggg gccagggggc | 300 |
| cggagagccg cctgcttgag ttctacctcg ccatgccttt cgcgacaccc atggaagcag | 360 |
| agctggcccg caggagcctg gcccaggatg ccccaccgct tcccgtgcca ggggtgcttc | 420 |
| tgaaggagtt cactgtgtcc ggcaacatac tgactatccg actgactgct gcagaccacc | 480 |
| gccaactgca gctctccatc agctcctgtc tccagcagct ttccctgttg atgtggatca | 540 |
| cgcagtgctt tctgcccgtg tttttggctc agcctccctc agggcagagg cgctaagccc | 600 |
| agcctggcgc cccttcctag gtcatgcctc ctcccctagg gaatggtccc agcacgagtg | 660 |
| gccagttcat tgtgggggcc tgattgtttg tcgctggagg aggacggctt acatgttttgt | 720 |
| ttctgtagaa aataaaactg agctacgaaa aa | 752 |

<210> SEQ ID NO 1064
<211> LENGTH: 2148
<212> TYPE: DNA
<213> ORGANISM: Homo sapiens
<220> FEATURE:
<221> NAME/KEY: misc_feature
<222> LOCATION: (1)...(2)
<223> OTHER INFORMATION: n = A,T,C or G

<400> SEQUENCE: 1064

| | |
|---|---|
| gcttcagggt acagctcccc cgcagccaga agccgggcct gcagcccctc agcaccgctc | 60 |
| cgggacaccc cacccgcttc ccaggcgtga cctgtcaaca gcaacttcgc ggtgtggtga | 120 |
| actctctgag gaaaaaccat tttgattatt actctcagac gtgcgtggca acaagtgact | 180 |

```
gagacctaga aatccaagcg ttggaggtcc tgaggccagc ctaagtcgct tcaaaatgga    240
acgaaggcgt ttgtggggtt ccattcagag ccgatacatc agcatgagtg tgtggacaag    300
cccacggaga cttgtggagc tggcagggca gagcctgctg aaggatgagg ccctggccat    360
tgccgccctg gagttgctgc ccagggagct cttcccgcca ctcttcatgg cagcctttga    420
cgggagacac agccagaccc tgaaggcaat ggtgcaggcc tggcccttca cctgcctccc    480
tctgggagtg ctgatgaagg acaacatct tcacctggag accttcaaag ctgtgcttga    540
tggacttgat gtgctccttg cccaggaggt tcgccccagg aggtggaaac ttcaagtgct    600
ggatttacgg aagaactctc atcaggactt ctggactgta tggtctggaa acagggccag    660
tctgtactca tttccagagc cagaagcagc tcagcccatg acaaagaagc gaaaagtaga    720
tggtttgagc acagaggcag agcagcccct cattccagta gaggtgctcg tagacctgtt    780
cctcaaggaa ggtgcctgtg atgaattgtt ctcctacctc attgagaaag tgaagcgaaa    840
gaaaaatgta ctacgcctgt gctgtaagaa gctgaagatt tttgcaatgc ccatgcagga    900
tatcaagatg atccctgaaaa tggtgcagct ggactctatt gaagatttgg aagtgacttg    960
tacctggaag ctacccacct tggcgaaatt ttctccttac ctgggccaga tgattaatct   1020
gcgtagactc ctcctctccc acatccatgc atcttcctac atttccccgg agaaggaaga   1080
gcagtatatc gcccagttca cctctcagtt cctcagtctg cagtgcctgc aggctctcta   1140
tgtggactct ttattttcc ttagaggccg cctggatcag ttgctcaggc acgtgatgaa   1200
ccccttggaa accctctcaa taactaactg ccggcttcg gaaggggatg tgatgcatct   1260
gtcccagagt cccagcgtca gtcagctaag tgtcctgagt ctaagtgggg tcatgctgac   1320
cgatgtaagt cccgagcccc tccaagctct gctggagaga gcctctgcca ccctccagga   1380
cctggtcttt gatgagtgtg ggatcacgga tgatcagctc cttgccctcc tgccttccct   1440
gagccactgc tcccagctta caaccttaag cttctacggg aattccatct ccatatctgc   1500
cttgcagagt ctcctgcagc acctcatcgg gctgagcaat ctgacccacg tgctgtatcc   1560 tgtcccctg gagagttatg aggacatcca tggtaccctc cacctggaga ggcttgccta   1620
tctgcatgcc aggctcaggg agttgctgtg tgagttgggg cggcccagca tggtctggct   1680
tagtgccaac ccctgtcctc actgtgggga cagaaccttc tatgacccgg agcccatcct   1740
gtgcccctgt ttcatgccta actagctggg tgcacatatc aaatgcttca ttctgcatac   1800
ttggacacta agccaggat gtgcatgcat cttgaagcaa caaagcagcc acagtttcag   1860
acaaatgttc agtgtgagtg aggaaaacat gttcagtgag gaaaaacat tcagacaaat   1920 gttcagtgag gaaaaaagg ggaagttggg gataggcaga tgttgacttg aggagttaat   1980
gtgatctttg gggagataca tcttatagag ttagaaatag aatctgaatt tctaaaggga   2040
gattctggct tgggaagtac atgtaggagt taatccctgt gtagactgtt gtaaagaaac   2100
tgttgaaaat aaagagaagc aatgtgaagc aaaaaaaaaa aaaaaaaa              2148
```

<210> SEQ ID NO 1065
<211> LENGTH: 1466
<212> TYPE: DNA
<213> ORGANISM: Homo sapiens

<400> SEQUENCE: 1065

```
agccccaagc ttaccacctg cacccggaga gctgtgtgtc accatgtggg tcccggttgt     60
cttcctcacc ctgtccgtga cgtggattgg tgctgcaccc ctcatcctgt ctcggattgt    120
gggaggctgg gagtgcgaga agcattccca accctggcag gtgcttgtgg cctctcgtgg    180
```

-continued

```
cagggcagtc tgcggcggtg ttctggtgca cccccagtgg gtcctcacag ctgcccactg        240
catcaggaac aaaagcgtga tcttgctggg tcggcacagc ctgtttcatc ctgaagacac        300
aggccaggta tttcaggtca gccacagctt cccacacccg ctctacgata tgagcctcct        360
gaagaatcga ttcctcaggc caggtgatga ctccagccac gacctcatgc tgctccgcct        420
gtcagagcct gccgagctca cggatgctgt gaaggtcatg gacctgccca cccaggagcc        480
agcactgggg accacctgct acgcctcagg ctggggcagc attgaaccag aggagttctt        540
gaccccaaag aaacttcagt gtgtggacct ccatgttatt ccaatgacg tgtgtgcgca         600
agttcaccct cagaaggtga ccaagttcat gctgtgtgct ggacgctgga cggggggcaa        660
aagcacctgc tcgggtgatt ctgggggccc acttgtctgt aatggtgtgc ttcaaggtat        720
cacgtcatgg ggcagtgaac catgtgccct gcccgaaagg ccttccctgt acaccaaggt        780
ggtgcattac cggaagtgga tcaaggacac catcgtggcc aaccctgag caccctatc         840
aacccctat tgtagtaaac ttggaaccct ggaaatgacc aggccaagac tcaagcctcc        900
ccagttctac tgacctttgt ccttaggtgt gaggtccagg gttgctagga aagaaatca        960
gcagacacag gtgtagacca gagtgttcct taaatggtgt aattttgtcc tctctgtgtc       1020
ctggggaata ctggccatgc ctggagacat atcactcaat ttctctgagg acacagatag       1080
gatggggtgt ctgtgttatt tgtggggtac agagatgaaa gaggggtggg atccacactg       1140
agagagtgga gagtgacatg tgctggacac tgtccatgaa gcactgagca gaagctggag       1200
gcacaacgca ccagacactc acagcaagga tggagctgaa aacataaccc actctgtcct       1260
ggaggcactg ggaagcctag agaaggctgt gagccaagga gggagggtct tcctttggca       1320
tgggatgggg atgaagtaag gagagggact ggacccctg gaagctgatt cactatgggg        1380
ggaggtgtat tgaagtcctc cagacaaccc tcagatttga tgatttccta gtagaactca       1440
cagaaataaa gagctgttat actgtg                                            1466
```

<210> SEQ ID NO 1066
<211> LENGTH: 990
<212> TYPE: DNA
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)...(990)
<223> OTHER INFORMATION: n = A,T,C or G

<400> SEQUENCE: 1066

```
agggagaggc agtgaccatg aaggctgtgc tgcttgccct gttgatggca ggcttggccc         60
tgcagccagg cactgccctg ctgtgctact cctgcaaagc ccaggtgagc aacgaggact        120
gcctgcaggt ggagaactgc acccagctgg gggagcagtg ctggaccgcg cgcatccgcg        180
cagttggcct cctgaccgtc atcagcaaag gctgcagctt gaactgcgtg atgactcac         240
aggactacta cgtgggcaag aagaacatca cgtgctgtga caccgacttg tgcaacgcca        300
gcggggccca tgccctgcag ccggctgccg ccatccttgc gctgctccct gcactcggcc        360
tgctgctctg ggacccggc cagctatagg ctctgggggg cccgctgca gcccacactg         420
ggtgtggtgc cccaggcctt tgtgccactc tcacagaac ctggcccagt gggagcctgt        480
cctggttcct gaggcacatc ctaacgcaag tttgaccatg tatgtttgca ccccttttcc       540
ccnaaccctg accttcccat gggccttttc caggattccn accnggcaga tcagttttag       600
tganacanat ccgcntgcag atggcccctc caaccntttn tgttgntgtt tccatggccc       660
```

```
agcattttcc acccttaacc ctgtgttcag gcacttnttc ccccaggaag ccttccctgc    720
ccaccccatt tatgaattga gccaggtttg gtccgtggtg tccccgcac ccagcagggg    780 acaggcaatc aggagggccc agtaaaggct gagatgaagt ggactgagta gaactggagg    840
acaagagttg acgtgagttc ctgggagttt ccagagatgg ggcctggagg cctggaggaa    900
ggggccaggc ctcacatttg tggggntccc gaatggcagc ctgagcacag cgtaggccct    960
taataaacac ctgttggata agccaaaaaa                                      990
```

<210> SEQ ID NO 1067
<211> LENGTH: 9
<212> TYPE: PRT
<213> ORGANISM: Homo sapiens

<400> SEQUENCE: 1067

Leu Pro His Ser Ser Ser His Trp Leu
1               5

<210> SEQ ID NO 1068
<211> LENGTH: 10
<212> TYPE: PRT
<213> ORGANISM: Homo sapiens

<400> SEQUENCE: 1068

Gln Leu Pro His Ser Ser Ser His Trp Leu
1               5                   10

<210> SEQ ID NO 1069
<211> LENGTH: 9
<212> TYPE: PRT
<213> ORGANISM: Homo sapiens

<400> SEQUENCE: 1069

Leu Ile Tyr Arg Arg Arg Leu Met Lys
1               5

<210> SEQ ID NO 1070
<211> LENGTH: 10
<212> TYPE: PRT
<213> ORGANISM: Homo sapiens

<400> SEQUENCE: 1070

Ser Leu Ile Tyr Arg Arg Arg Leu Met Lys
1               5                   10

<210> SEQ ID NO 1071
<211> LENGTH: 8
<212> TYPE: PRT
<213> ORGANISM: Homo sapiens

<400> SEQUENCE: 1071

Ile Tyr Arg Arg Arg Leu Met Lys
1               5

<210> SEQ ID NO 1072
<211> LENGTH: 9
<212> TYPE: PRT
<213> ORGANISM: Homo sapiens

<400> SEQUENCE: 1072

Leu Pro His Ser Ser Ser His Trp Leu
1               5

<210> SEQ ID NO 1073

```
<211> LENGTH: 10
<212> TYPE: PRT
<213> ORGANISM: Homo sapiens

<400> SEQUENCE: 1073

Gln Leu Pro His Ser Ser Ser His Trp Leu
1               5                   10

<210> SEQ ID NO 1074
<211> LENGTH: 8
<212> TYPE: PRT
<213> ORGANISM: Homo sapiens

<400> SEQUENCE: 1074

Glu Ser Leu Phe Arg Ala Val Ile
1               5

<210> SEQ ID NO 1075
<211> LENGTH: 10
<212> TYPE: PRT
<213> ORGANISM: Homo sapiens

<400> SEQUENCE: 1075

Ile Leu Glu Ser Leu Phe Arg Ala Val Ile
1               5                   10

<210> SEQ ID NO 1076
<211> LENGTH: 9
<212> TYPE: PRT
<213> ORGANISM: Homo sapiens

<400> SEQUENCE: 1076

Ile Leu Glu Ser Leu Phe Arg Ala Val
1               5

<210> SEQ ID NO 1077
<211> LENGTH: 10
<212> TYPE: PRT
<213> ORGANISM: Homo sapiens

<400> SEQUENCE: 1077

Cys Ile Leu Glu Ser Leu Phe Arg Ala Val
1               5                   10

<210> SEQ ID NO 1078
<211> LENGTH: 9
<212> TYPE: PRT
<213> ORGANISM: Homo sapiens

<400> SEQUENCE: 1078

Cys Ile Leu Glu Ser Leu Phe Arg Ala
1               5

<210> SEQ ID NO 1079
<211> LENGTH: 9
<212> TYPE: PRT
<213> ORGANISM: Homo sapiens

<400> SEQUENCE: 1079

Glu Phe Leu Trp Gly Pro Arg Ala Leu
1               5

<210> SEQ ID NO 1080
<211> LENGTH: 8
<212> TYPE: PRT
<213> ORGANISM: Homo sapiens
```

<400> SEQUENCE: 1080

Phe Leu Trp Gly Pro Arg Ala Leu
1               5

<210> SEQ ID NO 1081
<211> LENGTH: 10
<212> TYPE: PRT
<213> ORGANISM: Homo sapiens

<400> SEQUENCE: 1081

Phe Leu Trp Gly Pro Arg Ala Leu Ala Glu
1               5                  10

<210> SEQ ID NO 1082
<211> LENGTH: 10
<212> TYPE: PRT
<213> ORGANISM: Homo sapiens

<400> SEQUENCE: 1082

Leu Trp Gly Pro Arg Ala Leu Ala Glu Thr
1               5                  10

<210> SEQ ID NO 1083
<211> LENGTH: 9
<212> TYPE: PRT
<213> ORGANISM: Homo sapiens

<400> SEQUENCE: 1083

Pro Arg Ala Leu Ala Glu Thr Ser Tyr
1               5

<210> SEQ ID NO 1084
<211> LENGTH: 10
<212> TYPE: PRT
<213> ORGANISM: Homo sapiens

<400> SEQUENCE: 1084

Gly Pro Arg Ala Leu Ala Glu Thr Ser Tyr
1               5                  10

<210> SEQ ID NO 1085
<211> LENGTH: 9
<212> TYPE: PRT
<213> ORGANISM: Homo sapiens

<400> SEQUENCE: 1085

Arg Ala Leu Ala Glu Thr Ser Tyr Val
1               5

<210> SEQ ID NO 1086
<211> LENGTH: 9
<212> TYPE: PRT
<213> ORGANISM: Homo sapiens

<400> SEQUENCE: 1086

Leu Ala Glu Thr Ser Tyr Val Lys Val
1               5

<210> SEQ ID NO 1087
<211> LENGTH: 10
<212> TYPE: PRT
<213> ORGANISM: Homo sapiens

<400> SEQUENCE: 1087

```
Ala Leu Ala Glu Thr Ser Tyr Val Lys Val
1               5                   10

<210> SEQ ID NO 1088
<211> LENGTH: 9
<212> TYPE: PRT
<213> ORGANISM: Homo sapiens

<400> SEQUENCE: 1088

Ala Glu Thr Ser Tyr Val Lys Val Leu
1               5

<210> SEQ ID NO 1089
<211> LENGTH: 10
<212> TYPE: PRT
<213> ORGANISM: Homo sapiens

<400> SEQUENCE: 1089

Leu Ala Glu Thr Ser Tyr Val Lys Val Leu
1               5                   10

<210> SEQ ID NO 1090
<211> LENGTH: 9
<212> TYPE: PRT
<213> ORGANISM: Homo sapiens

<400> SEQUENCE: 1090

Thr Ser Tyr Val Lys Val Leu Glu Tyr
1               5

<210> SEQ ID NO 1091
<211> LENGTH: 10
<212> TYPE: PRT
<213> ORGANISM: Homo sapiens

<400> SEQUENCE: 1091

Glu Thr Ser Tyr Val Lys Val Leu Glu Tyr
1               5                   10

<210> SEQ ID NO 1092
<211> LENGTH: 9
<212> TYPE: PRT
<213> ORGANISM: Homo sapiens

<400> SEQUENCE: 1092

Lys Val Leu Glu Tyr Val Ile Lys Val
1               5

<210> SEQ ID NO 1093
<211> LENGTH: 10
<212> TYPE: PRT
<213> ORGANISM: Homo sapiens

<400> SEQUENCE: 1093

Ser Tyr Val Leu Val Thr Cys Leu Gly Leu
1               5                   10

<210> SEQ ID NO 1094
<211> LENGTH: 9
<212> TYPE: PRT
<213> ORGANISM: Homo sapiens

<400> SEQUENCE: 1094

Tyr Val Leu Val Thr Cys Leu Gly Leu
1               5
```

<210> SEQ ID NO 1095
<211> LENGTH: 8
<212> TYPE: PRT
<213> ORGANISM: Homo sapiens

<400> SEQUENCE: 1095

Val Leu Val Thr Cys Leu Gly Leu
1               5

<210> SEQ ID NO 1096
<211> LENGTH: 9
<212> TYPE: PRT
<213> ORGANISM: Homo sapiens

<400> SEQUENCE: 1096

Thr Gln Asp Leu Val Gln Glu Lys Tyr
1               5

<210> SEQ ID NO 1097
<211> LENGTH: 10
<212> TYPE: PRT
<213> ORGANISM: Homo sapiens

<400> SEQUENCE: 1097

Leu Thr Gln Asp Leu Val Gln Glu Lys Tyr
1               5                   10

<210> SEQ ID NO 1098
<211> LENGTH: 9
<212> TYPE: PRT
<213> ORGANISM: Homo sapiens

<400> SEQUENCE: 1098

Tyr Gly Glu Pro Arg Lys Leu Leu Thr
1               5

<210> SEQ ID NO 1099
<211> LENGTH: 9
<212> TYPE: PRT
<213> ORGANISM: Homo sapiens

<400> SEQUENCE: 1099

Leu Val Gln Glu Lys Tyr Leu Glu Tyr
1               5

<210> SEQ ID NO 1100
<211> LENGTH: 10
<212> TYPE: PRT
<213> ORGANISM: Homo sapiens

<400> SEQUENCE: 1100

Asp Leu Val Gln Glu Lys Tyr Leu Glu Tyr
1               5                   10

<210> SEQ ID NO 1101
<211> LENGTH: 9
<212> TYPE: PRT
<213> ORGANISM: Homo sapiens

<400> SEQUENCE: 1101

Ser Ala Tyr Gly Glu Pro Arg Lys Leu
1               5

<210> SEQ ID NO 1102
<211> LENGTH: 9

```
<212> TYPE: PRT
<213> ORGANISM: Homo sapiens

<400> SEQUENCE: 1102

Lys Val Leu Glu Tyr Val Ile Lys Val
1               5

<210> SEQ ID NO 1103
<211> LENGTH: 10
<212> TYPE: PRT
<213> ORGANISM: Homo sapiens

<400> SEQUENCE: 1103

Val Lys Val Leu Glu Tyr Val Ile Lys Val
1               5                   10

<210> SEQ ID NO 1104
<211> LENGTH: 9
<212> TYPE: PRT
<213> ORGANISM: Homo sapiens

<400> SEQUENCE: 1104

Tyr Val Lys Val Leu Glu Tyr Val Ile
1               5

<210> SEQ ID NO 1105
<211> LENGTH: 9
<212> TYPE: PRT
<213> ORGANISM: Homo sapiens

<400> SEQUENCE: 1105

Thr Ser Tyr Val Lys Val Leu Glu Tyr
1               5

<210> SEQ ID NO 1106
<211> LENGTH: 10
<212> TYPE: PRT
<213> ORGANISM: Homo sapiens

<400> SEQUENCE: 1106

Glu Thr Ser Tyr Val Lys Val Leu Glu Tyr
1               5                   10

<210> SEQ ID NO 1107
<211> LENGTH: 9
<212> TYPE: PRT
<213> ORGANISM: Homo sapiens

<400> SEQUENCE: 1107

Val Ile Lys Val Ser Ala Arg Val Arg
1               5

<210> SEQ ID NO 1108
<211> LENGTH: 10
<212> TYPE: PRT
<213> ORGANISM: Homo sapiens

<400> SEQUENCE: 1108

Tyr Val Ile Lys Val Ser Ala Arg Val Arg
1               5                   10

<210> SEQ ID NO 1109
<211> LENGTH: 8
<212> TYPE: PRT
<213> ORGANISM: Homo sapiens
```

```
<400> SEQUENCE: 1109

Glu Leu Val His Phe Leu Leu Leu
1               5

<210> SEQ ID NO 1110
<211> LENGTH: 10
<212> TYPE: PRT
<213> ORGANISM: Homo sapiens

<400> SEQUENCE: 1110

Met Val Glu Leu Val His Phe Leu Leu Leu
1               5                   10

<210> SEQ ID NO 1111
<211> LENGTH: 8
<212> TYPE: PRT
<213> ORGANISM: Homo sapiens

<400> SEQUENCE: 1111

Ile Ser Arg Lys Met Val Glu Leu
1               5

<210> SEQ ID NO 1112
<211> LENGTH: 9
<212> TYPE: PRT
<213> ORGANISM: Homo sapiens

<400> SEQUENCE: 1112

Ala Ile Ser Arg Lys Met Val Glu Leu
1               5

<210> SEQ ID NO 1113
<211> LENGTH: 10
<212> TYPE: PRT
<213> ORGANISM: Homo sapiens

<400> SEQUENCE: 1113

Ala Ala Ile Ser Arg Lys Met Val Glu Leu
1               5                   10

<210> SEQ ID NO 1114
<211> LENGTH: 9
<212> TYPE: PRT
<213> ORGANISM: Homo sapiens

<400> SEQUENCE: 1114

Lys Met Val Glu Leu Val His Phe Leu
1               5

<210> SEQ ID NO 1115
<211> LENGTH: 9
<212> TYPE: PRT
<213> ORGANISM: Homo sapiens

<400> SEQUENCE: 1115

Ile Ser Arg Lys Met Val Glu Leu Val
1               5

<210> SEQ ID NO 1116
<211> LENGTH: 10
<212> TYPE: PRT
<213> ORGANISM: Homo sapiens

<400> SEQUENCE: 1116

Ala Ile Ser Arg Lys Met Val Glu Leu Val
```

<210> SEQ ID NO 1117
<211> LENGTH: 9
<212> TYPE: PRT
<213> ORGANISM: Homo sapiens

<400> SEQUENCE: 1117

Leu Val His Phe Leu Leu Leu Lys Tyr
1               5

<210> SEQ ID NO 1118
<211> LENGTH: 10
<212> TYPE: PRT
<213> ORGANISM: Homo sapiens

<400> SEQUENCE: 1118

Glu Leu Val His Phe Leu Leu Leu Lys Tyr
1               5                   10

<210> SEQ ID NO 1119
<211> LENGTH: 9
<212> TYPE: PRT
<213> ORGANISM: Homo sapiens

<400> SEQUENCE: 1119

Arg Lys Met Val Glu Leu Val His Phe
1               5

<210> SEQ ID NO 1120
<211> LENGTH: 9
<212> TYPE: PRT
<213> ORGANISM: Homo sapiens

<400> SEQUENCE: 1120

Leu Gln Leu Val Phe Gly Ile Glu Val
1               5

<210> SEQ ID NO 1121
<211> LENGTH: 10
<212> TYPE: PRT
<213> ORGANISM: Homo sapiens

<400> SEQUENCE: 1121

Tyr Leu Gln Leu Val Phe Gly Ile Glu Val
1               5                   10

<210> SEQ ID NO 1122
<211> LENGTH: 9
<212> TYPE: PRT
<213> ORGANISM: Homo sapiens

<400> SEQUENCE: 1122

Gln Leu Val Phe Gly Ile Glu Val Val
1               5

<210> SEQ ID NO 1123
<211> LENGTH: 10
<212> TYPE: PRT
<213> ORGANISM: Homo sapiens

<400> SEQUENCE: 1123

Leu Gln Leu Val Phe Gly Ile Glu Val Val
1               5                   10

```
<210> SEQ ID NO 1124
<211> LENGTH: 9
<212> TYPE: PRT
<213> ORGANISM: Homo sapiens

<400> SEQUENCE: 1124

Ile Glu Val Val Glu Val Val Pro Ile
1               5

<210> SEQ ID NO 1125
<211> LENGTH: 10
<212> TYPE: PRT
<213> ORGANISM: Homo sapiens

<400> SEQUENCE: 1125

Gly Ile Glu Val Val Glu Val Val Pro Ile
1               5                   10

<210> SEQ ID NO 1126
<211> LENGTH: 9
<212> TYPE: PRT
<213> ORGANISM: Homo sapiens

<400> SEQUENCE: 1126

Phe Gly Ile Glu Val Val Glu Val Val
1               5

<210> SEQ ID NO 1127
<211> LENGTH: 9
<212> TYPE: PRT
<213> ORGANISM: Homo sapiens

<400> SEQUENCE: 1127

Ala Ser Glu Tyr Leu Gln Leu Val Phe
1               5

<210> SEQ ID NO 1128
<211> LENGTH: 10
<212> TYPE: PRT
<213> ORGANISM: Homo sapiens

<400> SEQUENCE: 1128

Lys Ala Ser Glu Tyr Leu Gln Leu Val Phe
1               5                   10

<210> SEQ ID NO 1129
<211> LENGTH: 8
<212> TYPE: PRT
<213> ORGANISM: Homo sapiens

<400> SEQUENCE: 1129

Glu Glu Lys Ile Trp Glu Glu Leu
1               5

<210> SEQ ID NO 1130
<211> LENGTH: 10
<212> TYPE: PRT
<213> ORGANISM: Homo sapiens

<400> SEQUENCE: 1130

Ala Pro Glu Glu Lys Ile Trp Glu Glu Leu
1               5                   10

<210> SEQ ID NO 1131
<211> LENGTH: 8
<212> TYPE: PRT
```

<213> ORGANISM: Homo sapiens

<400> SEQUENCE: 1131

Ala Pro Glu Glu Lys Ile Trp Glu
1               5

<210> SEQ ID NO 1132
<211> LENGTH: 9
<212> TYPE: PRT
<213> ORGANISM: Homo sapiens

<400> SEQUENCE: 1132

Lys Ile Trp Glu Glu Leu Ser Met Leu
1               5

<210> SEQ ID NO 1133
<211> LENGTH: 10
<212> TYPE: PRT
<213> ORGANISM: Homo sapiens

<400> SEQUENCE: 1133

Glu Lys Ile Trp Glu Glu Leu Ser Met Leu
1               5                   10

<210> SEQ ID NO 1134
<211> LENGTH: 8
<212> TYPE: PRT
<213> ORGANISM: Homo sapiens

<400> SEQUENCE: 1134

Phe Leu Trp Gly Pro Arg Ala Leu
1               5

<210> SEQ ID NO 1135
<211> LENGTH: 9
<212> TYPE: PRT
<213> ORGANISM: Homo sapiens

<400> SEQUENCE: 1135

Phe Leu Trp Gly Pro Arg Ala Leu Ile
1               5

<210> SEQ ID NO 1136
<211> LENGTH: 9
<212> TYPE: PRT
<213> ORGANISM: Homo sapiens

<400> SEQUENCE: 1136

Leu Ile Glu Thr Ser Tyr Val Lys Val
1               5

<210> SEQ ID NO 1137
<211> LENGTH: 10
<212> TYPE: PRT
<213> ORGANISM: Homo sapiens

<400> SEQUENCE: 1137

Ala Leu Ile Glu Thr Ser Tyr Val Lys Val
1               5                   10

<210> SEQ ID NO 1138
<211> LENGTH: 9
<212> TYPE: PRT
<213> ORGANISM: Homo sapiens

<400> SEQUENCE: 1138

Arg Ala Leu Ile Glu Thr Ser Tyr Val
1               5

<210> SEQ ID NO 1139
<211> LENGTH: 9
<212> TYPE: PRT
<213> ORGANISM: Homo sapiens

<400> SEQUENCE: 1139

Ile Glu Thr Ser Tyr Val Lys Val Leu
1               5

<210> SEQ ID NO 1140
<211> LENGTH: 10
<212> TYPE: PRT
<213> ORGANISM: Homo sapiens

<400> SEQUENCE: 1140

Leu Ile Glu Thr Ser Tyr Val Lys Val Leu
1               5                   10

<210> SEQ ID NO 1141
<211> LENGTH: 8
<212> TYPE: PRT
<213> ORGANISM: Homo sapiens

<400> SEQUENCE: 1141

Phe Leu Trp Gly Pro Arg Ala Leu
1               5

<210> SEQ ID NO 1142
<211> LENGTH: 9
<212> TYPE: PRT
<213> ORGANISM: Homo sapiens

<400> SEQUENCE: 1142

Glu Phe Leu Trp Gly Pro Arg Ala Leu
1               5

<210> SEQ ID NO 1143
<211> LENGTH: 9
<212> TYPE: PRT
<213> ORGANISM: Homo sapiens

<400> SEQUENCE: 1143

Phe Leu Trp Gly Pro Arg Ala Leu Val
1               5

<210> SEQ ID NO 1144
<211> LENGTH: 9
<212> TYPE: PRT
<213> ORGANISM: Homo sapiens

<400> SEQUENCE: 1144

Arg Ala Leu Val Glu Thr Ser Tyr Val
1               5

<210> SEQ ID NO 1145
<211> LENGTH: 9
<212> TYPE: PRT
<213> ORGANISM: Homo sapiens

<400> SEQUENCE: 1145

Leu Trp Gly Pro Arg Ala Leu Val Glu
1               5

```
<210> SEQ ID NO 1146
<211> LENGTH: 10
<212> TYPE: PRT
<213> ORGANISM: Homo sapiens

<400> SEQUENCE: 1146

Phe Leu Trp Gly Pro Arg Ala Leu Val Glu
1               5                   10

<210> SEQ ID NO 1147
<211> LENGTH: 10
<212> TYPE: PRT
<213> ORGANISM: Homo sapiens

<400> SEQUENCE: 1147

Leu Trp Gly Pro Arg Ala Leu Val Glu Thr
1               5                   10

<210> SEQ ID NO 1148
<211> LENGTH: 9
<212> TYPE: PRT
<213> ORGANISM: Homo sapiens

<400> SEQUENCE: 1148

Gly Pro Glu Ser Arg Leu Leu Glu Phe
1               5

<210> SEQ ID NO 1149
<211> LENGTH: 9
<212> TYPE: PRT
<213> ORGANISM: Homo sapiens

<400> SEQUENCE: 1149

Pro Glu Ser Arg Leu Leu Glu Phe Tyr
1               5

<210> SEQ ID NO 1150
<211> LENGTH: 10
<212> TYPE: PRT
<213> ORGANISM: Homo sapiens

<400> SEQUENCE: 1150

Gly Pro Glu Ser Arg Leu Leu Glu Phe Tyr
1               5                   10

<210> SEQ ID NO 1151
<211> LENGTH: 9
<212> TYPE: PRT
<213> ORGANISM: Homo sapiens

<400> SEQUENCE: 1151

Glu Ser Arg Leu Leu Glu Phe Tyr Leu
1               5

<210> SEQ ID NO 1152
<211> LENGTH: 9
<212> TYPE: PRT
<213> ORGANISM: Homo sapiens

<400> SEQUENCE: 1152

Arg Leu Leu Glu Phe Tyr Leu Ala Met
1               5

<210> SEQ ID NO 1153
```

```
<211> LENGTH: 9
<212> TYPE: PRT
<213> ORGANISM: Homo sapiens

<400> SEQUENCE: 1153

Leu Glu Phe Tyr Leu Ala Met Pro Phe
1               5

<210> SEQ ID NO 1154
<211> LENGTH: 10
<212> TYPE: PRT
<213> ORGANISM: Homo sapiens

<400> SEQUENCE: 1154

Leu Leu Glu Phe Tyr Leu Ala Met Pro Phe
1               5                   10

<210> SEQ ID NO 1155
<211> LENGTH: 10
<212> TYPE: PRT
<213> ORGANISM: Homo sapiens

<400> SEQUENCE: 1155

Ala Met Pro Phe Ala Thr Pro Met Glu Ala
1               5                   10

<210> SEQ ID NO 1156
<211> LENGTH: 9
<212> TYPE: PRT
<213> ORGANISM: Homo sapiens

<400> SEQUENCE: 1156

Met Pro Phe Ala Thr Pro Met Glu Ala
1               5

<210> SEQ ID NO 1157
<211> LENGTH: 9
<212> TYPE: PRT
<213> ORGANISM: Homo sapiens

<400> SEQUENCE: 1157

Pro Leu Pro Val Pro Gly Val Leu Leu
1               5

<210> SEQ ID NO 1158
<211> LENGTH: 10
<212> TYPE: PRT
<213> ORGANISM: Homo sapiens

<400> SEQUENCE: 1158

Pro Pro Leu Pro Val Pro Gly Val Leu Leu
1               5                   10

<210> SEQ ID NO 1159
<211> LENGTH: 8
<212> TYPE: PRT
<213> ORGANISM: Homo sapiens

<400> SEQUENCE: 1159

Leu Pro Val Pro Gly Val Leu Leu
1               5

<210> SEQ ID NO 1160
<211> LENGTH: 10
<212> TYPE: PRT
<213> ORGANISM: Homo sapiens
```

-continued

```
<400> SEQUENCE: 1160

Glu Leu Ala Arg Arg Ser Leu Ala Gln Asp
1               5                   10

<210> SEQ ID NO 1161
<211> LENGTH: 9
<212> TYPE: PRT
<213> ORGANISM: Homo sapiens

<400> SEQUENCE: 1161

Val Pro Gly Val Leu Leu Lys Glu Phe
1               5

<210> SEQ ID NO 1162
<211> LENGTH: 10
<212> TYPE: PRT
<213> ORGANISM: Homo sapiens

<400> SEQUENCE: 1162

Pro Val Pro Gly Val Leu Leu Lys Glu Phe
1               5                   10

<210> SEQ ID NO 1163
<211> LENGTH: 8
<212> TYPE: PRT
<213> ORGANISM: Homo sapiens

<400> SEQUENCE: 1163

Leu Pro Val Pro Gly Val Leu Leu
1               5

<210> SEQ ID NO 1164
<211> LENGTH: 9
<212> TYPE: PRT
<213> ORGANISM: Homo sapiens

<400> SEQUENCE: 1164

Thr Val Ser Gly Asn Ile Leu Thr Ile
1               5

<210> SEQ ID NO 1165
<211> LENGTH: 10
<212> TYPE: PRT
<213> ORGANISM: Homo sapiens

<400> SEQUENCE: 1165

Phe Thr Val Ser Gly Asn Ile Leu Thr Ile
1               5                   10

<210> SEQ ID NO 1166
<211> LENGTH: 9
<212> TYPE: PRT
<213> ORGANISM: Homo sapiens

<400> SEQUENCE: 1166

Gly Val Leu Leu Lys Glu Phe Thr Val
1               5

<210> SEQ ID NO 1167
<211> LENGTH: 10
<212> TYPE: PRT
<213> ORGANISM: Homo sapiens

<400> SEQUENCE: 1167
```

```
Val Leu Leu Lys Glu Phe Thr Val Ser Gly
1               5                   10

<210> SEQ ID NO 1168
<211> LENGTH: 9
<212> TYPE: PRT
<213> ORGANISM: Homo sapiens

<400> SEQUENCE: 1168

Leu Leu Lys Glu Phe Thr Val Ser Gly
1               5

<210> SEQ ID NO 1169
<211> LENGTH: 9
<212> TYPE: PRT
<213> ORGANISM: Homo sapiens

<400> SEQUENCE: 1169

Val Pro Gly Val Leu Leu Lys Glu Phe
1               5

<210> SEQ ID NO 1170
<211> LENGTH: 10
<212> TYPE: PRT
<213> ORGANISM: Homo sapiens

<400> SEQUENCE: 1170

Pro Val Pro Gly Val Leu Leu Lys Glu Phe
1               5                   10

<210> SEQ ID NO 1171
<211> LENGTH: 9
<212> TYPE: PRT
<213> ORGANISM: Homo sapiens

<400> SEQUENCE: 1171

Ala Ala Asp His Arg Gln Leu Gln Leu
1               5

<210> SEQ ID NO 1172
<211> LENGTH: 9
<212> TYPE: PRT
<213> ORGANISM: Homo sapiens

<400> SEQUENCE: 1172

Ser Ile Ser Ser Cys Leu Gln Gln Leu
1               5

<210> SEQ ID NO 1173
<211> LENGTH: 10
<212> TYPE: PRT
<213> ORGANISM: Homo sapiens

<400> SEQUENCE: 1173

Leu Ser Ile Ser Ser Cys Leu Gln Gln Leu
1               5                   10

<210> SEQ ID NO 1174
<211> LENGTH: 10
<212> TYPE: PRT
<213> ORGANISM: Homo sapiens

<400> SEQUENCE: 1174

Thr Ala Ala Asp His Arg Gln Leu Gln Leu
1               5                   10
```

```
<210> SEQ ID NO 1175
<211> LENGTH: 9
<212> TYPE: PRT
<213> ORGANISM: Homo sapiens

<400> SEQUENCE: 1175

Trp Ile Thr Gln Cys Phe Leu Pro Val
1               5

<210> SEQ ID NO 1176
<211> LENGTH: 9
<212> TYPE: PRT
<213> ORGANISM: Homo sapiens

<400> SEQUENCE: 1176

Ser Leu Leu Met Trp Ile Thr Gln Cys
1               5

<210> SEQ ID NO 1177
<211> LENGTH: 9
<212> TYPE: PRT
<213> ORGANISM: Homo sapiens

<400> SEQUENCE: 1177

Ser Ser Cys Leu Gln Gln Leu Ser Leu
1               5

<210> SEQ ID NO 1178
<211> LENGTH: 9
<212> TYPE: PRT
<213> ORGANISM: Homo sapiens

<400> SEQUENCE: 1178

Gln Gln Leu Ser Leu Leu Met Trp Ile
1               5

<210> SEQ ID NO 1179
<211> LENGTH: 9
<212> TYPE: PRT
<213> ORGANISM: Homo sapiens

<400> SEQUENCE: 1179

Ser Cys Leu Gln Gln Leu Ser Leu Leu
1               5

<210> SEQ ID NO 1180
<211> LENGTH: 10
<212> TYPE: PRT
<213> ORGANISM: Homo sapiens

<400> SEQUENCE: 1180

Ser Ser Cys Leu Gln Gln Leu Ser Leu Leu
1               5                   10

<210> SEQ ID NO 1181
<211> LENGTH: 9
<212> TYPE: PRT
<213> ORGANISM: Homo sapiens

<400> SEQUENCE: 1181

Thr Gln Cys Phe Leu Pro Val Phe Leu
1               5

<210> SEQ ID NO 1182
<211> LENGTH: 10
```

```
<212> TYPE: PRT
<213> ORGANISM: Homo sapiens

<400> SEQUENCE: 1182

Ile Thr Gln Cys Phe Leu Pro Val Phe Leu
1               5                   10

<210> SEQ ID NO 1183
<211> LENGTH: 9
<212> TYPE: PRT
<213> ORGANISM: Homo sapiens

<400> SEQUENCE: 1183

Pro Met Gln Asp Ile Lys Met Ile Leu
1               5

<210> SEQ ID NO 1184
<211> LENGTH: 10
<212> TYPE: PRT
<213> ORGANISM: Homo sapiens

<400> SEQUENCE: 1184

Met Pro Met Gln Asp Ile Lys Met Ile Leu
1               5                   10

<210> SEQ ID NO 1185
<211> LENGTH: 9
<212> TYPE: PRT
<213> ORGANISM: Homo sapiens

<400> SEQUENCE: 1185

Gln His Leu Ile Gly Leu Ser Asn Leu
1               5

<210> SEQ ID NO 1186
<211> LENGTH: 10
<212> TYPE: PRT
<213> ORGANISM: Homo sapiens

<400> SEQUENCE: 1186

Leu Gln His Leu Ile Gly Leu Ser Asn Leu
1               5                   10

<210> SEQ ID NO 1187
<211> LENGTH: 8
<212> TYPE: PRT
<213> ORGANISM: Homo sapiens

<400> SEQUENCE: 1187

His Leu Ile Gly Leu Ser Asn Leu
1               5

<210> SEQ ID NO 1188
<211> LENGTH: 9
<212> TYPE: PRT
<213> ORGANISM: Homo sapiens

<400> SEQUENCE: 1188

Ile Gly Leu Ser Asn Leu Thr His Val
1               5

<210> SEQ ID NO 1189
<211> LENGTH: 10
<212> TYPE: PRT
<213> ORGANISM: Homo sapiens
```

```
<400> SEQUENCE: 1189

Leu Ile Gly Leu Ser Asn Leu Thr His Val
1               5                   10

<210> SEQ ID NO 1190
<211> LENGTH: 9
<212> TYPE: PRT
<213> ORGANISM: Homo sapiens

<400> SEQUENCE: 1190

Val Leu Val His Pro Gln Trp Val Leu
1               5

<210> SEQ ID NO 1191
<211> LENGTH: 10
<212> TYPE: PRT
<213> ORGANISM: Homo sapiens

<400> SEQUENCE: 1191

Gly Val Leu Val His Pro Gln Trp Val Leu
1               5                   10

<210> SEQ ID NO 1192
<211> LENGTH: 9
<212> TYPE: PRT
<213> ORGANISM: Homo sapiens

<400> SEQUENCE: 1192

Gly Val Leu Val His Pro Gln Trp Val
1               5

<210> SEQ ID NO 1193
<211> LENGTH: 9
<212> TYPE: PRT
<213> ORGANISM: Homo sapiens

<400> SEQUENCE: 1193

Trp Val Leu Thr Ala Ala His Cys Ile
1               5

<210> SEQ ID NO 1194
<211> LENGTH: 10
<212> TYPE: PRT
<213> ORGANISM: Homo sapiens

<400> SEQUENCE: 1194

Leu Val His Pro Gln Trp Val Leu Thr Ala
1               5                   10

<210> SEQ ID NO 1195
<211> LENGTH: 10
<212> TYPE: PRT
<213> ORGANISM: Homo sapiens

<400> SEQUENCE: 1195

Val Leu Val His Pro Gln Trp Val Leu Thr
1               5                   10

<210> SEQ ID NO 1196
<211> LENGTH: 9
<212> TYPE: PRT
<213> ORGANISM: Homo sapiens

<400> SEQUENCE: 1196

Leu Val His Pro Gln Trp Val Leu Thr
```

```
<210> SEQ ID NO 1197
<211> LENGTH: 8
<212> TYPE: PRT
<213> ORGANISM: Homo sapiens

<400> SEQUENCE: 1197

Cys Ile Arg Asn Lys Ser Val Ile
1               5

<210> SEQ ID NO 1198
<211> LENGTH: 9
<212> TYPE: PRT
<213> ORGANISM: Homo sapiens

<400> SEQUENCE: 1198

His Cys Ile Arg Asn Lys Ser Val Ile
1               5

<210> SEQ ID NO 1199
<211> LENGTH: 9
<212> TYPE: PRT
<213> ORGANISM: Homo sapiens

<400> SEQUENCE: 1199

His Pro Gln Trp Val Leu Thr Ala Ala
1               5

<210> SEQ ID NO 1200
<211> LENGTH: 10
<212> TYPE: PRT
<213> ORGANISM: Homo sapiens

<400> SEQUENCE: 1200

Ala Ala His Cys Ile Arg Asn Lys Ser Val
1               5                   10

<210> SEQ ID NO 1201
<211> LENGTH: 8
<212> TYPE: PRT
<213> ORGANISM: Homo sapiens

<400> SEQUENCE: 1201

Leu Leu Trp Gly Pro Gly Gln Leu
1               5

<210> SEQ ID NO 1202
<211> LENGTH: 9
<212> TYPE: PRT
<213> ORGANISM: Homo sapiens

<400> SEQUENCE: 1202

Leu Leu Leu Trp Gly Pro Gly Gln Leu
1               5

<210> SEQ ID NO 1203
<211> LENGTH: 10
<212> TYPE: PRT
<213> ORGANISM: Homo sapiens

<400> SEQUENCE: 1203

Gly Leu Leu Leu Trp Gly Pro Gly Gln Leu
1               5                   10
```

```
<210> SEQ ID NO 1204
<211> LENGTH: 9
<212> TYPE: PRT
<213> ORGANISM: Homo sapiens

<400> SEQUENCE: 1204

Ala Leu Gln Pro Ala Ala Ala Ile Leu
1               5

<210> SEQ ID NO 1205
<211> LENGTH: 10
<212> TYPE: PRT
<213> ORGANISM: Homo sapiens

<400> SEQUENCE: 1205

His Ala Leu Gln Pro Ala Ala Ala Ile Leu
1               5                   10

<210> SEQ ID NO 1206
<211> LENGTH: 10
<212> TYPE: PRT
<213> ORGANISM: Homo sapiens

<400> SEQUENCE: 1206

Ala Pro Glu Lys Asp Lys Phe Phe Ala Tyr
1               5                   10

<210> SEQ ID NO 1207
<211> LENGTH: 9
<212> TYPE: PRT
<213> ORGANISM: Homo sapiens

<400> SEQUENCE: 1207

Pro Glu Lys Asp Lys Phe Phe Ala Tyr
1               5

<210> SEQ ID NO 1208
<211> LENGTH: 9
<212> TYPE: PRT
<213> ORGANISM: Homo sapiens

<400> SEQUENCE: 1208

Glu Lys Asp Lys Phe Phe Ala Tyr Leu
1               5

<210> SEQ ID NO 1209
<211> LENGTH: 8
<212> TYPE: PRT
<213> ORGANISM: Homo sapiens

<400> SEQUENCE: 1209

Lys Asp Lys Phe Phe Ala Tyr Leu
1               5

<210> SEQ ID NO 1210
<211> LENGTH: 9
<212> TYPE: PRT
<213> ORGANISM: Homo sapiens

<400> SEQUENCE: 1210

Pro Ala Phe Leu Pro Trp His Arg Leu
1               5

<210> SEQ ID NO 1211
<211> LENGTH: 10
<212> TYPE: PRT
```

<213> ORGANISM: Homo sapiens

<400> SEQUENCE: 1211

Ala Pro Ala Phe Leu Pro Trp His Arg Leu
1               5                   10

<210> SEQ ID NO 1212
<211> LENGTH: 10
<212> TYPE: PRT
<213> ORGANISM: Homo sapiens

<400> SEQUENCE: 1212

Phe Leu Leu Arg Trp Glu Gln Glu Ile Gln
1               5                   10

<210> SEQ ID NO 1213
<211> LENGTH: 9
<212> TYPE: PRT
<213> ORGANISM: Homo sapiens

<400> SEQUENCE: 1213

Arg Leu Phe Leu Leu Arg Trp Glu Gln
1               5

<210> SEQ ID NO 1214
<211> LENGTH: 10
<212> TYPE: PRT
<213> ORGANISM: Homo sapiens

<400> SEQUENCE: 1214

Gly Ser Glu Ile Trp Arg Asp Ile Asp Phe
1               5                   10

<210> SEQ ID NO 1215
<211> LENGTH: 9
<212> TYPE: PRT
<213> ORGANISM: Homo sapiens

<400> SEQUENCE: 1215

Ser Glu Ile Trp Arg Asp Ile Asp Phe
1               5

<210> SEQ ID NO 1216
<211> LENGTH: 9
<212> TYPE: PRT
<213> ORGANISM: Homo sapiens

<400> SEQUENCE: 1216

Arg Ile Trp Ser Trp Leu Leu Gly Ala
1               5

<210> SEQ ID NO 1217
<211> LENGTH: 9
<212> TYPE: PRT
<213> ORGANISM: Homo sapiens

<400> SEQUENCE: 1217

Ser Trp Leu Leu Gly Ala Ala Met Val
1               5

<210> SEQ ID NO 1218
<211> LENGTH: 10
<212> TYPE: PRT
<213> ORGANISM: Homo sapiens

<400> SEQUENCE: 1218

```
Trp Leu Leu Gly Ala Ala Met Val Gly Ala
1               5                   10

<210> SEQ ID NO 1219
<211> LENGTH: 9
<212> TYPE: PRT
<213> ORGANISM: Homo sapiens

<400> SEQUENCE: 1219

Leu Leu Gly Ala Ala Met Val Gly Ala
1               5

<210> SEQ ID NO 1220
<211> LENGTH: 9
<212> TYPE: PRT
<213> ORGANISM: Homo sapiens

<400> SEQUENCE: 1220

Leu Leu His Glu Thr Asp Ser Ala Val
1               5

<210> SEQ ID NO 1221
<211> LENGTH: 9
<212> TYPE: PRT
<213> ORGANISM: Homo sapiens

<400> SEQUENCE: 1221

Ala Thr Ala Arg Arg Pro Arg Trp Leu
1               5

<210> SEQ ID NO 1222
<211> LENGTH: 9
<212> TYPE: PRT
<213> ORGANISM: Homo sapiens

<400> SEQUENCE: 1222

Thr Pro Lys His Asn Met Lys Ala Phe
1               5

<210> SEQ ID NO 1223
<211> LENGTH: 10
<212> TYPE: PRT
<213> ORGANISM: Homo sapiens

<400> SEQUENCE: 1223

Glu Leu Lys Ala Glu Asn Ile Lys Lys Phe
1               5                   10

<210> SEQ ID NO 1224
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (7)...(7)
<223> OTHER INFORMATION: Xaa= His or Tyr

<400> SEQUENCE: 1224

Asn Ile Lys Lys Phe Leu Xaa Asn Phe
1               5

<210> SEQ ID NO 1225
<211> LENGTH: 10
<212> TYPE: PRT
```

<213> ORGANISM: Artificial Sequence
<220> FEATURE:
<223> OTHER INFORMATION: Synthetic peptide
<220> FEATURE:
<221> NAME/KEY: VARIANT
<222> LOCATION: (8)...(8)
<223> OTHER INFORMATION: Xaa = His or Tyr

<400> SEQUENCE: 1225

Glu Asn Ile Lys Lys Phe Leu Xaa Asn Phe
1               5                   10

<210> SEQ ID NO 1226
<211> LENGTH: 9
<212> TYPE: PRT
<213> ORGANISM: Homo sapiens

<400> SEQUENCE: 1226

Ala Gly Ala Lys Gly Val Ile Leu Tyr
1               5

<210> SEQ ID NO 1227
<211> LENGTH: 10
<212> TYPE: PRT
<213> ORGANISM: Homo sapiens

<400> SEQUENCE: 1227

Pro Leu Met Tyr Ser Leu Val His Asn Leu
1               5                   10

<210> SEQ ID NO 1228
<211> LENGTH: 9
<212> TYPE: PRT
<213> ORGANISM: Homo sapiens

<400> SEQUENCE: 1228

Leu Met Tyr Ser Leu Val His Asn Leu
1               5

<210> SEQ ID NO 1229
<211> LENGTH: 9
<212> TYPE: PRT
<213> ORGANISM: Homo sapiens

<400> SEQUENCE: 1229

Arg Val Asp Cys Thr Pro Leu Met Tyr
1               5

<210> SEQ ID NO 1230
<211> LENGTH: 9
<212> TYPE: PRT
<213> ORGANISM: Homo sapiens

<400> SEQUENCE: 1230

Asp Cys Thr Pro Leu Met Tyr Ser Leu
1               5

<210> SEQ ID NO 1231
<211> LENGTH: 9
<212> TYPE: PRT
<213> ORGANISM: Homo sapiens

<400> SEQUENCE: 1231

Ser Gly Met Pro Arg Ile Ser Lys Leu
1               5

```
<210> SEQ ID NO 1232
<211> LENGTH: 10
<212> TYPE: PRT
<213> ORGANISM: Homo sapiens

<400> SEQUENCE: 1232

Phe Ser Gly Met Pro Arg Ile Ser Lys Leu
 1               5                  10

<210> SEQ ID NO 1233
<211> LENGTH: 28
<212> TYPE: PRT
<213> ORGANISM: Homo sapiens

<400> SEQUENCE: 1233

Arg Leu Thr Ala Ala Asp His Arg Gln Leu Gln Leu Ser Ile Ser Ser
 1               5                  10                  15

Cys Leu Gln Gln Leu Ser Leu Leu Met Trp Ile Thr
            20                  25

<210> SEQ ID NO 1234
<211> LENGTH: 28
<212> TYPE: PRT
<213> ORGANISM: Homo sapiens

<400> SEQUENCE: 1234

Ser Ser Cys Leu Gln Gln Leu Ser Leu Leu Met Trp Ile Thr Gln Cys
 1               5                  10                  15

Phe Leu Pro Val Phe Leu Ala Gln Pro Pro Ser Gly
            20                  25

<210> SEQ ID NO 1235
<211> LENGTH: 8
<212> TYPE: PRT
<213> ORGANISM: Homo sapiens

<400> SEQUENCE: 1235

Lys Ala Glu Met Leu Glu Ser Val
 1               5

<210> SEQ ID NO 1236
<211> LENGTH: 9
<212> TYPE: PRT
<213> ORGANISM: Homo sapiens

<400> SEQUENCE: 1236

Thr Lys Ala Glu Met Leu Glu Ser Val
 1               5

<210> SEQ ID NO 1237
<211> LENGTH: 10
<212> TYPE: PRT
<213> ORGANISM: Homo sapiens

<400> SEQUENCE: 1237

Val Thr Lys Ala Glu Met Leu Glu Ser Val
 1               5                  10

<210> SEQ ID NO 1238
<211> LENGTH: 9
<212> TYPE: PRT
<213> ORGANISM: Homo sapiens

<400> SEQUENCE: 1238

Met Leu Glu Ser Val Ile Lys Asn Tyr
 1               5
```

<210> SEQ ID NO 1239
<211> LENGTH: 10
<212> TYPE: PRT
<213> ORGANISM: Homo sapiens

<400> SEQUENCE: 1239

Glu Met Leu Glu Ser Val Ile Lys Asn Tyr
1               5                   10

<210> SEQ ID NO 1240
<211> LENGTH: 9
<212> TYPE: PRT
<213> ORGANISM: Homo sapiens

<400> SEQUENCE: 1240

Lys Ala Glu Met Leu Glu Ser Val Ile
1               5

<210> SEQ ID NO 1241
<211> LENGTH: 8
<212> TYPE: PRT
<213> ORGANISM: Homo sapiens

<400> SEQUENCE: 1241

Lys Ala Ser Glu Ser Leu Gln Leu
1               5

<210> SEQ ID NO 1242
<211> LENGTH: 9
<212> TYPE: PRT
<213> ORGANISM: Homo sapiens

<400> SEQUENCE: 1242

Gly Lys Ala Ser Glu Ser Leu Gln Leu
1               5

<210> SEQ ID NO 1243
<211> LENGTH: 9
<212> TYPE: PRT
<213> ORGANISM: Homo sapiens

<400> SEQUENCE: 1243

Ala Ser Glu Ser Leu Gln Leu Val Phe
1               5

<210> SEQ ID NO 1244
<211> LENGTH: 9
<212> TYPE: PRT
<213> ORGANISM: Homo sapiens

<400> SEQUENCE: 1244

Leu Val Phe Gly Ile Asp Val Lys Glu
1               5

<210> SEQ ID NO 1245
<211> LENGTH: 8
<212> TYPE: PRT
<213> ORGANISM: Homo sapiens

<400> SEQUENCE: 1245

Leu Leu Lys Tyr Arg Ala Arg Glu
1               5

```
<210> SEQ ID NO 1246
<211> LENGTH: 8
<212> TYPE: PRT
<213> ORGANISM: Homo sapiens

<400> SEQUENCE: 1246

Val Ala Asp Leu Val Gly Phe Leu
1               5

<210> SEQ ID NO 1247
<211> LENGTH: 9
<212> TYPE: PRT
<213> ORGANISM: Homo sapiens

<400> SEQUENCE: 1247

Lys Val Ala Asp Leu Val Gly Phe Leu
1               5

<210> SEQ ID NO 1248
<211> LENGTH: 9
<212> TYPE: PRT
<213> ORGANISM: Homo sapiens

<400> SEQUENCE: 1248

Ala Asp Leu Val Gly Phe Leu Leu Leu
1               5

<210> SEQ ID NO 1249
<211> LENGTH: 10
<212> TYPE: PRT
<213> ORGANISM: Homo sapiens

<400> SEQUENCE: 1249

Val Ala Asp Leu Val Gly Phe Leu Leu Leu
1               5                   10

<210> SEQ ID NO 1250
<211> LENGTH: 10
<212> TYPE: PRT
<213> ORGANISM: Homo sapiens

<400> SEQUENCE: 1250

Leu Leu Lys Tyr Arg Ala Arg Glu Pro Val
1               5                   10

<210> SEQ ID NO 1251
<211> LENGTH: 9
<212> TYPE: PRT
<213> ORGANISM: Homo sapiens

<400> SEQUENCE: 1251

Leu Val Glu Thr Ser Tyr Val Lys Val
1               5

<210> SEQ ID NO 1252
<211> LENGTH: 10
<212> TYPE: PRT
<213> ORGANISM: Homo sapiens

<400> SEQUENCE: 1252

Ala Leu Val Glu Thr Ser Tyr Val Lys Val
1               5                   10

<210> SEQ ID NO 1253
<211> LENGTH: 9
<212> TYPE: PRT
```

```
<213> ORGANISM: Homo sapiens

<400> SEQUENCE: 1253

Lys Val Leu His His Met Val Lys Ile
 1               5

<210> SEQ ID NO 1254
<211> LENGTH: 9
<212> TYPE: PRT
<213> ORGANISM: Homo sapiens

<400> SEQUENCE: 1254

Tyr Val Lys Val Leu His His Met Val
 1               5

<210> SEQ ID NO 1255
<211> LENGTH: 9
<212> TYPE: PRT
<213> ORGANISM: Homo sapiens

<400> SEQUENCE: 1255

Pro Arg Ala Leu Val Glu Thr Ser Tyr
 1               5

<210> SEQ ID NO 1256
<211> LENGTH: 10
<212> TYPE: PRT
<213> ORGANISM: Homo sapiens

<400> SEQUENCE: 1256

Gly Pro Arg Ala Leu Val Glu Thr Ser Tyr
 1               5                  10

<210> SEQ ID NO 1257
<211> LENGTH: 10
<212> TYPE: PRT
<213> ORGANISM: Homo sapiens

<400> SEQUENCE: 1257

Leu Val Glu Thr Ser Tyr Val Lys Val Leu
 1               5                  10

<210> SEQ ID NO 1258
<211> LENGTH: 9
<212> TYPE: PRT
<213> ORGANISM: Homo sapiens

<400> SEQUENCE: 1258

Thr Ile Ile Pro Glu Val Pro Gln Leu
 1               5

<210> SEQ ID NO 1259
<211> LENGTH: 10
<212> TYPE: PRT
<213> ORGANISM: Homo sapiens

<400> SEQUENCE: 1259

Asp Thr Ile Ile Pro Glu Val Pro Gln Leu
 1               5                  10

<210> SEQ ID NO 1260
<211> LENGTH: 10
<212> TYPE: PRT
<213> ORGANISM: Homo sapiens

<400> SEQUENCE: 1260
```

Glu Val Pro Gln Leu Thr Asp Leu Ser Phe
1               5                   10

<210> SEQ ID NO 1261
<211> LENGTH: 8
<212> TYPE: PRT
<213> ORGANISM: Homo sapiens

<400> SEQUENCE: 1261

Thr Pro Leu Asn Ser Ser Thr Ile
1               5

<210> SEQ ID NO 1262
<211> LENGTH: 8
<212> TYPE: PRT
<213> ORGANISM: Homo sapiens

<400> SEQUENCE: 1262

Ile Gly Leu Arg Trp Thr Pro Leu
1               5

<210> SEQ ID NO 1263
<211> LENGTH: 9
<212> TYPE: PRT
<213> ORGANISM: Homo sapiens

<400> SEQUENCE: 1263

Ser Ile Gly Leu Arg Trp Thr Pro Leu
1               5

<210> SEQ ID NO 1264
<211> LENGTH: 9
<212> TYPE: PRT
<213> ORGANISM: Homo sapiens

<400> SEQUENCE: 1264

Leu Asn Ser Ser Thr Ile Ile Gly Tyr
1               5

<210> SEQ ID NO 1265
<211> LENGTH: 10
<212> TYPE: PRT
<213> ORGANISM: Homo sapiens

<400> SEQUENCE: 1265

Pro Leu Asn Ser Ser Thr Ile Ile Gly Tyr
1               5                   10

<210> SEQ ID NO 1266
<211> LENGTH: 9
<212> TYPE: PRT
<213> ORGANISM: Homo sapiens

<400> SEQUENCE: 1266

Thr Pro Leu Asn Ser Ser Thr Ile Ile
1               5

<210> SEQ ID NO 1267
<211> LENGTH: 8
<212> TYPE: PRT
<213> ORGANISM: Homo sapiens

<400> SEQUENCE: 1267

Ile Gly Tyr Arg Ile Thr Val Val
1               5

<210> SEQ ID NO 1268
<211> LENGTH: 9
<212> TYPE: PRT
<213> ORGANISM: Homo sapiens

<400> SEQUENCE: 1268

Ile Ile Gly Tyr Arg Ile Thr Val Val
1               5

<210> SEQ ID NO 1269
<211> LENGTH: 10
<212> TYPE: PRT
<213> ORGANISM: Homo sapiens

<400> SEQUENCE: 1269

Thr Ile Ile Gly Tyr Arg Ile Thr Val Val
1               5                   10

<210> SEQ ID NO 1270
<211> LENGTH: 9
<212> TYPE: PRT
<213> ORGANISM: Homo sapiens

<400> SEQUENCE: 1270

Ile Gly Tyr Arg Ile Thr Val Val Ala
1               5

<210> SEQ ID NO 1271
<211> LENGTH: 10
<212> TYPE: PRT
<213> ORGANISM: Homo sapiens

<400> SEQUENCE: 1271

Ile Ile Gly Tyr Arg Ile Thr Val Val Ala
1               5                   10

<210> SEQ ID NO 1272
<211> LENGTH: 8
<212> TYPE: PRT
<213> ORGANISM: Homo sapiens

<400> SEQUENCE: 1272

Ser Leu Pro Val Ser Pro Arg Leu
1               5

<210> SEQ ID NO 1273
<211> LENGTH: 9
<212> TYPE: PRT
<213> ORGANISM: Homo sapiens

<400> SEQUENCE: 1273

Gln Ser Leu Pro Val Ser Pro Arg Leu
1               5

<210> SEQ ID NO 1274
<211> LENGTH: 8
<212> TYPE: PRT
<213> ORGANISM: Homo sapiens

<400> SEQUENCE: 1274

Pro Val Ser Pro Arg Leu Gln Leu
1               5

<210> SEQ ID NO 1275

```
<211> LENGTH: 9
<212> TYPE: PRT
<213> ORGANISM: Homo sapiens

<400> SEQUENCE: 1275

Leu Pro Val Ser Pro Arg Leu Gln Leu
1               5

<210> SEQ ID NO 1276
<211> LENGTH: 10
<212> TYPE: PRT
<213> ORGANISM: Homo sapiens

<400> SEQUENCE: 1276

Ser Leu Pro Val Ser Pro Arg Leu Gln Leu
1               5                   10

<210> SEQ ID NO 1277
<211> LENGTH: 8
<212> TYPE: PRT
<213> ORGANISM: Homo sapiens

<400> SEQUENCE: 1277

Leu Pro Val Ser Pro Arg Leu Gln
1               5

<210> SEQ ID NO 1278
<211> LENGTH: 9
<212> TYPE: PRT
<213> ORGANISM: Homo sapiens

<400> SEQUENCE: 1278

Gln Leu Ser Asn Gly Asn Arg Thr Leu
1               5

<210> SEQ ID NO 1279
<211> LENGTH: 10
<212> TYPE: PRT
<213> ORGANISM: Homo sapiens

<400> SEQUENCE: 1279

Leu Gln Leu Ser Asn Gly Asn Arg Thr Leu
1               5                   10

<210> SEQ ID NO 1280
<211> LENGTH: 9
<212> TYPE: PRT
<213> ORGANISM: Homo sapiens

<400> SEQUENCE: 1280

Trp Val Asn Asn Gln Ser Leu Pro Val
1               5

<210> SEQ ID NO 1281
<211> LENGTH: 9
<212> TYPE: PRT
<213> ORGANISM: Homo sapiens

<400> SEQUENCE: 1281

Pro Val Ser Pro Arg Leu Gln Leu Ser
1               5

<210> SEQ ID NO 1282
<211> LENGTH: 8
<212> TYPE: PRT
<213> ORGANISM: Homo sapiens
```

<400> SEQUENCE: 1282

Ser Leu Pro Val Ser Pro Arg Leu
1               5

<210> SEQ ID NO 1283
<211> LENGTH: 9
<212> TYPE: PRT
<213> ORGANISM: Homo sapiens

<400> SEQUENCE: 1283

Gln Ser Leu Pro Val Ser Pro Arg Leu
1               5

<210> SEQ ID NO 1284
<211> LENGTH: 8
<212> TYPE: PRT
<213> ORGANISM: Homo sapiens

<400> SEQUENCE: 1284

Pro Val Ser Pro Arg Leu Gln Leu
1               5

<210> SEQ ID NO 1285
<211> LENGTH: 9
<212> TYPE: PRT
<213> ORGANISM: Homo sapiens

<400> SEQUENCE: 1285

Leu Pro Val Ser Pro Arg Leu Gln Leu
1               5

<210> SEQ ID NO 1286
<211> LENGTH: 10
<212> TYPE: PRT
<213> ORGANISM: Homo sapiens

<400> SEQUENCE: 1286

Ser Leu Pro Val Ser Pro Arg Leu Gln Leu
1               5                   10

<210> SEQ ID NO 1287
<211> LENGTH: 8
<212> TYPE: PRT
<213> ORGANISM: Homo sapiens

<400> SEQUENCE: 1287

Leu Pro Val Ser Pro Arg Leu Gln
1               5

<210> SEQ ID NO 1288
<211> LENGTH: 9
<212> TYPE: PRT
<213> ORGANISM: Homo sapiens

<400> SEQUENCE: 1288

Gln Leu Ser Asn Asp Asn Arg Thr Leu
1               5

<210> SEQ ID NO 1289
<211> LENGTH: 10
<212> TYPE: PRT
<213> ORGANISM: Homo sapiens

<400> SEQUENCE: 1289

Leu Gln Leu Ser Asn Asp Asn Arg Thr Leu
1               5                   10

<210> SEQ ID NO 1290
<211> LENGTH: 9
<212> TYPE: PRT
<213> ORGANISM: Homo sapiens

<400> SEQUENCE: 1290

Trp Val Asn Asn Gln Ser Leu Pro Val
1               5

<210> SEQ ID NO 1291
<211> LENGTH: 9
<212> TYPE: PRT
<213> ORGANISM: Homo sapiens

<400> SEQUENCE: 1291

Asn Gln Ser Leu Pro Val Ser Pro Arg
1               5

<210> SEQ ID NO 1292
<211> LENGTH: 8
<212> TYPE: PRT
<213> ORGANISM: Homo sapiens

<400> SEQUENCE: 1292

Ser Leu Pro Val Ser Pro Arg Leu
1               5

<210> SEQ ID NO 1293
<211> LENGTH: 9
<212> TYPE: PRT
<213> ORGANISM: Homo sapiens

<400> SEQUENCE: 1293

Gln Ser Leu Pro Val Ser Pro Arg Leu
1               5

<210> SEQ ID NO 1294
<211> LENGTH: 8
<212> TYPE: PRT
<213> ORGANISM: Homo sapiens

<400> SEQUENCE: 1294

Pro Val Ser Pro Arg Leu Gln Leu
1               5

<210> SEQ ID NO 1295
<211> LENGTH: 9
<212> TYPE: PRT
<213> ORGANISM: Homo sapiens

<400> SEQUENCE: 1295

Leu Pro Val Ser Pro Arg Leu Gln Leu
1               5

<210> SEQ ID NO 1296
<211> LENGTH: 10
<212> TYPE: PRT
<213> ORGANISM: Homo sapiens

<400> SEQUENCE: 1296

Ser Leu Pro Val Ser Pro Arg Leu Gln Leu
1               5                   10

```
<210> SEQ ID NO 1297
<211> LENGTH: 8
<212> TYPE: PRT
<213> ORGANISM: Homo sapiens

<400> SEQUENCE: 1297

Leu Pro Val Ser Pro Arg Leu Gln
 1               5

<210> SEQ ID NO 1298
<211> LENGTH: 9
<212> TYPE: PRT
<213> ORGANISM: Homo sapiens

<400> SEQUENCE: 1298

Gln Leu Ser Asn Gly Asn Arg Thr Leu
 1               5

<210> SEQ ID NO 1299
<211> LENGTH: 10
<212> TYPE: PRT
<213> ORGANISM: Homo sapiens

<400> SEQUENCE: 1299

Leu Gln Leu Ser Asn Gly Asn Arg Thr Leu
 1               5                   10

<210> SEQ ID NO 1300
<211> LENGTH: 9
<212> TYPE: PRT
<213> ORGANISM: Homo sapiens

<400> SEQUENCE: 1300

Trp Val Asn Gly Gln Ser Leu Pro Val
 1               5

<210> SEQ ID NO 1301
<211> LENGTH: 9
<212> TYPE: PRT
<213> ORGANISM: Homo sapiens

<400> SEQUENCE: 1301

Leu Trp Trp Val Asn Gly Gln Ser Leu
 1               5

<210> SEQ ID NO 1302
<211> LENGTH: 10
<212> TYPE: PRT
<213> ORGANISM: Homo sapiens

<400> SEQUENCE: 1302

Tyr Leu Trp Trp Val Asn Gly Gln Ser Leu
 1               5                   10

<210> SEQ ID NO 1303
<211> LENGTH: 9
<212> TYPE: PRT
<213> ORGANISM: Homo sapiens

<400> SEQUENCE: 1303

Gly Gln Ser Leu Pro Val Ser Pro Arg
 1               5

<210> SEQ ID NO 1304
<211> LENGTH: 8
```

```
<212> TYPE: PRT
<213> ORGANISM: Homo sapiens

<400> SEQUENCE: 1304

Asp Met Lys Leu Arg Leu Pro Ala
 1               5

<210> SEQ ID NO 1305
<211> LENGTH: 10
<212> TYPE: PRT
<213> ORGANISM: Homo sapiens

<400> SEQUENCE: 1305

Gly Thr Asp Met Lys Leu Arg Leu Pro Ala
 1               5                  10

<210> SEQ ID NO 1306
<211> LENGTH: 8
<212> TYPE: PRT
<213> ORGANISM: Homo sapiens

<400> SEQUENCE: 1306

His Leu Asp Met Leu Arg His Leu
 1               5

<210> SEQ ID NO 1307
<211> LENGTH: 9
<212> TYPE: PRT
<213> ORGANISM: Homo sapiens

<400> SEQUENCE: 1307

Thr His Leu Asp Met Leu Arg His Leu
 1               5

<210> SEQ ID NO 1308
<211> LENGTH: 10
<212> TYPE: PRT
<213> ORGANISM: Homo sapiens

<400> SEQUENCE: 1308

Glu Thr His Leu Asp Met Leu Arg His Leu
 1               5                  10

<210> SEQ ID NO 1309
<211> LENGTH: 8
<212> TYPE: PRT
<213> ORGANISM: Homo sapiens

<400> SEQUENCE: 1309

Pro Ala Ser Pro Glu Thr His Leu
 1               5

<210> SEQ ID NO 1310
<211> LENGTH: 9
<212> TYPE: PRT
<213> ORGANISM: Homo sapiens

<400> SEQUENCE: 1310

Leu Pro Ala Ser Pro Glu Thr His Leu
 1               5

<210> SEQ ID NO 1311
<211> LENGTH: 10
<212> TYPE: PRT
<213> ORGANISM: Homo sapiens
```

```
<400> SEQUENCE: 1311

Arg Leu Pro Ala Ser Pro Glu Thr His Leu
 1               5                  10

<210> SEQ ID NO 1312
<211> LENGTH: 9
<212> TYPE: PRT
<213> ORGANISM: Homo sapiens

<400> SEQUENCE: 1312

Ser Pro Glu Thr His Leu Asp Met Leu
 1               5

<210> SEQ ID NO 1313
<211> LENGTH: 10
<212> TYPE: PRT
<213> ORGANISM: Homo sapiens

<400> SEQUENCE: 1313

Ala Ser Pro Glu Thr His Leu Asp Met Leu
 1               5                  10

<210> SEQ ID NO 1314
<211> LENGTH: 9
<212> TYPE: PRT
<213> ORGANISM: Homo sapiens

<400> SEQUENCE: 1314

His Leu Asp Met Leu Arg His Leu Tyr
 1               5

<210> SEQ ID NO 1315
<211> LENGTH: 10
<212> TYPE: PRT
<213> ORGANISM: Homo sapiens

<400> SEQUENCE: 1315

Thr His Leu Asp Met Leu Arg His Leu Tyr
 1               5                  10

<210> SEQ ID NO 1316
<211> LENGTH: 8
<212> TYPE: PRT
<213> ORGANISM: Homo sapiens

<400> SEQUENCE: 1316

Glu Leu Arg Lys Val Lys Val Leu
 1               5

<210> SEQ ID NO 1317
<211> LENGTH: 9
<212> TYPE: PRT
<213> ORGANISM: Homo sapiens

<400> SEQUENCE: 1317

Thr Glu Leu Arg Lys Val Lys Val Leu
 1               5

<210> SEQ ID NO 1318
<211> LENGTH: 10
<212> TYPE: PRT
<213> ORGANISM: Homo sapiens

<400> SEQUENCE: 1318

Glu Thr Glu Leu Arg Lys Val Lys Val Leu
```

```
<210> SEQ ID NO 1319
<211> LENGTH: 9
<212> TYPE: PRT
<213> ORGANISM: Homo sapiens

<400> SEQUENCE: 1319

Leu Lys Glu Thr Glu Leu Arg Lys Val
1               5

<210> SEQ ID NO 1320
<211> LENGTH: 10
<212> TYPE: PRT
<213> ORGANISM: Homo sapiens

<400> SEQUENCE: 1320

Ile Leu Lys Glu Thr Glu Leu Arg Lys Val
1               5                   10

<210> SEQ ID NO 1321
<211> LENGTH: 9
<212> TYPE: PRT
<213> ORGANISM: Homo sapiens

<400> SEQUENCE: 1321

Met Arg Ile Leu Lys Glu Thr Glu Leu
1               5

<210> SEQ ID NO 1322
<211> LENGTH: 10
<212> TYPE: PRT
<213> ORGANISM: Homo sapiens

<400> SEQUENCE: 1322

Gln Met Arg Ile Leu Lys Glu Thr Glu Leu
1               5                   10

<210> SEQ ID NO 1323
<211> LENGTH: 9
<212> TYPE: PRT
<213> ORGANISM: Homo sapiens

<400> SEQUENCE: 1323

Glu Thr Glu Leu Arg Lys Val Lys Val
1               5

<210> SEQ ID NO 1324
<211> LENGTH: 10
<212> TYPE: PRT
<213> ORGANISM: Homo sapiens

<400> SEQUENCE: 1324

Lys Glu Thr Glu Leu Arg Lys Val Lys Val
1               5                   10

<210> SEQ ID NO 1325
<211> LENGTH: 9
<212> TYPE: PRT
<213> ORGANISM: Homo sapiens

<400> SEQUENCE: 1325

Met Pro Asn Gln Ala Gln Met Arg Ile
1               5
```

```
<210> SEQ ID NO 1326
<211> LENGTH: 10
<212> TYPE: PRT
<213> ORGANISM: Homo sapiens

<400> SEQUENCE: 1326

Ala Met Pro Asn Gln Ala Gln Met Arg Ile
1               5                   10

<210> SEQ ID NO 1327
<211> LENGTH: 10
<212> TYPE: PRT
<213> ORGANISM: Homo sapiens

<400> SEQUENCE: 1327

Met Pro Asn Gln Ala Gln Met Arg Ile Leu
1               5                   10

<210> SEQ ID NO 1328
<211> LENGTH: 8
<212> TYPE: PRT
<213> ORGANISM: Homo sapiens

<400> SEQUENCE: 1328

Arg Pro Arg Phe Arg Glu Leu Val
1               5

<210> SEQ ID NO 1329
<211> LENGTH: 9
<212> TYPE: PRT
<213> ORGANISM: Homo sapiens

<400> SEQUENCE: 1329

Cys Arg Pro Arg Phe Arg Glu Leu Val
1               5

<210> SEQ ID NO 1330
<211> LENGTH: 9
<212> TYPE: PRT
<213> ORGANISM: Homo sapiens

<400> SEQUENCE: 1330

Arg Phe Arg Glu Leu Val Ser Glu Phe
1               5

<210> SEQ ID NO 1331
<211> LENGTH: 10
<212> TYPE: PRT
<213> ORGANISM: Homo sapiens

<400> SEQUENCE: 1331

Pro Arg Phe Arg Glu Leu Val Ser Glu Phe
1               5                   10

<210> SEQ ID NO 1332
<211> LENGTH: 9
<212> TYPE: PRT
<213> ORGANISM: Homo sapiens

<400> SEQUENCE: 1332

Glu Cys Arg Pro Arg Phe Arg Glu Leu
1               5

<210> SEQ ID NO 1333
<211> LENGTH: 9
<212> TYPE: PRT
```

-continued

```
<213> ORGANISM: Homo sapiens

<400> SEQUENCE: 1333

Gly Ala Ala Ser Gly Leu Asn Gly Cys
1               5

<210> SEQ ID NO 1334
<211> LENGTH: 9
<212> TYPE: PRT
<213> ORGANISM: Homo sapiens

<400> SEQUENCE: 1334

Arg Ala Ser Gly Pro Gly Gly Gly Ala
1               5

<210> SEQ ID NO 1335
<211> LENGTH: 9
<212> TYPE: PRT
<213> ORGANISM: Homo sapiens

<400> SEQUENCE: 1335

Pro His Gly Gly Ala Ala Ser Gly Leu
1               5

<210> SEQ ID NO 1336
<211> LENGTH: 10
<212> TYPE: PRT
<213> ORGANISM: Homo sapiens

<400> SEQUENCE: 1336

Gly Pro His Gly Gly Ala Ala Ser Gly Leu
1               5                   10

<210> SEQ ID NO 1337
<211> LENGTH: 10
<212> TYPE: PRT
<213> ORGANISM: Homo sapiens

<400> SEQUENCE: 1337

Ala Pro Arg Gly Pro His Gly Gly Ala Ala
1               5                   10

<210> SEQ ID NO 1338
<211> LENGTH: 8
<212> TYPE: PRT
<213> ORGANISM: Homo sapiens

<400> SEQUENCE: 1338

Val Arg Pro Arg Arg Trp Lys Leu
1               5

<210> SEQ ID NO 1339
<211> LENGTH: 9
<212> TYPE: PRT
<213> ORGANISM: Homo sapiens

<400> SEQUENCE: 1339

Glu Val Arg Pro Arg Arg Trp Lys Leu
1               5

<210> SEQ ID NO 1340
<211> LENGTH: 9
<212> TYPE: PRT
<213> ORGANISM: Homo sapiens

<400> SEQUENCE: 1340
```

Arg Pro Arg Arg Trp Lys Leu Gln Val
1               5

<210> SEQ ID NO 1341
<211> LENGTH: 9
<212> TYPE: PRT
<213> ORGANISM: Homo sapiens

<400> SEQUENCE: 1341

Pro Arg Arg Trp Lys Leu Gln Val Leu
1               5

<210> SEQ ID NO 1342
<211> LENGTH: 10
<212> TYPE: PRT
<213> ORGANISM: Homo sapiens

<400> SEQUENCE: 1342

Arg Pro Arg Arg Trp Lys Leu Gln Val Leu
1               5                   10

<210> SEQ ID NO 1343
<211> LENGTH: 9
<212> TYPE: PRT
<213> ORGANISM: Homo sapiens

<400> SEQUENCE: 1343

Arg Trp Lys Leu Gln Val Leu Asp Leu
1               5

<210> SEQ ID NO 1344
<211> LENGTH: 10
<212> TYPE: PRT
<213> ORGANISM: Homo sapiens

<400> SEQUENCE: 1344

Arg Arg Trp Lys Leu Gln Val Leu Asp Leu
1               5                   10

<210> SEQ ID NO 1345
<211> LENGTH: 9
<212> TYPE: PRT
<213> ORGANISM: Homo sapiens

<400> SEQUENCE: 1345

Pro Val Glu Val Leu Val Asp Leu Phe
1               5

<210> SEQ ID NO 1346
<211> LENGTH: 8
<212> TYPE: PRT
<213> ORGANISM: Homo sapiens

<400> SEQUENCE: 1346

Val Lys Arg Lys Lys Asn Val Leu
1               5

<210> SEQ ID NO 1347
<211> LENGTH: 9
<212> TYPE: PRT
<213> ORGANISM: Homo sapiens

<400> SEQUENCE: 1347

Lys Val Lys Arg Lys Lys Asn Val Leu
1               5

<210> SEQ ID NO 1348
<211> LENGTH: 10
<212> TYPE: PRT
<213> ORGANISM: Homo sapiens

<400> SEQUENCE: 1348

Glu Lys Val Lys Arg Lys Lys Asn Val Leu
1               5                   10

<210> SEQ ID NO 1349
<211> LENGTH: 8
<212> TYPE: PRT
<213> ORGANISM: Homo sapiens

<400> SEQUENCE: 1349

Lys Val Lys Arg Lys Lys Asn Val
1               5

<210> SEQ ID NO 1350
<211> LENGTH: 8
<212> TYPE: PRT
<213> ORGANISM: Homo sapiens

<400> SEQUENCE: 1350

Arg Lys Lys Asn Val Leu Arg Leu
1               5

<210> SEQ ID NO 1351
<211> LENGTH: 9
<212> TYPE: PRT
<213> ORGANISM: Homo sapiens

<400> SEQUENCE: 1351

Lys Arg Lys Lys Asn Val Leu Arg Leu
1               5

<210> SEQ ID NO 1352
<211> LENGTH: 10
<212> TYPE: PRT
<213> ORGANISM: Homo sapiens

<400> SEQUENCE: 1352

Val Lys Arg Lys Lys Asn Val Leu Arg Leu
1               5                   10

<210> SEQ ID NO 1353
<211> LENGTH: 8
<212> TYPE: PRT
<213> ORGANISM: Homo sapiens

<400> SEQUENCE: 1353

Asp Glu Leu Phe Ser Tyr Leu Ile
1               5

<210> SEQ ID NO 1354
<211> LENGTH: 9
<212> TYPE: PRT
<213> ORGANISM: Homo sapiens

<400> SEQUENCE: 1354

Val Leu Arg Leu Cys Cys Lys Lys Leu
1               5

<210> SEQ ID NO 1355

```
<211> LENGTH: 10
<212> TYPE: PRT
<213> ORGANISM: Homo sapiens

<400> SEQUENCE: 1355

Asn Val Leu Arg Leu Cys Cys Lys Lys Leu
 1               5                  10

<210> SEQ ID NO 1356
<211> LENGTH: 9
<212> TYPE: PRT
<213> ORGANISM: Homo sapiens

<400> SEQUENCE: 1356

Tyr Leu Ile Glu Lys Val Lys Arg Lys
 1               5

<210> SEQ ID NO 1357
<211> LENGTH: 8
<212> TYPE: PRT
<213> ORGANISM: Homo sapiens

<400> SEQUENCE: 1357

Gln Ala Trp Pro Phe Thr Cys Leu
 1               5

<210> SEQ ID NO 1358
<211> LENGTH: 9
<212> TYPE: PRT
<213> ORGANISM: Homo sapiens

<400> SEQUENCE: 1358

Val Gln Ala Trp Pro Phe Thr Cys Leu
 1               5

<210> SEQ ID NO 1359
<211> LENGTH: 10
<212> TYPE: PRT
<213> ORGANISM: Homo sapiens

<400> SEQUENCE: 1359

Met Val Gln Ala Trp Pro Phe Thr Cys Leu
 1               5                  10

<210> SEQ ID NO 1360
<211> LENGTH: 8
<212> TYPE: PRT
<213> ORGANISM: Homo sapiens

<400> SEQUENCE: 1360

Leu Pro Leu Gly Val Leu Met Lys
 1               5

<210> SEQ ID NO 1361
<211> LENGTH: 9
<212> TYPE: PRT
<213> ORGANISM: Homo sapiens

<400> SEQUENCE: 1361

Cys Leu Pro Leu Gly Val Leu Met Lys
 1               5

<210> SEQ ID NO 1362
<211> LENGTH: 10
<212> TYPE: PRT
<213> ORGANISM: Homo sapiens
```

<400> SEQUENCE: 1362

Thr Cys Leu Pro Leu Gly Val Leu Met Lys
1               5                   10

<210> SEQ ID NO 1363
<211> LENGTH: 9
<212> TYPE: PRT
<213> ORGANISM: Homo sapiens

<400> SEQUENCE: 1363

Gly Val Leu Met Lys Gly Gln His Leu
1               5

<210> SEQ ID NO 1364
<211> LENGTH: 9
<212> TYPE: PRT
<213> ORGANISM: Homo sapiens

<400> SEQUENCE: 1364

Leu Pro Leu Gly Val Leu Met Lys Gly
1               5

<210> SEQ ID NO 1365
<211> LENGTH: 10
<212> TYPE: PRT
<213> ORGANISM: Homo sapiens

<400> SEQUENCE: 1365

Cys Leu Pro Leu Gly Val Leu Met Lys Gly
1               5                   10

<210> SEQ ID NO 1366
<211> LENGTH: 10
<212> TYPE: PRT
<213> ORGANISM: Homo sapiens

<400> SEQUENCE: 1366

Trp Pro Phe Thr Cys Leu Pro Leu Gly Val
1               5                   10

<210> SEQ ID NO 1367
<211> LENGTH: 9
<212> TYPE: PRT
<213> ORGANISM: Homo sapiens

<400> SEQUENCE: 1367

Glu Leu Phe Pro Pro Leu Phe Met Ala
1               5

<210> SEQ ID NO 1368
<211> LENGTH: 9
<212> TYPE: PRT
<213> ORGANISM: Homo sapiens

<400> SEQUENCE: 1368

Pro Arg Glu Leu Phe Pro Pro Leu Phe
1               5

<210> SEQ ID NO 1369
<211> LENGTH: 10
<212> TYPE: PRT
<213> ORGANISM: Homo sapiens

<400> SEQUENCE: 1369

Leu Pro Arg Glu Leu Phe Pro Pro Leu Phe
1               5                   10

<210> SEQ ID NO 1370
<211> LENGTH: 9
<212> TYPE: PRT
<213> ORGANISM: Homo sapiens

<400> SEQUENCE: 1370

Arg Glu Leu Phe Pro Pro Leu Phe Met
1               5

<210> SEQ ID NO 1371
<211> LENGTH: 10
<212> TYPE: PRT
<213> ORGANISM: Homo sapiens

<400> SEQUENCE: 1371

Pro Arg Glu Leu Phe Pro Pro Leu Phe Met
1               5                   10

<210> SEQ ID NO 1372
<211> LENGTH: 8
<212> TYPE: PRT
<213> ORGANISM: Homo sapiens

<400> SEQUENCE: 1372

Arg Pro Ser Leu Tyr Thr Lys Val
1               5

<210> SEQ ID NO 1373
<211> LENGTH: 9
<212> TYPE: PRT
<213> ORGANISM: Homo sapiens

<400> SEQUENCE: 1373

Glu Arg Pro Ser Leu Tyr Thr Lys Val
1               5

<210> SEQ ID NO 1374
<211> LENGTH: 8
<212> TYPE: PRT
<213> ORGANISM: Homo sapiens

<400> SEQUENCE: 1374

Leu Pro Glu Arg Pro Ser Leu Tyr
1               5

<210> SEQ ID NO 1375
<211> LENGTH: 9
<212> TYPE: PRT
<213> ORGANISM: Homo sapiens

<400> SEQUENCE: 1375

Ala Leu Pro Glu Arg Pro Ser Leu Tyr
1               5

<210> SEQ ID NO 1376
<211> LENGTH: 9
<212> TYPE: PRT
<213> ORGANISM: Homo sapiens

<400> SEQUENCE: 1376

Ser Leu Tyr Thr Lys Val Val His Tyr
1               5

```
<210> SEQ ID NO 1377
<211> LENGTH: 10
<212> TYPE: PRT
<213> ORGANISM: Homo sapiens

<400> SEQUENCE: 1377

Pro Ser Leu Tyr Thr Lys Val Val His Tyr
1               5                   10

<210> SEQ ID NO 1378
<211> LENGTH: 9
<212> TYPE: PRT
<213> ORGANISM: Homo sapiens

<400> SEQUENCE: 1378

Arg Pro Ser Leu Tyr Thr Lys Val Val
1               5

<210> SEQ ID NO 1379
<211> LENGTH: 8
<212> TYPE: PRT
<213> ORGANISM: Homo sapiens

<400> SEQUENCE: 1379

Gly Asn Lys Val Lys Asn Ala Gln
1               5

<210> SEQ ID NO 1380
<211> LENGTH: 8
<212> TYPE: PRT
<213> ORGANISM: Homo sapiens

<400> SEQUENCE: 1380

Ile Ala Arg Tyr Gly Lys Val Phe
1               5

<210> SEQ ID NO 1381
<211> LENGTH: 9
<212> TYPE: PRT
<213> ORGANISM: Homo sapiens

<400> SEQUENCE: 1381

Ala Gln Leu Ala Gly Ala Lys Gly Val
1               5

<210> SEQ ID NO 1382
<211> LENGTH: 9
<212> TYPE: PRT
<213> ORGANISM: Homo sapiens

<400> SEQUENCE: 1382

Lys Val Phe Arg Gly Asn Lys Val Lys
1               5

<210> SEQ ID NO 1383
<211> LENGTH: 9
<212> TYPE: PRT
<213> ORGANISM: Homo sapiens

<400> SEQUENCE: 1383

Gly Asn Lys Val Lys Asn Ala Gln Leu
1               5

<210> SEQ ID NO 1384
<211> LENGTH: 9
```

```
<212> TYPE: PRT
<213> ORGANISM: Homo sapiens

<400> SEQUENCE: 1384

Thr Pro Gly Tyr Pro Ala Asn Glu Tyr
1               5

<210> SEQ ID NO 1385
<211> LENGTH: 10
<212> TYPE: PRT
<213> ORGANISM: Homo sapiens

<400> SEQUENCE: 1385

Leu Thr Pro Gly Tyr Pro Ala Asn Glu Tyr
1               5                   10

<210> SEQ ID NO 1386
<211> LENGTH: 9
<212> TYPE: PRT
<213> ORGANISM: Homo sapiens

<400> SEQUENCE: 1386

Gly Tyr Pro Ala Asn Glu Tyr Ala Tyr
1               5

<210> SEQ ID NO 1387
<211> LENGTH: 10
<212> TYPE: PRT
<213> ORGANISM: Homo sapiens

<400> SEQUENCE: 1387

Pro Gly Tyr Pro Ala Asn Glu Tyr Ala Tyr
1               5                   10

<210> SEQ ID NO 1388
<211> LENGTH: 9
<212> TYPE: PRT
<213> ORGANISM: Homo sapiens

<400> SEQUENCE: 1388

Asp Pro Leu Thr Pro Gly Tyr Pro Ala
1               5

<210> SEQ ID NO 1389
<211> LENGTH: 9
<212> TYPE: PRT
<213> ORGANISM: Homo sapiens

<400> SEQUENCE: 1389

Ser Leu Tyr Glu Ser Trp Thr Lys Lys
1               5

<210> SEQ ID NO 1390
<211> LENGTH: 10
<212> TYPE: PRT
<213> ORGANISM: Homo sapiens

<400> SEQUENCE: 1390

Lys Ser Leu Tyr Glu Ser Trp Thr Lys Lys
1               5                   10

<210> SEQ ID NO 1391
<211> LENGTH: 9
<212> TYPE: PRT
<213> ORGANISM: Homo sapiens
```

```
<400> SEQUENCE: 1391

Glu Gly Phe Glu Gly Lys Ser Leu Tyr
1               5

<210> SEQ ID NO 1392
<211> LENGTH: 10
<212> TYPE: PRT
<213> ORGANISM: Homo sapiens

<400> SEQUENCE: 1392

Asp Glu Gly Phe Glu Gly Lys Ser Leu Tyr
1               5                   10

<210> SEQ ID NO 1393
<211> LENGTH: 9
<212> TYPE: PRT
<213> ORGANISM: Homo sapiens

<400> SEQUENCE: 1393

Thr Lys Lys Ser Pro Ser Pro Glu Phe
1               5

<210> SEQ ID NO 1394
<211> LENGTH: 10
<212> TYPE: PRT
<213> ORGANISM: Homo sapiens

<400> SEQUENCE: 1394

Trp Thr Lys Lys Ser Pro Ser Pro Glu Phe
1               5                   10

<210> SEQ ID NO 1395
<211> LENGTH: 10
<212> TYPE: PRT
<213> ORGANISM: Homo sapiens

<400> SEQUENCE: 1395

Ser Leu Tyr Glu Ser Trp Thr Lys Lys Ser
1               5                   10

<210> SEQ ID NO 1396
<211> LENGTH: 8
<212> TYPE: PRT
<213> ORGANISM: Homo sapiens

<400> SEQUENCE: 1396

Trp Gly Glu Val Lys Arg Gln Ile
1               5

<210> SEQ ID NO 1397
<211> LENGTH: 9
<212> TYPE: PRT
<213> ORGANISM: Homo sapiens

<400> SEQUENCE: 1397

Ala Trp Gly Glu Val Lys Arg Gln Ile
1               5

<210> SEQ ID NO 1398
<211> LENGTH: 10
<212> TYPE: PRT
<213> ORGANISM: Homo sapiens

<400> SEQUENCE: 1398

Lys Ala Trp Gly Glu Val Lys Arg Gln Ile
```

<210> SEQ ID NO 1399
<211> LENGTH: 8
<212> TYPE: PRT
<213> ORGANISM: Homo sapiens

<400> SEQUENCE: 1399

Lys Ala Trp Gly Glu Val Lys Arg
1               5

<210> SEQ ID NO 1400
<211> LENGTH: 9
<212> TYPE: PRT
<213> ORGANISM: Homo sapiens

<400> SEQUENCE: 1400

Ser Lys Ala Trp Gly Glu Val Lys Arg
1               5

<210> SEQ ID NO 1401
<211> LENGTH: 9
<212> TYPE: PRT
<213> ORGANISM: Homo sapiens

<400> SEQUENCE: 1401

Gln Ile Tyr Val Ala Ala Phe Thr Val
1               5

<210> SEQ ID NO 1402
<211> LENGTH: 9
<212> TYPE: PRT
<213> ORGANISM: Homo sapiens

<400> SEQUENCE: 1402

Tyr Val Ala Ala Phe Thr Val Gln Ala
1               5

<210> SEQ ID NO 1403
<211> LENGTH: 9
<212> TYPE: PRT
<213> ORGANISM: Homo sapiens

<400> SEQUENCE: 1403

Trp Gly Glu Val Lys Arg Gln Ile Tyr
1               5

<210> SEQ ID NO 1404
<211> LENGTH: 9
<212> TYPE: PRT
<213> ORGANISM: Homo sapiens

<400> SEQUENCE: 1404

Glu Val Lys Arg Gln Ile Tyr Val Ala
1               5

<210> SEQ ID NO 1405
<211> LENGTH: 9
<212> TYPE: PRT
<213> ORGANISM: Homo sapiens

<400> SEQUENCE: 1405

Thr Val Gln Ala Ala Ala Glu Thr Leu
1               5

```
<210> SEQ ID NO 1406
<211> LENGTH: 10
<212> TYPE: PRT
<213> ORGANISM: Homo sapiens

<400> SEQUENCE: 1406

Phe Thr Val Gln Ala Ala Ala Glu Thr Leu
 1               5                   10

<210> SEQ ID NO 1407
<211> LENGTH: 9
<212> TYPE: PRT
<213> ORGANISM: Homo sapiens

<400> SEQUENCE: 1407

Lys Arg Gln Ile Tyr Val Ala Ala Phe
 1               5

<210> SEQ ID NO 1408
<211> LENGTH: 9
<212> TYPE: PRT
<213> ORGANISM: Homo sapiens

<400> SEQUENCE: 1408

Pro Ser Lys Ala Trp Gly Glu Val Lys
 1               5

<210> SEQ ID NO 1409
<211> LENGTH: 9
<212> TYPE: PRT
<213> ORGANISM: Homo sapiens

<400> SEQUENCE: 1409

Lys Ala Trp Gly Glu Val Lys Arg Gln
 1               5

<210> SEQ ID NO 1410
<211> LENGTH: 9
<212> TYPE: PRT
<213> ORGANISM: Homo sapiens

<400> SEQUENCE: 1410

Trp Lys Glu Phe Gly Leu Asp Ser Val
 1               5

<210> SEQ ID NO 1411
<211> LENGTH: 10
<212> TYPE: PRT
<213> ORGANISM: Homo sapiens

<400> SEQUENCE: 1411

Gln Trp Lys Glu Phe Gly Leu Asp Ser Val
 1               5                   10

<210> SEQ ID NO 1412
<211> LENGTH: 10
<212> TYPE: PRT
<213> ORGANISM: Homo sapiens

<400> SEQUENCE: 1412

Glu Phe Gly Leu Asp Ser Val Glu Leu Ala
 1               5                   10

<210> SEQ ID NO 1413
<211> LENGTH: 9
<212> TYPE: PRT
```

<213> ORGANISM: Homo sapiens

<400> SEQUENCE: 1413

Glu Leu Arg Gln Lys Glu Ser Lys Leu
1               5

<210> SEQ ID NO 1414
<211> LENGTH: 10
<212> TYPE: PRT
<213> ORGANISM: Homo sapiens

<400> SEQUENCE: 1414

Ala Glu Leu Arg Gln Lys Glu Ser Lys Leu
1               5                   10

<210> SEQ ID NO 1415
<211> LENGTH: 9
<212> TYPE: PRT
<213> ORGANISM: Homo sapiens

<400> SEQUENCE: 1415

Lys Leu Gln Glu Asn Arg Lys Ile Ile
1               5

<210> SEQ ID NO 1416
<211> LENGTH: 8
<212> TYPE: PRT
<213> ORGANISM: Homo sapiens

<400> SEQUENCE: 1416

Gln Leu Glu Glu Lys Thr Lys Leu
1               5

<210> SEQ ID NO 1417
<211> LENGTH: 9
<212> TYPE: PRT
<213> ORGANISM: Homo sapiens

<400> SEQUENCE: 1417

Asn Gln Leu Glu Glu Lys Thr Lys Leu
1               5

<210> SEQ ID NO 1418
<211> LENGTH: 9
<212> TYPE: PRT
<213> ORGANISM: Homo sapiens

<400> SEQUENCE: 1418

Leu Leu Glu Glu Ser Arg Asp Lys Val
1               5

<210> SEQ ID NO 1419
<211> LENGTH: 10
<212> TYPE: PRT
<213> ORGANISM: Homo sapiens

<400> SEQUENCE: 1419

Phe Leu Leu Glu Glu Ser Arg Asp Lys Val
1               5                   10

<210> SEQ ID NO 1420
<211> LENGTH: 9
<212> TYPE: PRT
<213> ORGANISM: Homo sapiens

<400> SEQUENCE: 1420

Glu Ser Arg Asp Lys Val Asn Gln Leu
1               5

<210> SEQ ID NO 1421
<211> LENGTH: 10
<212> TYPE: PRT
<213> ORGANISM: Homo sapiens

<400> SEQUENCE: 1421

Glu Glu Ser Arg Asp Lys Val Asn Gln Leu
1               5                   10

<210> SEQ ID NO 1422
<211> LENGTH: 9
<212> TYPE: PRT
<213> ORGANISM: Homo sapiens

<400> SEQUENCE: 1422

Glu Lys Glu Val His Asp Leu Glu Tyr
1               5

<210> SEQ ID NO 1423
<211> LENGTH: 10
<212> TYPE: PRT
<213> ORGANISM: Homo sapiens

<400> SEQUENCE: 1423

Arg Glu Lys Glu Val His Asp Leu Glu Tyr
1               5                   10

<210> SEQ ID NO 1424
<211> LENGTH: 9
<212> TYPE: PRT
<213> ORGANISM: Homo sapiens

<400> SEQUENCE: 1424

Asp Leu Glu Tyr Ser Tyr Cys His Tyr
1               5

<210> SEQ ID NO 1425
<211> LENGTH: 9
<212> TYPE: PRT
<213> ORGANISM: Homo sapiens

<400> SEQUENCE: 1425

Glu Val His Asp Leu Glu Tyr Ser Tyr
1               5

<210> SEQ ID NO 1426
<211> LENGTH: 10
<212> TYPE: PRT
<213> ORGANISM: Homo sapiens

<400> SEQUENCE: 1426

Glu Val His Asp Leu Glu Tyr Ser Tyr Cys
1               5                   10

<210> SEQ ID NO 1427
<211> LENGTH: 8
<212> TYPE: PRT
<213> ORGANISM: Homo sapiens

<400> SEQUENCE: 1427

Lys Leu Ser Ser Lys Arg Glu Leu
1               5

<210> SEQ ID NO 1428
<211> LENGTH: 8
<212> TYPE: PRT
<213> ORGANISM: Homo sapiens

<400> SEQUENCE: 1428

Glu Leu Lys Asn Thr Glu Tyr Phe
1               5

<210> SEQ ID NO 1429
<211> LENGTH: 9
<212> TYPE: PRT
<213> ORGANISM: Homo sapiens

<400> SEQUENCE: 1429

Arg Glu Leu Lys Asn Thr Glu Tyr Phe
1               5

<210> SEQ ID NO 1430
<211> LENGTH: 8
<212> TYPE: PRT
<213> ORGANISM: Homo sapiens

<400> SEQUENCE: 1430

Lys Arg Gly Gln Arg Pro Lys Leu
1               5

<210> SEQ ID NO 1431
<211> LENGTH: 10
<212> TYPE: PRT
<213> ORGANISM: Homo sapiens

<400> SEQUENCE: 1431

Leu Pro Lys Arg Gly Gln Arg Pro Lys Leu
1               5                   10

<210> SEQ ID NO 1432
<211> LENGTH: 9
<212> TYPE: PRT
<213> ORGANISM: Homo sapiens

<400> SEQUENCE: 1432

Leu Lys Asn Thr Glu Tyr Phe Thr Leu
1               5

<210> SEQ ID NO 1433
<211> LENGTH: 10
<212> TYPE: PRT
<213> ORGANISM: Homo sapiens

<400> SEQUENCE: 1433

Glu Leu Lys Asn Thr Glu Tyr Phe Thr Leu
1               5                   10

<210> SEQ ID NO 1434
<211> LENGTH: 9
<212> TYPE: PRT
<213> ORGANISM: Homo sapiens

<400> SEQUENCE: 1434

Lys Arg Glu Leu Lys Asn Thr Glu Tyr
1               5

<210> SEQ ID NO 1435

```
<211> LENGTH: 9
<212> TYPE: PRT
<213> ORGANISM: Homo sapiens

<400> SEQUENCE: 1435

Lys Leu Ser Ser Lys Arg Glu Leu Lys
 1               5

<210> SEQ ID NO 1436
<211> LENGTH: 9
<212> TYPE: PRT
<213> ORGANISM: Homo sapiens

<400> SEQUENCE: 1436

Gly Gln Arg Pro Lys Leu Ser Ser Lys
 1               5

<210> SEQ ID NO 1437
<211> LENGTH: 10
<212> TYPE: PRT
<213> ORGANISM: Homo sapiens

<400> SEQUENCE: 1437

Arg Gly Gln Arg Pro Lys Leu Ser Ser Lys
 1               5                  10

<210> SEQ ID NO 1438
<211> LENGTH: 9
<212> TYPE: PRT
<213> ORGANISM: Homo sapiens

<400> SEQUENCE: 1438

Arg Pro Lys Leu Ser Ser Lys Arg Glu
 1               5

<210> SEQ ID NO 1439
<211> LENGTH: 8
<212> TYPE: PRT
<213> ORGANISM: Homo sapiens

<400> SEQUENCE: 1439

Leu Glu Tyr Val Arg Glu Glu Leu
 1               5

<210> SEQ ID NO 1440
<211> LENGTH: 9
<212> TYPE: PRT
<213> ORGANISM: Homo sapiens

<400> SEQUENCE: 1440

Glu Leu Glu Tyr Val Arg Glu Glu Leu
 1               5

<210> SEQ ID NO 1441
<211> LENGTH: 10
<212> TYPE: PRT
<213> ORGANISM: Homo sapiens

<400> SEQUENCE: 1441

Asn Glu Leu Glu Tyr Val Arg Glu Glu Leu
 1               5                  10

<210> SEQ ID NO 1442
<211> LENGTH: 10
<212> TYPE: PRT
<213> ORGANISM: Homo sapiens
```

```
<400> SEQUENCE: 1442

Glu Leu Lys Gln Lys Arg Glu Asp Glu Val
1               5                   10

<210> SEQ ID NO 1443
<211> LENGTH: 9
<212> TYPE: PRT
<213> ORGANISM: Homo sapiens

<400> SEQUENCE: 1443

Tyr Val Arg Glu Glu Leu Lys Gln Lys
1               5

<210> SEQ ID NO 1444
<211> LENGTH: 9
<212> TYPE: PRT
<213> ORGANISM: Homo sapiens

<400> SEQUENCE: 1444

Gln Leu Asn Val Tyr Glu Ile Lys Val
1               5

<210> SEQ ID NO 1445
<211> LENGTH: 9
<212> TYPE: PRT
<213> ORGANISM: Homo sapiens

<400> SEQUENCE: 1445

Ser Lys Gln Leu Asn Val Tyr Glu Ile
1               5

<210> SEQ ID NO 1446
<211> LENGTH: 9
<212> TYPE: PRT
<213> ORGANISM: Homo sapiens

<400> SEQUENCE: 1446

Ala Glu Ser Lys Gln Leu Asn Val Tyr
1               5

<210> SEQ ID NO 1447
<211> LENGTH: 10
<212> TYPE: PRT
<213> ORGANISM: Homo sapiens

<400> SEQUENCE: 1447

Thr Ala Glu Ser Lys Gln Leu Asn Val Tyr
1               5                   10

<210> SEQ ID NO 1448
<211> LENGTH: 8
<212> TYPE: PRT
<213> ORGANISM: Homo sapiens

<400> SEQUENCE: 1448

Ile Lys Val Asn Lys Leu Glu Leu
1               5

<210> SEQ ID NO 1449
<211> LENGTH: 9
<212> TYPE: PRT
<213> ORGANISM: Homo sapiens

<400> SEQUENCE: 1449
```

```
Glu Ile Lys Val Asn Lys Leu Glu Leu
 1               5

<210> SEQ ID NO 1450
<211> LENGTH: 10
<212> TYPE: PRT
<213> ORGANISM: Homo sapiens

<400> SEQUENCE: 1450

Tyr Glu Ile Lys Val Asn Lys Leu Glu Leu
 1               5                  10

<210> SEQ ID NO 1451
<211> LENGTH: 9
<212> TYPE: PRT
<213> ORGANISM: Homo sapiens

<400> SEQUENCE: 1451

Lys Leu Glu Leu Glu Leu Glu Ser Ala
 1               5

<210> SEQ ID NO 1452
<211> LENGTH: 9
<212> TYPE: PRT
<213> ORGANISM: Homo sapiens

<400> SEQUENCE: 1452

Val Tyr Glu Ile Lys Val Asn Lys Leu
 1               5

<210> SEQ ID NO 1453
<211> LENGTH: 10
<212> TYPE: PRT
<213> ORGANISM: Homo sapiens

<400> SEQUENCE: 1453

Asn Val Tyr Glu Ile Lys Val Asn Lys Leu
 1               5                  10

<210> SEQ ID NO 1454
<211> LENGTH: 9
<212> TYPE: PRT
<213> ORGANISM: Homo sapiens

<400> SEQUENCE: 1454

Glu Leu Glu Ser Ala Lys Gln Lys Phe
 1               5

<210> SEQ ID NO 1455
<211> LENGTH: 9
<212> TYPE: PRT
<213> ORGANISM: Homo sapiens

<400> SEQUENCE: 1455

Lys Leu Glu Leu Glu Leu Glu Ser Ala
 1               5

<210> SEQ ID NO 1456
<211> LENGTH: 9
<212> TYPE: PRT
<213> ORGANISM: Homo sapiens

<400> SEQUENCE: 1456

Glu Leu Glu Ser Ala Lys Gln Lys Phe
 1               5
```

```
<210> SEQ ID NO 1457
<211> LENGTH: 8
<212> TYPE: PRT
<213> ORGANISM: Homo sapiens

<400> SEQUENCE: 1457

Lys Glu Lys Leu Lys Arg Glu Ala
1               5

<210> SEQ ID NO 1458
<211> LENGTH: 9
<212> TYPE: PRT
<213> ORGANISM: Homo sapiens

<400> SEQUENCE: 1458

Glu Ala Lys Glu Asn Thr Ala Thr Leu
1               5

<210> SEQ ID NO 1459
<211> LENGTH: 10
<212> TYPE: PRT
<213> ORGANISM: Homo sapiens

<400> SEQUENCE: 1459

Arg Glu Ala Lys Glu Asn Thr Ala Thr Leu
1               5                   10

<210> SEQ ID NO 1460
<211> LENGTH: 10
<212> TYPE: PRT
<213> ORGANISM: Homo sapiens

<400> SEQUENCE: 1460

Lys Leu Lys Arg Glu Ala Lys Glu Asn Thr
1               5                   10

<210> SEQ ID NO 1461
<211> LENGTH: 8
<212> TYPE: PRT
<213> ORGANISM: Homo sapiens

<400> SEQUENCE: 1461

Glu Ala Glu Lys Ile Lys Lys Trp
1               5

<210> SEQ ID NO 1462
<211> LENGTH: 9
<212> TYPE: PRT
<213> ORGANISM: Homo sapiens

<400> SEQUENCE: 1462

Gly Leu Ser Arg Val Tyr Ser Lys Leu
1               5

<210> SEQ ID NO 1463
<211> LENGTH: 10
<212> TYPE: PRT
<213> ORGANISM: Homo sapiens

<400> SEQUENCE: 1463

Glu Gly Leu Ser Arg Val Tyr Ser Lys Leu
1               5                   10

<210> SEQ ID NO 1464
<211> LENGTH: 9
```

<212> TYPE: PRT
<213> ORGANISM: Homo sapiens

<400> SEQUENCE: 1464

Lys Leu Tyr Lys Glu Ala Glu Lys Ile
1               5

<210> SEQ ID NO 1465
<211> LENGTH: 9
<212> TYPE: PRT
<213> ORGANISM: Homo sapiens

<400> SEQUENCE: 1465

Asn Ser Glu Gly Leu Ser Arg Val Tyr
1               5

<210> SEQ ID NO 1466
<211> LENGTH: 10
<212> TYPE: PRT
<213> ORGANISM: Homo sapiens

<400> SEQUENCE: 1466

Glu Asn Ser Glu Gly Leu Ser Arg Val Tyr
1               5                   10

<210> SEQ ID NO 1467
<211> LENGTH: 9
<212> TYPE: PRT
<213> ORGANISM: Homo sapiens

<400> SEQUENCE: 1467

Leu Ser Arg Val Tyr Ser Lys Leu Tyr
1               5

<210> SEQ ID NO 1468
<211> LENGTH: 10
<212> TYPE: PRT
<213> ORGANISM: Homo sapiens

<400> SEQUENCE: 1468

Gly Leu Ser Arg Val Tyr Ser Lys Leu Tyr
1               5                   10

<210> SEQ ID NO 1469
<211> LENGTH: 10
<212> TYPE: PRT
<213> ORGANISM: Homo sapiens

<400> SEQUENCE: 1469

Leu Glu Asn Ser Glu Gly Leu Ser Arg Val
1               5                   10

<210> SEQ ID NO 1470
<211> LENGTH: 10
<212> TYPE: PRT
<213> ORGANISM: Homo sapiens

<400> SEQUENCE: 1470

Lys Leu Tyr Lys Glu Ala Glu Lys Ile Lys
1               5                   10

<210> SEQ ID NO 1471
<211> LENGTH: 8
<212> TYPE: PRT
<213> ORGANISM: Homo sapiens

```
<400> SEQUENCE: 1471

Arg Glu Asp Arg Trp Ala Val Ile
1               5

<210> SEQ ID NO 1472
<211> LENGTH: 9
<212> TYPE: PRT
<213> ORGANISM: Homo sapiens

<400> SEQUENCE: 1472

Met Arg Glu Asp Arg Trp Ala Val Ile
1               5

<210> SEQ ID NO 1473
<211> LENGTH: 10
<212> TYPE: PRT
<213> ORGANISM: Homo sapiens

<400> SEQUENCE: 1473

Lys Met Arg Glu Asp Arg Trp Ala Val Ile
1               5                   10

<210> SEQ ID NO 1474
<211> LENGTH: 9
<212> TYPE: PRT
<213> ORGANISM: Homo sapiens

<400> SEQUENCE: 1474

Lys Met Arg Glu Asp Arg Trp Ala Val
1               5

<210> SEQ ID NO 1475
<211> LENGTH: 9
<212> TYPE: PRT
<213> ORGANISM: Homo sapiens

<400> SEQUENCE: 1475

Thr Thr Pro Gly Ser Thr Leu Lys Phe
1               5

<210> SEQ ID NO 1476
<211> LENGTH: 10
<212> TYPE: PRT
<213> ORGANISM: Homo sapiens

<400> SEQUENCE: 1476

Leu Thr Thr Pro Gly Ser Thr Leu Lys Phe
1               5                   10

<210> SEQ ID NO 1477
<211> LENGTH: 8
<212> TYPE: PRT
<213> ORGANISM: Homo sapiens

<400> SEQUENCE: 1477

Gly Ser Thr Leu Lys Gly Ala Ile
1               5

<210> SEQ ID NO 1478
<211> LENGTH: 9
<212> TYPE: PRT
<213> ORGANISM: Homo sapiens

<400> SEQUENCE: 1478

Ile Arg Lys Met Arg Glu Asp Arg Trp
```

```
<210> SEQ ID NO 1479
<211> LENGTH: 8
<212> TYPE: PRT
<213> ORGANISM: Homo sapiens

<400> SEQUENCE: 1479

Arg Leu Glu Met His Phe Lys Leu
1               5

<210> SEQ ID NO 1480
<211> LENGTH: 9
<212> TYPE: PRT
<213> ORGANISM: Homo sapiens

<400> SEQUENCE: 1480

Ser Arg Leu Glu Met His Phe Lys Leu
1               5

<210> SEQ ID NO 1481
<211> LENGTH: 9
<212> TYPE: PRT
<213> ORGANISM: Homo sapiens

<400> SEQUENCE: 1481

Lys Leu Lys Glu Asp Tyr Glu Lys Ile
1               5

<210> SEQ ID NO 1482
<211> LENGTH: 9
<212> TYPE: PRT
<213> ORGANISM: Homo sapiens

<400> SEQUENCE: 1482

Lys Ile Gln His Leu Glu Gln Glu Tyr
1               5

<210> SEQ ID NO 1483
<211> LENGTH: 10
<212> TYPE: PRT
<213> ORGANISM: Homo sapiens

<400> SEQUENCE: 1483

Glu Lys Ile Gln His Leu Glu Gln Glu Tyr
1               5                   10

<210> SEQ ID NO 1484
<211> LENGTH: 9
<212> TYPE: PRT
<213> ORGANISM: Homo sapiens

<400> SEQUENCE: 1484

Glu Asn Ser Arg Leu Glu Met His Phe
1               5

<210> SEQ ID NO 1485
<211> LENGTH: 10
<212> TYPE: PRT
<213> ORGANISM: Homo sapiens

<400> SEQUENCE: 1485

Arg Leu Glu Met His Phe Lys Leu Lys Glu
1               5                   10
```

```
<210> SEQ ID NO 1486
<211> LENGTH: 8
<212> TYPE: PRT
<213> ORGANISM: Homo sapiens

<400> SEQUENCE: 1486

Leu Glu Asp Ile Lys Val Ser Leu
 1               5

<210> SEQ ID NO 1487
<211> LENGTH: 9
<212> TYPE: PRT
<213> ORGANISM: Homo sapiens

<400> SEQUENCE: 1487

Glu Leu Glu Asp Ile Lys Val Ser Leu
 1               5

<210> SEQ ID NO 1488
<211> LENGTH: 10
<212> TYPE: PRT
<213> ORGANISM: Homo sapiens

<400> SEQUENCE: 1488

Lys Glu Leu Glu Asp Ile Lys Val Ser Leu
 1               5                  10

<210> SEQ ID NO 1489
<211> LENGTH: 8
<212> TYPE: PRT
<213> ORGANISM: Homo sapiens

<400> SEQUENCE: 1489

Leu Thr Lys Glu Leu Glu Asp Ile
 1               5

<210> SEQ ID NO 1490
<211> LENGTH: 9
<212> TYPE: PRT
<213> ORGANISM: Homo sapiens

<400> SEQUENCE: 1490

His Leu Thr Lys Glu Leu Glu Asp Ile
 1               5

<210> SEQ ID NO 1491
<211> LENGTH: 9
<212> TYPE: PRT
<213> ORGANISM: Homo sapiens

<400> SEQUENCE: 1491

Ser Leu Gln Arg Ser Val Ser Thr Gln
 1               5

<210> SEQ ID NO 1492
<211> LENGTH: 9
<212> TYPE: PRT
<213> ORGANISM: Homo sapiens

<400> SEQUENCE: 1492

Thr Lys Glu Leu Glu Asp Ile Lys Val
 1               5

<210> SEQ ID NO 1493
<211> LENGTH: 10
<212> TYPE: PRT
```

<213> ORGANISM: Homo sapiens

<400> SEQUENCE: 1493

Leu Thr Lys Glu Leu Glu Asp Ile Lys Val
1               5                   10

<210> SEQ ID NO 1494
<211> LENGTH: 10
<212> TYPE: PRT
<213> ORGANISM: Homo sapiens

<400> SEQUENCE: 1494

Asp Ile Lys Val Ser Leu Gln Arg Ser Val
1               5                   10

<210> SEQ ID NO 1495
<211> LENGTH: 8
<212> TYPE: PRT
<213> ORGANISM: Homo sapiens

<400> SEQUENCE: 1495

Lys Met Lys Asp Leu Thr Phe Leu
1               5

<210> SEQ ID NO 1496
<211> LENGTH: 9
<212> TYPE: PRT
<213> ORGANISM: Homo sapiens

<400> SEQUENCE: 1496

Asn Lys Met Lys Asp Leu Thr Phe Leu
1               5

<210> SEQ ID NO 1497
<211> LENGTH: 10
<212> TYPE: PRT
<213> ORGANISM: Homo sapiens

<400> SEQUENCE: 1497

Glu Asn Lys Met Lys Asp Leu Thr Phe Leu
1               5                   10

<210> SEQ ID NO 1498
<211> LENGTH: 9
<212> TYPE: PRT
<213> ORGANISM: Homo sapiens

<400> SEQUENCE: 1498

Leu Leu Glu Glu Ser Arg Asp Lys Val
1               5

<210> SEQ ID NO 1499
<211> LENGTH: 10
<212> TYPE: PRT
<213> ORGANISM: Homo sapiens

<400> SEQUENCE: 1499

Phe Leu Leu Glu Glu Ser Arg Asp Lys Val
1               5                   10

<210> SEQ ID NO 1500
<211> LENGTH: 9
<212> TYPE: PRT
<213> ORGANISM: Homo sapiens

<400> SEQUENCE: 1500

```
Glu Ser Arg Asp Lys Val Asn Gln Leu
 1               5
```

<210> SEQ ID NO 1501
<211> LENGTH: 10
<212> TYPE: PRT
<213> ORGANISM: Homo sapiens

<400> SEQUENCE: 1501

```
Glu Glu Ser Arg Asp Lys Val Asn Gln Leu
 1               5                   10
```

<210> SEQ ID NO 1502
<211> LENGTH: 9
<212> TYPE: PRT
<213> ORGANISM: Homo sapiens

<400> SEQUENCE: 1502

```
Glu Lys Glu Asn Lys Met Lys Asp Leu
 1               5
```

<210> SEQ ID NO 1503
<211> LENGTH: 10
<212> TYPE: PRT
<213> ORGANISM: Homo sapiens

<400> SEQUENCE: 1503

```
Thr Glu Lys Glu Asn Lys Met Lys Asp Leu
 1               5                   10
```

<210> SEQ ID NO 1504
<211> LENGTH: 9
<212> TYPE: PRT
<213> ORGANISM: Homo sapiens

<400> SEQUENCE: 1504

```
Glu Asn Lys Met Lys Asp Leu Thr Phe
 1               5
```

<210> SEQ ID NO 1505
<211> LENGTH: 8
<212> TYPE: PRT
<213> ORGANISM: Homo sapiens

<400> SEQUENCE: 1505

```
Ile Glu Lys Met Ile Thr Ala Phe
 1               5
```

<210> SEQ ID NO 1506
<211> LENGTH: 9
<212> TYPE: PRT
<213> ORGANISM: Homo sapiens

<400> SEQUENCE: 1506

```
Asn Ile Glu Lys Met Ile Thr Ala Phe
 1               5
```

<210> SEQ ID NO 1507
<211> LENGTH: 10
<212> TYPE: PRT
<213> ORGANISM: Homo sapiens

<400> SEQUENCE: 1507

```
Ser Asn Ile Glu Lys Met Ile Thr Ala Phe
 1               5                   10
```

<210> SEQ ID NO 1508
<211> LENGTH: 8
<212> TYPE: PRT
<213> ORGANISM: Homo sapiens

<400> SEQUENCE: 1508

Thr Ala Phe Glu Glu Leu Arg Val
1               5

<210> SEQ ID NO 1509
<211> LENGTH: 9
<212> TYPE: PRT
<213> ORGANISM: Homo sapiens

<400> SEQUENCE: 1509

Ile Thr Ala Phe Glu Glu Leu Arg Val
1               5

<210> SEQ ID NO 1510
<211> LENGTH: 10
<212> TYPE: PRT
<213> ORGANISM: Homo sapiens

<400> SEQUENCE: 1510

Met Ile Thr Ala Phe Glu Glu Leu Arg Val
1               5                   10

<210> SEQ ID NO 1511
<211> LENGTH: 9
<212> TYPE: PRT
<213> ORGANISM: Homo sapiens

<400> SEQUENCE: 1511

Lys Met Ile Thr Ala Phe Glu Glu Leu
1               5

<210> SEQ ID NO 1512
<211> LENGTH: 10
<212> TYPE: PRT
<213> ORGANISM: Homo sapiens

<400> SEQUENCE: 1512

Glu Lys Met Ile Thr Ala Phe Glu Glu Leu
1               5                   10

<210> SEQ ID NO 1513
<211> LENGTH: 9
<212> TYPE: PRT
<213> ORGANISM: Homo sapiens

<400> SEQUENCE: 1513

Glu Leu Arg Val Gln Ala Glu Asn Ser
1               5

<210> SEQ ID NO 1514
<211> LENGTH: 10
<212> TYPE: PRT
<213> ORGANISM: Homo sapiens

<400> SEQUENCE: 1514

Asp Leu Asn Ser Asn Ile Glu Lys Met Ile
1               5                   10

<210> SEQ ID NO 1515

```
<211> LENGTH: 8
<212> TYPE: PRT
<213> ORGANISM: Homo sapiens

<400> SEQUENCE: 1515

Trp Thr Ser Ala Lys Asn Thr Leu
 1               5

<210> SEQ ID NO 1516
<211> LENGTH: 9
<212> TYPE: PRT
<213> ORGANISM: Homo sapiens

<400> SEQUENCE: 1516

Thr Pro Leu Pro Lys Ala Tyr Thr Val
 1               5

<210> SEQ ID NO 1517
<211> LENGTH: 10
<212> TYPE: PRT
<213> ORGANISM: Homo sapiens

<400> SEQUENCE: 1517

Ser Thr Pro Leu Pro Lys Ala Tyr Thr Val
 1               5                  10

<210> SEQ ID NO 1518
<211> LENGTH: 9
<212> TYPE: PRT
<213> ORGANISM: Homo sapiens

<400> SEQUENCE: 1518

Leu Ser Thr Pro Leu Pro Lys Ala Tyr
 1               5

<210> SEQ ID NO 1519
<211> LENGTH: 10
<212> TYPE: PRT
<213> ORGANISM: Homo sapiens

<400> SEQUENCE: 1519

Thr Leu Ser Thr Pro Leu Pro Lys Ala Tyr
 1               5                  10

<210> SEQ ID NO 1520
<211> LENGTH: 9
<212> TYPE: PRT
<213> ORGANISM: Homo sapiens

<400> SEQUENCE: 1520

Asn Thr Leu Ser Thr Pro Leu Pro Lys
 1               5

<210> SEQ ID NO 1521
<211> LENGTH: 10
<212> TYPE: PRT
<213> ORGANISM: Homo sapiens

<400> SEQUENCE: 1521

Lys Asn Thr Leu Ser Thr Pro Leu Pro Lys
 1               5                  10

<210> SEQ ID NO 1522
<211> LENGTH: 8
<212> TYPE: PRT
<213> ORGANISM: Homo sapiens
```

<400> SEQUENCE: 1522

Ile Ser Lys Asp Lys Arg Asp Tyr
1               5

<210> SEQ ID NO 1523
<211> LENGTH: 10
<212> TYPE: PRT
<213> ORGANISM: Homo sapiens

<400> SEQUENCE: 1523

His Gly Ile Ser Lys Asp Lys Arg Asp Tyr
1               5                   10

<210> SEQ ID NO 1524
<211> LENGTH: 9
<212> TYPE: PRT
<213> ORGANISM: Homo sapiens

<400> SEQUENCE: 1524

Lys Arg Asp Tyr Leu Trp Thr Ser Ala
1               5

<210> SEQ ID NO 1525
<211> LENGTH: 10
<212> TYPE: PRT
<213> ORGANISM: Homo sapiens

<400> SEQUENCE: 1525

Ser Lys Asp Lys Arg Asp Tyr Leu Trp Thr
1               5                   10

<210> SEQ ID NO 1526
<211> LENGTH: 8
<212> TYPE: PRT
<213> ORGANISM: Homo sapiens

<400> SEQUENCE: 1526

Glu Asn Lys Met Lys Asp Leu Thr
1               5

<210> SEQ ID NO 1527
<211> LENGTH: 9
<212> TYPE: PRT
<213> ORGANISM: Homo sapiens

<400> SEQUENCE: 1527

Glu Ile Asn Asp Lys Glu Lys Gln Val
1               5

<210> SEQ ID NO 1528
<211> LENGTH: 9
<212> TYPE: PRT
<213> ORGANISM: Homo sapiens

<400> SEQUENCE: 1528

Gln Ile Thr Glu Lys Glu Asn Lys Met
1               5

<210> SEQ ID NO 1529
<211> LENGTH: 9
<212> TYPE: PRT
<213> ORGANISM: Homo sapiens

<400> SEQUENCE: 1529

Ser Leu Leu Leu Ile Gln Ile Thr Glu
1               5

<210> SEQ ID NO 1530
<211> LENGTH: 8
<212> TYPE: PRT
<213> ORGANISM: Homo sapiens

<400> SEQUENCE: 1530

Phe Glu Lys Ile Ala Glu Glu Leu
1               5

<210> SEQ ID NO 1531
<211> LENGTH: 9
<212> TYPE: PRT
<213> ORGANISM: Homo sapiens

<400> SEQUENCE: 1531

Gln Phe Glu Lys Ile Ala Glu Glu Leu
1               5

<210> SEQ ID NO 1532
<211> LENGTH: 10
<212> TYPE: PRT
<213> ORGANISM: Homo sapiens

<400> SEQUENCE: 1532

Lys Gln Phe Glu Lys Ile Ala Glu Glu Leu
1               5                   10

<210> SEQ ID NO 1533
<211> LENGTH: 8
<212> TYPE: PRT
<213> ORGANISM: Homo sapiens

<400> SEQUENCE: 1533

Asp Asn Lys Gln Phe Glu Lys Ile
1               5

<210> SEQ ID NO 1534
<211> LENGTH: 9
<212> TYPE: PRT
<213> ORGANISM: Homo sapiens

<400> SEQUENCE: 1534

Tyr Asp Asn Lys Gln Phe Glu Lys Ile
1               5

<210> SEQ ID NO 1535
<211> LENGTH: 10
<212> TYPE: PRT
<213> ORGANISM: Homo sapiens

<400> SEQUENCE: 1535

Leu Tyr Asp Asn Lys Gln Phe Glu Lys Ile
1               5                   10

<210> SEQ ID NO 1536
<211> LENGTH: 8
<212> TYPE: PRT
<213> ORGANISM: Homo sapiens

<400> SEQUENCE: 1536

Leu Gly Glu Lys Glu Thr Leu Leu
1               5

<210> SEQ ID NO 1537
<211> LENGTH: 9
<212> TYPE: PRT
<213> ORGANISM: Homo sapiens

<400> SEQUENCE: 1537

Val Leu Gly Glu Lys Glu Thr Leu Leu
1               5

<210> SEQ ID NO 1538
<211> LENGTH: 10
<212> TYPE: PRT
<213> ORGANISM: Homo sapiens

<400> SEQUENCE: 1538

Lys Val Leu Gly Glu Lys Glu Thr Leu Leu
1               5                   10

<210> SEQ ID NO 1539
<211> LENGTH: 9
<212> TYPE: PRT
<213> ORGANISM: Homo sapiens

<400> SEQUENCE: 1539

Leu Leu Arg Thr Glu Gln Gln Arg Leu
1               5

<210> SEQ ID NO 1540
<211> LENGTH: 10
<212> TYPE: PRT
<213> ORGANISM: Homo sapiens

<400> SEQUENCE: 1540

Glu Leu Leu Arg Thr Glu Gln Gln Arg Leu
1               5                   10

<210> SEQ ID NO 1541
<211> LENGTH: 9
<212> TYPE: PRT
<213> ORGANISM: Homo sapiens

<400> SEQUENCE: 1541

Thr Glu Gln Gln Arg Leu Glu Asn Tyr
1               5

<210> SEQ ID NO 1542
<211> LENGTH: 10
<212> TYPE: PRT
<213> ORGANISM: Homo sapiens

<400> SEQUENCE: 1542

Arg Thr Glu Gln Gln Arg Leu Glu Asn Tyr
1               5                   10

<210> SEQ ID NO 1543
<211> LENGTH: 9
<212> TYPE: PRT
<213> ORGANISM: Homo sapiens

<400> SEQUENCE: 1543

Glu Asp Gln Leu Ile Ile Leu Thr Met
1               5

<210> SEQ ID NO 1544
<211> LENGTH: 10

```
<212> TYPE: PRT
<213> ORGANISM: Homo sapiens

<400> SEQUENCE: 1544

Arg Leu Glu Asn Tyr Glu Asp Gln Leu Ile
 1               5                  10

<210> SEQ ID NO 1545
<211> LENGTH: 8
<212> TYPE: PRT
<213> ORGANISM: Homo sapiens

<400> SEQUENCE: 1545

Lys Ala Arg Ala Ala His Ser Phe
 1               5

<210> SEQ ID NO 1546
<211> LENGTH: 9
<212> TYPE: PRT
<213> ORGANISM: Homo sapiens

<400> SEQUENCE: 1546

Val Val Thr Glu Phe Glu Thr Thr Val
 1               5

<210> SEQ ID NO 1547
<211> LENGTH: 10
<212> TYPE: PRT
<213> ORGANISM: Homo sapiens

<400> SEQUENCE: 1547

Phe Val Val Thr Glu Phe Glu Thr Thr Val
 1               5                  10

<210> SEQ ID NO 1548
<211> LENGTH: 9
<212> TYPE: PRT
<213> ORGANISM: Homo sapiens

<400> SEQUENCE: 1548

Val Thr Glu Phe Glu Thr Thr Val Cys
 1               5

<210> SEQ ID NO 1549
<211> LENGTH: 10
<212> TYPE: PRT
<213> ORGANISM: Homo sapiens

<400> SEQUENCE: 1549

Val Val Thr Glu Phe Glu Thr Thr Val Cys
 1               5                  10

<210> SEQ ID NO 1550
<211> LENGTH: 9
<212> TYPE: PRT
<213> ORGANISM: Homo sapiens

<400> SEQUENCE: 1550

Asp Leu Gln Ile Ala Thr Asn Thr Ile
 1               5

<210> SEQ ID NO 1551
<211> LENGTH: 9
<212> TYPE: PRT
<213> ORGANISM: Homo sapiens
```

-continued

```
<400> SEQUENCE: 1551

Ile Ala Thr Asn Thr Ile Cys Gln Leu
1               5

<210> SEQ ID NO 1552
<211> LENGTH: 10
<212> TYPE: PRT
<213> ORGANISM: Homo sapiens

<400> SEQUENCE: 1552

Gln Ile Ala Thr Asn Thr Ile Cys Gln Leu
1               5                   10

<210> SEQ ID NO 1553
<211> LENGTH: 9
<212> TYPE: PRT
<213> ORGANISM: Homo sapiens

<400> SEQUENCE: 1553

Val Met Thr Lys Leu Gly Phe Lys Tyr
1               5

<210> SEQ ID NO 1554
<211> LENGTH: 9
<212> TYPE: PRT
<213> ORGANISM: Homo sapiens

<400> SEQUENCE: 1554

Leu Asn Tyr Glu Val Met Thr Lys Leu
1               5

<210> SEQ ID NO 1555
<211> LENGTH: 10
<212> TYPE: PRT
<213> ORGANISM: Homo sapiens

<400> SEQUENCE: 1555

Lys Leu Asn Tyr Glu Val Met Thr Lys Leu
1               5                   10

<210> SEQ ID NO 1556
<211> LENGTH: 9
<212> TYPE: PRT
<213> ORGANISM: Homo sapiens

<400> SEQUENCE: 1556

Thr Leu Pro Pro Phe Met Arg Ser Lys
1               5

<210> SEQ ID NO 1557
<211> LENGTH: 9
<212> TYPE: PRT
<213> ORGANISM: Homo sapiens

<400> SEQUENCE: 1557

Lys Ile Met Pro Lys Lys Pro Ala Glu
1               5

<210> SEQ ID NO 1558
<211> LENGTH: 10
<212> TYPE: PRT
<213> ORGANISM: Homo sapiens

<400> SEQUENCE: 1558

Ser Leu Gln Arg Ile Phe Pro Lys Ile Met
```

```
                1               5                    10
```

<210> SEQ ID NO 1559
<211> LENGTH: 9
<212> TYPE: PRT
<213> ORGANISM: Homo sapiens

<400> SEQUENCE: 1559

```
Tyr Ile Lys Ser Tyr Leu Glu Gln Ala
 1               5
```

<210> SEQ ID NO 1560
<211> LENGTH: 9
<212> TYPE: PRT
<213> ORGANISM: Homo sapiens

<400> SEQUENCE: 1560

```
Ser Phe Gln Asp Tyr Ile Lys Ser Tyr
 1               5
```

<210> SEQ ID NO 1561
<211> LENGTH: 10
<212> TYPE: PRT
<213> ORGANISM: Homo sapiens

<400> SEQUENCE: 1561

```
Asp Ser Phe Gln Asp Tyr Ile Lys Ser Tyr
 1               5                   10
```

<210> SEQ ID NO 1562
<211> LENGTH: 8
<212> TYPE: PRT
<213> ORGANISM: Homo sapiens

<400> SEQUENCE: 1562

```
Leu Pro Glu Glu Lys Gln Pro Leu
 1               5
```

<210> SEQ ID NO 1563
<211> LENGTH: 9
<212> TYPE: PRT
<213> ORGANISM: Homo sapiens

<400> SEQUENCE: 1563

```
Gln Leu Pro Glu Glu Lys Gln Pro Leu
 1               5
```

<210> SEQ ID NO 1564
<211> LENGTH: 10
<212> TYPE: PRT
<213> ORGANISM: Homo sapiens

<400> SEQUENCE: 1564

```
Lys Gln Leu Pro Glu Glu Lys Gln Pro Leu
 1               5                   10
```

<210> SEQ ID NO 1565
<211> LENGTH: 9
<212> TYPE: PRT
<213> ORGANISM: Homo sapiens

<400> SEQUENCE: 1565

```
Leu Pro Glu Glu Lys Gln Pro Leu Leu
 1               5
```

-continued

<210> SEQ ID NO 1566
<211> LENGTH: 10
<212> TYPE: PRT
<213> ORGANISM: Homo sapiens

<400> SEQUENCE: 1566

Gln Leu Pro Glu Glu Lys Gln Pro Leu Leu
1               5                   10

<210> SEQ ID NO 1567
<211> LENGTH: 9
<212> TYPE: PRT
<213> ORGANISM: Homo sapiens

<400> SEQUENCE: 1567

Ser Leu Leu Cys Arg His Lys Arg Lys
1               5

<210> SEQ ID NO 1568
<211> LENGTH: 91
<212> TYPE: PRT
<213> ORGANISM: Homo sapiens

<400> SEQUENCE: 1568

Glu Val Pro Gln Leu Thr Asp Leu Ser Phe Val Asp Ile Thr Asp Ser
1               5                   10                  15

Ser Ile Gly Leu Arg Trp Thr Pro Leu Asn Ser Ser Thr Ile Ile Gly
            20                  25                  30

Tyr Arg Ile Thr Val Val Ala Ala Gly Glu Gly Ile Pro Ile Phe Glu
        35                  40                  45

Asp Phe Val Asp Ser Ser Val Gly Tyr Tyr Thr Val Thr Gly Leu Glu
    50                  55                  60

Pro Gly Ile Asp Tyr Asp Ile Ser Val Ile Thr Leu Ile Asn Gly Gly
65                  70                  75                  80

Glu Ser Ala Pro Thr Thr Leu Thr Gln Gln Thr
            85                  90

<210> SEQ ID NO 1569
<211> LENGTH: 147
<212> TYPE: PRT
<213> ORGANISM: Homo sapiens

<400> SEQUENCE: 1569

Cys Thr Phe Asp Asn Leu Ser Pro Gly Leu Glu Tyr Asn Val Ser Val
1               5                   10                  15

Tyr Thr Val Lys Asp Asp Lys Glu Ser Val Pro Ile Ser Asp Thr Ile
            20                  25                  30

Ile Pro Glu Val Pro Gln Leu Thr Asp Leu Ser Phe Val Asp Ile Thr
        35                  40                  45

Asp Ser Ser Ile Gly Leu Arg Trp Thr Pro Leu Asn Ser Ser Thr Ile
    50                  55                  60

Ile Gly Tyr Arg Ile Thr Val Val Ala Ala Gly Glu Gly Ile Pro Ile
65                  70                  75                  80

Phe Glu Asp Phe Val Asp Ser Ser Val Gly Tyr Tyr Thr Val Thr Gly
            85                  90                  95

Leu Glu Pro Gly Ile Asp Tyr Asp Ile Ser Val Ile Thr Leu Ile Asn
            100                 105                 110

Gly Gly Glu Ser Ala Pro Thr Thr Leu Thr Gln Gln Thr Ala Val Pro
        115                 120                 125

Pro Pro Thr Asp Leu Arg Phe Thr Asn Ile Gly Pro Asp Thr Met Arg

Val Thr Trp
145

<210> SEQ ID NO 1570
<211> LENGTH: 2823
<212> TYPE: DNA
<213> ORGANISM: Homo sapiens

<400> SEQUENCE: 1570

```
ctgcactttt gataacctga gtcccggcct ggagtacaat gtcagtgttt acactgtcaa      60
ggatgacaag gaaagtgtcc ctatctctga taccatcatc ccaggtaata gaaaataagc     120
tgctatcctg agagtgacat tccaataaga gtggggatta gcatcttaat ccccagatgc     180
ttaagggtgt caactatatt tgggatttaa ttccgatctc ccagctgcac tttccaaaac     240
caagaagtca agcagcgat ttggacaaaa tgcttgctgt taacactgct ttactgtctg     300
tgcttcactg ggatgctgtg tgttgcagcg agtatgtaat ggagtggcag ccatggcttt     360
aactctgtat tgtctgctca catggaagta tgactaaaac actgtcacgt gtctgtactc     420
agtactgata ggctcaaagt aatatggtaa atgcatccca tcagtacatt tctgcccgat     480
tttacaatcc atatcaattt ccaacagctg cctatttcat cttgcagttt caaatccttc     540
ttttgaaaa ttggattta aaaaaagtt aagtaaagt cacaccttca gggttgttct     600
ttcttgtggc cttgaaagac aacattgcaa aggcctgtcc taaggatagg cttgtttgtc     660
cattgggtta acataatg aaagcattgg acagatcgtg tccccctttg gactcttcag     720
tagaatgctt ttactaacgc taattacatg ttttgattat gaatgaacct aaaaatagtgg    780
caatggcctt aacctaggcc tgtctttcct cagcctgaat gtgcttttga atggcacatt     840
tcacaccata cattcataat gcattagcgt tatggccatg atgttgtcat gagttttgta     900
tgggagaaaa aaaatcaatt tatcacccat ttattatttt ttccggttgt tcatgcaagc     960
ttatttttcta ctaaaacagt tttggaatta ttaaaagcat tgctgatact tacttcagat    1020
attatgtcta ggctctaaga atggtttcga catcctaaac agccatatga tttttaggaa    1080
tctgaacagt tcaaattgta ccctttaagg atgttttcaa aatgtaaaaa atatatatat    1140
atatatatat tccctaaaag aatattcctg tttattcttc tagggaagca aactgttcat    1200
gatgcttagg aagtctttc agagaattta aaacagattg catattacca tcattgcttt    1260
aacattccac caatttttact actagtaacc tgatatacac tgctttattt tttcctcttt    1320
ttttcctct atttttccttt tgcctccccc tcccttgct ttgtaactca atagaggtgc    1380
cccaactcac tgacctaagc tttgttgata taaccgattc aagcatcggc ctgaggtgga    1440
ccccgctaaa ctcttccacc attattgggt accgcatcac agtagttgcg gcaggagaag    1500
gtatccctat ttttgaagat tttgtggact cctcagtagg atactacaca gtcacgggc    1560
tggagccggg cattgactat gatatcagcg ttatcactct cattaatggc ggcgagagtg    1620
cccctactac actgacacaa caaacggtg aattttgaaa acttctgcgt ttgagacata    1680
gatggtgttg catgctgcca ccagttactc cggttaaata tggatgtttc atggggggaag    1740
tcagcaattg gccaaagatt cagataggtg gaattggggg gataaggaat caaatgcatc    1800
tgctaaactg attggagaaa aacacatgca atatcttcag tacactctca tttaaaccac    1860
aagtagatat aaagcctaga gaaatacaga tgtctgctct gttaaatata aatagcaaa    1920
tgttcattca atttgaagac ctagaatttt tcttcttaaa taccaaacac gaataccaaa    1980
ttgcgtaagt accaattgat aagaatatat caccaaaatg taccatcatg ctcttccttc    2040
```

```
tacccttga taaactctac catgctcctt ctttgtagct aaaaacccat caaaatttag   2100
ggtagagtgg atgggcattg tttttgaggta ggagaaaagt aaacttggga ccattctagg  2160
ttttgttgct gtcactaggt aaagaaacac ctctttaacc acagtctggg acaagcatg   2220 caacatttta aaggttctct gctgtgcatg ggaaaagaaa catgctgaga accaatttgc   2280
atgaacatgt tcacttgtaa gtagaattca ctgaatggaa ctgtagctct agatatctca   2340
catgggggga agtttaggac cctcttgtct ttttgtctgt gtgcatgtat ttctttgtaa   2400
agtactgcta tgtttctctt tgctgtgtgg caacttaagc ctcttcggcc tgggataaaa   2460
taatctgcag tggtattaat aatgtacata aagtcaacat atttgaaagt agattaaaat   2520 ctttttaaa tatatcaatg atggcaaaaa ggttaaaggg ggcctaacag tactgtgtgt   2580
agtgttttat ttttaacagt agtacactat aacttaaaat agacttagat tagactgttt   2640
gcatgattat gattctgttt cctttatgca tgaaatattg attttaccttt tccagctact   2700 tcgttagctt taattttaaa atacattaac tgagtcttcc ttcttgttcg aaaccagctg   2760
ttcctcctcc cactgacctg cgattcacca acattggtcc agacaccatg cgtgtcacct   2820
ggg                                                                 2823

<210> SEQ ID NO 1571
<211> LENGTH: 702
<212> TYPE: PRT
<213> ORGANISM: Homo sapiens

<400> SEQUENCE: 1571

Met Glu Ser Pro Ser Ala Pro Pro His Arg Trp Cys Ile Pro Trp Gln
 1               5                  10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
```

```
                    225                 230                 235                 240
Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655
```

```
Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
            675                 680                 685

Val Gly Ile Met Ile Gly Val Leu Val Gly Val Ala Leu Ile
            690                 695                 700

<210> SEQ ID NO 1572
<211> LENGTH: 2974
<212> TYPE: DNA
<213> ORGANISM: Homo sapiens

<400> SEQUENCE: 1572
```

| | | | | |
|---|---|---|---|---|
| ctcagggcag agggaggaag gacagcagac cagacagtca cagcagcctt gacaaaacgt | | | | 60 |
| tcctggaact caagctcttc tccacagagg aggacagagc agacagcaga gaccatggag | | | | 120 |
| tctccctcgg ccctccca cagatggtgc atccctggc agaggctcct gctcacagcc | | | | 180 |
| tcacttctaa ccttctggaa cccgcccacc actgccaagc tcactattga atccacgccg | | | | 240 |
| ttcaatgtcg cagaggggaa ggaggtgctt ctacttgtcc acaatctgcc ccagcatctt | | | | 300 |
| tttggctaca gctggtacaa aggtgaaaga gtggatggca accgtcaaat tataggatat | | | | 360 |
| gtaataggaa ctcaacaagc taccccaggg cccgcataca gtggtcgaga gataatatac | | | | 420 |
| cccaatgcat ccctgctgat ccagaacatc atccagaatg acacaggatt ctacacccta | | | | 480 |
| cacgtcataa agtcagatct tgtgaatgaa aagcaactg ccagttccg ggtatacccg | | | | 540 |
| gagctgccca gccctccat ctccagcaac aactccaaac ccgtggagga caaggatgct | | | | 600 |
| gtggccttca cctgtgaacc tgagactcag gacgcaacct acctgtggtg ggtaaacaat | | | | 660 |
| cagagcctcc cggtcagtcc caggctgcag ctgtccaatg caacaggac cctcactcta | | | | 720 |
| ttcaatgtca agaaatga cacagcaagc tacaaatgtg aaacccagaa cccagtgagt | | | | 780 |
| gccaggcgca gtgattcagt catcctgaat gtcctctatg gccggatgc ccccaccatt | | | | 840 |
| tcccctctaa acacatctta cagatcaggg gaaaatctga acctctcctg ccacgcagcc | | | | 900 |
| tctaacccac ctgcacagta ctcttggttt gtcaatggga cttccagca atccaccaa | | | | 960 |
| gagctcttta tccccaacat cactgtgaat aatagtggat cctatacgtg ccaagcccat | | | | 1020 |
| aactcagaca ctggcctcaa taggaccaca gtcacgacga tcacagtcta tgcagagcca | | | | 1080 |
| cccaaaccct tcatcaccag caacaactcc aaccccgtgg aggatgagga tgctgtagcc | | | | 1140 |
| ttaacctgtg aacctgagat tcagaacaca acctacctgt ggtgggtaaa taatcagagc | | | | 1200 |
| ctcccggtca gtcccaggct gcagctgtcc aatgacaaca ggaccctcac tctactcagt | | | | 1260 |
| gtcacaagga atgatgtagg accctatgag tgtggaatcc agaacgaatt aagtgttgac | | | | 1320 |
| cacagcgacc cagtcatcct gaatgtcctc tatggcccag acgaccccac catttccccc | | | | 1380 |
| tcatacacct attaccgtcc aggggtgaac ctcagcctct cctgccatgc agcctctaac | | | | 1440 |
| ccacctgcac agtattcttg gctgattgat gggaacatcc agcaacacac acaagagctc | | | | 1500 |
| tttatctcca acatcactga gaagaacagc ggactctata cctgccaggc caataactca | | | | 1560 |
| gccagtggcc acagcaggac tacagtcaag acaatcacag tctctgcgga gctgcccaag | | | | 1620 |
| ccctccatct ccagcaacaa ctccaaaccc gtggaggaca aggatgctgt ggccttcacc | | | | 1680 |
| tgtgaacctg aggctcagaa cacaacctac ctgtggtggg taaatggtca gagcctccca | | | | 1740 |
| gtcagtccca ggctgcagct gtccaatggc aacaggaccc tcactctatt caatgtcaca | | | | 1800 |
| agaaatgacg caagagccta tgtatgtgga atccagaact cagtgagtgc aaaccgcagt | | | | 1860 |
| gacccagtca ccctggatgt cctctatggg ccggacaccc catcatttc cccccagac | | | | 1920 |

-continued

```
tcgtcttacc tttcgggagc gaacctcaac ctctcctgcc actcggcctc taacccatcc    1980
ccgcagtatt cttggcgtat caatgggata ccgcagcaac acacacaagt tctctttatc    2040
gccaaaatca cgccaaataa taacgggacc tatgcctgtt ttgtctctaa cttggctact    2100
ggccgcaata attccatagt caagagcatc acagtctctg catctggaac ttctcctggt    2160
ctctcagctg gggccactgt cggcatcatg attggagtgc tggttggggt tgctctgata    2220
tagcagccct ggtgtagttt cttcatttca ggaagactga cagttgtttt gcttcttcct    2280
taaagcattt gcaacagcta cagtctaaaa ttgcttcttt accaaggata tttacagaaa    2340
agactctgac cagagatcga gaccatccta gccaacatcg tgaaacccca tctctactaa    2400
aaatacaaaa atgagctggg cttggtggcg cgcacctgta gtcccagtta ctcgggaggc    2460
tgaggcagga gaatcgcttg aacccgggag gtggagattg cagtgagccc agatcgcacc    2520
actgcactcc agtctggcaa cagagcaaga ctccatctca aaagaaaag aaaagaagac    2580 tctgacctgt actcttgaat acaagtttct gataccactg cactgtctga aatttccaa    2640 aactttaatg aactaactga cagcttcatg aaactgtcca ccaagatcaa gcagagaaaa    2700
taattaattt catgggacta aatgaactaa tgaggattgc tgattcttta aatgtcttgt    2760
ttcccagatt tcaggaaact ttttttcttt taagctatcc actcttacag caatttgata    2820
aaatatactt ttgtgaacaa aaattgagac atttacattt tctccctatg tggtcgctcc    2880
agacttggga aactattcat gaatatttat attgtatggt aatatagtta ttgcacaagt    2940
tcaataaaaa tctgctcttt gtataacaga aaaa                                2974
```

<210> SEQ ID NO 1573
<211> LENGTH: 1255
<212> TYPE: PRT
<213> ORGANISM: Homo sapiens

<400> SEQUENCE: 1573

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190
```

```
His Pro Cys Ser Pro Met Cys Lys Gly Ser Arg Cys Trp Gly Glu Ser
        195                 200                 205
Ser Glu Asp Cys Gln Ser Leu Thr Arg Thr Val Cys Ala Gly Gly Cys
        210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                245                 250                 255
His Phe Asn His Ser Gly Ile Cys Glu Leu His Cys Pro Ala Leu Val
                260                 265                 270
Thr Tyr Asn Thr Asp Thr Phe Glu Ser Met Pro Asn Pro Glu Gly Arg
            275                 280                 285
Tyr Thr Phe Gly Ala Ser Cys Val Thr Ala Cys Pro Tyr Asn Tyr Leu
        290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
                340                 345                 350
Val Arg Ala Val Thr Ser Ala Asn Ile Gln Glu Phe Ala Gly Cys Lys
            355                 360                 365
Lys Ile Phe Gly Ser Leu Ala Phe Leu Pro Glu Ser Phe Asp Gly Asp
        370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
                420                 425                 430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
        450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
                500                 505                 510
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
        530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
                580                 585                 590
Pro Pro Phe Cys Val Ala Arg Cys Pro Ser Gly Val Lys Pro Asp Leu
            595                 600                 605
Ser Tyr Met Pro Ile Trp Lys Phe Pro Asp Glu Glu Gly Ala Cys Gln
```

```
                610                 615                 620
Pro Cys Pro Ile Asn Cys Thr His Ser Cys Val Asp Leu Asp Lys
625                 630                 635                 640

Gly Cys Pro Ala Glu Gln Arg Ala Ser Pro Leu Thr Ser Ile Val Ser
                645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
                690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
                850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
                915                 920                 925

Arg Glu Ile Pro Asp Leu Leu Glu Lys Gly Glu Arg Leu Pro Gln Pro
                930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
                995                 1000                1005

Leu Glu Asp Asp Asp Met Gly Asp Leu Val Asp Ala Glu Glu Tyr Leu
                1010                1015                1020

Val Pro Gln Gln Gly Phe Phe Cys Pro Asp Pro Ala Pro Gly Ala Gly
1025                1030                1035                1040
```

```
Gly Met Val His His Arg His Arg Ser Ser Ser Thr Arg Ser Gly Gly
            1045                1050                1055

Gly Asp Leu Thr Leu Gly Leu Glu Pro Ser Glu Glu Ala Pro Arg
        1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
        1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
            1125                1130                1135

Pro Glu Tyr Val Asn Gln Pro Asp Val Arg Pro Gln Pro Ser Pro
            1140                1145                1150

Arg Glu Gly Pro Leu Pro Ala Ala Arg Pro Ala Gly Ala Thr Leu Glu
            1155                1160                1165

Arg Ala Lys Thr Leu Ser Pro Gly Lys Asn Gly Val Val Lys Asp Val
        1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
            1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
            1235                1240                1245

Leu Gly Leu Asp Val Pro Val
    1250                1255

<210> SEQ ID NO 1574
<211> LENGTH: 4530
<212> TYPE: DNA
<213> ORGANISM: Homo sapiens

<400> SEQUENCE: 1574
aattctcgag ctcgtcgacc ggtcgacgag ctcgagggtc gacgagctcg agggcgcgcg    60
cccggccccc acccctcgca gcaccccgcg ccccgcgccc tcccagccgg gtccagccgg   120
agccatgggg ccggagccgc agtgagcacc atggagctgg cggccttgtg ccgctggggg   180
ctcctcctcg ccctcttgcc ccccggagcc gcgagcaccc aagtgtgcac ggcacagac    240
atgaagctgc ggctccctgc cagtcccgag acccacctgg acatgctccg ccacctctac   300
cagggctgcc aggtggtgca gggaaacctg gaactcacct acctgcccac caatgccagc   360
ctgtccttcc tgcaggatat ccaggaggtg cagggctacg tgctcatcgc tcacaaccaa   420
gtgaggcagg tcccactgca gaggctgcgg attgtgcgag caccagct ctttgaggac    480
aactatgccc tggccgtgct agacaatgga cccgctga caataccac ccctgtcaca     540
ggggcctccc caggaggcct gcgggagctg cagcttcgaa gcctcacaga gatcttgaaa   600
ggagggtct tgatccagcg gaaccccag ctctgctacc aggacacgat tttgtggaag    660
gacatcttcc acaagaacaa ccagctggct ctcacactga tagacaccaa ccgctctcgg   720
gcctgccacc cctgttctcc gatgtgtaag ggctcccgct gctggggaga gagttctgag   780
gattgtcaga gctgacgcg cactgtctgt gccggtggct gtgccgctg caagggcca     840
ctgcccactg actgctgcca tgagcagtgt gctgccggct gcacgggccc caagcactct   900
```

```
gactgcctgg cctgcctcca cttcaaccac agtggcatct gtgagctgca ctgcccagcc    960
ctggtcacct acaacacaga cacgtttgag tccatgccca atcccgaggg ccggtataca   1020
ttcggcgcca gctgtgtgac tgcctgtccc tacaactacc tttctacgga cgtgggatcc   1080
tgcaccctcg tctgccccct gcacaaccaa gaggtgacag cagaggatgg aacacagcgg   1140
tgtgagaagt gcagcaagcc ctgtgcccga gtgtgctatg gtctgggcat ggagcacttg   1200
cgagaggtga gggcagttac cagtgccaat atccaggagt tgctggctg caagaagatc   1260
tttgggagcc tggcatttct gccggagagc tttgatgggg acccagcctc caacactgcc   1320
ccgctccagc cagagcagct ccaagtgttt gagactctgg aagagatcac aggttaccta   1380
tacatctcag catggccgga cagcctgcct gacctcagcg tcttccagaa cctgcaagta   1440
atccggggac gaattctgca caatggcgcc tactcgctga ccctgcaagg gctgggcatc   1500
agctggctgg ggctgcgctc actgagggaa ctgggcagtg gactggccct catccaccat   1560
aacacccacc tctgcttcgt gcacacggtg ccctgggacc agctctttcg gaacccgcac   1620
caagctctgc tccacactgc caaccggcca gaggacgagt gtgtgggcga gggcctggcc   1680
tgccaccagc tgtgcgcccg agggcactgc tggggtccag ggcccaccca gtgtgtcaac   1740
tgcagccagt tccttcgggg ccaggagtgc gtggaggaat gccgagtact gcaggggctc   1800
cccagggagt atgtgaatgc caggcactgt ttgccgtgcc accctgagtg tcagccccag   1860
aatggctcag tgacctgttt tggaccggag gctgaccagt gtgtggcctg tgcccactat   1920
aaggaccctc ccttctgcgt ggcccgctgc cccagcggtg tgaaacctga cctctcctac   1980
atgcccatct ggaagtttcc agatgaggag ggcgcatgcc agccttgccc catcaactgc   2040
acccactcct gtgtggacct ggatgacaag ggctgccccg ccgagcagag agccagccct   2100
ctgacgtcca tcgtctctgc ggtggttggc attctgctgg tcgtggtctt ggggtggtc   2160
tttgggatcc tcatcaagcg acggcagcag aagatccgga gtacacgat gcggagactg   2220
ctgcaggaaa cggagctggt ggagccgctg acacctagcg gagcgatgcc caaccaggcg   2280
cagatgcgga tcctgaaaga gacggagctg aggaaggtga aggtgcttgg atctggcgct   2340
tttggcacag tctacaaggg catctggatc cctgatgggg agaatgtgaa aattccagtg   2400
gccatcaaag tgttgaggga aaacacatcc cccaaagcca caaagaaat cttagacgaa   2460
gcatacgtga tggctggtgt gggctcccca tatgtctccc gccttctggg catctgcctg   2520
acatccacgg tgcagctggt gacacagctt atgccctatg gctgcctctt agaccatgtc   2580
cgggaaaacc gcgacgcct gggctcccag gacctgctga actggtgtat gcagattgcc   2640
aaggggatga gctacctgga ggatgtgcgg ctcgtacaca gggacttggc cgctcggaac   2700
gtgctggtca gagtcccaa ccatgtcaaa attacagact cgggctggc tcggctgctg   2760
gacattgacg agacagagta ccatgcagat ggggcaagg tgcccatcaa gtggatggcg   2820
ctggagtcca ttctccgccg gcggttcacc accagagtg atgtgtggag ttatggtgtg   2880
actgtgtggg agctgatgac ttttggggcc aaaccttacg atgggatccc agcccgggag   2940
atccctgacc tgctggaaaa ggggagcgg ctgcccagc cccccatctg caccattgat   3000
gtctacatga tcatggtcaa atgttggatg attgactctg aatgtcggcc aagattccgg   3060
gagttggtgt ctgaattctc ccgcatggcc agggaccccc agcgctttgt ggtcatccag   3120
aatgaggact ttgggccagc cagtcccttg gacagcacct tctaccgctc actgctggag   3180
gacgatgaca tgggggacct ggtggatgct gaggagtatc tggtacccca gcagggcttc   3240
ttctgtccag accctgcccc gggcgctggg ggcatggtcc accacaggca ccgcagctca   3300
```

```
tctaccagga gtggcggtgg ggacctgaca ctagggctgg agccctctga gaggaggcc     3360
cccaggtctc cactggcacc ctccgaaggg gctggctccg atgtatttga tggtgacctg    3420
ggaatggggg cagccaaggg gctgcaaagc ctccccacac atgacccag ccctctacag     3480
cggtacagtg aggaccccac agtacccctg ccctctgaga ctgatggcta cgttgccccc    3540
ctgacctgca gccccagcc tgaatatgtg aaccagccag atgttcggcc ccagccccct    3600
tcgcccgag agggccctct gcctgctgcc cgacctgctg gtgccactct ggaagggcc     3660
aagactctct ccccagggaa gaatggggtc gtcaaagacg ttttttgcctt tggggtgcc    3720
gtggagaacc ccgagtactt gacacccag ggaggagctg cccctcagcc ccaccctcct    3780
cctgccttca gcccagcctt cgacaacctc tattactggg accaggaccc accagagcgg   3840
ggggctccac ccagcacctt caaagggaca cctacggcag agaacccaga gtacctgggt   3900
ctggacgtgc cagtgtgaac cagaaggcca agtccgcaga agccctgatg tgtcctcagg   3960
gagcagggaa ggcctgactt ctgctggcat caagaggtgg gagggccctc cgaccacttc   4020
caggggaacc tgccatgcca ggaacctgtc ctaaggaacc ttccttcctg cttgagttcc   4080
cagatggctg gaaggggtcc agcctcgttg gaagaggaac agcactgggg agtctttgtg   4140
gattctgagg ccctgcccaa tgagactcta gggtccagtg gatgccacag cccagcttgg   4200
cccttttcctt ccagatcctg ggtactgaaa gccttaggga agctggcctg agaggggaag  4260
cggccctaag ggagtgtcta gaacaaaag cgacccattc agagactgtc cctgaaacct    4320
agtactgccc cccatgagga aggaacagca atggtgtcag tatccaggct ttgtacagag   4380
tgctttttctg tttagttttt acttttttg ttttgttttt taaagacga aataaagacc    4440
caggggagaa tgggtgttgt atggggaggc aagtgtgggg ggtccttctc cacacccact   4500
ttgtccattt gcaaatatat tttggaaaac                                    4530
```

<210> SEQ ID NO 1575
<211> LENGTH: 976
<212> TYPE: PRT
<213> ORGANISM: Homo sapiens

<400> SEQUENCE: 1575

```
Met Glu Lys Gln Lys Pro Phe Ala Leu Phe Val Pro Pro Arg Ser Ser
1               5                   10                  15

Ser Ser Gln Val Ser Ala Val Lys Pro Gln Thr Leu Gly Gly Asp Ser
            20                  25                  30

Thr Phe Phe Lys Ser Phe Asn Lys Cys Thr Glu Asp Asp Leu Glu Phe
        35                  40                  45

Pro Phe Ala Lys Thr Asn Leu Ser Lys Asn Gly Glu Asn Ile Asp Ser
    50                  55                  60

Asp Pro Ala Leu Gln Lys Val Asn Phe Leu Pro Val Leu Glu Gln Val
65                  70                  75                  80

Gly Asn Ser Asp Cys His Tyr Gln Glu Gly Leu Lys Asp Ser Asp Leu
                85                  90                  95

Glu Asn Ser Glu Gly Leu Ser Arg Val Phe Ser Lys Leu Tyr Lys Glu
            100                 105                 110

Ala Glu Lys Ile Lys Lys Trp Lys Val Ser Thr Glu Ala Glu Leu Arg
        115                 120                 125

Gln Lys Glu Ser Lys Leu Gln Glu Asn Arg Lys Ile Ile Glu Ala Gln
    130                 135                 140

Arg Lys Ala Ile Gln Glu Leu Gln Phe Gly Asn Glu Lys Val Ser Leu
145                 150                 155                 160
```

```
Lys Leu Glu Glu Gly Ile Gln Glu Asn Lys Asp Leu Ile Lys Glu Asn
                165                 170                 175
Asn Ala Thr Arg His Leu Cys Asn Leu Leu Lys Glu Thr Cys Ala Arg
            180                 185                 190
Ser Ala Glu Lys Thr Lys Lys Tyr Glu Tyr Glu Arg Glu Glu Thr Arg
        195                 200                 205
Gln Val Tyr Met Asp Leu Asn Asn Asn Ile Glu Lys Met Ile Thr Ala
    210                 215                 220
His Gly Glu Leu Arg Val Gln Ala Glu Asn Ser Arg Leu Glu Met His
225                 230                 235                 240
Phe Lys Leu Lys Glu Asp Tyr Glu Lys Ile Gln His Leu Glu Gln Glu
                245                 250                 255
Tyr Lys Lys Glu Ile Asn Asp Lys Glu Lys Gln Val Ser Leu Leu Leu
            260                 265                 270
Ile Gln Ile Thr Glu Lys Glu Asn Lys Met Lys Asp Leu Thr Phe Leu
        275                 280                 285
Leu Glu Glu Ser Arg Asp Lys Val Asn Gln Leu Glu Glu Lys Thr Lys
    290                 295                 300
Leu Gln Ser Glu Asn Leu Lys Gln Ser Ile Glu Lys Gln His His Leu
305                 310                 315                 320
Thr Lys Glu Leu Glu Asp Ile Lys Val Ser Leu Gln Arg Ser Val Ser
                325                 330                 335
Thr Gln Lys Ala Leu Glu Glu Asp Leu Gln Ile Ala Thr Lys Thr Ile
            340                 345                 350
Cys Gln Leu Thr Glu Glu Lys Glu Thr Gln Met Glu Gly Ser Asn Lys
        355                 360                 365
Ala Arg Ala Ala His Ser Phe Val Val Thr Glu Phe Glu Thr Thr Val
    370                 375                 380
Cys Ser Leu Glu Glu Leu Leu Arg Thr Glu Gln Gln Arg Leu Glu Lys
385                 390                 395                 400
Asn Glu Asp Gln Leu Lys Ile Leu Thr Met Glu Leu Gln Lys Lys Ser
                405                 410                 415
Ser Glu Leu Glu Glu Met Thr Lys Leu Thr Asn Asn Lys Glu Val Glu
            420                 425                 430
Leu Glu Glu Leu Lys Lys Val Leu Gly Glu Lys Glu Thr Leu Leu Tyr
        435                 440                 445
Glu Asn Lys Gln Phe Glu Lys Ile Ala Glu Glu Leu Lys Gly Thr Glu
    450                 455                 460
Gln Glu Leu Ile Gly Leu Leu Gln Ala Arg Glu Lys Glu Val His Asp
465                 470                 475                 480
Leu Glu Ile Gln Leu Thr Ala Ile Thr Thr Ser Glu Gln Tyr Tyr Ser
                485                 490                 495
Lys Glu Val Lys Asp Leu Lys Thr Glu Leu Glu Asn Glu Lys Leu Lys
            500                 505                 510
Asn Thr Glu Leu Thr Ser His Cys Asn Lys Leu Ser Leu Glu Asn Lys
        515                 520                 525
Glu Leu Thr Gln Glu Thr Ser Asp Met Thr Leu Glu Leu Lys Asn Gln
    530                 535                 540
Gln Glu Asp Ile Asn Asn Asn Lys Lys Gln Glu Glu Arg Met Leu Lys
545                 550                 555                 560
Gln Ile Glu Asn Leu Gln Glu Thr Thr Gln Leu Arg Asn Glu Leu
                565                 570                 575
Glu Tyr Val Arg Glu Glu Leu Lys Gln Lys Arg Asp Glu Val Lys Cys
            580                 585                 590
```

```
Lys Leu Asp Lys Ser Glu Glu Asn Cys Asn Asn Leu Arg Lys Gln Val
            595                 600                 605

Glu Asn Lys Asn Lys Tyr Ile Glu Glu Leu Gln Gln Glu Asn Lys Ala
610                 615                 620

Leu Lys Lys Gly Thr Ala Glu Ser Lys Gln Leu Asn Val Tyr Glu
625                 630                 635                 640

Ile Lys Val Asn Lys Leu Glu Leu Glu Leu Glu Ser Ala Lys Gln Lys
                645                 650                 655

Phe Gly Glu Ile Thr Asp Thr Tyr Gln Lys Glu Ile Glu Asp Lys Lys
            660                 665                 670

Ile Ser Glu Glu Asn Leu Leu Glu Glu Val Glu Lys Ala Lys Val Ile
        675                 680                 685

Ala Asp Glu Ala Val Lys Leu Gln Lys Glu Ile Asp Lys Arg Cys Gln
    690                 695                 700

His Lys Ile Ala Glu Met Val Ala Leu Met Glu Lys His Lys His Gln
705                 710                 715                 720

Tyr Asp Lys Ile Ile Glu Glu Arg Asp Ser Glu Leu Gly Leu Tyr Lys
                725                 730                 735

Ser Lys Glu Gln Glu Gln Ser Ser Leu Arg Ala Ser Leu Glu Ile Glu
            740                 745                 750

Leu Ser Asn Leu Lys Ala Glu Leu Leu Ser Val Lys Lys Gln Leu Glu
        755                 760                 765

Ile Glu Arg Glu Glu Lys Glu Lys Leu Lys Arg Glu Ala Lys Glu Asn
    770                 775                 780

Thr Ala Thr Leu Lys Glu Lys Lys Asp Lys Lys Thr Gln Thr Phe Leu
785                 790                 795                 800

Leu Glu Thr Pro Glu Ile Tyr Trp Lys Leu Asp Ser Lys Ala Val Pro
                805                 810                 815

Ser Gln Thr Val Ser Arg Asn Phe Thr Ser Val Asp His Gly Ile Ser
            820                 825                 830

Lys Asp Lys Arg Asp Tyr Leu Trp Thr Ser Ala Lys Asn Thr Leu Ser
        835                 840                 845

Thr Pro Leu Pro Lys Ala Tyr Thr Val Lys Thr Pro Lys Pro Lys
    850                 855                 860

Leu Gln Gln Arg Glu Asn Leu Asn Ile Pro Ile Glu Glu Ser Lys Lys
865                 870                 875                 880

Lys Arg Lys Met Ala Phe Glu Phe Asp Ile Asn Ser Asp Ser Ser Glu
                885                 890                 895

Thr Thr Asp Leu Leu Ser Met Val Ser Glu Glu Thr Leu Lys Thr
            900                 905                 910

Leu Tyr Arg Asn Asn Asn Pro Pro Ala Ser His Leu Cys Val Lys Thr
        915                 920                 925

Pro Lys Lys Ala Pro Ser Ser Leu Thr Thr Pro Gly Pro Thr Leu Lys
    930                 935                 940

Phe Gly Ala Ile Arg Lys Met Arg Glu Asp Arg Trp Ala Val Ile Ala
945                 950                 955                 960

Lys Met Asp Arg Lys Lys Lys Leu Lys Glu Ala Glu Lys Leu Phe Val
                965                 970                 975

<210> SEQ ID NO 1576
<211> LENGTH: 3393
<212> TYPE: DNA
<213> ORGANISM: Homo sapiens

<400> SEQUENCE: 1576
```

```
gccctcatag accgtttgtt gtagttcgcg tgggaacagc aacccacggt ttcccgatag      60
ttcttcaaag atatttacaa ccgtaacaga gaaaatggaa aagcaaaagc cctttgcatt     120
gttcgtacca ccgagatcaa gcagcagtca ggtgtctgcg gtgaaacctc agaccctggg    180
aggcgattcc actttcttca agagtttcaa caaatgtact gaagatgatt tggagtttcc    240
atttgcaaag actaatctct ccaaaaatgg ggaaaacatt gattcagatc ctgctttaca    300
aaaagttaat ttcttgcccg tgcttgagca ggttggtaat tctgactgtc actatcagga    360
aggactaaaa gactctgatt tggagaattc agagggattg agcagagtgt tttcaaaact    420
gtataaggag gctgaaaaga taaaaaaatg gaaagtaagt acagaagctg aactgagaca    480
gaaagaaagt aagttgcaag aaaacagaaa gataattgaa gcacagcgaa aagccattca    540
ggaactgcaa tttggaaatg aaaaagtaag tttgaaatta gaagaaggaa tacaagaaaa    600
taaagattta ataaaagaga ataatgccac aaggcattta tgtaatctac tcaaagaaac    660
ctgtgctaga tctgcagaaa agacaaagaa atatgaatat gaacgggaag aaaccaggca    720
agtttatatg gatctaaata ataacattga gaaaatgata acagctcatg gggaacttcg    780
tgtgcaagct gagaattcca gactggaaat gcattttaag ttaaaggaag attatgaaaa    840
aatccaacac cttgaacaag aatacaagaa ggaaataaat gacaaggaaa gcaggtatc    900 actactattg atccaaatca ctgagaaaga aaataaaatg aaagatttaa catttctgct    960
agaggaatcc agagataaag ttaatcaatt agaggaaaag acaaaattac agagtgaaaa   1020
cttaaaacaa tcaattgaga acagcatca tttgactaaa gaactagaag atattaaagt    1080
gtcattacaa agaagtgtga gtactcaaaa ggctttagag gaagatttac agatagcaac    1140
aaaaacaatt tgtcagctaa ctgaagaaaa agaaactcaa atggaagaat ctaataaagc    1200
tagagctgct cattcgtttg tggttactga atttgaaact actgtctgca gcttggaaga    1260
attattgaga acagaacagc aaagattgga aaaaaatgaa gatcaattga aaatacttac    1320
catggagctt caaaagaaat caagtgagct ggaagagatg actaagctta caaataacaa    1380
agaagtagaa cttgaagaat tgaaaaaagt cttgggagaa aaggaaacac ttttatatga    1440
aaataaacaa tttgagaaga ttgctgaaga attaaaagga acagaacaag aactaattgg    1500
tcttctccaa gccagagaga aagaagtaca tgatttggaa atacagttaa ctgccattac    1560
cacaagtgaa cagtattatt caaaagaggt taaagatcta aaaactgagc ttgaaaacga    1620
gaagcttaag aatactgaat taacttcaca ctgcaacaag cttttcactag aaaacaaaga    1680 gctcacacag gaaacaagtg atatgaccct agaactcaag aatcagcaag aagatattaa    1740
taataacaaa aagcaagaag aaaggatgtt gaaacaaata gaaaatcttc aagaaacaga    1800
aacccaatta agaaatgaac tagaatatgt gagagaagag ctaaaacaga aaagagatga    1860
agttaaatgt aaattggaca agagtgaaga aaattgtaac aatttaagga aacaagttga    1920
aaataaaaac aagtatattg aagaacttca gcaggagaat aaggccttga aaaaaaagg    1980 tacagcagaa agcaagcaac tgaatgtttta tgagataaag gtcaataaat tagagttaga    2040
actagaaagt gccaaacaga aatttggaga atcacagac acctatcaga aagaaattga    2100
ggacaaaaag atatcagaag aaaatctttt ggaagaggtt gagaaagcaa agtaatagc    2160 tgatgaagca gtaaaattac agaagaaat tgataagcga tgtcaacata aaatagctga    2220
aatggtagca cttatggaaa acataagca ccaatatgat aagatcattg aagaaagaga    2280
ctcagaatta ggactttata agagcaaaga acaagaacag tcatcactga gagcatcttt    2340
ggagattgaa ctatccaatc tcaaagctga acttttgtct gttaagaagc aacttgaaat    2400
```

```
agaaagagaa gagaaggaaa aactcaaaag agaggcaaaa gaaaacacag ctactcttaa    2460
agaaaaaaaa gacaagaaaa cacaaacatt tttattggaa acacctgaaa tttattggaa    2520
attggattct aaagcagttc cttcacaaac tgtatctcga aatttcacat cagttgatca    2580
tggcatatcc aaagataaaa gagactatct gtggacatct gccaaaaata ctttatctac    2640
accattgcca aaggcatata cagtgaagac accaacaaaa ccaaaactac agcaaagaga    2700
aaacttgaat atacccattg aagaaagtaa aaaaaagaga aaaatggcct ttgaatttga    2760
tattaattca gatagttcag aaactactga tcttttgagc atggtttcag aagaagagac    2820
attgaaaaca ctgtatagga acaataatcc accagcttct catctttgtg tcaaaacacc    2880
aaaaaaggcc ccttcatctc taacaacccc tggacctaca ctgaagtttg gagctataag    2940
aaaaatgcgg gaggaccgtt gggctgtaat tgctaaaatg gatagaaaaa aaaaactaaa    3000
agaagctgaa aagttatttg tttaatttca gagaatcagt gtagttaagg agcctaataa    3060
cgtgaaactt atagttaata ttttgttctt atttgccaga gccacatttt atctggaagt    3120
tgagacttaa aaaatacttg catgaatgat ttgtgtttct ttatattttt agcctaaatg    3180
ttaactacat attgtctgga aacctgtcat tgtattcaga taattagatg attatatatt    3240
gttgttactt tttcttgtat tcatgaaaac tgttttttact aagttttcaa atttgtaaag    3300
ttagcctttg aatgctagga atgcattatt gagggtcatt ctttattctt tactattaaa    3360
atattttgga tgcaaaaaaa aaaaaaaaaa aaa                                 3393
```

<210> SEQ ID NO 1577
<211> LENGTH: 188
<212> TYPE: PRT
<213> ORGANISM: Homo sapiens

<400> SEQUENCE: 1577

```
Met Asn Gly Asp Asp Ala Phe Ala Arg Arg Pro Arg Asp Asp Ala Gln
 1               5                  10                  15

Ile Ser Glu Lys Leu Arg Lys Ala Phe Asp Asp Ile Ala Lys Tyr Phe
             20                  25                  30

Ser Lys Lys Glu Trp Glu Lys Met Lys Ser Ser Glu Lys Ile Val Tyr
         35                  40                  45

Val Tyr Met Lys Leu Asn Tyr Glu Val Met Thr Lys Leu Gly Phe Lys
     50                  55                  60

Val Thr Leu Pro Pro Phe Met Arg Ser Lys Arg Ala Ala Asp Phe His
 65                  70                  75                  80

Gly Asn Asp Phe Gly Asn Asp Arg Asn His Arg Asn Gln Val Glu Arg
                 85                  90                  95

Pro Gln Met Thr Phe Gly Ser Leu Gln Arg Ile Phe Pro Lys Ile Met
            100                 105                 110

Pro Lys Lys Pro Ala Glu Glu Glu Asn Gly Leu Lys Glu Val Pro Glu
        115                 120                 125

Ala Ser Gly Pro Gln Asn Asp Gly Lys Gln Leu Cys Pro Pro Gly Asn
    130                 135                 140

Pro Ser Thr Leu Glu Lys Ile Asn Lys Thr Ser Gly Pro Lys Arg Gly
145                 150                 155                 160

Lys His Ala Trp Thr His Arg Leu Arg Glu Arg Lys Gln Leu Val Val
                165                 170                 175

Tyr Glu Glu Ile Ser Asp Pro Glu Glu Asp Asp Glu
            180                 185
```

```
<210> SEQ ID NO 1578
<211> LENGTH: 576
<212> TYPE: DNA
<213> ORGANISM: Homo sapiens

<400> SEQUENCE: 1578
atgaacggag acgacgcctt tgcaaggaga cccagggatg atgctcaaat atcagagaag      60
ttacgaaagg ccttcgatga tattgccaaa tacttctcta agaaagagtg ggaaaagatg     120
aaatcctcgg agaaaatcgt ctatgtgtat atgaagctaa actatgaggt catgactaaa     180
ctaggtttca aggtcaccct cccacctttc atgcgtagta acgggctgc agacttccac      240 gggaatgatt ttggtaacga tcgaaaccac aggaatcagg ttgaacgtcc tcagatgact     300
ttcggcagcc tccagagaat cttcccgaag atcatgccca agaagccagc agaggaagaa     360
aatggtttga ggaagtgcc agaggcatct ggcccacaaa atgatgggaa acagctgtgc      420
cccccgggaa atccaagtac cttggagaag attaacaaga catctggacc caaaaggggg     480
aaacatgcct ggaccacag actgcgtgag agaaagcagc tggtggttta tgaagagatc      540
agcgaccctg aggaagatga cgagtaactc ccctcg                               576

<210> SEQ ID NO 1579
<211> LENGTH: 28
<212> TYPE: PRT
<213> ORGANISM: Homo sapiens

<400> SEQUENCE: 1579

Ser Ser Cys Leu Gln Gln Leu Ser Leu Leu Met Trp Ile Thr Gln Cys
  1               5                  10                  15

Phe Leu Pro Val Phe Leu Ala Gln Pro Pro Ser Gly
             20                  25

<210> SEQ ID NO 1580
<211> LENGTH: 38
<212> TYPE: PRT
<213> ORGANISM: Homo sapiens

<400> SEQUENCE: 1580

Tyr Phe Ser Lys Glu Glu Trp Glu Lys Met Lys Ala Ser Glu Lys Ile
  1               5                  10                  15

Phe Tyr Val Tyr Met Lys Arg Lys Tyr Glu Ala Met Thr Lys Leu Gly
             20                  25                  30

Phe Lys Ala Thr Leu Pro
         35

<210> SEQ ID NO 1581
<211> LENGTH: 74
<212> TYPE: PRT
<213> ORGANISM: Homo sapiens

<400> SEQUENCE: 1581

Ser Leu Leu Met Trp Ile Thr Gln Cys Lys Ala Ser Glu Lys Ile Phe
  1               5                  10                  15

Tyr Val Gly Leu Pro Ser Ile Pro Val His Pro Ile Gly Leu Pro Ser
             20                  25                  30

Ile Pro Val His Pro Ile Lys Ala Ser Glu Lys Ile Phe Tyr Val Ser
         35                  40                  45

Leu Leu Met Trp Ile Thr Gln Cys Lys Ala Ser Glu Lys Ile Phe Tyr
     50                  55                  60

Val Lys Ala Ser Glu Lys Ile Phe Tyr Val
 65                  70
```

<210> SEQ ID NO 1582
<211> LENGTH: 75
<212> TYPE: PRT
<213> ORGANISM: Homo sapiens

<400> SEQUENCE: 1582

Met Ser Leu Leu Met Trp Ile Thr Gln Cys Lys Ala Ser Glu Lys Ile
1               5                   10                  15

Phe Tyr Val Gly Leu Pro Ser Ile Pro Val His Pro Ile Gly Leu Pro
            20                  25                  30

Ser Ile Pro Val His Pro Ile Lys Ala Ser Glu Lys Ile Phe Tyr Val
        35                  40                  45

Ser Leu Leu Met Trp Ile Thr Gln Cys Lys Ala Ser Glu Lys Ile Phe
    50                  55                  60

Tyr Val Lys Ala Ser Glu Lys Ile Phe Tyr Val
65                  70                  75

<210> SEQ ID NO 1583
<211> LENGTH: 72
<212> TYPE: PRT
<213> ORGANISM: Homo sapiens

<400> SEQUENCE: 1583

Ser Leu Leu Met Trp Ile Thr Gln Cys Lys Ala Ser Glu Lys Ile Phe
1               5                   10                  15

Tyr Val Thr Gln Cys Phe Leu Pro Val Phe Leu Ser Leu Leu Met Trp
            20                  25                  30

Ile Thr Gln Cys Ser Leu Leu Met Trp Ile Thr Gln Cys Ser Leu Leu
        35                  40                  45

Met Trp Ile Thr Gln Cys Thr Gln Cys Phe Leu Pro Val Phe Leu Lys
    50                  55                  60

Ala Ser Glu Lys Ile Phe Tyr Val
65                  70

<210> SEQ ID NO 1584
<211> LENGTH: 73
<212> TYPE: PRT
<213> ORGANISM: Homo sapiens

<400> SEQUENCE: 1584

Met Ser Leu Leu Met Trp Ile Thr Gln Cys Lys Ala Ser Glu Lys Ile
1               5                   10                  15

Phe Tyr Val Thr Gln Cys Phe Leu Pro Val Phe Leu Ser Leu Leu Met
            20                  25                  30

Trp Ile Thr Gln Cys Ser Leu Leu Met Trp Ile Thr Gln Cys Ser Leu
        35                  40                  45

Leu Met Trp Ile Thr Gln Cys Thr Gln Cys Phe Leu Pro Val Phe Leu
    50                  55                  60

Lys Ala Ser Glu Lys Ile Phe Tyr Val
65                  70

EXPRESSION VECTORS ENCODING EPITOPES OF TARGET-ASSOCIATED ANTIGENS AND METHODS FOR THEIR DESIGN

CROSS REFERENCE TO RELATED APPLICATIONS

This application claims priority under 35 U.S.C. §119(e) to U.S. Provisional Application No. 60/336,968 filed Nov. 7, 2001, which is hereby incorporated by reference in its entirety.

BACKGROUND OF THE INVENTION

1. Field of the Invention

The invention disclosed herein is directed to methods for the design of epitope-encoding vectors for use in compositions, including for example, pharmaceutical compositions capable of inducing an immune response in a subject to whom the compositions are administered. The invention is further directed to the vectors themselves. The epitope(s) expressed using such vectors can stimulate a cellular immune response against a target cell displaying the epitope(s).

2. Description of the Related Art

The immune system can be categorized into two discrete effector arms. The first is innate immunity, which involves numerous cellular components and soluble factors that respond to all infectious challenges. The other is the adaptive immune response, which is customized to respond specifically to precise epitopes from infectious agents. The adaptive immune response is further broken down into two effector arms known as the humoral and cellular immune systems. The humoral arm is centered on the production of antibodies by B-lymphocytes while the cellular arm involves the killer cell activity of cytotoxic T Lymphocytes.

Cytotoxic T Lymphocytes (CTL) do not recognize epitopes on the infectious agents themselves. Rather, CTL detect fragments of antigens derived from infectious agents that are displayed on the surface of infected cells. As a result antigens are visible to CTL only after they have been processed by the infected cell and thus displayed on the surface of the cell.

The antigen processing and display system on the surface of cells has been well established. CTL recognize short peptide antigens, which are displayed on the surface in non-covalent association with class I major histocompatibility complex molecules (MHC). These class I peptides are in turn derived from the degradation of cytosolic proteins.

SUMMARY OF THE INVENTION

Embodiments of the invention provide expression cassettes, for example, for use in vaccine vectors, which encode one or more embedded housekeeping epitopes, and methods for designing and testing such expression cassettes. Housekeeping epitopes can be liberated from the translation product of such cassettes through proteolytic processing by the immunoproteasome of professional antigen presenting cells (pAPC). In one embodiment of the invention, sequences flanking the housekeeping epitope(s) can be altered to promote cleavage by the immunoproteasome at the desired location(s). Housekeeping epitopes, their uses, and identification are described in U.S. patent application Ser. Nos. 09/560,465 and 09/561,074 entitled EPITOPE SYNCHRONIZATION IN ANTIGEN PRESENTING CELLS, and METHOD OF EPITOPE DISCOVERY, respectively; both of which were filed on Apr. 28, 2000, and which are both incorporated herein by reference in their entireties.

Examples of housekeeping epitopes are disclosed in provisional U.S. Patent Applications entitled EPITOPE SEQUENCES, Nos. 60/282,211, filed on Apr. 6, 2001; 60/337,017, filed on Nov. 7, 2001; 60/363210 filed Mar. 7, 2002; and 60/409,123, filed on Sep. 5, 2002; and U.S. application Ser. No. 10/117,937, filed on Apr. 4, 2002, which is also entitled EPITOPE SEQUENCES; which are all incorporated herein by reference in their entirety.

In other embodiments of the invention, the housekeeping epitope(s) can be flanked by arbitrary sequences or by sequences incorporating residues known to be favored in immunoproteasome cleavage sites. As used herein the term "arbitrary sequences" refers to sequences chosen without reference to the native sequence context of the epitope, their ability to promote processing, or immunological function. In further embodiments of the invention multiple epitopes can be arrayed head-to-tail. These arrays can be made up entirely of housekeeping epitopes. Likewise, the arrays can include alternating housekeeping and immune epitopes. Alternatively, the arrays can include housekeeping epitopes flanked by immune epitopes, whether complete or distally truncated. Further, the arrays can be of any other similar arrangement. There is no restriction on placing a housekeeping epitope at the terminal positions of the array. The vectors can additionally contain authentic protein coding sequences or segments thereof containing epitope clusters as a source of immune epitopes. The term "authentic" refers to natural protein sequences.

Epitope clusters and their uses are described in U.S. patent application Ser. No. 09/561,571 entitled EPITOPE CLUSTERS, filed on Apr. 28, 2000; Ser. No. 10/005,905, entitled EPITOPE SYNCHRONIZATION IN ANTIGEN PRESENTING CELLS, filed on Nov. 7, 2001; and Ser. No. 10/026,066, filed on Dec. 7, 2001, also entitled EPITOPE SYNCHRONIZATION IN ANTIGEN PRESENTING CELLS; all of which are incorporated herein by reference in their entirety.

Embodiments of the invention can encompass screening the constructs to determine whether the housekeeping epitope is liberated. In constructs containing multiple housekeeping epitopes, embodiments can include screening to determine which epitopes are liberated. In a preferred embodiment, a vector containing an embedded epitope can be used to immunize HLA transgenic mice and the resultant CTL can be tested for their ability to recognize target cells presenting the mature epitope. In another embodiment, target cells expressing immunoproteasome can be transformed with the vector. The target cell may express immunoproteasome either constitutively, because of treatment with interferon (IFN), or through genetic manipulation, for example. CTL that recognize the mature epitope can be tested for their ability to recognize these target cells. In yet another embodiment, the embedded epitope can be prepared as a synthetic peptide. The synthetic peptide then can be subjected to digestion by an immunoproteasome preparation in vitro and the resultant fragments can be analyzed to determine the sites of cleavage. Such polypeptides, recombinant or synthetic, from which embedded epitopes can be successfully liberated, can also be incorporated into immunogenic compositions.

The invention disclosed herein relates to the identification of a polypeptide suitable for epitope liberation. One embodiment of the invention, relates to a method of identifying a polypeptide suitable for epitope liberation including, for example, the steps of identifying an epitope of interest; providing a substrate polypeptide sequence including the epitope, wherein the substrate polypeptide permits processing by a proteasome; contacting the substrate polypeptide with a composition including the proteasome, under conditions that support processing of the substrate polypeptide by the proteasome; and assaying for liberation of the epitope.

The epitope can be embedded in the substrate polypeptide, and in some aspects the substrate polypeptide can include more than one epitope, for example. Also, the epitope can be a housekeeping epitope.

In one aspect, the substrate polypeptide can be a synthetic peptide. Optionally, the substrate polypeptide can be included in a formulation promoting protein transfer. Alternatively, the substrate polypeptide can be a fusion protein. The fusion protein can further include a protein domain possessing protein transfer activity. Further, the contacting step can include immunization with the substrate polypeptide.

In another aspect, the substrate polypeptide can be encoded by a polynucleotide. The contacting step can include immunization with a vector including the polynucleotide, for example. The immunization can be carried out in an HLA-transgenic mouse or any other suitable animal, for example. Alternatively, the contacting step can include transforming a cell with a vector including the polynucleotide. In some embodiments the transformed cell can be a target cell that is targeted by CTL for purposes of assaying for proper liberation of epitope.

The proteasome processing can take place intracellularly, either in vitro or in vivo. Further, the proteasome processing can take place in a cell-free system.

The assaying step can include a technique selected from the group including, but not limited to, mass spectrometry, N-terminal pool sequencing, HPLC, and the like. Also, the assaying step can include a T cell target recognition assay. The T cell target recognition assay can be selected from the group including, but not limited to, a cytolytic activity assay, a chromium release assay, a cytokine assay, an ELISPOT assay, tetramer analysis, and the like.

In still another aspect, the amino acid sequence of the substrate polypeptide including the epitope can be arbitrary. Also, the substrate polypeptide in which the epitope is embedded can be derived from an authentic sequence of a target-associated antigen. Further, the substrate polypeptide in which the epitope is embedded can be conformed to a preferred immune proteasome cleavage site flanking sequence.

In another aspect, the substrate polypeptide can include an array of additional epitopes. Members of the array can be arranged head-to-tail, for example. The array can include more than one housekeeping epitope. The more than one housekeeping epitope can include copies of the same epitope. The array can include a housekeeping and an immune epitope, or alternating housekeeping and immune epitopes, for example. Also, the array can include a housekeeping epitope positioned between two immune epitopes in an epitope battery. The array can include multiple epitope batteries, so that there are two immune epitopes between each housekeeping epitope in the interior of the array. Optionally, at least one of the epitopes can be truncated distally to its junction with an adjacent epitope. The truncated epitopes can be immune epitopes, for example. The truncated epitopes can have lengths selected from the group including, but not limited to, 9, 8, 7, 6, 5, 4 amino acids, and the like.

In still another aspect, the substrate polypeptide can include an array of epitopes and epitope clusters. Members of the array can be arranged head-to-tail, for example.

In yet another aspect, the proteasome can be an immune proteasome.

Another embodiment of the disclosed invention relates to vectors including a housekeeping epitope expression cassette. The housekeeping epitope(s) can be derived from a target-associated antigen, and the housekeeping epitope can be liberatable, that is capable of liberation, from a translation product of the cassette by immunoproteasome processing.

In one aspect of the invention the expression cassette can encode an array of two or more epitopes or at least one epitope and at least one epitope cluster. The members of the array can be arranged head-to-tail, for example. Also, the members of the array can be arranged head-to-tail separated by spacing sequences, for example. Further, the array can include a plurality of housekeeping epitopes. The plurality of housekeeping epitopes can include more than one copy of the same epitope or single copies of distinct epitopes, for example. The array can include at least one housekeeping epitope and at least one immune epitope. Also, the array can include alternating housekeeping and immune epitopes. Further, the array includes a housekeeping epitope sandwiched between two immune epitopes so that there are two immune epitopes between each housekeeping epitope in the interior of the array. The immune epitopes can be truncated distally to their junction with the adjacent housekeeping epitope.

In another aspect, the expression cassette further encodes an authentic protein sequence, or segment thereof, including at least one immune epitope. Optionally, the segment can include at least one epitope cluster. The housekeeping epitope expression cassette and the authentic sequence including at least one immune epitope can be encoded in a single reading frame or transcribed as a single mRNA species, for example. Also, the housekeeping epitope expression cassette and the authentic sequence including at least one immune epitope may not be transcribed as a single mRNA species.

In yet another aspect, the vector can include a DNA molecule or an RNA molecule. The vector can encode, for example, SEQ ID NO. 4, SEQ ID NO. 17, SEQ ID NO. 20, SEQ ID NO. 26, SEQ ID NO. 27, SEQ ID NO. 29, SEQ ID NO. 33, and the like. Also, the vector can include SEQ ID NO. 9, SEQ ID NO. 19, SEQ ID NO. 21, SEQ ID NO. 30, SEQ ID NO. 34, and the like. Also, the vector can encode SEQ ID NO. 5 or SEQ ID NO. 18, for example.

In still another aspect, the target-associated antigen can be an antigen derived from or associated with a tumor or an intracellular parasite, and the intracellular parasite can be, for example, a virus, a bacterium, a protozoan, or the like.

Another embodiment of the invention relates to vectors including a housekeeping epitope identified according to any of the methods disclosed herein, claimed or otherwise. For example, embodiments can relate to vector encoding a substrate polypeptide that includes a housekeeping epitope by any of the methods described herein.

In one aspect, the housekeeping epitope can be liberated from the cassette translation product by immune proteasome processing Another embodiment of the disclosed invention relates to methods of activating a T cell. The methods can include, for example, the steps of contacting a vector including a housekeeping epitope expression cassette with an APC. The housekeeping epitope can be derived from a target-associated antigen, for example, and the housekeeping epitope can be liberatable from a translation product of the cassette by immunoproteasome processing. The methods can further include contacting the APC with a T cell. The contacting of the vector with the APC can occur in vitro or in vivo.

Another embodiment of the disclosed invention relates to a substrate polypeptide including a housekeeping epitope wherein the housekeeping epitope can be liberated by immunoproteasome processing in a pAPC.

Another embodiment of the disclosed invention relates to a method of activating a T cell comprising contacting a substrate polypeptide including a housekeeping epitope with an APC wherein the housekeeping epitope can be liberated by immunoproteasome processing and contacting the APC with a T cell.

BRIEF DESCRIPTION OF THE DRAWINGS

FIG. 1. An illustrative drawing depicting pMA2M.

FIG. 2. Assay results showing the % of specific lysis of ELAGIGILTV pulsed and unpulsed T2 target cells by mock immunized CTL.

FIG. 3. Assay results showing the % of specific lysis of ELAGIGILTV pulsed and unpulsed T2 target cells by pVAXM3 immunized CTL.

FIG. 4. Assay results showing the % of specific lysis of ELAGIGILTV pulsed and unpulsed T2 target cells by pVAXM2 immunized CTL.

FIG. 5. Assay results showing the % of specific lysis of ELAGIGILTV pulsed and unpulsed T2 target cells by pVAXM1 immunized CTL.

FIG. 9. Shows the differential processing of SSX-$2_{31-68}$ by housekeeping and immunoproteasome.

DETAILED DESCRIPTION OF THE PREFERRED EMBODIMENT

Definitions

Figure 6:
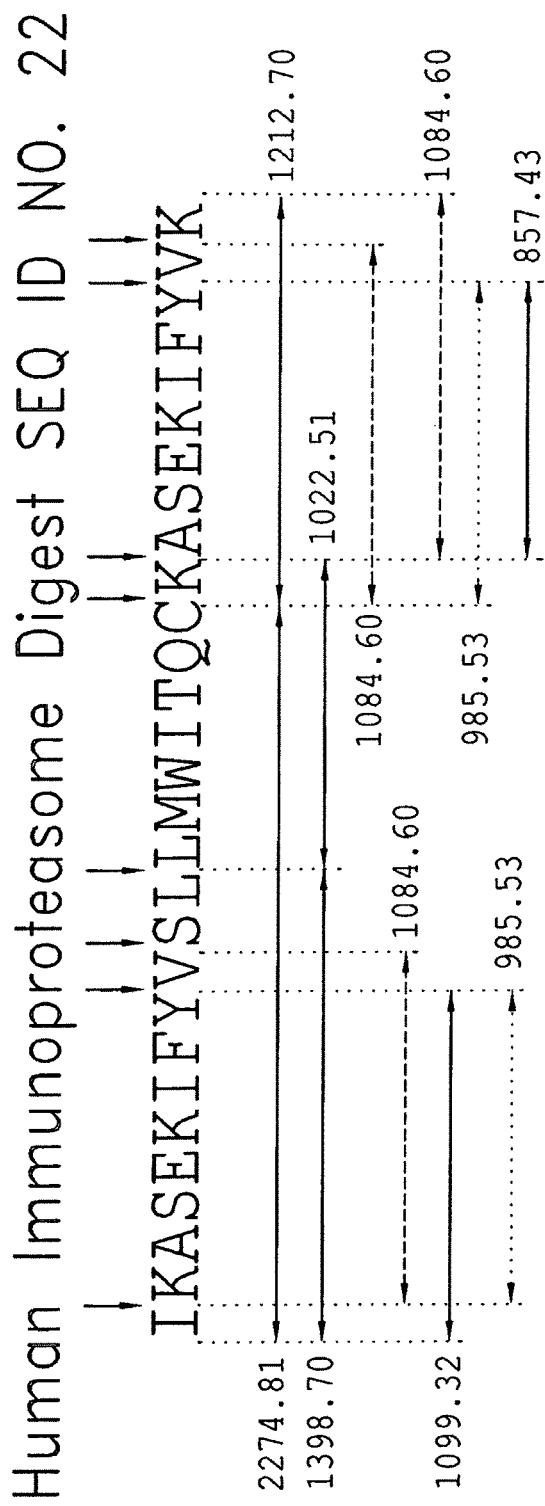
FIG. 6. Illustrates a sequence of SEQ ID NO. 22 from which the NY-ESO-$1_{157-165}$ epitope is liberated by immunoproteasomal processing.

Unless otherwise clear from the context of the use of a term herein, the following listed terms shall generally have the indicated meanings for purposes of this description.

PROFESSIONAL ANTIGEN-PRESENTING CELL (pAPC)—a cell that possesses T cell costimulatory molecules and is able to induce a T cell response. Well characterized pAPCs include dendritic cells, B cells, and macrophages.

PERIPHERAL CELL—a cell that is not a pAPC.

HOUSEKEEPING PROTEASOME—a proteasome normally active in peripheral cells, and generally not present or not strongly active in pAPCs.

IMMUNOPROTEASOME—a proteasome normally active in pAPCs; the immunoproteasome is also active in some peripheral cells in infected tissues or following exposure to interferon.

EPITOPE—a molecule or substance capable of stimulating an immune response. In preferred embodiments, epitopes according to this definition include but are not necessarily limited to a polypeptide and a nucleic acid encoding a polypeptide, wherein the polypeptide is capable of stimulating an immune response. In other preferred embodiments, epitopes according to this definition include but are not necessarily limited to peptides presented on the surface of cells, the peptides being non-covalently bound to the binding cleft of class I MHC, such that they can interact with T cell receptors (TCR). Epitopes presented by class I MHC may be in immature or mature form. "Mature" refers to an MHC epitope in distinction to any precursor ("immature") that may include or consist essentially of a housekeeping epitope, but also includes other sequences in a primary translation product that are removed by processing, including without limitation, alone or in any combination, proteasomal digestion, N-terminal trimming, or the action of exogenous enzymatic activities. Thus, a mature epitope may be provided embedded in a somewhat longer polypeptide, the immunological potential of which is due, at least in part, to the embedded epitope; or in its ultimate form that can bind in the MHC binding cleft to be recognized by TCR, respectively.

MHC EPITOPE—a polypeptide having a known or predicted binding affinity for a mammalian class I or class II major histocompatibility complex (MHC) molecule.

HOUSEKEEPING EPITOPE—In a preferred embodiment, a housekeeping epitope is defined as a polypeptide fragment that is an MHC epitope, and that is displayed on a cell in which housekeeping proteasomes are predominantly active. In another preferred embodiment, a housekeeping epitope is defined as a polypeptide containing a housekeeping epitope according to the foregoing definition, that is flanked by one to several additional amino acids. In another preferred embodiment, a housekeeping epitope is defined as a nucleic acid that encodes a housekeeping epitope according to the foregoing definitions. Exemplary housekeeping epitopes are provide in U.S. application Ser. No. 10/117,937, filed on Apr. 4, 2002; and U.S. Provisional Application Nos. 60/282,211, filed on Apr. 6, 2001; 60/337,017, filed on Nov. 7, 2001; 60/363210 filed Mar. 7, 2002; and 60/409,123, filed on Sep. 5, 2002; all of which are entitled EPITOPE SEQUENCES, and all of which above were incorporated herein by reference in their entireties.

IMMUNE EPITOPE—In a preferred embodiment, an immune epitope is defined as a polypeptide fragment that is an MHC epitope, and that is displayed on a cell in which immunoproteasomes are predominantly active. In another preferred embodiment, an immune epitope is defined as a polypeptide containing an immune epitope according to the foregoing definition, that is flanked by one to several additional amino acids. In another preferred embodiment, an immune epitope is defined as a polypeptide including an epitope cluster sequence, having at least two polypeptide sequences having a known or predicted affinity for a class I MHC. In yet another preferred embodiment, an immune epitope is defined as a nucleic acid that encodes an immune epitope according to any of the foregoing definitions.

TARGET CELL—a cell to be targeted by the vaccines and methods of the invention. Examples of target cells according to this definition include but are not necessarily limited to: a neoplastic cell and a cell harboring an intracellular parasite, such as, for example, a virus, a bacterium, or a protozoan. Target cells can also include cells that are targeted by CTL as a part of assays to determine or confirm proper epitope liberation and processing by a cell expressing immunoproteasome, to determine T cell specificity or immunogenicity for a desired epitope. Such cells may be transformed to express the substrate or liberation sequence, or the cells can simply be pulsed with peptide/epitope.

TARGET-ASSOCIATED ANTIGEN (TAA)—a protein or polypeptide present in a target cell. TUMOR-ASSOCIATED ANTIGENS (TuAA)—a TAA, wherein the target cell is a neoplastic cell.

HLA EPITOPE—a polypeptide having a known or predicted binding affinity for a human class I or class II HLA complex molecule.

ANTIBODY—a natural immunoglobulin (Ig), poly- or monoclonal, or any molecule composed in whole or in part of an Ig binding domain, whether derived biochemically or by use of recombinant DNA. Examples include inter alia, F(ab), single chain Fv, and Ig variable region-phage coat protein fusions.

ENCODE—an open-ended term such that a nucleic acid encoding a particular amino acid sequence can consist of codons specifying that (poly)peptide, but can also comprise additional sequences either translatable, or for the control of transcription, translation, or replication, or to facilitate manipulation of some host nucleic acid construct.

SUBSTANTIAL SIMILARITY—this term is used to refer to sequences that differ from a reference sequence in an inconsequential way as judged by examination of the sequence. Nucleic acid sequences encoding the same amino acid sequence are substantially similar despite differences in degenerate positions or modest differences in length or composition of any non-coding regions. Amino acid sequences differing only by conservative substitution or minor length variations are substantially similar. Additionally, amino acid sequences comprising housekeeping epitopes that differ in the number of N-terminal flanking residues, or immune epitopes and epitope clusters that differ in the number of flanking residues at either terminus, are substantially similar. Nucleic acids that encode substantially similar amino acid sequences are themselves also substantially similar.

FUNCTIONAL SIMILARITY—this term is used to refer to sequences that differ from a reference sequence in an inconsequential way as judged by examination of a biological or biochemical property, although the sequences may not be substantially similar. For example, two nucleic acids can be useful as hybridization probes for the same sequence but encode differing amino acid sequences. Two peptides that induce cross-reactive CTL responses are functionally similar even if they differ by non-conservative amino acid substitutions (and thus do not meet the substantial similarity definition). Pairs of antibodies, or TCRs, that recognize the same epitope can be functionally similar to each other despite whatever structural differences exist. In testing for functional similarity of immunogenicity one would generally immunize with the "altered" antigen and test the ability of the elicited response (Ab, CTL, cytokine production, etc.) to recognize the target antigen. Accordingly, two sequences may be designed to differ in certain respects while retaining the same function. Such designed sequence variants are among the embodiments of the present invention.

EXPRESSION CASSETTE—a polynucleotide sequence encoding a polypeptide, operably linked to a promoter and other transcription and translation control elements, including but not limited to enhancers, termination codons, internal ribosome entry sites, and polyadenylation sites. The cassette can also include sequences that facilitate moving it from one host molecule to another.

EMBEDDED EPITOPE—an epitope contained within a longer polypeptide, also can include an epitope in which either the N-terminus or the C-terminus is embedded such that the epitope is not in an interior position.

MATURE EPITOPE—a peptide with no additional sequence beyond that present when the epitope is bound in the MHC peptide-binding cleft.

EPITOPE CLUSTER—a polypeptide, or a nucleic acid sequence encoding it, that is a segment of a native protein sequence comprising two or more known or predicted epitopes with binding affinity for a shared MHC restriction element, wherein the density of epitopes within the cluster is greater than the density of all known or predicted epitopes with binding affinity for the shared MHC restriction element within the complete protein sequence, and as disclosed in U.S. patent application Ser. No. 09/561,571 entitled EPITOPE CLUSTERS.

SUBSTRATE OR LIBERATION SEQUENCE—a designed or engineered sequence comprising or encoding a housekeeping epitope (according to the first of the definitions offered above) embedded in a larger sequence that provides a context allowing the housekeeping epitope to be liberated by immunoproteasomal processing, directly or in combination with N-terminal trimming or other processes. terminal Degradation of cytosolic proteins takes place via the ubiquitin-dependent multi-catalytic multi-subunit protease system known as the proteasome. The proteasome degrades cytosolic proteins generating fragments that can then be translocated from the cytosol into the endoplasmic reticulum (ER) for loading onto class I MHC. Such protein fragments shall be referred to as class I peptides. The peptide loaded MHC are subsequently transported to the cell surface where they can be detected by CTL.

The multi-catalytic activity of the proteasome is the result of its multi-subunit structure. Subunits are expressed from different genes and assembled post-translationally into the proteasome complex. A key feature of the proteasome is its bimodal activity, which enables it to exert its protease, or cleavage function, with two discrete kinds of cleavage patterns. This bimodal action of the proteasome is extremely fundamental to understanding how CTL are targeted to recognize peripheral cells in the body and how this targeting requires synchronization between the immune system and the targeted cells.

The housekeeping proteasome is constitutively active in all peripheral cells and tissues of the body. The first mode of operation for the housekeeping proteasome is to degrade cellular protein, recycling it into amino acids. Proteasome function is therefore a necessary activity for cell life. As a corollary to its housekeeping protease activity, however, class I peptides generated by the housekeeping proteasome are presented on all of the peripheral cells of the body.

The proteasome's second mode of function is highly exclusive and occurs specifically in pAPCs or as a consequence of a cellular response to interferons (IFNs). In its second mode of activity the proteasome incorporates unique subunits, which replace the catalytic subunits of the constitutive housekeeping proteasome. This "modified" proteasome has been called the immunoproteasome, owing to its expression in pAPC and as a consequence of induction by IFN in body cells.

APC define the repertoire of CTL that recirculate through the body and are potentially active as killer cells. CTL are activated by interacting with class I peptide presented on the surface of a pAPC. Activated CTL are induced to proliferate and caused to recirculate through the body in search of diseased cells. This is why the CTL response in the body is defined specifically by the class I peptides produced by the pAPC. It is important to remember that pAPCs express the immunoproteasome, and that as a consequence of the bimodal activity of the proteasome, the cleavage pattern of proteins (and the resultant class I peptides produced) are different from those in peripheral body cells which express housekeeping proteasome. The differential proteasome activity in pAPC and peripheral body cells, therefore, is important to consider during natural infection and with therapeutic CTL vaccination strategies.

All cells of the body are capable of producing IFN in the event that they are infected by a pathogen such as a virus. IFN production in turn results in the expression of the immunoproteasome in the infected cell. Viral antigens are thereby processed by the immunoproteasome of the infected cell and the consequent peptides are displayed with class I MHC on the cell surface. At the same time, pAPC are sequestering virus antigens and are processing class I peptides with their immunoproteasome activity, which is normal for the pAPC cell type. The CTL response in the body is being stimulated specifically by the class I peptides produced by the pAPC. Fortunately, the infected cell is also producing class I peptides from the immunoproteasome, rather than the normal housekeeping proteasome. Thus, virus-related class I peptides are being produced that enable detection by the ensuing CTL response. The CTL immune response is induced by pAPC, which normally produce different class I peptides compared to peripheral body cells, owing to different proteasome activity. Therefore, during infection there is epitope synchronization between the infected cell and the immune system.

This is not the case with tumors and chronic viruses, which block the interferon system. For tumors there is no infection in the tumor cell to induce the immunoproteasome expression, and chronic virus infection either directly or indirectly blocks immunoproteasome expression. In both cases the diseased cell maintains its display of class I peptides derived from housekeeping proteasome activity and avoids effective surveillance by CTL.

In the case of therapeutic vaccination to eradicate tumors or chronic infections, the bimodal function of the proteasome and its differential activity in APC and peripheral cells of the body is significant. Upon vaccination with protein antigen, and before a CTL response can occur, the antigen must be acquired and processed into peptides that are subsequently presented on class I MHC on the pAPC surface. The activated CTL recirculate in search of cells with similar class I peptide on the surface. Cells with this peptide will be subjected to destruction by the cytolytic activity of the CTL. If the targeted diseased cell does not express the immunoproteasome, which is present in the pAPC, then the epitopes are not synchronized and CTL fail to find the desired peptide target on the surface of the diseased cell.

Preferably, therapeutic vaccine design takes into account the class I peptide that is actually present on the target tissue. That is, effective antigens used to stimulate CTL to attack diseased tissue are those that are naturally processed and presented on the surface of the diseased tissue. For tumors and chronic infection this generally means that the CTL epitopes are those that have been processed by the housekeeping proteasome. In order to generate an effective therapeutic vaccine, CTL epitopes are identified based on the knowledge that such epitopes are, in fact, produced by the housekeeping proteasome system. Once identified, these epitopes, embodied as peptides, can be used to successfully immunize or induce therapeutic CTL responses against housekeeping proteasome expressing target cells in the host.

However, in the case of DNA vaccines, there can be an additional consideration. The immunization with DNA requires that APCs take up the DNA and express the encoded proteins or peptides. It is possible to encode a discrete class I peptide on the DNA. By immunizing with this construct, APCs can be caused to express a housekeeping epitope, which is then displayed on class I MHC on the surface of the cell for stimulating an appropriate CTL response. Constructs for generation of proper termini of housekeeping epitopes have been described in U.S. patent application Ser. No. 09/561,572 entitled EXPRESSION VECTORS ENCODING EPITOPES OF TARGET-ASSOCIATED ANTIGENS, filed on Apr. 28, 2000, which is incorporated herein by reference in its entirety.

Embodiments of the invention provide expression cassettes that encode one or more embedded housekeeping epitopes, and methods for designing and testing such expression cassettes. The expression cassettes and constructs can encode epitopes, including housekeeping epitopes, derived from antigens that are associated with targets. Housekeeping epitopes can be liberated from the translation product(s) of the cassettes. For example, in some embodiments of the invention, the housekeeping epitope(s) can be flanked by arbitrary sequences or by sequences incorporating residues known to be favored in immunoproteasome cleavage sites. In further embodiments of the invention multiple epitopes can be arrayed head-to-tail. In some embodiments, these arrays can be made up entirely of housekeeping epitopes. Likewise, the arrays can include alternating housekeeping and immune epitopes. Alternatively, the arrays can include housekeeping epitopes flanked by immune epitopes, whether complete or distally truncated. In some preferred embodiments, each housekeeping epitope can be flanked on either side by an immune epitope, such that an array of such arrangements has two immune epitopes between each housekeeping epitope. Further, the arrays can be of any other similar arrangement. There is no restriction on placing a housekeeping epitope at the terminal positions of the array. The vectors can additionally contain authentic protein coding sequences or segments thereof containing epitope clusters as a source of immune epitopes.

Several disclosures make reference to polyepitopes or string-of-bead arrays. See, for example, WO0119408A1, Mar. 22, 2001; WO9955730A2, Nov. 4, 1999; WO0040261A2, Jul. 13, 2000; WO9603144A1, Feb. 8, 1996; EP1181314A1, Feb. 27, 2002; WO0123577A3, April 5; U.S. Pat No. 6,074,817, Jun. 13, 2000; U.S. Pat. No. 5,965,381, Oct. 12, 1999; WO9741440A1, Nov. 6, 1997; U.S. Pat. No. 6,130,066, Oct. 10, 2000; U.S. Pat. No.6,004,777, Dec. 21, 1999; U.S. Pat. No. 5,990,091, Nov. 23, 1999; WO9840501A1, Sep. 17, 1998; WO9840500A1, Sep. 17, 1998; WO018035A2, Mar. 15, 2001; WO02068654A2, Sep. 6, 2002; WO0189281A2, Nov. 29, 2001; WO0158478A, Aug. 16, 2001; EP1118860A1, Jul. 25, 2001; WO011040A1, Feb. 15, 2001; WO0073438A1, Dec. 7, 2000; WO0071158A1, Nov. 30, 2000; WO0066727A1, Nov. 9, 2000; WO0052451A1, Sep. 8, 2000; WO0052157A1, Sep. 8, 2000; WO0029008A2, May 25, 2000; WO0006723A1, Feb. 10, 2000; all of which are incorporated by reference in their entirety. Additional disclosures, all of which are hereby incorporated by reference in their entirety, include Palmowski M J, et al—J Immunol 2002;168(9):4391-8; Fang Z Y, et al—Virology 2001;291(2):272-84; Firat H, et al—J Gene Med 2002;4(1):38-45; Smith S G, et al—Clin Cancer Res 2001;7 (12):4253-61; Vonderheide R H, et al—Clin Cancer Res 2001; 7(11):3343-8; Firat H, et al—Eur J Immunol 2001;31 (10):3064-74; Le T T, et al—Vaccine 2001;19(32):4669-75; Fayolle C, et al—J Virol 2001;75(16):7330-8; Smith S G—Curr Opin Mol Ther 1999;1(1):10-5; Firat H, et al—Eur J Immunol 1999;29(10):3112-21; Mateo L, et al—J Immunol 1999;163(7):4058-63; Heemskerk M H, et al—Cell Immunol 1999;195(1):10-7; Woodberry T, et al—J Virol 1999;73(7): 5320-5; Hanke T, et al—Vaccine 1998;16(4):426-35; Thomson S A, et al—J Immunol 1998;160(4):1717-23; Toes R E, et al—Proc Natl Acad Sci USA 1997;94(26):14660-5; Thomson S A, et al—J Immunol 1996;157(2):822-6; Thomson S A, et al—Proc Natl Acad Sci USA 1995;92(13):5845-9; Street M D, et al—Immunology 2002;106(4):526-36; Hirano K, et al—Histochem Cell Biol 2002;117(1):41-53; Ward S M, et al—Virus Genes 2001;23(1):97-104; Liu W J, et al—Virology 2000;273(2):374-82; Gariglio P, et al—Arch Med Res 1998;29(4):279-84; Suhrbier A—Immunol Cell Biol 1997; 75(4):402-8; Fomsgaard A, et al—Vaccine 1999;18(7-8): 681-91; An L L, et al—J Virol 1997;71(3):2292-302; Whitton J L, et al—J Virol 1993;67(1):348-52; Ripalti A, et al—J Clin Microbiol 1994;32(2):358-63; and Gilbert, S. C., et al., Nat. Biotech. 15:1280-1284, 1997.

One important feature that the disclosures in the preceding paragraph all share is their lack of appreciation for the desirability of regenerating housekeeping epitopes when the construct is expressed in a pAPC. This understanding was not apparent until the present invention. Embodiments of the invention include sequences, that when processed by an immune proteasome, liberate or generate a housekeeping epitope. Embodiments of the invention also can liberate or generate such epitopes in immunogenically effective amounts. Accordingly, while the preceding references contain disclosures relating to polyepitope arrays, none is enabling of the technology necessary to provide or select a polyepitope capable of liberating a housekeeping epitope by action of an immunoproteasome in a pAPC. In contrast, embodiments of the instant invention are based upon a recognition of the desirability of achieving this result. Accordingly, embodiments of the instant invention include any nucleic acid construct that encodes a polypeptide containing at least one housekeeping epitope provided in a context that promotes its generation via immunoproteasomal activity, whether the housekeeping epitope is embedded in a string-of-beads array or some other arrangement. Some embodiments of the invention include uses of one or more of the nucleic acid constructs or their products that are specifically disclosed in any one or more of the above-listed references. Such uses include, for example, screening a polyepitope for proper liberation context of a housekeeping epitope and/or an immune epitope, designing an effective immunogen capable of causing presentation of a housekeeping epitope and/or an immune epitope on a pAPC, immunizing a patient, and the like. Alternative embodiments include use of only a subset of such nucleic acid constructs or a single such construct, while specifically excluding one or more other such constructs, for any of the purposes disclosed herein. Some preferred embodiments employ these and/or other nucleic acid sequences encoding polyepitope arrays alone or in combination. For example, some embodiments exclude use of polyepitope arrays from one or more of the above-mentioned references. Other embodiments may exclude any combination or all of the polyepitope arrays from the above-mentioned references collectively. Some embodiments include viral and/or bacterial vectors encoding polyepitope arrays, while other embodiments specifically exclude such vectors. Such vectors can encode carrier proteins that may have some immunostimulatory effect. Some embodiments include such vectors with such immunostimulatory/immunopotentiating effects, as opposed to immunogenic effects, while in other embodiments such vectors may be included. Further, in some instances viral and bacterial vectors encode the desired epitope as a part of substantially complete proteins which are not associated with the target cell. Such vectors and products are included in some embodiments, while excluded from others. Some embodiments relate to repeated administration of vectors. In some of those embodiments, nonviral and nonbacterial vectors are included. Likewise, some embodiments include arrays that contain extra amino acids between epitopes, for example anywhere from 1-6 amino acids, or more, in some embodiments, while other embodiments specifically exclude such arrays.

Embodiments of the present invention also include methods, uses, therapies, and compositions directed to various types of targets. Such targets can include, for example, neoplastic cells such as those listed below, for example; and cells infected with any virus, bacterium, protozoan, fungus, or other agents, examples of which are listed below, in Tables 1-5, or which are disclosed in any of the references listed above. Alternative embodiments include the use of only a subset of such neoplastic cells and infected cells listed below, in Tables 1-5, or in any of the references disclosed herein, or a single one of the neoplastic cells or infected cells, while specifically excluding one or more other such neoplastic cells or infected cells, for any of the purposes disclosed herein. The following are examples of neoplastic cells that can be targeted: human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non Hodgkin's disease), multiple myeloma, Waldenstrom's macroglobulinemia, heavy chain disease, hepatocellular cancer, brain cancer, stomach cancer, liver cancer, and the like. Examples of infectious agents that infect the target cells can include the following: adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus JC, hepatitis C virus, measles virus, rubella virus, human immunodeficiency virus (HIV), human T cell leukemia virus I, human T cell leukemia virus II, *Chlamydia, Listeria, Salmonella, Legionella, Brucella, Coxiella, Rickettsia, Mycobacterium, Leishmania, Trypanasoma, Toxoplasma, Plasmodium*, and the like. Exemplary infectious agents and neoplastic cells are also included in Tables 1-5 below.

Furthermore the targets can include neoplastic cells described in or cells infected by agents that are described in any of the following references: Jäger, E. et al., "Granulocyte-macrophage-colony-stimulating factor enhances immune responses to melanoma-associated peptides in vivo," *Int. J Cancer*, 67:54-62 (1996); Kündig, T.M., Althage, A., Hengartner, H. & Zinkernagel, R. M., "A skin test to assess CD8+ cytotoxic T cell activity," *Proc. Natl. Acad Sci. USA*, 89:7757-76 (1992); Bachmann, M.F. & Kundig, T. M., "In vitro vs. in vivo assays for the assessment of T- and B-cell function,"

Curr. Opin. Immunol., 6:320-326 (1994); Kundig et al., "On the role of antigen in maintaining cytotoxic T cell memory," *Proceedings of the National Academy of Sciences of the United States of America*, 93:9716-23 (1996); Steinmann, R.M., "The dendritic cells system and its role in immunogenicity," *Annual Review of Immunology* 9:271-96 (1991); Inaba, K. et al., "Identification of proliferating dendritic cell precursors in mouse blood," *Journal of Experimental Medicine*, 175:1157-67 (1992); Young, J. W. & Inaba, K., "Dendritic cells as adjuvants for class I major histocompatibility complex-restricted anti-tumor immunity," *Journal of Experimental Medicine*, 183:7-11 (1996); Kuby, Janis, *Immunology*, Second Edition, Chapter 15, W. H. Freeman and Company (1991); Austenst, E., Stahl, T., and de Gruyter, Walter, *Insulin Pump Therapy*, Chapter 3, Berlin, N.Y. (1990); Remington, *The Science and Practice of Pharmacy*, Nineteenth Edition, Chapters 86-88 (1985); Cleland, Jeffery L. and Langer, Robert (Editor), "Formulation and delivery of proteins and peptides," *American Chemical Society* (ACS Symposium Series, No. 567) (1994); Santus, Giancarlo and Baker, Richard, "Osmotic drug delivery: A review of the patent literature," *Journal of Controlled Release*, 35:1-21 (1995); Rammensee, U.S. Pat. No. 5,747,269, issued May 5, 1998; Magruder, U.S. Pat. No. 5,059,423, issued Oct. 22, 1991; Sandbrook, U.S. Pat. No. 4,552,651, issued Nov. 25, 1985; Eckenhoff et al., U.S. Pat. No. 3,987,790, issued Oct. 26, 1976; Theeuwes, U.S. Pat. No. 4,455,145, issued Jun. 19, 1984; Roth et al. U.S. Pat. No. 4,929,233, issued May 29 1990; van der Bruggen et al., U.S. Pat. No. 5,554,506, issued Sep. 10, 1996; Pfreundschuh, U.S. Pat. No. 5,698,396, issued Dec. 16, 1997; Magruder, U.S. Pat. No. 5,110,596, issued May 5, 1992; Eckenhoff, U.S. Pat. No. 4,619,652, issued Oct. 28, 1986; Higuchi et al., U.S. Pat. No. 3,995,631, issued Dec. 7, 1976; Maruyama, U.S. Pat. No. 5,017,381, issued May 21, 1991; Eckenhoff, U.S. Pat. No. 4,963,141, issued Oct. 16, 1990; van der Bruggen et al., U.S. Pat. No. 5,558,995, issued Sep. 24, 1996; Stolzenberg et al. U.S. Pat. No. 3,604,417, issued Sep. 14, 1971; Wong et al., U.S. Pat. No. 5,110,597, issued May 5, 1992; Eckenhoff, U.S. Pat. No. 4,753,651, issued Jun. 28, 1988; Theeuwes, U.S. Pat. No. 4,203,440, issued May 20, 1980; Wong et al. U.S. Pat. No. 5,023,088, issued Jun. 11, 1991; Wong et al., U.S. Pat. No. 4,976,966, issued Dec. 11, 1990; Van den Eynde et al., U.S. Pat. No. 5,648,226, issued Jul. 15, 1997; Baker et al., U.S. Pat. No. 4,838,862, issued Jun. 13, 1989; Magruder, U.S. Pat. No. 5,135,523, issued Aug. 4, 1992; Higuchi et al., U.S. Pat. No. 3,732,865, issued May 15, 1975; Theeuwes, U.S. Pat. No. 4,286,067, issued Aug. 25, 1981; Theeuwes et al., U.S. Pat. No. 5,030,216, issued Jul. 9, 1991; Boon et al., U.S. Pat. No. 5,405,940, issued Apr. 11, 1995; Faste, U.S. Pat. No. 4,898, 582, issued Feb. 6, 1990; Eckenhoff, U.S. Pat. No. 5,137,727, issued Aug. 11, 1992; Higuchi et al., U.S. Pat. No. 3,760,804, issued Sep. 25, 1973; Eckenhoff et al., U.S. Pat. No. 4,300, 558, issued Nov. 12, 1981; Magruder et al., U.S. Pat. No. 5,034,229, issued Jul. 23, 1991; Boon et al., U.S. Pat. No. 5,487,974, issued Jan. 30, 1996; Kam et al., U.S. Pat. No. 5,135,498, issued Aug. 4, 1992; Magruder et al., U.S. Pat. No. 5,174,999, issued Dec. 29, 1992; Higuchi, U.S. Pat. No. 3,760,805, Sep. 25, 1973; Michaels, U.S. Pat. No. 4,304,232, issued Dec. 8, 1981; Magruder et al., U.S. Pat. No. 5,037,420, issued Oct. 15, 1991; Wolfel et al., U.S. Pat. No. 5,530,096, issued Jun. 25, 1996; Athadye et al., U.S. Pat. No. 5,169,390, issued Dec. 8, 1992; Balaban et al., U.S. Pat. No. 5,209,746, issued May 11, 1993; Higuchi, U.S. Pat. No. 3,929,132, issued Dec. 30, 1975; Michaels, U.S. Pat. No. 4,340,054, issued Jul. 20, 1982; Magruder et al., U.S. Pat. No. 5,057,318, issued Oct. 15, 1991; Wolfel et al., U.S. Pat. No. 5,519,117, issued May 21, 1996; Athadye et al., U.S. Pat. No. 5,257,987, issued Nov. 2, 1993; Linkwitz et al., U.S. Pat. No. 5,221,278, issued Jun. 22, 1993; Nakano et al., U.S. Pat. No. 3,995,632, issued Dec. 7, 1976; Michaels, U.S. Pat. No. 4,367,741, issued January 11, 1983; Eckenhoff, U.S. Pat. No. 4,865,598, issued Sep. 12, 1989; Lethe et al., U.S. Pat. No. 5,774,316, issued Apr. 28, 1998; Eckenhoff, U.S. Pat. No. 4,340,048, issued Jul. 20, 1982; Wong, U.S. Pat. No. 5,223,265, issued Jun. 29, 1993; Higuchi et al., U.S. Pat. No. 4,034,756, issued Jul. 12, 1977; Michaels, U.S. Pat. No. 4,450,198, issued May 22, 1984; Eckenhoff et al., U.S. Pat. No. 4,865,845, issued Sep. 12, 1989; Melief et. al., U.S. Pat. No. 5,554,724, issued Sep. 10, 1996; Eckenhoff et al., U.S. Pat. No. 4,474,575, issued Oct. 2, 1984; Theeuwes, U.S. Pat. No. 3,760,984, issued Sep. 25, 1983; Eckenhoff, U.S. Pat. No. 4,350,271, issued Sep. 21, 1982; Eckenhoff et al., U.S. Pat. No. 4,855, 141, issued Aug. 8, 1989; Zingerman, U.S. Pat. No. 4,872, 873, issued Oct. 10, 1989; Townsend et al., U.S. Pat. No. 5,585,461, issued Dec. 17, 1996; Carulli, J.P. et al., *J. Cellular Biochem Suppl.*, 30/31:286-96 (1998); Tiireci, Ö., Sahin, U., and Pfreundschuh, M., "Serological analysis of human tumor antigens: molecular definition and implications," *Molecular Medicine Today*, 3:342 (1997); Rammensee et al., *MHC Ligands and Peptide Motifs*, Landes Bioscience Austin, Tex., 224-27, (1997); Parker et al., "Scheme for ranking potential HLA-A2 binding peptides based on independent binding of individual peptide side-chains," *J. Immunol.* 152:163-175 (1994); Kido & Ohshita, *Anal. Biochem.*, 230:41-47 (1995); Yamada et al., *J. Biochem.* (Tokyo), 95:1155-60 (1984); Kawashima et al., *Kidney Int.*, 54:275-8 (1998); Nakabayshi & Ikezawa, *Biochem. Int.* 16:1119-25 (1988); Kanaseki & Ohkuma, *J. Biochem.* (Tokyo), 110:541-7 (1991); Wattiaux et al., *J. Cell Biol.*, 78:349-68 (1978); Lisman et al., *Biochem. J.*, 178:79-87 (1979); Dean, B., *Arch. Biochem. Biophys.*, 227: 154-63 (1983); Overdijk et al., *Adv. Exp. Med. Biol.*, 101:601-10 (1978); Stromhaug et al., *Biochem. J.*, 335:217-24 (1998); Escola et al., *J. Biol. Chem.*, 271:27360-05 (1996); Hammond et al., *Am. J. Physiol.*, 267:F516-27 (1994); Williams & Smith, *Arch. Biochem. Biophys.*, 305:298-306 (1993); Marsh, M., *Methods Cell Biol.*, 31:319-34 (1989); Schmid & Mellman, *Prog. Clin. Biol. Res.*, 270:35-49 (1988); Falk, K. et al., *Nature*, 351:290, (1991); Ausubel et al., *Short Protocols in Molecular Biology*, Third Edition, Unit 11.2 (1997); hypertext transfer protocol address syfpeithi.de/Scripts/MHC-Server.dl1/EpitopePrediction.htm; Levy, Morel, S. et al., *Immunity* 12:107-117 (2000); Seipelt et al., "The structures of picornaviral proteinases," *Virus Research*, 62:159-68, 1999; Storkus et al., U.S. Pat. No. 5,989,565, issued Nov. 23, 1999; Morton, U.S. Pat. No. 5,993,828, issued Nov. 30, 1999; *Virus Research* 62:159-168, (1999); Simard et al., U.S. patent application Ser No. 10/026,066, filed Dec. 7, 2001; Simard et al., U.S. patent application Ser No. 09/561,571, filed Apr. 28, 2000; Simard et al., U.S. patent application Ser. No. 09/561, 572, filed Apr. 28, 2000; Kundig et al., WO 99/02183, Jan. 21, 1999; Simard et al., U.S. patent application Ser No. 09/561, 074, filed Apr. 28, 2000; Simard et al., U.S. patent application Ser No. 10/225,568, filed Aug. 20, 2002; Simard et al., U.S. patent application Ser No. 10/005,905, filed Nov. 7, 2001; Simard et al., U.S. patent application Ser No. 09/561,074, filed Apr. 28, 2000.

Additional embodiments of the invention include methods, uses, therapies, and compositions relating to a particular antigen, whether the antigen is derived from, for example, a target cell or an infective agent, such as those mentioned above. Some preferred embodiments employ the antigens listed herein, in Tables 1-5, or in the list below, alone, as subsets, or in any combination. For example, some embodiments exclude use of one or more of those antigens. Other embodiments may exclude any combination or all of those antigens. Several examples of such antigens include MelanA (MART-I), gp100 (Pmel 17), tyrosinase, TRP-1, TRP-2, MAGE-1, MAGE-3, BAGE, GAGE-1, GAGE-2, CEA, RAGE, NY-ESO, SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nmn-23H1, PSA, TAG-72-4, CAM 17.1, NuMa, K-ras, β-Catenin, CDK4, Mum-1, p16, as well as any of those set forth in the above mentioned references. Other antigens are included in Tables 1-4 below.

Further embodiments include methods, uses, compositions, and therapies relating to epitopes, including, for example those epitopes listed in Tables 1-5. These epitopes can be useful to flank housekeeping epitopes in screening vectors, for example. Some embodiments include one or more epitopes from Tables 1-5, while other embodiments specifically exclude one or more of such epitopes or combinations thereof.

TABLE 1

| Virus | Protein | AA Position | T cell epitope MHC ligand (Antigen) | MHC molecule |
|---|---|---|---|---|
| Adenovirus 3 | E3 9Kd | 30-38 | LIVIGILIL (SEQ. ID NO.: 44) | HLA-A*0201 |
| Adenovirus 5 | EIA | 234-243 | SGPSNTPPEI (SEQ. ID NO.: 45) | H2-Db |
| Adenovirus 5 | E1B | 192-200 | VNIRNCCYI (SEQ. ID NO.: 46) | H2-Db |
| Adenovirus 5 | EIA | 234-243 | SGPSNIPPEI (T > I) (SEQ. ID NO.: 47) | H2-Db |
| CSFV | NS polyprotein | 2276-2284 | ENALLVALF (SEQ. ID NO.: 48) | SLA, haplotype d/d |
| Dengue virus 4 | NS3 | 500-508 | TPEGIIPTL (SEQ. ID NO.: 49) | HLA-B*3501 |
| EBV | LMP-2 | 426-434 | CLGGLLTMV (SEQ. ID NO.: 50) | HLA-A*0201 |
| EBV | EBNA-1 | 480-484 | NIAEGLRAL (SEQ. ID NO.: 51) | HLA-A*0201 |
| EBV | EBNA-1 | 519-527 | NLRRGTALA (SEQ. ID NO.: 52) | HLA-A*0201 |
| EBV | EBNA-1 | 525-533 | ALAIPQCRL (SEQ. ID NO.: 53) | HLA-A*0201 |
| EBV | EBNA-1 | 575-582 | VLKDAIKDL (SEQ. ID NO.: 54) | HLA-A*0201 |
| EBV | EBNA-1 | 562-570 | FMVFLQTHI (SEQ. ID NO.: 55) | HLA-A*0201 |
| EBV | EBNA-2 | 15-23 | HLIVDTDSL (SEQ. ID NO.: 56) | HLA-A*0201 |
| EBV | EBNA-2 | 22-30 | SLGNPSLSV (SEQ. ID NO.: 57) | HLA-A*0201 |
| EBV | EBNA-2 | 126-134 | PLASAMRML (SEQ. ID NO.: 58) | HLA-A*0201 |
| EBV | EBNA-2 | 132-140 | RMLWMANYI (SEQ. ID NO.: 59) | HLA-A*0201 |
| EBV | EBNA-2 | 133-141 | MLWMANYIV (SEQ. ID NO.: 60) | HLA-A*0201 |
| EBV | EBNA-2 | 151-159 | ILPQGPQTA (SEQ. ID NO.: 61) | HLA-A*0201 |
| EBV | EBNA-2 | 171-179 | PLRPTAPTI (SEQ. ID NO.: 62) | HLA-A*0201 |
| EBV | EBNA-2 | 205-213 | PLPPATLTV (SEQ. ID NO.: 63) | HLA-A*0201 |
| EBV | EBNA-2 | 246-254 | RMHLPVLHV (SEQ. ID NO.: 64) | HLA-A*0201 |
| EBV | EBNA-2 | 287-295 | PMPLPPSQL (SEQ. ID NO.: 65) | HLA-A*0201 |
| EBV | EBNA-2 | 294-302 | QLPPPAAPA (SEQ. ID NO.: 66) | HLA-A*0201 |
| EBV | EBNA-2 | 381-389 | SMPELSPVL (SEQ. ID NO.: 67) | HLA-A*0201 |
| EBV | EBNA-2 | 453-461 | DLDESWDYI (SEQ. ID NO.: 68) | HLA-A*0201 |
| EBV | BZLF1 | 43-51 | PLPCVLWPV (SEQ. ID NO.: 69) | HLA-A*0201 |
| EBV | BZLF1 | 167-175 | SLEECDSEL (SEQ. ID NO.: 70) | HLA-A*0201 |
| EBV | BZLF1 | 176-184 | EIKRYKNRV (SEQ. ID NO.: 71) | HLA-A*0201 |
| EBV | BZLF1 | 195-203 | QLLQHYREV (SEQ. ID NO.: 72) | HLA-A*0201 |
| EBV | BZLF1 | 196-204 | LLQHYREVA (SEQ. ID NO.: 73) | HLA-A*0201 |
| EBV | BZLFI | 217-225 | LLKQMCPSL (SEQ. ID NO.: 74) | HLA-A*0201 |

TABLE 1-continued

| Virus | Protein | AA Position | T cell epitope MHC ligand (Antigen) | MHC molecule |
|---|---|---|---|---|
| EBV | BZLF1 | 229-237 | SIIPRTPDV (SEQ. ID NO.: 75) | HLA-A*0201 |
| EBV | EBNA-6 | 284-293 | LLDFVRFMGV (SEQ. ID NO.: 76) | HLA-A*0201 |
| EBV | EBNA-3 | 464-472 | SVRDRLARL (SEQ. ID NO.: 77) | HLA-A*0203 |
| EBV | EBNA-4 | 416-424 | IVTDFSVIK (SEQ. ID NO.: 78) | HLA-A*1101 |
| EBV | EBNA-4 | 399-408 | AVFDRKSDAK (SEQ. ID NO.: 79) | HLA-A*0201 |
| EBV | EBNA-3 | 246-253 | RYSIFFDY (SEQ. ID NO.: 80) | HLA-A24 |
| EBV | EBNA-6 | 881-889 | QPRAPIRPI (SEQ. ID NO.: 81) | HLA-B7 |
| EBV | EBNA-3 | 379-387 | RPPIFIRRI (SEQ. ID NO.: 82) | HLA-B7 |
| EBV | EBNA-1 | 426-434 | EPDVPPGAI (SEQ. ID NO.: 83) | HLA-B7 |
| EBV | EBNA-1 | 228-236 | IPQCRLTPL (SEQ. ID NO.: 84) | HLA-B7 |
| EBV | EBNA-1 | 546-554 | GPGPQPGPL (SEQ. ID NO.: 85) | HLA-B7 |
| EBV | EBNA-1 | 550-558 | QPGPLRESI (SEQ. ID NO.: 86) | HLA-B7 |
| EBV | EBNA-1 | 72-80 | R.PQKRPSCI (SEQ. ID NO.: 87) | HLA-B7 |
| EBV | EBNA-2 | 224-232 | PPTPLLTVL (SEQ. ID NO.: 88) | HLA-B7 |
| EBV | EBNA-2 | 241-249 | TPSPPRMHL (SEQ. ID NO.: 89) | HLA-B7 |
| EBV | EBNA-2 | 244-252 | PPRMHLPVL (SEQ. ID NO.: 90) | HLA-B7 |
| EBV | EBNA-2 | 254-262 | VPDQSMHPL (SEQ. ID NO.: 91) | HLA-B7 |
| EBV | EBNA-2 | 446-454 | PPSIDPADL (SEQ. ID NO.: 92) | HLA-B7 |
| EBV | BZLFI | 44-52 | LPCVLWPVL (SEQ. ID NO.: 93) | HLA-B7 |
| EBV | BZLF1 | 222-231 | CPSLDVDSII (SEQ. ID NO.: 94) | HLA-B7 |
| EBV | BZLFI | 234-242 | TPDVLHEDL (SEQ. ID NO.: 95) | HLA-B7 |
| EBV | EBNA-3 | 339-347 | FLRGRAYGL (SEQ. ID NO.: 96) | HLA-B8 |
| EBV | EBNA-3 | 26-34 | QAKWRLQTL (SEQ. ID NO.: 97) | HLA-B8 |
| EBV | EBNA-3 | 325-333 | AYPLHEQHG (SEQ. ID NO.: 98) | HLA-B8 |
| EBV | EBNA-3 | 158-166 | YIKSFVSDA (SEQ. ID NO.: 99) | HLA-B8 |
| EBV | LMP-2 | 236-244 | RRRWRRLTV (SEQ. ID NO.: 100) | HLA-B*2704 |
| EBV | EBNA-6 | 258-266 | RRIYDLIEL (SEQ. ID NO.: 101) | HLA-B*2705 |
| EBV | EBNA-3 | 458-466 | YPLHEQHGM (SEQ. ID NO.: 102) | HLA-B*3501 |
| EBV | EBNA-3 | 458-466 | YPLHEQHGM (SEQ. ID NO.: 103) | HLA-B*3503 |
| HCV | NS3 | 389-397 | HSKKKCDEL (SEQ. ID NO.: 104) | HLA-B8 |
| HCV | env E | 44-51 | ASRCWVAM (SEQ. ID NO.: 105) | HLA-B*3501 |
| HCV | core protein | 27-35 | GQIVGGVYL (SEQ. ID NO.: 106) | HLA-B*40012 |
| HCV | NSI | 77-85 | PPLTDFDQGW (SEQ. ID NO.: 107) | HLA-B*5301 |
| HCV | core protein | 18-27 | LMGYIPLVGA (SEQ. ID NO.: 108) | H2-Dd |
| HCV | core protein | 16-25 | ADLMGYIPLV (SEQ. ID NO.: 109) | H2-Dd |
| HCV | NS5 | 409-424 | MSYSWTGALVTPCAEE (SEQ. ID NO.: 110) | H2-Dd |
| HCV | NS1 | 205-213 | KHPDATYSR (SEQ. ID NO.: 111) | Papa-A06 |
| HCV-1 | NS3 | 400-409 | KLVALGINAV (SEQ. ID NO.: 112) | HLA-A*0201 |

TABLE 1-continued

| Virus | Protein | AA Position | T cell epitope MHC ligand (Antigen) | MHC molecule |
|---|---|---|---|---|
| HCV-1 | NS3 | 440-448 | GDFDSVIDC (SEQ. ID NO.: 113) | Patr-B16 |
| HCV-1 | env E | 118-126 | GNASRCWVA (SEQ. ID NO.: 114) | Patr-BI6 |
| HCV-1 | NSI | 159-167 | TRPPLGNWF (SEQ. ID NO.: 115) | Patr-B13 |
| HCV-1 | NS3 | 351-359 | VPHPNIEEV (SEQ. ID NO.: 116) | Patr-B13 |
| HCV-1 | NS3 | 438-446 | YTGDFDSVI (SEQ. ID NO.: 117) | Patr-B01 |
| HCV-1 | NS4 | 328-335 | SWAIKWEY (SEQ. ID NO.: 118) | Patr-A1 1 |
| HCV-1 | NSI | 205-213 | KHPDATYSR (SEQ. ID NO.: 119) | Patr-A04 |
| HCV-1 | NS3 | 440-448 | GDFDSVIDC (SEQ. ID NO.: 120) | Patr-A04 |
| HIV | gp41 | 583-591 | RYLKDQQLL (SEQ. ID NO.: 121) | HLA_A24 |
| HIV | gagp24 | 267-275 | IVGLNKIVR (SEQ. ID NO.: 122) | HLA-A*3302 |
| HIV | gagp24 | 262-270 | EIYKRWIIL (SEQ. ID NO.: 123) | HLA-B8 |
| HIV | gagp24 | 261-269 | GE1YKRWI1 (SEQ. ID NO.: 124) | HLA-B8 |
| HIV | gagp17 | 93-101 | EIKDTKEAL (SEQ. ID NO.: 125) | HLA-B8 |
| HIV | gp41 | 586-593 | YLKDQQLL (SEQ. ID NO.: 126) | HLA-B8 |
| HIV | gagp24 | 267-277 | ILGLNKIVRMY (SEQ. ID NO.: 127) | HLA-B* 1501 |
| HIV | gp41 | 584-592 | ERYLKDQQL (SEQ. ID NO.: 128) | HLA-B14 |
| HIV | nef | 115-125 | YHTQGYFPQWQ (SEQ. ID NO.: 129) | HLA-B17 |
| HIV | nef | 117-128 | TQGYFPQWQNYT (SEQ. ID NO.: 130) | HLA-B17 |
| HIV | gp120 | 314-322 | GRAFVT1GK (SEQ. ID NO.: 131) | HLA-B*2705 |
| HIV | gagp24 | 263-271 | KRWIILGLN (SEQ. ID NO.: 132) | HLA-B*2702 |
| HIV | nef | 72-82 | QVPLRPMTYK (SEQ. ID NO.: 133) | HLA-B*3501 |
| HIV | nef | 117-125 | TQGYFPQWQ (SEQ. ID NO.: 134) | HLA-B*3701 |
| HIV | gagp24 | 143-151 | HQAISPRTI, (SEQ. ID NO.: 135) | HLA-Cw*0301 |
| HIV | gagp24 | 140-151 | QMVHQAISPRTL (SEQ. ID NO.: 136) | HLA-Cw*0301 |
| HIV | gp120 | 431-440 | MYAPPIGGQI (SEQ. ID NO.: 137) | H2-Kd |
| HIV | gp160 | 318-327 | RGPGRAFVTI (SEQ. ID NO.: 138) | H2-Dd |
| HIV | gp120 | 17-29 | MPGRAFVTI (SEQ. ID NO.: 139) | H2-Ld |
| HIV-1 | RT | 476-484 | ILKEPVHGV (SEQ. ID NO.: 140) | HLA-A*0201 |
| HIV-1 | nef | 190-198 | AFHHVAREL (SEQ. ID NO.: 141) | HLA-A*0201 |
| HIV-1 | gpI60 | 120-128 | KLTPLCVTL (SEQ. ID NO.: 142) | HLA-A*0201 |
| HIV-1 | gp]60 | 814-823 | SLLNATDIAV (SEQ. ID NO.: 143) | HLA-A*0201 |
| HIV-1 | RT | 179-187 | VIYQYMDDL (SEQ. ID NO.: 144) | HLA-A*0201 |
| HIV-1 | gagp 17 | 77-85 | SLYNTVATL (SEQ. ID NO.: 145) | HLA-A*0201 |
| HIV-1 | gp160 | 315-329 | RGPGRAFVT1 (SEQ. ID NO.: 146) | HLA-A*0201 |
| HIV-1 | gp41 | 768-778 | RLRDLLLIVTR (SEQ. ID NO.: 147) | HLA-A3 |
| HIV-1 | nef | 73-82 | QVPLRPMTYK (SEQ. ID NO.: 148) | HLA-A3 |
| HIV-1 | gp120 | 36-45 | TVYYGVPVWK (SEQ. ID NO.: 149) | HLA-A3 |
| HIV-1 | gagp17 | 20-29 | RLRPGGKKK (SEQ. ID NO.: 150) | HLA-A3 |

TABLE 1-continued

| Virus | Protein | AA Position | T cell epitope MHC ligand (Antigen) | MHC molecule |
|---|---|---|---|---|
| HIV-1 | gp120 | 38-46 | VYYGVPVWK (SEQ. ID NO.: 151) | HLA-A3 |
| HIV-1 | nef | 74-82 | VPLRPMTYK (SEQ. ID NO.: 152) | HLA-a*1101 |
| HIV-1 | gagp24 | 325-333 | AIFQSSMTK (SEQ. ID NO.: 153) | HLA-A*1101 |
| HIV-1 | nef | 73-82 | QVPLRPMTYK (SEQ. ID NO.: 154) | HLA-A*1101 |
| HIV-1 | nef | 83-94 | AAVDLSHFLKEK (SEQ. ID NO.: 155) | HLA-A*1101 |
| HIV-1 | gagp24 | 349-359 | ACQGVGGPGGHK (SEQ. ID NO.: 156) | HLA-A*1101 |
| HIV-1 | gagp24 | 203-212 | ETINEEAAEW (SEQ. ID NO.: 157) | HLA-A25 |
| HIV-1 | nef | 128-137 | TPGPGVRYPL (SEQ. ID NO.: 158) | HLA-B7 |
| HIV-1 | gagp 17 | 24-31 | GGKKKYKL (SEQ. ID NO.: 159) | HLA-B8 |
| HIV-1 | gp120 | 2-10 | RVKEKYQHL (SEQ. ID NO.: 160) | HLA-B8 |
| HIV-1 | gagp24 | 298-306 | DRFYKTLRA (SEQ. ID NO.: 161) | HLA-B 14 |
| HIV-1 | NEF | 132-147 | GVRYPLTFGWCYKLVP (SEQ. ID NO.: 162) | HLA-B18 |
| HIV-1 | gagp24 | 265-24 | KRWIILGLNK (SEQ. ID NO.: 163) | HLA-B*2705 |
| HIV-1 | nef | 190-198 | AFHHVAREL (SEQ. ID NO.: 164) | HLA-B*5201 |
| EBV | EBNA-6 | 335-343 | KEHVIQNAF (SEQ. ID NO.: 165) | HLA-B44 |
| EBV | EBNA-6 | 130-139 | EENLLDFVRF (SEQ. ID NO.: 166) | HLA-B*4403 |
| EBV | EBNA-2 | 42-51 | DTPLIPLTIF (SEQ. ID NO.: 167) | HLA-B51 |
| EBV | EBNA-6 | 213-222 | QNGALAINTF (SEQ. ID NO.: 168) | HLA-1362 |
| EBV | EBNA-3 | 603-611 | RLRAEAGVK (SEQ. ID NO.: 169) | HLA-A3 |
| HBV | sAg | 348-357 | GLSPTVWLSV (SEQ. ID NO.: 170) | HLA-A*0201 |
| HBV | SAg | 335-343 | WLSLLVPFV (SEQ. ID NO.: 171) | HLA-A*0201 |
| HBV | cAg | 18-27 | FLPSDFFPSV (SEQ. ID NO.: 172) | HLA-A*0201 |
| HBV | cAg | 18-27 | FLPSDFFPSV (SEQ. ID NO.: 173) | HLA-A*0202 |
| HBV | cAg | 18-27 | FLPSDFFPSV (SEQ. ID NO.: 174) | HLA-A*0205 |
| HBV | cAg | 18-27 | FLPSDFFPSV (SEQ. ID NO.: 175) | HLA-A*0206 |
| HBV | pol | 575-583 | FLLSLGIHIL (SEQ. ID NO.: 176) | HLA-A*0201 |
| HBV | pol | 816-824 | SLYADSPSV (SEQ. ID NO.: 177) | HLA-A*0201 |
| HBV | pol | 455-463 | GLSRYVARL (SEQ. ID NO.: 178) | HLA-A*0201 |
| HBV | env | 338-347 | LLVPFVQWFV (SEQ. ID NO.: 179) | HLA-A*0201 |
| HBV | pol | 642-650 | ALMPLYACI (SEQ. ID NO.: 180) | HLA-A*0201 |
| HBV | env | 378-387 | LPIFFCLWV (SEQ. ID NO.: 181) | HLA-A*0201 |
| HBV | pol | 538-546 | YMDDVVLGA (SEQ. ID NO.: 182) | HLA-A*0201 |
| HBV | env | 250-258 | LLLCLIFLL (SEQ. ID NO.: 183) | HLA-A*0201 |
| HBV | env | 260-269 | LLDYQGMLPV (SEQ. ID NO.: 184) | HLA-A*0201 |
| HBV | env | 370-379 | SIVSPFIPLL (SEQ. ID NO.: 185) | HLA-A*0201 |
| HBV | env | 183-191 | FLLTRILTI (SEQ. ID NO.: 186) | HLA-A*0201 |
| HBV | cAg | 88-96 | YVNVNMGLK (SEQ. ID NO.: 187) | HLA-A* 1101 |
| HBV | cAg | 141-151 | STLPETTVVRR (SEQ. ID NO.: 188) | HLA-A*3101 |

TABLE 1-continued

| Virus | Protein | AA Position | T cell epitope MHC ligand (Antigen) | MHC molecule |
|---|---|---|---|---|
| HBV | cAg | 141-151 | STLPETTVVRR (SEQ. ID NO.: 189) | HLA-A*6801 |
| HBV | cAg | 18-27 | FLPSDFFPSV (SEQ. ID NO.: 190) | HLA-A*6801 |
| HBV | sAg | 28-39 | IPQSLDSWWTSL (SEQ. ID NO.: 191) | H2-Ld |
| HBV | cAg | 93-100 | MGLKFRQL (SEQ. ID NO.: 192) | H2-Kb |
| HBV | preS | 141-149 | STBXQSGXQ (SEQ. ID NO.: 193) | HLA-A*0201 |
| HCMV | gp B | 618-628 | FIAGNSAYEYV (SEQ. ID NO.: 194) | HLA-A*0201 |
| HCMV | E1 | 978-989 | SDEEFAIVAYTL (SEQ. ID NO.: 195) | HLA-B18 |
| HCMV | pp65 | 397-411 | DDVWTSGSDSDEELV (SEQ. ID NO.: 196) | HLA-b35 |
| HCMV | pp65 | 123-131 | IPSINVHHY (SEQ. ID NO.: 197) | HLA-B*3501 |
| HCMV | pp65 | 495-504 | NLVPMVATVO (SEQ. ID NO.: 198) | HLA-A*0201 |
| HCMV | pp65 | 415-429 | RKTPRVTOGGAMAGA (SEQ. ID NO.: 199) | HLA-B7 |
| HCV | MP | 17-25 | DLMGYIPLV (SEQ. ID NO.: 200) | HLA-A*0201 |
| HCV | MP | 63-72 | LLALLSCLTV (SEQ. ID NO.: 201) | HLA-A*0201 |
| HCV | MP | 105-112 | ILHTPGCV (SEQ. ID NO.: 202) | HLA-A*0201 |
| HCV | env E | 66-75 | QLRRHIDLLV (SEQ. ID NO.: 203) | HLA-A*0201 |
| HCV | env E | 88-96 | DLCGSVFLV (SEQ. ID NO.: 204) | HLA-A*0201 |
| HCV | env E | 172-180 | SMVGNWAKV (SEQ. ID NO.: 205) | HLA-A*0201 |
| HCV | NSI | 308-316 | HLIIQNIVDV (SEQ. ID NO.: 206) | HLA-A*0201 |
| HCV | NSI | 340-348 | FLLLADARV (SEQ. ID NO.: 207) | HLA-A*0201 |
| HCV | NS2 | 234-246 | GLRDLAVAVEPVV (SEQ. ID NO.: 208) | HLA-A*0201 |
| HCV | NSI | 18-28 | SLLAPGAKQNV (SEQ. ID NO.: 209) | HLA-A*0201 |
| HCV | NSI | 19-28 | LLAPGAKQNV (SEQ. ID NO.: 210) | HLA-A*0201 |
| HCV | NS4 | 192-201 | LLFNILGGWV (SEQ. ID NO.: 211) | HLA-A*0201 |
| HCV | NS3 | 579-587 | YLVAYQATV (SEQ. ID NO.: 212) | HLA-A*0201 |
| HCV | core protein | 34-43 | YLLPRRGPRL (SEQ. ID NO.: 213) | HLA-A*0201 |
| HCV | MP | 63-72 | LLALLSCLTI (SEQ. ID NO.: 214) | HLA-A*0201 |
| HCV | NS4 | 174-182 | SLMAFTAAV (SEQ. ID NO.: 215) | HLA-A*0201 |
| HCV | NS3 | 67-75 | CINGVCWTV (SEQ. ID NO.: 216) | HLA-A*0201 |
| HCV | NS3 | 163-171 | LLCPAGHAV (SEQ. ID NO.: 217) | HLA-A*0201 |
| HCV | NS5 | 239-247 | ILDSFDPLV (SEQ. ID NO.: 218) | HLA-A*0201 |
| HCV | NS4A | 236-244 | ILAGYGAGV (SEQ. ID NO.: 219) | HLA-A*0201 |
| HCV | NS5 | 714-722 | GLQDCTMLV (SEQ. ID NO.: 220) | HLA-A*0201 |
| HCV | NS3 | 281-290 | TGAPVTYSTY (SEQ. ID NO.: 221) | HLA-A*0201 |
| HCV | NS4A | 149-157 | HMWNFISGI (SEQ. ID NO.: 222) | HLA-A*0201 |
| HCV | NS5 | 575-583 | RVCEKMALY (SEQ. ID NO.: 223) | HLA-A*0201-A3 |
| HCV | NS1 | 238-246 | TINYTIFK (SEQ. ID NO.: 224) | HLA-A*1101 |
| HCV | NS2 | 109-116 | YISWCLWW (SEQ. ID NO.: 225) | HLA-A23 |
| HCV | core protein | 40-48 | GPRLGVRAT (SEQ. ID NO.: 226) | HLA-B7 |

TABLE 1-continued

| Virus | Protein | AA Position | T cell epitope MHC ligand (Antigen) | MHC molecule |
|---|---|---|---|---|
| HIV-1 | gp120 | 380-388 | SFNCGGEFF (SEQ. ID NO.: 227) | HLA-Cw*0401 |
| HIV-1 | RT | 206-214 | TEMEKEGKI (SEQ. ID NO.: 228) | H2-Kk |
| HIV-1 | p17 | 18-26 | KIRLRPGGK (SEQ. ID NO.: 229) | HLA-A*0301 |
| HIV-1 | P17 | 20-29 | RLRPGGKKKY (SEQ. ID NO.: 230) | HLA-A*0301 |
| HIV-1 | RT | 325-333 | AIFQSSMTK (SEQ. ID NO.: 231) | HLA-A*0301 |
| HIV-1 | p17 | 84-92 | TLYCVHQRI (SEQ. ID NO.: 232) | HLA-A11 |
| HIV-1 | RT | 508-517 | IYQEPFKNLK (SEQ. ID NO.: 233) | HLA-A11 |
| HIV-1 | p17 | 28-36 | KYKLKHIVW (SEQ. ID NO.: 234) | HLA-A24 |
| HIV-1 | gp120 | 53-62 | LFCASDAKAY (SEQ. ID NO.: 235) | HLA-A24 |
| HIV-1 | gagp24 | 145-155 | QAISPRTLNAW (SEQ. ID NO.: 236) | HLA-A25 |
| HIV-1 | gagp24 | 167-175 | EVIPMFSAL (SEQ. ID NO.: 237) | HLA-A26 |
| HIV-1 | RT | 593-603 | ETFYVDGAANR (SEQ. ID NO.: 238) | HLA-A26 |
| HIV-1 | gp41 | 775-785 | RLRDLLLIVTR (SEQ. ID NO.: 239) | HLA-A31 |
| HIV-1 | RT | 559-568 | PIQKETWETW (SEQ. ID NO.: 240) | HLA-A32 |
| HIV-1 | gp120 | 419-427 | RIKQIINMW (SEQ. ID NO.: 241) | HLA-A32 |
| HIV-1 | RT | 71-79 | ITLWQRPLV (SEQ. ID NO.: 242) | HLA-A*6802 |
| HIV-1 | RT | 85-93 | DTVLEEMNL (SEQ. ID NO.: 243) | HLA-A*6802 |
| HIV-1 | RT | 71-79 | ITLWQRPLV (SEQ. ID NO.: 244) | HLA-A*7401 |
| HIV-1 | gag p24 | 148-156 | SPRTLNAWV (SEQ. ID NO.: 245) | HLA-B7 |
| HIV-1 | gagp24 | 179-187 | ATPQDLNTM (SEQ. ID NO.: 246) | HLA-B7 |
| HIV-1 | gp120 | 303-312 | RPNNNTRKSI (SEQ. ID NO.: 247) | HLA-B7 |
| HIV-1 | gp41 | 843-851 | IPRRIRQGL (SEQ. ID NO.: 248) | HLA-B7 |
| HIV-1 | p17 | 74-82 | ELRSLYNTV (SEQ. ID NO.: 249) | HLA-B8 |
| HIV-1 | nef | 13-20 | WPTVRERM (SEQ. ID NO.: 250) | HLA-B8 |
| HIV-1 | nef | 90-97 | FLKEKGGL (SEQ. ID NO.: 251) | HLA-B8 |
| HIV-1 | gag p24 | 183-191 | DLNTMLNTV (SEQ. ID NO.: 252) | HLA-B14 |
| HIV-1 | P17 | 18-27 | KIRLRPGGKK (SEQ. ID NO.: 253) | HLA-B27 |
| HIV-1 | p17 | 19-27 | IRLRPGGKK (SEQ. ID NO.: 254) | HLA-B27 |
| HIV-1 | gp41 | 791-799 | GRRGWEALKY (SEQ. ID NO.: 255) | HLA-B27 |
| HIV-1 | nef | 73-82 | QVPLRPMTYK (SEQ. ID NO.: 256) | HLA-B27 |
| HIV-1 | GP41 | 590-597 | RYLKDQQL (SEQ. ID NO.: 257) | HLA-B27 |
| HIV-1 | nef | 105-114 | RRQDILDLWI (SEQ. ID NO.: 258) | HLA-B*2705 |
| HIV-1 | nef | 134-141 | RYPLTFGW (SEQ. ID NO.: 259) | HLA-B*2705 |
| HIV-1 | p17 | 36-44 | WASRELERF (SEQ. ID NO.: 260) | HLA-B35 |
| HIV-1 | GAG P24 | 262-270 | TVLDVGDAY (SEQ. ID NO.: 261) | HLA-B35 |
| HIV-1 | gp120 | 42-52 | VPVWKEATTTL (SEQ. ID NO.: 262) | HLA-B35 |
| HIV-1 | P17 | 36-44 | NSSKVSQNY (SEQ. ID NO.: 263) | HLA-B35 |
| HIV-1 | gag p24 | 254-262 | PPIPVGDIY (SEQ. ID NO.: 264) | HLA-B35 |

TABLE 1-continued

| Virus | Protein | AA Position | T cell epitope MHC ligand (Antigen) | MHC molecule |
|---|---|---|---|---|
| HIV-1 | RT | 342-350 | HPDIVIYQY (SEQ. ID)NO.: 265) | HLA-B35 |
| HIV-1 | gp41 | 611-619 | TAVPWNASW (SEQ. ID NO.: 266) | HLA-B35 |
| HIV-1 | gag | 245-253 | NPVPVGN1Y (SEQ. ID NO.: 267) | HLA-B35 |
| HIV-1 | nef | 120-128 | YFPDWQNYT (SEQ. ID NO.: 268) | HLA-B37 |
| HIV-1 | gag p24 | 193-201 | GHQAAMQML (SEQ. ID NO.: 269) | HLA-B42 |
| HIV-1 | p17 | 20-29 | RLRPGGKKKY (SEQ. ID NO.: 270) | HLA-B42 |
| HIV-1 | RT | 438-446 | YPGIKVRQL (SEQ. ID NO.: 271) | HLA-B42 |
| HIV-1 | RT | 591-600 | GAETFYVDGA (SEQ. ID NO.: 272) | HLA-B45 |
| HIV-1 | gag p24 | 325-333 | NANPDCKTI (SEQ. ID NO.: 273) | HLA-B51 |
| HIV-1 | gag p24 | 275-282 | RMYSPTSI (SEQ. ID NO.: 274) | HLA-B52 |
| HIV-1 | gp120 | 42-51 | VPVWKEATTT (SEQ. ID NO.: 275) | HLA-B*5501 |
| HIV-1 | gag p24 | 147-155 | ISPRTLNAW (SEQ. ID NO.: 276) | HLA-B57 |
| HIV-1 | gag p24 | 240-249 | TSTLQEQIGW (SEQ. ID NO.: 277) | HLA-B57 |
| HIV-1 | gag p24 | 162-172 | KAFSPEVIPMF (SEQ. ID NO.: 278) | HLA-B57 |
| HIV-1 | gag p24 | 311-319 | QASQEVKNW (SEQ. ID NO.: 279) | HLA-B57 |
| HIV-1 | gag p24 | 311-319 | QASQDVKNW (SEQ. ID NO.: 280) | HLA-B57 |
| HIV-1 | nef | 116-125 | HTQGYFPDWQ (SEQ. ID NO.: 281) | HLA-B57 |
| HIV-1 | nef | 120-128 | YFPDWQNYT (SEQ. ID NO.: 282) | HLA-B57 |
| HIV-1 | gag p24 | 240-249 | TSTLQEQIGW (SEQ. ID NO.: 283) | HLA-B58 |
| HIV-1 | p17 | 20-29 | RLRPGGKKKY (SEQ. ID NO.: 284) | HLA-B62 |
| HIV-1 | p24 | 268-277 | LGLNKJVRMY (SEQ. ID NO.: 285) | HLA-B62 |
| HIV-1 | RT | 415-426 | LVGKLNWASQIY (SEQ. ID NO.: 286) | HLA-B62 |
| HIV-1 | RT | 476-485 | ILKEPVHGVY (SEQ. ID NO.: 287) | HLA-B62 |
| HIV-1 | nef | 117-127 | TQGYFPDWQNY (SEQ. ID NO.: 288) | HLA-B62 |
| HIV-1 | nef | 84-91 | AVDLSHFL (SEQ. ID NO.: 289) | HLA-B62 |
| HIV-1 | gag p24 | 168-175 | VIPMFSAL (SEQ. ID NO.: 290) | HLA-Cw*0102 |
| HIV-1 | gp120 | 376-384 | FNCGGEFFY (SEQ. ID NO.: 291) | HLA-A29 |
| HIV-1 | gp120 | 375-383 | SFNCGGEFF (SEQ. ID NO.: 292) | HLA-B15 |
| HIV-1 | nef | 136-145 | PLTFGWCYKL (SEQ. ID NO.: 293) | HLA-A*0201 |
| HIV-1 | nef | 180-189 | VLEWRFDSRL (SEQ. ID NO.: 294) | HLA-A*0201 |
| HIV-1 | nef | 68-77 | FPVTPQVPLR (SEQ. ID NO.: 295) | HLA-B7 |
| HIV-1 | nef | 128-137 | TPGPGVRYPL (SEQ. ID NO.: 296) | HLA-B7 |
| HIV-1 | gag p24 | 308-316 | QASQEVKNW (SEQ. ID NO.: 297) | HLA-Cw*0401 |
| HIV-1 IIIB | RT | 273-282 | VPLDEDFRKY (SEQ. ID NO.: 298) | HLA-B35 |
| HIV-1 IIIB | RT | 25-33 | NPDIVIYQY (SEQ. ID NO.: 299) | HLA-B35 |
| HIV-1 IIIB | gp41 | 557-565 | RAIEAQAHL (SEQ. ID NO.: 300) | HLA-B51 |
| HIV-1 IIIB | RT | 231-238 | TAFTIPSI (SEQ. ID NO.: 301) | HLA-B51 |
| HIV-1 IIIB | p24 | 215-223 | VHPVHAGPIA (SEQ. ID NO.: 302) | HLA-B*5501 |

TABLE 1-continued

| Virus | Protein | AA Position | T cell epitope MHC ligand (Antigen) | MHC molecule |
|---|---|---|---|---|
| HIV-1 IIIB | gp120 | 156-165 | NCSFNISTSI (SEQ. ID NO.: 303) | HLA-Cw8 |
| HIV-1 IIIB | gp120 | 241-249 | CTNVSTVQC (SEQ. ID NO.: 304) | HLA-Cw8 |
| HIV-1 5F2 | gp120 | 312-320 | IGPGRAFHT (SEQ. ID NO.: 305) | H2-Dd |
| HIV-1 5F2 | pol | 25-33 | NPDIVIYQY (SEQ. ID NO.: 306) | HLA-B*3501 |
| HIV-1 5F2 | pol | 432-441 | EPIVGAETFY (SEQ. ID NO.: 307) | HLA-B*3501 |
| HIV-1 5F2 | pol | 432-440 | EPIVGAETF (SEQ. ID NO.: 308) | HLA-B*3501 |
| HIV-1 5F2 | pol | 6-14 | SPAIFQSSM (SEQ. ID NO.: 309) | HLA-B*3501 |
| HIV-1 5F2 | pol | 59-68 | VPLDKDFRKY (SEQ. ID NO.: 310) | HLA-B*3501 |
| HIV-1 5F2 | pol | 6-14 | IPLTEEAEL (SEQ. ID NO.: 311) | HLA-B*3501 |
| HIV-1 5F2 | nef | 69-79 | RPQVPLRPMTY (SEQ. ID NO.: 312) | HLA-B*3501 |
| HIV-1 5F2 | nef | 66-74 | FPVRPQVPL (SEQ. ID NO.: 313) | HLA-B*3501 |
| HIV-1 5F2 | env | 10-18 | DPNPQEVVL (SEQ. ID NO.: 314) | HLA-B*3501 |
| HIV-1 5F2 | env | 7-15 | RPIVSTQLL (SEQ. ID NO.: 315) | HLA-B*3501 |
| HIV-1 5F2 | pol | 6-14 | IPLTEEAEL (SEQ. ID NO.: 316) | HLA-B51 |
| HIV-1 5F2 | env | 10-18 | DPNPQEVVL (SEQ. ID NO.: 317) | HLA-B51 |
| HIV-1 5F2 | gagp24 | 199-207 | AMQMLKETI (SEQ. ID NO.: 318) | H2-Kd |
| HIV-2 | gagp24 | 182-190 | TPYDrNQML (SEQ. ID NO.: 319) | HLA-B*5301 |
| HIV-2 | gag | 260-269 | RRWIQLGLQKV (SEQ. ID NO.: 320) | HLA-B*2703 |
| HIV-1 5F2 | gp41 | 593-607 | GIWGCSGKLICTTAV (SEQ. ID NO.: 321) | HLA-B17 |
| HIV-1 5F2 | gp41 | 753-767 | ALIWEDLRSLCLFSY (SEQ. ID NO.: 322) | HLA-B22 |
| HPV 6b | E7 | 21-30 | GLHCYEQLV (SEQ. ID NO.: 323) | HLA-A*0201 |
| HPV 6b | E7 | 47-55 | PLKQHFQIV (SEQ. ID NO.: 324) | HLA-A*0201 |
| HPV11 | E7 | 4-12 | RLVTLKDIV (SEQ. ID NO.: 325) | HLA-A*0201 |
| HPV16 | E7 | 86-94 | TLGIVCPIC (SEQ. ID NO.: 326) | HLA-A*0201 |
| HPV16 | E7 | 85-93 | GTLGIVCPI (SEQ. ID NO.: 327) | HLA-A*0201 |
| HPV16 | E7 | 12-20 | MLDLQPETT (SEQ. ID NO.: 328) | HLA-A*0201 |
| HPV16 | E7 | 11-20 | YMLDLQPETT (SEQ. ID NO.: 329) | HLA-A*0201 |
| HPV16 | E6 | 15-22 | RPRKLPQL (SEQ. ID NO.: 330) | HLA-B7 |
| HPV16 | E6 | 49-57 | RAHYNIVTF (SEQ. ID NO.: 331) | HW-Db |
| HSV | gp B | 498-505 | SSIEFARL (SEQ. ID NO.: 332) | H2-Kb |
| HSV-1 | gp C | 480-488 | GIGIGVLAA (SEQ. ID NO.: 333) | HLA-A*0201 |
| HSV-1 | ICP27 | 448-456 | DYATLGVGV (SEQ. ID NO.: 334) | H2-Kd |
| HSV-1 | ICP27 | 322-332 | LYRTFAGNPRA (SEQ. ID NO.: 335) | H2-Kd |
| HSV-1 | UL39 | 822-829 | QTFDFGRL (SEQ.ID NO.: 336) | H2-Kb |
| HSV-2 | gpC | 446-454 | GAGIGVAVL (SEQ. ID NO.: 337) | HLA-A*0201 |
| HLTV-1 | TAX | 11-19 | LLFGYPVYV (SEQ. ID NO.: 338) | HLA-A*0201 |
| Influenza | MP | 58-66 | GILGFVFTL (SEQ. ID NO.: 339) | HLA-A*0201 |
| Influenza | MP | 59-68 | ILGFVFTLTV (SEQ. ID NO.: 340) | HLA-A*0201 |

TABLE 1-continued

| Virus | Protein | AA Position | T cell epitope MHC ligand (Antigen) | MHC molecule |
|---|---|---|---|---|
| Influenza | NP | 265-273 | ILRGSVAHK (SEQ. ID NO.: 341) | HLA-A3 |
| Influenza | NP | 91-99 | KTGGPIYKR (SEQ. ID NO.: 342) | HLA-A*6801 |
| Influenza | NP | 380-388 | ELRSRYWAI (SEQ. ID NO.: 343) | HLA-B8 |
| Influenza | NP | 381-388 | LRSRYWAI (SEQ. ID NO.: 344) | HLA-B*2702 |
| Influenza | NP | 339-347 | EDLRVLSFI (SEQ. ID NO.: 345) | HLA-B*3701 |
| Influenza | NSI | 158-166 | GEISPLPSL (SEQ. ID NO.: 346) | HLA-B44 |
| Influenza | NP | 338-346 | FEDLRVLSF (SEQ. ID NO.: 347) | HLA-B44 |
| Influenza | NSI | 158-166 | GEISPLPSL (SEQ. ID NO.: 348) | HLA-B*4402 |
| Influenza | NP | 338-346 | FEDLRVLSF (SEQ. ID NO.: 349) | HLA-B*4402 |
| Influenza | PBI | 591-599 | VSDGGPKLY (SEQ. ID NO.: 350) | HLA-A1 |
| Influenza A | NP | 44-52 | CTELKLSDY (SEQ. ID NO.: 351) | HLA-A1 |
| Influenza | NSI | 122-130 | AIMDKNIIL (SEQ. ID NO.: 352) | HLA-A*0201 |
| Influenza A | NSI | 123-132 | IMDKNIILKA (SEQ. ID NO.: 353) | HLA-A*0201 |
| Influenza A | NP | 383-391 | SRYWAIRTR (SEQ. ID NO.: 354) | HLA-B*2705 |
| Influenza A | NP | 147-155 | TYQRTRALV (SEQ. ID NO.: 355) | H2-Kd |
| Influenza A | HA | 210-219 | TYVSVSTSTL (SEQ. ID NO.: 356) | H2-Kd |
| Influenza A | HA | 518-526 | IYSTVASSL (SEQ. ID NO.: 357) | H2-Kd |
| Influenza A | HA | 259-266 | FEANGNLI (SEQ. ID NO.: 358) | H2-Kk |
| Influenza A | HA | 10-18 | IEGGWTGM1 (SEQ. ID NO.: 359) | H2-Kk |
| Influenza A | NP | 50-57 | SDYEGRLI (SEQ. ID NO.: 360) | H2-Kk |
| Influenza a | NSI | 152-160 | EEGAIVGEI (SEQ. ID NO.: 361) | H2-Kk |
| Influenza A34 | NP | 336-374 | ASNENMETM (SEQ. ID NO.: 362) | H2Db |
| Influenza A68 | NP | 366-374 | ASNENMDAM (SEQ. ID NO.: 363) | H2Db |
| Influenza B | NP | 85-94 | KLGEFYNQMM (SEQ. ID NO.: 364) | HLA-A*0201 |
| Influenza B | NP | 85-94 | KAGEFYNQMM (SEQ. ID NO.: 365) | HLA-A*0201 |
| Influenza JAP | HA | 204-212 | LYQNVGTYV (SEQ. ID NO.: 366) | H2Kd |
| Influenza JAP | HA | 210-219 | TYVSVGTSTL (SEQ. ID NO.: 367) | H2-Kd |
| Influenza JAP | HA | 523-531 | VYQILATYA (SEQ. ID NO.: 368) | H2-Kd |
| Influenza JAP | HA | 529-537 | IYATVAGSL (SEQ. ID NO.: 369) | H2-Kd |
| Influenza JAP | HA | 210-219 | TYVSVGTSTI(L>I) (SEQ. ID NO.: 370) | H2-Kd |
| Influenza JAP | HA | 255-262 | FESTGNLI (SEQ. ID NO.: 371) | H2-Kk |
| JHMV | cAg | 318-326 | APTAGAFFF (SEQ. ID NO.: 372) | H2-Ld |
| LCMV | NP | 118-126 | RPQASGVYM (SEQ. ID NO.: 373) | H2-Ld |
| LCMV | NP | 396-404 | FQPQNGQFI (SEQ. ID NO.: 374) | H2-Db |
| LCMV | GP | 276-286 | SGVENPGGYCL (SEQ. ID NO.: 375) | H2-Db |
| LCMV | GP | 33-42 | KAVYNFATCG (SEQ. ID NO.: 376) | H2-Db |
| MCMV | pp89 | 168-176 | YPHFMPTNL (SEQ. ID NO.: 377) | H2-Ld |
| MHV | spike protein | 510-518 | CLSWNGPHL (SEQ. ID NO.: 378) | H2-Db |

TABLE 1-continued

| Virus | Protein | AA Position | T cell epitope MHC ligand (Antigen) | MHC molecule |
|---|---|---|---|---|
| MMTV | env gp 36 | 474-482 | SFAVATTAL (SEQ. ID NO.: 379) | H2-Kd |
| MMTV | gag p27 | 425-433 | SYETFISRL (SEQ. ID NO.: 380) | H2-Kd |
| MMTV | env gp73 | 544-551 | ANYDFICV (SEQ. ID NO.: 381) | H2-Kb |
| MuLV | env p15E | 574-581 | KSPWFTTL (SEQ. ID NO.: 382) | H2-Kb |
| MuLV | env gp70 | 189-196 | SSWDFITV (SEQ. ID NO.: 383) | H2-Kb |
| MuLV | gag 75K | 75-83 | CCLCLTVFL (SEQ. ID NO.: 384) | H2-Db |
| MuLV | env gp70 | 423-431 | SPSYVYHQF (SEQ. ID NO.: 385) | H2Ld |
| MV | F protein | 437-447 | SRRYPDAVYLH (SEQ. ID NO.: 386) | HLA-B*2705 |
| Mv | F protein | 438-446 | RRYPDAVYL (SEQ. ID NO.: 387) | HLA-B*2705 |
| Mv | NP | 281-289 | YPALGLHEF (SEQ. ID NO.: 388) | H2-Ld |
| Mv | HA | 343-351 | DPVIDRLYL (SEQ. ID NO.: 389) | H2-Ld |
| MV | HA | 544-552 | SPGRSFSYF (SEQ. ID NO.: 390) | H2-Ld |
| Poliovirus | VP1 | 111-118 | TYKDTVQL (SEQ. ID NO.: 391) | H2-kd |
| Poliovirus | VP1 | 208-217 | FYDGFSKVPL (SEQ. ID NO.: 392) | H2-Kd |
| Pseudorabies virus gp | G111 | 455-463 | IAGIGILAI (SEQ. ID NO.: 393) | HLA-A*0201 |
| Rabiesvirus | NS | 197-205 | VEAEIAHQI (SEQ. ID NO.: 394) | H2-Kk |
| Rotavirus | VP7 | 33-40 | 11YRFLL1 (SEQ. ID NO.: 395) | H2-Kb |
| Rotavirus | VP6 | 376-384 | VGPVFPPGM (SEQ. ID NO.: 396) | H2-Kb |
| Rotavirus | VP3 | 585-593 | YSGYIFRDL (SEQ. ID NO.: 397) | H2-Kb |
| RSV | M2 | 82-90 | SYIGSINNI (SEQ. ID NO.: 398) | H2-Kd |
| SIV | gagp11C | 179-190 | EGCTPYDTNQML (SEQ. ID NO.: 399) | Mamu-A*01 |
| SV | NP | 324-332 | FAPGNYPAL (SEQ. ID NO.: 400) | H2-Db |
| SV | NP | 324-332 | FAPCTNYPAL (SEQ. ID NO.: 401) | H2-Kb |
| SV40 | T | 404-411 | VVYDFLKC (SEQ. ID NO.: 402) | H2-Kb |
| SV40 | T | 206-215 | SAINNYAQKL (SEQ. ID NO.: 403) | H2-Db |
| SV40 | T | 223-231 | CKGVNKEYL (SEQ. ID NO.: 404) | H2-Db |
| SV40 | T | 489-497 | QGINNLDNL (SEQ. ID NO.: 405) | H2-Db |
| SV40 | T | 492-500 (501) | NNLDNLRDY(L) (SEQ. ID NO.: 406) | H2-Db |
| SV40 | T | 560-568 | SEFLLEKRI (SEQ. ID NO.: 407) | H2-Kk |
| VSV | NP | 52-59 | RGYVYQGL (SEQ. ID NO.: 408) | H2-Kb |

TABLE 2

| HLA-A1 | Position (Antigen) | Source |
|---|---|---|
| T cell epitopes | EADPTGHSY (SEQ. ID NO.: 409) | MAGE-1 161-169 |
| | VSDGGPNLY (SEQ. ID NO.: 410) | Influenza A PB 1591-599 |
| | CTELKLSDY (SEQ. ID NO.: 411) | Influenza A NP 44-52 |
| | EVDPIGHLY (SEQ. ID NO.: 412) | MAGE-3 168-176 |
| HLA-A201 | MLLSVPLLLG (SEQ. ID NO.: 413) | Calreticulin signal sequence I-10 |
| | STBXQSGXQ (SEQ. ID NO.: 414) | HBV PRE-S PROTEIN 141-149 |
| | YMDGTMSQV (SEQ. ID NO.: 415) | Tyrosinase 369-377 |
| | ILKEPVHGV (SEQ. ID NO.: 416) | HIV-I RT 476-484 |

TABLE 2-continued

| HLA-A1 | Position (Antigen) | Source |
|---|---|---|
| LLGFVFTLTV (SEQ. ID NO.: 417) | Influenza MP 59-68 | |
| LLFGYPVYVV (SEQ. ID NO.: 418) | HTLV-1 tax 11-19 | |
| GLSPTVWLSV (SEQ. ID NO.: 419) | HBV sAg 348-357 | |
| WLSLLVPFV (SEQ. ID NO.: 420) | HBV sAg 335-343 | |
| FLPSDFFPSV (SEQ. ID NO.: 421) | HBV cAg 18-27 | |
| CLGOLLTMV (SEQ. ID NO.: 422) | EBV LMP-2 426-434 | |
| FLAGNSAYEYV (SEQ. ID NO.: 423) | HCMV gp 618-628B | |
| KLGEFYNQMM (SEQ. ID NO.: 424) | Influenza BNP 85-94 | |
| KLVALGINAV (SEQ. ID NO.: 425) | HCV-1 NS3 400-409 | |
| DLMGYIPLV (SEQ. ID NO.: 426) | HCV MP 17-25 | |
| RLVTLKDIV (SEQ. ID NO.: 427) | HPV 11 EZ 4-12 | |
| MLLAVLYCL (SEQ. ID NO.: 428) | Tyrosinase 1-9 | |
| AAGIGILTV (SEQ. ID NO.: 429) | Melan A\Mart-1 27-35 | |
| YLEPGPVTA (SEQ. ID NO.: 430) | Pmel 17/gp 100 480-488 | |
| ILDGTATLRL (SEQ. ID NO.: 431) | Pmel 17/gp 100 457-466 | |
| LLDGTATLRL (SEQ. ID NO.: 432) | Pmel gplOO 457-466 | |
| ITDQVPFSV (SEQ. ID NO.: 433) | Pmel gp 100 209-217 | |
| KTWGQYWQV (SEQ. ID NO.: 434) | Pmel gp 100 154-162 | |
| TITDQVPFSV (SEQ. ID NO.: 435) | Pmel gp 100 208-217 | |
| AFHIIVAREL (SEQ. ID NO.: 436) | HIV-I nef 190-198 | |
| YLNKIQNSL (SEQ. ID NO.: 437) | *P. falciparum* CSP 334-342 | |
| MMRKLAELSV (SEQ. ID NO.: 438) | *P. falciparum* CSP 1-10 | |
| KAGEFYNQMM (SEQ. ID NO.: 439) | Influenza BNP 85-94 | |
| NIAEGLRAL (SEQ. ID NO.: 440) | EBNA-1 480-488 | |
| NLRRGTALA (SEQ. ID NO.: 441) | EBNA-1 519-527 | |
| ALAIPQCRL (SEQ. ID NO.: 442) | EBNA-1 525-533 | |
| VLKDAIKDL (SEQ. ID NO.: 443) | EBNA-1 575-582 | |
| FMVFLQTHI (SEQ. ID NO.: 444) | EBNA-1 562-570 | |
| HLIVDTDSL (SEQ. ID NO.: 445) | EBNA-2 15-23 | |
| SLGNPSLSV (SEQ. ID NO.: 446) | EBNA-2 22-30 | |
| PLASAMRML (SEQ. ID NO.: 447) | EBNA-2 126-134 | |
| RMLWMANYI (SEQ. ID NO.: 448) | EBNA-2 132-140 | |
| MLWMANYIV (SEQ. ID NO.: 449) | EBNA-2 133-141 | |
| ILPQGPQTA (SEQ. ID NO.: 450) | EBNA-2 151-159 | |
| PLRPTAPTTI (SEQ. ID NO.: 451) | EBNA-2 171-179 | |
| PLPPATLTV (SEQ. ID NO.: 452) | EBNA-2 205-213 | |
| RMHLPVLHV (SEQ. ID NO.: 453) | EBNA-2 246-254 | |
| PMPLPPSQL (SEQ. ID NO.: 454) | EBNA-2 287-295 | |
| QLPPPAAPA (SEQ. ID NO.: 455) | EBNA-2 294-302 | |
| SMPELSPVL (SEQ. ID NO.: 456) | EBNA-2 381-389 | |
| DLDESWDY1 (SEQ. ID NO.: 457) | EBNA-2 453-461 | |
| PLPCVLWPVV (SEQ. ID NO.: 458) | BZLF1 43-51 | |
| SLEECDSEL (SEQ. ID NO.: 459) | BZLF1 167-175 | |
| EIKRYKNRV (SEQ. ID NO.: 460) | BZLF1 176-184 | |
| QLLQFIYREV (SEQ. ID NO.: 461) | BZLF1 195-203 | |
| LLQHYREVA (SEQ. ID NO.: 462) | BZLFI 196-204 | |
| LLKQMCPSL (SEQ. ID NO.: 463) | BZLFI 217-225 | |
| SIIPRTPDV (SEQ. ID NO.: 464) | BZLFI 229-237 | |
| AIMDKNIIL (SEQ. ID NO.: 465) | Influenza A NSI 122-130 | |
| IMDKNIILKA (SEQ. ID NO.: 466) | Influenza A NSI 123-132 | |
| LLALLSCLTV (SEQ. ID NO.: 467) | HCV MP 63-72 | |
| ILHTPGCV (SEQ. ID NO.: 468) | HCV MP 105-112 | |
| QLRRHIDLLV (SEQ. ID NO.: 469) | HCV env E 66-75 | |
| DLCGSVFLV (SEQ. ID NO.: 470) | HCV env E 88-96 | |
| SMVGNWAKV (SEQ. ID NO.: 471) | HCV env E 172-180 | |
| HLHQNIVDV (SEQ. ID NO.: 472) | HCV NSI 308-316 | |
| FLLLADARV (SEQ. ID NO.: 473) | HCV NSI 340-348 | |
| GLRDLAVAVEPVV (SEQ. ID NO.: 474) | HCV NS2 234-246 | |
| SLLAPGAKQNV (SEQ. ID NO.: 475) | HCV NS1 18-28 | |
| LLAPGAKQNV (SEQ. ID NO.: 476) | HCV NS1 19-28 | |
| FLLSLGIHL (SEQ. ID NO.: 477) | HBV pol 575-583 | |
| SLYADSPSV (SEQ. ID NO.: 478) | HBV pol 816-824 | |
| GLSRYVARL (SEQ. ID NO.: 479) | HBV POL 455-463 | |
| KIFGSLAFL (SEQ. ID NO.: 480) | HER-2 369-377 | |
| ELVSEFSRM (SEQ. ID NO.: 481) | HER-2 971-979 | |
| KLTPLCVTL (SEQ. ID NO.: 482) | HIV-I gp 160 120-128 | |
| SLLNATDIAV (SEQ. ID NO.: 483) | HIV-I GP 160 814-823 | |
| VLYRYGSFSV (SEQ. ID NO.: 484) | Pmel gp100 476-485 | |
| YIGEVLVSV (SEQ. ID NO.: 485) | Non-filament forming class I myosin family (HA-2)** | |
| LLFNILGGWV (SEQ. ID NO.: 486) | HCV NS4 192-201 | |
| LLVPFVQWFW (SEQ. ID NO.: 487) | HBV env 338-347 | |
| ALMPLYACI (SEQ. ID NO.: 488) | HBV pol 642-650 | |
| YLVAYQATV (SEQ. ID NO.: 489) | HCV NS3 579-587 | |
| TLGIVCPIC (SEQ. ID NO.: 490) | HIPV 16 E7 86-94 | |
| YLLPRRGPRL (SEQ. ID NO.: 491) | HCV core protein 34-43 | |
| LLPIFFCLWV (SEQ. ID NO.: 492) | HBV env 378-387 | |
| YMDDVVLGA (SEQ. ID NO.: 493) | HBV Pol 538-546 | |

TABLE 2-continued

| HLA-A1 | Position (Antigen) | Source |
|---|---|---|
| | GTLGIVCPI (SEQ. ID NO.: 494) | HPV16 E7 85-93 |
| | LLALLSCLTI (SEQ. ID NO.: 495) | HCV MP 63-72 |
| | MLDLQPETT (SEQ. ID NO.: 496) | HPV 16 E7 12-20 |
| | SLMAFTAAV (SEQ. ID NO.: 497) | HCV NS4 174-182 |
| | CINGVCWTV (SEQ. ID NO.: 498) | HCV NS3 67-75 |
| | VMNILLQYVV (SEQ. ID NO.: 499) | Glutarnic acid decarboxylase 114-123 |
| | ILTVILGVL (SEQ. ID NO.: 500) | Melan A/Mart- 32-40 |
| | FLWGPRALV (SEQ. ID NO.: 501) | MAGE-3 271-279 |
| | LLCPAGHAV (SEQ. ID NO.: 502) | HCV NS3 163-171 |
| | ILDSFDPLV (SEQ. ID NO.: 503) | HCV NSS 239-247 |
| | LLLCLIFLL (SEQ. ID NO.: 504) | HBV env 250-258 |
| | LIDYQGMLPV (SEQ. ID NO.: 505) | HBV env 260-269 |
| | SIVSPFIPLL (SEQ. ID NO.: 506) | HBV env 370-379 |
| | FLLTRILTI (SEQ. ID NO.: 507) | HBV env 183-191 |
| | HLGNVKYLV (SEQ. ID NO.: 508) | *P. faciparum* TRAP 3-11 |
| | GIAGGLALL (SEQ. ID NO.: 509) | *P. faciparum* TRAP 500-508 |
| | ILAGYGAGV (SEQ. ID NO.: 510) | HCV NS S4A 236-244 |
| | GLQDCTMLV (SEQ. ID NO.: 511) | HCV NS5 714-722 |
| | TGAPVTYSTY (SEQ. ID NO.: 512) | HCV NS3 281-290 |
| | VIYQYMDDLV (SEQ. ID NO.: 513) | HIV-1RT 179-187 |
| | VLPDVFIRCV (SEQ. ID NO.: 514) | N-acetylglucosaminyl- transferase V Gnt-V intron |
| | VLPDVFIRC (SEQ. ID NO.: 515) | N-acetylglucosaminyl- transferase V Gnt-V intron |
| | AVGIGIAVV (SEQ. ID NO.: 516) | Human CD9 |
| | LVVLGLLAV (SEQ. ID NO.: 517) | Human glutamyltransferase |
| | ALGLGLLPV (SEQ. ID NO.: 5 18) | Human G protein coupled receptor 164-172 |
| | GIGIGVLAA (SEQ. ID NO.: 519) | HSV-I gp C 480-488 |
| | GAGIGVAVL (SEQ. ID NO.: 520) | HSV-2 gp C 446-454 |
| | IAGIGILAI (SEQ. ID NO.: 521) | Pseudorabies gpGIN 455-463 |
| | LIVIGILIL (SEQ. ID NO.: 522) | Adenovirus 3 E3 9 kD 30-38 |
| | LAGIGLIAA (SEQ. ID NO.: 523) | *S. Lincolnensis* ImrA |
| | VDGIGILTI (SEQ. ID NO.: 524) | Yeast ysa-1 77-85 |
| | GAGIGVLTA (SEQ. ID NO.: 525) 157 | *B. polymyxa*, βendoxylanase 149-157 |
| | AAGIGHQI (SEQ. ID NO.: 526) | *E. coli*methionine synthase 590-598 |
| | QAGIGILLA (SEQ. ID NO.: 527) | *E. coli*hypothetical protein 4-12 |
| | KARDPHSGHFV (SEQ. ID NO.: 528) | CDK4wl 22-32 |
| | KACDPI-ISGIIFV (SEQ. ID NO.: 529) | CDK4-R24C 22-32 |
| | ACDPFISGHFV (SEQ. ID NO.: 530) | CDK4-R24C 23-32 |
| | SLYNTVATL (SEQ. ID NO.: 531) | HIV-I gag p17 77-85 |
| | ELVSEFSRV (SEQ. ID NO.: 532) | HER-2, m > V substituted 971-979 |
| | RGPGRAFVTI (SEQ. ID NO.: 533) | HIV-I gp 160 315-329 |
| | HMWNFISGI (SEQ. ID NO.: 534) | HCV NS4A 149-157 |
| | NLVPMVATVQ (SEQ. ID NO.: 535) | HCMV pp65 495-504 |
| | GLHCYEQLV (SEQ. ID NO.: 536) | HPV 6b E7 21-30 |
| | PLKQHFQIV (SEQ. ID NO.: 537) | HPV 6b E7 47-55 |
| | LLDFVRFMGV (SEQ. ID NO.: 538) | EBNA-6 284-293 |
| | AIMEKNIML (SEQ. ID NO.: 539) | Influenza Alaska NS 1 122-130 |
| | YLKTIQNSL (SEQ. ID NO.: 540) | *P. falciparum* cp36 CSP |
| | YLNKIQNSL (SEQ. ID NO.: 541) | *P. falciparum* cp39 CSP |
| | YMLDLQPETT (SEQ. ID NO.: 542) | HPV 16 E7 11-20* |
| | LLMGTLGIV (SEQ. ID NO.: 543) | HPV16 E7 82-90** |
| | TLGIVCPI (SEQ. ID NO.: 544) | HPV 16 E7 86-93 |
| | TLTSCNTSV (SEQ. ID NO.: 545) | HIV-1 gp120 197-205 |
| | KLPQLCTEL (SEQ. ID NO.: 546) | HPV 16 E6 18-26 |
| | TIHDIILEC (SEQ. ID NO.: 547) | HPV 16 E6 29-37 |
| | LGIVCPICS (SEQ. ID NO.: 548) | HPV16 E7 87-95 |
| | VILGVLLLI (SEQ. ID NO.: 549) | Melan A/Mart-1 35-43 |
| | ALMDKSLHV (SEQ. ID NO.: 550) | Melan A/Mart-1 56-64 |
| T cell epitopes | GILTVILGV (SEQ. ID NO.: 551) | Melan A/Mart-1 31-39 |
| | MINAYLDKL (SEQ. ID NO.: 552) | *P. Falciparum* STARP 523-531 |
| | AAGIGILTV (SEQ. ID NO.: 553) | Melan A/Mart- 127-35 |
| | FLPSDFFPSV (SEQ. ID NO.: 554) | HBV cAg 18-27 |
| Motif unknown T cell epitopes | SVRDRLARL (SEQ. ID NO.: 555) | EBNA-3 464-472 |
| T cell epitopes | AAGIGILTV (SEQ. ID NO.: 556) | Melan A/Mart-1 27-35 |
| | FAYDGKDYI (SEQ. ID NO.: 557) | Human MHC I-ot 140-148 |
| T cell epitopes | AAGIGILTV (SEQ. ID NO.: 558) | Melan A/Mart-1 27-35 |
| | FLPSDFFPSV (SEQ. ID NO.: 559) | HBV cAg 18-27 |
| Motif unknown T cell epitopes | AAGIGILTV (SEQ. ID NO.: 560) | Meland A/Mart-1 27-35 |
| | FLPSDFFPSV (SEQ. ID NO.: 561) | HBV cAg 18-27 |
| | AAGIGILTV (SEQ. ID NO.: 562) | Melan A/Mart-1 27-35 |
| | ALLAVGATK (SEQ. ID NO.: 563) | Pme117 gp 100 17-25 |
| T cell epitopes | RLRDLLLIVTR (SEQ. ID NO.: 564) | HIV-1 gp41 768-778 |
| | QVPLRPMTYK (SEQ. ID NO.: 565) | HIV-1 nef 73-82 |
| | TVYYGVPVWK (SEQ. ID NO.: 566) | HIV-1 gp120-36-45 |
| | RLRPGGKKK (SEQ. ID NO.: 567) | HIV-1 gag p 17 20-29 |
| | ILRGSVAHK (SEQ. ID NO.: 568) | Influenza NP 265-273 |

TABLE 2-continued

| HLA-A1 | Position (Antigen) | Source |
|---|---|---|
| | RLRAEAGVK (SEQ. ID NO.: 569) | EBNA-3 603-611 |
| | RLRDLLLIVTR (SEQ. ID NO.: 570) | HIV-1 gp41 770-780 |
| | VYYGVPVWK (SEQ. ID NO.: 571) | HIV-I GP 120 38-46 |
| | RVCEKMALY (SEQ. ID NO.: 572) | HCV NS5 575-583 |
| Motif unknown T cell epitope | KIFSEVTLK (SEQ. ID NO.: 573) | Unknown; muta melanoma peptide ted (p I 83L) 175-183 |
| | YVNVNMGLK* (SEQ. ID NO.: 574) | HBV cAg 88-96 |
| T cell epitopes | IVTDFSVIK (SEQ. ID NO.: 575) | EBNA-4 416-424 |
| | ELNEALELK (SEQ. ID NO.: 576) | P53 343-351 |
| | VPLRPMTYK (SEQ. ID NO.: 577) | HIV-1 NEF 74-82 |
| | AIFQSSMTK (SEQ. ID NO.: 578) | HIV-I gag p24 325-333 |
| | QVPLRPMTYK (SEQ. ID NO.: 579) | HIV-1 nef 73-82 |
| | TINYTIFK HCV (SEQ. ID NO.: 580) | NSI 238-246 |
| | AAVDLSHFLKEK (SEQ. ID NO.: 581) | HIV-1 nef 83-94 |
| | ACQGVGGPGGHK (SEQ. ID NO.: 582) | HIV-1 II 1B p24 349-359 |
| HLA-A24 | SYLDSGIHF* (SEQ. ID NO.: 583) | β-catenin, mutated (proto-onocogen) 29-37 |
| T cell epitopes | RYLKDQQLL (SEQ. ID NO.: 584) | HIV GP 41 583-591 |
| | AYGLDFYIL (SEQ. ID NO.: 585) | P15 melanoma Ag 10-18 |
| | AFLPWHRLFL (SEQ. ID NO.: 586) | Tyrosinase 206-215 |
| | AFLPWHRLF (SEQ. ID NO.: 587) | Tyrosinase 206-214 |
| | RYSIFFDY (SEQ. ID NO.: 588) | Ebna-3 246-253 |
| T cell epitope | ETINEEAAEW (SEQ. ID NO.: 589) | HIV-1 gag p24 203-212 |
| T cell epitopes | STLPETTVVRR (SEQ. ID NO.: 590) | HBV cAg 141-151 |
| | MSLQRQFLR (SEQ. ID NO.: 591) | ORF 3P-gp75 294-321 (bp) |
| | LLPGGRPYR (SEQ. ID NO.: 592) | TRP (tyrosinase rel.) 197-205 |
| T cell epitope | IVGLNKIVR (SEQ. ID NO.: 593) | HIV gag p24 267-267-275 |
| | AAGIGILTV (SEQ. ID NO.: 594) | Melan A/Mart-127 35 |

Table 3 sets forth additional antigens useful in the invention that are available from the Ludwig Cancer Institute. The Table refers to patents in which the identified antigens can be found and as such are incorporated herein by reference. TRA refers to the tumor-related antigen and the LUD No. refers to the Ludwig Institute number.

TABLE 3

| TRA | LUD No. | Patent No. | Date Patent Issued | Peptide (Antigen) | HLA |
|---|---|---|---|---|---|
| MAGE-4 | 5293 | 5,405,940 | 11 Apr. 1995 | EVDPASNTY (SEQ. ID NO.: 979) | HLA-A1 |
| MAGE-41 | 5293 | 5,405,940 | 11 Apr. 1995 | EVDPTSNTY (SEQ ID NO: 595) | HLA-A I |
| MAGE-5 | 5293 | 5,405,940 | 11 Apr. 1995 | EADPTSNTY (SEQ ID NO: 596) | HLA-A I |
| MAGE-51 | 5293 | 5,405,940 | 11 Apr. 1995 | EADPTSNTY (SEQ ID NO: 597) | HLA-A I |
| MAGE-6 | 5294 | 5,405,940 | 11 Apr. 1995 | EVDPIGHVY (SEQ ID NO: 598) | HLA-A1 |
| | 5299.2 | 5,487,974 | 30 Jan. 1996 | MLLAVLYCLL (SEQ ID NO: 599) | HLA-A2 |
| | 5360 | 5,530,096 | 25 Jun. 1996 | MLLAVLYCL (SEQ ID NO: 600) | HLA-B44 |
| Tyrosinase | 5360.1 | 5,519,117 | 21 May 1996 | SEIWRDIDFA (SEQ ID NO: 601) SEIWRDIDF (SEQ ID NO: 602) | HLA-B44 |
| Tyrosinase | 5431 | 5,774,316 | 28 Apr. 1998 | XEIWRDIDF (SEQ ID NO: 603) | HLA-B44 |
| MAGE-2 | 5340 | 5,554,724 | 10 Sep. 1996 | STLVEVTLGEV (SEQ ID NO: 604) LVEVTLGEV (SEQ ID NO: 605) VIFSKASEYL (SEQ ID NO: 606) IIVLAIIAI (SEQ ID NO: 607) KIWEELSMLEV (SEQ ID NO: 608) LIETSYVKV (SEQ ID NO: 609) | HLA-A2 |
| | 5327 | 5,585,461 | 17 Dec. 1996 | FLWGPRALV (SEQ ID NO: 610) TLVEVTLGEV (SEQ ID NO: 611) ALVETSYVKV (SEQ ID NO: 612) | HLA-A2 |

TABLE 3-continued

| TRA | LUD No. | Patent No. | Date Patent Issued | Peptide (Antigen) | HLA |
|---|---|---|---|---|---|
| MAGE-3 | 5344 | 5,554,506 | 10 Sep. 1996 | KIWEELSVL (SEQ ID NO: 613) | HLA-A2 |
| MAGE-3 | 5393 | 5,405,940 | 11 Apr. 1995 | EVDPIGHLY (SEQ ID NO: 614) | HLA-A1 |
| MAGE | 5293 | 5,405,940 | 11 Apr. 1995 | EXDX5Y (SEQ. ID NO.: 615) (but not EADPTGHSY) (SEQ. ID NO.: 616) E (A/V) D X5 Y (SEQ. ID NO.: 617) E (A/V) D P X4 Y (SEQ. ID NO.: 618) E (A/V) D P (I/A/T) X3 Y (SEQ. ID NO.: 619) E (A/V) D P (I/A/T) (G/S) X2 Y (SEQ. ID NO.: 620) E (A/V) D P (I/A/T) (G/S) (H/N) X Y (SEQ. ID NO.: 621) E (A/V) DP (I/A/T) (G/S) (H/N) (L/T/V) Y (SEQ. ID NO.: 622) | HLA-A1 |
| MAGE-1 | 5361 | 5,558,995 | 24 Sep. 1996 | ELHSAYGEPRKLLTQD (SEQ ID NO: 623) EHSAYGEPRKLL (SEQ ID NO: 624) SAYGEPRKL (SEQ ID NO: 625) | HLA-C Clone 10 |
| MAGE-1 | 5253.4 | TBA | TBA | EADPTGHSY (SEQ ID NO: 626) | HLA-A I |
| BAGE | 5310.1 | TBA | TBA | MAARAVFLALSAQLLQARLMKE (SEQ ID NO: 627) MAARAVFLALSAQLLQ (SEQ ID NO: 628) AARAVFLAL (SEQ ID NO: 629) | HLA-C Clone 10 HLA-C Clone 10 HLA-C Clone 10 |
| GAGE | 5323.2 | 5,648,226 | 15 Jul. 1997 | YRPRPRRY (SEQ. ID NO.: 630) | HLA-CW6 |

TABLE 4

| Source | Protein | AA Position | MHC molecules | T cell epitope MHC ligand (Antigen) | SEQ ID NO: | Ref. |
|---|---|---|---|---|---|---|
| synthetic peptides | synthetic peptides | synthetic peptides | HLA-A2 | ALFAAAAAV | 631 | Parker, et al., "Scheme for ranking potential HLA-A2 binding peptides based on independent binding of individual peptide side-chains," J. Immunol. 152:163-175 |
| | | | " | GIFGGVGGV | 632 | Parker, et al., "Scheme for ranking potential HLA-A2 binding peptides based on independent binding of individual peptide side-chains," J. Immunol. 152:163-175 |
| | | | " | GLDKGGGV | 633 | Parker, et al., "Scheme for ranking potential HLA-A2 binding peptides based on independent binding of individual peptide side-chains," J. Immunol. 152:163-175 |
| | | | " | GLFGGFGGV | 634 | Parker, et al., "Scheme for ranking potential HLA-A2 binding peptides based on independent binding of individual peptide side-chains," J. Immunol. 152:163-175 |
| | | | " | GLFGGGAGV | 635 | Parker, et al., "Scheme for ranking potential HLA-A2 binding peptides based on independent binding of individual peptide side-chains," J. Immunol. 152:163-175 |
| | | | " | GLFGGGEGV | 636 | Parker, et al., "Scheme for ranking potential HLA-A2 binding peptides based on independent binding of individual peptide side-chains," J. Immunol. 152:163-175 |
| | | | " | GLFGGGFGV | 637 | Parker, et al., "Scheme for ranking potential HLA-A2 binding peptides based on independent binding of individual peptide side-chains," J. Immunol. 152:163-175 |
| | | | " | GLFGGGGL | 638 | Parker, et al., "Scheme for ranking potential HLA-A2 binding peptides based on independent binding of individual peptide side-chains," J. Immunol. 152:163-175 |
| | | | " | GLFGGGGV | 639 | Parker, et al., "Scheme for ranking potential HLA-A2 binding peptides based on independent binding of individual peptide side-chains," J. Immunol. 152:163-175 |
| | | | " | GLFGGGVGV | 640 | Parker, et al., "Scheme for ranking potential HLA-A2 binding peptides based on independent binding of individual peptide side-chains," J. Immunol. 152:163-175 |
| | | | " | GLFGGVGGV | 641 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO: | Ref. |
|---|---|---|---|---|---|---|
| | | | " | GLFGGVGKV | 642 | Parker, et al., "Scheme for ranking potential HLA-A2 binding peptides based on independent binding of individual peptide side-chains," J. Immunol. 152:163-175 |
| | | | " | GLFKGVGGV | 643 | Parker, et al., "Scheme for ranking potential HLA-A2 binding peptides based on independent binding of individual peptide side-chains," J. Immunol. 152:163-175 |
| | | | " | GLGGGFGV | 644 | Parker, et al., "Scheme for ranking potential HLA-A2 binding peptides based on independent binding of individual peptide side-chains," J. Immunol. 152:163-175 |
| | | | " | GLLGGGVGV | 645 | Parker, et al., "Scheme for ranking potential HLA-A2 binding peptides based on independent binding of individual peptide side-chains," J. Immunol. 152:163-175 |
| | | | " | GLYGGGGGV | 646 | Parker, et al., "Scheme for ranking potential HLA-A2 binding peptides based on independent binding of individual peptide side-chains," J. Immunol. 152:163-175 |
| | | | " | GMFGGGGV | 647 | Parker, et al., "Scheme for ranking potential HLA-A2 binding peptides based on independent binding of individual peptide side-chains," J. Immunol. 152:163-175 |
| | | | " | GMFGGVGGV | 648 | Parker, et al., "Scheme for ranking potential HLA-A2 binding peptides based on independent binding of individual peptide side-chains," J. Immunol. 152:163-175 |
| | | | " | GQFGGVGGV | 649 | Parker, et al., "Scheme for ranking potential HLA-A2 binding peptides based on independent binding of individual peptide side-chains," J. Immunol. 152:163-175 |
| | | | " | GVFGGVGGV | 650 | Parker, et al., "Scheme for ranking potential HLA-A2 binding peptides based on independent binding of individual peptide side-chains," J. Immunol. 152:163-175 |
| | | | " | KLFGGGGGV | 651 | Parker, et al., "Scheme for ranking potential HLA-A2 binding peptides based on independent binding of individual peptide side-chains," J. Immunol. 152:163-175 |
| | | | " | KLFGGVGGV | 652 | Parker, et al., "Scheme for ranking potential HLA-A2 binding peptides based on independent binding of individual peptide side-chains," J. Immunol. 152:163-175 |
| | | | " | AILGFVFTL | 653 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO.: | Ref. |
|---|---|---|---|---|---|---|
| | | | " | GAIGFVFTL | 654 | Parker, et al., "Scheme for ranking potential HLA-A2 binding peptides based on independent binding of individual peptide side-chains," J. Immunol. 152:163-175 |
| | | | " | GALGFVFTL | 655 | Parker, et al., "Scheme for ranking potential HLA-A2 binding peptides based on independent binding of individual peptide side-chains," J. Immunol. 152:163-175 |
| | | | " | GELGFVFTL | 656 | Parker, et al., "Scheme for ranking potential HLA-A2 binding peptides based on independent binding of individual peptide side-chains," J. Immunol. 152:163-175 |
| | | | " | GIAGFVFTL | 657 | Parker, et al., "Scheme for ranking potential HLA-A2 binding peptides based on independent binding of individual peptide side-chains," J. Immunol. 152:163-175 |
| | | | " | GIEGFVFTL | 658 | Parker, et al., "Scheme for ranking potential HLA-A2 binding peptides based on independent binding of individual peptide side-chains," J. Immunol. 152:163-175 |
| | | | " | GILAFVFTL | 659 | Parker, et al., "Scheme for ranking potential HLA-A2 binding peptides based on independent binding of individual peptide side-chains," J. Immunol. 152:163-175 |
| | | | " | GILGAVFTL | 660 | Parker, et al., "Scheme for ranking potential HLA-A2 binding peptides based on independent binding of individual peptide side-chains," J. Immunol. 152:163-175 |
| | | | " | GILGEVFTL | 661 | Parker, et al., "Scheme for ranking potential HLA-A2 binding peptides based on independent binding of individual peptide side-chains," J. Immunol. 152:163-175 |
| | | | " | GILFGAFTL | 662 | Parker, et al., "Scheme for ranking potential HLA-A2 binding peptides based on independent binding of individual peptide side-chains," J. Immunol. 152:163-175 |
| | | | " | GILGFEFTL | 663 | Parker, et al., "Scheme for ranking potential HLA-A2 binding peptides based on independent binding of individual peptide side-chains," J. Immunol. 152:163-175 |
| | | | " | GILGFKFTL | 664 | Parker, et al., "Scheme for ranking potential HLA-A2 binding peptides based on independent binding of individual peptide side-chains," J. Immunol. 152:163-175 |
| | | | " | GILGFVATL | 665 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO: | Ref. |
|---|---|---|---|---|---|---|
| | | | " | GILGFVETL | 666 | Parker, et al., "Scheme for ranking potential HLA-A2 binding peptides based on independent binding of individual peptide side-chains," J. Immunol. 152:163-175 |
| | | | " | GILGFVFAL | 667 | Parker, et al., "Scheme for ranking potential HLA-A2 binding peptides based on independent binding of individual peptide side-chains," J. Immunol. 152:163-175 |
| | | | " | GILGFVFEL | 668 | Parker, et al., "Scheme for ranking potential HLA-A2 binding peptides based on independent binding of individual peptide side-chains," J. Immunol. 152:163-175 |
| | | | " | GILGFVFKL | 669 | Parker, et al., "Scheme for ranking potential HLA-A2 binding peptides based on independent binding of individual peptide side-chains," J. Immunol. 152:163-175 |
| | | | " | GILGFVFTA | 670 | Parker, et al., "Scheme for ranking potential HLA-A2 binding peptides based on independent binding of individual peptide side-chains," J. Immunol. 152:163-175 |
| | | | " | GILGFVFTL | 671 | Parker, et al., "Scheme for ranking potential HLA-A2 binding peptides based on independent binding of individual peptide side-chains," J. Immunol. 152:163-175 |
| | | | " | GILGFVFVL | 672 | Parker, et al., "Scheme for ranking potential HLA-A2 binding peptides based on independent binding of individual peptide side-chains," J. Immunol. 152:163-175 |
| | | | " | GILGFVKTL | 673 | Parker, et al., "Scheme for ranking potential HLA-A2 binding peptides based on independent binding of individual peptide side-chains," J. Immunol. 152:163-175 |
| | | | " | GILGKVFTL | 674 | Parker, et al., "Scheme for ranking potential HLA-A2 binding peptides based on independent binding of individual peptide side-chains," J. Immunol. 152:163-175 |
| | | | " | GILKFVFTL | 675 | Parker, et al., "Scheme for ranking potential HLA-A2 binding peptides based on independent binding of individual peptide side-chains," J. Immunol. 152:163-175 |
| | | | " | GILPFVFTL | 676 | Parker, et al., "Scheme for ranking potential HLA-A2 binding peptides based on independent binding of individual peptide side-chains," J. Immunol. 152:163-175 |
| | | | " | GIVGFVFTL | 677 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO.: | Ref. |
|---|---|---|---|---|---|---|
| | | | " | GKLGFVFTL | 678 | Parker, et al., "Scheme for ranking potential HLA-A2 binding peptides based on independent binding of individual peptide side-chains," J. Immunol. 152:163-175 |
| | | | " | GLLGFVFTL | 679 | Parker, et al., "Scheme for ranking potential HLA-A2 binding peptides based on independent binding of individual peptide side-chains," J. Immunol. 152:163-175 |
| | | | " | GQLGFVFTL | 680 | Parker, et al., "Scheme for ranking potential HLA-A2 binding peptides based on independent binding of individual peptide side-chains," J. Immunol. 152:163-175 |
| | | | " | KALGFVFTL | 681 | Parker, et al., "Scheme for ranking potential HLA-A2 binding peptides based on independent binding of individual peptide side-chains," J. Immunol. 152:163-175 |
| | | | " | KILGFVFTL | 682 | Parker, et al., "Scheme for ranking potential HLA-A2 binding peptides based on independent binding of individual peptide side-chains," J. Immunol. 152:163-175 |
| | | | " | KILGKVFTL | 683 | Parker, et al., "Scheme for ranking potential HLA-A2 binding peptides based on independent binding of individual peptide side-chains," J. Immunol. 152:163-175 |
| | | | " | AILLGVFML | 684 | Parker, et al., "Scheme for ranking potential HLA-A2 binding peptides based on independent binding of individual peptide side-chains," J. Immunol. 152:163-175 |
| | | | " | AIYKRWIIL | 685 | Parker, et al., "Scheme for ranking potential HLA-A2 binding peptides based on independent binding of individual peptide side-chains," J. Immunol. 152:163-175 |
| | | | " | ALFFFDIDL | 686 | Parker, et al., "Scheme for ranking potential HLA-A2 binding peptides based on independent binding of individual peptide side-chains," J. Immunol. 152:163-175 |
| | | | " | ATVELLSEL | 687 | Parker, et al., "Scheme for ranking potential HLA-A2 binding peptides based on independent binding of individual peptide side-chains," J. Immunol. 152:163-175 |
| | | | " | CLFGYPVYV | 688 | Parker, et al., "Scheme for ranking potential HLA-A2 binding peptides based on independent binding of individual peptide side-chains," J. Immunol. 152:163-175 |
| | | | " | FIFPNYTIV | 689 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO: | Ref. |
|---|---|---|---|---|---|---|
| | | | " | IISLWDSQL | 690 | Parker, et al., "Scheme for ranking potential HLA-A2 binding peptides based on independent binding of individual peptide side-chains," J. Immunol. 152:163-175 |
| | | | " | ILASLFAAV | 691 | Parker, et al., "Scheme for ranking potential HLA-A2 binding peptides based on independent binding of individual peptide side-chains," J. Immunol. 152:163-175 |
| | | | " | ILESLFAAV | 692 | Parker, et al., "Scheme for ranking potential HLA-A2 binding peptides based on independent binding of individual peptide side-chains," J. Immunol. 152:163-175 |
| | | | " | KLGEFFNQM | 693 | Parker, et al., "Scheme for ranking potential HLA-A2 binding peptides based on independent binding of individual peptide side-chains," J. Immunol. 152:163-175 |
| | | | " | KLGEFYNQM | 694 | Parker, et al., "Scheme for ranking potential HLA-A2 binding peptides based on independent binding of individual peptide side-chains," J. Immunol. 152:163-175 |
| | | | " | LLFGYPVYV | 695 | Parker, et al., "Scheme for ranking potential HLA-A2 binding peptides based on independent binding of individual peptide side-chains," J. Immunol. 152:163-175 |
| | | | " | LLWKGEGAV | 696 | Parker, et al., "Scheme for ranking potential HLA-A2 binding peptides based on independent binding of individual peptide side-chains," J. Immunol. 152:163-175 |
| | | | " | LMFGYPVYV | 697 | Parker, et al., "Scheme for ranking potential HLA-A2 binding peptides based on independent binding of individual peptide side-chains," J. Immunol. 152:163-175 |
| | | | " | LNFGYPVYV | 698 | Parker, et al., "Scheme for ranking potential HLA-A2 binding peptides based on independent binding of individual peptide side-chains," J. Immunol. 152:163-175 |
| | | | " | LQFGYPVYV | 699 | Parker, et al., "Scheme for ranking potential HLA-A2 binding peptides based on independent binding of individual peptide side-chains," J. Immunol. 152:163-175 |
| | | | " | NIVAHTFKV | 700 | Parker, et al., "Scheme for ranking potential HLA-A2 binding peptides based on independent binding of individual peptide side-chains," J. Immunol. 152:163-175 |
| | | | " | NLPMVATV | 701 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO: | Ref. |
|---|---|---|---|---|---|---|
| | | | " | QMLLAIARL | 702 | Parker, et al., "Scheme for ranking potential HLA-A2 binding peptides based on independent binding of individual peptide side-chains," J. Immunol. 152:163-175 |
| | | | " | QMWQARLTV | 703 | Parker, et al., "Scheme for ranking potential HLA-A2 binding peptides based on independent binding of individual peptide side-chains," J. Immunol. 152:163-175 |
| | | | " | RLLQTGIHV | 704 | Parker, et al., "Scheme for ranking potential HLA-A2 binding peptides based on independent binding of individual peptide side-chains," J. Immunol. 152:163-175 |
| | | | " | RLVNGSLAL | 705 | Parker, et al., "Scheme for ranking potential HLA-A2 binding peptides based on independent binding of individual peptide side-chains," J. Immunol. 152:163-175 |
| | | | " | SLYNTVATL | 706 | Parker, et al., "Scheme for ranking potential HLA-A2 binding peptides based on independent binding of individual peptide side-chains," J. Immunol. 152:163-175 |
| | | | " | TLNAWVKVV | 707 | Parker, et al., "Scheme for ranking potential HLA-A2 binding peptides based on independent binding of individual peptide side-chains," J. Immunol. 152:163-175 |
| | | | " | WLYRETCNL | 708 | Parker, et al., "Scheme for ranking potential HLA-A2 binding peptides based on independent binding of individual peptide side-chains," J. Immunol. 152:163-175 |
| | | | " | YLFKRMIDL | 709 | Parker, et al., "Scheme for ranking potential HLA-A2 binding peptides based on independent binding of individual peptide side-chains," J. Immunol. 152:163-175 |
| | | | " | GAFGGVGGV | 710 | Parker, et al., "Scheme for ranking potential HLA-A2 binding peptides based on independent binding of individual peptide side-chains," J. Immunol. 152:163-175 |
| | | | " | GAFGGVGGY | 711 | Parker, et al., "Scheme for ranking potential HLA-A2 binding peptides based on independent binding of individual peptide side-chains," J. Immunol. 152:163-175 |
| | | | " | GEFGGVGGV | 712 | Parker, et al., "Scheme for ranking potential HLA-A2 binding peptides based on independent binding of individual peptide side-chains," J. Immunol. 152:163-175 |
| | | | " | GGFGGVGGV | 713 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO.: | Ref. |
|---|---|---|---|---|---|---|
| | | | " | GIFGGGGGV | 714 | Parker, et al., "Scheme for ranking potential HLA-A2 binding peptides based on independent binding of individual peptide side-chains," J. Immunol. 152:163-175 |
| | | | " | GIGGFGGGL | 715 | Parker, et al., "Scheme for ranking potential HLA-A2 binding peptides based on independent binding of individual peptide side-chains," J. Immunol. 152:163-175 |
| | | | " | GIGGGGGGL | 716 | Parker, et al., "Scheme for ranking potential HLA-A2 binding peptides based on independent binding of individual peptide side-chains," J. Immunol. 152:163-175 |
| | | | " | GLDGGGGGV | 717 | Parker, et al., "Scheme for ranking potential HLA-A2 binding peptides based on independent binding of individual peptide side-chains," J. Immunol. 152:163-175 |
| | | | " | GLDGKGGGV | 718 | Parker, et al., "Scheme for ranking potential HLA-A2 binding peptides based on independent binding of individual peptide side-chains," J. Immunol. 152:163-175 |
| | | | " | GLDKKGGGV | 719 | Parker, et al., "Scheme for ranking potential HLA-A2 binding peptides based on independent binding of individual peptide side-chains," J. Immunol. 152:163-175 |
| | | | " | GLFGGGFGF | 720 | Parker, et al., "Scheme for ranking potential HLA-A2 binding peptides based on independent binding of individual peptide side-chains," J. Immunol. 152:163-175 |
| | | | " | GLFGGGFGG | 721 | Parker, et al., "Scheme for ranking potential HLA-A2 binding peptides based on independent binding of individual peptide side-chains," J. Immunol. 152:163-175 |
| | | | " | GLFGGGFGN | 722 | Parker, et al., "Scheme for ranking potential HLA-A2 binding peptides based on independent binding of individual peptide side-chains," J. Immunol. 152:163-175 |
| | | | " | GLFGGGFGS | 723 | Parker, et al., "Scheme for ranking potential HLA-A2 binding peptides based on independent binding of individual peptide side-chains," J. Immunol. 152:163-175 |
| | | | " | GLFGGGGGI | 724 | Parker, et al., "Scheme for ranking potential HLA-A2 binding peptides based on independent binding of individual peptide side-chains," J. Immunol. 152:163-175 |
| | | | " | GLFGGGGGM | 725 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO: | Ref. |
|---|---|---|---|---|---|---|
| | | | " | GLFGGGGGT | 726 | Parker, et al., "Scheme for ranking potential HLA-A2 binding peptides based on independent binding of individual peptide side-chains," J. Immunol. 152:163-175 |
| | | | " | GLFGGGGGY | 727 | Parker, et al., "Scheme for ranking potential HLA-A2 binding peptides based on independent binding of individual peptide side-chains," J. Immunol. 152:163-175 |
| | | | " | GLGFGGGGV | 728 | Parker, et al., "Scheme for ranking potential HLA-A2 binding peptides based on independent binding of individual peptide side-chains," J. Immunol. 152:163-175 |
| | | | " | GLGGFGGGV | 729 | Parker, et al., "Scheme for ranking potential HLA-A2 binding peptides based on independent binding of individual peptide side-chains," J. Immunol. 152:163-175 |
| | | | " | GLGGGFGGV | 730 | Parker, et al., "Scheme for ranking potential HLA-A2 binding peptides based on independent binding of individual peptide side-chains," J. Immunol. 152:163-175 |
| | | | " | GLGGGGGFV | 731 | Parker, et al., "Scheme for ranking potential HLA-A2 binding peptides based on independent binding of individual peptide side-chains," J. Immunol. 152:163-175 |
| | | | " | GLGGGGGGY | 732 | Parker, et al., "Scheme for ranking potential HLA-A2 binding peptides based on independent binding of individual peptide side-chains," J. Immunol. 152:163-175 |
| | | | " | GLGGGVGGV | 733 | Parker, et al., "Scheme for ranking potential HLA-A2 binding peptides based on independent binding of individual peptide side-chains," J. Immunol. 152:163-175 |
| | | | " | GLLGGGGGV | 734 | Parker, et al., "Scheme for ranking potential HLA-A2 binding peptides based on independent binding of individual peptide side-chains," J. Immunol. 152:163-175 |
| | | | " | GLPGGGGGV | 735 | Parker, et al., "Scheme for ranking potential HLA-A2 binding peptides based on independent binding of individual peptide side-chains," J. Immunol. 152:163-175 |
| | | | " | GNFGGVGGV | 736 | Parker, et al., "Scheme for ranking potential HLA-A2 binding peptides based on independent binding of individual peptide side-chains," J. Immunol. 152:163-175 |
| | | | " | GSFGGVGGV | 737 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO: | Ref. |
|---|---|---|---|---|---|---|
| | | | " | GTFGGVGGV | 738 | Parker, et al., "Scheme for ranking potential HLA-A2 binding peptides based on independent binding of individual peptide side-chains," J. Immunol. 152:163-175 |
| | | | " | AGNSAYEYV | 739 | Parker, et al., "Scheme for ranking potential HLA-A2 binding peptides based on independent binding of individual peptide side-chains," J. Immunol. 152:163-175 |
| | | | " | GLFPGQFAY | 740 | Parker, et al., "Scheme for ranking potential HLA-A2 binding peptides based on independent binding of individual peptide side-chains," J. Immunol. 152:163-175 |
| | | | " | HILLGVFML | 741 | Parker, et al., "Scheme for ranking potential HLA-A2 binding peptides based on independent binding of individual peptide side-chains," J. Immunol. 152:163-175 |
| | | | " | ILESLFRAV | 742 | Parker, et al., "Scheme for ranking potential HLA-A2 binding peptides based on independent binding of individual peptide side-chains," J. Immunol. 152:163-175 |
| | | | " | KKKYKLKHI | 743 | Parker, et al., "Scheme for ranking potential HLA-A2 binding peptides based on independent binding of individual peptide side-chains," J. Immunol. 152:163-175 |
| | | | " | MLASIDLKY | 744 | Parker, et al., "Scheme for ranking potential HLA-A2 binding peptides based on independent binding of individual peptide side-chains," J. Immunol. 152:163-175 |
| | | | " | MLERELVRK | 745 | Parker, et al., "Scheme for ranking potential HLA-A2 binding peptides based on independent binding of individual peptide side-chains," J. Immunol. 152:163-175 |
| | | | " | KLFGVFTV | 746 | Parker, et al., "Scheme for ranking potential HLA-A2 binding peptides based on independent binding of individual peptide side-chains," J. Immunol. 152:163-175 |
| | | | " | ILDKKVEKV | 747 | Parker, et al., "Scheme for ranking potential HLA-A2 binding peptides based on independent binding of individual peptide side-chains," J. Immunol. 152:163-175 |
| | | | " | ILKEPVHGV | 748 | Parker, et al., "Scheme for ranking potential HLA-A2 binding peptides based on independent binding of individual peptide side-chains," J. Immunol. 152:163-175 |
| | | | " | ALFAAAAAY | 749 | Parker, et al., "Scheme for ranking potential HLA-A2 binding peptides based on independent binding of individual peptide side-chains," J. Immunol. 152:163-175 |

TABLE 4-continued

| Source | Protein | AA Position | MHC molecules | T cell epitope MHC ligand (Antigen) | SEQ ID NO: | Ref. |
|---|---|---|---|---|---|---|
| | | | " | GIGFGGGGL | 750 | Parker, et al., "Scheme for ranking potential HLA-A2 binding peptides based on independent binding of individual peptide side-chains." J. Immunol. 152:163-175 |
| | | | " | GKFGGVGGV | 751 | Parker, et al., "Scheme for ranking potential HLA-A2 binding peptides based on independent binding of individual peptide side-chains." J. Immunol. 152:163-175 |
| | | | " | GLFGGGGGK | 752 | Parker, et al., "Scheme for ranking potential HLA-A2 binding peptides based on independent binding of individual peptide side-chains." J. Immunol. 152:163-175 |
| | | | " | EILGFVFTL | 753 | Parker, et al., "Scheme for ranking potential HLA-A2 binding peptides based on independent binding of individual peptide side-chains." J. Immunol. 152:163-175 |
| | | | " | GIKGFVFTL | 754 | Parker, et al., "Scheme for ranking potential HLA-A2 binding peptides based on independent binding of individual peptide side-chains." J. Immunol. 152:163-175 |
| | | | " | GQLGFVFTK | 755 | Parker, et al., "Scheme for ranking potential HLA-A2 binding peptides based on independent binding of individual peptide side-chains." J. Immunol. 152:163-175 |
| | | | " | ILGFVFTLT | 756 | Parker, et al., "Scheme for ranking potential HLA-A2 binding peptides based on independent binding of individual peptide side-chains." J. Immunol. 152:163-175 |
| | | | " | KILGFVFTK | 757 | Parker, et al., "Scheme for ranking potential HLA-A2 binding peptides based on independent binding of individual peptide side-chains." J. Immunol. 152:163-175 |
| | | | " | KKLGFVFTL | 758 | Parker, et al., "Scheme for ranking potential HLA-A2 binding peptides based on independent binding of individual peptide side-chains." J. Immunol. 152:163-175 |
| | | | " | KLFEKVYNY | 759 | Parker, et al., "Scheme for ranking potential HLA-A2 binding peptides based on independent binding of individual peptide side-chains." J. Immunol. 152:163-175 |
| | | | " | LRFGYPVYV | 760 | Parker, et al., "Scheme for ranking potential HLA-A2 binding peptides based on independent binding of individual peptide side-chains." J. Immunol. 152:163-175 |
| Human | HSP60 | 140-148 | HLA-B27 | IRRGVMLAV | 761 | Rammensee et al. 1997 160 |
| " | | 369-377 | " | KRIQEIIEQ | 762 | Rammensee et al. 1997 160 |

TABLE 4-continued

| Source | Protein | AA Position | MHC molecules | T cell epitope MHC ligand (Antigen) | SEQ ID NO: | Ref. |
|---|---|---|---|---|---|---|
| " | " | 469-477 | " | KRTLKIPAM | 763 | Rammensee et al. 1997 160 |
| Yersinia | HSP60 | 35-43 | " | GRNVVLDKS | 764 | Rammensee et al. 1997 160 |
| " | " | 117-125 | " | KRGIDKAVI | 765 | Rammensee et al. 1997 160 |
| " | " | 420-428 | " | IRAASAITA | 766 | Rammensee et al. 1997 160 |
| " | HSP60 | 284-292 | HLA-B*2705 | RRKAMFEDI | 767 | Rammensee et al. 1997 160 |
| P. falciparum | LSA-1 | 1850-1857 | HLA-B3501 | KPKDELDY | 768 | 169 |
| Influenza NP | | 379-387 | HLA-B*4402 | LELRSRYWA | 769 | 183 |
| Rotavirus | Tum-P35B | 4-13 | HLA-D$^d$ | GPPHSNNFGY | 770 | 230 |
| | VP7 | 33-40 | | IIYRFLLI | 771 | 262 |
| | OGDH (F108Y) | 104-112 | H2-L$^d$ | QLSPYPFDL | 772 | 253 |
| | TRP-2 | 181-188 | p287 | VYDFFVWL | 773 | 284 |
| | DEAD box p 68 | 547-554 | p287 | SNFVFAGI | 774 | 283 |
| | Vector "artefact" | | p287 | SVVEFSSL | 775 | 260 |
| | Epiope mimic of tumor Ag | | p287 | AHYLFRNL | 776 | 278 |
| | Epitope mimic of H-3 | | " | THYLFRNL | 777 | " |
| | Epitope mimic of H-3 | | " | LIVIYNTL | 778 | 279 |
| | miHAg" | | | LIYEFNTL | 779 | " |
| | | | " | IPYIYNTL | 780 | " |
| | | | " | IIYIYHRL | 781 | " |
| | | | " | LIYIFNTL | 782 | " |
| | | 93-100 | " | MGLKFRQL | 783 | 280 |
| | | 51-58 | " | IMIKFRNRL | 784 | 281 |
| Human | HBV cAg autoantigen LA | | H2D$^b$ | WMHHNMDLI | 785 | 303 |
| Mouse | UTY protein | | | | | |
| Mouse | p53 | 232-240 | " | KYMCNSSCM | 786 | 302 |
| | MDM2 | 441-449 | " | GRPKNGCIV | 787 | 277 |
| | Epitope mimic of natural | | " | AQHPNAELL | 788 | 278 |
| MURINE | MuLV gag75K | 75-83 | " | CCLCITVFL | 789 | 301 |

TABLE 4-continued

| Source | Protein | AA Position | MHC molecules | T cell epitope MHC ligand (Antigen) | SEQ ID NO.: | Ref. |
|---|---|---|---|---|---|---|
| P. falciparum | CSP | 375-383 | p290 | YENDIEKK | 790 | 315 |
| " | " | 371-379 | " | DELDYENDI | 791 | 315 |
| HIV | -1RT | 206-214 | " | TEMEKEGKI | 792 | 316 |
| Rabies | NS | 197-205 | " | VEAEIAHQI | 793 | 309, 310 |
| Influenza A | NS1 | 152-160 | " | EEGAIVGEI | 794 | 304 |
| Murine | SMCY | 3-11 | p291 | TENSGKDI | 795 | 317 |
| | MHC class 1 leader | | p293 | AMAPRTLLL | 796 | 318 |
| | ND1 alpha | 1-12 | p293 | FFINLTLLVP | 797 | 323 |
| | ND Beta | 1-12 | p293 | FFINLTLLVP | 798 | 323 |
| | ND alpha | 1-17 | " | FFINLTLLVPILLIAM | 799 | 324 |
| | ND Beta | 1-17 | " | FFINALTLLVPILLIAM | 800 | " |
| | COI mitochondrial | 1-6 | " | FINRW | 801 | 325 |
| L. monocytogenes | LemA | 1-6 | " | IGWII | 802 | 326 |
| | SIV gag | 179-190 | Mamu-A*01 | EGCTPYDINQML | 803 | 334 |
| | p11C MAGE-3 | | HLA-A2 | ALSRKVAEL | 804 | 5,554,506 |
| | | | " | IMPKAGLLI | 805 | " |
| | | | " | KIWEELSVL | 806 | " |
| | | | " | ALVETSYVKV | 807 | " |
| | | | " | Thr Leu Val Glu Val Thr Leu Gly Glu Val | 808 | " |
| | | | " | Ala Leu Ser Arg Lys Val Ala Glu Leu | 809 | " |
| | | | " | Ile Met Pro Lys Ala Gly Leu Leu Ile | 810 | " |
| | | | " | Lys Ile Trp Glu Glu Leu Ser Val Leu | 811 | " |
| | | | " | Ala Leu Val Glu Thr Ser Tyr Val Lys Val | 812 | " |
| | peptides which bind to MHCs | | HLA-A2 | Lys Gly Ile Leu Gly Phe Val Phe Thr Leu Thr Val | 813 | 5,989,565 |
| | | | " | Gly Ile Ile Gly Phe Val Phe Thr Ile | 814 | " |
| | | | " | Gly Ile Ile Gly Phe Val Phe Thr Leu | 815 | " |
| | | | " | Gly Ile Leu Gly Phe Val Phe Thr Leu | 816 | " |
| | | | " | Gly Leu Leu Gly Phe Val Phe Thr Leu | 817 | " |
| | | | " | XXTVXXGVX, X = Leu or Ile (6-37) | 818 | " |
| | | | " | Ile Leu Thr Val Ile Leu Gly Val Leu | 819 | " |
| | | | " | Tyr Leu Glu Pro Gly Pro Val Thr Ala | 820 | " |

TABLE 4-continued

| Source | Protein | AA Position | MHC molecules | T cell epitope MHC ligand (Antigen) | SEQ ID NO: | Ref. |
|---|---|---|---|---|---|---|
| | | | " | Gln Val Pro Leu Arg Pro Met Thr Tyr Lys | 821 | " |
| | | | " | Asp Gly Leu Ala Pro Pro Gln His Leu Ile Arg | 822 | " |
| | | | " | Leu Leu Gly Arg Asn Ser Phe Glu Val | 823 | " |
| | Peptides from MAGE-1 | | HLA-C clone 10 | Glu His Ser Ala Tyr Gly Glu Pro Arg Lys Leu Leu Thr Gln Asp Leu | 824 | 5,558,995 |
| | | | HLA-C clone 10 | Glu His Ser Ala Tyr Gly Glu Pro Arg Lys Leu Leu | 825 | " |
| | | | HLA-C clone 10 | Ser Ala Tyr Gly Glu Pro Arg Lys Leu | 826 | " |
| | GAGE | | HLA-Cw6 | Tyr Arg Pro Arg Pro Arg Arg Tyr | 827 | 5,648,226 |
| | | | " | Thr Tyr Arg Pro Arg Pro Arg Arg Tyr | 828 | " |
| | | | " | Tyr Arg Pro Arg Pro Arg Arg Tyr Val | 829 | " |
| | | | " | Thr Tyr Arg Pro Arg Pro Arg Arg Tyr Val | 830 | " |
| | | | " | Arg Pro Arg Pro Arg Arg Tyr Val Glu | 831 | " |
| | | | " | Met Ser Trp Arg Gly Arg Ser Thr Tyr Arg Pro Arg Pro Arg Arg | 832 | " |
| | | | " | Thr Tyr Arg Pro Arg Pro Arg Arg Tyr Val Glu Pro Pro Glu Met Ile | 833 | " |
| | MAGE | | HLA-A1, primarily | Isolated nonapeptide having Glu at its N terminal, Tyr at its C-terminal, and Asp at the third residue from its N terminal, with the proviso that said isolated nonapeptide is not Glu Ala Asp Pro Thr Gly His Ser Tyr (SEQ ID NO: 1), and wherein said isolated nonapeptide binds to a human leukocyte antigen molecule on a cell to | 834 | 5,405,940 |

TABLE 4-continued

| Source | Protein | AA Position | MHC molecules | T cell epitope MHC ligand (Antigen) | SEQ. ID NO.: | Ref. |
|---|---|---|---|---|---|---|
| | | | | form a complex, said complex provoking lysis of said cell by a cytolytic T cell specific to said complex | | |
| | | | HLA-A1, primarily | Glu Val Val Pro Ile Ser His Leu Tyr | 835 | " |
| | | | HLA-A1, primarily | Glu Val Val Arg Ile Gly His Leu Tyr | 836 | " |
| | | | HLA-A1, primarily | Glu Val Asp Pro Ile Gly His Leu Tyr | 837 | " |
| | | | HLA-A1, primarily | Glu Val Asp Pro Ala Ser Asn Thr Tyr | 838 | " |
| | | | HLA-A1, primarily | Glu Val Asp Pro Thr Ser Asn Thr Tyr | 839 | " |
| | | | HLA-A1, primarily | Glu Ala Asp Pro Thr Ser Asn Thr Tyr | 840 | " |
| | | | HLA-A1, primarily | Glu Val Asp Pro Ile Gly His Val Tyr | 841 | " |
| | | | HLA-A1, primarily | GAAGTGGTCCCC ATCAGCCACTTGTAC | 842 | " |
| | | | HLA-A1, primarily | GAAGTGGTCCGC ATCGGCCACTTGTAC | 843 | " |
| | | | HLA-A1, primarily | GAAGTGGACCCC ATCGGCCACTTGTAC | 844 | " |
| | | | HLA-A1, primarily | GAAGTGGACCCC GCCAGCAACACCTAC | 845 | " |
| | | | HLA-A1, primarily | GAAGTGGACCCC ACCAGCAACACCTAC | 846 | " |
| | | | HLA-A1, primarily | GAAGCGGACCCC ACCAGCAACACCTAC | 847 | " |
| | | | HLA-A1, primarily | GAAGCGGACCCC ACCAGCAACACCTAC | 848 | " |
| | | | HLA-A1, primarily | GAAGTGGACCCC ATCGGCCACGTGTAC | 849 | " |
| | | | HLA-A1, primarily | Glu Ala Asp Pro Thr Gly His Ser | 850 | " |
| | | | HLA-A1, primarily | Ala Asp Pro Trp Gly His Ser Tyr | 851 | " |
| | MAGE peptides | | HLA-A2 | Ser Thr Leu Val Glu Val Thr Leu Gly Glu Val | 852 | 5,554,724 |
| | " | | " | Leu Val Glu Val Thr Leu Gly Glu Val | 853 | " |
| | " | | " | Lys Met Val Glu Leu Val His Phe Leu | 854 | " |
| | " | | " | Val Ile Phe Ser Lys Ala Ser Glu Tyr Leu | 855 | " |

| Source | Protein | AA Position | MHC molecules | T cell epitope MHC ligand (Antigen) | SEQ ID NO: | Ref. |
|---|---|---|---|---|---|---|
| " | " | | " | Tyr Leu Gln Leu Val Phe Gly Ile Glu Val | 856 | " |
| " | " | | " | Gln Leu Val Phe Gly Ile Glu Val Val | 857 | " |
| " | " | | " | Gln Leu Val Phe Gly Ile Glu Val Val Glu Val | 858 | " |
| " | " | | " | Ile Ile Val Leu Ala Ile Ile Ala Ile | 859 | " |
| " | " | | " | Lys Ile Trp Glu Glu Leu Ser Met Leu Glu Val | 860 | " |
| " | " | | " | Ala Leu Ile Glu Thr Ser Tyr Val Lys Val | 861 | " |
| " | " | | " | Leu Ile Glu Thr Ser Tyr Val Lys Val | 862 | " |
| " | " | | " | Gly Leu Glu Ala Arg Gly Glu Ala Leu Gly Leu | 863 | " |
| " | " | | " | Gly Leu Glu Ala Arg Gly Glu Ala Leu | 864 | " |
| " | " | | " | Ala Leu Gly Leu Val Gly Ala Gln Ala | 865 | " |
| " | " | | " | Gly Leu Val Gly Ala Gln Ala Pro Ala | 866 | " |
| " | " | | " | Asp Leu Glu Ser Glu Phe Gln Ala Ala | 867 | " |
| " | " | | " | Asp Leu Glu Ser Glu Phe Gln Ala Ala Ile | 868 | " |
| " | " | | " | Ala Ile Ser Arg Lys Met Val Glu Leu Val | 869 | " |
| " | " | | " | Ala Ile Ser Arg Lys Met Val Glu Leu | 870 | " |
| " | " | | " | Lys Met Val Glu Leu Val His Phe Leu Leu | 871 | " |
| " | " | | " | Lys Met Val Glu Leu Val His Phe Leu Leu Leu | 872 | " |
| " | " | | " | Leu Leu Leu Lys Tyr Arg Ala Arg Glu Pro Val | 873 | " |
| " | " | | " | Leu Leu Lys Tyr Arg Ala Arg Glu Pro Val | 874 | " |
| " | " | | " | Val Leu Arg Asn Cys Gln Asp Phe Phe Pro Val | 875 | " |
| " | " | | " | Tyr Leu Gln Leu Val Phe Gly Ile Glu Val Val | 876 | " |

TABLE 4-continued

| Source | Protein | AA Position | MHC molecules | T cell epitope MHC ligand (Antigen) | SEQ ID NO: | Ref. |
|---|---|---|---|---|---|---|
| " | " | | " | Gly Ile Glu Val Val | 877 | " |
| " | " | | " | Glu Val Val Pro Ile | 878 | " |
| " | " | | " | Pro Ile Ser His Leu Tyr Ile Leu Val | 879 | " |
| " | " | | " | His Leu Tyr Ile Leu Val Thr Cys Leu | 880 | " |
| " | " | | " | His Leu Tyr Ile Leu Val Thr Cys Leu Gly Leu | | |
| " | " | | " | Tyr Ile Leu Val Thr Cys Leu Gly Leu | 881 | " |
| " | " | | " | Cys Leu Gly Leu Ser Tyr Asp Gly Leu | 882 | " |
| " | " | | " | Cys Leu Gly Leu Ser Tyr Asp Gly Leu Leu | 883 | " |
| " | " | | " | Val Met Pro Lys Thr Gly Leu Leu Ile | 884 | " |
| " | " | | " | Val Met Pro Lys Thr Gly Leu Leu Ile Ile | 885 | " |
| " | " | | " | Val Met Pro Lys Thr Gly Leu eu Ile Ile Val | 886 | " |
| " | " | | " | Gly Leu Leu Ile Ile Val Leu Ala Ile | 887 | " |
| " | " | | " | Gly Leu Leu Ile Ile Val Leu Ala Ile Ile | 888 | " |
| " | " | | " | Gly Leu Leu Ile Ile Val Leu Ala Ile Ile Ala | 889 | " |
| " | " | | " | Leu Leu Ile Ile Val Leu Ala Ile Ile | 890 | " |
| " | " | | " | Leu Leu Ile Ile Val Leu Ala Ile Ile Ala | 891 | " |
| " | " | | " | Leu Leu Ile Ile Val Leu Ala Ile Ile Ala Ile | 892 | " |
| " | " | | " | Leu Ile Ile Val Leu Ala Ile Ile Ala | 893 | " |
| " | " | | " | Leu Ile Ile Val Leu Ala Ile Ile Ala Ile | 894 | " |
| " | " | | " | Ile Ile Ala Ile Glu Gly Asp Cys Ala | 895 | " |
| " | " | | " | Lys Ile Trp Glu Glu Leu Ser Met Leu | 896 | " |
| " | " | | " | Leu Met Gln Asp Leu Val Gln Glu Asn Tyr Leu | 897 | " |
| " | " | | " | Phe Leu Trp Gly Pro Arg Ala Leu Ile | 898 | " |

TABLE 4-continued

| Source | Protein | AA Position | MHC molecules | T cell epitope MHC ligand (Antigen) | SEQ ID NO: | Ref. |
|---|---|---|---|---|---|---|
| " | " | | " | Leu Ile Glu Thr Ser Tyr Val Lys Val | 899 | " |
| " | " | | " | Ala Leu Ile Glu Thr Ser Tyr Val Lys Val Leu | 900 | " |
| " | " | | " | Thr Leu Lys Ile Gly Gly Glu Pro His Ile | 901 | " |
| " | " | | " | His Ile Ser Tyr Pro Pro Leu His Glu Arg Ala | 902 | " |
| " | " | | " | Gln Thr Ala Ser Ser Ser Ser Thr Leu | 903 | " |
| " | " | | " | Gln Thr Ala Ser Ser Ser Ser Thr Leu Val | 904 | " |
| " | " | | " | Val Thr Leu Gly Glu Val Pro Ala Ala | 905 | " |
| " | " | | " | Val Thr Lys Ala Glu Met Leu Glu Ser Val | 906 | " |
| " | " | | " | Val Thr Lys Ala Glu Met Leu Glu Ser Val Leu | 907 | " |
| " | " | | " | Val Thr Cys Leu Gly Leu Ser Tyr Asp Gly Leu | 908 | " |
| " | " | | " | Lys Thr Gly Leu Leu Ile Ile Val Leu | 909 | " |
| " | " | | " | Lys Thr Gly Leu Leu Ile Ile Val Leu Ala | 910 | " |
| " | " | | " | Lys Thr Gly Leu Leu Ile Ile Val Leu Ala Ile | 911 | " |
| " | " | | " | His Thr Leu Lys Ile Gly Gly Glu Pro His Ile | 912 | " |
| " | " | | " | Met Leu Asp Leu Gln Pro Glu Thr Thr | 913 | " |
| Mage-3 peptides | | | HLA-A2 | Gly Leu Glu Ala Arg Gly Glu Ala Leu | 914 | 5,585,461 |
| " | | | " | Ala Leu Ser Arg Lys Val Ala Glu Leu | 915 | " |
| " | | | " | Phe Leu Trp Gly Pro Arg Ala Leu Val | 916 | " |
| " | | | " | Thr Leu Val Glu Val | 917 | " |
| " | | | " | Thr Leu Gly Glu Val | 918 | " |
| " | | | " | Ala Leu Ser Arg Lys Val Ala Glu Leu Val | 918 | " |
| " | | | " | Ala Leu Val Glu Thr Ser Tyr Val Lys Val | 919 | " |

TABLE 4-continued

| Source | Protein | AA Position | MHC molecules | T cell epitope MHC ligand (Antigen) | SEQ ID NO: | Ref. |
|---|---|---|---|---|---|---|
| | Tyrosinase | | HLA-A2 | Tyr Met Asn Gly Thr Met Ser Gln Val | 920 | 5,487,974 |
| | " | | " | Met Leu Leu Ala Val Leu Tyr Cys Leu Leu | 921 | " |
| | Tyrosinase | | HLA-A2 | Met Leu Leu Ala Val Leu Tyr Cys Leu | 922 | 5,530,096 |
| | " | | " | Leu Leu Ala Val Leu Tyr Cys Leu Leu | 923 | " |
| | Tyrosinase | | HLA-A2 and HLA-B44 | Ser Glu Ile Trp Arg Asp Ile Asp Phe Ala His Glu Ala | 924 | 5,519,117 |
| | " | | HLA-A2 and HLA-B44 | Ser Glu Ile Trp Arg Asp Ile Asp Phe | 925 | " |
| | " | | HLA-A2 and HLA-B44 | Glu Glu Asn Leu Leu Asp Phe Val Arg Phe | 926 | " |
| | Melan A/MART-1 | | | EAAGIGILTV | 927 | Jäger, E. et al. Granulocyte-macrophage-colony-stimulating Factor Enhances Immune Responses To Melanoma-'associated Peptides in vivo Int. J Cancer 67, 54-62 (1996) |
| | Tyrosinase | | | MLLAVLYCL | 928 | Jäger, E. et al. Granulocyte-macrophage-colony-stimulating Factor Enhances Immune Responses To Melanoma-'associated Peptides in vivo Int. J Cancer 67, 54-62 (1996) |
| | " | | | YMDGTMSQV | 929 | Jäger, E. et al. Granulocyte-macrophage-colony-stimulating Factor Enhances Immune Responses To Melanoma-'associated Peptides in vivo Int. J Cancer 67, 54-62 (1996) |
| | gp100/Pme 117 | | | YLEPGPVTA | 930 | Jäger, E. et al. Granulocyte-macrophage-colony-stimulating Factor Enhances Immune Responses To Melanoma-'associated Peptides in vivo Int. J Cancer 67, 54-62 (1996) |
| | " | | | LLDGTATLRL | 931 | Jäger, E. et al. Granulocyte-macrophage-colony-stimulating Factor Enhances Immune Responses To Melanoma-'associated Peptides in vivo Int. J Cancer 67, 54-62 (1996) |
| | Influenza matrix | | | GILGFVFTL | 932 | Jäger, E. et al. Granulocyte-macrophage-colony-stimulating Factor Enhances Immune Responses To Melanoma-'associated Peptides in vivo Int. J Cancer 67, 54-62 (1996) |
| | MAGE-1 | | | EADPTGHSY | 933 | Jäger, E. et al. Granulocyte-macrophage-colony-stimulating Factor Enhances Immune Responses To Melanoma-'associated Peptides in vivo Int. J Cancer 67, 54-62 (1996) |

TABLE 4-continued

| Source | Protein | AA Position | MHC molecules | T cell epitope MHC ligand (Antigen) | SEQ ID NO.: | Ref. |
|---|---|---|---|---|---|---|
| | MAGE-1 | | HLA-A1 | EADPTGHSY | 934 | Int. J Cancer 67, 54-62 (1996) Jäger, E. et al. Granulocyte-macrophage-colony-stimulating Factor Enhances Immune Responses To Melanoma-'associated Peptides in vivo Int. J Cancer 67, 54-62 (1996) DIRECTLY FROM DAVID'S LIST |
| | BAGE | | HLA-C | MAARAVFLALSA QLLQARLMKE | 935 | DIRECTLY FROM DAVID'S LIST |
| | " | | " | MAARAVFLALSA QLLQ | 936 | DIRECTLY FROM DAVID'S LIST |
| | " | | " | AARAVFLAL | 937 | DIRECTLY FROM DAVID'S LIST |
| Influenza | PR8 NP | 147-154 | $K^d$ | IYQRIRALV | 938 | Falk et al., Allele-specific motifs revealed by sequencing of self-peptides eluted from MHC molecules |
| SELF PEPTIDE | P815 | | " | SYFPEITHI | 939 | Falk et al., Allele-specific motifs revealed by sequencing of self-peptides eluted from MHC molecules |
| Influenza | Jap HA 523-549 | | " | IYAIVAGSL | 940 | Falk et al., Allele-specific motifs revealed by sequencing of self-peptides eluted from MHC molecules |
| " | Jap HA 523-549 | | " | VYQILAIYA | 941 | Falk et al., Allele-specific motifs revealed by sequencing of self-peptides eluted from MHC molecules |
| " | Jap HA 523-549 | | " | IYSTVASSL | 942 | Falk et al., Allele-specific motifs revealed by sequencing of self-peptides eluted from MHC molecules |
| " | JAP HA 202-221 | | " | LYQNVGTYV | 943 | Falk et al., Allele-specific motifs revealed by sequencing of self-peptides eluted from MHC molecules |
| | HLA-A24 | | " | RYLENQKRT | 944 | Falk et al., Allele-specific motifs revealed by sequencing of self-peptides eluted from MHC molecules |
| | HLA-Cw3 | | " | RYLKNGKET | 945 | Falk et al., Allele-specific motifs revealed by sequencing of self-peptides eluted from MHC molecules |
| | P815 | | " | KYQAVTTTL | 946 | Falk et al., Allele-specific motifs revealed by sequencing of self-peptides eluted from MHC molecules |
| Plasmodium berghen | CSP | | " | SYIPSAEKI | 947 | Falk et al., Allele-specific motifs revealed by sequencing of self-peptides eluted from MHC molecules |
| Plasmodium yoelii | CSP | | " | SYVPSAFQI | 948 | Falk et al., Allele-specific motifs revealed by sequencing of self-peptides eluted from MHC molecules |

TABLE 4-continued

| Source | Protein | AA Position | MHC molecules | T cell epitope MHC ligand (Antigen) | SEQ ID NO.: | Ref. |
|---|---|---|---|---|---|---|
| Vesicular stomatitis viruse Ovalbumin | NP 52-59 | | $K^b$ | RGYVYQGL | 949 | Falk et al., Allele-specific motifs revealed by sequencing of self-peptides eluted from MHC molecules |
| | | | " | SIINFEKL | 950 | Falk et al., Allele-specific motifs revealed by sequencing of self-peptides eluted from MHC molecules |
| Sandal Virus | NP 321-332 | | " | APGNYPAL | 951 | Falk et al., Allele-specific motifs revealed by sequencing of self-peptides eluted from MHC molecules |
| | | | " | VPYGSFKHV | 952 | Morel et al., Processing of some antigens by the standard proteasome but not by the immunoproteasome results in poor presentation by dendritic cells, Immunity, vol. 12:107-117, 2000. |
| MOTIFS |
| influenza | PR8 NP | | $K^d$ restricted peptide motif | TYQRTRALV | 953 | 5,747,269 |
| self peptide | P815 | | $K^d$ restricted peptide motif | SYFPEITHI | 954 | " |
| influenza | JAP HA | | $K^d$ restricted peptide motif | IYATVAGSL | 955 | " |
| influenza | JAP HA | | $K^d$ restricted peptide motif | VYQILAIYA | 956 | " |
| influenza | PR8 HA | | $K^d$ restricted peptide motif | IYSTVASSL | 957 | " |
| influenza | JAP HA | | $K^d$ restricted peptide motif | LYQNVGTYV | 958 | " |
| | P815 tumour antigen | | HLA-A24 HLA-Cw3 " | RYLENGKETL RYLKNGKETL KYQAVTTTL | 959 960 961 | " " " |
| Plasmodium berghei | CSP | | " | SYIPSAEKI | 962 | " |

TABLE 4-continued

| Source | Protein | AA Position | MHC molecules | T cell epitope MHC ligand (Antigen) | SEQ ID NO.: | Ref. |
|---|---|---|---|---|---|---|
| *Plasmodium yoelii* | CSP | | " | SYVPSAEQI | 963 | " |
| influenza | NP | | D^b-restricted peptide motif | ASNENMETM | 964 | " |
| adenovirus | E1A | | D^b-restricted peptide motif | SGPSNTPPEI | 965 | " |
| lymphocytic choriomeningitis | | | D^b-restricted peptide motif | SGVENPGGYCL | 966 | " |
| simian virus | 40 T | | D^b-restricted peptide motif | SAINNY.... | 967 | " |
| HIV | reverse transcriptase | | HLA-A2.1-restricted peptide motif | ILKEPVHGV | 968 | " |
| influenza | influenza matrix protein | | HLA-A2.1-restricted peptide motif | GILGFVFTL | 969 | " |
| influenza | influenza matrix protein | | HLA-A2.1-restricted peptide motif | ILGFVFTLTV | 970 | " |
| HIV | Gag protein | | | FLQSRPEPT | 971 | " |
| HIV | Gag protein | | | AMQMLKE... | 972 | " |
| HIV | Gag protein | | | PLAPGQMRE | 973 | " |
| HIV | Gag protein | | | QMKDCTERQ | 974 | " |
| | | | HLA-A*0205-restricted peptide motif | VYGVIQK | 975 | " |

TABLE 5

| | |
|---|---|
| SEQ. ID NO.: 976 | VSV-NP peptide (49-62) |
| SEQ. ID NO.: 977 | LCMV-NP peptide (118-132) |
| SEQ. ID NO.: 978 | LCMV glycoprotein peptide. 33-41 |

Embodiments of the present invention provide polypeptide compositions, including vaccines, therapeutics, diagnostics, pharmacological and pharmaceutical compositions. The various compositions include newly identified epitopes of TAAs, as well as variants of these epitopes. Other embodiments of the invention provide polynucleotides encoding the polypeptide epitopes of the invention. The invention further provides vectors for expression of the polypeptide epitopes for purification. In addition, the invention provides vectors for the expression of the polypeptide epitopes in an APC for use as an anti-tumor vaccine. Any of the epitopes or antigens, or nucleic acids encoding the same, from Appendix A can be used. Other embodiments relate to methods of making and using the various compositions.

A general architecture for a class I MHC-binding epitope can be described, and has been reviewed more extensively in Madden, D.R. *Annu. Rev. Immunol.* 13:587-622, 1995. Much of the binding energy arises from main chain contacts between conserved residues in the MHC molecule and the N- and C-termini of the peptide. Additional main chain contacts are made but vary among MHC alleles. Sequence specificity is conferred by side chain contacts of so-called anchor residues with pockets that, again, vary among MHC alleles. Anchor residues can be divided into primary and secondary. Primary anchor positions exhibit strong preferences for relatively well-defined sets of amino acid residues. Secondary positions show weaker and/or less well-defined preferences that can often be better described in terms of less favored, rather than more favored, residues. Additionally, residues in some secondary anchor positions are not always positioned to contact the pocket on the MHC molecule at all. Thus, a subset of peptides exists that bind to a particular MHC molecule and have a side chain-pocket contact at the position in question and another subset exists that show binding to the same MHC molecule that does not depend on the conformation the peptide assumes in the peptide-binding groove of the MHC molecule. The C-terminal residue (P?;omega) is preferably a primary anchor residue. For many of the better studied HLA molecules (e.g. A2, A68, B27, B7, B35, and B53) the second position (P2) is also an anchor residue. However, central anchor residues have also been observed including P3 and P5 in HLA-B8, as well as P5 and P? (omega)-3 in the murine MHC molecules H-2$D^b$ and H-2$K^b$, respectively. Since more stable binding will generally improve immunogenicity, anchor residues are preferably conserved or optimized in the design of variants, regardless of their position.

Because the anchor residues are generally located near the ends of the epitope, the peptide can buckle upward out of the peptide-binding groove allowing some variation in length. Epitopes ranging from 8-11 amino acids have been found for HLA-A68, and up to 13 amino acids for HLA-A2. In addition to length variation between the anchor positions, single residue truncations and extensions have been reported and the N- and C-termini, respectively. Of the non-anchor residues, some point up out of the groove, making no contact with the MHC molecule but being available to contact the TCR, very often P1, P4, and P? (omega)-1 for HLA-A2. Others of the non-anchor residues can become interposed between the upper edges of the peptide-binding groove and the TCR, contacting both. The exact positioning of these side chain residues, and thus their effects on binding, MHC fine conformation, and ultimately immunogenicity, are highly sequence dependent. For an epitope to be highly immunogenic it must not only promote stable enough TCR binding for activation to occur, but the TCR must also have a high enough off-rate that multiple TCR molecules can interact sequentially with the same peptide-MHC complex (Kalergis, A.M. et al., *Nature Immunol.* 2:229-234, 2001). Thus, without further information about the ternary complex, both conservative and non-conservative substitutions at these positions merit consideration when designing variants.

The polypeptide epitope variants can be made, for example, using any of the techniques and guidelines for conservative and non-conservative mutations. Variants can be derived from substitution, deletion or insertion of one or more amino acids as compared with the native sequence. Amino acid substitutions can be the result of replacing one amino acid with another amino acid having similar structural and/or chemical properties, such as the replacement of a threonine with a serine, for example. Such replacements are referred to as conservative amino acid replacements, and all appropriate conservative amino acid replacements are considered to be embodiments of one invention. Insertions or deletions can optionally be in the range of about 1 to 4, preferably 1 to 2, amino acids. It is generally preferable to maintain the "anchor positions" of the peptide which are responsible for binding to the MHC molecule in question. Indeed, immunogenicity of peptides can be improved in many cases by substituting more preferred residues at the anchor positions (Franco, et al., *Nature Immunology,* 1(2):145-150, 2000). Immunogenicity of a peptide can also often be improved by substituting bulkier amino acids for small amino acids found in non-anchor positions while maintaining sufficient cross-reactivity with the original epitope to constitute a useful vaccine. The variation allowed can be determined by routine insertions, deletions or substitutions of amino acids in the sequence and testing the resulting variants for activity exhibited by the polypeptide epitope. Because the polypeptide epitope is often 9 amino acids, the substitutions preferably are made to the shortest active epitope, for example, an epitope of 9 amino acids.

Variants can also be made by adding any sequence onto the N-terminus of the polypeptide epitope variant. Such N-terminal additions can be from 1 amino acid up to at least 25 amino acids. Because peptide epitopes are often trimmed by N-terminal exopeptidases active in the pAPC, it is understood that variations in the added sequence can have no effect on the activity of the epitope. In preferred embodiments, the amino acid residues between the last upstream proteasomal cleavage site and the N-terminus of the MHC epitope do not include a proline residue. Serwold, T. at al., Nature Immunol. 2:644-651, 2001. Accordingly, effective epitopes can be generated from precursors larger than the preferred 9-mer class I motif.

Generally, peptides are useful to the extent that they correspond to epitopes actually displayed by MHC I on the surface of a target cell or a pACP. A single peptide can have varying affinities for different MHC molecules, binding some well, others adequately, and still others not appreciably (Appendix B). MHC alleles have traditionally been grouped according to serologic reactivity which does not reflect the structure of the peptide-binding groove, which can differ among different alleles of the same type. Similarly, binding properties can be shared across types; groups based on shared binding properties have been termed supertypes. There are numerous alleles of MHC I in the human population; epitopes specific to certain alleles can be selected based on the genotype of the patient.

Still further embodiments are directed to methods, uses, therapies and compositions related to epitopes with specificity for MHC, including, for example, those listed in Tables 6-10. Other embodiments include one or more of the MHCs listed in Tables 6-10, including combinations of the same, while other embodiments specifically exclude any one or more of the MHCs or combinations thereof. Tables 8-10 include frequencies for the listed HLA antigens.

TABLE 6

Class I MHC Molecules

Class I

Human

HLA-A1
HLA-A*0101
HLA-A*0201
HLA-A*0202
HLA-A*0203
HLA-A*0204
HLA-A*0205
HLA-A*0206
HLA-A*0207
HLA-A*0209
HLA-A*0214
HLA-A3
HLA-A*0301
HLA-A*1101
HLA-A23
HLA-A24
HLA-A25
HLA-A*2902
HLA-A*3101
HLA-A*3302
HLA-A*6801
HLA-A*6901
HLA-B7
HLA-B*0702
HLA-B*0703
HLA-B*0704
HLA-B*0705
HLA-B8
HLA-B13
HLA-B14
HLA-B*1501 (B62)
HLA-B17
HLA-B18
HLA-B22
HLA-B27
HLA-B*2702
HLA-B*2704
HLA-B*2705
HLA-B*2709
HLA-B35
HLA-B*3501
HLA-B*3502
HLA-B*3701
HLA-B*3801
HLA-B*39011
HLA-B*3902
HLA-B40
HLA-B*40012 (B60)
HLA-B*4006 (B61)
HLA-B44
HLA-B*4402
HLA-B*4403
HLA-B*4501
HLA-B*4601
HLA-B51
HLA-B*5101
HLA-B*5102
HLA-B*5103
HLA-B*5201
HLA-B*5301
HLA-B*5401
HLA-B*5501
HLA-B*5502

TABLE 6-continued

Class I MHC Molecules

Class I

HLA-B*5601
HLA-B*5801
HLA-B*6701
HLA-B*7301
HLA-B*7801
HLA-Cw*0102
HLA-Cw*0301
HLA-Cw*0304
HLA-Cw*0401
HLA-Cw*0601
HLA-Cw*0602
HLA-Cw*0702
HLA-Cw8
HLA-Cw*1601M
HLA-G

Murine

H2-K$^d$
H2-D$^d$
H2-L$^d$
H2-K$^b$
H2-D$^b$
H2-K$^k$
H2-K$^{km1}$
Qa-1$^a$
Qa-2
H2-M3

Rat

RT1.A$^a$
RT1.A$^l$

Bovine

Bota-A11
Bota-A20

Chicken

B-F4
B-F12
B-F15
B-F19

Chimpanzee

Patr-A*04
Patr-A*11
Patr-B*01
Patr-B*13
Patr-B*16

Baboon

Papa-A*06

Macaque

Mamu-A*01

Swine

SLA (haplotype d/d)
Virus homolog hCMV class I homolog UL18

TABLE 7

Class I MHC Molecules

Class I

Human

HLA-A1
HLA-A*0101
HLA-A*0201
HLA-A*0202

TABLE 7-continued

Class I MHC Molecules

Class I

HLA-A*0204
HLA-A*0205
HLA-A*0206
HLA-A*0207
HLA-A*0214
HLA-A3
HLA-A*1101
HLA-A24
HLA-A*2902
HLA-A*3101
HLA-A*3302
HLA-A*6801
HLA-A*6901
HLA-B7
HLA-B*0702
HLA-B*0703
HLA-B*0704
HLA-B*0705
HLA-B8
HLA-B14
HLA-B*1501 (B62)
HLA-B27
HLA-B*2702
HLA-B*2705
HLA-B35
HLA-B*3501
HLA-B*3502
HLA-B*3701
HLA-B*3801
HLA-B*39011
HLA-B*3902
HLA-B40
HLA-B*40012 (B60)
HLA-B*4006 (B61)
HLA-B44
HLA-B*4402
HLA-B*4403
HLA-B*4601
HLA-B51
HLA-B*5101
HLA-B*5102
HLA-B*5103
HLA-B*5201
HLA-B*5301
HLA-B*5401
HLA-B*5501
HLA-B*5502
HLA-B*5601
HLA-B*5801
HLA-B*6701
HLA-B*7301
HLA-B*7801
HLA-Cw*0102
HLA-Cw*0301
HLA-Cw*0304
HLA-Cw*0401
HLA-Cw*0601
HLA-Cw*0602
HLA-Cw*0702
HLA-G

Murine

$H2\text{-}K^d$
$H2\text{-}D^d$
$H2\text{-}L^d$
$H2\text{-}K^b$
$H2\text{-}D^b$
$H2\text{-}K^k$
$H2\text{-}K^{kml}$
Qa-2

Rat

$RT1.A^a$
$RT1.A^1$

Bovine

Bota-A11
Bota-A20

Chicken

B-F4
B-F12
B-F15
B-F19

Virus homolog hCMV class I homolog UL18

TABLE 8

Estimated gene frequencies of HLA-A antigens

| Antigen | CAU Gf[a] | CAU SE[b] | AFR Gf | AFR SE | ASI Gf | ASI SE | LAT Gf | LAT SE | NAT Gf | NAT SE |
|---|---|---|---|---|---|---|---|---|---|---|
| A1 | 15.1843 | 0.0489 | 5.7256 | 0.0771 | 4.4818 | 0.0846 | 7.4007 | 0.0978 | 12.0316 | 0.2533 |
| A2 | 28.6535 | 0.0619 | 18.8849 | 0.1317 | 24.6352 | 0.1794 | 28.1198 | 0.1700 | 29.3408 | 0.3585 |
| A3 | 13.3890 | 0.0463 | 8.4406 | 0.0925 | 2.6454 | 0.0655 | 8.0789 | 0.1019 | 11.0293 | 0.2437 |
| A28 | 4.4652 | 0.0280 | 9.9269 | 0.0997 | 1.7657 | 0.0537 | 8.9446 | 0.1067 | 5.3856 | 0.1750 |
| A36 | 0.0221 | 0.0020 | 1.8836 | 0.0448 | 0.0148 | 0.0049 | 0.1584 | 0.0148 | 0.1545 | 0.0303 |
| A23 | 1.8287 | 0.0181 | 10.2086 | 0.1010 | 0.3256 | 0.0231 | 2.9269 | 0.0628 | 1.9903 | 0.1080 |
| A24 | 9.3251 | 0.0395 | 2.9668 | 0.0560 | 22.0391 | 0.1722 | 13.2610 | 0.1271 | 12.6613 | 0.2590 |
| A9 unsplit | 0.0809 | 0.0038 | 0.0367 | 0.0063 | 0.0858 | 0.0119 | 0.0537 | 0.0086 | 0.0356 | 0.0145 |
| A9 total | 11.2347 | 0.0429 | 13.2121 | 0.1128 | 22.4505 | 0.1733 | 16.2416 | 0.1382 | 14.6872 | 0.2756 |
| A25 | 2.1157 | 0.0195 | 0.4329 | 0.0216 | 0.0990 | 0.0128 | 1.1937 | 0.0404 | 1.4520 | 0.0924 |
| A26 | 3.8795 | 0.0262 | 2.8284 | 0.0547 | 4.6628 | 0.0862 | 3.2612 | 0.0662 | 2.4292 | 0.1191 |
| A34 | 0.1508 | 0.0052 | 3.5228 | 0.0610 | 1.3529 | 0.0470 | 0.4928 | 0.0260 | 0.3150 | 0.0432 |
| A43 | 0.0018 | 0.0006 | 0.0334 | 0.0060 | 0.0231 | 0.0062 | 0.0055 | 0.0028 | 0.0059 | 0.0059 |
| A66 | 0.0173 | 0.0018 | 0.2233 | 0.0155 | 0.0478 | 0.0089 | 0.0399 | 0.0074 | 0.0534 | 0.0178 |
| A10 unsplit | 0.0790 | 0.0038 | 0.0939 | 0.0101 | 0.1255 | 0.0144 | 0.0647 | 0.0094 | 0.0298 | 0.0133 |
| A10 total | 6.2441 | 0.0328 | 7.1348 | 0.0850 | 6.3111 | 0.0993 | 5.0578 | 0.0816 | 4.2853 | 0.1565 |
| A29 | 3.5796 | 0.0252 | 3.2071 | 0.0582 | 1.1233 | 0.0429 | 4.5156 | 0.0774 | 3.4345 | 0.1410 |
| A30 | 2.5067 | 0.0212 | 13.0969 | 0.1129 | 2.2025 | 0.0598 | 4.4873 | 0.0772 | 2.5314 | 0.1215 |
| A31 | 2.7386 | 0.0221 | 1.6556 | 0.0420 | 3.6005 | 0.0761 | 4.8328 | 0.0800 | 6.0881 | 0.1855 |
| A32 | 3.6956 | 0.0256 | 1.5384 | 0.0405 | 1.0331 | 0.0411 | 2.7064 | 0.0604 | 2.5521 | 0.1220 |
| A33 | 1.2080 | 0.0148 | 6.5607 | 0.0822 | 9.2701 | 0.1191 | 2.6593 | 0.0599 | 1.0754 | 0.0796 |
| A74 | 0.0277 | 0.0022 | 1.9949 | 0.0461 | 0.0561 | 0.0096 | 0.2027 | 0.0167 | 0.1068 | 0.0252 |

TABLE 8-continued

Estimated gene frequencies of HLA-A antigens

| Antigen | CAU Gf[a] | SE[b] | AFR Gf | SE | ASI Gf | SE | LAT Gf | SE | NAT Gf | SE |
|---|---|---|---|---|---|---|---|---|---|---|
| A19 unsplit | 0.0567 | 0.0032 | 0.2057 | 0.0149 | 0.0990 | 0.0128 | 0.1211 | 0.0129 | 0.0475 | 0.0168 |
| A19 total | 13.8129 | 0.0468 | 28.2593 | 0.1504 | 17.3846 | 0.1555 | 19.5252 | 0.1481 | 15.8358 | 0.2832 |
| AX | 0.8204 | 0.0297 | 4.9506 | 0.0963 | 2.9916 | 0.1177 | 1.6332 | 0.0878 | 1.8454 | 0.1925 |

[a]Gene frequency.
[b]Standard error.

TABLE 9

Estimated gene frequencies for HLA-B antigens

| Antigen | CAU Gf[a] | SE[b] | AFR Gf | SE | ASI Gf | SE | LAT Gf | SE | NAT Gf | SE |
|---|---|---|---|---|---|---|---|---|---|---|
| B7 | 12.1782 | 0.0445 | 10.5960 | 0.1024 | 4.2691 | 0.0827 | 6.4477 | 0.0918 | 10.9845 | 0.2432 |
| B8 | 9.4077 | 0.0397 | 3.8315 | 0.0634 | 1.3322 | 0.0467 | 3.8225 | 0.0715 | 8.5789 | 0.2176 |
| B13 | 2.3061 | 0.0203 | 0.8103 | 0.0295 | 4.9222 | 0.0886 | 1.2699 | 0.0416 | 1.7495 | 0.1013 |
| B14 | 4.3481 | 0.0277 | 3.0331 | 0.0566 | 0.5004 | 0.0287 | 5.4166 | 0.0846 | 2.9823 | 0.1316 |
| B18 | 4.7980 | 0.0290 | 3.2057 | 0.0582 | 1.1246 | 0.0429 | 4.2349 | 0.0752 | 3.3422 | 0.1391 |
| B27 | 4.3831 | 0.0278 | 1.2918 | 0.0372 | 2.2355 | 0.0603 | 2.3724 | 0.0567 | 5.1970 | 0.1721 |
| B35 | 9.6614 | 0.0402 | 8.5172 | 0.0927 | 8.1203 | 0.1122 | 14.6516 | 0.1329 | 10.1198 | 0.2345 |
| B37 | 1.4032 | 0.0159 | 0.5916 | 0.0252 | 1.2327 | 0.0449 | 0.7807 | 0.0327 | 0.9755 | 0.0759 |
| B41 | 0.9211 | 0.0129 | 0.8183 | 0.0296 | 0.1303 | 0.0147 | 1.2818 | 0.0418 | 0.4766 | 0.0531 |
| B42 | 0.0608 | 0.0033 | 5.6991 | 0.0768 | 0.0841 | 0.0118 | 0.5866 | 0.0284 | 0.2856 | 0.0411 |
| B46 | 0.0099 | 0.0013 | 0.0151 | 0.0040 | 4.9292 | 0.0886 | 0.0234 | 0.0057 | 0.0238 | 0.0119 |
| B47 | 0.2069 | 0.0061 | 0.1305 | 0.0119 | 0.0956 | 0.0126 | 0.1832 | 0.0159 | 0.2139 | 0.0356 |
| B48 | 0.0865 | 0.0040 | 0.1316 | 0.0119 | 2.0276 | 0.0575 | 1.5915 | 0.0466 | 1.0267 | 0.0778 |
| B53 | 0.4620 | 0.0092 | 10.9529 | 0.1039 | 0.4315 | 0.0266 | 1.6982 | 0.0481 | 1.0804 | 0.0798 |
| B59 | 0.0020 | 0.0006 | 0.0032 | 0.0019 | 0.4277 | 0.0265 | 0.0055 | 0.0028 | 0[c] | — |
| B67 | 0.0040 | 0.0009 | 0.0086 | 0.0030 | 0.2276 | 0.0194 | 0.0055 | 0.0028 | 0.0059 | 0.0059 |
| B70 | 0.3270 | 0.0077 | 7.3571 | 0.0866 | 0.8901 | 0.0382 | 1.9266 | 0.0512 | 0.6901 | 0.0639 |
| B73 | 0.0108 | 0.0014 | 0.0032 | 0.0019 | 0.0132 | 0.0047 | 0.0261 | 0.0060 | 0[c] | — |
| B51 | 5.4215 | 0.0307 | 2.5980 | 0.0525 | 7.4751 | 0.1080 | 6.8147 | 0.0943 | 6.9077 | 0.1968 |
| B52 | 0.9658 | 0.0132 | 1.3712 | 0.0383 | 3.5121 | 0.0752 | 2.2447 | 0.0552 | 0.6960 | 0.0641 |
| B5 unsplit | 0.1565 | 0.0053 | 0.1522 | 0.0128 | 0.1288 | 0.0146 | 0.1546 | 0.0146 | 0.1307 | 0.0278 |
| B5 total | 6.5438 | 0.0435 | 4.1214 | 0.0747 | 11.1160 | 0.1504 | 9.2141 | 0.1324 | 7.7344 | 0.2784 |
| B44 | 13.4858 | 0.0465 | 7.0137 | 0.0847 | 5.6807 | 0.0948 | 9.9253 | 0.1121 | 11.8024 | 0.2511 |
| B45 | 0.5771 | 0.0102 | 4.8069 | 0.0708 | 0.1816 | 0.0173 | 1.8812 | 0.0506 | 0.7603 | 0.0670 |
| B12 unsplit | 0.0788 | 0.0038 | 0.0280 | 0.0055 | 0.0049 | 0.0029 | 0.0193 | 0.0051 | 0.0654 | 0.0197 |
| B12 total | 14.1440 | 0.0474 | 11.8486 | 0.1072 | 5.8673 | 0.0963 | 11.8258 | 0.1210 | 12.6281 | 0.2584 |
| B62 | 5.9117 | 0.0320 | 1.5267 | 0.0404 | 9.2249 | 0.1190 | 4.1825 | 0.0747 | 6.9421 | 0.1973 |
|  |  |  |  |  |  |  |  |  | 0.3738 |  |
| B63 | 0.4302 | 0.0088 | 1.8865 | 0.0448 | 0.4438 | 0.0270 | 0.8083 | 0.0333 | 0.0356 | 0.0471 |
| B75 | 0.0104 | 0.0014 | 0.0226 | 0.0049 | 1.9673 | 0.0566 | 0.1101 | 0.0123 | 0 | 0.0145 |
| B76 | 0.0026 | 0.0007 | 0.0065 | 0.0026 | 0.0874 | 0.0120 | 0.0055 | 0.0028 | 0[c] | — |
| B77 | 0.0057 | 0.0010 | 0.0119 | 0.0036 | 0.0577 | 0.0098 | 0.0083 | 0.0034 | 0.0059 | 0.0059 |
| B15 unsplit | 0.1305 | 0.0049 | 0.0691 | 0.0086 | 0.4301 | 0.0266 | 0.1820 | 0.0158 | 0.0715 | 0.0206 |
| B15 total | 6.4910 | 0.0334 | 3.5232 | 0.0608 | 12.2112 | 0.1344 | 5.2967 | 0.0835 | 7.4290 | 0.2035 |
| B38 | 2.4413 | 0.0209 | 0.3323 | 0.0189 | 3.2818 | 0.0728 | 1.9652 | 0.0517 | 1.1017 | 0.0806 |
| B39 | 1.9614 | 0.0188 | 1.2893 | 0.0371 | 2.0352 | 0.0576 | 6.3040 | 0.0909 | 4.5527 | 0.1615 |
| B16 unsplit | 0.0638 | 0.0034 | 0.0237 | 0.0051 | 0.0644 | 0.0103 | 0.1226 | 0.0130 | 0.0593 | 0.0188 |
| B16 total | 4.4667 | 0.0280 | 1.6453 | 0.0419 | 5.3814 | 0.0921 | 8.3917 | 0.1036 | 5.7137 | 0.1797 |
| B57 | 3.5955 | 0.0252 | 5.6746 | 0.0766 | 2.5782 | 0.0647 | 2.1800 | 0.0544 | 2.7265 | 0.1260 |
| B58 | 0.7152 | 0.0114 | 5.9546 | 0.0784 | 4.0189 | 0.0803 | 1.2481 | 0.0413 | 0.9398 | 0.0745 |
| B17 unsplit | 0.2845 | 0.0072 | 0.3248 | 0.0187 | 0.3751 | 0.0248 | 0.1446 | 0.0141 | 0.2674 | 0.0398 |
| B17 total | 4.5952 | 0.0284 | 11.9540 | 0.1076 | 6.9722 | 0.1041 | 3.5727 | 0.0691 | 3.9338 | 0.1503 |
| B49 | 1.6452 | 0.0172 | 2.6286 | 0.0528 | 0.2440 | 0.0200 | 2.3353 | 0.0562 | 1.5462 | 0.0953 |
| B50 | 1.0580 | 0.0138 | 0.8636 | 0.0304 | 0.4421 | 0.0270 | 1.8883 | 0.0507 | 0.7862 | 0.0681 |
| B21 unsplit | 0.0702 | 0.0036 | 0.0270 | 0.0054 | 0.0132 | 0.0047 | 0.0771 | 0.0103 | 0.0356 | 0.0145 |
| B21 total | 2.7733 | 0.0222 | 3.5192 | 0.0608 | 0.6993 | 0.0339 | 4.3007 | 0.0755 | 2.3680 | 0.1174 |
| B54 | 0.0124 | 0.0015 | 0.0183 | 0.0044 | 2.6873 | 0.0660 | 0.0289 | 0.0063 | 0.0534 | 0.0178 |
| B55 | 1.9046 | 0.0185 | 0.4895 | 0.0229 | 2.2444 | 0.0604 | 0.9515 | 0.0361 | 1.4054 | 0.0909 |
| B56 | 0.5527 | 0.0100 | 0.2686 | 0.0170 | 0.8260 | 0.0368 | 0.3596 | 0.0222 | 0.3387 | 0.0448 |
| B22 unsplit | 0.1682 | 0.0055 | 0.0496 | 0.0073 | 0.2730 | 0.0212 | 0.0372 | 0.0071 | 0.1246 | 0.0272 |
| B22 total | 2.0852 | 0.0217 | 0.8261 | 0.0297 | 6.0307 | 0.0971 | 1.3771 | 0.0433 | 1.9221 | 0.1060 |
| B60 | 5.2222 | 0.0302 | 1.5299 | 0.0404 | 8.3254 | 0.1135 | 2.2538 | 0.0553 | 5.7218 | 0.1801 |
| B61 | 1.1916 | 0.0147 | 0.4709 | 0.0225 | 6.2072 | 0.0989 | 4.6691 | 0.0788 | 2.6023 | 0.1231 |
| B40 unsplit | 0.2696 | 0.0070 | 0.0388 | 0.0065 | 0.3205 | 0.0230 | 0.2473 | 0.0184 | 0.2271 | 0.0367 |
| B40 total | 6.6834 | 0.0338 | 2.0396 | 0.0465 | 14.8531 | 0.1462 | 7.1702 | 0.0963 | 8.5512 | 0.2168 |
| BX | 1.0922 | 0.0252 | 3.5258 | 0.0802 | 3.8749 | 0.0988 | 2.5266 | 0.0807 | 1.9867 | 0.1634 |

TABLE 9-continued

Estimated gene frequencies for HLA-B antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |

[a]Gene frequency.
[b]Standard error.
[c]The observed gene count was zero.

TABLE 10

Estimated gene frequencies of HLA-DR antigens

| | CAU | | AFR | | ASI | | LAT | | NAT | |
|---|---|---|---|---|---|---|---|---|---|---|
| Antigen | Gf[a] | SE[b] | Gf | SE | Gf | SE | Gf | SE | Gf | SE |
| DR1 | 10.2279 | 0.0413 | 6.8200 | 0.0832 | 3.4628 | 0.0747 | 7.9859 | 0.1013 | 8.2512 | 0.2139 |
| DR2 | 15.2408 | 0.0491 | 16.2373 | 0.1222 | 18.6162 | 0.1608 | 11.2389 | 0.1182 | 15.3932 | 0.2818 |
| DR3 | 10.8708 | 0.0424 | 13.3080 | 0.1124 | 4.7223 | 0.0867 | 7.8998 | 0.1008 | 10.2549 | 0.2361 |
| DR4 | 16.7589 | 0.0511 | 5.7084 | 0.0765 | 15.4623 | 0.1490 | 20.5373 | 0.1520 | 19.8264 | 0.3123 |
| DR6 | 14.3937 | 0.0479 | 18.6117 | 0.1291 | 13.4471 | 0.1404 | 17.0265 | 0.1411 | 14.8021 | 0.2772 |
| DR7 | 13.2807 | 0.0463 | 10.1317 | 0.0997 | 6.9270 | 0.1040 | 10.6726 | 0.1155 | 10.4219 | 0.2378 |
| DR8 | 2.8820 | 0.0227 | 6.2673 | 0.0800 | 6.5413 | 0.1013 | 9.7731 | 0.1110 | 6.0059 | 0.1844 |
| DR9 | 1.0616 | 0.0139 | 2.9646 | 0.0559 | 9.7527 | 0.1218 | 1.0712 | 0.0383 | 2.8662 | 0.1291 |
| DR10 | 1.4790 | 0.0163 | 2.0397 | 0.0465 | 2.2304 | 0.0602 | 1.8044 | 0.0495 | 1.0896 | 0.0801 |
| DR11 | 9.3180 | 0.0396 | 10.6151 | 0.1018 | 4.7375 | 0.0869 | 7.0411 | 0.0955 | 5.3152 | 0.1740 |
| DR12 | 1.9070 | 0.0185 | 4.1152 | 0.0655 | 10.1365 | 0.1239 | 1.7244 | 0.0484 | 2.0132 | 0.1086 |
| DR5 unsplit | 1.2199 | 0.0149 | 2.2957 | 0.0493 | 1.4118 | 0.0480 | 1.8225 | 0.0498 | 1.6769 | 0.0992 |
| DR5 total | 12.4449 | 0.0045 | 17.0260 | 0.1243 | 16.2858 | 0.1516 | 10.5880 | 0.1148 | 9.0052 | 0.2218 |
| DRX | 1.3598 | 0.0342 | 0.8853 | 0.0760 | 2.5521 | 0.1089 | 1.4023 | 0.0930 | 2.0834 | 0.2037 |

[a]Gene frequency.
[b]Standard error.

It can be desirable to express housekeeping peptides in the context of a larger protein. Processing can be detected even when a small number of amino acids are present beyond the terminus of an epitope. Small peptide hormones are usually proteolytically processed from longer translation products, often in the size range of approximately 60-120 amino acids. This fact has led some to assume that this is the minimum size that can be efficiently translated. In some embodiments, the housekeeping peptide can be embedded in a translation product of at least about 60 amino acids, in others 70, 80, 90 amino acids, and in still others 100, 110 or 120 amino acids, for example. In other embodiments the housekeeping peptide can be embedded in a translation product of at least about 50, 30, or 15 amino acids.

Due to differential proteasomal processing, the immunoproteasome of the pAPC produces peptides that are different from those produced by the housekeeping proteasome in peripheral body cells. Thus, in expressing a housekeeping peptide in the context of a larger protein, it is preferably expressed in the pAPC in a context other than its full-length native sequence, because, as a housekeeping epitope, it is generally only efficiently processed from the native protein by the housekeeping proteasome, which is not active in the pAPC. In order to encode the housekeeping epitope in a DNA sequence encoding a larger polypeptide, it is useful to find flanking areas on either side of the sequence encoding the epitope that permit appropriate cleavage by the immunoproteasome in order to liberate that housekeeping epitope. Such a sequence promoting appropriate processing is referred to hereinafter as having substrate or liberation sequence function. Altering flanking amino acid residues at the N-terminus and C-terminus of the desired housekeeping epitope can facilitate appropriate cleavage and generation of the housekeeping epitope in the pAPC. Sequences embedding housekeeping epitopes can be designed de novo and screened to determine which can be successfully processed by immunoproteasomes to liberate housekeeping epitopes.

Alternatively, another strategy is very effective for identifying sequences allowing production of housekeeping epitopes in APC. A contiguous sequence of amino acids can be generated from head to tail arrangement of one or more housekeeping epitopes. A construct expressing this sequence is used to immunize an animal, and the resulting T cell response is evaluated to determine its specificity to one or more of the epitopes in the array. These immune responses indicate housekeeping epitopes that are processed in the pAPC effectively. The necessary flanking areas around this epitope are thereby defined. The use of flanking regions of about 4-6 amino acids on either side of the desired peptide can provide the necessary information to facilitate proteasome processing of the housekeeping epitope by the immunoproteasome. Therefore, a substrate or liberation sequence of approximately 16-22 amino acids can be inserted into, or fused to, any protein sequence effectively to result in that housekeeping epitope being produced in an APC. In some embodiments, a broader context of a substrate sequence can also influence processing. In such embodiments, comparisons of a liberaton sequence in a variety of contexts can be useful in further optimizing a particular substrate sequence. In alternate embodiments the whole head-to-tail array of epitopes, or just the epitopes immediately adjacent to the correctly processed housekeeping epitope can be similarly transferred from a test construct to a vaccine vector.

In a preferred embodiment, the housekeeping epitopes can be embedded between known immune epitopes, or segments of such, thereby providing an appropriate context for processing. The abutment of housekeeping and immune epitopes can generate the necessary context to enable the immunoproteasome to liberate the housekeeping epitope, or a larger fragment, preferably including a correct C-terminus. It can be useful to screen constructs to verify that the desired epitope is produced. The abutment of housekeeping epitopes can generate a site cleavable by the immunoproteasome. Some embodiments of the invention employ known epitopes to flank housekeeping epitopes in test substrates; in others, screening as described below is used, whether the flanking regions are arbitrary sequences or mutants of the natural flanking sequence, and whether or not knowledge of proteasomal cleavage preferences are used in designing the substrates.

Cleavage at the mature N-terminus of the epitope, while advantageous, is not required, since a variety of N-terminal trimming activities exist in the cell that can generate the mature N-terminus of the epitope subsequent to proteasomal processing. It is preferred that such N-terminal extension be less than about 25 amino acids in length and it is further preferred that the extension have few or no proline residues. Preferably, in screening, consideration is given not only to cleavage at the ends of the epitope (or at least at its C-terminus), but consideration also can be given to ensure limited cleavage within the epitope.

Shotgun approaches can be used in designing test substrates and can increase the efficiency of screening. In one embodiment multiple epitopes can be assembled one after the other, with individual epitopes possibly appearing more than once. The substrate can be screened to determine which epitopes can be produced. In the case where a particular epitope is of concern, a substrate can be designed in which it appears in multiple different contexts. When a single epitope appearing in more than one context is liberated from the substrate additional secondary test substrates, in which individual instances of the epitope are removed, disabled, or are unique, can be used to determine which are being liberated and truly confer substrate or liberation sequence function.

Several readily practicable screens exist. A preferred in vitro screen utilizes proteasomal digestion analysis, using purified immunoproteasomes, to determine if the desired housekeeping epitope can be liberated from a synthetic peptide embodying the sequence in question. The position of the cleavages obtained can be determined by techniques such as mass spectrometry, HPLC, and N-terminal pool sequencing; as described in greater detail in U.S. patent application Ser. Nos. 09/561,074, 09/560,465 and 10/117,937, and Provisional U.S. Patent Application Nos. 60/282,211, 60/337,017, and 60/363,210, which were all cited and incorporated by reference above.

Alternatively, in vivo and cell-based screens such as immunization or target sensitization can be employed. For immunization a nucleic acid construct capable of expressing the sequence in question is used. Harvested CTL can be tested for their ability to recognize target cells presenting the housekeeping epitope in question. Such targets cells are most readily obtained by pulsing cells expressing the appropriate MHC molecule with synthetic peptide embodying the mature housekeeping epitope. Alternatively, immunization can be carried out using cells known to express housekeeping proteasome and the antigen from which the housekeeping epitope is derived, either endogenously or through genetic engineering. To use target sensitization as a screen, CTL, or preferably a CTL clone, that recognizes the housekeeping epitope can be used. In this case it is the target cell that expresses the embedded housekeeping epitope (instead of the pAPC during immunization) and it must express immunoproteasome. Generally, the cell or target cell can be transformed with an appropriate nucleic acid construct to confer expression of the embedded housekeeping epitope. Loading with a synthetic peptide embodying the embedded epitope using peptide loaded liposomes, or complexed with cationic lipid protein transfer reagents such as BIOPORTER™ (Gene Therapy Systems, San Diego, Calif.), represents an alternative.

Once sequences with substrate or liberation sequence function are identified they can be encoded in nucleic acid vectors, chemically synthesized, or produced recombinantly. In any of these forms they can be incorporated into immunogenic compositions. Such compositions can be used in vitro in vaccine development or in the generation or expansion of CTL to be used in adoptive immunotherapy. In vivo they can be used to induce, amplify or sustain and active immune response. The uptake of polypeptides for processing and presentation can be greatly enhanced by packaging with cationic lipid, the addition of a tract of cationic amino acids such as poly-L-lysine (Ryser, H. J. et al., *J. Cell Physiol.* 113:167-178, 1982; Shen, W. C. & Ryser, H. J., *Proc. Natl. Aced. Sci. USA* 75:1872-1876, 1978), the incorporation into branched structures with importation signals (Sheldon, K. et al., *Proc. Natl. Aced. Sci. USA* 92:2056-2060, 1995), or mixture with or fusion to polypeptides with protein transfer function including peptide carriers such as pep-1 (Morris, M. C., et al., *Nat. Biotech.* 19:1173-1176, 2001), the PreS2 translocation motif of hepatitis B virus surface antigen, VP22 of herpes viruses, and HIV-TAT protein (Oess, S. & Hildt, E., *Gene Ther.* 7:750-758, 2000; Ford, K. G., et al., *Gene Ther.* 8:1-4, 2001; Hung, C. F. et al., *J. Virol.* 76:2676-2682, 2002; Oliveira, S. C., et a;. *Hum. Gene Ther.* 12:1353-1359, 2001; Normand, N. et al., *J. Biol. Chem.* 276:15042-15050, 2001; Schwartz, J. J. & Zhang, S., *Curr. Opin. Mol. Ther.* 2:162-167, 2000; Elliot G., 7 Hare, P. Cell 88:223-233, 1997), among other methodologies. Particularly for fusion proteins the immunogen can be produced in culture and the purified protein administered or, in the alternative, the nucleic acid vector can be administered so that the immunogen is produced and secreted by cells transformed in vivo. In either scenario the transport function of the fusion protein facilitates uptake by pAPC.

EXAMPLES

Example 1

A recombinant DNA plasmid vaccine, pMA2M, which encodes one polypeptide with an HLA A2-specific CTL epitope ELAGIGILTV (SEQ ID NO. 1) from melan-A (26-35A27L), and a portion (amino acids 31-96) of melan-A (SEQ ID NO. 2) including the epitope clusters at amino acids 31-48 and 56-69, was constructed. These clusters were previously disclosed in U.S. patent application Ser. No. 09/561,571 entitled EPITOPE CLUSTERS incorporated by reference above. Flanking the defined melan-A CTL epitope are short amino acid sequences derived from human tyrosinase (SEQ ID NO. 3) to facilitate liberation of the melan-A housekeeping epitope by processing by the immunoproteasome. In addition, these amino acid sequences represent potential CTL epitopes themselves. The cDNA sequence for the polypeptide in the plasmid is under the control of promoter/enhancer sequence from cytomegalovirus (CMVp) (see FIG. 1), which allows efficient transcription of messenger for the polypeptide upon uptake by APCs. The bovine growth hormone polyadenylation signal (BGH polyA) at the 3' end of the encoding sequence provides a signal for polyadenylation of the messenger to increase its stability as well as for translocation out of nucleus into the cytoplasm for translation. To facilitate plasmid transport into the nucleus after uptake, a nuclear import sequence (NIS) from simian virus 40 (SV40) has been inserted in the plasmid backbone. The plasmid carries two copies of a CpG immunostimulatory motif, one in the NIS sequence and one in the plasmid backbone. Lastly, two prokaryotic genetic elements in the plasmid are responsible for amplification in *E. coli*, the kanamycin resistance gene (Kan R) and the pMB1 bacterial origin of replication.

SUBSTRATE or LIBERATION Sequence

The amino acid sequence of the encoded polypeptide (94 amino acid residues in length) (SEQ ID NO. 4) containing a 28 amino acid substrate or liberation sequence at its N-terminus (SEQ ID NO. 5) is given below:

MLLAVLYCL-ELAGIGTLTV-YMDGTMSQV-
GILTVILGVLLLIGCWYCRRRNGYRALMDKSLHVGTQCALTRRCPQEGFDHRDSKVSLQ
EKNCEPV

The first 9 amino acid residues are derived from tyrosinase$_{1-9}$ (SEQ ID NO. 6), the next ten constitute melan-A (26-35A27L) (SEQ ID NO. 1), and amino acid residues 20 to 28 are derived from tyrosinase$_{369-377}$ (SEQ ID NO. 7). These two tyrosinase nonamer sequences both represent potential HLA A2-specific CTL epitopes. Amino acid residues 10-19 constitute melan-A (26-35A27L) an analog of an HLA A2-specific CTL epitope from melan-A, EAAGIGILTV (SEQ ID NO. 8), with an elevated potency in inducing CTL responses during in vitro immunization of human PBMC and in vivo immunization in mice. The segment of melan-A constituting the rest of the polypeptide (amino acid residues 29 to 94) contain a number of predicted HLA A2-specific epitopes, including the epitope clusters cited above, and thus can be useful in generating a response to immune epitopes as described at length in the patent applications 'Epitope Synchronization in Antigen Presenting Cells' and 'Epitope Clusters' cited and incorporated by reference above. This region was also included to overcome any difficulties that can be associated with the expression of shorter sequences. A drawing of pMA2M is shown in FIG. 1.

Plasmid Construction

A pair of long complementary oligonucleotides was synthesized which encoded the first 30 amino acid residues. In addition, upon annealing, these oligonucleotides generated the cohensive ends of Afl II at the 5' end and that of EcoR I at the 3' end. The melan A$_{31-96}$ region was amplified with PCR using oligonucleotides carrying restriction sites for EcoR I at the 5' end and Not I at the 3' end. The PCR product was digested with EcoR I and Not I and ligated into the vector backbone, described in Example 1, that had been digested with Afl II and Not I, along with the annealed oligonucleotides encoding the amino terminal region in a three-fragment ligation. The entire coding sequence was verified by DNA sequencing. The sequence of the entire insert, from the Afl II site at the 5' end to the Not I site at the 3' end is disclosed as SEQ ID NO. 9. Nucleotides 12-293 encode the polypeptide.

Example 2

Three vectors containing melan-A (26-35A27L) (SEQ ID NO. 1) as an embedded housekeeping epitope were tested for their ability to induce a CTL response to this epitope in HLA-A2 transgenic HHD mice (Pascolo et al. *J Exp. Med.* 185:2043-2051, 1997). One of the vectors was pMA2M described above (called pVAXM3 in FIG. 3). In pVAXM2 the same basic group of 3 epitopes was repeated several times with the flanking epitopes truncated by differing degrees in the various repeats of the array. Specifically the cassette consisted of:

M-Tyr(5-9)-ELA-Tyr(369-373)-     (SEQ ID NO. 10)
Tyr(4-9)-ELA-Tyr(369-374)-Tyr
(3-9)-ELA-Tyr(369-375)-Tyr(2-
9)-ELA where ELA represents melan-A (26-35A27L) (SEQ ID NO. 1). This cassette was inserted in the same plasmid backbone as used for pVAXM3. The third, pVAXM1 is identical to pVAXM2 except that the epitope array is followed by an IRES (internal ribosome entry site for encephalomyocarditis virus) linked to a reading frame encoding melan-A 31-70.

Four groups of three HHD A2.1 mice were injected intranodally in surgically exposed inguinal lymph nodes with 25 μl of 1 mg/ml plasmid DNA in PBS on days 0, 3, and 6, each group receiving one of the three vectors or PBS alone. On day 14 the spleens were harvested and restimulated in vitro one time with 3-day LPS blasts pulsed with peptide (melan-A (26-35A27L)(SEQ ID NO. 1)). The in vitro cultures were supplemented with Rat T-Stim (Collaborative Biomedical Products) on the 3$^{rd}$ day and assayed for cytolytic activity on the 7$^{th}$ day using a standard $^{51}$Cr-release assay. FIGS. 2 to 5 show % specific lysis obtained using the cells immunized with PBS, pVAXM1, pVAXM2, and pVAXM3, respectively on T2 target cells and T2 target cells pulsed with melan-A (26-35A27L) (ELA) (SEQ ID NO. 1). All three vectors generated strong CTL responses. These data indicated that the plasmids have been taken up by APCs, the encoded polypeptide has been synthesized and proteolytically processed to produce the decamer epitope in question (that is, it had substrate or liberation sequence function), and that the epitope became HLA-A2 bound for presentation. Also, an isolated variant of pVAXM2, that terminates after the 55$^{th}$ amino acid, worked similarly well as the full length version (data not shown). Whether other potential epitopes within the expression cassette can also be produced and be active in inducing CTL responses can be determined by testing for CTL activity against target cells pulsed with corresponding synthetic peptides.

Example 3

An NY-ESO-1 (SEQ ID NO. 11) SUBSTRATE/LIBERATION Sequence

Six other epitope arrays were tested leading to the identification of a substrate/liberation sequence for the housekeeping epitope NY-ESO-1$_{157-165}$ (SEQ ID NO. 12). The component epitopes of the arrays were:

SSX-2$_{41-49}$:    KASEKTFYV    Array       (SEQ ID NO. 13)
                                element A NY-ESO-1$_{157-165}$: SLLMWITQC  Array       (SEQ ID NO. 12)
                                element B NY-ESO-1$_{163-171}$: TQCFLPVFL  Array       (SEQ ID NO. 14)
                                element C -continued

| | | | |
|---|---|---|---|
| PSMA$_{288-297}$: | GLPSIPVHPI | Array element D | (SEQ ID NO. 15) |
| TYR$_{4-9}$: | AVLYCL | Array element E | (SEQ ID NO. 16) |

The six arrays had the following arrangements of elements after starting with an initiator methionine:

| | |
|---|---|
| pVAX-PC-A: | B-A-D-D-A-B-A-A |
| pVAX-PC-B: | D-A-B-A-A-D-B-A |
| pVAX-PC-C: | E-A-D-B-A-B-E-A-A |
| pVAX-BC-A: | B-A-C-B-A-A-C-A |
| pVAX-BC-B: | C-A-B-C-A-A-B-A |
| pVAX-BC-C: | E-A-A-B-C-B-A-A |

These arrays were inserted into the same vector backbone described in the examples above. The plasmid vectors were used to immunize mice essentially as described in Example 2 and the resulting CTL were tested for their ability to specifically lyse target cells pulsed with the peptide NY-ESO-1 157-165, corresponding to element B above. Both pVAX-PC-A and pVAX-BC-A were found to induce specific lytic activity. Comparing the contexts of the epitope (element B) in the various arrays, and particularly between pVAX-PC-A and pVAX-BC-A, between pVAX-PC-A and pVAX-PC-B, and between pVAX-BC-A and pVAX-BC-C, it was concluded that it was the first occurrence of the epitope in pVAX-PC-A and pVAX-BC-A that was being correctly processed and presented. In other words an initiator methionine followed by elements B-A constitute a substrate/liberation sequence for the presentation of element B. On this basis a new expression cassette for use as a vaccine was constructed encoding the following elements:

An initiator methionine,
NY-ESO-1$_{157-165}$ (bold)—a housekeeping epitope,
SSX2$_{41-49}$ (italic)—providing appropriate context for processing, and
NY-ESO-1$_{77-180}$—to avoid "short sequence" problems and provide immune epitopes.

Thus the construct encodes the amino acid sequence:
M-SLLMWITQC-KASEKIFYV-RCGARGPESRLLE-FYLAMPFATPMEAELARRSLAQDAP-PLPVPGVLLKEFTVSGNILTIRL TAADHRQLQLSISS-CLQQLSLLMWITQCFLPVFLAQPPSGQRR (SEQ ID NO. 17) and MSLLMWITQCKASEKIFYV (SEQ ID NO. 18) constitutes the liberation or substrate sequence. A polynucleotide encoding SEQ ID NO. 17 (SEQ ID NO. 19: nucleotides 12-380) was inserted into the same plasmid backbone as used for pMA2M generating the plasmid pN157.

Example 4

A construct similar to pN157 containing the whole epitope array from pVAX-PC-A was also made and designated pBPL. Thus the encoded amino acid sequence in pBPL is:

M-SLLMWITQC-KASEKIFYV-GLPSIPVHPI-GLPSIPVHPI-KASEKIFYV-SLLMWITQC-KASEKIFYV-KASEKIFYV-RCGARGPESRLLEFYLAMPFATPMEAELARRSLAQDAPPLPVPGVLLKEFTVSGNILTIRL TAADHRQLQLSISSCLQQLSLLMWITQCFLPVFLAQPPSGQRR. (SEQ ID NO. 20)

SEQ ID NO. 21 is the polynucleotide encoding SEQ ID NO. 20 used in pBPL.

Figure 7:
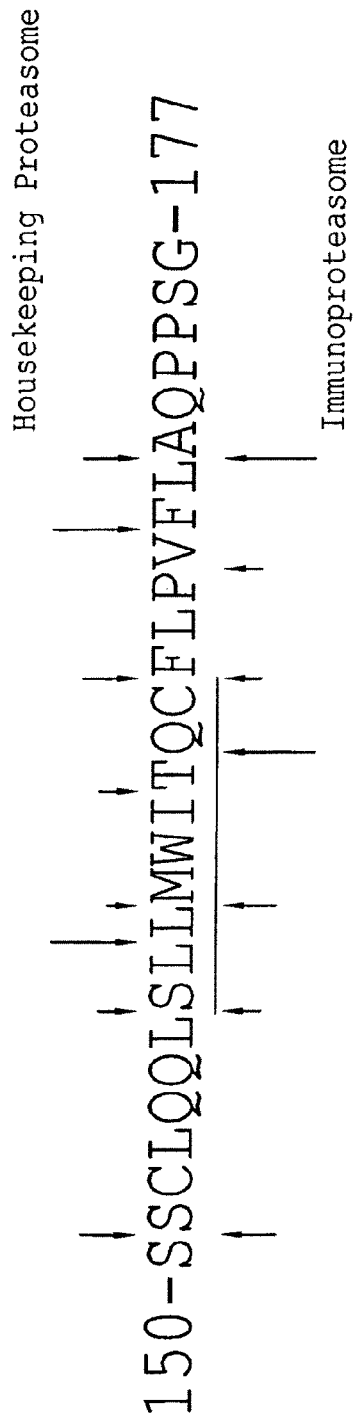
FIG. 7. Shows the differential processing by immunoproteasome and housekeeping proteasome of the SLLMWITQC epitope (SEQ ID NO. 12) in its native context where the cleavage following the C is more efficiently produced by housekeeping than immunoproteasome.

A portion of SEQ ID NO. 20, IKASEKIFYVSLLM-WITQCKASEKIFYVK (SEQ ID NO. 22) was made as a synthetic peptide and subjected to in vitro proteasomal digestion analysis with human immunoproteasome, utilizing both mass spectrometry and N-terminal pool sequencing. The identification of a cleavage after the C residue indicates that this segment of the construct can function as a substrate or liberation sequence for NY-ESO-1$_{157-165}$ (SEQ ID NO. 12) epitope (see FIG. 6). FIG. 7 shows the differential processing of the SLLMWITQC epitope (SEQ ID NO. 12) in its native context where the cleavage following the C is more efficiently produced by housekeeping than immunoproteasome. The immunoproteasome also produces a major cleavage internal to the epitope, between the T and the Q when the epitope is in its native context, but not in the context of SEQ ID NO. 22 (compare FIG. 6 and 7).

Example 5

Screening of further epitope arrays led to the identification of constructs promoting the expression of the epitope SSX-2$_{41-49}$ (SEQ ID NO. 13). In addition to some of the array elements defined in Example 3, the following additional elements were also used:

| | | | |
|---|---|---|---|
| SSX-4$_{57-65}$: | VMTKLGFKV | Array element F. | (SEQ ID NO. 23) |
| PSMA$_{730-739}$: | RQIYVAAFTV | Array element G. | (SEQ ID NO. 24) |

A construct, denoted CTLA02, encoding an initiator methionine and the array F-A-G-D-C-F-G-A, was found to successfully immunize HLA-A2 transgenic mice to generate a CTL response recognizing the peptide SSX-2$_{41-49}$ (SEQ ID NO. 13).

As described above, it can be desirable to combine a sequence with substrate or liberation sequence function with one that can be processed into immune epitopes. Thus SSX-2$_{15-183}$ (SEQ ID NO. 25) was combined with all or part of the array as follows:

| | |
|---|---|
| CTLS1: | |
| F-A-G-D-C-F-G-A-SSX-2$_{15-183}$ | (SEQ ID NO. 26) |
| CTLS2: | |
| SSX-2$_{15-183}$-F-A-G-D-C-F-G-A | (SEQ ID NO. 27) |
| CTLS3: | |
| F-A-G-D-SSX-2$_{15-183}$ | (SEQ ID NO. 28) |
| CTLS4: | |
| SSX-2$_{15-183}$-C-F-G-A | (SEQ ID NO. 29). |

All of the constructs except CTLS3 were able to induce CTL recognizing the peptide SSX-2$_{41-49}$ (SEQ ID NO. 13). CTLS3 was the only one of these four constructs which did not include the second element A from CTLA02 suggesting that it was this second occurrence of the element that provided substrate or liberation sequence function. In CTLS2 and CTLS4 the A element is at the C-terminal end of the array, as in CTLA02. In CTLS1 the A element is immediately followed by the SSX-$2_{15-183}$ segment which begins with an alanine, a residue often found after proteasomal cleavage sites (Toes, R. E. M., et al., *J. Exp. Med.* 194:1-12, 2001). SEQ ID NO. 30 is the polynucleotide sequence encoding SEQ ID NO. 26 used in CTLS1, also called pCBP.

A portion of CTLS1 (SEQ ID NO. 26), encompassing array elements F-A-SSX-$2_{15-23}$ with the sequence RQIY-VAAFTV-KASEKIFYV-AQIPEKIQK (SEQ ID NO. 31), was made as a synthetic peptide and subjected to in vitro proteasomal digestion analysis with human immunoproteasome, utilizing both mass spectrometry and N-terminal pool sequencing. The observation that the C-terminus of the SSX-$2_{41-49}$ epitope (SEQ ID NO. 13) was generated (see FIG. 8) provided further evidence in support of substrate or liberation sequence function. The data in FIG. 9 showed the differential processing of the SSX-$2_{41-49}$ epitope, KASEKIFYV (SEQ ID NO. 13), in its native context, where the cleavage following the V was the predominant cleavage produced by housekeeping proteasome, while the immunoproteasome had several major cleavage sites elsewhere in the sequence. By moving this epitope into the context provided by SEQ ID NO. 31 the desired cleavage became a major one and its relative frequency compared to other immunoproteasome cleavages was increased (compare FIGS. 8 and 9). The data in FIG. 8B also showed the similarity in specificity of mouse and human immunoproteasome lending support to the usefulness of the transgenic mouse model to predict human antigen processing.

Example 6

Screening also revealed substrate or liberation sequence function for a tyrosinase epitope, Tyr$_{207-215}$ (SEQ ID NO. 32), as part of an array consisting of the sequence [Tyr$_{1-17}$-Tyr$_{207-215}$]$_4$, [MLLAVLYCLLWSFQTSA-FLPWHRLFL]$_4$, (SEQ ID NO. 33). The same vector backbone described above was used to express this array. This array differs from those of the other examples in that the Tyr$_{1-17}$ segment, which was included as a source of immune epitopes, is used as a repeated element of the array. This is in contrast with the pattern shown in the other examples where sequence included as a source of immune epitopes and/or length occurred a single time at the beginning or end of the array, the remainder of which was made up of individual epitopes or shorter sequences.
Plasmid Construction The polynucleotide encoding SEQ ID NO. 33 was generated by assembly of annealed synthetic oligonucleotides. Four pairs of complementary oligonucleotides were synthesized which span the entire coding sequence with cohesive ends of the restriction sites of Afl II and EcoR I at either terminus. Each complementary pair of oligonucleotides were first annealed, the resultant DNA fragments were ligated stepwise, and the assembled DNA fragment was inserted into the same vector backbone described above pre-digested with Afl II/EcoR I. The construct was called CTLT2/pMEL and SEQ ID NO. 34 is the polynucleotide sequence used to encode SEQ ID NO. 33.

Example 7

Administration of a DNA Plasmid Formulation of a Immunotherapeutic for Melanoma to Humans An MA2M melanoma vaccine with a sequence as described in Example 1 above, was formulated in 1% Benzyl alcohol, 1% ethyl alcohol, 0.5 mM EDTA, citrate-phosphate, pH 7.6. Aliquots of 200, 400, and 600 μg DNA/ml were prepared for loading into MINIMED 407C infusion pumps. The catheter of a SILHOUETTE infusion set was placed into an inguinal lymph node visualized by ultrasound imaging. The pump and infusion set assembly was originally designed for the delivery of insulin to diabetics. The usual 17 mm catheter was substituted with a 31 mm catheter for this application. The infusion set was kept patent for 4 days (approximately 96 hours) with an infusion rate of about 25 μl/hour resulting in a total infused volume of approximately 2.4 ml. Thus the total administered dose per infusion was approximately 500, and 1000 μg; and can be 1500 μg, respectively, for the three concentrations described above. Following an infusion, subjects were given a 10 day rest period before starting a subsequent infusion. Given the continued residency of plasmid DNA in the lymph node after administration and the usual kinetics of CTL response following disappearance of antigen, this schedule will be sufficient to maintain the immunologic CTL response.

Example 8

SEQ ID NO. 22 is made as a synthetic peptide and packaged with a cationic lipid protein transfer reagent. The composition is infused directly into the inguinal lymph node (see example 7) at a rate of 200 to 600 μg of peptide per day for seven days, followed by seven days rest. An initial treatment of 3-8 cycles are conducted.

Example 9

A fusion protein is made by adding SEQ ID NO. 34 to the 3' end of a nucleotide sequence encoding herpes simplex virus 1 VP22 (SEQ ID NO. 42) in an appropriate mammalian expression vector; the vector used above is suitable. The vector is used to transform HEK 293 cells and 48 to 72 hours later the cells are pelleted, lysed and a soluble extract prepared. The fusion protein is purified by affinity chromatagraphy using an anti-VP22 monoclonal antibody. The purified fusion protein is administered intranodally at a rate of 10 to 100 μg per day for seven days, followed by seven days rest. An initial treatment of 3-8 cycles are conducted.

All references mentioned herein are hereby incorporated by reference in their entirety. Further, the present invention can utilize various aspects of the following, which are all incorporated by reference in their entirety: U.S. patent application Ser. No. 09/380,534, filed on Sep. 1, 1999, entitled A METHOD OF INDUCING A CTL RESPONSE; Ser. No. 09/776,232, filed on Feb. 2, 2001, entitled METHOD OF INDUCING A CTL RESPONSE; Ser. No. 09/715,835, filed on Nov. 16, 2000, entitled AVOIDANCE OF UNDESIRABLE REPLICATION INTERMEDIATES IN PLASMID PROPOGATION; Ser. No. 09/999,186, filed on Nov. 7, 2001, entitled METHODS OF COMMERCIALIZING AN ANTIGEN; and Provisional U.S. Patent Application No. 60/274,063, filed on Mar. 7, 2001, entitled ANTI-NEOVASCULAR VACCINES FOR CANCER.

TABLE 11

| | Partial listing of SEQ ID NOS. | |
|---|---|---|
| 1 | ELAGIGILTV | melan-A 26-3 5 (A27L) |
| 2 | Melan-A protein | Accession number: NP 005502 |
| 3 | Tyrosinase protein | Accession number: P14679 |
| 4 | MLLAVLYCLELAGIGILTVYMDGTMSQVG ILTVILGVLLLIGCWYCRRRNGYRALMDK SLHVGTQCALTRRCPQEGFDHRDSKVSLQ EKNCEPV | pMA2M expression product |
| 5 | MLLAVLYCLELAGIGILTVYMDGTMSQV | Liberation or substrate sequence for SEQ ID NO. 1 from pMA2M |
| 6 | MLLAVLYCL | tyrosinase 1-9 |
| 7 | YMDGTMSQV | tyrosinase 369-377 |
| 8 | EAAGIGILTV | melan-A 26-35 |
| 9 | cttaagccaccatgttactagctgttttgtactgcctggaact agcagggatcggcatattgacagtgtatatgga tggaacaatgtcccaggtaggaattctgacagtgatcctggga gtcttactgctcatcggctgttggtattgtaga agacgaaatggatacagagccttgatgataaaagtcttcatg ttggcactcaatgtgccttaacaagaagatgcc cacaagaagggtttgatcatcgggacagcaaagtgtctcttca agagaaaaactgtgaacctgtgtagtgagcggc cgc | pMA2M insert |
| 10 | MVLYCLELAGIGILTVYMDGTAVLYCLEL AGIGILTVYMDGTMLAVLYCLELAGIGILT VYMDGTMSLLAVLYCLELAGIGILTV | Epitope array from pVAXM2 and pVAXM1 |
| 11 | NY-ESO-1 protein | Accession number: P78358 |
| 12 | SLLMWITQC | NY-ESO-1 157-165 |
| 13 | KASEKIFYV | SSX-2 41-49 |
| 14 | TQCFLPVFL | NY-ESO-1 163-171 |
| 15 | GLPSIPVHPI | PSMA 288-297 |
| 16 | AVLYCL | tyrosinase 4-9 |
| 17 | MSLLMWITQCKASEKIFYVRCGARGPESR LLEFYLAMPFATPMEAELARRSLAQDAPP LPVPGVLLKEFTVSGNTLTTRLTAADHRQL QLSISSCLQQLSLLMWITQCFLPVFLAQPPS GQRR | pN157 expression product |
| 18 | MSLLMWITQCKASEKTFYV | liberation or substrate sequence for SEQ NO. 12 from pN157 |
| 19 | cttaagccaccatgtccctgttgatgtggatcacgcagtgcaa agcttcggagaaaatcttctacgtacggtgcgg tgccaggggccggagagccgcctgcttgagttctacctcgcc atgcctttcgcgacacccatggaagcagagctg gcccgcaggagcctggcccaggatgccccaccgcttcccgtgc caggggtgcttctgaaggagttcactgtgtccg gcaacatactgactatccgactgactgctgcagaccaccgcca actgcagctctccatcagctcctgtctccagca gcttttcccctgttgatgtggatcacgcagtgctttctgcccgtg tttttggctcagcctccctcagggcagaggcgc tagtgagaattc | Insert for pN157 |
| 20 | MSLLMWITQCKASEKIFYVGLPSIPVHPIGL PSIPVHPIKASEKTFYVSLLMWITQCKASEK IFYVKASEKIFYVRCGARGPESRLLEFYLA MPFATPMEAELARRSLAQDAPPLPVPGVL LKEFTVSGNILTIRLTAADHRQLQLSISSCL QQLSLLMWITQCFLPVFLAQPPSGQRR | pBPL expression product |
| 21 | atgtccctgttgatgtggatcacgcaqtgcaaagcttcggaga aaatcttctatgtgggtcttccaagtattcctg ttcatccaattggtcttccaagtattcctgttcatccaattaa agcttcggagaaaatcttctatgtgtccctgtt gatgtggatcacgcagtgcaaagcttcggagaaaatcttctat gtgaaagcttcggagaaaatcttctacgtacgg tgcggtgccaggggccggagagccgcctgcttgagttctacc tcgccatgcctttcgcgacacccatggaagcag agctggcccgcaggagcctggcccaggatgccccaccgcttcc cgtgccaggggtgcttctgaaggagttcactgt gtccggcaacatactgactatccgactgactgctgcagaccac cgccaactgcagctctccatcagctcctgtctc cagcagctttcccctgttgatgtggatcacgcagtgctttctgc ccgtgttttggctcagcctccctcagggcaga ggcgctagtga | pBPL insert coding region |
| 22 | IKASEKIFYVSLLMWITQCKASEKIIFYVK | Substrate in FIG. 6 |
| 23 | VMTKLGFKV | SSX-4$_{57-65}$ |
| 24 | RQLYVAAFTV | PSMA$_{730-739}$ |

TABLE 11-continued

Partial listing of SEQ ID NOS.

Figure 8A:
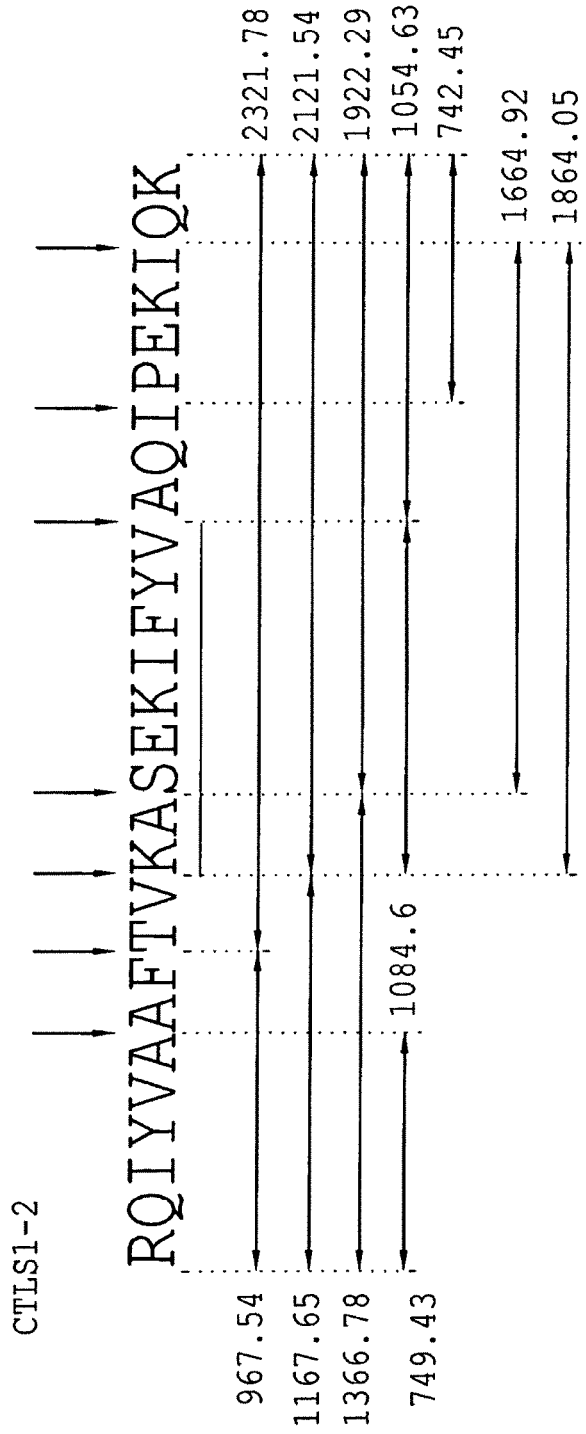
FIG. 8. 8A: Shows the results of the human immunoproteasome digest of SEQ ID NO. 31. 8B: Shows the comparative results of mouse versus human immunoproteasome digestion of SEQ ID NO. 31.
Figure 8B:
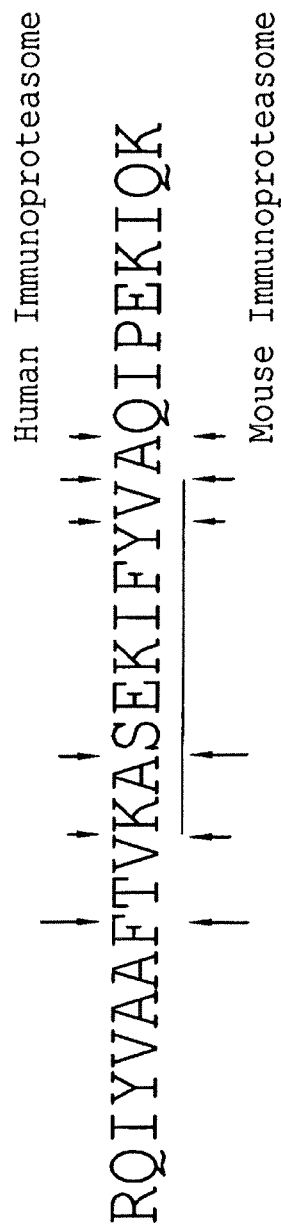

| | | |
|---|---|---|
| 25 | AQTPEKIQKAFDDIAKYFSKEEWEKMKAS EKIFYVYMKRKYEAMTKLGFKATLPPFMC NKRAEDFQGNDLDNDPNRGNQVERPQMT FGRLQGISPKIMPKKPAEEGNDSEEVPEAS GPQNDGKELCPPGKIPTTSEKIHERSGPKRG EHAWTHRLRERKQLVIYEEISDP | SSX-2$_{15-183}$ |
| 26 | MVMTKLGFKVKASEKJIFYVRQJYVAAFTV GLPSIPVHPITQCFLPVFLVMTKLGFKVRQI YVAETVKASEKJFYVAQTPEKIQKAFDDI AKYFSKEEWEKMKASEKIFYVYMKRKYE AMTKLGFKATLPPFMCNKRAEDFQGNDL DNDPNRGNQVERPQMTFGRLQGISPKIMP KKPAEEGNDSEEVPEASGPQNDGKELCPP GKPTTSEKIHERSGPKRGEHAWTHRLRER KQLVTYEEISDP | CTLS1/pCBP expression product |
| 27 | MAQIPEKIQKAFDDIAKYFSKEEWEKMKA SEKIFYVYMKRKYEAMTKLGFKATLPPFM CNKRAEDFQGNDLDNDPNRGNQVERPQM TFGRLQGISPKIMPKKPAEEGNPSEEVPEA SGPQNDGKELCPPGKPTTSEKIHERSGPKR GEHAWTHRLRERKQLVIYEEISDPVMTKL GFKVKASEKIFYVRQIYVAAFTVGLPSIIW HPITQCFLPVFLVMTKLGFKVRQIYVAAFT VKASEKIFYV | CTLS2 expression product |
| 28 | MVMTKLGFKVKASEKIFYVRQIYVAAFTV GLPSIPVHPIAQTPEKIQKAFDDIAKYFSKEE WEKMKASEKIFYVYMKRKYEAMTKLGF KATLPPFMCNKRAEDFQGNDLDNDPNRG NQVERPQMTFGRLQGISPKIMPKKPAEEG NDSEEVPEASGPQNDGKELCPPGKPTTSE KIHERSGPKRGEHAWTHRLRERKQLVJYE EISDP | CTLS3 expression product |
| 29 | MAQIPEKIQKAFDDIAKYFSKEEWEKMKA SEKIFYVYMKRKYEAMTKLGFKATLPPFM CNKRAEDFQGNPLDNDPNRGNQVERPQM TFGRLQGISPKIMPKKPAEEGNDSEEVPEA SGPQNDGKELCPPGKPTTSEKIHERSGPKR GEHAWTHRLRERKQLVLYEEISDPTQCFLP VFLVMTKLGFKVRQIYVAAFTVKASEKIF YV | CTLS4 expression product |
| 30 | atggtcatgactaaactaggttttcaaggtcaaagcttcggaga aaatcttctatgtgagacagatttatgttgcag ccttcacagtgggtcttccaagtattcctgttcatccaattac gcagtgctttctgcccgtgttttggtcatgac taaactaggtttcaaggtcagacagatttatgttgcagccttc acagtgaaagcttcggagaaaatcttctacgta gctcaaataccagagaagatccaaaaggccttcgatgatattg ccaaatacttctctaaggaagagtgggaaaaga tgaaagcctcggagaaaatcttctatgtgtatatgaagagaaa gtatgaggctatgactaaactaggtttcaaggc cacccctccaccttcatgtgtaataaacgggccgaagacttc caggggaatgatttggataatgaccctaaccgt gggaatcaggttgaacgtcctcagatgactttcggcaggctcc agggaatctccccgaagatcatgcccaagaagc cagcagaggaaggaaatgattcggaggaagtgccagaagcatc tggcccacaaaatgatgggaaagagctgtgccc cccgggaaaaccaactacctctgagaagattcacgagagatct ggacccaaaaggggggaacatgcctggacccac agactgcgtgagagaaaacagctggtgatttatgaagagatca gcgaccccttagtga | pcBP insert coding region |
| 31 | RQIYVAAFTVKASEKTFYVAQIPEKIQK | FIG. 8 substrate/CTLS1-2 |
| 32 | FLPWHRLFL | TYR$_{207-215}$ |
| 33 | MLLAVLYCLLWSFQTSAFLPWHRLFLMLL AVLYCLLWSFQTSAFLPWHRLFLMLLAVL YCLLWSFQTSAFLPWHRLFLMLLAVLYCL LWSFQTSAFLPWHRLFL | CTLT2/pMEL expression product |
| 34 | atgctcctggctgttttgtactgcctgctgtggagtttccaga cctccgcttttctgccttggcatagactcttct tgatgctcctggctgttttgtactgcctgctgtggagtttcca gacctccgcttttctgccttggcatagactctt cttgatgctcctggctgttttgtactgcctgctgtggagtttc cagacctccgcttttctgccttggcatagactc ttcttgatgctcctggctgttttgtactgcctgctgtggagtt tccagacctccgcttttctgccttggcatagac tcttcttgtagtga | CTLT2/pMEL insert coding region |
| 35 | MELAN-A cDNA | Accession number: NM_005511 |
| 36 | Tyrosinase cDNA | Accession number: NM_000372 |
| 37 | NY-ESO-1 cDNA | Accession number: U87459 |

TABLE 11-continued

Partial listing of SEQ ID NOS.

| | | |
|---|---|---|
| 38 | PSMA protein | Accession number: NP_004467 |
| 39 | PSMA cDNA | Accession number: NM_004476 |
| 40 | SSX-2 protein | Accession number: NP_003138 |
| 41 | SSX-2 cDNA | Accession number: NM_003147 |
| 42 | atgacctctcgccgctccgtgaagtcgggtccgcgggaggttccg cgcgatgagtacgaggatctgtactacaccccgtcttcaggtatgg cgagtcccgatagtccgcctgacacctcccgccgtggcgccctac agacacgctcgcgccagaggggcgaggtccgtttcgtccagtac gacgagtcggattatgccctctacggggctcgtcatccgaagac gacgaacacccggaggtcccccggacgcggcgtcccgtttccgg ggcggttttgtccggcccggggcctgcgcgggcgcctccgccac ccgctgggtccggaggggccggacgcacacccaccaccgcccc ccgggccccccgaacccagcgggtggcgactaaggcccccgcg gcccggcggcggagaccacccgcggcaggaaatcggcccag ccagaatccgccgcactcccagacgccccgcgtcgacggcgc caacccgatccaagacacccgcgcaggggctggccagaaagct gcactttagcaccgccccccaaaccccgacgcgccatggaccc cccggggtggccggctttaacaagcgcgtcttctgcgccgcggtcg ggcgcctggcggccatgcatgcccggatggcggcggtccagctc tgggacatgtcgcgtccgcgcacagacgaagacctcaacgaact ccttggcatcaccaccatccgcgtgacggtctgcgagggcaaaaa cctgcttcagcgcgccaacgagttggtgaatccagacgtggtgca ggacgtcgacgcggccacggcgactcgagggcgttctgcggcgt cgcgcccaccgagcgacctcgagcccagcccgctccgcttct cgccccagacggccgtcgag | From accession number: D10879 Herpes Simplex virus 1 UL49 coding sequence (VP22) |
| 43 | MTSRRSVKSGPREVPRDEYEDLYYTPSSG MASPDSPPDTSRRGALFTQTRSRQRGEVR FVQYDESDYALYGGSSSEDDEHPEVPRTR RPVSGAVLSGPGPARAPPPFTPAGSGGAG RTPTTAPRAPRTQRVATKAPAAPAAETTR GRKSAQPESAALPDAPASTAPTFTRSKTPA QGLARKLHFSTAPPNPDAPWTPRVAGFNK RVFCAAVGRLAAMHARMAAVQLWDFTM SRPRTDEDLNELLGITTIRVTVCEGKNLLQ RANELVNPDVVQDVDAATATRGRSAASR FTPTERPRAPARSASRPRRPVE | Accession number: P10233 Herpes Simplex virus 1 UL49/VP22 protein sequence |

Melan-A mRNA Sequence
LOCUS NM_005511 1524 bp mRNA PRI 14-OCT-2001
DEFINITION Homo sapiens melan-A (MLANA), mRNA.
ACCESSION NM_005511
VERSION NM_005511.1 GI:5031912

/translation ="MPREDAHFIYGYPKKGHGHSYTTAEEAAGIGILTVILGVLLLIGCWYCRRRN (SEQ ID NO.2)

GYRALMDKSLHVGTQCALTRRCPQEGFDHRDSKVSLQEKNCEPVVPNAPPAYEKLSAE

QSPPPYSP"

ORIGIN (SEQ ID NO. 35)

```
  1 agcagacaga ggactctcat taaggaaggt gtcctgtgcc ctgaccctac aagatgccaa
 61 gagaagatgc tcacttcatc tatggttacc ccaagaaggg gcacggccac tcttacacca
121 cggctgaaga ggccgctggg atcggcatcc tgacagtgat cctgggagtc ttactgctca
181 tcggctgttg gtattgtaga agacgaaatg gatacagagc cttgatggat aaaagtcttc
241 atgttggcac tcaatgtgcc ttaacaagaa gatgcccaca agaagggttt gatcatcggg
301 acagcaaagt gtctcttcaa gagaaaaact gtgaacctgt ggttcccaat gctccacctg
361 cttatgagaa actctctgca gaacagtcac caccacctta tcaccttaa gagccagcga
421 gacacctgag acatgctgaa attatttctc tcacactttt gcttgaattt aatacagaca
481 tctaatgttc tcctttggaa tggtgtagga aaaatgcaag ccatctctaa taataagtca
541 gtgttaaaat tttagtaggt ccgctagcag tactaatcat gtgaggaaat gatgagaaat
```

-continued

| | ORIGIN |
|---|---|
| 601 | attaaattgg gaaaactcca tcaataaatg ttgcaatgca tgatactatc tgtgccagag |
| 661 | gtaatgttag taaatccatg gtgttatttt ctgagagaca gaattcaagt gggtattctg |
| 721 | gggccatcca atttctcttt acttgaaatt tggctaataa caaactagtc aggttttcga |
| 781 | accttgaccg acatgaactg tacacagaat tgttccagta ctatggagtg ctcacaaagg |
| 841 | atacttttac aggttaagac aaagggttga ctggcctatt tatctgatca agaacatgtc |
| 901 | agcaatgtct ctttgtgctc taaaattcta ttatactaca ataatatatt gtaaagatcc |
| 961 | tatagctctt ttttttttgag atggagtttc gcttttgttg cccaggctgg agtgcaatgg |
| 1021 | cgcgatcttg gctcaccata acctccgcct cccaggttca agcaattctc ctgccttagc |
| 1081 | ctcctgagta gctgggatta caggcgtgcg ccactatgcc tgactaattt tgtagtttta |
| 1141 | gtagagacgg ggtttctcca tgttggtcag gctggtctca aactcctgac ctcaggtgat |
| 1201 | ctgcccgcct cagcctccca aagtgctgga attacaggcg tgagccacca cgcctggctg |
| 1261 | gatcctatat cttaggtaag acataaacg cagtctaatt acatttcact tcaaggctca |
| 1321 | atgctattct aactaatgac aagtattttc tactaaacca gaaattggta gaaggattta |
| 1381 | aataagtaaa agctactatg tactgcctta gtgctgatgc ctgtgtactg ccttaaatgt |
| 1441 | acctatggca atttagctct cttgggttcc caaatccctc tcacaagaat gtgcagaaga |
| 1501 | aatcataaag gatcagagat tctg |

Tyrosinase mRNA Sequence
LOCUS NM_000372 1964 bp mRNA PRI 31-OCT-2000
DEFINITION Homo sapiens tyrosinase (oculocutaneous
 albinism IA) (TYR), mRNA.
ACCESSION NM_000372
VERSION NM_000372.1 GI:4507752

/translation ="MLLAVLYCLLWSFQTSAGHFPRACVSSKNLMEKECCPPWSGDRS     (SEQ ID NO.3)

PCGQLSGRGSCQNILLSNAPLGPQFPFTGVDDRESWPSVFYNRTCQCSGNFMGFNCGNC

KFGFWGPNCTERRLLVRRNWDLSAPEKDKFFAYLTLAKHTISSDYVTPIGTYGQMKNGS

TPMFNDINIYDLFVWMHYYVSMDALLGGSEIWRDIDFAHEAPAYLPWHRLFLLRWEQEI

QKLTGDENFTIPYWDWRDAEKCDICTDEYMGGQHPTNPNLLSPASFFSSWQIVCSRLEE

YNSHQSLCNGTPEGPLRRNPGNHDKSRTPRLPSSADVEFCLSLTQYESGSMDKAANFSFR

NTLEGFASPLTGIADASQSSMHNALHIYMNGTMSQVQGSANDPTFLLHHAFVDSIFEQWL

RRHRPLQEVYPEANAPIGHNRESYMVPFIPLYRNGDFFISSKDLGYDYSYLQDSDPDSFQ

DYIKSYLEQASRIWSWLLGAAMVGAVLTALLAGLVSLLCRHKRKQLP

EEKQPLLMEKEDYHSLYQSHL"

| | ORIGIN |
|---|---|
| | (SEQ ID NO. 36) |
| 1 | atcactgtag tagtagctgg aaagagaaat ctgtgactcc aattagccag ttcctgcaga |
| 61 | ccttgtgagg actagaggaa gaatgctcct ggctgttttg tactgcctgc tgtggagttt |
| 121 | ccagacctcc gctggccatt tccctagagc ctgtgtctcc tctaagaacc tgatggagaa |
| 181 | ggaatgctgt ccaccgtgga gcggggacag gagtccctgt ggccagcttt caggcagagg |

-continued

```
ORIGIN
 241 ttcctgtcag aatatccttc tgtccaatgc accacttggg cctcaatttc ccttcacagg
 301 ggtggatgac cgggagtcgt ggccttccgt cttttataat aggacctgcc agtgctctgg
 361 caacttcatg ggattcaact gtggaaactg caagtttggc ttttggggac caaactgcac
 421 agagagacga ctcttggtga agaaaacat cttcgatttg agtgccccag agaaggacaa
 481 attttttgcc tacctcactt tagcaaagca taccatcagc tcagactatg tcatccccat
 541 agggacctat ggccaaatga aaaatggatc aacacccatg tttaacgaca tcaatattta
 601 tgacctcttt gtctggatgc attattatgt gtcaatggat gcactgcttg ggggatctga
 661 aatctggaga gacattgatt ttgcccatga agcaccagct tttctgcctt ggcatagact
 721 cttcttgttg cggtgggaac aagaaatcca gaagctgaca ggagatgaaa acttcactat
 781 tccatattgg gactggcggg atgcagaaaa gtgtgacatt gcacagatg agtacatggg
 841 aggtcagcac cccacaaatc ctaacttact cagcccagca tcattcttct cctcttggca
 901 gattgtctgt agccgattgg aggagtacaa cagccatcag tctttatgca atggaacgcc
 961 cgagggacct ttacggcgta atcctggaaa ccatgacaaa tccagaaccc caaggctccc
1021 ctcttcagct gatgtagaat tttgcctgag tttgacccaa tatgaatctg gttccatgga
1081 taaagctgcc aatttcagct ttagaaatac actggaagga tttgctagtc cacttactgg
1141 gatagcggat gcctctcaaa gcagcatgca caatgccttg cacatctata tgaatggaac
1201 aatgtcccag gtacagggat ctgccaacga tcctatcttc cttcttcacc atgcatttgt
1261 tgacagtatt tttgagcagt ggctccgaag gcaccgtcct cttcaagaag tttatccaga
1321 agccaatgca cccattggac ataaccggga atcctacatg gttccttta taccactgta
1381 cagaaatggt gatttctta tttcatccaa agatctgggc tatgactata gctatctaca
1441 agattcagac ccagactctt ttcaagacta cattaagtcc tatttggaac aagcgagtcg
1501 gatctggtca tggctccttg gggcggcgat ggtaggggcc gtcctcactg ccctgctggc
1561 agggcttgtg agcttgctgt gtcgtcacaa gagaaagcag cttcctgaag aaaagcagcc
1621 actcctcatg gagaaagagg attaccacag cttgtatcag agccatttat aaaaggctta
1681 ggcaatagag tagggccaaa aagcctgacc tcactctaac tcaaagtaat gtccaggttc
1741 ccagagaata tctgctggta ttttctgta aagaccattt gcaaaattgt aacctaatac
1801 aaagtgtagc cttcttccaa ctcaggtaga acacacctgt ctttgtcttg ctgtttcac
1861 tcagcccttt taacattttc ccctaagccc atatgtctaa ggaaaggatg ctatttggta
1921 atgaggaact gttatttgta tgtgaattaa agtgctctta tttt
```

NY-ESO-1 mRNA Sequence
LOCUS HSU87459 752 bp. mRNA PRI 22-DEC-1999
DEFINITION Human autoimmunogenic cancer/testis anti-
  gen NY-ESO-1 mRNA, complete cds.
ACCESSION U87459
VERSION U87459.1 GI:1890098

/translation ="MQAEGRGTGGSTGDADGPGGPGWDGPGGNAGGPGEAGATGGRGPRGAG   (SEQ ID NO. 11)

AARASGPGGGAPRGPHGGAASGLNGCCRCGARGPESRLLEFYLAMPFATPMEAELARR

SLAQDAPPLPVPGVLLKEFTVSGNILTIRLTAADHRQLQLSISSCLQQLSLLM

WITQCFLPVFLAQPPSGQRR"

| ORIGIN | |
|---|---|
| | (SEQ ID NO. 37) |

```
  1 atcctcgtgg gccctgacct tctctctgag agccgggcag aggctccgga gccatgcagg
 61 ccgaaggccg gggcacaggg ggttcgacgg gcgatgctga tggcccagga ggccctggca
121 ttcctgatgg cccaggggc aatgctggcg gcccaggaga ggcgggtgcc acgggcggca
181 gaggtccccg gggcgcaggg gcagcaaggg cctcggggcc gggaggaggc gccccgcggg
241 gtccgcatgg cggcgcggct tcagggctga atggatgctg cagatgcggg gccaggggggc
301 cggagagccg cctgcttgag ttctacctcg ccatgccttt cgcgacaccc atggaagcag
361 agctggcccg caggagcctg gcccaggatg ccccaccgct tcccgtgcca ggggtgcttc
421 tgaaggagtt cactgtgtcc ggcaacatac tgactatccg actgactgct gcagaccacc
481 gccaactgca gctctccatc agctcctgtc tccagcagct ttccctgttg atgtggatca
541 cgcagtgctt tctgcccgtg tttttggctc agcctccctc agggcagagg cgctaagccc
601 agcctggcgc cccttcctag gtcatgcctc ctccctagg gaatggtccc agcacgagtg
661 gccagttcat tgtggggggcc tgattgtttg tcgctggagg aggacggctt acatgttttgt
721 ttctgtagaa aataaaactg agctacgaaa aa
```

PSMA cDNA Sequence
LOCUS NM_004476 2653 bp mRNA PRI 01-NOV-2000
DEFINITION Homo sapiens folate hydrolase (prostate-specific membrane antigen) 1 (FOLH1), mRNA.
ACCESSION NM_004476
VERSION NM_004476.1 GI:4758397

/translation ="MWNLLHETDSAVATARRPRWLCAGALVLAGGFFLLGFLFGWIKSSNEAT     (SEQ ID NO. 38)

NITPKHNMKAFLDELKAENIKKFLYNFTQIPHLAGTEQNFQLAKQIQSQWKEFGLDSVEL

AHYDVLLSYPNKTHPNYISIINEDGNEIFNTSLFEPPPPGYENVSDIVPPFSAFSPQGMPEG

DLVYVNYARTEDFFKLERDMKINCSGKIVIARYGKVFRGNKVKNAQLAGAKGVILYSDP

ADYFAGVKSYPDGWNLPGGGVQRGNILNLNGAGDPLTPGYPANEYAYRRGIAEAVGL

PSIPVHPIGYYDAQKLLEKMGGSAPPDSSWRGSLKVPYNVGPGFTGNFSTQKVKMHIHS

TNEVTRIYNVIGTLRGAVEPDRYVILGGHRDSWVFGGDPQSGAAVVHEIVRSFGTLKKE

GWRPRRTILFASWDAEEFGLLGSTEWAEENSRLLQERGVAYINADSSIEGNYTLRVDCTP

LMYSLVHNLTKELKSPDEGFEGKSLYESWTKKSPSPEFSGMPRISKLGSGNDFEVFFQRL

GIASGRARYTKNWETNKFSGYPLYHSVYETYELVEKFYDPMFKYHLTVAQVRGGMVFE

LANSIVLPFDCRDYAVVLRKYADMYSISMKHPQEMKTYSVSFDSLFSAVKNFTEIASKFS

ERLQDFDKSNPIVLRMMNPQLMFLERAIUDPLGLPDRPFYRHVIYAPSSHNKYAGESFPGI

YDALFDIESKVDPSKAWGEVKRQIYVAAFTVQAAAETLSEVA"

| ORIGIN | |
|---|---|
| | (SEQ ID NO. 39) |

```
  1 ctcaaaaggg gccggatttc cttctcctgg aggcagatgt tgcctctctc tctcgctcgg
 61 attggttcag tgcactctag aaacactgct gtggtggaga aactggaccc caggtctgga
121 gcgaattcca gcctgcaggg ctgataagcg aggcattagt gagattgaga gagactttac
```

-continued

```
ORIGIN
 181 cccgccgtgg tggttggagg gcgcgcagta gagcagcagc acaggcgcgg gtcccgggag
 241 gccggctctg ctcgcgccga gatgtggaat ctccttcacg aaaccgactc ggctgtggcc
 301 accgcgcgcc gcccgcgctg gctgtgcgct ggggcgctgg tgctggcggg tggcttcttt
 361 ctcctcggct tcctcttcgg gtggtttata aaatcctcca atgaagctac taacattact
 421 ccaaagcata atatgaaagc attttggat gaattgaaag ctgagaacat caagaagttc
 481 ttatataatt ttacacagat accacattta gcaggaacag aacaaaactt tcagcttgca
 541 aagcaaattc aatcccagtg gaaagaattt ggcctggatt ctgttgagct agcacattat
 601 gatgtcctgt tgtcctaccc aaataagact catcccaact acatctcaat aattaatgaa
 661 gatggaaatg agattttcaa cacatcatta tttgaaccac ctcctccagg atatgaaaat
 721 gtttcggata ttgtaccacc tttcagtgct ttctctcctc aaggaatgcc agagggcgat
 781 ctagtgtatg ttaactatgc acgaactgaa gacttcttta aattggaacg ggacatgaaa
 841 atcaattgct ctgggaaaat tgtaattgcc agatatggga aagttttcag aggaaataag
 901 gttaaaaatg cccagctggc aggggccaaa ggagtcattc tctactccga ccctgctgac
 961 tactttgctc ctggggtgaa gtcctatcca gatggttgga atcttcctgg aggtggtgtc
1021 cagcgtggaa atatcctaaa tctgaatggt gcaggagacc ctctcacacc aggttaccca
1081 gcaaatgaat atgcttatag gcgtggaatt gcagaggctg ttggtcttcc aagtattcct
1141 gttcatccaa ttggatacta tgatgcacag aagctcctag aaaaaatggg tggctcagca
1201 ccaccagata gcagctggag aggaagtctc aaagtgccct acaatgttgg acctggcttt
1261 actggaaact tttctacaca aaaagtcaag atgcacatcc actctaccaa tgaagtgaca
1321 agaatttaca atgtgatagg tactctcaga ggagcagtgg aaccagacag atatgtcatt
1381 ctgggaggtc accgggactc atgggtgttt ggtggtattg accctcagag tggagcagct
1441 gttgttcatg aaattgtgag gagctttgga acactgaaaa aggaagggtg agagacctaga
1501 agaacaattt tgtttgcaag ctgggatgca gaagaatttg gtcttcttgg ttctactgag
1561 tgggcagagg agaattcaag actccttcaa gagcgtggcg tggcttatat taatgctgac
1621 tcatctatag aaggaaacta cactctgaga gttgattgta caccgctgat gtacagcttg
1681 gtacacaacc taacaaaaga gctgaaaagc cctgatgaag ctttgaagg caaatctctt
1741 tatgaaagtt ggactaaaaa aagtccttcc ccagagttca gtggcatgcc aggataagc
1801 aaattgggat ctggaaatga ttttgaggtg ttcttccaac gacttggaat tgcttcaggc
1861 agagcacggt atactaaaaa ttgggaaaca aacaaattca gcggctatcc actgtatcac
1921 agtgtctatg aaacatatga gttggtggaa agtttttatg atccaatgtt taaatatcac
1981 ctcactgtgg cccaggttcg aggagggatg gtgtttgagc tagccaattc catagtgctc
2041 cctttttgatt gtcgagatta tgctgtagtt ttaagaaagt atgctgacaa aatctacagt
2101 atttctatga aacatccaca ggaaatgaag acatacagtg tatcatttga ttcacttttt
2161 tctgcagtaa agaattttac agaaattgct tccaagttca gtgagagact ccaggacttt
2221 gacaaaagca acccaatagt attaagaatg atgaatgatc aactcatgtt tctggaaaga
2281 gcatttattg atccattagg gttaccagac aggccttttt ataggcatgt catctatgct
2341 ccaagcagcc acaacaagta tgcagggggag tcattcccag gaatttatga tgctctgttt
2401 gatattgaaa gcaaagtgga cccttccaag gcctggggag aagtgaagag acagatttat
2461 gttgcagcct tcacagtgca ggcagctgca gagactttga gtgaagtagc ctaagaggat
```

-continued

```
ORIGIN
2521 tctttagaga atccgtattg aatttgtgtg gtatgtcact cagaaagaat cgtaatgggt
2581 atattgataa attttaaaat tggtatattt gaaataaagt tgaatattat ataaaaaaa
2641 aaaaaaaaaa aaa
```

NM 003147 Homo Sapiens Synovial Sarcoma, X Breakpoint 2 (SSX2), mRNA
LOCUS NM_003147 766 bp mRNA PRI 14-MAR-2001
DEFINITION Homo sapiens synovial sarcoma, X breakpoint 2 (SSX2), mRNA.
ACCESSION NM_003147
VERSION NM_003147.1 GI:10337582

/translation ="MNGDDAFARRPTVGAQIPEKIQKAFDDTAKYFSKEEWEKMKASE SEQ ID NO. 40
KIFYVYMKRKYEANTKLGFKATLPPFMCNKRAEDFQGNDLDNDPNRGNQVERPQMTFG
RLQGISPKIMPKKPAEEGNDSEEVPEASGPQNDGKELCPPGKPTTSEKIHERSGPKRG
EHAWTHRLRERKQLVIYEEISDPEEDDE"

```
                                                              SEQ ID NO 41
  1 ctctctttcg attcttccat actcagagta cgcacggtct gatttctct ttggattctt
 61 ccaaaatcag agtcagactg ctcccggtgc catgaacgga gacgacgcct tgcaaggag
121 acccacggtt ggtgctcaaa taccagaaa gatccaaaag gccttcgatg atattgccaa
181 atacttctct aaggaagagt gggaaaagat gaaagcctcg gagaaaatCt tctatgtgta
241 tatgaagaga aagtatgagg ctatgactaa actaggtttc aaggccaccc tcccacctt
301 catgtgtaat aaacgggccg aagacttcca ggggaatgat ttggataatg accctaaccg
361 tgggaatcag gttgaacgtc ctcagatgac tttcggcagg ctccagggaa tctccccgaa
421 gatcatgccc aagaagccag cagaggaagg aaatgattcg gaggaagtgc cagaagcatc
481 tggcccacaa aatgatggga aagagctgtg cccccggga aaaccaacta cctctgagaa
541 gattcacgag agatctggac ccaaaagggg ggaacatgcc tggacccaca gactgcgtga
601 gagaaaacag ctggtgattt atgaagagat cagcgaccct gaggaagatg acgagtaact
661 cccctcaggg atacgacaca tgcccatgat gagaagcaga acgtggtgac cttcacgaa
721 catgggcatg gctgcggacc cctcgtcatc aggtgcatag caagtg
```

APPENDIX A

| SEQ ID NO | IDENTITY | SEQUENCE |
|---|---|---|
| 980 | Tyr 207-216 | FLPWHRLFLL |
| 981 | Tyrosinase protein | Accession number**: P14679 |
| 982 | SSX-2 protein | Accession number: NP_003138 |
| 983 | PSMA protein | Accession number: NP_004467 |
| 984 | Tyrosinase cDNA | Accession number: NM_000372 |
| 985 | SSX-2 cDNA | Accession number: NM_003147 |
| 986 | PSMA cDNA | Accession number: NM_004476 |
| 987 | Tyr 207-215 | FLPWHRLFL |
| 988 | Tyr 208-216 | LPWHRLFLL |
| 989 | SSX-2 31-68 | YFSKEEWEKMKASEKIFYV YMKRKYEAMTKLGFKATLP |
| 990 | SSX-2 32-40 | FSKEEWEKM |
| 991 | SSX-2 39-47 | KMKASEKIF |
| 992 | SSX-2 40-48 | MKASEKIFY |
| 993 | SSX-2 39-48 | KMKASEKIFY |

APPENDIX A-continued

| SEQ ID NO | IDENTITY | SEQUENCE |
|---|---|---|
| 994 | SSX-2 41-49 | KASEKIFYV |
| 995 | SSX-2 40-49 | MKASEKIFYV |
| 996 | SSX-2 41-50 | KASEKIFYVY |
| 997 | SSX-2 42-49 | ASEKIFYVY |
| 998 | SSX-2 53-61 | RKYEAMTKL |
| 999 | SSX-2 52-61 | KRKYEAMTKL |
| 1000 | SSX-2 54-63 | KYEAMTKLGF |
| 1001 | SSX-2 55-63 | YEAMTKLGF |
| 1002 | SSX-2 56-63 | EAMTKLGF |
| 1003 | HBV18-27 | FLPSDYFPSV |
| 1004 | HLA-B44 binder | AEMGKYSFY |
| 1005 | SSX-1 41-49 | KYSEKISYV |
| 1006 | SSX-3 41-49 | KVSEKIVYV |
| 1007 | SSX-4 41-49 | KSSEKIVYV |
| 1008 | SSX-5 41-49 | KASEKIIYV |
| 1009 | PSMA163-192 | AFSPQGMPEGDLVYV NYARTEDFFKLERDM |

APPENDIX A-continued

| SEQ ID NO | IDENTITY | SEQUENCE |
|---|---|---|
| 1010 | PSMA 168-190 | GMPEGDLVYVNYARTEDFFKLER |
| 1011 | PSMA 169-177 | MPEGDLVYV |
| 1012 | PSMA 168-177 | GMPEGDLVYV |
| 1013 | PSMA 168-176 | GMPEGDLVY |
| 1014 | PSMA 167-176 | QGMPEGDLVY |
| 1015 | PSMA 169-176 | MPEGDLVY |
| 1016 | PSMA 171-179 | EGDLVYVNY |
| 1017 | PSMA 170-179 | PEGDLVYVNY |
| 1018 | PSMA 174-183 | LVYVNYARTE |
| 1019 | PSMA 177-185 | VNYARTEDF |
| 1020 | PSMA 176-185 | YVNYARTEDF |
| 1021 | PSMA 178-186 | NYARTEDFF |
| 1022 | PSMA 179-186 | YARTEDFF |
| 1023 | PSMA 181-189 | RTEDFFKLE |
| 1024 | PSMA 281-310 | RGIAEAVGLPSIPVHPIGYYDAQKLLEKMG |
| 1025 | PSMA 283-307 | IAEAVGLPSIPVHPIGYYDAQKLLE |
| 1026 | PSMA 289-297 | LPSIPVHPI |
| 1027 | PSMA 288-297 | GLPSIPVHPI |
| 1028 | PSMA 297-305 | IGYYDAQKL |
| 1029 | PSMA 296-305 | PIGYYDAQKL |
| 1030 | PSMA 291-299 | SIPVHPIGY |
| 1031 | PSMA 290-299 | PSIPVHPIGY |
| 1032 | PSMA 292-299 | IPVHPIGY |
| 1033 | PSMA 299-307 | YYDAQKLLE |
| 1034 | PSMA454-481 | SSIEGNYTLRVDCTPLMYSLVHLTKEL |
| 1035 | PSMA 456-464 | IEGNYTLRV |
| 1036 | PSMA 455-464 | SIEGNYTLRV |
| 1037 | PSMA 457-464 | EGNYTLRV |
| 1038 | PSMA 461-469 | TLRVDCTPL |
| 1039 | PSMA 460-469 | YTLRVDCTPL |
| 1040 | PSMA 462-470 | LRVDCTPLM |
| 1041 | PSMA 463-471 | RVDCTPLMY |
| 1042 | PSMA 462-471 | LRVDCTPLMY |
| 1043 | PSMA653-687 | FDKSNPIVLRMMNDQLMFLERAFIDPLGLPDRPFY |
| 1044 | PSMA 660-681 | VLRMMNDQLMFLERAFIDPLGL |
| 1045 | PSMA 663-671 | MMNDQLMFL |
| 1046 | PSMA 662-671 | RMMNDQLMFL |
| 1047 | PSMA 662-670 | RMMNDQLMF |
| 1048 | Tyr1-17 | MLLAVLYCLLWSFQTSA |
| 1049 | GP100 protein[2] | **Accession number: P40967 |
| 1050 | MAGE-1 protein | Accession number: P43355 |
| 1051 | MAGE-2 protein | Accession number: P43356 |
| 1052 | MAGE-3 protein | Accession number: P43357 |
| 1053 | NY-ESO-1 protein | Accession number: P78358 |
| 1054 | LAGE-1a protein | Accession number: CAA11116 |
| 1055 | LAGE-1b protein | Accession number: CAA11117 |
| 1056 | PRAME protein | Accession number: NP 006106 |
| 1057 | PSA protein | Accession number: P07288 |
| 1058 | PSCA protein | Accession number: O43653 |
| 1059 | GP100 cds | Accession number: U20093 |
| 1060 | MAGE-1 cds | Accession number: M77481 |
| 1061 | MAGE-2 cds | Accession number: L18920 |
| 1062 | MAGE-3 cds | Accession number: U03735 |
| 1063 | NY-ESO-1 cDNA | Accession number: U87459 |
| 1064 | PRAME cDNA | Accession number: NM_006115 |
| 1065 | PSA cDNA | Accession number: NM_001648 |
| 1066 | PSCA cDNA | Accession number: AF043498 |
| 1067 | GP100 630-638 | LPHSSSHWL |
| 1068 | GP100 629-638 | QLPHSSSHWL |
| 1069 | GP100 614-622 | LIYRRRLMK |
| 1070 | GP100 613-622 | SLIYRRRLMK |
| 1071 | GP100 615-622 | IYRRRLMK |
| 1072 | GP100 630-638 | LPHSSSHWL |
| 1073 | GP100 629-638 | QLPHSSSHWL |
| 1074 | MAGE-1 95-102 | ESLFRAVI |
| 1075 | MAGE-1 93-102 | ILESLFRAVI |
| 1076 | MAGE-1 93-101 | ILESLFRAV |
| 1077 | MAGE-1 92-101 | CILESLFRAV |
| 1078 | MAGE-1 92-100 | CILESLFRA |
| 1079 | MAGE-1 263-271 | EFLWGPRAL |
| 1080 | MAGE-1 264-271 | FLWGPRAL |
| 1081 | MAGE-1 264-273 | FLWGPRALAE |
| 1082 | MAGE-1 265-274 | LWGPRALAET |
| 1083 | MAGE-1 268-276 | PRALAETSY |
| 1084 | MAGE-1 267-276 | GPRALAETSY |
| 1085 | MAGE-1 269-277 | RALAETSYV |
| 1086 | MAGE-1 271-279 | LAETSYVKV |
| 1087 | MAGE-1 270-279 | ALAETSYVKV |
| 1088 | MAGE-1 272-280 | AETSYVKVL |
| 1089 | MAGE-1 271-280 | LAETSYVKVL |
| 1090 | MAGE-1 274-282 | TSYVKVLEY |
| 1091 | MAGE-1 273-282 | ETSYVKVLEY |
| 1092 | MAGE-1 278-286 | KVLEYVIKV |
| 1093 | MAGE-1 168-177 | SYVLVTCLGL |
| 1094 | MAGE-1 169-177 | YVLVTCLGL |
| 1095 | MAGE-1 170-177 | VLVTCLGL |
| 1096 | MAGE-1 240-248 | TQDLVQEKY |
| 1097 | MAGE-1 239-248 | LTQDLVQEKY |
| 1098 | MAGE-1 232-240 | YGEPRKLLT |
| 1099 | MAGE-1 243-251 | LVQEKYLEY |
| 1100 | MAGE-1 242-251 | DLVQEKYLEY |
| 1101 | MAGE-1 230-238 | SAYGEPRKL |
| 1102 | MAGE-1 278-286 | KVLEYVIKV |
| 1103 | MAGE-1 277-286 | VKVLEYVIKV |
| 1104 | MAGE-1 276-284 | YVKVLEYVI |
| 1105 | MAGE-1 274-282 | TSYVKVLEY |
| 1106 | MAGE-1 273-282 | ETSYVKVLEY |
| 1107 | MAGE-1 283-291 | VIKVSARVR |
| 1108 | MAGE-1 282-291 | YVIKVSARVR |
| 1109 | MAGE-2 115-122 | ELVHFLLL |
| 1110 | MAGE-2 113-122 | MVELVHFLLL |
| 1111 | MAGE-2 109-116 | ISRKMVEL |
| 1112 | MAGE-2 108-116 | AISRKMVEL |
| 1113 | MAGE-2 107-115 | AAISRKMVEL |
| 1114 | MAGE-2 112-120 | KMVELVHFL |
| 1115 | MAGE-2 109-117 | ISRKMVELV |
| 1116 | MAGE-2 108-117 | AISRKMVELV |
| 1117 | MAGE-2 116-124 | LVHFLLLKY |
| 1118 | MAGE-2 115-124 | ELVHFLLLKY |
| 1119 | MAGE-2 111-119 | RKMVELVHF |
| 1120 | MAGE-2 158-166 | LQLVFGIEV |
| 1121 | MAGE-2 157-166 | YLQLVFGIEV |
| 1122 | MAGE-2 159-167 | QLVFGIEVV |
| 1123 | MAGE-2 158-167 | LQLVFGIEVV |
| 1124 | MAGE-2 164-172 | IEVVEVVPI |
| 1125 | MAGE-2 163-172 | GIEVVEVVPI |
| 1126 | MAGE-2 162-170 | FGIEVVEVV |
| 1127 | MAGE-2 154-162 | ASEYLQLVF |
| 1128 | MAGE-2 153-162 | KASEYLQLVF |
| 1129 | MAGE-2 218-225 | EEKIWEEL |
| 1130 | MAGE-2 216-225 | APEEKIWEEL |
| 1131 | MAGE-2 216-223 | APEEKIWE |
| 1132 | MAGE-2 220-228 | KIWEELSML |
| 1133 | MAGE-2 219-228 | EKIWEELSML |
| 1134 | MAGE-2 271-278 | FLWGPRAL |
| 1135 | MAGE-2 271-279 | FLWGPRALI |
| 1136 | MAGE-2 278-286 | LIETSYVKV |
| 1137 | MAGE-2 277-286 | ALIETSYVKV |
| 1138 | MAGE-2 276-284 | RALIETSYV |
| 1139 | MAGE-2 279-287 | IETSYVKVL |
| 1140 | MAGE-2 278-287 | LIETSYVKVL |
| 1141 | MAGE-3 271-278 | FLWGPRAL |
| 1142 | MAGE-3 270-278 | EFLWGPRAL |
| 1143 | MAGE-3 271-279 | FLWGPRALV |
| 1144 | MAGE-3 276-284 | RALVETSYV |
| 1145 | MAGE-3 272-280 | LWGPRALVE |
| 1146 | MAGE-3 271-280 | FLWGPRALVE |
| 1147 | MAGE-3 27 2-281 | LWGPRALVET |
| 1148 | NY-ESO-1 82-90 | GPESRLLEF |
| 1149 | NY-ESO-1 83-91 | PESRLLEFY |
| 1150 | NY-ESO-1 82-91 | GPESRLLEFY |
| 1151 | NY-ESO-1 84-92 | ESRLLEFYL |
| 1152 | NY-ESO-1 86-94 | RLLEFYLAM |
| 1153 | NY-ESO-1 88-96 | LEFYLAMPF |
| 1154 | NY-ESO-1 87-96 | LLEFYLAMPF |
| 1155 | NY-ESO-1 93-102 | AMPFATPMEA |
| 1156 | NY-ESO-1 94-102 | MPFATPMEA |
| 1157 | NY-ESO-1 115-123 | PLPVPGVLL |
| 1158 | NY-ESO-1 114-123 | PPLPVPGVLL |
| 1159 | NY-ESO-1 116-123 | LPVPGVLL |
| 1160 | NY-ESO-1 103-112 | ELARRSLAQD |

APPENDIX A-continued

| SEQ ID NO | IDENTITY | SEQUENCE |
|---|---|---|
| 1161 | NY-ESO-1 118-126 | PGVLLKEF |
| 1162 | NY-ESO-1 117-126 | PVPGVLLKEF |
| 1163 | NY-ESO-1 116-123 | LPVPGVLL |
| 1164 | NY-ESO-1 127-135 | TVSGNILTI |
| 1165 | NY-ESO-1 126-135 | FTVSGNILTI |
| 1166 | NY-ESO-1 120-128 | GVLLKEFTV |
| 1167 | NY-ESO-1 121-130 | VLLKEFTVSG |
| 1168 | NY-ESO-1 122-130 | LLKEFTVSG |
| 1169 | NY-ESO-1 118-126 | VPGVLLKEF |
| 1170 | NY-ESO-1 117-126 | PVPGVLLKEF |
| 1171 | NY-ESO-1 139-147 | AADHRQLQL |
| 1172 | NY-ESO-1 148-156 | SISSCLQQL |
| 1173 | NY-ESO-1 147-156 | LSISSCLQQL |
| 1174 | NY-ESO-1 138-147 | TAADHRQLQL |
| 1175 | NY-ESO-1 161-169 | WITQCFLPV |
| 1176 | NY-ESO-1 157-165 | SLLMWITQC |
| 1177 | NY-ESO-1 150-158 | SSCLQQLSL |
| 1178 | NY-ESO-1 154-162 | QQLSLLMWI |
| 1179 | NY-ESO-1 151-159 | SCLQQLSLL |
| 1180 | NY-ESO-1 150-159 | SSCLQQLSLL |
| 1181 | NY-ESO-1 163-171 | TQCFLPVFL |
| 1182 | NY-ESO-1 162-171 | ITQCFLPVFL |
| 1183 | PRAME 219-227 | PMQDIKMIL |
| 1184 | PRAME 218-227 | MPMQDIKMIL |
| 1185 | PRAME 428-436 | QHLIGLSNL |
| 1186 | PRAME 427-436 | LQHLIGLSNL |
| 1187 | PRAME 429-436 | HLIGLSNL |
| 1188 | PRAME 431-439 | IGLSNLTHV |
| 1189 | PRAME 430-439 | LIGLSNLTHV |
| 1190 | PSA 53-61 | VLVHPQWVL |
| 1191 | PSA 52-61 | GVLVHPQWVL |
| 1192 | PSA 52-60 | GVLVHPQWV |
| 1193 | PSA 59-67 | WVLTAAHCI |
| 1194 | PSA 54-63 | LVHPQWVLTA |
| 1195 | PSA 53-62 | VLVHPQWVLT |
| 1196 | PSA 54-62 | LVHPQWVLT |
| 1197 | PSA 66-73 | CIRNKSVI |
| 1198 | PSA 65-73 | HCIRNKSVI |
| 1199 | PSA 56-64 | HPQWVLTAA |
| 1200 | PSA 63-72 | AAHCIRNKSV |
| 1201 | PSCA 116-123 | LLWGPGQL |
| 1202 | PSCA 115-123 | LLLWGPGQL |
| 1203 | PSCA 114-123 | GLLLWGPGQL |
| 1204 | PSCA 99-107 | ALQPAAAIL |
| 1205 | PSCA 98-107 | HALQPAAAIL |
| 1206 | Tyr 128-137 | APEKDKFFAY |
| 1207 | Tyr 129-137 | PEKDKFFAY |
| 1208 | Tyr 130-138 | EKDKFFAYL |
| 1209 | Tyr 131-138 | KDKFFAYL |
| 1210 | Tyr 205-213 | PAFLPWHRL |
| 1211 | Tyr 204-213 | APAFLPWHRL |
| 1212 | Tyr 214-223 | FLLRWEQEIQ |
| 1213 | Tyr 212-220 | RLFLLRWEQ |
| 1214 | Tyr 191-200 | GSEIWRDIDF |
| 1215 | Tyr 192-200 | SEIWRDIDF |
| 1216 | Tyr 473-481 | RIWSWLLGA |
| 1217 | Tyr 476-484 | SWLLGAAMV |
| 1218 | Tyr 477-486 | WLLGAAMVGA |
| 1219 | Tyr 478-486 | LLGAAMVGA |
| 1220 | PSMA 4-12 | LLHETDSAV |
| 1221 | PSMA 13-21 | ATARRPRWL |
| 1222 | PSMA 53-61 | TPKHNMKAF |
| 1223 | PSMA 64-73 | ELKAENIKKF |
| 1224 | PSMA 69-77 | NIKKFLH$^1$NF |
| 1225 | PSMA 68-77 | ENIKKFLH$^1$NF |
| 1226 | PSMA 220-228 | AGAKGVILY |
| 1227 | PSMA 468-477 | PLMYSLVHNL |
| 1228 | PSMA 469-477 | LMYSLVHNL |
| 1229 | PSMA 463-471 | RVDCTPLMY |
| 1230 | PSMA 465-473 | DCTPLMYSL |
| 1231 | PSMA 507-515 | SGMPRISKL |
| 1232 | PSMA 506-515 | FSGMPRISKL |
| 1233 | NY-ESO-1 136-163 | RLTAADHRQLQLSISSCLQQLSLLMWIT |
| 1234 | NY-ESO-1 150-177 | SSCLQQLSLLMWITQCFLPVFLAQPPSG |
| 1235 | Mage-1 125-132 | KAEMLESV |
| 1236 | Mage-1 124-132 | TKAEMLESV |
| 1237 | Mage-1 123-132 | VTKAEMLESV |
| 1238 | Mage-1 128-136 | MLESVIKNY |
| 1239 | Mage-1 127-136 | EMLESVIKNY |
| 1240 | Mage-1 125-133 | KAEMLESVI |
| 1241 | Mage-1 146-153 | KASESLQL |
| 1242 | Mage-1 145-153 | GKASESLQL |
| 1243 | Mage-1 147-155 | ASESLQLVF |
| 1244 | Mage-1 153-161 | LVFGIDVKE |
| 1245 | Mage-1 114-121 | LLKYRARE |
| 1246 | Mage-1 106-113 | VADLVGFL |
| 1247 | Mage-1 105-113 | KVADLVGFL |
| 1248 | Mage-1 107-115 | ADLVGFLLL |
| 1249 | Mage-1 106-115 | VADLVGFLLL |
| 1250 | Mage-1 114-123 | LLKYRAREPV |
| 1251 | Mage-3 278-286 | LVETSYVKV |
| 1252 | Mage-3 277-286 | ALVETSYVKV |
| 1253 | Mage-3 285-293 | KVLHHMVKI |
| 1254 | Mage-3 283-291 | YVKVLHHMV |
| 1255 | Mage-3 275-283 | PRALVETSY |
| 1256 | Mage-3 274-283 | GPRALVETSY |
| 1257 | Mage-3 278-287 | LVETSYVKVL |
| 1258 | ED-B 4'-5 | TIIPEVPQL |
| 1259 | ED-B 5'-5 | DTIIPEVPQL |
| 1260 | ED-B 1-10 | EVPQLTDLSF |
| 1261 | ED-B 23-30 | TPLNSSTI |
| 1262 | ED-B 18-25 | IGLRWTPL |
| 1263 | ED-B 17-25 | SIGLRWTPL |
| 1264 | ED-B 25-33 | LNSSTIIGY |
| 1265 | ED-B 24-33 | PLNSSTIIGY |
| 1266 | ED-B 23-31 | TPLNSSTII |
| 1267 | ED-B 31-38 | IGYRITVV |
| 1268 | ED-B 30-38 | IIGYRITVV |
| 1269 | ED-B 29-38 | TIIGYRITVV |
| 1270 | ED-B 31-39 | IGYRITVVA |
| 1271 | ED-B 30-39 | IIGYRITVVA |
| 1272 | CEA 184-191 | SLPVSPRL |
| 1273 | CEA 183-191 | QSLPVSPRL |
| 1274 | CEA 186-193 | PVSPRLQL |
| 1275 | CEA 185-193 | LPVSPRLQL |
| 1276 | CEA 184-193 | SLPVSPRLQL |
| 1277 | CEA 185-192 | LPVSPRLQ |
| 1278 | CEA 192-200 | QLSNGNRTL |
| 1279 | CEA 191-200 | LQLSNGNRTL |
| 1280 | CEA 179-187 | WVNNQSLPV |
| 1281 | CEA 186-194 | PVSPRLQLS |
| 1282 | CEA 362-369 | SLPVSPRL |
| 1283 | CEA 361-369 | QSLPVSPRL |
| 1284 | CEA 364-371 | PVSPRLQL |
| 1285 | CEA 363-371 | LPVSPRLQL |
| 1286 | CEA 362-371 | SLPVSPRLQL |
| 1287 | CEA 363-370 | LPVSPRLQ |
| 1288 | CEA 370-378 | QLSNDNRTL |
| 1289 | CEA 369-378 | LQLSNDNRTL |
| 1290 | CEA 357-365 | WVNNQSLPV |
| 1291 | CEA 360-368 | NQSLPVSPR |
| 1292 | CEA 540-547 | SLPVSPRL |
| 1293 | CEA 539-547 | QSLPVSPRL |
| 1294 | CEA 542-549 | PVSPRLQL |
| 1295 | CEA 541-549 | LPVSPRLQL |
| 1296 | CEA 540-549 | SLPVSPRLQL |
| 1297 | CEA 541-548 | LPVSPRLQ |
| 1298 | CEA 548-556 | QLSNGNRTL |
| 1299 | CEA 547-556 | LQLSNGNRTL |
| 1300 | CEA 535-543 | WVNGQSLPV |
| 1301 | CEA 533-541 | LWWVNGQSL |
| 1302 | CEA 532-541 | YLWWVNGQSL |
| 1303 | CEA 538-546 | GQSLPVSPR |
| 1304 | Her-2 30-37 | DMKLRLPA |
| 1305 | Her-2 28-37 | GTDMKLRLPA |
| 1306 | Her-2 42-49 | HLDMLRHL |
| 1307 | Her-2 41-49 | THLDMLRHL |
| 1308 | Her-2 40-49 | ETHLDMLRHL |
| 1309 | Her-2 36-43 | PASPETHL |
| 1310 | Her-2 35-43 | LPASPETHL |
| 1311 | Her-2 34-43 | RLPASPETHL |
| 1312 | Her-2 38-46 | SPETHLDML |
| 1313 | Her-2 37-46 | ASPETHLDML |
| 1314 | Her-2 42-50 | HLDMLRHLY |

APPENDIX A-continued

| SEQ ID NO | IDENTITY | SEQUENCE |
|---|---|---|
| 1315 | Her-2 41-50 | THLDMLRHLY |
| 1316 | Her-2 719-726 | ELRKVKVL |
| 1317 | Her-2 718-726 | TELRKVKVL |
| 1318 | Her-2 717-726 | ETELRKVKVL |
| 1319 | Her-2 715-723 | LKETELRKV |
| 1320 | Her-2 714-723 | ILKETELRKV |
| 1321 | Her-2 712-720 | MRILKETEL |
| 1322 | Her-2 711-720 | QMRILKETEL |
| 1323 | Her-2 717-725 | ETELRKVKV |
| 1324 | Her-2 716-725 | KETELRKVKV |
| 1325 | Her-2 706-714 | MPNQAQMRI |
| 1326 | Her-2 705-714 | AMPNQAQMRI |
| 1327 | Her-2 706-715 | MPNQAQMRIL |
| 1328 | HER-2 966-973 | RPRFRELV |
| 1329 | HER-2 965-973 | CRPRFRELV |
| 1330 | HER-2 968-976 | RFRELVSEF |
| 1331 | HER-2 967-976 | PRFRELVSEF |
| 1332 | HER-2 964-972 | ECRPRFREL |
| 1333 | NY-ESO-1 67-75 | GAASGLNGC |
| 1334 | NY-ESO-1 52-60 | RASGPGGGA |
| 1335 | NY-ESO-1 64-72 | PHGGAASGL |
| 1336 | NY-ESO-1 63-72 | GPHGGAASGL |
| 1337 | NY-ESO-1 60-69 | APRGPHGGAA |
| 1338 | PRAME 112-119 | VRPRRWKL |
| 1339 | PRAME 111-119 | EVRPRRWKL |
| 1340 | PRAME 113-121 | RPRRWKLQV |
| 1341 | PRAME 114-122 | PRRWKLQVL |
| 1342 | PRAME 113-122 | RPRRWKLQVL |
| 1343 | PRAME 116-124 | RWKLQVLDL |
| 1344 | PRAME 115-124 | RRWKLQVLDL |
| 1345 | PRAME 174-182 | PVEVLVDLF |
| 1346 | PRAME 199-206 | VKRKKNVL |
| 1347 | PRAME 198-206 | KVKRKKNVL |
| 1348 | PRAME 197-206 | EKVKRKKNVL |
| 1349 | PRAME 198-205 | KVKRKKNV |
| 1350 | PRAME 201-208 | RKKNVLRL |
| 1351 | PRAME 200-208 | KRKKNVLRL |
| 1352 | PRAME 199-208 | VKRKKNVLRL |
| 1353 | PRAME 189-196 | DELFSYLI |
| 1354 | PRAME 205-213 | VLRLCCKKL |
| 1355 | PRAME 204-213 | NVLRLCCKKL |
| 1356 | PRAME 194-202 | YLIEKVKRK |
| 1357 | PRAME 74-81 | QAWPFTCL |
| 1358 | PRAME 73-81 | VQAWPFTCL |
| 1359 | PRAME 72-81 | MVQAWPFTCL |
| 1360 | PRAME 81-88 | LPLGVLMK |
| 1361 | PRAME 80-88 | CLPLGVLMK |
| 1362 | PRAME 79-88 | TCLPLGVLMK |
| 1363 | PRAME 84-92 | GVLMKGQHL |
| 1364 | PRAME 81-89 | LPLGVLMKG |
| 1365 | PRAME 80-89 | CLPLGVLMKG |
| 1366 | PRAME 76-85 | WPFTCLPLGV |
| 1367 | PRAME 51-59 | ELFPPLFMA |
| 1368 | PRAME 49-57 | PRELFPPLF |
| 1369 | PRAME 48-57 | LPRELFPPLF |
| 1370 | PRAME 50-58 | RELFPPLFM |
| 1371 | PRAME 49-58 | PRELFPPLFM |
| 1372 | PSA 239-246 | RPSLYTKV |
| 1373 | PSA 238-246 | ERPSLYTKV |
| 1374 | PSA 236-243 | LPERPSLY |
| 1375 | PSA 235-243 | ALPERPSLY |
| 1376 | PSA 241-249 | SLYTKVVHY |
| 1377 | PSA 240-249 | PSLYTKVVHY |
| 1378 | PSA 239-247 | RPSLYTKVV |
| 1379 | PSMA 211-218 | GNKVKNAQ |
| 1380 | PSMA 202-209 | IARYGKVF |
| 1381 | PSMA 217-225 | AQLAGAKGV |
| 1382 | PSMA 207-215 | KVFRGNKVK |
| 1383 | PSMA 211-219 | GNKVKNAQL |
| 1384 | PSMA 269-277 | TPGYPANEY |
| 1385 | PSMA 268-277 | LTPGYPANEY |
| 1386 | PSMA 271-279 | GYPANEYAY |
| 1387 | PSMA 270-279 | PGYPANEYAY |
| 1388 | PSMA 266-274 | DPLTGYPA |
| 1389 | PSMA 492-500 | SLYESWTKK |
| 1390 | PSMA 491-500 | KSLYESWTKK |
| 1391 | PSMA 486-494 | EGFEGKSLY |
| 1392 | PSMA 485-494 | DEGFEGKSLY |
| 1393 | PSMA 498-506 | TKKSPSPEF |
| 1394 | PSMA 497-506 | WTKKSPSPEF |
| 1395 | PSMA 492-501 | SLYESWTKKS |
| 1396 | PSMA 725-732 | WGEVKRQI |
| 1397 | PSMA 724-732 | AWGEVKRQI |
| 1398 | PSMA 723-732 | KAWGEVKRQI |
| 1399 | PSMA 723-730 | KAWGEVKR |
| 1400 | PSMA 722-730 | SKAWGEVKR |
| 1401 | PSMA 731-739 | QIYVAAFTV |
| 1402 | PSMA 733-741 | YVAAFTVQA |
| 1403 | PSMA 725-733 | WGEVKRQIY |
| 1404 | PSMA 727-735 | EVKRQIYVA |
| 1405 | PSMA 738-746 | TVQAAAETL |
| 1406 | PSMA 737-746 | FTVQAAAETL |
| 1407 | PSMA 729-737 | KRQIYVAAF |
| 1408 | PSMA 721-729 | PSKAWGEVK |
| 1409 | PSMA 723-731 | KAWGEVKRQ |
| 1410 | PSMA 100-108 | WKEFGLDSV |
| 1411 | PSMA 99-108 | QWKEFGLDSV |
| 1412 | PSMA 102-111 | EFGLDSVELA |
| 1413 | SCP-1 126-134 | ELRQKESKL |
| 1414 | SCP-1 125-134 | AELRQKESKL |
| 1415 | SCP-1 133-141 | KLQENRKII |
| 1416 | SCP-1 298-305 | QLEEKTKL |
| 1417 | SCP-1 297-305 | NQLEEKTKL |
| 1418 | SCP-1 288-296 | LLEESRDKV |
| 1419 | SCP-1 287-296 | FLLEESRDKV |
| 1420 | SCP-1 291-299 | ESRDKVNQL |
| 1421 | SCP-1 290-299 | EESRDKVNQL |
| 1422 | SCP-1 475-483 | EKEVHDLEY |
| 1423 | SCP-1 474-483 | REKEVHDLEY |
| 1424 | SCP-1 480-488 | DLEYSYCHY |
| 1425 | SCP-1 477-485 | EVHDLEYSY |
| 1426 | SCP-1 477-486 | EVHDLEYSYC |
| 1427 | SCP-1 502-509 | KLSSKREL |
| 1428 | SCP-1 508-515 | ELKNTEYF |
| 1429 | SCP-1 507-515 | RELKNTEYF |
| 1430 | SCP-1 496-503 | KRGQRPKL |
| 1431 | SCP-1 494-503 | LPKRGQRPKL |
| 1432 | SCP-1 509-517 | LKNTEYFTL |
| 1433 | SCP-1 508-517 | ELKNTEYFTL |
| 1434 | SCP-1 506-514 | KRELKNTEY |
| 1435 | SCP-1 502-510 | KLSSKRELK |
| 1436 | SCP-1 498-506 | GQRPKLSSK |
| 1437 | SCP-1 497-506 | RGQRPICLSSK |
| 1438 | SCP-1 500-508 | RPKLSSKRE |
| 1439 | SCP-1 573-580 | LEYVREEL |
| 1440 | SCP-1 572-580 | ELEYVREEL |
| 1441 | SCP-1 571-580 | NELEYVREEL |
| 1442 | SCP-1 579-587 | ELKQKREDEV |
| 1443 | SCP-1 575-583 | YVREELKQK |
| 1444 | SCP-1 632-640 | QLNVYEIKV |
| 1445 | SCP-1 630-638 | SKQLNVYEI |
| 1446 | SCP-1 628-636 | AESKQLNVY |
| 1447 | SCP-1 627-636 | TAESKQLNVY |
| 1448 | SCP-1 638-645 | IKVNKLEL |
| 1449 | SCP-1 637-645 | EIKVNKLEL |
| 1450 | SCP-1 636-645 | YEIKVNKLEL |
| 1451 | SCP-1 642-650 | KLELELESA |
| 1452 | SCP-1 635-643 | VYEIKVNKL |
| 1453 | SCP-1 634-643 | NVYEIKVNKL |
| 1454 | SCP-1 646-654 | ELESAKQKF |
| 1455 | SCP-1 642-650 | KLELELESA |
| 1456 | SCP-1 646-654 | ELESAKQKF |
| 1457 | SCP-1 771-778 | KEKLKREA |
| 1458 | SCP-1 777-785 | EAKENTATL |
| 1459 | SCP-1 776-785 | REAKENTATL |
| 1460 | SCP-1 773-782 | KLKREAKENT |
| 1461 | SCP-1 112-119 | EAEKIKKW |
| 1462 | SCP-1 101-109 | GLSRVYSKL |
| 1463 | SCP-1 100-109 | EGLSRVYSKL |
| 1464 | SCP-1 108-116 | KLYKEAEKI |
| 1465 | SCP-1 98-106 | NSEGLSRVY |
| 1466 | SCP-1 97-106 | ENSEGLSRVY |
| 1467 | SCP-1 102-110 | LSRVYSKLY |
| 1468 | SCP-1 101-110 | GLSRVYSKLY |
| 1469 | SCP-1 96-105 | LENSEGLSRV |
| 1470 | SCP-1 108-117 | KLYKEAEKIK |

APPENDIX A-continued

| SEQ ID NO | IDENTITY | SEQUENCE |
|---|---|---|
| 1471 | SCP-1 949-956 | REDRWAVI |
| 1472 | SCP-1 948-956 | MREDRWAVI |
| 1473 | SCP-1 947-956 | KMREDRWAVI |
| 1474 | SCP-1 947-955 | KMREDRWAV |
| 1475 | SCP-1 934-942 | TTPGSTLKF |
| 1476 | SCP-1 933-942 | LTTPGSTLKF |
| 1477 | SCP-1 937-945 | GSTLKGAI |
| 1478 | SCP-1 945-953 | IRKMREDRW |
| 1479 | SCP-1 236-243 | RLEMHFKL |
| 1480 | SCP-1 235-243 | SRLEMHFKL |
| 1481 | SCP-1 242-250 | KLKEDYEKI |
| 1482 | SCP-1 249-257 | KIQHLEQEY |
| 1483 | SCP-1 248-257 | EKIQHLEQEY |
| 1484 | SCP-1 233-242 | ENSRLEMHF |
| 1485 | SCP-1 236-245 | RLEMHFKLKE |
| 1486 | SCP-1 324-331 | LEDIKVSL |
| 1487 | SCP-1 323-331 | ELEDIKVSL |
| 1488 | SCP-1 322-331 | KELEDIKVSL |
| 1489 | SCP-1 320-327 | LTKELEDI |
| 1490 | SCP-1 319-327 | HLTKELEDI |
| 1491 | SCP-1 330-338 | SLQRSVSTQ |
| 1492 | SCP-1 321-329 | TKELEDIKV |
| 1493 | SCP-1 320-329 | LTKELEDIKV |
| 1494 | SCP-1 326-335 | DIKVSLQRSV |
| 1495 | SCP-1 281-288 | KMKDLTFL |
| 1496 | SCP-1 280-288 | NKMKDLTFL |
| 1497 | SCP-1 279-288 | ENKMKDLTFL |
| 1498 | SCP-1 288-296 | LLEESRDKV |
| 1499 | SCP-1 287-296 | FLLEESRDKV |
| 1500 | SCP-1 291-299 | ESRDKVNQL |
| 1501 | SCP-1 290-299 | EESRDKVNQL |
| 1502 | SCP-1 277-285 | EKENKMKDL |
| 1503 | SCP-1 276-285 | TEKENKMKDL |
| 1504 | SCP-1 279-287 | ENKMKDLTF |
| 1505 | SCP-1 218-225 | IEKMITAF |
| 1506 | SCP-1 217-225 | NIEKMITAF |
| 1507 | SCP-1 216-225 | SNIEKMITAF |
| 1508 | SCP-1 223-230 | TAFEELRV |
| 1509 | SCP-1 222-230 | ITAFEELRV |
| 1510 | SCP-1 221-230 | MITAFEELRV |
| 1511 | SCP-1 220-228 | KMITAFEEL |
| 1512 | SCP-1 219-228 | EKMITAFEEL |
| 1513 | SCP-1 227-235 | ELRVQAENS |
| 1514 | SCP-1 213-222 | DLNSNIEKMI |
| 1515 | SCP-1 837-844 | WTSAKNTL |
| 1516 | SCP-1 846-854 | TPLPKAYTV |
| 1517 | SCP-1 845-854 | STPLPKAYTV |
| 1518 | SCP-1 844-852 | LSTPLPKAY |
| 1519 | SCP-1 843-852 | TLSTPLPKAY |
| 1520 | SCP-1 842-850 | NTLSTPLPK |
| 1521 | SCP-1 841-850 | KNTLSTPLPK |
| 1522 | SCP-1 828-835 | ISKDKRDY |
| 1523 | SCP-1 826-835 | HGISKDKRDY |
| 1524 | SCP-1 832-840 | KRDYLWTSA |
| 1525 | SCP-1 829-838 | SKDKRDYLWT |
| 1526 | SCP-1 279-286 | ENKMKDLT |
| 1527 | SCP-1 260-268 | EINDKEKQV |
| 1528 | SCP-1 274-282 | QITEKENKM |
| 1529 | SCP-1 269-277 | SLLLIQITE |
| 1530 | SCP-1 453-460 | FEKIAEEL |
| 1531 | SCP-1 452-460 | QFEKIAEEL |
| 1532 | SCP-1 451-460 | KQFEKIAEEL |
| 1533 | SCP-1 449-456 | DNKQFEKI |
| 1534 | SCP-1 448-456 | YDNKQFEKI |
| 1535 | SCP-1 447-456 | LYDNKQFEKI |
| 1536 | SCP-1 440-447 | LGEKETLL |
| 1537 | SCP-1 439-447 | VLGEKETLL |
| 1538 | SCP-1 438-447 | KVLGEKETLL |
| 1539 | SCP-1 390-398 | LLRTEQQRL |
| 1540 | SCP-1 389-398 | ELLRTEQQRL |
| 1541 | SCP-1 393-401 | TEQQRLENY |
| 1542 | SCP-1 392-401 | RTEQQRLENY |
| 1543 | SCP-1 402-410 | EDQLIILTM |
| 1544 | SCP-1 397-406 | RLENYEDQLI |
| 1545 | SCP-1 368-375 | KARAAHSF |
| 1546 | SCP-1 376-384 | VVTEFETTV |
| 1547 | SCP-1 375-384 | FVVTEFETTV |
| 1548 | SCP-1 377-385 | VTEFETTVC |
| 1549 | SCP-1 376-385 | VVTEFETTVC |
| 1550 | SCP-1 344-352 | DLQIATNTI |
| 1551 | SCP-1 347-355 | IATNTICQL |
| 1552 | SCP-1 346-355 | QIATNTICQL |
| 1553 | SSX4 57-65 | VMTKLGFKY |
| 1554 | SSX4 53-61 | LNYEVMTKL |
| 1555 | SSX4 52-61 | KLNYEVMTKL |
| 1556 | SSX4 66-74 | TLPPFMRSK |
| 1557 | SSX4 110-118 | KIMPKKPAE |
| 1558 | SSX4 103-112 | SLQRIFPKIM |
| 1559 | Tyr 463-471 | YIKSYLEQA |
| 1560 | Tyr 459-467 | SFQDYIKSY |
| 1561 | Tyr 458-467 | DSFQDYIKSY |
| 1562 | Tyr 507-514 | LPEEKQPL |
| 1563 | Tyr 506-514 | QLPEEKQPL |
| 1564 | Tyr 505-514 | KQLPEEKQPL |
| 1565 | Tyr 507-515 | LPEEKQPLL |
| 1566 | Tyr 506-515 | QLPEEKQPLL |
| 1567 | Tyr 497-505 | SLLCRHKRK |
| 1568 | ED-B domain of Fibronectin | EVPQLTDLSFVDIT DSSIGLRWTPLNSSTIIGYRI TVVAAGEGIPIFEDFVDSSV GYYTVTGLEPGIDYDISVIT LINGGESAPTTLTQQT |
| 1569 | ED-B domain of Fibronectin with flanking sequence from Fribronectin | CTFDNLSPGLEYNVSVY TVKDDKESVPISDTIIP EVPQLTDLSFVDITDS SIGLRWTPLNSSTIIGYRI TVVAAGEGIPIFEDFVDS SSVGYYTVTGLEPGID YDISVITLINGGESAPTTLTQQT AVPPPTDLRFTNIGPDTMRVTW |
| 1570 | ED-B domain of Fibronectin cds | Accession number: X07717 |
| 1571 | CEA protein | Accession number: P06731 |
| 1572 | CEA cDNA | Accession number: NM_004363 |
| 1573 | Her2/Neu protein | Accession number: P04626 |
| 1574 | Her2/Neu cDNA | Accession number: M11730 |
| 1575 | SCP-1 protein | Accession number: Q15431 |
| 1576 | SCP-1 cDNA | Accession number: X95654 |
| 1577 | SSX-4 protein | Accession number: O60224 |
| 1578 | SSX-4 cDNA | Accession number: NM_005636 |

[1]This H was reported as Y in the SWISSPROT database.
[2]The amino acid at position 274 may be Pro or Leu depending upon the database. The particular analysis presented herein used the Pro.
**All accession numbers used here and throughout can be accessed through the NCBI databases, for example, through the Entrez seek and retrieval system on the world wide web.

APPENDIX B

Predicted Binding of Tyrosinase$_{207-216}$
(SEQ ID NO. 980) to Various MHC types

| MHC I type | *Half time of dissociation (min) |
|---|---|
| A1 | 0.05 |
| A*0201 | 1311. |
| A*0205 | 50.4 |
| A3 | 2.7 |
| A*1101 | 0.012 |
| (part of the A3 supertype) | |
| A24 | 6.0 |
| B7 | 4.0 |
| B8 | 8.0 |
| B14 | 60.0 |
| (part of the B27 supertype) | |
| B*2702 | 0.9 |
| B*2705 | 30.0 |
| B*3501 | 2.0 |
| (part of the B7 supertype) | |
| B*4403 | 0.1 |
| B*5101 | 26.0 |

APPENDIX B-continued

Predicted Binding of Tyrosinase$_{207-216}$ (SEQ ID NO. 980) to Various MHC types

| MHC I type | *Half time of dissociation (min) |
|---|---|
| (part of the B7 supertype) | |
| B*5102 | 55.0 |
| B*5801 | 0.20 |
| B60 | 0.40 |
| B62 | 2.0 |

*HLA Peptide Binding Predictions (world wide web hypertext transfer protocol "access at bimas.dcrt.nih.gov/molbio/hla_bin").

APPENDIX C

Class I HLA peptide binding anchor residues*
Amino acids in boldface indicate anchor residues, underline represents auxiliary anchor positions.

| | Position | | | | | | | | |
|---|---|---|---|---|---|---|---|---|---|
| HLA-A1 | 1 | 2 | 3 | 4 | 5 | 6 | 7 | 8 | 9 |
| Anchor or auxiliary anchor residues | | T̲ S̲ | D E | | | | L̲ | | Y |

| | Position | | | | | | | | |
|---|---|---|---|---|---|---|---|---|---|
| HLA-A*0201 | 1 | 2 | 3 | 4 | 5 | 6 | 7 | 8 | 9 |
| Anchor or auxiliary anchor residues | | L M | | | | V̲ | | | V L |

| | Position | | | | | | | | |
|---|---|---|---|---|---|---|---|---|---|
| HLA-A*0202 | 1 | 2 | 3 | 4 | 5 | 6 | 7 | 8 | 9 |
| Anchor residues | | L | | | | | | | L V |

| | Position | | | | | | | | |
|---|---|---|---|---|---|---|---|---|---|
| HLA-A*0204 | 1 | 2 | 3 | 4 | 5 | 6 | 7 | 8 | 9 |
| Anchor or auxiliary anchor residues | | L | | | | | | | L |

| | Position | | | | | | | | |
|---|---|---|---|---|---|---|---|---|---|
| HLA-A*0205 | 1 | 2 | 3 | 4 | 5 | 6 | 7 | 8 | 9 |
| Anchor or auxiliary anchor residues | | V L I M Q | | | | I̲ V̲ L̲ A̲ | | | L |

| | Position | | | | | | | | |
|---|---|---|---|---|---|---|---|---|---|
| HLA-A*0206 | 1 | 2 | 3 | 4 | 5 | 6 | 7 | 8 | 9 |
| Anchor or auxiliary anchor residues | | V | | | | | | | V |

| | Position | | | | | | | | |
|---|---|---|---|---|---|---|---|---|---|
| HLA-A*0207 | 1 | 2 | 3 | 4 | 5 | 6 | 7 | 8 | 9 |
| Anchor or auxiliary anchor residues | | L | D | | | | | | L |

| | Position | | | | | | | | |
|---|---|---|---|---|---|---|---|---|---|
| HLA-A*0214 | 1 | 2 | 3 | 4 | 5 | 6 | 7 | 8 | 9 |
| Anchor or auxiliary anchor residues | | V, Q L̲ | | | | I, L V̲, F̲ | | | L V |

APPENDIX C-continued

Class I HLA peptide binding anchor residues*
Amino acids in boldface indicate anchor residues, underline
represents auxiliary anchor positions.

| HLA-A3 | 1 | 2 | 3 | 4 | 5 | 6 | 7 | 8 | 9 |
|---|---|---|---|---|---|---|---|---|---|
| Anchor or auxiliary anchor residues | | L V M | F Y | | | I M F V L | I L M F | | K Y F |

| HLA-A*1101 | 1 | 2 | 3 | 4 | 5 | 6 | 7 | 8 | 9 |
|---|---|---|---|---|---|---|---|---|---|
| Anchor or auxiliary anchor residues | | V I F Y | M L F Y I A | | | | L I Y V F | | K |

| HLA-A24 | 1 | 2 | 3 | 4 | 5 | 6 | 7 | 8 | 9 |
|---|---|---|---|---|---|---|---|---|---|
| Anchor or auxiliary anchor residues | | Y | | | I V | F | | | I L F |

| HLA-A*2902 | 1 | 2 | 3 | 4 | 5 | 6 | 7 | 8 | 9 |
|---|---|---|---|---|---|---|---|---|---|
| Anchor or auxiliary anchor residues | | E | F | | | | | | Y |

| HLA-A*3101 | 1 | 2 | 3 | 4 | 5 | 6 | 7 | 8 | 9 |
|---|---|---|---|---|---|---|---|---|---|
| Anchor or auxiliary anchor residues | | L V Y F | F L Y W | | | L F V I | | | R |

| HLA-A*3302 | 1 | 2 | 3 | 4 | 5 | 6 | 7 | 8 | 9 |
|---|---|---|---|---|---|---|---|---|---|
| Anchor or auxiliary anchor residues | | A I L F Y V | | | | | | | R |

| HLA-A*6801 | 1 | 2 | 3 | 4 | 5 | 6 | 7 | 8 | 9 |
|---|---|---|---|---|---|---|---|---|---|
| Anchor residues | D E | V T | | | | | | | R K |

| HLA-A*6901 | 1 | 2 | 3 | 4 | 5 | 6 | 7 | 8 | 9 |
|---|---|---|---|---|---|---|---|---|---|
| Anchor or auxiliary Residues | | V T A | I F L M | | | I F L | | | V L |

APPENDIX C-continued

Class I HLA peptide binding anchor residues*
Amino acids in boldface indicate anchor residues, underline
represents auxiliary anchor positions.

| HLA-B7 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | R | | | | | | L F |

| HLA-B*0702 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | | | | | | | L |

| HLA-B*0703 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | R | | | | | E | L |

| HLA-B*0705 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | | | | | | | L |

| HLA-B8 | Position | | | | | | | | |
|---|---|---|---|---|---|---|---|---|---|
| | 1 | 2 | 3 | 4 | 5 | 6 | 7 | 8 | 9 |
| Anchor residues | | | K | | K R | | | | L |

| HLA-B14 | Position | | | | | | | | |
|---|---|---|---|---|---|---|---|---|---|
| | 1 | 2 | 3 | 4 | 5 | 6 | 7 | 8 | 9 |
| Anchor or auxiliary anchor Residues | | R K | L Y F | | R H | I L | | | L |

| HLA-B*1501(B62) | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | Q L | | | I V | | | | F Y |

| HLA-B27 | Position | | | | | | | | |
|---|---|---|---|---|---|---|---|---|---|
| | 1 | 2 | 3 | 4 | 5 | 6 | 7 | 8 | 9 |
| Anchor residues | | R | | | | | | | |

| HLA-B*2702 | Position | | | | | | | | |
|---|---|---|---|---|---|---|---|---|---|
| | 1 | 2 | 3 | 4 | 5 | 6 | 7 | 8 | 9 |
| Anchor residues | | R | | | | | | | F Y I L W |

| HLA-B*2705 | Position | | | | | | | | |
|---|---|---|---|---|---|---|---|---|---|
| | 1 | 2 | 3 | 4 | 5 | 6 | 7 | 8 | 9 |
| Anchor or auxiliary anchor Residues | | R | | | | | | | L F |

APPENDIX C-continued

Class I HLA peptide binding anchor residues*
Amino acids in boldface indicate anchor residues, underline
represents auxiliary anchor positions.

| HLA-B*35 | Position | | | | | | | | |
|---|---|---|---|---|---|---|---|---|---|
| | 1 | 2 | 3 | 4 | 5 | 6 | 7 | 8 | 9 |
| Anchor or Auxiliary anchor residues | | P | | | | | | | Y F M L I |

| HLA-B*3501 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | | | | | | | Y F M L I |

| HLA-B*3503 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | | | | | | | M L F |

| HLA-B*3701 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | D E | | | V I | | | F M L | I L |

| HLA-B*3801 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | H | D E | | | | | | F L |

| HLA-B*39011 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | R H | | | | I V L | | | L |

| HLA-B*3902 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | K Q | | | I L F V | | | | L |

| HLA-B40* | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | E | F I V | | | | | | L W M A T R |

APPENDIX C-continued

Class I HLA peptide binding anchor residues*
Amino acids in boldface indicate anchor residues, underline
represents auxiliary anchor positions.

| HLA-B*40012 (B60) | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | E | | | | | I V | | L |

| HLA-B*4006 (B61) | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | E | F I L V Y W | | | I | | | V |

| HLA-B44 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | E | I | P | | V | | | Y |

| HLA-B*4402 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | E | | | | | | | F Y |

| HLA-B*4403 | Position | | | | | | | | |
|---|---|---|---|---|---|---|---|---|---|
| | 1 | 2 | 3 | 4 | 5 | 6 | 7 | 8 | 9 |
| | | E | | | | | | | Y F |

| HLA-B*4601 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | M | K R, N | D E, V | P I | S | E | V A | Y F |

| HLA-B*5101 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | A P G | | | | | | | F I |

| HLA-B*5102 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P A G | Y | | | | | | I V |

| HLA-B*5103 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | A P G | Y | | | | | | V I F |

APPENDIX C-continued

Class I HLA peptide binding anchor residues*
Amino acids in boldface indicate anchor residues, underline
represents auxiliary anchor positions.

| HLA-B*5201 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | Q | F Y W | | L I V | | | I V | I V |

| HLA-B*5301 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | | | | | | | L, I |

| HLA-B*5401 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | | | | | | | |

| HLA-B*5501 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | | | | | | | |

| HLA-B*5502 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | | | | | | | |

| HLA-B*5601 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | A | P | Y | | | | | | A |

| HLA-B*5801 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | A S T | | P E K | V I L M F | | | | F W |

| HLA-B*6701 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P | | | | | | | L |

| HLA-B*7301 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | R | | | | | | | P |

| HLA-B*7801 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | P A G | | | | I L F V | | A | |

APPENDIX C-continued

Class I HLA peptide binding anchor residues*
Amino acids in boldface indicate anchor residues, underline
represents auxiliary anchor positions.

| HLA-Cw*0102 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | A<br>L | | | | | | | L |

| HLA-Cw*0301 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | | V<br>I<br>Y<br>L<br>M | P | | F<br>Y | | | L<br>F<br>M<br>I |

| HLA-Cw*0304 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | A | V<br>I<br>P<br>Y<br>M | P<br>E | | | M<br>E | | L<br>M |

| HLA-Cw*0401 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | Y<br>P<br>F | | | | V<br>I<br>L | | | L<br>F<br>M |

| HLA-Cw*0601 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | | | | I<br>L<br>F<br>M | V<br>I<br>L | | | L<br>I<br>V<br>Y |

| HLA-Cw*0602 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | | | | I<br>L<br>F<br>M | V<br>I<br>L | | | L<br>I<br>V<br>Y |

| HLA-Cw*0702 | Position | | | | | | | | |
|---|---|---|---|---|---|---|---|---|---|
| | 1 | 2 | 3 | 4 | 5 | 6 | 7 | 8 | 9 |
| Anchor or auxiliary anchor residues | | Y<br>P | | | V<br>Y<br>I<br>L<br>F<br>M | V<br>I<br>L<br>M | | | Y<br>F<br>L |

*(Extracted from Table 4.2 of Rammensee et al., previously incorporated by reference.)

What is claimed is:

1. A vector comprising a housekeeping epitope expression cassette, wherein the housekeeping epitope is derived from a target-associated antigen, wherein the housekeeping epitope is liberatable from a translation product of the cassette by immunoproteasome processing, wherein the antigen is NY-ESO-1, wherein the housekeeping epitope is NY-ESO-$1_{157-165}$ (SEQ ID NO:12), and wherein the vector comprises a nucleic acid sequence encoding SEQ ID NO:18.

2. A vector comprising a housekeeping epitope expression cassette, wherein the housekeeping epitope is derived from a target-associated antigen, wherein the housekeeping epitope is liberatable from a translation product of the cassette by immunoproteasome processing, wherein the antigen is NY- ESO-1, wherein the housekeeping epitope is NY-ESO-$1_{157-165}$ (SEQ ID NO:12), and wherein the vector comprises a nucleic acid sequence encoding SEQ ID NO:22.

3. The vector of claim 2, comprising a nucleic acid sequence encoding SEQ ID NO:20.

4. A vector comprising a housekeeping epitope expression cassette, wherein the housekeeping epitope is derived from a target-associated antigen, wherein the housekeeping epitope is liberatable from a translation product of the cassette by immunoproteasome processing, wherein the antigen is NY-ESO-1, wherein the housekeeping epitope is NY-ESO-$1_{157-165}$ (SEQ ID NO:12), and wherein the vector comprises a nucleic acid sequence encoding the polypeptide sequence M-(B-A-D-D-A-B-A-A), and wherein M is an initiator Methionine, B is the sequence of SEQ ID NO:12, A is the sequence of SEQ ID NO:13, and D is the sequence of SEQ ID NO:15 (SEQ ID NO:1582).

\* \* \* \* \*

UNITED STATES PATENT AND TRADEMARK OFFICE
CERTIFICATE OF CORRECTION

Page 1 of 1

PATENT NO.       : 8,637,305 B2
APPLICATION NO.  : 10/292413
DATED            : January 28, 2014
INVENTOR(S)      : Simard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1637 days.

Signed and Sealed this
Twenty-first Day of July, 2015

Michelle K. Lee
*Director of the United States Patent and Trademark Office*